US010953034B2

(12) United States Patent
Kammler et al.

(10) Patent No.: US 10,953,034 B2
(45) Date of Patent: Mar. 23, 2021

(54) NUCLEIC ACID MOLECULE FOR REDUCTION OF PAPD5 AND PAPD7 MRNA FOR TREATING HEPATITIS B INFECTION

(71) Applicant: HOFFMANN-LA ROCHE INC., Little Falls, NJ (US)

(72) Inventors: Susanne Kammler, Hørsholm (DK); Anaïs Lopez, Basel (CH); Henrik Mueller, Basel (CH); Søren Ottosen, Hørsholm (DK); Lykke Pedersen, Hørsholm (DK)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/162,279

(22) Filed: Oct. 16, 2018

(65) Prior Publication Data
US 2019/0111073 A1 Apr. 18, 2019

(30) Foreign Application Priority Data

Oct. 16, 2017 (EP) .................................... 17196554
Dec. 18, 2017 (EP) .................................... 17208056

(51) Int. Cl.
A61K 31/7105 (2006.01)
A61P 31/20 (2006.01)
C12N 15/113 (2010.01)
C07H 21/02 (2006.01)
A61K 31/712 (2006.01)

(52) U.S. Cl.
CPC ........ A61K 31/7105 (2013.01); A61K 31/712 (2013.01); A61P 31/20 (2018.01); C07H 21/02 (2013.01); C12N 15/113 (2013.01); C12N 15/1137 (2013.01); C12N 2310/11 (2013.01); C12N 2310/315 (2013.01); C12N 2310/3231 (2013.01); C12N 2310/341 (2013.01); C12N 2310/343 (2013.01); C12N 2310/346 (2013.01); C12N 2310/351 (2013.01); C12Y 207/07 (2013.01); C12Y 207/07007 (2013.01)

(58) Field of Classification Search
CPC .............. C12N 15/113; C12N 2310/11; C12N 2310/31; C12N 2310/32; C12N 2310/33; A01K 2207/05
See application file for complete search history.

(56) References Cited

U.S. PATENT DOCUMENTS

| 4,711,955 | A | 12/1987 | Ward et al. |
| 5,525,711 | A | 6/1996 | Hawkins et al. |
| 5,792,608 | A | 8/1998 | Swaminathan et al. |
| 5,885,968 | A | 3/1999 | Biessen et al. |
| 8,090,542 | B2 | 1/2012 | Khvorova et al. |
| 8,349,809 | B2 | 1/2013 | Brown |
| 8,513,207 | B2 | 8/2013 | Brown |
| 9,458,153 | B2 | 10/2016 | Han et al. |
| 10,093,671 | B2 | 10/2018 | Han et al. |
| 2004/0157780 | A1 | 8/2004 | Grey et al. |
| 2005/0272080 | A1 | 12/2005 | Palma et al. |
| 2006/0257851 | A1 | 11/2006 | Bentwich |
| 2010/0173974 | A1 | 7/2010 | Brown |
| 2011/0118337 | A1 | 5/2011 | Chau et al. |
| 2012/0040460 | A1 | 2/2012 | Rigoutsos et al. |
| 2017/0235368 | A1 | 8/2017 | El-Ouardi et al. |
| 2019/0194768 | A1 | 6/2019 | Han et al. |
| 2019/0211339 | A1 | 7/2019 | Agarwal et al. |
| 2019/0216846 | A1 | 7/2019 | Javanbakht et al. |
| 2020/0147123 | A1 | 5/2020 | Kammler et al. |

FOREIGN PATENT DOCUMENTS

| EP | 0302175 | A2 | 2/1989 |
| EP | 1013661 | A1 | 6/2000 |
| EP | 1152009 | A1 | 7/2001 |
| EP | 1752536 | A1 | 12/2005 |
| EP | 2213738 | A2 | 8/2010 |
| WO | 1993007883 | | 4/1993 |
| WO | 1998039352 | A1 | 9/1998 |
| WO | 1999014226 | A2 | 3/1999 |
| WO | 2000047599 | A1 | 8/2000 |
| WO | 2000066604 | A2 | 11/2000 |
| WO | 2001023613 | A1 | 4/2001 |
| WO | 20030022987 | A2 | 3/2003 |
| WO | 2004046160 | A2 | 6/2004 |
| WO | 2005014806 | A2 | 2/2005 |
| WO | 2007031091 | A2 | 3/2007 |
| WO | 2007090071 | A2 | 8/2007 |
| WO | 20070106407 | A2 | 9/2007 |
| WO | 2007134181 | A2 | 11/2007 |
| WO | 2007146511 | A2 | 12/2007 |
| WO | 2008049085 | A1 | 4/2008 |
| WO | 2008082730 | A2 | 7/2008 |
| WO | 2008113832 | A2 | 9/2008 |
| WO | 2008150729 | A2 | 12/2008 |
| WO | 2008154401 | A2 | 12/2008 |

(Continued)

OTHER PUBLICATIONS

Ansel, H.C., Pharmaceutical Dosage Forms and Drug Delivery Systems, 1995, Williams & Wilkins, ppxi-xii, 105-116, 194-200, 497-514, cover pages.

Bastin, R.J. et al., Salt Selection and Optimisation Procedures for Pharmaceutical New Chemical Entities, Organic Process Research & Development, (2000), vol. 4, pp. 427-435.

(Continued)

Primary Examiner — Brian Whiteman
(74) Attorney, Agent, or Firm — Holland & Hart LLP

(57) ABSTRACT

The present invention relates to nucleic acid molecules that are complementary to both PAP associated domain containing 5 (PAPD5) and PAP associated domain containing 7 (PAPD7), leading to inhibition of the expression of both PAPD5 and PAPD7 when using a single nucleic acid molecule. The invention also provides for PAPD5 and PAPD7 specific nucleic acid molecules for use in treating and/or preventing a HBV infection, in particular a chronic HBV infection. Also comprised in the present invention is a pharmaceutical composition for use in the treatment and/or prevention of a HBV infection.

24 Claims, 21 Drawing Sheets

Figure 1A:
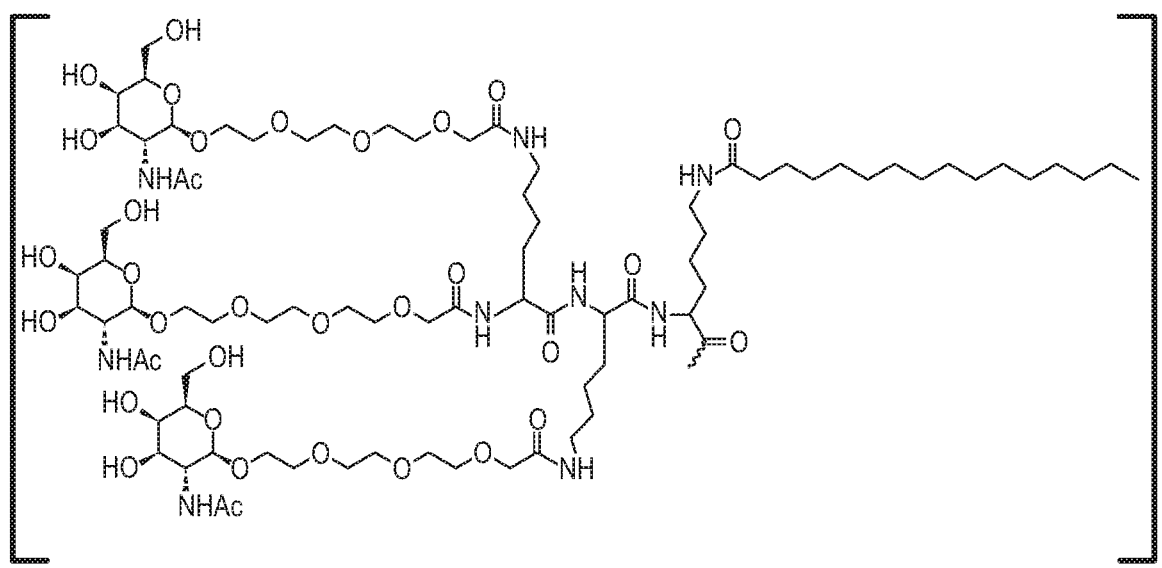
Figure 1B:
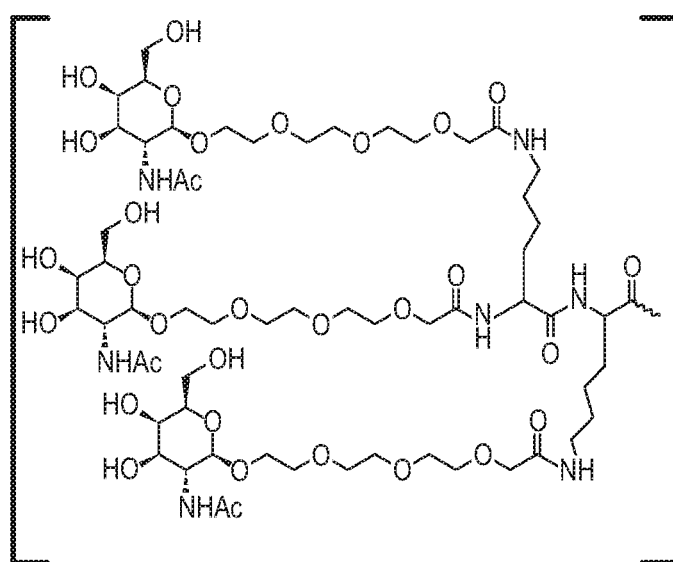
Figure 1C:
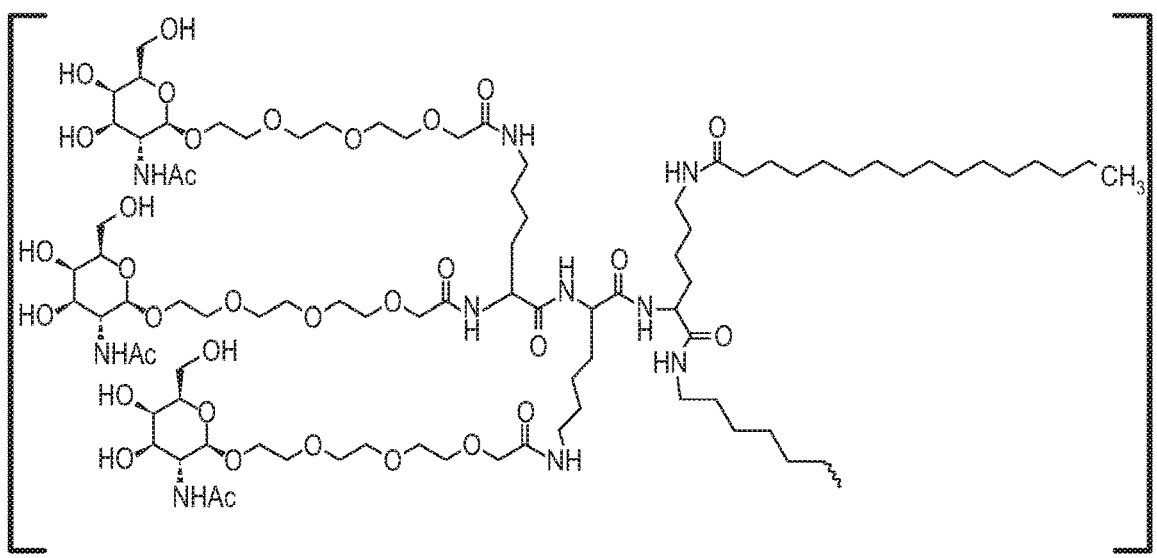

Specification includes a Sequence Listing.

(56) References Cited

FOREIGN PATENT DOCUMENTS

| | | | |
|---|---|---|---|
| WO | 2009006478 A2 | 1/2009 | |
| WO | 2009067647 A1 | 5/2009 | |
| WO | 2009090182 A1 | 7/2009 | |
| WO | 2009124238 A1 | 10/2009 | |
| WO | 2010036698 A1 | 4/2010 | |
| WO | 20100040571 A2 | 4/2010 | |
| WO | 2010077578 A1 | 7/2010 | |
| WO | 2010093788 A2 | 8/2010 | |
| WO | 2011017521 A2 | 2/2011 | |
| WO | 2011108699 A1 | 9/2011 | |
| WO | 2011156202 A1 | 12/2011 | |
| WO | 2012024170 A2 | 2/2012 | |
| WO | 2012055362 A1 | 5/2012 | |
| WO | 2012109395 A1 | 8/2012 | |
| WO | 2012145697 A1 | 10/2012 | |
| WO | 2013003520 A1 | 1/2013 | |
| WO | 2013022984 A1 | 2/2013 | |
| WO | 2013033230 A1 | 3/2013 | |
| WO | 2013036868 A1 | 3/2013 | |
| WO | 2013113501 A1 | 8/2013 | |
| WO | 2013154798 A1 | 10/2013 | |
| WO | 2013159109 A1 | 10/2013 | |
| WO | 20130166264 A2 | 11/2013 | |
| WO | 2014012081 A2 | 1/2014 | |
| WO | 20140036429 A1 | 3/2014 | |
| WO | 2014076195 A1 | 5/2014 | |
| WO | 2014076196 A1 | 5/2014 | |
| WO | 2014179620 A1 | 11/2014 | |
| WO | 2014179629 A2 | 11/2014 | |
| WO | 2014207232 A1 | 12/2014 | |
| WO | 2015031694 A2 | 3/2015 | |
| WO | 2015113922 A1 | 8/2015 | |
| WO | 20150113990 A1 | 8/2015 | |
| WO | 2015173164 A1 | 11/2015 | |
| WO | 2015173208 A2 | 11/2015 | |
| WO | 2016051116 A1 | 4/2016 | |
| WO | 2016055601 A1 | 4/2016 | |
| WO | 2016079181 A1 | 5/2016 | |
| WO | 2016127002 A1 | 8/2016 | |
| WO | 20160177655 A1 | 11/2016 | |
| WO | 2017015175 A1 | 1/2017 | |
| WO | 2017027350 A2 | 2/2017 | |
| WO | 2017066712 A2 | 4/2017 | |
| WO | 2017178656 A1 | 10/2017 | |
| WO | 2017216390 A1 | 12/2017 | |
| WO | 2017216391 A1 | 12/2017 | |
| WO | 2018059718 A1 | 4/2018 | |
| WO | WO-2019145543 A1 * | 8/2019 | ............... C07H 1/00 |

OTHER PUBLICATIONS

Biessen, E.A.L. et al., Synthesis of Cluster Galactosides with High Affinity for the Hepatic Asialoglycoprotein Receptor, J. Med. Chem., 1995, vol. 38(9), pp. 1538-1546.

Biessen, E.A.L. et al., Receptor-Dependent Cell Specific Delivery of Antisense Oligonucleotides, Developments in Cardiovascular Medicine, (1999), p. 285-299.

Buster, E.H. et al., Peginterferon alpha-2b is safe and effective in HBeAg-positive chronic hepatitis B patients with advanced fibrosis, Hepatology, 2007, vol. 46, No. 2, pp. 388-394.

Cahn, R.S., et al., Specification of Molecular Chirality, Angewandte Chemie International Edition, 1966, vol. 5, No. 4, pp. 385-415.

Caruthers, M.H. et al., Chemical Synthesis of Deoxyoligonucleotides by the Phosphoramidite Method, Methods in Enzymology, 1987, vol. 154, pp. 287-313.

Chang, Mei-Hwei, Hepatitis B virus infection, Elsevier, Seminars in Fetal Neonatal Medicine, 2007, vol. 12, pp. 160-167.

Deleavey, G.F. et al., Designing Chemically Modified Oligonucleotides for Targeted Gene Silencing, Chemistry and Biology, 2012, vol. 19(8), pp. 937-954.

Duff, R.J. et al., Intrabody Tissue-Specific Delivery of Antisense Conjugates in Animals: Ligand-Linker-Antisense Oligomer Conjugates, Methods in Enzymolology, 2000, vol. 313(17), pp. 297-321.

Fluiter, K. et al., Filling the gap in LNA antisense oligo gapmers: the effects of unlocked nucleic acid (UNA) and 4'-C-hydroxymethyl-DNA modifications on RNase H recruitment and efficacy of an LNA gapmer, Molecular Biosystems, 2009, vol. 5, pp. 838-843.

Freier, S.M. et al., The ups and downs of nucleic acid duplex stability: structure-stability studies on chemically-modified DNA:RNA duplexes, Nucleic Acids Research, 1997, vol. 25(22), pp. 4429-4443.

Hansen, L.D. et al., Entropy Titration. A calorimetric method for the determination of $\Delta G°(K)$, $\Delta H°$ and $\Delta S°1$, Chemical Communications, 1965, No. 3, pp. 36-38.

Hantz, O. et al., Persistence of the hepatitis B virus covalently closed circular DNA in HepaRG human hepatocyte-like cells, Journal of General Virology, 2009, vol. 90, Part 1, pp. 127-135.

Hirao, I. et al., Natural versus Artificial Creation of Base Pairs in DNA: Origin of Nucleobases from the Perspectives of Unnatural Base Pair Studies, Accounts of Chemical Research, 2012, vol. 45, No. 12, pp. 2055-2065.

Ishida, Y. et al., Novel Robust in Vitro Hepatitis B Virus Infection Model Using Fresh Human Hepatocytes Isolated from Humanized Mice, American Journal of Pathology, 2015, vol. 185, No. 5, pp. 1275-1285.

Khorev, O. et al., Trivalent, Gal/GalNAc-containing ligands designed for the asialoglycoprotein receptor, Bioorganic & Medicinal Chemistry, 2008, vol. 16(9), pp. 5216-5231.

Knowles, B.B. et al., Human Hepatocellular Carcinoma Cell Lines Secrete the Major Plasma Proteins and Hepatitis B Surface Antigen, Science, 1980, vol. 209(4455), pp. 497-499.

Langer, R., New Methods of Drug Delivery, Science, 1990, vol. 249, issue 4976, pp. 1527-1533.

Mangos, M.M. et al., Efficient RNase H-Directed Cleavage of RNA Promoted by Antisense DNA or 2'F-ANA Constructs Containing Acyclic Nucleotide Inserts, J. Am. Chem. Soc., 2003, vol. 125(3), pp. 654-661.

McTigue, P.M. et al., Sequence-Dependent Thermodynamic Parameters for Locked Nucleic Acid (LNA)-DNA Duplex Formation, Biochemistry, 2004, vol. 43(18), pp. 5388-5405.

Mergny, J.L. et al., Analysis of Thermal Melting Curves, Oligonucleotides, 2003, vol. 13(6), pp. 515-537.

Milich, D.R., Influence of T-helper cell subsets and crossregulation in hepatitis B virus infection, Journal of Viral Hepatitis, (1997), vol. 4 (suppl 2), pp. 48-59.

Mitsuoka, Y. et al., A bridged nucleic acid, 2',4'-BNACOC: synthesis of fully modified oligonucleotides bearing thymine, 5-methylcytosine, adenine and guanine 2',4'-BNACOC monomers and RNA-selective nucleic-acid recognition, Nucleic Acids Research, 2009, vol. 37, No. 4, pp. 1225-1238.

Morita, K. et al., 2'-O,4'-C-ethylene-bridged nucleic acids (ENA): highly nuclease-resistant and thermodynamically stable oligonucleotides for antisense drug, Bioorganic & Medicinal Chemistry Letters, 2002, vol. 12(1), pp. 73-76.

Nayersina, R. et al, HLA A2 restricted cytotoxic T lymphocyte responses to multiple hepatitis B surface antigen epitopes during hepatitis B virus infection, Journal of Immunology, (1993), vol. 150(10), pp. 4659-4671.

Rukov, J.L. et al., Dissecting the target specificity of RNase H recruiting oligonucleotides using massively parallel reporter analysis of short RNA motifs, Nucleic Acids Research, 2015, vol. 43(17), pp. 8476-8487.

Santalucia, J. Jr., A unified view of polymer, dumbbell, and oligonucleotide DNA nearest-neighbor thermodynamics, Proc. National Academy Science USA., 1998, vol. 95(4), pp. 1460-1465.

Sells, M.A. et al., Production of hepatitis B virus particles in Hep G2 cells transfected with cloned hepatitis B virus DNA, Proceedings of National Academy Science USA, 1987, vol. 84(4), pp. 1005-1009.

Seth, P.P. et al.,Synthesis and Biophysical Evaluation of 2',4'-Constrained 2'O-Methoxyethyl and 2',4'-Constrained 2'O-Ethyl Nucleic Acid Analogues, J. Org. Chem., 2010, vol. 75, No. 5, pp. 1569-1581.

Shi, C.C. et al., Hepatitis B virus suppresses the functional interaction between natural killer cells and plasmacytoid dendritic cells, Journal Viral Hepatitas, 2012, vol. 19(2), e26-e33.

(56) References Cited

OTHER PUBLICATIONS

Sugimoto, N. et al., Thermodynamic Parameters to Predict Stability of RNA/DNA Hybrid Duplexes, Biochemistry, 1995, vol. 34(35), pp. 11211-11216.
Uhlmann, E., Recent advances in the medicinal chemistry of antisense olignonucleotides, Current Opinion in Drug Discovery & Development, 2000, vol. 3, No. 2, pp. 203-213.
Vester, B. et al., Chemically modified oligonucleotides with efficient RNase H response, Bioorganic & Medicinal Chemistry Letters, 2008, vol. 18 (7), pp. 2296-2300.
Walsh, R. et al., Targeting the hepatits B virus procore antigen with a novel IgNAR singel variable domain intrabody, Virology, 2011, vol. 411, No. 1, pp. 132-141.
Wooddell, C.I. et al., RNAi-based treatment of chronically infected patients and chimpanzees reveals that Integrated hepatitis B virus DNA is a source of HBsAg, Science Translational Medicine, 2017, vol. 9, No. 409, eaan0241.
Yang, D. et al., A mouse model for HBV immunotolerance and immunotherapy, Cellular & Molecular Immunology, 2014, vol. 11, pp. 71-78.
N.N: database entry: ATJ17241, Sep. 20, 2007 (Sep. 20, 2007), pp. 1-1, XP055404262, Retrieved from the Internet: URL:file:///C:/Users/TL23249/Documents/Downloads/GSN_ATJ17241.pdf [retrieved on Sep. 6, 2017].
Database EMBL, Aug. 18, 2010, (Aug. 18, 2010) Sequence 593709 from Patent EP2213738., XP002787331, retrieved from EBI accession No. EM PAT:HD716993 Database accession No. HD716993 sequence.
Database EMBL, Apr. 19, 2011, (Apr. 19, 2011) WO 2005116204-A/507823: Double strand polynucleotides generating RNA interference., XP002787332, retrieved from EBI accession No. EM PAT:FZ101298 Database accession No. FZ101298 sequence.
Database EMBL, Aug. 18, 2011, (Aug. 18, 2011) 11 Sequence 447635 from Patent EP2213738. II XP002787330, retrieved from EBI accession No. EM PAT:HD570919 Database accession No. HD570919 sequence.
N.N: database entry: GZ986077, Jun. 4, 2013 (Jun. 4, 2013), pp. 1-1, XP055404295, Retrieved from the Internet: URL:file:///C:/Users/TL23249/Documents/Downloads/EM_PAT_GZ986077.pdf [retrieved on Sep. 6, 2017].
N.N: database entry: miRTarBase—targets for hsa-mir-192-5p, Jun. 3, 2014 (Jun. 3, 2014), XP055404326, Retrieved from the Internet: URL:file:///C:/Users/TL23249/Documents/Downloads/miRNA-Target Interaction Search Results.pdf [retrieved on Sep. 6, 2017].
N.N: database entry GS_NUC ALERT:W02015031694.237191, Mar. 5, 2015 (Mar. 5, 2015), pp. 1-1, XP055404257, Retrieved from the Internet: URL:www [retrieved on Sep. 6, 2017].
Block, Timothy M. et al., Chronic hepatitis B: A wave of new therapies on the horizon, Antiviral Research, Elsevier BV, NL, vol. 121, Jun. 22, 2015 (Jun. 22, 2015), pp. 69-81.
Buster et al., Withdrawal Flares After Treatment with Peginterferon Alpha-2b alone or in Combination with Lamivudine in HBeAg-Positive Chronic Hepatitis B, Hepatology, (2007), 46, 388-94.
Chen et al., Immune Tolerance Split between Hepatitis B Virus Precore and Core Proteins, 2005, Journal of Virology, 79: 3016-3027.
Fisicaro et al., Antiviral Intrahepatic T-Cell Responses Can Be Restored by Blocking Programmed Death-1 Pathway in Chronic Hepatitis B, Gastroenterology, (2010), 138, 682-93.
Geng, Ca et al., Small-molecule inhibitors for the treatment of hepatitis B virus documented in patents, Mini Reviews in Medicinal Chemistry, Bentham Science Publ, NL, vol. 13, No. 5, Apr. 1, 2013 (Apr. 1, 2013), pp. 749-776.
Hadziyannis, Natural history of chronic hepatitis B in Euro-Mediterranean and African Countries, 2011, Journal of hepatology, 55: 183-191.
Hui Wang et al., Identification of acetyltransferase genes (HAT1 and KAT8) regulating HBV replication by RNAi screening, Cell & Bioscience, vol. 3, No. 9, Dec. 1, 2015 (Dec. 1, 2015), p. 715.

Janssen et al., Pegylated interferon alfa-2b alone or in combination with lamivudine for HBeAg-positive chronic hepatitis B: a randomised trial, Lancet, (2005), 365, 123-9.
Kondo et al., Recovery of Functional Cytotoxic T LymphocytesDuring Lamivudine Therapy by AcquiringMulti-Specificity, Journal of Medical Virology (2004), 74, 425-433.
Kondo et al., Hepatitis B Surface Antigen Could Contribute to the Immunopathogenesis of Hepatitis B Virus Infection, ISRN Gasteroenterology, (2013), Article ID 935295.
Kumar et al., Hepatitis B Virus Regulatory HBx Protein Binds to Adaptor Protein IPS-1 and Inhibits the Activation of Beta Interferon, J Virol, (2011), 85, 987-95.
Liaw et al., Hepatitis B virus infection, Lancet, 2009, 373: 582-592.
Liaw, Hepatitis B e Antigen Seroconversion: A Critical Event in Chronic Hepatitis B Virus Infection, Dig. Dis. Sci., 2010, 55: 2727-2734.
Marcellin et al., Peginterferon Alfa-2a Alone, Lamivudine Alone, and the Two in Combination in Patients with HBeAg-Negative Chronic Hepatitis B, N. Engl. J. Med., (2004), 351, 1206-17.
Milich et al., The Secreted Hepatitis B Precore Antigen Can Modulate the Immune Response to the Nucleocapsid: A Mechanism for Persistence, 1998, J. Immunol. 160: 2013-2021.
Mueller Henrik et al: PAPD5/7 are novel host factors that are required for Hepatitis B virus RNA stabilization, Hepatology, Oct. 26, 2018, pp. 1527-3350.
Op Den Brouw et al., Hepatitis B virus surface antigen impairs myeloid dendritic cellfunction: a possible immune escape mechanism of hepatitis B virus, Immunology, (2009b), 126, 280-9.
Ra Palma et al., database entry: GC056445, Aug. 12, 2005 (Aug. 12, 2005), pp. 1-1, XP055404289, Retrieved from the Internet: URL:file:///C:/Users/TL23249/Documents/Downloads/EM_PAT_GC056445.pdf [retrieved on Sep. 6, 2017].
Schulze et al., Detection of CD4+ T Cell Responses in Patients with acute HCV Infection Irrespective of Clinical Outcome, Hepatology, 46, (2007), 1759-68.
Shin et al, Prediction of response to entecavir therapy in patients withHBeAg-positive chronic hepatitis B based on on-treatmentHBsAg, HBeAg and HBV DNA levels, J Viral Hepat. (2012), 19, e26-33.
Tavis John E. et al., The hepatitis B virus ribonuclease H as a drug target, Antiviral Research, vol. 118, Apr. 8, 2015 (Apr. 8, 2015), pp. 132-138.
Wieland, S. F. & F. V. Chisari, Stealth and Cunning: Hepatitis B and Hepatitis C Viruses, J Virol, (2005), 79, 9369-80.
Woltman et al., Hepatitis B Virus Lacks Immune Activating Capacity, but Actively Inhibits Plasmacytoid Dendritic Cell Function; PLoS One, (2011), 6, e15324.
Yan et al., Molecular Determinants of Hepatitis B and D Virus Entry Restriction in Mouse Sodium Taurocholate Cotransporting Polypeptide, J Virol, 87, (2013), 7977-91.
PCT International Search Report for PCT International Patent Application No. PCT/EP2017/064981, dated Oct. 2, 2017.
Altschul, SF et al., "Basic Local Alignment Search Tool," J Mol Biol, 1990, vol. 215, pp. 403-410, 8 pages.
Bergstrom DE, "Unnatural Nucleosides with Unusual Base Pairing Properties," Current Protocols in Nucleic Acid Chemistry, 2001, Suppl. 5, pp. 1.4.1-1.4.13, 13 pages.
Holdgate, GA et al., "Measurements of binding thermodynamics in drug discovery," Drug Discovery Today, 2005, vol 10, No. 22, pp. 1543-1550, 8 pages.
Manoharan, M., "Oligonucleotide Conjugates in Antisense Technology," Antisense Drug Technology, Marcel Dekker, Inc., 2001, Ch. 16, pp. 391-469, 81 pages.
N.N: database entry: mRNA—"EM_EST:AW015126; SV 1; linear; mRNA; EST; HUM; 244 BP," Sep. 13, 1999; Retrieved from the Internet: URL:file:///ibis.internal.epo.org/exam/dbfetch.jsp?id=EM_EST:AW015126 [retrieved on Jan. 15, 2020], 1 page.
Ogami, K et al., "Molecular cloning and characterization of a novel isoform of the non-canonical poly(A) polymerase PAPD7", Biochemical and Biophysical Research Communications, 2013, 432.1, pp. 135-140, 6 pages.

(56) References Cited

OTHER PUBLICATIONS

Winther, TH et al., "Circulating MicroRNAs in Plasma of Hepatitis B e Antigent Positive Children Reveal Liver-Specifc Target Genes", International Journal of Hepatology, 2014, article ID791045, pp. 1-10, 10 pages.

Wu Q et al., "EM_EST:EH352838; SV 1; linear; mRNA; EST; HUM; 105 BP," Mar. 2, 2007; Retrieved from the Internet: URL:file:///ibis.internal.epo.org/exam/dbfetch.jsp?id=EM_EST:EH352838 [retrieved on Jan. 15, 2020], 1 page.

Altschul SF, "A Protein Alignment Scoring System Sensitive at All Evolutionary Distances," Journal Molecular Evolution, 1993, vol. 36, pp. 290-300; 11 pages.

Altschul, SF et al., "Gapped BLAST and PSI-BLAST: a new generation of protein database search programs," Nucleic Acids Research, 1997, vol. 25:17, pp. 3389-3402, 14 pages.

Bartel et al., "Cellular interactions in Development: A practical approach." Oxford University Press, pp. 153-179, 28 pages.

Brutlag et al., "Improved sensitivity of biological sequence database searches," 1990, vol. 6:3, pp. 237-245, 9 pages.

Chidley, C. et al., "A yeast-based screen reveals that sulfasalazine inhibits tetrahydrobiopterin biosynthesis", Nature Chemical Biology, 2011, vol. 7, pp. 375-383, 9 pages.

Heidenreich, M et al., "Applications of CRISPR-Cas systems in neuroscience", Nat Rev Neurosci, 2016, vol. 17(1) pp. 36-44, 23 pages.

Lagos-Quintana, M et al. "New microRNAs from mouse and human," RNA, 2003, vol. 9, pp. 175-179, 5 pages.

Lewis BP et al., "Conserved Seed Pairing, Often Flanked by Adenosines, Indicates that Thousands of Human Genes are MicroRNA Targets," Cell, 2005, vol. 120, pp. 15-20, 6 pages.

Licitra, EJ et al., "A three-hybrid system for detecting small ligand—protein receptor interactions", Proc Natl Academy of Science USA, 1996, vol. 93, pp. 12817-12821, 5 pages.

Rammelt, C et al, "PAPD5, a noncanonical poly(A) polymerase with an unusual RNA-binding motif", RNA, 2011, vol. 17, pp. 1737-1746, 10 pages.

Thompson, JD et al., Clustal W: improving the sensitivity of progressive multiple sequence alignment through sequence weighting, position-specific gap penalties and weight matrix choice, Nucleic Acids Res., 1994, vol. 22(22), pp. 4673-4680, 8 pages.

Walsh, R. et al., "Targeting the hepatitis B virus procore antigen with a novel IgNAR singel variable domain intrabody," Virology, 2011, vol. 411, pp. 132-141, 10 pages.

Ward, ES et al., "Binding activities of a repertoire of single immunoglobulin variable domains secreted from *Escherichia coli*," Nature, 1989, vol. 341, pp. 544-546, 3 pages.

Zhou, T et al., HBsAg mRNA degradation induced by a dihydroquinolizinone compound depends on the HBV posttranscription regulatory element, Antiviral Research, 2018, vol. 149, pp. 191-201, 11 pages.

PCT International Search Report for PCT International Patent Application No. PCT/EP2017/064980, dated Oct. 2, 2017.

miRTasBase accession No. MIRT026642 [miRNA, hsa-miR-192-5p : PAPD5, target gene], downloaded Jun. 28, 2019, 4 pages.

miRTasBase accession No. MIRT026248 [miRNA, hsa-miR-192-5p : PAPD7, target gene], downloaded Jun. 28, 2019, 4 pages.

Schulze A. et al., Hepatitis B virus infection initiates with a large surface protein-dependent binding to heparan sulfate proteoglycans, Hepatology, 2007, vol. 46(6), pp. 1759-1768.

U.S. Centers for Disease Control and Prevention ("CDC"), "Hepatitis B FAQs for the Public", retrieved Jan. 28, 2020, 7 pages.

World Health Organization ("Who"), "Hepatitis B Fact sheet No 204", Jul. 2014, retrieved Jan. 28, 2020, 4 pages.

Examination Report issued in EP Application No. 17732082.7 dated Aug. 5, 2020, 5 pages.

Berry M N and Friend D S, High-yield Preparation of Isolated Rat Liver Parenchymal Cells: A Biochemical and Fine Structural Study , J. Cell Biol., 1969, Dec;43(3):506-20. doi: 10.1083/jcb.43.3.506.

Iobst, S. T. and Drickamer, K. JB. C. Selective Sugar Binding to the Carbohydrate Recognition Domains of the Rat Hepatic and Macrophage Asialoglycoprotein Receptors, 1996, 271, 6686.

Paterna J C et al., Antioxidant and Cytoprotective Properties ofd-Tagatose in Cultured Murine Hepatocytes, 1998, Toxicol. Appl. Pharmacol., 1998, vol. 148, Issue 1, pp. 117-125.

Boelea J. et al., "PAPD5-mediated 3'adenylation and subsequent degradation of miR-21 is disrupted in proliferative disease", PNAS, 2014, vol. 111, Issue 31, pp. 11467-11472.

Fakhr et al., Cancer Gene Therapy 23, 73-82 (2016).

Hagedorn et al., Nucleic Acid Research vol. 45, pp. 2262-2282 (2017).

A-fang Ji et al., "Status and research progress in clinical medication of hepatitis B drugs", Anti infect. Pharm., 2019, vol. 16, Issue 12, pp. 2034-2039.

\* cited by examiner

NUCLEIC ACID MOLECULE FOR REDUCTION OF PAPD5 AND PAPD7 MRNA FOR TREATING HEPATITIS B INFECTION

The present application claims the benefit of priority from EP 17196554.4, entitled "NUCLEIC ACID MOLECULE FOR REDUCTION OF PAPD5 AND PAPD7 mRNA FOR TREATING HEPATITIS B INFECTION," filed on 16 Oct. 2017, and from EP 17208056.6, entitled "NUCLEIC ACID MOLECULE FOR REDUCTION OF PAPD5 AND PAPD7 mRNA FOR TREATING HEPATITIS B INFECTION," filed on 18 Dec. 2017, the contents of each of which is incorporated herein by reference.

FIELD OF THE INVENTION

The present invention relates to nucleic acid molecules that are complementary to both PAP associated domain containing 5 (PAPD5) and PAP associated domain containing 7 (PAPD7), leading to inhibition of the expression of both PAPD5 and PAPD7 when using a single oligonucleotide. The invention also provides for PAPD5 and PAPD7 specific nucleic acid molecules for use in treating and/or preventing a HBV infection, in particular a chronic HBV infection. Also comprised in the present invention is a pharmaceutical composition for use in the treatment and/or prevention of a HBV infection.

BACKGROUND

HBV infection remains a major health problem worldwide which concerns an estimated 350 million chronic carriers. Approximately 25% of carriers die from chronic hepatitis, cirrhosis, or liver cancer. Hepatitis B virus is the second most significant carcinogen behind tobacco, causing from 60% to 80% of all primary liver cancer. HBV is 100 times more contagious than HIV.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, *Hepatology*, 46, (2007), 1759-68) and via the specific binding of HBV surface antigens (HBsAg) to the hepatocyte sodium-taurocholate cotransporting polypeptide (NTCP) receptor (Yan, *J Virol*, 87, (2013), 7977-91). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence.

The secretion of antiviral cytokines in response to a HBV infection by the hepatocytes and/or the intra-hepatic immune cells plays a central role in the viral clearance of the infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signalling system and subsequently the interferon (IFN) antiviral activity. Among these, the excessive secretion of HBV empty sub-viral particles (SVPs, HBsAg) are thought to participate to the maintenance of the immunological tolerant state observed in chronically infected patients (CHB). The persistent exposure to HBsAg and other viral antigens can lead to HBV-specific T-cell deletion or to progressive functional impairment (Kondo, *Journal of Immunology* (1993), 150, 4659-4671; Kondo, *Journal of Medical Virology* (2004), 74, 425-433; Fisicaro, *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw, *Immunology*, (2009b), 126, 280-9; Woltman, *PLoS One*, (2011), 6, e15324; Shi, *J Viral Hepat*. (2012), 19, e26-33; Kondo, *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains one of the ultimate goals of therapy. Current therapy such as Nucleos(t)ide analogues are molecules that inhibit HBV DNA synthesis but are not directed at reducing HBsAg level. Nucleos(t)ide analogs, even with prolonged therapy, only show weak HBsAg clearance comparable to those observed naturally (between −1%-2%) (Janssen, *Lancet*, (2005), 365, 123-9; Marcellin, *N. Engl. J. Med.*, (2004), 351, 1206-17; Buster, *Hepatology*, (2007), 46, 388-94). It was recently shown that completely or patially integrated hepatitis B virus DNA is a source of HBsAg expression in chronically infected individuals (see Wooddell et all 2017 Sci. Transl. Med. Vol 9, Issue 409, eaan0241).

Hepatitis B e-antigen (also called HBV envelope antigen or HBeAg) is a viral protein that is secreted by hepatitis B infected cells. HBeAg is associated with chronic hepatitis B infections and is used as a marker of active viral disease and a patient's degree of infectiousness.

The function of the hepatitis B virus precore or HBeAg is not completely known. However HBeAg is well known to play a key role in viral persistence. HBeAg is thought to promote HBV chronicity by functioning as an immunoregulatory protein. In particular, the HBeAg is a secreted accessory protein, which appears to attenuate the host immune response to the intracellular nucleocapsid protein (Walsh, Virology, 2011, 411(1):132-141). The HBeAg acts as an immune tolerogen contributing to HBV persistence, and possibly functions in utero considering that soluble HBeAg traverses the placenta (Walsh, Virology, 2011, 411(1):132-141). Furthermore, HBeAg downregulates: i) cellular genes controlling intracellular signaling; and ii) the Toll-like receptor 2 (TLR-2) to dampen the innate immune response to viral infection (Walsh, Virology, 2011, 411(1):132-141). In the absence of HBeAg, HBV replication is associated with upregulation of the TLR2 pathway (Walsh, Virology, 2011, 411(1):132-141). Accordingly, HBeAg has a significant role in modulating virus/host interactions to influence the host immune response (Walsh, Virology, 2011, 411(1): 132-141). Thus, reducing HBeAg in HBeAg positive patient population may lead to reversal of HBV specific immunedysfunction (Milich, 1997, J. Viral. Hep. 4: 48-59; Milich, 1998, J. Immunol. 160: 2013-2021). In addition, the secreted HBeAg is significantly more efficient than the intracellular hepatitis core antigen (HBcAg) at eliciting T-cell tolerance, and the split T-cell tolerance between the HBeAg and the HBcAg and the clonal heterogeneity of HBc/HBeAg-specific T-cell tolerance may have significant implications for natural HBV infection and especially for precore-negative chronic hepatitis (Chen, 2005, Journal of Virology, 79: 3016-3027).

Figure 18A:
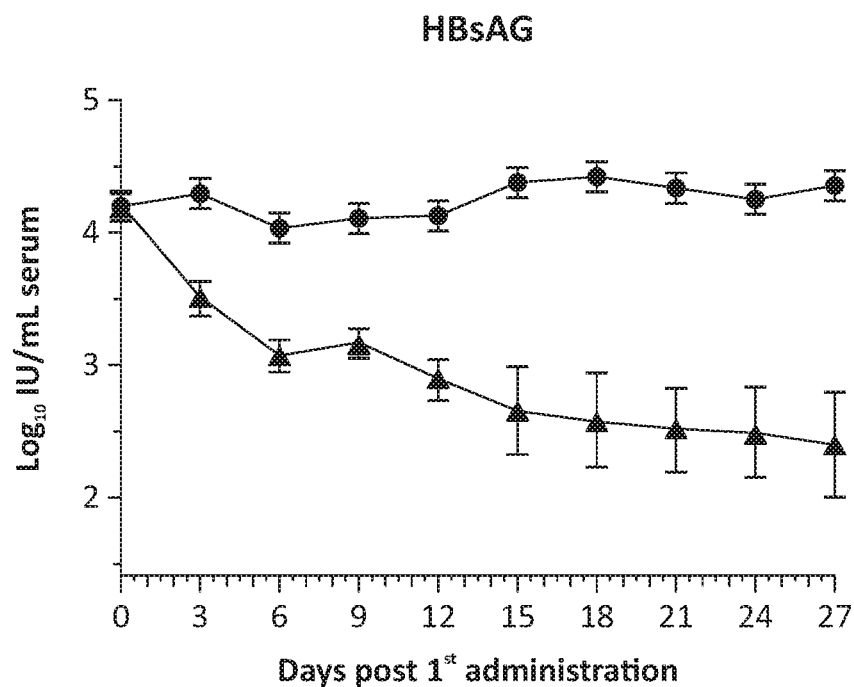
Figure 18B:
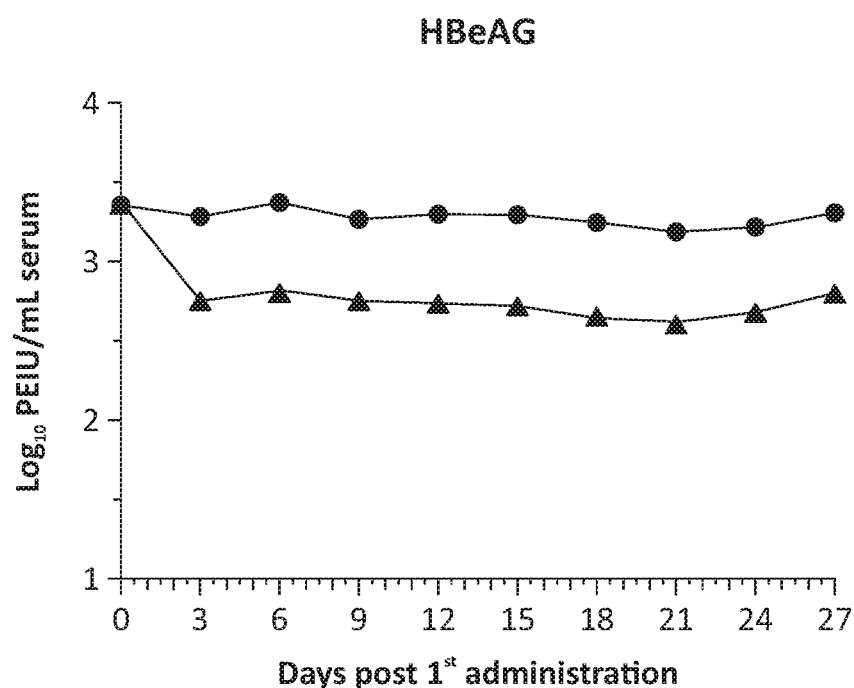

Accordingly, reducing secretion of HBeAg in addition to secretion of HBsAg would lead to an improved inhibition of development of a chronic HBV infection as compared to the inhibition of secretion of HBsAg alone. In addition, the highest rates of transmission of an acute infection to chronic (>80%) have been reported in cases of materno-fetal and neonatal HBV transmission from HBeAg-positive mothers (Liaw, Lancet, 2009, 373: 582-592; Liaw, Dig. Dis. Sci., 2010, 55: 2727-2734; and Hadziyannis, 2011, Journal of hepatology, 55: 183-191). Therefore, reducing HBeAg in an expected mother may not only reduce the patient's degree of infectiousness, but may also inhibit the development of a chronic HBV infection of her child.

Therefore, in the therapy of HBV there is an unmet medical need to inhibit viral expression, particularly to inhibit secretion of HBsAg and HBeAg (Wieland, S. F. & F. V. Chisari. J Virol, (2005), 79, 9369-80; Kumar et al. J Virol, (2011), 85, 987-95; Woltman et al. PLoS One, (2011), 6, e15324; Op den Brouw et al. Immunology, (2009b), 126, 280-9).

In WO 2017/066712 down regulation of PAPD5 in relation to the treatment and diagnosis of telomere diseases has been described. Five shRNA structures for this purpose have been described.

PCT/EP2017/064980 discloses targeting PAPD5 or PAPD7 with a nucleic acid molecule and the combination of such molecules to treatment HBV infections.

Objective of the Invention

The present invention identifies novel nucleic acid molecules which are capable of inhibiting the expression of both PAPD5 and PAPD7 in vivo and in vitro. The ability to inhibit two target nucleic acids with a single molecule has distinct advantages in terms of production, simplicity of delivery to the target cell, simplicity of pharmacokinetic/pharmacodynamic (PK/PD) and the concentration needed to achieve a therapeutic benefit. Furthermore the present invention shows that there is a correlation between the PAPD5 and PAPD7 knock down and the HBV antigen inhibition, such as HBsAg inhibition.

BRIEF DESCRIPTION OF THE FIGURES

The Figures show:

FIG. 1: Illustrates exemplary antisense oligonucleotide conjugates, where the oligonucleotide either is represented as a wavy line (A-D) or as "oligonucleotide" (E-H) or as $T_2$ (I) and the asialoglycoprotein receptor targeting conjugate moieties are trivalent N-acetylgalactosamine moieties. Compounds A to D comprise a di-lysine brancher molecule, a PEG3 spacer and three terminal GalNAc carbohydrate moieties. In compound A and B the oligonucleotide is attached directly to the asialoglycoprotein receptor targeting conjugate moiety without a linker. In compound C and D the oligonucleotide is attached to the asialoglycoprotein receptor targeting conjugate moiety via a C6 linker. Compounds E-I comprise a commercially available trebler brancher molecule and spacers of varying length and structure and three terminal GalNAc carbohydrate moieties.

FIG. 2: Structural formula of the trivalent GalNAc cluster (GN2). GN2 is useful as conjugation moiety in the present invention. The wavy line illustrates the site of conjugation of the cluster to e.g. a C6 amino linker or directly to the oligonucleotide FIG. 3: Shows the correlation between PAPD5 and PAPD7 knock down in Hela cells from example 1 with HBsAg reduction in dHepRG cells from example 2.

FIG. 4: Structural formula of CMP ID NO: 20_12. Pharmaceutical salts thereof include monovalent or divalent cations, such as $Na^+$, $K^+$, and $Ca^{2+}$ or a mixture of these being associated with the compound.

FIG. 5: Structural formula of CMP ID NO: 20_13. Pharmaceutical salts thereof include monovalent or divalent cations, such as $Na^+$, $K^+$, and $Ca^{2+}$ or a mixture of these being associated with the compound.

FIG. 6: Structural formula of CMP ID NO: 20_14. Pharmaceutical salts thereof include monovalent or divalent cations, such as $Na^+$, $K^+$, and $Ca^{2+}$ or a mixture of these being associated with the compound.

FIG. 7: Structural formula of CMP ID NO: 20_15. Pharmaceutical salts thereof include monovalent or divalent cations, such as $Na^+$, $K^+$, and $Ca^{2+}$ or a mixture of these being associated with the compound.

FIG. 8: Structural formula of CMP ID NO: 20_18. Pharmaceutical salts thereof include monovalent or divalent cations, such as $Na^+$, $K^+$, and $Ca^{2+}$ or a mixture of these being associated with the compound.

FIG. 9: Structural formula of CMP ID NO: 20_36. Pharmaceutical salts thereof include monovalent or divalent cations, such as $Na^+$, $K^+$, and $Ca^{2+}$ or a mixture of these being associated with the compound.

FIG. 10: Structural formula of CMP ID NO: 20_30. Pharmaceutical salts thereof include monovalent or divalent cations, such as $Na^+$, $K^+$, and $Ca^{2+}$ or a mixture of these being associated with the compound.

FIG. 11: Representation of in vitro PAPD5 and PAPD7 reduction achieved with oligonucleotides targeting the human and mouse transcripts (table 5) in the human HeLa cell line (A) and in primary mouse hepatocytes (PMH, B).

FIG. 12: Structural formula of CMP ID NO: 20_20. Pharmaceutical salts thereof include monovalent or divalent cations, such as $Na^+$, $K^+$, and $Ca^{2+}$ or a mixture of these being associated with the compound.

FIG. 13: Structural formula of CMP ID NO: 20_21. Pharmaceutical salts thereof include monovalent or divalent cations, such as $Na^+$, $K^+$, and $Ca^{2+}$ or a mixture of these being associated with the compound.

FIG. 14: Structural formula of CMP ID NO: 21_2. Pharmaceutical salts thereof include monovalent or divalent cations, such as $Na^+$, $K^+$, and $Ca^{2+}$ or a mixture of these being associated with the compound.

FIG. 15: Structural formula of CMP ID NO: 20_22. Pharmaceutical salts thereof include monovalent or divalent cations, such as $Na^+$, $K^+$, and $Ca^{2+}$ or a mixture of these being associated with the compound.

FIG. 16: Structural formula of CMP ID NO: 21_33. Pharmaceutical salts thereof include monovalent or divalent cations, such as $Na^+$, $K^+$, and $Ca^{2+}$ or a mixture of these being associated with the compound.

FIG. 17: Structural formula of CMP ID NO: 21_34. Pharmaceutical salts thereof include monovalent or divalent cations, such as $Na^+$, $K^+$, and $Ca^{2+}$ or a mixture of these being associated with the compound.

FIG. 18: Effect on HBsAg and HBeAg over time in vivo in the AAV/HBV mouse model following a single treatment with 10 mg/kg of two oligonucleotides one targeting PAPD5 and one targeting PAPD7.

SUMMARY OF THE INVENTION

Definitions

Nucleic Acid Molecule

The term "nucleic acid molecule" or "therapeutic nucleic acid molecule" as used herein is defined as it is generally understood by the skilled person as a molecule comprising two or more covalently linked nucleosides (i.e. a nucleotide sequence). The nucleic acid molecule(s) referred to in the method of the invention are generally therapeutic oligonucleotides below 50 nucleotides in length. The nucleic acid molecules may be or comprise an antisense oligonucleotide, or may be another oligomeric nucleic acid molecule, such as a CRISPR RNA, a siRNA, shRNA, an aptamer, or a ribozyme. Nucleic acid molecules are compositions that are commonly made in the laboratory by solid-phase chemical synthesis followed by purification. When referring to a sequence of the nucleic acid molecule, reference is made to the sequence or order of nucleobase moieties, or modifications thereof, of the covalently linked nucleotides or nucleosides. The nucleic acid molecule of the invention is man-made, and is chemically synthesized, and is typically purified or isolated. The nucleic acid molecule of the invention may comprise one or more modified nucleosides or nucleotides.

In some embodiments, the nucleic acid molecule of the invention comprises or consists of 12 to 50 nucleotides in length, such as from 13 to 40, such as from 14 to 35, such as from 15 to 30, such as from 16 to 22, such as from 16 to 18 or 15 to 17 contiguous nucleotides in length.

In some embodiments, the nucleic acid molecule or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if a nucleic acid molecule is said to include from 10 to 30 nucleotides, both 10 and 30 nucleotides are included.

In some embodiments, the contiguous nucleotide sequence comprises or consists of 12, 13, 14, 15, 16, 17, 18, 19, 20, 21 or 22 contiguous nucleotides in length The nucleic acid molecule(s) are for modulating the expression of a target nucleic acid in a mammal. In some embodiments the nucleic acid molecules, such as for siRNAs, shRNAs and antisense oligonucleotides, are typically for inhibiting the expression of a target nucleic acid(s).

In one embodiment of the invention the nucleic acid molecule is selected from a RNAi agent, such as a siRNA or shRNA. In another embodiment the nucleic acid molecule is a single stranded antisense oligonucleotide, such as a high affinity modified antisense oligonucleotide.

In some embodiments the nucleic acid molecule is a phosphorothioate nucleic acid molecule. In some embodiments the nucleic acid molecule comprises phosphorothioate internucleoside linkages.

In some embodiments the nucleic acid molecule may be conjugated to non-nucleosidic moieties (conjugate moieties).

A library of nucleic acid molecules is to be understood as a collection of variant nucleic acid molecules. The purpose of the library of nucleic acid molecules can vary. In some embodiments, the library of nucleic acid molecules is composed of oligonucleotides with overlapping nucleobase sequence targeting a region in common between the PAPD5 and PAPD7 target nucleic acids with the purpose of identifying the most potent sequence within the library of nucleic acid molecules. In some embodiments, the library of nucleic acid molecules is a library of nucleic acid molecule design variants (child nucleic acid molecules) of a parent or ancestral nucleic acid molecule, wherein the nucleic acid molecule design variants retaining the core nucleobase sequence of the parent nucleic acid molecule.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. The term single stranded is generally understood by the skilled person in the art. Especially it is understood that single stranded oligonucleotides of the present invention can form hairpins or intermolecular duplex structures (duplex between two molecules of the same oligonucleotide), as long as the degree of intra or inter self complementarity is less than 50% across of the full length of the oligonucleotide.

In one embodiment of the invention the antisense oligonucleotide is an RNaseH recruiting oligonucleotide. Contrary to RNAi molecules antisense oligonucleotides also act in the nucleous of the cell. For targeting pre-mRNA sequences and antisense oligonucleotide is preferable since it acts in the nucleus of the cell.

RNAi

Herein, the term "RNA interference (RNAi) molecule" refers to short double-stranded RNA molecule capable of inducing RNA-dependent gene silencing via the RNA-induced silencing complex (RISC) in a cell's cytoplasm, where they interact with the catalytic RISC component argonaute. One type of RNAi molecule is a small interfering RNA (siRNA), which is a double-stranded RNA molecule that, by binding complementary mRNA after transcription, leads to their degradation and loss in translation. A small hairpin RNA (shRNA) is an artificial RNA molecule with a hairpin structure which upon expression is able to reduce mRNA via the DICER and RNA reducing silencing complex (RISC). RNAi molecules can be designed on the base of the RNA sequence of the gene of interest. Corresponding RNAi can then be synthesized chemically or by in vitro transcription, or expressed from a vector or PCR product siRNA and shRNA molecules are generally between 20 and 50 nucleotides in length, such as between 25 and 35 nucleotides in length, and interacts with the endonuclease known as Dicer which is believed to processes dsRNA into 19-23 base pair short interfering RNAs with characteristic two base 3' overhangs which are then incorporated into an RNA-induced silencing complex (RISC). Effective extended forms of Dicer substrates have been described in U.S. Pat. Nos. 8,349,809 and 8,513,207, hereby incorporated by reference. Upon binding to the appropriate target mRNA, one or more endonucleases within the RISC cleave the target to induce silencing. RNAi agents may be chemically modified using modified internucleotide linkages and high affinity nucleosides, such as 2'-4' bicyclic ribose modified nucleosides, including LNA and cET.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the nucleic acid molecules of the invention compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides as well as siRNA's for in vivo use, and may serve to protect against nuclease cleavage at regions of DNA or RNA nucleosides in the oligonucleotide or siRNA of the invention, for example within the gap region of a gapmer oligonucleotide, as well as in regions of modified nucleosides.

In an embodiment, the nucleic acid molecule, e.g. antisense oligonucleotide, shRNA or siRNA, comprises one or more internucleoside linkages modified from the natural phosphodiester to a linkage that is for example more resistant to nuclease attack. Nuclease resistance may be determined by incubating the oligonucleotide in blood serum or by using a nuclease resistance assay (e.g. snake venom phosphodiesterase (SVPD), both are well known in the art. Internucleoside linkages which are capable of enhancing the nuclease resistance of an oligonucleotide are referred to as nuclease resistant internucleoside linkages. In some embodiments at least 50% of the internucleoside linkages in the antisense oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmakokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 75%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate. In some embodiments at least one of the phosphorothioate internucleoside linkages is stereodefined, such as at least 20%, 30%, 40%, 50%, 60%, such as at least 70%, such as at least 75%, such as at least 80% or such as at least 90% of the internucleoside linkages in the oligonucleotide are stereo defined. The synthesis of stereodefined phosphorothiate linkages are for example described in WO2014/012081 and WO2016/079181.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(S)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR"—CO—O—, —NR$^H$—CO—NR$^H$—, and/or the internucleoside linker may be selected form the group consisting of: —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—CH$_2$—NCH$_3$—O—CH$_2$—, where R$^H$ is selected from hydrogen and C1-4-alkyl.

Nuclease resistant linkages, such as phosphothioate linkages, are particularly useful in antisense oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the antisense oligonucleotide are phosphorothioate and/or boranophosphate linkages. Preferably, all the internucleoside linkages in the oligonucleotide are phosphorothioate linkages.

Stereorandom Phosphorothioate Linkages

Phosphorothioate linkages are internucleoside phosphate linkages where one of the non-bridging oxygens has been substituted with a sulfur. The substitution of one of the non-bridging oxygens with a sulfur introduces a chiral center, and as such within a single phosphorothioate oligonucleotide, each phosphorothioate internucleoside linkage will be either in the S (Sp) or R (Rp) stereoisoforms. Such internucleoside linkages are referred to as "chiral internucleoside linkages". By comparison, phosphodiester internucleoside linkages are non-chiral as they have two non-terminal oxygen atoms.

The designation of the chirality of a stereocenter is determined by standard Cahn-Ingold-Prelog rules (CIP priority rules) first published in Cahn, R. S.; Ingold, C. K.; Prelog, V. (1966). "Specification of Molecular Chirality". Angewandte Chemie International Edition. 5 (4): 385-415. doi:10.1002/anie.196603851.

During standard oligonucleotide synthesis the stereoselectivity of the coupling and the following sulfurization is not controlled. For this reason the stereochemistry of each phosphorothioate internucleoside linkages is randomly Sp or Rp, and as such a phosphorothioate oligonucleotide produced by traditional oligonucleotide synthesis actually can exist in as many as 2$^X$ different phosphorothioate diastereoisomers, where X is the number of phosphorothioate internucleoside linkages. Such oligonucleotides are referred to as stereorandom phosphorothioate oligonucleotides herein, and do not contain any stereodefined internucleoside linkages. Stereorandom phosphorothioate oligonucleotides are therefore mixtures of individual diastereoisomers originating from the non-stereodefined synthesis. In this context the mixture is defined as up to 2$^X$ different phosphorothioate diastereoisomers.

Stereodefined Internucleoside Linkages

A stereodefined internucleoside linkage is an internucleoside linkage which introduces a chiral center into the oligonucleotide, which exists in predominantly one stereoisomeric form, either R or S within a population of individual oligonucleotide molecules.

It should be recognized that stereoselective oligonucleotide synthesis methods used in the art typically provide at least about 90% or at least about 95% stereoselectivity at each internucleoside linkage stereocenter, and as such up to about 10%, such as about 5% of oligonucleotide molecules may have the alternative stereo isomeric form.

In some embodiments the stereoselectivity of each stereodefined phosphorothioate stereocenter is at least about 90%. In some embodiments the stereoselectivity of each stereodefined phosphorothioate stereocenter is at least about 95%.

Stereodefined Phosphorothioate Linkages

Stereodefined phosphorothioate linkages are phosphorothioate linkages which have been chemically synthesized in either the Rp or Sp configuration within a population of individual oligonucleotide molecules, such as at least about 90% or at least about 95% stereoselectivity at each stereocenter (either Rp or Sp), and as such up to about 10%, such as about 5% of oligonucleotide molecules may have the alternative stereo isomeric form.

The stereo configurations of the phosphorothioate internucleoside linkages are presented below

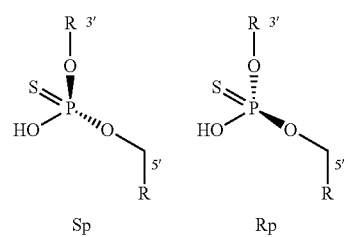

Sp    Rp

Where the 3' R group represents the 3' position of the adjacent nucleoside (a 5' nucleoside), and the 5' R group represents the 5' position of the adjacent nucleoside (a 3' nucleoside).

Rp internucleoside linkages may also be represented as srP, and Sp internucleoside linkages may be represented as ssP herein.

In some embodiments the stereoselectivity of each stereodefined phosphorothioate stereocenter is at least about 97%. In some embodiments the stereoselectivity of each stereodefined phosphorothioate stereocenter is at least about 98%. In some embodiments the stereoselectivity of each stereodefined phosphorothioate stereocenter is at least about 99%.

In some embodiments a stereoselective internucleoside linkage is in the same stereoisomeric form in at least 97%, such as at least 98%, such as at least 99%, or (essentially) all of the oligonucleotide molecules present in a population of the oligonucleotide molecule.

Stereoselectivity can be measured in a model system only having an achiral backbone (i.e. phosphodiesters) it is possible to measure the stereoselectivity of each monomer by e.g. coupling a stereodefined monomer to the following model-system "5' t-po-t-po-t-po 3". The result of this will then give: 5' DMTr-t-srp-t-po-t-po-t-po 3' or 5' DMTr-t-ssp-t-po-t-po-t-po 3' which can be separated using HPLC. The stereoselectivity is determined by integrating the UV signal from the two possible compounds and giving a ratio of these e.g. 98:2, 99:1 or >99:1.

It will be understood that the stereo % purity of a specific single diastereoisomer (a single stereodefined oligonucleotide molecule) will be a function of the coupling selectivity for the defined stereocenter at each internucleoside position, and the number of stereodefined internucleoside linkages to be introduced. By way of example, if the coupling selectivity at each position is 97%, the resulting purity of the stereodefined oligonucleotide with 15 stereodefined internucleoside linkages will be $0.97^{15}$, i.e. 63% of the desired diastereoisomer as compared to 37% of the other diastereoisomers. The purity of the defined diastereoisomer may after synthesis be improved by purification, for example by HPLC, such as ion exchange chromatography or reverse phase chromatography.

In some embodiments, a stereodefined oligonucleotide refers to a population of an oligonucleotide wherein at least about 40%, such as at least about 50% of the population is of the desired diastereoisomer.

Alternatively stated, in some embodiments, a stereodefined oligonucleotide refers to a population of oligonucleotides wherein at least about 40%, such as at least about 50%, of the population consists of the desired (specific) stereodefined internucleoside linkage motif (also termed stereodefined motif).

For stereodefined oligonucleotides which comprise both stereorandom and stereodefined internucleoside stereocenters, the purity of the stereodefined oligonucleotide is determined with reference to the % of the population of the oligonucleotide which retains the defined stereodefined internucleoside linkage motif(s), the stereorandom linkages are disregarded in the calculation.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide or modified nucleic acid molecule describes an oligonucleotide or nucleic acid molecule comprising one or more sugar-modified nucleosides and/or modified internucleoside linkages. The term "chimeric" is a term that has been used in the literature to describe oligonucleotides or nucleic acid molecules with modified nucleosides, in particular gapmer oligonucleotides.

Stereodefined Oligonucleotide

A stereodefined oligonucleotide is an oligonucleotide wherein at least one of the internucleoside linkages is a stereodefined internucleoside linkage.

A stereodefined phosphorothioate oligonucleotide is an oligonucleotide wherein at least one of the internucleoside linkages is a stereodefined phosphorothioate internucleoside linkage.

Stereodefined Internucleoside Motif

A stereodefined internucleoside motif, also termed stereodefined motif herein, refers to the pattern of stereodefined R and S internucleoside linkages in a stereodefined oligonucleotide, and is written 5'-3'. For example, the stereodefined oligonucleotide (SEQ ID NO 18)
5'-$T_{srP}$ $C_{ssP}$ $A_{ssP}$ $a_{srP}$ $C_{srP}$ $t_{ssP}$ $t_{srP}$ $t_{srP}$ $C_{ssP}$ $a_{srP}$ $C_{ssP}$ $t_{srP}$ $t_{ssP}$ $C_{ssP}$ $A_{ssP}$ G-3', has a stereodefined internucleoside motif of RSSRRSRRSRSRSSS.

With respect to sub-libraries of stereodefined oligonucleotides, these will contain a common stereodefined internucleoside motif in an otherwise stereorandom background (optionally with one or more non chiral internucleoside linkages, e.g. phosphodiester linkages).

For example, the oligonucleotide (SEQ ID NO 18)
5'-$T_s$ $C_s$ $A_s$ $a_s$ $C_{srP}$ $t_{ssP}$ $t_{srP}$ $C_s$ $a_s$ $C_s$ $t_s$ $t_s$ $C_s$ $A_s$

G-3 has a stereodefined internucleoside motif of XXXXRSSRXXXXXXX, with X representing a stereorandom phosphorothioate internucleoside linkage (shown as subscript s in the compound). It will be noted that in this example the first 5' stereodefined internucleoside linkage is the $5^{th}$ internucleoside linkage from the 5' end (between the nucleosides at position 4 and 5), and as such the above motif is also referred to as a "RSSR" motif at (internucleoside linkage) position 5.

When the stereodefined internucleoside motif (stereodefined motif) is made up on a series of adjacent stereodefined internucleoside linkages (i.e. positioned between contiguous nucleosides), it is referred to herein as a contiguous stereodefined internucleoside motif (a contiguous stereodefined motif). It will be understood that a contiguous stereodefined motif must comprise two or more adjacent stereodefined internucleoside linkages.

In a sub-library mixture, a stereodefined internucleoside motif may also be dis-contiguous, the stereodefined internucleoside linkages are dispersed with one or more stereorandom internucleoside linkages.

For example the compound

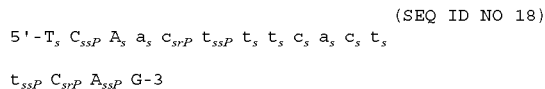
(SEQ ID NO 18)

has a dis-contiguous motif XSXXRSXXXXXXSRS.

Parent Oligonucleotide A parent oligonucleotide is an oligonucleotide which has a defined nucleobase sequence (motif sequence). In the methods of the invention, a parent oligonucleotide is typically an oligonucleotide which is to be improved by the use of the method of the invention by creating one or more libraries.

Typically a library can vary the nucleoside modifications (design libraries) while maintaining the nucleobase sequence of the parent and the stereochemistry (typically stereorandom).

Alternative a library can vary the stereochemistry of the parent oligonucleotide while maintaining the nucleobase sequence (motif sequence) and nucleoside modification pattern (design). In such a library the stereochemistry of one, or more (2+), of the internucleoside linkages is stereodefined and is different to that of the parent oligonucleotide.

In some embodiments, the parent oligonucleotide is a stereorandom phosphorothioate oligonucleotide. In some embodiments, the parent oligonucleotide is a stereorandom phosphorothioate oligonucleotide gapmer.

In some embodiments, the parent oligonucleotide may be a sub-library which comprises a common stereodefined motif.

Stereodefined Variants (Child Oligonucleotides)

A stereodefined variant of an oligonucleotide is an oligonucleotide which retain the same sequence and nucleoside modifications as a parent oligonucleotide (i.e. the same sequence and nucleoside modification chemistry and design), but differs with respect to one or more stereodefined internucleoside linkages, such as one or more stereodefined phosphorothioate internucleoside linkages (a stereodefined phosphorothioate variant).

A stereodefined variant may be a sub-library, or may be a fully stereodefined oligonucleotide.

Sub-Library of Stereodefined Oligonucleotides

An oligonucleotide which comprises both stereorandom and stereodefined oligonucleotides is referred to herein as a sub-library. Sub-libraries are less complex mixtures of the diastereoisomeric mixture of a fully stereorandom oligonucleotide thus representing a sub-set of all possible diastereoisomers. For example, theoretically, a fully phosphorothioate stereorandom 16mer is a mixture of $2^{15}$ diastereoisomer (32768), whereas a sub-library where one of the phosphorothioate internucleoside linkages is stereodefined will have half the library complexity (16384 diastereoisomer), (2 stereodefined linkages=8192 diastereoisomer; 3 stereodefined linkages=4096 diastereoisomer, 4 stereodefined linkages=2048 diastereoisomer, 5 stereodefined linkages=1024 diastereoisomer) assuming 100% stereoselective coupling efficacy.

Fully Stereodefined Oligonucleotides

A fully stereodefined oligonucleotide is an oligonucleotide wherein all the chiral internucleoside linkages present within the oligonucleotide are stereodefined. A fully stereodefined phosphorothioate oligonucleotide is an oligonucleotides wherein all the chiral internucleoside linkages present within the oligonucleotide are stereodefined phosphorothioate internucleoside linkages.

It will be understood that, in some embodiments, a fully stereodefined oligonucleotide may comprise one or more, non-chiral internucleosides, such as phosphodiester internucleoside linkages, for example phosphodiester linkages can be used within the flanking regions of gapmers, and/or when linking terminal nucleosides, such as between short regions of DNA nucleosides (biocleavable linker) linking a gapmer sequence and a conjugate group.

In some embodiments of fully stereodefined oligonucleotide, all of the internucleoside linkages present in the oligonucleotide, or contiguous nucleotide region thereof, such as an F-G-F' gapmer, are stereodefined internucleoside linkages, such as stereodefined phosphorothioate internucleoside linkages.

Complementarity

The term "complementarity" describes the capacity for Watson-Crick base-pairing of nucleosides/nucleotides. Watson-Crick base pairs are guanine (G)-cytosine (C) and adenine (A)—thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol. 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences (when aligned with the target sequence 5'-3' and the oligonucleotide sequence from 3'-5'), dividing by the total number of nucleotides in the oligonucleotide and multiplying by 100. In such a comparison a nucleobase/nucleotide which does not align (form a base pair) is termed a mismatch. Preferably, insertions and deletions are not allowed in the calculation of % complementarity of a contiguous nucleotide sequence.

The term "fully complementary", refers to 100% complementarity.

The following is an example of an oligonucleotide (SEQ ID NO: 12) that is fully complementary to a region of a target nucleic acid.

```
759 ctgtggatgcagatctgggaga    781 (Pos. 759-781 of SEQ ID NO: 1)
    |||||||||||||||||
  1-3'-ACCTACGTCTAGACCC-5'---  16 (SEQ ID NO: 12)
```

Identity

The term "Identity" as used herein, refers to the number of nucleotides in percent of a contiguous nucleotide sequence in a nucleic acid molecule (e.g. oligonucleotide) which, at a given position, are identical to (i.e. in their ability to form Watson Crick base pairs with the complementary nucleoside) a contiguous nucleotide sequence, at a given position of a separate nucleic acid molecule (e.g. the target nucleic acid). The percentage is calculated by counting the number of aligned bases that are identical between the two sequences dividing by the total number of nucleotides in the oligonucleotide and multiplying by 100. Percent Identity= (Matches×100)/Length of aligned region. Preferably, insertions and deletions are not allowed in the calculation of % complementarity of a contiguous nucleotide sequence.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, O*ligonucleotides* 13:515-537). The standard state Gibbs free energy $\Delta G°$ is a more accurate representation of binding affinity and is related to the dissociation constant ($K_d$) of the reaction by $\Delta G°=-RT\ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem, Comm,* 36-38 and Hoidgate et al., 2005, *Drug Discov Today*. The skilled person will know that commercial equipment is available for $\Delta G°$ measurements. $\Delta G°$ can also be estimated numerically by using the nearest neighbor model as described by SantaLucia, 1998, *Proc Nati Acad Sci USA.* 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated $\Delta G°$ value of −10 to −60 kcal, such as −12 to −40, such as from −15 to −30 kcal or −16 to −27 kcal such as −18 to −25 kcal.

Target Nucleic Acid

According to the present invention, there are two target nucleic acids which are to be modulated by the same oligonucleotide. The target nucleic acids are i) a nucleic acid which encodes mammalian PAPD5 (target nucleic acid 1) and ii) a nucleic acid which encodes mammalian PAPD7 (target nucleic acid 2). The target nucleic acids may for example be a gene, a RNA, a mRNA, and pre-mRNA, a mature mRNA or a cDNA sequence. Suitably, the target nucleic acid encodes a PAPD5 or PAPD7 protein, in particular mammalian PAPD5 or PAPD7, such as human PAPD5 or PAPD7 (See for example table 1 and 2) which provides the pre-mRNA sequences for human, monkey, and mouse PAPD5 and PAPD7).

In some embodiments, the target nucleic acid is selected from the group consisting of SEQ ID NO: 1,3 and/or 5 naturally occurring variants thereof (e.g. sequences encoding a mammalian PAPD5).

In some embodiments, the target nucleic acid is selected from the group consisting of SEQ ID NO: 2, 4, and/or 6 or 11 or naturally occurring variants thereof (e.g. sequences encoding a mammalian PAPD7).

TABLE 1

A. Genome and assembly information for PAPD5 across species.

| | | | | Genomic coordinates | | | |
|---|---|---|---|---|---|---|---|
| Species | Chr. | Band | Strand | Start | End | ensembl_gene_id | Assembly |
| Human | 16 | q12.1 | fwd | 50152918 | 50235310 | ENSG00000121274 | GRCh38.p7 |
| Cynomolgus monkey | 20 | | fwd | 37953893 | 38040642 | RefSeq ID: NC_022291.1 | Macaca_fascicularis_5.0 (GCF_000364345.1) |
| mouse | 8 | C3 | fwd | 88199213 | 88259722 | ENSMUSG00000036779 | GRCm38.p5 |
| Rat | 19 | p11 | rev | 19771677 | 19832812 | ENSRNOG00000024212 | Rnor_6.0 |

B. Genome and assembly information for PAPD7 across species.

| | | | | Genomic coordinates | | | |
|---|---|---|---|---|---|---|---|
| Species | Chr | Band | Strand | Start | End | ensembl_gene_id | Assembly |
| Human | 5 | p15.31 | fwd | 6713007 | 6757048 | ENSG00000112941 | GRCh38.p7 |
| Cynomolgus monkey | 6 | | fwd | 6740764 | 6790723 | RefSeq NC_022277.1 | Macaca_fascicularis_5.0 (GCF_000364345.1) |
| mouse | 13 | B3 | rev | 69497959 | 69534617 | ENSMUSG00000034575 | GRCm38.p5 |
| Rat | 1 | p11 | fwd | 36400443 | 36433238 | ENSRNOG00000017613 | Rnor_6.0 |

Fwd = forward strand. Rev = reverse strand. The genome coordinates provide the pre-mRNA sequence (genomic sequence).

If employing the oligonucleotide of the invention in research or diagnostics the target nucleic acid may be a cDNA or a synthetic nucleic acid derived from DNA or RNA.

For in vivo or in vitro application, the oligonucleotide of the invention is typically capable of inhibiting the expression of the PAPD5 and PAPD7 target nucleic acid in a cell which is expressing the PAPD5 and PAPD7 target nucleic acid. The contiguous sequence of nucleobases of the oligonucleotide of the invention is typically complementary a conserved region of the PAPD5 and PAPD7 target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D' or D"). Further information on exemplary target nucleic acids is provided in table 2.

TABLE 2

Sequence details for PAPD5 and PAPD7 across species.

| Species | Target | RNA type | Length (nt) | SEQ ID NO |
|---|---|---|---|---|
| Human | PAPD5 | Pre-mRNA | 82393 | 1 |
| Human | PAPD7 | Pre-mRNA | 44042 | 2 |
| Cyno monkey | PAPD5 | Pre-mRNA | 86750 | 3 |
| Cyno monkey | PAPD7 | Pre-mRNA | 49960 | 4 |
| Mouse | PAPD5 | Pre-mRNA | 60510 | 5 |
| Mouse | PAPD7 | Pre-mRNA | 36659 | 6 |

Target Sequence

The term "target sequence" as used herein refers to a sequence of nucleotides present in the target nucleic acid which comprises the nucleobase sequence which is complementary to the oligonucleotide or nucleic acid molecule of the invention. In some embodiments, the target sequence consists of a region on the target nucleic acid which is complementary to the contiguous nucleotide sequence of the oligonucleotide of the invention (i.e. a sub-sequence).

In the present invention the target sequence is present both in the human PAPD5 and human PAPD7 target nucleic acid. The target sequence may therefore be referred to as a bispecific target sequence present in both the PAPD5 and PAPD7 target nucleic acid. In advantageous embodiments the target sequence is also present in at least one additional species, such as PAPD5 and PAPD7 from cynomolgus monkey, and/or PAPD5 and PAPD7 from mouse.

The oligonucleotide or nucleic acid molecule of the invention comprises a contiguous nucleotide sequence which is complementary to or hybridizes to a region on the target nucleic acid, such as a target sequence described herein.

The target nucleic sequence to which the oligonucleotide is complementary to or hybridizes to generally comprises a stretch of contiguous nucleobases of at least 10 nucleotides. The contiguous nucleotide sequence is between 10 to 50 nucleotides, such as 12-30, such as 13 to 25, such as 14 to 20, such as 15 to 18 contiguous nucleotides.

Naturally Occurring Variant

The term "naturally occurring variant" refers to variants of PAPD5 or PAPD7 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms, and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian PAPD5 target nucleic acid, such as a target nucleic acid selected form the group consisting of SEQ ID NO: 1, 3 or 5. In some embodiments the naturally occurring variants have at least 99% homology to the human PAPD5 target nucleic acid of SEQ ID NO: 1. In some embodiments the naturally occurring variants are the polymorphisms listed in table 3A.

In some embodiments, the naturally occurring variants have at least 95% such as at least 98% or at least 99% homology to a mammalian PAPD5 target nucleic acid, such as a target nucleic acid selected form the group consisting of SEQ ID NO: 2 or 4 or 6. In some embodiments the naturally occurring variants have at least 99% homology to the human PAPD7 target nucleic acid of SEQ ID NO: 2. In some embodiments the naturally occurring variants are the polymorphisms listed in table 3B.

Numerous single nucleotide polymorphisms are known in the PAPD5 or PAPD7 gene, for example those disclosed in Table 3A (human PAPD5 premRNA start/reference sequence is SEQ ID NO: 1) and Table 3B human PAPD7 premRNA start/reference sequence is SEQ ID NO: 2).

TABLE 3A

PAPD5 polymorphisms (naturally occurring variants)

| minor allele | Minor allele frequency | Start on SEQ ID NO: 1 |
|---|---|---|
| G | 0.00399361 | 29 |
| G | 0.000199681 | 34 |
| T | 0.000399361 | 39 |
| A | 0.000599042 | 62 |
| A | 0.000599042 | 97 |
| G | 0.000199681 | 141 |
| A | 0.000199681 | 142 |
| T | 0.000199681 | 158 |
| A | 0.0241613 | 235 |
| A | 0.00239617 | 279 |
| − | 0.214058 | 370 |
| G | 0.000798722 | 450 |
| CAGCA | 0.000798722 | 603 |
| A | 0.0223642 | 1028 |
| C | 0.000199681 | 1044 |
| A | 0.0189696 | 1068 |
| T | 0.000199681 | 1181 |
| T | 0.0249601 | 1199 |
| T | 0.000998403 | 1258 |
| A | 0.000199681 | 1261 |

TABLE 3A-continued

PAPD5 polymorphisms (naturally occurring variants)

| minor allele | Minor allele frequency | Start on SEQ ID NO: 1 |
|---|---|---|
| T | 0.000599042 | 1441 |
| T | 0.000199681 | 1443 |
| C | 0.000599042 | 1469 |
| A | 0.000399361 | 1535 |

TABLE 3B

PAPD7 polymorphisms (naturally occurring variants)

| minor allele | Minor allele frequency | Start on SEQ ID NO: 2 |
|---|---|---|
| A | 0.293331 | 21 |
| T | 0.00119808 | 50 |
| T | 0.000199681 | 64 |
| A | 0.00279553 | 127 |
| A | 0.0597045 | 224 |
| G | 0.000199681 | 234 |
| T | 0.000599042 | 270 |
| A | 0.128994 | 284 |
| C | 0.000399361 | 316 |
| T | 0.000199681 | 349 |
| G | 0.00778754 | 362 |
| A | 0.000199681 | 409 |
| G | 0.000199681 | 425 |
| A | 0.000199681 | 448 |
| T | 0.000199681 | 473 |
| C | 0.000199681 | 491 |
| C | 0.327676 | 564 |
| T | 0.0203674 | 606 |
| — | 0.389577 | 837 |
| — | 0.00139776 | 1317 |
| T | 0.000599042 | 1331 |
| T | 0.000199681 | 1475 |
| T | 0.000399361 | 1483 |
| C | 0.01877 | 1673 |
| A | 0.000199681 | 1682 |
| T | 0.00339457 | 1726 |
| GGTCCTGGCCGGCGCCCGC (SEQ ID NO: 35) | 0.258586 | 1736 |
| G | 0.000599042 | 1760 |

TABLE 3B-continued

PAPD7 polymorphisms (naturally occurring variants)

| minor allele | Minor allele frequency | Start on SEQ ID NO: 2 |
|---|---|---|
| C | 0.000199681 | 1777 |
| G | 0.000399361 | 1780 |
| T | 0.000199681 | 1852 |
| T | 0.000199681 | 1861 |
| T | 0.000199681 | 1889 |
| C | 0.000399361 | 1923 |
| G | 0.000399361 | 1962 |
| T | 0.0147764 | 1987 |
| G | 0.000998403 | 1996 |
| T | 0.000399361 | 2036 |

Modulation of Expression

The term "modulation of expression" as used herein is to be understood as an overall term for a nucleic acid molecules ability to alter the amount of PAPD5 and PAPD7 when compared to the amount of PAPD5 and PAPD7 before administration of the nucleic acid molecule. Alternatively, modulation of expression may be determined by reference to a control experiment. It is generally understood that the control is an individual or target cell treated with a saline composition or an individual or target cell treated with a non-targeting or nucleic acid molecule (mock). It may however also be an individual treated with the standard of care.

One type of modulation is a nucleic acid molecules, such as an antisense oligonucleotides, ability to inhibit, down-regulate, reduce, remove, stop, prevent, lessen, lower, avoid or terminate expression of PAPD5 and PAPD7, e.g. by degradation of mRNA or blockage of transcription.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T_m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' sugar modified nucleosides, such as 2' substituted nucleosides like Ome and MOE as well as 2' to 4' bridged nucleic acids such as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The nucleic acid molecule of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of nucleic acid molecules, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the —OH groups naturally found in RNA or DNA nucleosides. Substituents may, for example be introduced at the 2', 3', 4' or 5' positions.

2' Sugar Modified Nucleosides.

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

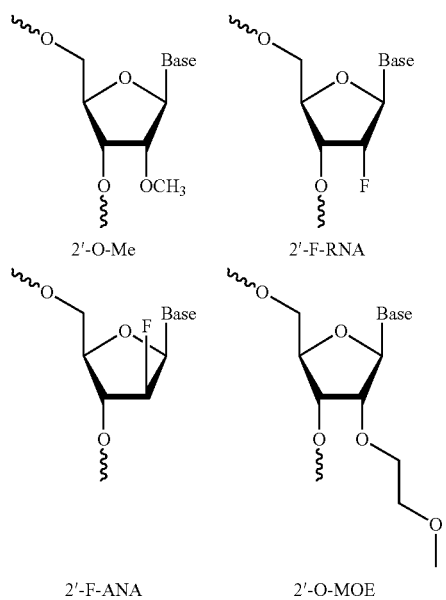

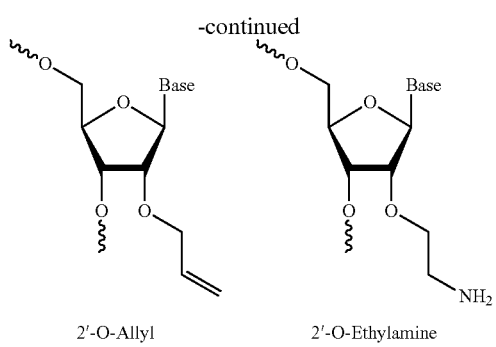

In relation to the present invention 2' substituted does not include 2' bridged molecules like LNA.

Locked Nucleic Acid Nucleosides (LNA).

An "LNA nucleoside" is 2'-sugar modified nucleoside which comprises a biradical linking the C2' and C4' of the ribose sugar ring of a said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

In some embodiments, the 2'-sugar modified nucleoside(s) or the LNA nucleoside(s) of the oligomer of the invention has a general structure of the formula I or II:

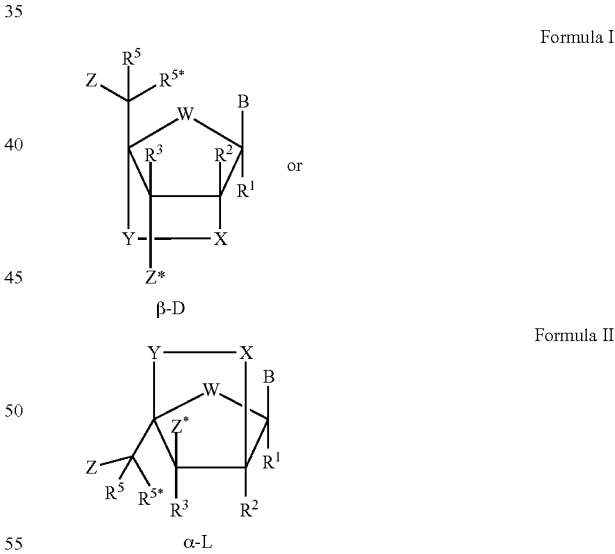

wherein W is selected from —O—, —S—, —N(R$^a$)—, —C(R$^a$R$^b$)—, such as, in some embodiments —O—;

B designates a nucleobase or modified nucleobase moiety;

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z In some embodiments, X is selected from the group consisting of: —O—, —S—, NH—, NR$^a$R$^b$, —CH$_2$—, CR$^a$R$^b$, —C(=CH$_2$)—, and —C(=CR$^a$R$_b$)—

In some embodiments, X is —O—

Y designates a group selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z In some embodiments, Y is selected from the group consisting of: —CH$_2$—, —C(R$^a$R$^b$)—, —CH$_2$CH$_2$—, —C(R$^a$R$^b$)—C(R$^a$R$^b$)—, —CH$_2$CH$_2$CH$_2$—, —C(R$^a$R$^b$)C(R$^a$R$^b$)C(R$^a$R$^b$)—, —C(R$^a$)=C(R$^b$)—, and —C(R$^a$)=N—

In some embodiments, Y is selected from the group consisting of: —CH$_2$—, —CHR$^a$—, —CHCH$_3$—, CR$^a$R$^b$— or —X—Y— together designate a bivalent linker group (also referred to as a radicle) together designate a bivalent linker group consisting of 1, 2, 3 or 4 groups/atoms selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z, In some embodiments, —X—Y— designates a biradicle selected from the groups consisting of: —X—CH$_2$—, —X—CR$^a$R$^b$—, —X—CHR$^a$—, —X—C(HCH$_3$)—, —O—Y—, —O—CH$_2$—, —S—CH$_2$—, —NH—CH$_2$—, —O—CHCH$_3$—, —CH$_2$—O—CH$_2$, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—CR$^a$R$^b$— and —S—CHR$^a$—.

In some embodiments —X—Y— designates —O—CH$_2$— or —O—CH(CH$_3$)—.

wherein Z is selected from —O—, —S—, and —N(R$^a$)—, and R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents R$^a$ and R$^b$ together may designate optionally substituted methylene (=CH$_2$), wherein for all chiral centers, asymmetric groups may be found in either R or S orientation.

wherein R$^1$, R$^2$, R$^3$, R$^5$ and R$^{5*}$ are independently selected from the group consisting of: hydrogen, optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted, and where two geminal substituents together may designate oxo, thioxo, imino, or optionally substituted methylene.

In some embodiments R$^1$, R$^2$, R$^3$, R$^5$ and R$^{5*}$ are independently selected from C$_{1-6}$ alkyl, such as methyl, and hydrogen.

In some embodiments R$^1$, R$^2$, R$^3$, R$^5$ and R$^{5*}$ are all hydrogen.

In some embodiments R$^1$, R$^2$, R$^3$, are all hydrogen, and either R$^5$ and R$^{5*}$ is also hydrogen and the other of R$^5$ and R$^{5*}$ is other than hydrogen, such as C$_{1-6}$ alkyl such as methyl.

In some embodiments, R$^a$ is either hydrogen or methyl. In some embodiments, when present, R$^b$ is either hydrogen or methyl.

In some embodiments, one or both of R$^a$ and R$^b$ is hydrogen

In some embodiments, one of R$^a$ and R$^b$ is hydrogen and the other is other than hydrogen In some embodiments, one of R$^a$ and R$^b$ is methyl and the other is hydrogen In some embodiments, both of R$^a$ and R$^b$ are methyl.

In some embodiments, the biradicle —X—Y— is —O—CH$_2$—, W is O, and all of R$^1$, R$^2$, R$^3$, R$^5$ and R$^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—CH$_2$—, W is O, and all of R$^1$, R$^2$, R$^3$, R$^5$ and R$^{5*}$ are all hydrogen. Such thio LNA nucleosides are disclosed in WO99/014226 and WO2004/046160 which are hereby incorporated by reference.

In some embodiments, the biradicle —X—Y— is —NH—CH$_2$—, W is O, and all of R$^1$, R$^2$, R$^3$, R$^5$ and R$^{5*}$ are all hydrogen. Such amino LNA nucleosides are disclosed in WO99/014226 and WO2004/046160 which are hereby incorporated by reference.

In some embodiments, the biradicle —X—Y— is —O—CH$_2$—CH$_2$— or —O—CH$_2$—CH$_2$— CH$_2$—, W is O, and all of R$^1$, R$^2$, R$^3$, R$^5$ and R$^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—CH$_2$—, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such 5' substituted LNA nucleosides are disclosed in WO2007/134181 which is hereby incorporated by reference.

In some embodiments, the biradicle —X—Y— is —O—CR$^a$R$^b$—, wherein one or both of R$^a$ and R$^b$ are other than hydrogen, such as methyl, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—CH(CH$_2$OCH$_3$)— (2' O-methoxyethyl bicyclic nucleic acid—Seth at al., 2010, J. Org. Chem. Vol 75(5) pp. 1569-81). In some embodiments, the biradicle —X—Y— designate the bivalent linker group —O—CH(CH$_2$CH$_3$)— (2'O-ethyl bicyclic nucleic acid—Seth at al., 2010, J. Org. Chem. Vol 75(5) pp. 1569-81). In some embodiments, the biradicle —X—Y— is —O—CHR$^a$—, W is O, and all of R$^1$, R$^2$, R$^3$, R$^5$ and R$^{5*}$ are all hydrogen. Such 6' substituted LNA nucleosides are disclosed in WO10036698 and WO07090071 which are both hereby incorporated by reference.

In some embodiments, the biradicle —X—Y— is —O—CH(CH$_2$OCH$_3$)—, W is O, and all of R$^1$, R$^2$, R$^3$, R$^5$ and R$^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)—. —in either the R- or S-configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH(CH$_3$)—, W is O, and all of R$^1$, R$^2$, R$^3$, R$^5$ and R$^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—CR$^a$R$^b$—, wherein in neither R$^a$ or R$^b$ is hydrogen, W is O, and all of R$^1$, R$^2$, R$^3$, R$^5$ and R$^{5*}$ are all hydrogen. In some embodiments, R$^a$ and R$^b$ are both methyl. Such 6' di-substituted LNA nucleosides are disclosed in WO 2009006478 which is hereby incorporated by reference.

In some embodiments, the biradicle —X—Y— is —S—CHR$^a$—, W is O, and all of R$^1$, R$^2$, R$^3$, R$^5$ and R$^{5*}$ are all hydrogen. Such 6' substituted thio LNA nucleosides are disclosed in WO11156202 which is hereby incorporated by reference. In some 6' substituted thio LNA embodiments R$^a$ is methyl.

In some embodiments, the biradicle —X—Y— is —C(=CH$_2$)—C(R$^a$R$^b$)—, such as —C(=CH$_2$)—CH$_2$—, or —C(=CH$_2$)—CH(CH$_3$)—W is O, and all of R$^1$, R$^2$, R$^3$, R$^5$ and R$^{5*}$ are all hydrogen. Such vinyl carbo LNA nucleosides are disclosed in WO08154401 and WO09067647 which are both hereby incorporated by reference.

In some embodiments the biradicle —X—Y— is —N(OR$^a$)—, W is O, and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as N substituted LNAs and are disclosed in WO2008/150729 which is hereby incorporated by reference. In some embodiments, the biradicle —X—Y— together designate the bivalent linker group —O—NR$^a$—CH$_3$— (Seth at al., 2010, J. Org. Chem). In some embodiments the biradicle —X—Y— is —N(R$^a$)—, W is O, and all of R$^1$, R$^2$, R$^3$, R$^5$ and R$^{5*}$ are all hydrogen. In some embodiments R$^a$ is C$_{1-6}$ alkyl such as methyl.

In some embodiments, one or both of R$^5$ and R$^{5*}$ is hydrogen and, when substituted the other of R$^5$ and R$^{5*}$ is C$_{1-6}$ alkyl such as methyl. In such an embodiment, R$^1$, R$^2$, R$^3$, may all be hydrogen, and the biradicle —X—Y— may be selected from —O—CH$_2$— or —O—C(HCRa)—, such as —O—C(HCH$_3$)—.

In some embodiments, the biradicle is —CR$^a$R$^b$—O—CR$^a$R$^b$—, such as CH$_2$—O—CH$_2$—, W is O and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—CR$^a$R$^b$—O—CR$^a$R$^b$—, such as O—CH$_2$—O—CH$_2$—, W is O and all of R$^1$, R$^2$, R$^3$, R$^5$ and R$^{5*}$ are all hydrogen. In some embodiments R$^a$ is C$_{1-6}$alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238.

Certain examples of LNA nucleosides are presented in Scheme 1.

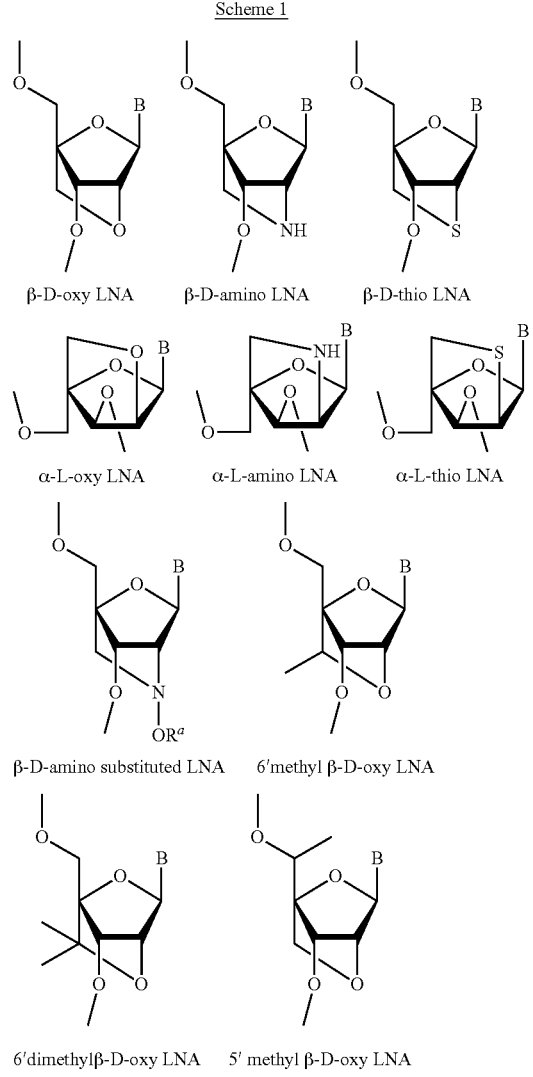

Scheme 1

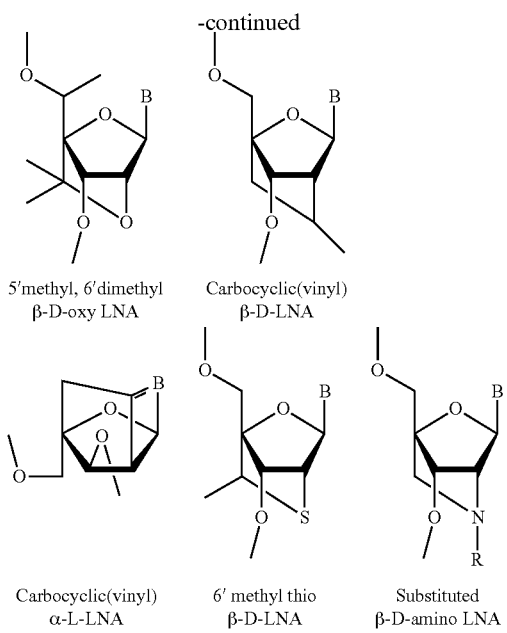

5'methyl, 6'dimethyl β-D-oxy LNA

Carbocyclic(vinyl) β-D-LNA

Carbocyclic(vinyl) α-L-LNA

6' methyl thio β-D-LNA

Substituted β-D-amino LNA

As illustrated in the examples, in some embodiments of the invention the LNA nucleosides in the oligonucleotides are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland Gapmer The antisense oligonucleotide of the invention, or contiguous nucleotide sequence thereof may be a gapmer. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5->3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further defined by having at least one sugar modified nucleoside at the end most distant from the gap region, i.e. at the 5' end of the 5' flank and at the 3' end of the 3' flank. Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides.

By way of example, the gapmer oligonucleotide of the present invention can be represented by the following formulae:

$F_{1-8}-G_{5-16}-F'_{1-8}$, such as $F_{1-8}-G_{7-16}-F'_{2-8}$ with the proviso that the overall length of the gapmer regions F-G-F' is at least 12, such as at least 14 nucleotides in length.

Regions F, G and F' are further defined below and can be incorporated into the F-G-F' formula.

Gapmer—Gap, Region G

Region G (gap region) of the gapmer is a region of nucleosides which enables the oligonucleotide to recruit RNaseH, such as human RNase H1, typically DNA nucleosides.

RNaseH is a cellular enzyme which recognizes the duplex between DNA and RNA, and enzymatically cleaves the RNA molecule. Suitably gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments consist of 6, 7, 8, 9, 10, 11, 12, 13, 14, 15 or 16 contiguous DNA nucleosides. Cytosine (C) DNA in the gap region may in some instances be methylated, such residues are either annotated as 5-methyl-cytosine (meC or with an e instead of a c). Methylation of Cytosine DNA in the gap is advantageous if cg dinucleotides are present in the gap to reduce potential toxicity, the modification is not expected to have significant impact on efficacy of the oligonucleotides.

In some embodiments the gap region G may consist of 6, 7, 8, 9, 10, 11, 12, 13, 14, 15 or 16 contiguous phosphorothioate linked DNA nucleosides. In some embodiments, all internucleoside linkages in the gap are phosphorothioate linkages.

Whilst traditional gapmers have a DNA gap region, there are numerous examples of modified nucleosides which allow for RNaseH recruitment when they are used within the gap region. Modified nucleosides which have been reported as being capable of recruiting RNaseH when included within a gap region include, for example, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue. The modified nucleosides used in such gapmers may be nucleosides which adopt a 2' endo (DNA like) structure when introduced into the gap region, i.e. modifications which allow for RNaseH recruitment). In some embodiments the DNA Gap region (G) described herein may optionally contain 1 to 3 sugar modified nucleosides which adopt a 2' endo (DNA like) structure when introduced into the gap region.

Region G—"Gap-Breaker"

Alternatively, there are numerous reports of the insertion of a modified nucleoside which confers a 3' endo conformation into the gap region of gapmers, whilst retaining some RNaseH activity. Such gapmers with a gap region comprising one or more 3'endo modified nucleosides are referred to as "gap-breaker" or "gap-disrupted" gapmers, see for example WO2013/022984. Gap-breaker oligonucleotides retain sufficient region of DNA nucleosides within the gap region to allow for RNaseH recruitment. The ability of gapbreaker oligonucleotide design to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA. Modified nucleosides used within the gap region of gap-breaker oligonucleotides may for example be modified nucleosides which confer a 3'endo confirmation, such 2'-O-methyl (OMe) or 2'-O-MOE (MOE) nucleosides, or beta-D LNA nucleosides (the bridge between C2' and C4' of the ribose sugar ring of a nucleoside is in the beta conformation), such as beta-D-oxy LNA or ScET nucleosides.

As with gapmers containing region G described above, the gap region of gap-breaker or gap-disrupted gapmers, have a DNA nucleosides at the 5' end of the gap (adjacent to the 3' nucleoside of region F), and a DNA nucleoside at the 3' end of the gap (adjacent to the 5' nucleoside of region F'). Gapmers which comprise a disrupted gap typically retain a region of at least 3 or 4 contiguous DNA nucleosides at either the 5' end or 3' end of the gap region.

Exemplary designs for gap-breaker oligonucleotides include

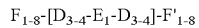

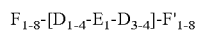

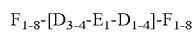

wherein region G is within the brackets $[D_n\text{-}E_r\text{-}D_m]$, D is a contiguous sequence of DNA nucleosides, E is a modified nucleoside (the gap-breaker or gap-disrupting nucleoside), and F and F' are the flanking regions as defined herein, and with the proviso that the overall length of the gapmer regions F-G-F' is at least 12, such as at least 14 nucleotides in length.

In some embodiments, region G of a gap disrupted gapmer comprises at least 6 DNA nucleosides, such as 6, 7, 8, 9, 10, 11, 12, 13, 14, 15 or 16 DNA nucleosides. As described above, the DNA nucleosides may be contiguous or may optionally be interspersed with one or more modified nucleosides, with the proviso that the gap region G is capable of mediating RNaseH recruitment.

Gapmer—Flanking Regions, F and F'

Region F is positioned immediately adjacent to the 5' DNA nucleoside of region G. The 3' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 1-6, such as 2-6, such as 3-4 contiguous nucleotides in length. Advantageously the 5' most nucleoside of region F is a sugar modified nucleoside. In some embodiments the two 5' most nucleoside of region F are sugar modified nucleoside. In some embodiments the 5' most nucleoside of region F is an LNA nucleoside. In some embodiments the two 5' most nucleoside of region F are LNA nucleosides. In some embodiments the two 5' most nucleoside of region F are 2' substituted nucleoside nucleosides, such as two 3' MOE nucleosides. In some embodiments the 5' most nucleoside of region F is a 2' substituted nucleoside, such as a MOE nucleoside.

Region F' is 2-8 contiguous nucleotides in length, such as 3-6, such as 4-5 contiguous nucleotides in length. Advantageously, embodiments the 3' most nucleoside of region F' is a sugar modified nucleoside. In some embodiments the two 3' most nucleoside of region F' are sugar modified nucleoside. In some embodiments the two 3' most nucleoside of region F' are LNA nucleosides. In some embodiments the 3' most nucleoside of region F' is an LNA nucleoside. In some embodiments the two 3' most nucleoside of region F' are 2' substituted nucleoside nucleosides, such as two 3' MOE nucleosides. In some embodiments the 3' most nucleoside of region F' is a 2' substituted nucleoside, such as a MOE nucleoside.

It should be noted that when the length of region F or F' is one, it is advantageously an LNA nucleoside.

In some embodiments, region F and F' independently consists of or comprises a contiguous sequence of sugar modified nucleosides. In some embodiments, the sugar modified nucleosides of region F may be independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments, region F and F' independently comprises both LNA and a 2' substituted modified nucleosides (mixed wing design).

In some embodiments, region F and F' consists of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as independently selected from beta-D-oxy LNA, ENA or ScET nucleosides. In some embodiments region F consists of 1-5, such as 2-4, such as 3-4 such as 1, 2, 3, 4 or 5 contiguous LNA nucleosides. In some embodiments, all the nucleosides of region F and F' are beta-D-oxy LNA nucleosides.

In some embodiments, all the nucleosides of region F or F', or F and F' are 2' substituted nucleosides, such as OMe or MOE nucleosides. In some embodiments region F consists of 1, 2, 3, 4, 5, 6, 7, or 8 contiguous OMe or MOE nucleosides. In some embodiments only one of the flanking regions can consist of 2' substituted nucleosides, such as OMe or MOE nucleosides. In some embodiments it is the 5' (F) flanking region that consists 2' substituted nucleosides, such as OMe or MOE nucleosides whereas the 3' (F') flanking region comprises at least one LNA nucleoside, such as beta-D-oxy LNA nucleosides or cET nucleosides. In some embodiments it is the 3' (F') flanking region that consists 2' substituted nucleosides, such as OMe or MOE nucleosides whereas the 5' (F) flanking region comprises at least one LNA nucleoside, such as beta-D-oxy LNA nucleosides or cET nucleosides.

In some embodiments, all the modified nucleosides of region F and F' are LNA nucleosides, such as independently selected from beta-D-oxy LNA, ENA or ScET nucleosides, wherein region F or F', or F and F' may optionally comprise DNA nucleosides (an alternating flank, see definition of these for more details). In some embodiments, all the modified nucleosides of region F and F' are beta-D-oxy LNA nucleosides, wherein region F or F', or F and F' may optionally comprise DNA nucleosides (an alternating flank, see definition of these for more details).

In some embodiments the 5' most and the 3' most nucleosides of region F and F' are LNA nucleosides, such as beta-D-oxy LNA nucleosides or ScET nucleosides.

In some embodiments, the internucleoside linkage between region F and region G is a phosphorothioate internucleoside linkage. In some embodiments, the internucleoside linkage between region F' and region G is a phosphorothioate internucleoside linkage. In some embodiments, the internucleoside linkages between the nucleosides of region F or F', F and F' are phosphorothioate internucleoside linkages.

Further gapmer designs are disclosed in WO2004/046160, WO2007/146511 and WO2008/113832, hereby incorporated by reference.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments the LNA gapmer is of formula: $[LNA]_{1-5}$-[region G]-$[LNA]_{1-5}$, wherein region G is as defined in the Gapmer region G definition.

In some embodiments the LNA is beta-D-oxy-LNA and the gapmer has the formula;

$F_{2-5\ LNA,\ 0-2\ DNA}$-$G_{7-11\ DNA}$-$F'_{3-5\ LNA,\ 0-2\ DNA}$

MOE Gapmers

A MOE gapmers is a gapmer wherein regions F and F' consist of MOE nucleosides. In some embodiments the MOE gapmer is of design $[MOE]_{1-8}$-[Region G]-$[MOE]_{1-8}$, such as $[MOE]_{2-7}$-[Region G]$_{5-16}$-$[MOE]_{2-7}$, such as $[MOE]_{3-6}$-[Region G]-$[MOE]_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as a MOE nucleosides. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Mixed wing gapmer designs are disclosed in WO2008/049085 and WO2012/109395, both of which are hereby incorporated by reference.

Alternating Flank Gapmers

Oligonucleotides with alternating flanks are LNA gapmer oligonucleotides where at least one of the flanks (F or F') comprises DNA in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides.

In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F or F' region are LNA nucleosides, and the. Flanking regions which comprise both LNA and DNA nucleoside are referred to as alternating flanks, as they comprise an alternating motif of LNA-DNA-LNA nucleosides. Alternating flank LNA gapmers are disclosed in WO2016/127002.

An alternating flank region may comprise up to 3 contiguous DNA nucleosides, such as 1 to 2 or 1 or 2 or 3 contiguous DNA nucleosides.

The alternating flak can be annotated as a series of integers, representing a number of LNA nucleosides (L) followed by a number of DNA nucleosides (D), for example $[L]_{1-3}$-$[D]_{1-4}$-$[L]_{1-3}$ $[L]_{1-2}$-$[D]_{1-2}$-$[L]_{1-2}$-$[D]_{1-2}$-$[L]_{1-2}$ In oligonucleotide designs these will often be represented as numbers such that 2-2-1 represents 5' $[L]_2$-$[D]_2$-$[L]$ 3', and 1-1-1-1-1 represents 5' $[L]$-$[D]$-$[L]$-$[D]$-$[L]$ 3'. The length of the flank (region F and F') in oligonucleotides with alternating flanks may independently be 3 to 10 nucleotides, such as 4 to 8, such as 5 to 6 nucleotides, such as 4, 5, 6 or 7 modified nucleotides. In some embodiments only one of the flanks in the gapmer oligonucleotide is alternating while the other is constituted of LNA nucleotides. It may be advantageous to have at least two LNA nucleotides at the 3' end of the 3' flank (F'), to confer additional exonuclease resistance. Some examples of oligonucleotides with alternating flanks are:

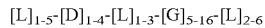

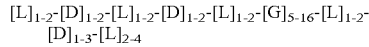

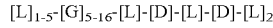

with the proviso that the overall length of the gapmer is at least 12, such as at least 14 nucleotides in length.

Region D' or D" in an Oligonucleotide

The oligonucleotide of the invention may in some embodiments comprise or consist of the contiguous nucleotide sequence of the oligonucleotide which is complementary to the target nucleic acid, such as the gapmer F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively it may be used to provide exonucleoase protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitute the gapmer.

In some embodiments, the oligonucleotide of the present invention can be represented by the following formulae:

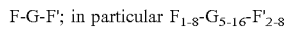

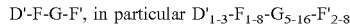

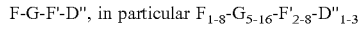

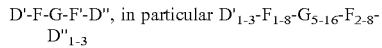

In some embodiments the internucleoside linkage positioned between region D' and region F is a phosphodiester linkage. In some embodiments the internucleoside linkage positioned between region F' and region D" is a phosphodiester linkage.

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs, e.g. off target activity or activity in non-target cell types, tissues or organs.

WO 93/07883 and WO2013/033230 provides suitable conjugate moieties, which are hereby incorporated by reference. Further suitable conjugate moieties are those capable of binding to the asialoglycoprotein receptor (ASGPR). In particular tri-valent N-acetylgalactosamine conjugate moieties are suitable for binding to the ASGPR, see for example WO 2014/076196, WO 2014/207232 and WO 2014/179620 (hereby incorporated by reference). Such conjugates serve to enhance uptake of the oligonucleotide to the liver while reducing its presence in the kidney, thereby increasing the liver/kidney ratio of a conjugated oligonucleotide compared to the unconjugated version of the same oligonucleotide.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Conjugate Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect one region, e.g. a conjugate moiety to another region, e.g. an oligonucleotide (e.g. the termini of region A or C).

In some embodiments of the invention the conjugate or oligonucleotide conjugate of the invention may optionally, comprise a linker region which is positioned between the oligonucleotide and the conjugate moiety. In some embodiments, the linker between the conjugate and oligonucleotide is biocleavable. The linker and the oligonucleotide is often attached via a phosphodiester linkage.

Biocleavable linkers (Region B) comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to 51 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA.

In one embodiment the linker between the oligonucleotide and the conjugate moiety is a physiologically labile linker composed of 2 to 5 consecutive phosphodiester linked nucleosides at the 5' or 3' terminal of the contiguous nucleotide sequence of the antisense compound. In some embodiments the consecutive phosphodiester linkages are a dinucleotide with a sequence selected from the group consisting of AA, AT, AC, AG, TA, TT, TC, TG, CA, CT, CC, CG, GA, GT, GC, or GG. In some embodiments the consecutive phosphodiester linkages are a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, or GGG. In specific examples phosphodiester linked CA dinucleotide, with three consecutive phosphodiester linkages, has been used as biocleavable linker between the contiguous nucleotide sequence and the conjugate moiety. Phosphodiester containing biocleavable linkers are described in more detail in WO 2014/076195 (hereby incorporated by reference). In a conjugate compound with a biocleavable linker at least about 50% of the conjugate moiety is cleaved from the oligonucleotide, such as at least about 60% cleaved, such as at least about 70% cleaved, such as at least about 80% cleaved, such as at least about 85% cleaved, such as at least about 90% cleaved, such as at least about 95% of the conjugate moiety is cleaved from the oligonucleotide cleaved when compared against a standard.

Conjugates may also be linked to the oligonucleotide via non-biocleavable linkers, or in some embodiments the conjugate may comprise a non-cleavable linker which is covalently attached to the biocleavable linker. Linkers that are not necessarily biocleavable primarily serve to covalently connect a conjugate moiety to an oligonucleotide or biocleavable linker, and potentially generate some distance between the conjugate moiety and the oligonucleotide. Some example linkers (region Y) include 8-amino-3,6-dioxaoctanoic acid (ADO), succinimidyl 4-(N-maleimidomethyl)cyclohexane-1-carboxylate (SMCC), 6-aminohexanoic acid (AHEX or AHA), 6-aminohexyloxy, 4-aminobutyric acid, 4-aminocyclohexylcarboxylic acid, succinimidyl 4-(N-maleimidomethyl)cyclohexane-1-carboxy-(6-amido-caproate) (LCSMCC), succinimidyl m-maleimido-benzoylate (MBS), succinimidyl N-e-maleimido-caproylate (EMCS), succinimidyl 6-(beta-maleimido-propionamido) hexanoate (SMPH), succinimidyl N-(a-maleimido acetate) (AMAS), succinimidyl 4-(p-maleimidophenyl)butyrate (SMPB), beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like. Non-cleavable linkers may also comprise a chain structure or an oligomer of repeating units such as ethylene glycol, amino acid units or amino alkyl groups. In some embodiments the linker (region Y) is an amino alkyl, such as a $C_2$-$C_{36}$ amino alkyl group, including, for example $C_6$ to $C_{12}$ amino alkyl groups. In some embodiments the linker (region Y) is a $C_6$ amino alkyl group (also termed a C6 linker). Conjugate linker groups may be routinely attached to an oligonucleotide via use of an amino modified oligonucleotide, and an activated ester group on the conjugate group. The linkage group between the amino alkyl and the oligonucleotide may for example be a phosphorothioate or a phosphodiester, or one of the other nucleoside linkage groups referred to herein. A conjugate compound of the present invention may be composed of the following regions C-B-A (Conjugate moiety-biocleavable linker-oligonucleotide/contiguous nucleotide sequence) or C-Y-B-A (conjugate moiety-non-cleavable linker-biocleavable linker-oligonucleotide/contiguous nucleotide sequence).

Treatment

The terms "treatment", "treating", "treats" or the like are used herein generally mean obtaining a desired pharmacological and/or physiological effect. This effect is therapeutic in terms of partially or completely curing a disease and/or adverse effect attributed to the disease. The term "treatment" as used herein covers any treatment of a disease in a subject and includes: (a) inhibiting the disease, i.e. arresting its development like the inhibition of increase of HBsAg and/or HBeAg; or (b) ameliorating (i.e. relieving) the disease, i.e. causing regression of the disease, like the repression of HBsAg and/or HBeAg production. Thus, a compound that ameliorates and/or inhibits a HBV infection is a compound that treats a HBV invention. Preferably, the term "treatment" as used herein relates to medical intervention of an already manifested disorder, like the treatment of an already defined and manifested HBV infection.

Prevention

Herein the term "preventing", "prevention" or "prevents" relates to a prophylactic treatment, i.e. to a measure or procedure the purpose of which is to prevent, rather than to cure a disease. Prevention means that a desired pharmacological and/or physiological effect is obtained that is prophylactic in terms of completely or partially preventing a disease or symptom thereof. Accordingly, herein "preventing a HBV infection" includes preventing a HBV infection from occurring in a subject, and preventing the occurrence of symptoms of a HBV infection. In the present invention in particular the prevention of HBV infection in children from HBV infected mothers are contemplated.

Patient

For the purposes of the present invention the "subject" (or "patient") may be a vertebrate. In context of the present invention, the term "subject" includes both humans and other animals, particularly mammals, and other organisms. Thus, the herein provided means and methods are applicable to both human therapy and veterinary applications. Accordingly, herein the subject may be an animal such as a mouse, rat, hamster, rabbit, guinea pig, ferret, cat, dog, chicken, sheep, bovine species, horse, camel, or primate. Preferably, the subject is a mammal. More preferably the subject is human.

HBV Infection

The term "hepatitis B virus infection" or "HBV infection" is commonly known in the art and refers to an infectious disease that is caused by the hepatitis B virus (HBV) and affects the liver. A HBV infection can be an acute or a chronic infection. Some infected persons have no symptoms during the initial infection and some develop a rapid onset of sickness with vomiting, yellowish skin, tiredness, dark urine and abdominal pain ("Hepatitis B Fact sheet N°204". who. int. July 2014. Retrieved 4 Nov. 2014). Often these symptoms last a few weeks and can result in death. It may take 30 to 180 days for symptoms to begin. In those who get infected around the time of birth 90% develop a chronic hepatitis B infection while less than 10% of those infected after the age of five do ("Hepatitis B FAQs for the Public—Transmission", U.S. Centers for Disease Control and Prevention (CDC), retrieved 2011-11-29). Most of those with chronic disease have no symptoms; however, cirrhosis and liver cancer may eventually develop (Chang, 2007, Semin Fetal Neonatal Med, 12: 160-167). These complications result in the death of 15 to 25% of those with chronic disease ("Hepatitis B Fact sheet N°204". who. int. July 2014, retrieved 4 Nov. 2014). Herein, the term "HBV infection" includes the acute and chronic hepatitis B infection. The term "HBV infection" also includes the asymptotic stage of the initial infection, the symptomatic stages, as well as the asymptotic chronic stage of the HBV infection.

Compound

Herein, the term "compound" means any nucleic acid molecule, such as RNAi molecules or antisense oligonucleotides according to the invention or any conjugate comprising such a nucleic acid molecule. For example, herein the compound may be a nucleic acid molecule targeting PAPD5 and PAPD7, in particular an antisense oligonucleotide.

Composition

The term "composition" may also be used to describe a nucleic acid molecule compound. A nucleic acid molecule composition has less than 20% impurities, preferably less than 15% or 10% impurities, more preferably less than 9, 8, 7 or 6% impurities, most preferably less than 5 impurities. The impurities are typically nucleic acid molecules which are one or two nucleotides shorter (n-1 or n-2) than the primary nucleic acid molecule component.

The present invention is further described by reference to the non-limiting figures and examples.

DETAILED DESCRIPTION OF THE INVENTION

PAPD5 and PAPD7 are non-canonical poly(A)-polymerases that belong to the superfamily of polymerase β-like nucleotidyl transferases. In PCT/EP2017/064981 PAPD5 and PAPD7 were identified as relevant targets for inhibition of an HBV infection by inhibiting the production of HBV surface antigen (HBsAg) and the expression of HBV RNA during HBV infection with two small molecules followed by confirmation with pools of siRNA compounds. In PCT/EP2017/064980 antisense oligonucleotides targeting either PAPD5 or PAPD7 were described and combined to achieve in vitro inhibition of an HBV infection.

The present invention has identified target sequences of 12 to 22 nucleotides in length which are shared between human PAPD5 and human PAPD7 mRNA in order to be able to inhibit both targets with a single nucleic acid molecule. There are around 4500 shared target sites between human PAPD5 and human PAPD7 pre-mRNA. In terms of generating a pharmaceutical acceptable molecule other parameters needs to be taken into account such as the number of off-targets as well as conservation to other species to allow in vivo proof of concept as well as meaningful pharmacokinetic/pharmacodynamic (PK/PD) modelling.

Oligonucleotides of the Invention

The present invention has identified novel antisense oligonucleotides which are capable of inhibiting the expression of both PAPD5 and PAPD7 in vitro and in vivo. The oligonucleotides are complementary to one of three target sites of between 16 and 22 nucleotides in length which are present in both human PAPD5 and human PAPD7.

The inhibition is achieved by hybridizing the antisense oligonucleotide to a target nucleic acid encoding PAPD5 and a target nucleic acid encoding PAPD7. It is understood that the same molecule does not need to hybridize to the two targets simultaneously in order to be effective.

Target nucleic acid 1 may be a mammalian PAPD5 sequence, such as a sequence selected from the group consisting of SEQ ID NO: 1, 3 and 5.

Target nucleic acid 2 may be a mammalian PAPD7 sequence, such as a sequence selected from the group consisting of SEQ ID NO: 2, 4 and 6.

In some embodiments the antisense oligonucleotide of the invention is capable of modulating the expression of target 1 and target 2 by inhibiting or down-regulating them. Preferably, such modulation produces an inhibition of expression of at least 50% compared to the normal expression level of the targets, more preferably at least 60%, 70%, 80%, 90%, 95% or 98% inhibition compared to the normal expression level of the targets. In some embodiments oligonucleotides of the invention are capable of inhibiting expression levels of PAPD5 and PAPD7 mRNA by at least 65%-98%, such as 70% to 95%, in vitro using HeLa cells, this range of target reduction is advantageous in terms of selecting oligonucleotides with good correlation to the HBV antigen reduction, such as HBsAg and/or HBeAg reduction. In some embodiments compounds of the invention may be capable of inhibiting expression levels of PAPD5 and PAPD7 protein by at least 50% in vitro using HeLa cells. The materials and Method section and the Examples herein provide assays which may be used to measure target RNA inhibition in HeLa cells. The target modulation is triggered by the hybridization between a contiguous nucleotide sequence, such as the gapmer region, of the oligonucleotide and the target nucleic acids. In some embodiments the oligonucleotide of the invention comprises mismatches between the oligonucleotide or the contiguous nucleotide sequence and one or both of the target nucleic acids. Despite mismatches hybridization to the target nucleic acid may still be sufficient to show a desired modulation of PAPD5 and PAPD7 expression. Reduced binding affinity resulting from mismatches may advantageously be compensated by increased length of the oligonucleotide and/or an increased number of modified nucleosides capable of increasing the binding affinity to the target within the oligonucleotide sequence. Advantageously, the oligonucleotides of the present invention contain modified nucleosides capable of increasing the binding affinity, such as 2' sugar modified nucleosides, including LNA.

An aspect of the present invention relates to an antisense oligonucleotide of 12 to 32 nucleotides in length, which comprises a contiguous nucleotide sequence of 12 to 22 nucleotides in length which is capable of inhibiting the expression of both PAPD5 and PAPD7.

In some embodiments, the oligonucleotide comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary to the target nucleic acids of SEQ ID NO: 1 and SEQ ID NO: 2, or natural variants thereof.

In one embodiment the antisense oligonucleotide of the invention, or contiguous nucleotide sequence thereof is fully complementary (100% complementary) to a region of the target nucleic acids, or in some embodiments may comprise one or two mismatches between the oligonucleotide and the target nucleic acids.

In some embodiments the antisense oligonucleotide comprises a contiguous nucleotide sequence of 12 to 22 nucleotides in length with at least 93% complementary, such as fully (or 100%) complementary, to a target nucleic acid region present in SEQ ID NO: 1 and SEQ ID NO: 2.

In some embodiments the antisense oligonucleotide or the contiguous nucleotide sequence of the invention is at least 93% complementarity, such as fully (or 100%) complementary, to the target nucleic acid of SEQ ID NO: 1, SEQ ID NO: 2, SEQ ID NO: 3 and SEQ ID NO: 4.

In some embodiments the antisense oligonucleotide or the contiguous nucleotide sequence of the invention is at least 93% complementarity, such as fully (or 100%) complementary, to the target nucleic acid of SEQ ID NO: 1, SEQ ID NO: 2, SEQ ID NO: 5 and SEQ ID NO: 6.

In some embodiments the antisense oligonucleotide or the contiguous nucleotide sequence is 100% complementary to position 64669 to 69429 on SEQ ID NO: 1 and position 29514 to 29530 on SEQ ID NO: 2.

In some embodiments the antisense oligonucleotide or the contiguous nucleotide sequence is 100% complementary to position 64670 to 64685 on SEQ ID NO: 1 and position 29515 to 29530 on SEQ ID NO: 2.

In some embodiments the antisense oligonucleotide or the contiguous nucleotide sequence is 100% complementary to position 69414 to 69429 on SEQ ID NO: 1 and position 30731 to 30746 on SEQ ID NO: 2.

In some embodiments the antisense oligonucleotide or the contiguous nucleotide sequence is 100% complementary to position 759 to 781 on SEQ ID NO: 1 and position 1032 to 1054 on SEQ ID NO: 2.

In some embodiments, the antisense oligonucleotide of the invention comprises or consists of 12 to 32 nucleotides in length, such as from 14 to 25, such as 15 to 22, such as from 16 to 20 contiguous nucleotides in length.

In some embodiments, the contiguous nucleotide sequence of the antisense oligonucleotide which is complementary to the target nucleic acids comprises or consists of 12 to 22, such as from 14 to 20, such as from 16 to 20, such as from 15 to 18, such as from 16 to 18, such as from 16 to 17 contiguous nucleotides in length.

In some embodiments, the antisense oligonucleotide or the contiguous nucleotide sequence thereof comprises or consists of 22 or less nucleotides, such as 20 or less nucleotides, such as 17 or less nucleotides. It is to be understood that any range given herein includes the range endpoints. Accordingly, if an oligonucleotide is said to include from 12 to 32 nucleotides, both 12 and 32 nucleotides are included.

In some embodiments, the antisense oligonucleotide or contiguous nucleotide sequence comprises or consists of 12 to 32 nucleotides in length with at least 93% identity, preferably 100% identity, to a sequence selected from the group consisting of SEQ ID NO: 7 to 16.

In some embodiments, the antisense oligonucleotide or contiguous nucleotide sequence comprises or consists of 12 to 32 nucleotides in length with at least 93% identity, preferably 100% identity, to a sequence selected from the group consisting of SEQ ID NO: 17 to 19.

In some embodiments, the antisense oligonucleotide or contiguous nucleotide sequence comprises or consists of 12 to 32 nucleotides in length with at least 93% identity, preferably 100% identity, to a sequence of SEQ ID NO: 17 or 18.

In some embodiments, the antisense oligonucleotide or contiguous nucleotide sequence comprises or consists of 12 to 32 nucleotides in length with at least 93% identity, preferably 100% identity, to a sequence of SEQ ID NO: 19.

In a further aspect the invention relates to siRNA molecules where the antisense strand has at least 93% identity, preferably 100% identity, to a sequence selected from the group consisting of SEQ ID NO: 17 to 19.

In a further aspect the invention relates to shRNA molecules where a region of the molecule has at least 93% identity, preferably 100% identity, to a sequence selected from the group consisting of SEQ ID NO: 17 to 19.

It is understood that the contiguous nucleobase sequences (motif sequence) can be modified to for example increase nuclease resistance and/or binding affinity to the target nucleic acid.

The pattern in which the high affinity modified nucleotides are incorporated into the oligonucleotide sequence is generally termed oligonucleotide design.

The oligonucleotides of the invention are designed with modified nucleosides and DNA nucleosides. Advantageously, high affinity modified nucleosides are used.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the oligonucleotide comprises one or more sugar modified nucleosides, such as 2' sugar modified nucleosides. Preferably the oligonucleotide of the invention comprise one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA). Often used LNA LNA nucleosides are oxy-LNA, or cET.

In a further embodiment the oligonucleotide comprises at least one modified internucleoside linkage. Suitable internucleoside modifications are described in the "Definitions" section under "Modified internucleoside linkage". It is advantageous if at least 75%, such as all, the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In some embodiments, the oligonucleotide of the invention comprises at least one LNA nucleoside, such as 1, 2, 3, 4, 5, 6, 7, or 8 LNA nucleosides, such as from 2 to 6 LNA nucleosides, such as from 3 to 7 LNA nucleosides, 4 to 8 LNA nucleosides or 3, 4, 5, 6, 7 or 8 LNA nucleosides. In some embodiments, at least 75% of the modified nucleosides in the oligonucleotide are LNA nucleosides, such as 80%, such as 85%, such as 90% of the modified nucleosides are LNA nucleosides. In a still further embodiment all the modified nucleosides in the oligonucleotide are LNA nucleosides. In a further embodiment, the oligonucleotide may comprise both beta-D-oxy-LNA, and one or more of the following LNA nucleosides: thio-LNA, amino-LNA, oxy-LNA, ScET and/or ENA in either the beta-D or alpha-L configurations or combinations thereof. In a further embodiment, all LNA cytosine units are 5-methyl-cytosine. It is advantageous for the nuclease stability of the oligonucleotide or contiguous nucleotide sequence to have at least 1 LNA nucleoside at the 5' end and at least 2 LNA nucleosides at the 3' end of the nucleotide sequence.

In an embodiment of the invention the oligonucleotide of the invention is capable of recruiting RNase H.

In the current invention an advantageous structural design is a gapmer design as described in the "Definitions" section under for example "Gapmer", "LNA Gapmer", "MOE gapmer" and "Mixed Wing Gapmer" "Alternating Flank Gapmer". The gapmer design includes gapmers with uniform flanks, mixed wing flanks, alternating flanks, and gapbreaker designs. In the present invention it is advantageous if the oligonucleotide of the invention is a gapmer with an F-G-F' design. In addition to the F-G-F' designs described in the definitions sections one design may be where the F and F' wing regions independently comprise 1-8 2' sugar modified nucleosides and G is a gap region between 5 and 16 nucleosides which are capable of recruiting RNaseH.

In some embodiments the gapmer is an LNA gapmer with uniform flanks or with alternating flanks.

In some embodiments of the invention the LNA gapmer is selected from the following designs uniform flank designs 2-11-3, 2-11-4, 2-12-2, 2-12-3, 2-13-2, 2-9-6, 3-10-3, 3-10-4, 3-11-2, 3-11-3, 3-12-2, 3-9-4, 4-10-2, 4-10-3, 4-11-2, 4-7-5, 4-8-4, 4-9-3, 5-10-2, 5-6-5, 5-7-4, 5-7-5, 5-8-3, 5-8-4, 5-9-2 or 6-9-2.

In some embodiments of the invention the LNA gapmer is selected from the following alternating flanks designs 4-7-1-1-3, 4-9-1-1-2, 1-1-3-7-1-1-2, 1-1-3-9-2, 2-1-1-9-2, 2-1-1-9-3

Table 5 and 7 (Materials and Method section) lists preferred designs of each motif sequence.

In all instances the F-G-F' design may further include region D' and/or D" as described in the "Definitions" section under "Region D' or D" in an oligonucleotide". In some embodiments the oligonucleotide of the invention has 1, 2 or 3 phosphodiester linked nucleoside units, such as DNA units, at the 5' or 3' end of the gapmer region. In some embodiments the oligonucleotide of the invention consists of two 5' phosphodiester linked DNA nucleosides followed by a F-G-F' gapmer region as defined in the "Definitions" section. In addition to the D'-F-G-F'-D" designs described in the definitions sections one design may be an antisense oligonucleotide wherein a) the F region is between 1 and 6 nucleotides in length and consists of 2-5 identical LNA nucleosides, such as beta-D-oxy LNA or cET, and 0-3 DNA nucleosides; and b) the F' region is between 2 and 6 nucleotides in length and consists of 2-5 identical LNA nucleosides, such as beta-D-oxy LNA or cET, and 0-3 DNA nucleosides; and c) the G region consists of between 5 and 11, such as from 7-10 DNA nucleotides and d) optionally region D' consists of between 1 and 3 phosphodiester linked DNA nucleosides. Oligonucleotides that contain phosphodiester linked DNA units at the 5' or 3' end are suitable for conjugation and may further comprise a conjugate moiety as described herein. For delivery to the liver ASGPR targeting moieties are particular advantageous as conjugate moieties, see the Conjugate section below for further details.

For certain embodiments of the invention, the oligonucleotide is selected from the group of oligonucleotide compounds with CMP ID NO: 7_1 to 7_83 (see oligonucleotides listed in table 5), or pharmaceutically acceptable salts thereof.

For certain embodiments of the invention, the oligonucleotide is selected from the group of oligonucleotide compounds with CMP-ID-NO: 8_1 to 8_81 (see oligonucleotides listed in table 5, or pharmaceutically acceptable salts thereof.

For certain embodiments of the invention, the oligonucleotide is selected from the group of oligonucleotide compounds with CMP-ID-NO: 9_1 to 9_12 (see oligonucleotides listed in table 5), or pharmaceutically acceptable salts thereof.

For certain embodiments of the invention, the oligonucleotide is selected from the group of oligonucleotide compounds with CMP-ID-NO: 10_1 to 10_18 (see oligonucleotides listed in table 5), or pharmaceutically acceptable salts thereof.

For certain embodiments of the invention, the oligonucleotide is selected from the group of oligonucleotide compounds with CMP-ID-NO: 11_1 to 11_26 (see oligonucleotides listed in table 5), or pharmaceutically acceptable salts thereof.

For certain embodiments of the invention, the oligonucleotide is selected from the group of oligonucleotide compounds with CMP-ID-NO: 12_1 to 12_15 (see oligonucleotides listed in table 5), or pharmaceutically acceptable salts thereof.

For certain embodiments of the invention, the oligonucleotide is selected from the group of oligonucleotide compounds with CMP-ID-NO: 13_1 or 13_2 (see oligonucleotides listed in table 5).

For certain embodiments of the invention, the oligonucleotide is selected from the group of oligonucleotide compounds with CMP-ID-NO: 14_1 to 14_13 (see oligonucleotides listed in table 5), or pharmaceutically acceptable salts thereof.

For certain embodiments of the invention, the oligonucleotide is selected from the group of oligonucleotide compounds with CMP-ID-NO: 15_1 to 15_21 (see oligonucleotides listed in table 5), or pharmaceutically acceptable salts thereof.

For certain embodiments of the invention, the oligonucleotide is selected from the group of oligonucleotide compounds with CMP-ID-NO: 16_1 to 16_5 (see oligonucleotides listed in table 5).

For certain embodiments of the invention, the oligonucleotide is selected from the group of oligonucleotide compounds with CMP-ID-NO: 17_1 to 17_183 (see oligonucleotides listed in table 7), or pharmaceutically acceptable salts thereof.

For certain embodiments of the invention, the oligonucleotide is selected from the group of oligonucleotide compounds with CMP-ID-NO: 18_1 to 18_31 or 18_250 to 18_361 (see oligonucleotides listed in table 7), or pharmaceutically acceptable salts thereof.

For certain embodiments of the invention, the oligonucleotide is selected from the group of oligonucleotide compounds with CMP-ID-NO: 18_32 to 18_249 or 18_362 to 18_610 (see oligonucleotides listed in table 7), or pharmaceutically acceptable salts thereof.

For certain embodiments of the invention, the oligonucleotide is selected from the group of oligonucleotide compounds with CMP-ID-NO: 19_1 to 19_22 (see oligonucleotides listed in table 7), or pharmaceutically acceptable salts thereof.

In an embodiment of the invention the oligonucleotide is selected from the group of oligonucleotide with the compound with CMP-ID-NO: 18_1, 18_5, 18_10, 18_15, 18_18, 18_19, 18_24, 18_27, 18_30, 18_346, 18_347, 18_357, 17_10, 17_137 and 17_139.

In an embodiment of the invention the oligonucleotide is selected from the group of oligonucleotide with the compound with CMP-ID-NO: 18_1, 18_15, 18_30, 17_10, 17_137 and 17_139.

In a further embodiment of the invention the oligonucleotide may comprise at least one stereodefined internucleoside linkages, such as a stereodefined phosphorothioate internucleoside linkage.

A key advantage of generating stereodefined oligonucleotide variants is the ability to increase the diversity across a sequence motif, and select stereodefined oligonucleotides including sub-libraries of stereodefined oligonucleotides, which have improved medicinal chemical properties as compared to a parent oligonucleotide.

In some embodiments, the improved medicinal chemical property (or improved properties) is selected from one or more of enhanced potency, enhanced specific activity, enhanced tissue uptake, enhanced cellular uptake, enhanced efficacy, altered biodistribution, reduced off-target effects, enhanced mismatch discrimination, reduced toxicity, reduced immunogenicity, altered serum protein binding, improved duration of action, and stability. Improvement in one or more property is assessed as compared to the parent oligonucleotide, such as a stereorandom parent oligonucleotide.

In some embodiments the improved property may be the ability of the oligonucleotide to modulate target expression, such as via an improved interaction with the cellular machinery involved in modulating target expression, by way of example, an enhanced RNase H activity, an improved splice modulating activity, or an improved microRNA inhibition.

In some embodiments, the improved property is RNaseH specificity, RNaseH allelic discrimination (i.e. discrimination between single nucleotide polymorphisms (SNPs) and/ or RNaseH activity. In some embodiments, the improved property is other than RNaseH specificity, RNaseH allelic discrimination and/or RNaseH activity. In some embodiments the improved property is improved intracellular uptake. In some embodiments the improved property is reduced toxicity, such as cytotoxicity or hepatotoxicity.

A stereodefined oligonucleotide which exhibits one or more improved property as compared to a parent oligonucleotide, or other stereodefined oligonucleotides, is referred to as an improved phosphorothioate variant.

In an embodiment of the invention the oligonucleotide is selected from the group of oligonucleotide with the compound with CMP-ID-NO: 18_223, 18_36, 18_196, 18_188, 18_243.

In a further aspect of the invention the nucleic acid molecules, such as the antisense oligonucleotide, of the invention can be targeted directly to the liver by covalently attaching them to a conjugate moiety capable of binding to the asialoglycoprotein receptor (ASGPr), such as divalent or trivalent GalNAc cluster.

Conjugates

Since HBV infection primarily affects the hepatocytes in the liver it is advantageous to conjugate the antisense oligonucleotides of the invention to a conjugate moiety that will increase the delivery of the oligonucleotide to the liver compared to the unconjugated oligonucleotide. In one embodiment liver targeting moieties are selected from moieties comprising cholesterol or other lipids or conjugate moieties capable of binding to the asialoglycoprotein receptor (ASGPR).

In some embodiments the invention provides a conjugate comprising an antisense oligonucleotide of the invention covalently attached to a conjugate moiety.

The asialoglycoprotein receptor (ASGPR) conjugate moiety comprises one or more carbohydrate moieties capable of binding to the asialoglycoprotein receptor (ASPGR targeting moieties) with affinity equal to or greater than that of galactose. The affinities of numerous galactose derivatives for the asialoglycoprotein receptor have been studied (see for example: Jobst, S. T. and Drickamer, K. JB. C. 1996, 271, 6686) or are readily determined using methods typical in the art.

In one embodiment the conjugate moiety comprises at least one asialoglycoprotein receptor targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine. Advantageously the asialoglycoprotein receptor targeting moiety is N-acetylgalactosamine (GalNAc).

To generate the ASGPR conjugate moiety the ASPGR targeting moieties (preferably GalNAc) can be attached to a conjugate scaffold. Generally the ASPGR targeting moieties can be at the same end of the scaffold. In one embodiment the conjugate moiety consists of two to four terminal GalNAc moieties linked to a spacer which links each GalNAc moiety to a brancher molecule that can be conjugated to the antisense oligonucleotide.

In a further embodiment the conjugate moiety is monovalent, di-valent, tri-valent or tetra-valent with respect to asialoglycoprotein receptor targeting moieties. Advantageously the asialoglycoprotein receptor targeting moiety comprises N-acetylgalactosamine (GalNAc) moieties.

The the ASPGR targeting scaffold which constitute the conjugate moiety can for example be generated by linking the GalNAc moiety to the spacer through its C—I carbon. A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a PEG3 spacer. The branch point can be any small molecule which permits attachment of two to three GalNAc moieties or other asialoglycoprotein receptor targeting moieties and further permits attachment of the branch point to the oligonucleotide, such constructs are termed GalNAc clusters or GalNAc conjugate moieties. An exemplary branch point group is a di-lysine. A di-lysine molecule contains three amine groups through which three GalNAc moieties or other asialoglycoprotein receptor targeting moieties may be attached and a carboxyl reactive group through which the di-lysine may be attached to the oligomer. Khorev, et al 2008 Bioorg. Med. Chem. Vol 16, pp. 5216 also describes the synthesis of a suitable trivalent brancher. Other commercially available branchers are 1,3-bis-[5-(4,4'-dimethoxytrityloxy)pentylamido]propyl-2-[(2-cyanoethyl)-(N,N-diisopropyl)] phosphoramidite (Glen Research Catalogue Number: 10-1920-xx); tris-2,2,2-[3-(4, 4'-dimethoxytrityloxy)propyloxymethyl]ethyl-[(2-cyanoethyl)-(N,N-diisopropyl)]-phosphoramidite (Glen Research Catalogue Number: 10-1922-xx); and tris-2,2,2-[3-(4,4'-dimethoxytrityloxy)propyloxymethyl]methyleneoxpropyl-[(2-cyanoethyl)-(N,N-diisopropyl)]-phosphoramidite; and 1-[5-(4,4'-dimethoxy-trityloxy)pentylamido]-3-[5-fluorenomethoxy-carbonyl-oxy-pentylamido]-propyl-2-[(2-cyanoethyl)-(N,N-diisopropyl)]-phosphoramidite (Glen Research Catalogue Number: 10-1925-xx).

Other GalNAc conjugate moieties can include, for example, those described in WO 2014/179620 and WO 2016/055601 and PCT/EP2017/059080 (hereby incorporated by reference), as well as small peptides with GalNAc moieties attached such as Tyr-Glu-Glu-(aminohexyl Gal-NAc)3 (YEE(ahGalNAc)3; a glycotripeptide that binds to asialoglycoprotein receptor on hepatocytes, see, e.g., Duff, et al., Methods Enzymol, 2000, 313, 297); lysine-based galactose clusters (e.g., L3G4; Biessen, et al., Cardovasc. Med., 1999, 214); and cholane-based galactose clusters (e.g., carbohydrate recognition motif for asialoglycoprotein receptor).

The ASGPR conjugate moiety, in particular a trivalent GalNAc conjugate moiety, may be attached to the 3'- or 5'-end of the oligonucleotide using methods known in the art. In one embodiment the ASGPR conjugate moiety is linked to the 5'-end of the oligonucleotide.

One or more linkers may be inserted between the conjugate moiety (such as at the brancher molecule) and the oligonucleotide. It is advantageous to have a biocleavable linker between the conjugate moiety and the antisense oligonucleotide, optionally in combination with a non-cleavable linker such as a C6 linker. The linker(s) may be selected from the linkers described in the "Definitions" section under "Conjugate linkers" in particular biocleavable region D' or D" linkers are advantageous.

Figure 1D:
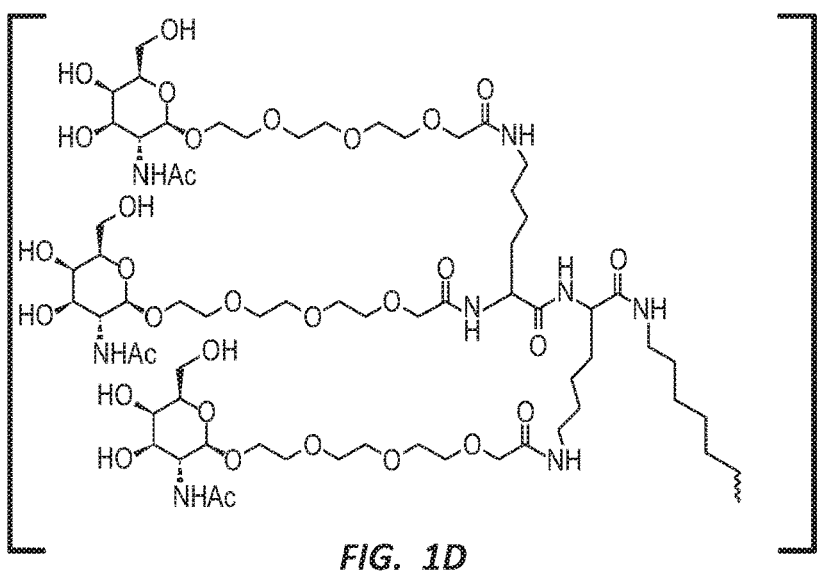
Figure 1E:
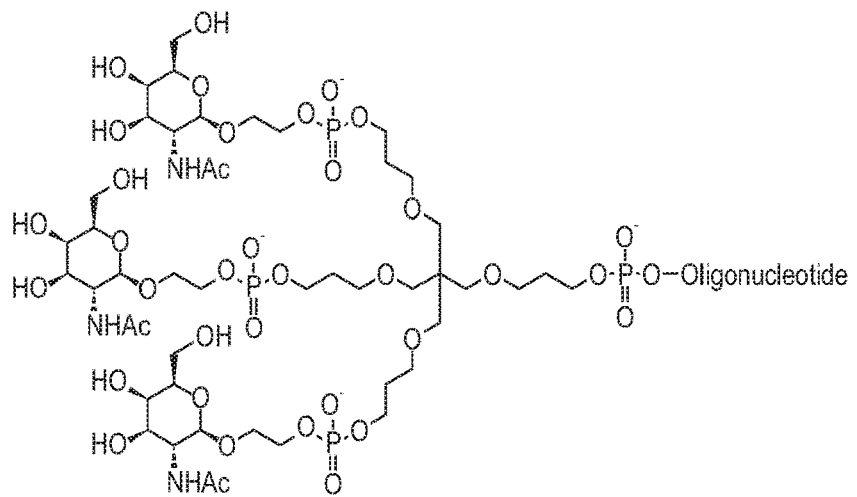
Figure 1F:
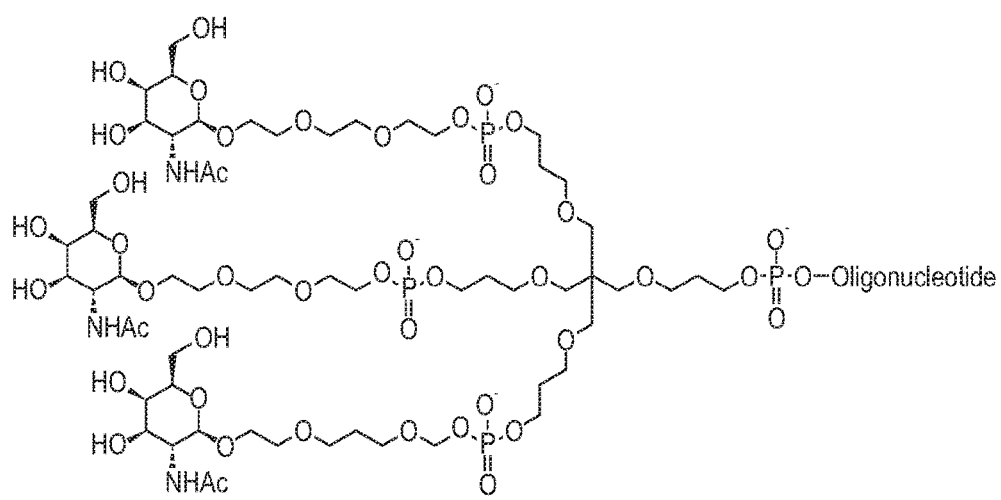
Figure 1G:
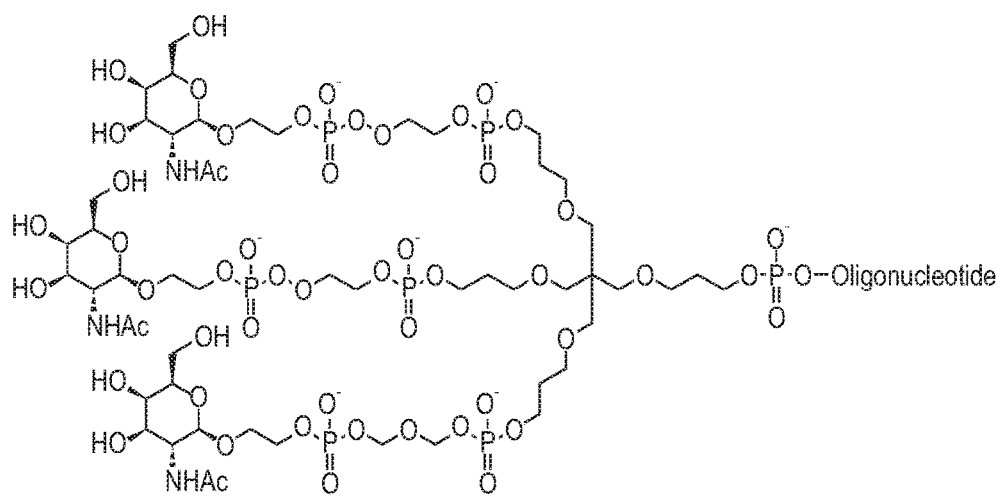
Figure 1H:
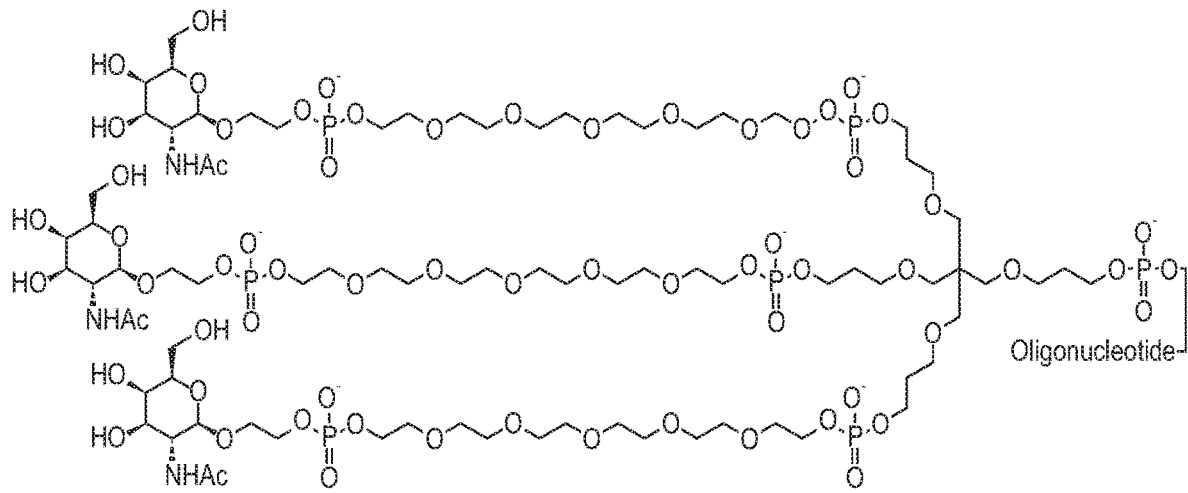
Figure 1I:
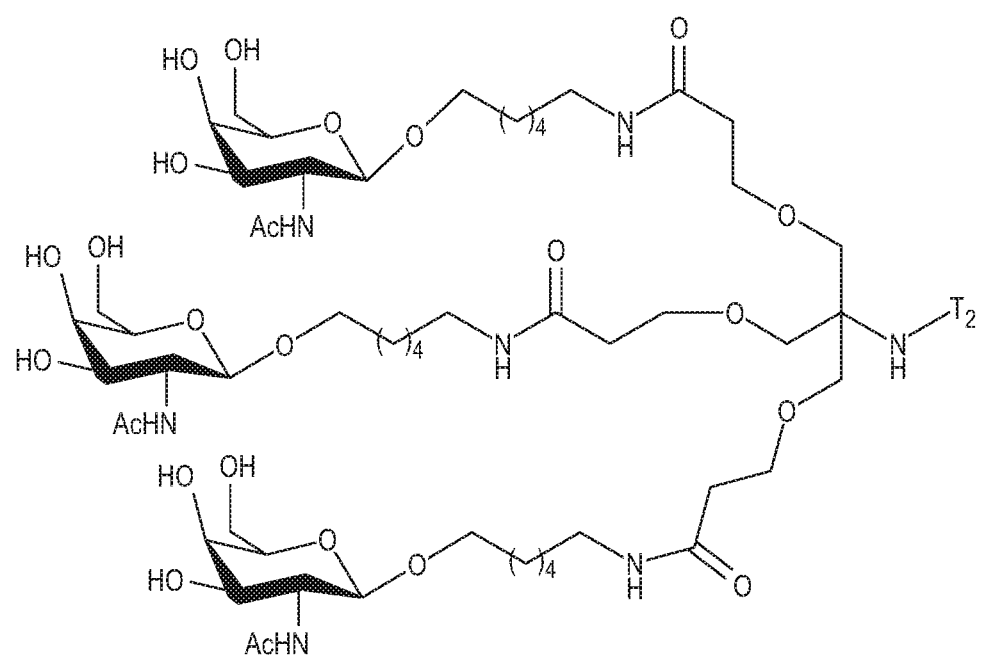

In one embodiment the conjugate moiety is a tri-valent N-acetylgalactosamine (GalNAc), such as those shown in FIG. 1, in particular as shown in FIG. 1D.

In an embodiment of the invention the conjugate compound is selected from the group of compounds in table 9 in the Material and Method section.

In an embodiment of the invention the conjugate compound is CMP-ID-NO: 20_12.

In an embodiment of the invention the conjugate compound is CMP-ID-NO 20_13.

In an embodiment of the invention the conjugate compound is CMP-ID-NO 20_14.

In an embodiment of the invention the conjugate compound is CMP-ID-NO 20_15.

In an embodiment of the invention the conjugate compound is CMP-ID-NO 20_16.

In an embodiment of the invention the conjugate compound is CMP-ID-NO 20_18.

In an embodiment of the invention the conjugate compound is CMP-ID-NO 20_20.

In an embodiment of the invention the conjugate compound is CMP-ID-NO 20_21.

In an embodiment of the invention the conjugate compound is CMP-ID-NO 20_22.

In an embodiment of the invention the conjugate compound is CMP-ID-NO 20_30.

In an embodiment of the invention the conjugate compound is CMP-ID-NO 20_35.

In an embodiment of the invention the conjugate compound is CMP-ID-NO 20_36.

In an embodiment of the invention the conjugate compound is CMP-ID-NO 21_2.

In an embodiment of the invention the conjugate compound is CMP-ID-NO 21_33.

In an embodiment of the invention the conjugate compound is CMP-ID-NO 21_34.

Method of Manufacture

In a further aspect, the invention provides methods for manufacturing the antisense oligonucleotides of the invention comprising reacting nucleotide units and thereby forming covalently linked contiguous nucleotide units comprised in the oligonucleotide. Preferably, the method uses phosphoramidite chemistry (see for example Caruthers et al, 1987, Methods in Enzymology vol. 154, pages 287-313). In a further embodiment the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Compositions

In a further aspect, the invention provides pharmaceutical compositions comprising an antisense oligonucleotides and/or conjugate compounds of the invention or salts thereof and a pharmaceutically acceptable diluent, carrier, salt and/or adjuvant. A typical pharmaceutical composition is prepared by mixing antisense oligonucleotide or conjugate compound of the invention and a diluent, carrier, or excipient.

A pharmaceutically acceptable diluent includes phosphate-buffered saline (PBS). In some embodiments the pharmaceutically acceptable diluent is sterile phosphate buffered saline. In some embodiments the oligonucleotide is used in the pharmaceutically acceptable diluent at a concentration of 50-300 µM solution.

For nucleic acid molecules, antisense oligonucleotides and conjugate compound comprising these suitable formulations are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt or potassium salt.

Applications

The oligonucleotides of the invention may be utilized as research reagents for, for example, diagnostics, therapeutics and prophylaxis.

In research, such oligonucleotides may be used to specifically modulate the synthesis of PAPD5 and PAPD7 protein in cells (e.g. in vitro cell cultures) and experimental animals thereby facilitating functional analysis of the target or an appraisal of its usefulness as a target for therapeutic intervention. Typically the target modulation is achieved by degrading or inhibiting the mRNA producing the protein, thereby prevent protein formation or by degrading or inhibiting a modulator of the gene or mRNA producing the protein.

If employing the oligonucleotide of the invention in research or diagnostics the target nucleic acid may be a cDNA or a synthetic nucleic acid derived from DNA or RNA.

Also encompassed by the present invention is an in vivo or in vitro method for modulating PAPD5 and PAPD7 expression in a target cell which is expressing PAPD5 and PAPD7, said method comprising administering an antisense oligonucleotide, conjugate compound or pharmaceutical composition of the invention in an effective amount to said cell.

In some embodiments, the target cell, is a mammalian cell in particular a human cell. The target cell may be an in vitro cell culture or an in vivo cell forming part of a tissue in a mammal. In preferred embodiments the target cell is present in in the liver. The target cell may be a hepatocyte.

One aspect of the present invention is related the antisense oligonucleotides, conjugate compounds or pharmaceutical compositions of the invention for use as a medicament.

In an aspect of the invention the antisense oligonucleotide, conjugate compound or pharmaceutical composition of the invention is capable of inhibiting the propagation of HBV. In particular the antisense oligonucleotide is capable of affecting one or more of the following parameters i) reduce the expression of viral RNA; ii) reduce the production of viral DNA (HBV DNA) derived from viral RNA (HBV RNA), iii) reduce the production of new viral particles (HBV particles); iv) reduce production of HBV antigens, in particular HBsAg and/or HBeAg.

For example, an antisense oligonucleotide that inhibits propagation of HBV may reduce i) the expression of viral RNA (HBV RNA) by at least 40% such as 50%, 60%, 70%, 80%, or 90% reduction compared to controls; ii) the production of viral DNA (HBV DNA) by at least 40% such as 50%, 60%, 70%, 80%, or 90% reduction compared to controls; iii) the production of new viral particles (HBV particles) by at least 40% such as 50%, 60%, 70%, 80%, or 90% reduction compared to controls; or iv) the production and/or secretion of HBsAg and/or HBeAg by at least 50%, such as at least 60%, 70%, 80%, 90% or even up to complete depletion of one or both of the antigens compared to controls. The controls may be untreated cells or animals or cell or animal treated with an appropriate control.

Inhibition of propagation of HBV may be measured in vitro using HBV infected dHepaRG cells or ASGPR-dHepaRG cells or in vivo for oligonucleotides complementary to mouse PAPD5 and PAPD7 using the AAV/HBV mouse model as described in the Materials and Methods section. Inhibition of secretion of HBsAg and/or HBeAg may be measured by ELISA, e.g. by using the CLIA ELISA Kit (Autobio Diagnostic) according to the manufacturers' instructions. Inhibition of production of intracellular HBV mRNA may be measured by real-time PCR, e.g. as described in the Materials and Methods section. Further methods for evaluating whether a test compound inhibits propagation of HBV are measuring secretion of HBV DNA by RT-qPCR e.g. as described in WO 2015/173208 or as described in Materials and method section; Northern Blot; in-situ hybridization, or immuno-fluorescence.

Due to the reduction of HBsAg secretion the antisense oligonucleotides, conjugate compounds or pharmaceutical compositions of the present invention can be used to inhibit development of or in the treatment of HBV infection. In particular, due to inhibition of HBeAg secretion, the antisense oligonucleotides, conjugate compounds or pharmaceutical compositions of the present invention more efficiently inhibits development of or treats a chronic HBV infection as compared to a compound that only reduces secretion of HBsAg. In addition, reducing HBeAg in an expecting mother may also inhibit the development of a chronic HBV infection of her child. Thus, due to the reduction of HBeAg secretion the antisense oligonucleotides, conjugate compounds or pharmaceutical compositions of the present invention inhibits development of a chronic HBV infection (such as development of a chronic HBV infection in the offspring of an HBV infected mother) and reduces the infectiousness of a HBV infected person.

Accordingly, one aspect of the present invention is related to use of the antisense oligonucleotides, conjugate compounds or pharmaceutical compositions of the invention to reduce secretion of HBsAg and HBeAg in an HBV infected individual. It is advantageous if the antisense oligonucleotides, conjugate compounds or pharmaceutical compositions of the invention are capable of reducing HBsAg expression from HBV DNA integrated into the host genome.

A further aspect of the invention relates to the use of the antisense oligonucleotides, conjugate compounds or pharmaceutical compositions of the invention to inhibit development of or treat a chronic HBV infection.

A further aspect of the invention relates to the use of the antisense oligonucleotides, conjugate compounds or pharmaceutical compositions of the invention to and reduces the infectiousness of a HBV infected person. In a particular aspect of the invention, the antisense oligonucleotides, conjugate compounds or pharmaceutical compositions of the invention inhibits development of a chronic HBV infection in the offspring of a HBV infected mother. This mother is preferably HBeAg positive.

The subject to be treated with the antisense oligonucleotides, conjugate compounds or pharmaceutical compositions of the invention (or which prophylactically receives antisense oligonucleotides, conjugate compounds or pharmaceutical compositions of the present invention) is preferably a human, more preferably a human patient who is HBsAg positive and/or HBeAg positive, even more preferably a human patient that is HBsAg positive and HBeAg positive. Said human patient may be an expected mother, e.g. an expected mother who is HBeAg positive and/or HBsAg positive, more preferably an expected mother who is HBeAg positive and HBsAg positive.

Accordingly, the present invention relates to a method of treating and/or preventing a HBV infection, wherein the method comprises administering an effective amount of the antisense oligonucleotides, conjugate compounds or pharmaceutical compositions of the invention.

The invention also provides for the use of a nucleic acid molecule, an antisense oligonucleotide, a conjugate compound or a pharmaceutical composition of the invention for the manufacture of a medicament, in particular a medicament for use in the treatment or prevention of HBV infection or chronic HBV infection or reduction of the infectiousness of a HBV infected person. In preferred embodiments the medicament is manufactured in a dosage form for subcutaneous administration.

The invention also provides for the use of a nucleic acid molecule, an antisense oligonucleotide, a conjugate compound, the pharmaceutical composition of the invention for the manufacture of a medicament wherein the medicament is in a dosage form for intravenous administration.

The nucleic acid molecule, antisense oligonucleotide or the pharmaceutical composition of the invention may be used in a combination therapy. For example, nucleic acid molecule, antisense oligonucleotide, or the pharmaceutical composition of the invention may be combined with other anti-HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti-HBV agents such as a HBV RNA replication inhibitor, a HBsAg secretion inhibitor, a HBV capsid inhibitor, an antisense oligomer (e.g. as described in WO2012/145697 and WO 2014/179629), a siRNA (e.g. described in WO 2005/014806, WO 2012/024170, WO 2012/2055362, WO 2013/003520, WO 2013/159109, WO 2017/027350 and WO2017/015175), a HBV therapeutic vaccine, a HBV prophylactic vaccine, a HBV antibody therapy (monoclonal or polyclonal), or TLR 2, 3, 7, 8 or 9 agonists for the treatment and/or prophylaxis of HBV.

Administration

The antisense oligonucleotides, conjugate compounds or pharmaceutical composition of the invention is formulated, dosed, and administered in a fashion consistent with good medical practice. Factors for consideration in this context include the particular mammal being treated, the clinical condition of the individual patient, the site of delivery of the agent, the method of administration, the scheduling of administration, the age and sex of the patients and other factors known to medical practitioners. Herein, an "effective amount" (also known as "(therapeutically) effective dose") means the amount of a compound that will elicit the biological or medical response of a subject that is being sought by a medical doctor or other clinician. The "effective amount" of an antisense oligonucleotide, conjugate compound or pharmaceutical composition of the invention, will be governed by such considerations, and is the minimum amount necessary to inhibit HBsAg and/or HBeAg. For example, such amount may be below the amount that is toxic to the cells of the recipient, or to the mammal as a whole.

In some embodiments, the oligonucleotide, oligonucleotide conjugate or pharmaceutical composition of the invention is administered at a dose of 0.1-15 mg/kg, such as from 0.2-10 mg/kg, such as from 0.25-5 mg/kg. The administration can be once a week, every $2^{nd}$ week, every third week or even once a month.

The nucleic acid molecules or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intramuscular, intracerebral, intracerebroventricular or intrathecal).

In a preferred embodiment the nucleic acid molecule, antisense oligonucleotide, conjugate compounds or pharmaceutical compositions of the present invention are administered by a parenteral route including intravenous, intraarterial, subcutaneous, intraperitoneal or intramuscular injection or infusion. In one embodiment the active oligonucleotide or oligonucleotide conjugate is administered intravenously. With GalNAc conjugated compounds it may be advantageous to administer subcutaneously in order to delay saturation of the ASGP reseptor.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above.

By way of example, the oligomer or the oligomer conjugate of the present invention may be used in combination with other actives, such as oligonucleotide-based antivirals—such as sequence specific oligonucleotide-based antivirals—acting either through antisense (including other LNA oligomers), siRNAs (such as ARC520), aptamers, morpholinos or any other antiviral, nucleotide sequence-dependent mode of action.

By way of further example, the oligomer or the oligomer conjugate of the present invention may be used in combination with other actives, such as immune stimulatory antiviral compounds, such as interferon (e.g. pegylated interferon alpha), TLR7 agonists (e.g. GS-9620), or therapeutic vaccines.

By way of further example, the oligomer or the oligomer conjugate of the present invention may be used in combination with other actives, such as small molecules, with antiviral activity. These other actives could be, for example, nucleoside/nucleotide inhibitors (eg entecavir or tenofovir disoproxil fumarate), encapsidation inhibitors, entry inhibitors (eg Myrcludex B).

In certain embodiments, the additional therapeutic agent may be an HBV agent, an Hepatitis C virus (HCV) agent, a chemotherapeutic agent, an antibiotic, an analgesic, a nonsteroidal anti-inflammatory (NSAID) agent, an antifungal agent, an antiparasitic agent, an anti-nausea agent, an antidiarrheal agent, or an immunosuppressant agent.

In particular related embodiments, the additional HBV agent may be interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In other particular related embodiments, the additional HCV agent may be interferon alpha-2b, interferon alpha-2a, and interferon alphacon-1 (pegylated and unpegylated); ribavirin; pegasys; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

Embodiments of the Invention

The following embodiments of the present invention may be used in combination with any other embodiments described herein.

1. A nucleic acid molecule of 12 to 32 nucleotides in length, which comprises a contiguous nucleotide sequence of 12 to 22 nucleotides in length which is capable of inhibiting the expression of both PAPD5 and PAPD7.

2. The nucleic acid molecule of embodiment 1, wherein the contiguous nucleotide sequence is at least 93% complementarity to target nucleic acid of SEQ ID NO: 1 and SEQ ID NO: 2.

3. The nucleic acid molecule of embodiment 1 or 2, wherein the contiguous nucleotide sequence is at least 100% complementarity to target nucleic acid of SEQ ID NO: 1 and SEQ ID NO: 2.

4. The nucleic acid molecule of embodiment 1 or 3, wherein the contiguous nucleotide sequence is complementary to target nucleic acid of SEQ ID NO: 1, SEQ ID NO: 2, SEQ ID NO: 3 and SEQ ID NO: 4.

5. The nucleic acid molecule of embodiment 1 or 3, wherein the contiguous nucleotide sequence is complementary to target nucleic acid of SEQ ID NO: 1, SEQ ID NO: 2, SEQ ID NO: 5 and SEQ ID NO: 6.

6. The nucleic acid molecule of embodiment 1 to 3 or 5, wherein the nucleic acid molecule is complementary to position 759 to 781 on SEQ ID NO: 1 and position 1032 to 1054 on SEQ ID NO: 2.

7. The nucleic acid molecule of embodiment 1 to 4, wherein the nucleic acid molecule is complementary to position 64669 to 69429 on SEQ ID NO: 1 and position 29514 to 29530 on SEQ ID NO: 2.

8. The nucleic acid molecule of embodiment 1 to 4, wherein the nucleic acid molecule is complementary to position 69414 to 69429 on SEQ ID NO: 1 and position 30731 to 30746 on SEQ ID NO: 2.

9. The nucleic acid molecule of embodiment 1 to 8 is capable of hybridizing to a target nucleic acid of SEQ ID NO: 1 and SEQ ID NO: 2 with a $\Delta G°$ below −15 kcal.

10. The nucleic acid molecule of embodiment 2 to 9, wherein the target nucleic acid is RNA.

11. The nucleic acid molecule of embodiment 10, wherein the RNA is pre-mRNA.

12. The nucleic acid molecule of embodiment 1-11, wherein the nucleic acid molecule is selected from antisense oligonucleotide, siRNA or shRNA.

13. The nucleic acid molecule of embodiment 1-11, wherein the nucleic acid molecule is a single stranded antisense oligonucleotide.

14. The antisense oligonucleotide of embodiment 12 or 13, wherein the contiguous nucleotide sequence comprises or consists of at least 14 contiguous nucleotides, particularly 15, 16, 17, 18, 19 or 20 contiguous nucleotides.

15. The antisense oligonucleotide of embodiment 12 or 13, wherein the contiguous nucleotide sequence comprises or consists of from 14 to 20 nucleotides.

16. The antisense oligonucleotide of embodiment 15, wherein the contiguous nucleotide sequence comprises or consists of from 16 to 18 nucleotides.

17. The antisense oligonucleotide of embodiment 1 to 16, wherein the oligonucleotide comprises or consists of 14 to 25 nucleotides in length.

18. The antisense oligonucleotide of embodiment 17, wherein the antisense oligonucleotide comprises or consists of 15 to 22 nucleotides in length.

19. The antisense oligonucleotide of embodiment 17 or 18, wherein the antisense oligonucleotide comprises or consists of 16 to 20 nucleotides in length.

20. The antisense oligonucleotide of embodiment 12-19, wherein the contiguous nucleotide sequence comprises or consists of a sequence selected from the group consisting of SEQ ID NO: 7, 8, 9, 10, 11, 12, 13, 14, 15, 16, 17, 18 and 19.

21. The antisense oligonucleotide of embodiment 12-20, wherein the contiguous nucleotide sequence comprises or consists of a sequence selected from the group consisting of SEQ ID NO: 7, 8, 9, 10, 11, 12, 13, 14, 15 and 16.

22. The antisense oligonucleotide of embodiment 12-20, wherein the contiguous nucleotide sequence comprises or consists of a sequence selected from SEQ ID NO: 17 or SEQ ID NO: 18.

23. The antisense oligonucleotide of embodiment 12-20, wherein the contiguous nucleotide sequence comprises or consists of SEQ ID NO: 19.

24. The antisense oligonucleotide of embodiment 12-23, wherein the contiguous nucleotide sequence has zero to three mismatches compared to the target nucleic acids it is complementary to.

25. The antisense oligonucleotide of embodiment 24, wherein the contiguous nucleotide sequence has one mismatch compared to the target nucleic acids.

26. The antisense oligonucleotide of embodiment 24, wherein the contiguous nucleotide sequence has two mismatches compared to the target nucleic acids.

27. The antisense oligonucleotide of embodiment 24, wherein the contiguous nucleotide sequence is fully complementary to both target nucleic acid sequences.

28. The antisense oligonucleotide of embodiment 12-27, comprising one or more modified nucleosides.

29. The antisense oligonucleotide of embodiment 28, wherein the one or more modified nucleoside is a high-affinity modified nucleosides.

30. The antisense oligonucleotide of embodiment 28 or 29, wherein the one or more modified nucleoside is a 2' sugar modified nucleoside.

31. The antisense oligonucleotide of embodiment 30, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, 2'-fluoro-ANA and LNA nucleosides.

32. The antisense oligonucleotide of embodiment 28-31, wherein the one or more modified nucleoside is a LNA nucleoside.

33. The antisense oligonucleotide of embodiment 32, wherein the modified LNA nucleoside is selected from oxy-LNA, amino-LNA, thio-LNA, cET, and ENA.

34. The antisense oligonucleotide of embodiment 32 or 33, wherein the modified LNA nucleoside is oxy-LNA with the following 2'-4' bridge —O—CH$_2$—.

35. The antisense oligonucleotide of embodiment 34, wherein the oxy-LNA is beta-D-oxy-LNA.

36. The antisense oligonucleotide of embodiment 32 or 33, wherein the modified LNA nucleoside is cET with the following 2'-4' bridge —O—CH(CH$_3$)—.

37. The antisense oligonucleotide of embodiment 36, wherein the cET is (S)cET, i.e. 6'(S)methyl-beta-D-oxy-LNA.

38. The antisense oligonucleotide of embodiment 32 or 33, wherein the LNA is ENA, with the following 2'-4' bridge —O—CH$_2$—CH$_2$—.

39. The antisense oligonucleotide of any one of embodiments 12-33, wherein the antisense oligonucleotide comprises at least one modified internucleoside linkage.

40. The antisense oligonucleotide of embodiment 39, wherein the modified internucleoside linkage is nuclease resistant.

41. The antisense oligonucleotide of embodiment 39 or 40, wherein at least 75% of the internucleoside linkages within the contiguous nucleotide sequence are phosphorothioate internucleoside linkages or boranophosphate internucleoside linkages.

42. The antisense oligonucleotide of embodiment 39 or 40, wherein all the internucleoside linkages within the contiguous nucleotide sequence are phosphorothioate internucleoside linkages.

43. The antisense oligonucleotide of embodiment 41 or 42, wherein at least one of the phosphorothioate internucleoside linkages are stereodefined 44. The antisense oligonucleotide of embodiment 12-43, wherein the antisense oligonucleotide is capable of recruiting RNase H.

45. The antisense oligonucleotide of embodiment 44, wherein the antisense oligonucleotide or the contiguous nucleotide sequence is a gapmer.

46. The antisense oligonucleotide of embodiment 45, wherein the gapmer has the formula 5'-F-G-F'-3', where the F and F' wing regions independently comprise or consist of 1-7 2' sugar modified nucleosides in accordance with embodiments 31 to 38 and G is a region between 5 and 16 nucleosides which are capable of recruiting RNaseH.

47. The antisense oligonucleotide of embodiment 46, wherein each wing (F and F') is characterized by having at least one 2' sugar modified nucleoside at the 5' terminal and the 3' terminal of the wing and the G region has at least one DNA nucleoside adjacent to the wing regions (e.g. 5' and 3' terminal of the G region).

48. The antisense oligonucleotide of embodiment 46 or 47, wherein all the 2' sugar modified nucleosides in region F and F' are identical LNA nucleosides.

49. The oligonucleotide of embodiment 46-48, wherein
   a. the F region is between 1 and 6 nucleotides in length and consists of 1-5 identical LNA nucleosides and 0-3 DNA nucleosides; and
   b. the F' region is between 2 and 6 nucleotides in length and consists of 2-5 identical LNA nucleosides and 0-3 DNA nucleosides; and
   c. the G region is between 5 and 11 nucleotides which are capable of recruiting RNaseH, and
   d. optionally a D' region with 1 to 3 phosphodiester linked DNA nucleosides are positioned at the 5' end of the F region 50. The antisense oligonucleotide of embodiment 47, wherein region F and F' consist of identical LNA nucleosides.

51. The antisense oligonucleotide of embodiment 46-48, wherein all the 2' sugar modified nucleosides in region F and F' are oxy-LNA nucleosides.

52. The antisense oligonucleotide of embodiment 46 or 47, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.

53. The antisense oligonucleotide of embodiment 46-52, wherein the RNaseH recruiting nucleosides in region G are independently selected from DNA, alpha-L-LNA, C4' alkylated DNA, ANA and 2' F-ANA and UNA.

54. The antisense oligonucleotide of embodiment 53, wherein the nucleosides in region G is DNA and/or alpha-L-LNA nucleosides.

55. The antisense oligonucleotide of embodiment 46 or 53 or 54, wherein region G consists of at least 75% DNA nucleosides.

56. The antisense oligonucleotide of embodiment 55, where all the nucleosides in region G are DNA nucleosides.

57. The antisense oligonucleotide of embodiment 12-55, wherein the antisense oligonucleotide is selected from CMP ID NO: 7_1 to 7_83, or pharmaceutically acceptable salts thereof.

58. The antisense oligonucleotide of embodiment 12-55, wherein the antisense oligonucleotide is selected from CMP ID NO: 8_1 to 8_81, or pharmaceutically acceptable salts thereof.

59. The antisense oligonucleotide of embodiment 12-55, wherein the antisense oligonucleotide is selected from CMP ID NO: 9_1 to 9_12, or pharmaceutically acceptable salts thereof.

60. The antisense oligonucleotide of embodiment 12-55, wherein the antisense oligonucleotide is selected from CMP ID NO: 10_1 to 10_18, or pharmaceutically acceptable salts thereof.

61. The antisense oligonucleotide of embodiment 12-55, wherein the antisense oligonucleotide is selected from CMP ID NO: 11_1 to 11_26, or pharmaceutically acceptable salts thereof.

62. The antisense oligonucleotide of embodiment 12-55, wherein the antisense oligonucleotide is selected from CMP ID NO: 12_1 to 12_15, or pharmaceutically acceptable salts thereof.

63. The antisense oligonucleotide of embodiment 12-55, wherein the antisense oligonucleotide is selected from CMP ID NO: 13_1 or 13_2, or pharmaceutically acceptable salts thereof.

64. The antisense oligonucleotide of embodiment 12-55, wherein the antisense oligonucleotide is selected from CMP ID NO: 14_1 to 14_13, or pharmaceutically acceptable salts thereof.

65. The antisense oligonucleotide of embodiment 12-55, wherein the antisense oligonucleotide is selected from CMP ID NO: 15_1 to 15_21, or pharmaceutically acceptable salts thereof.

66. The antisense oligonucleotide of embodiment 12-55, wherein the antisense oligonucleotide is selected from CMP ID NO: 16_1 to 16_5, or pharmaceutically acceptable salts thereof.

67. The antisense oligonucleotide of embodiment 12-55, wherein the antisense oligonucleotide is selected from CMP ID NO: 17_1 to 17_183, or pharmaceutically acceptable salts thereof.

68. The antisense oligonucleotide of embodiment 12-55, wherein the antisense oligonucleotide is selected from CMP ID NO: 18_1 to 18_31 or 18_250 to 18_361, or pharmaceutically acceptable salts thereof.

69. The antisense oligonucleotide of embodiment 68, wherein the antisense oligonucleotide is selected from CMP ID NO: 18_1, 18_5, 18_10, 18_15, 18_18, 18_19, 18_24, 18_27, 18_30, 18_346, 18_347, 18_357, 17_10, 17_137 and 17_139, or pharmaceutically acceptable salts thereof.

70. The antisense oligonucleotide of embodiment 69, wherein the antisense oligonucleotide is selected from CMP ID NO: 18_1, 18_15, 18_27, 18_30, 17_10, 17_137 and 17_139.

71. The antisense oligonucleotide of embodiment 12-55, wherein the antisense oligonucleotide is selected from CMP ID NO: 18_32 to 18_249 or 18_362 to 18_610, or pharmaceutically acceptable salts thereof.

72. The antisense oligonucleotide of embodiment 71, wherein the antisense oligonucleotide is selected from CMP ID NO: 18_223, 18_36, 18_196, 18_188 and 18_243.

73. The antisense oligonucleotide of embodiment 12-55, wherein the antisense oligonucleotide is selected from CMP ID NO: 19_1 to 19_22, or pharmaceutically acceptable salts thereof.

74. A conjugate compound comprising a nucleic acid molecule according to any one of claims 1 to 11 or an antisense oligonucleotide according to any one of claims 12-57, and at least one conjugate moiety covalently attached to said antisense oligonucleotide.

75. The conjugate compound of embodiment 74, wherein the conjugate moiety is selected from carbohydrates, cell surface receptor ligands, drug substances, hormones, lipophilic substances, polymers, proteins, peptides, toxins, vitamins, viral proteins or combinations thereof.

76. The conjugate compound of embodiment 74 or 75, wherein the conjugate moiety is capable of binding to the asialoglycoprotein receptor.

77. The conjugate compound of embodiment 76, wherein the conjugate moiety comprises at least one asialoglycoprotein receptor targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine.

78. The conjugate compound of embodiment 77, wherein the asialoglycoprotein receptor targeting moiety is N-acetylgalactosamine (GalNAc).

79. The conjugate compound of embodiment 77 or 78, wherein the conjugate moiety is mono-valent, di-valent, tri-valent or tetra-valent with respect to asialoglycoprotein receptor targeting moieties.

80. The conjugate compound of embodiment 79, wherein the conjugate moiety consists of two to four terminal GalNAc moieties and a spacer linking each GalNAc moiety to a brancher molecule that can be conjugated to the antisense compound.

81. The conjugate compound of embodiment 80, wherein the spacer is a PEG spacer.

82. The conjugate compound of embodiment 76 to 81, wherein the conjugate moiety is a tri-valent N-acetylgalactosamine (GalNAc) moiety.

83. The conjugate compound of embodiment 76 to 82, wherein the conjugate moiety is selected from one of the trivalent GalNAc moieties in FIG. 1.

84. The conjugate compound of embodiment 83, wherein the conjugate moiety is the trivalent GalNAc moiety in FIG. 1D.

85. The conjugate compound of embodiment 74-84, comprising a linker which is positioned between the nucleic acid molecule or the antisense oligonucleotide and the conjugate moiety.

86. The conjugate compound of embodiment 85, wherein the linker is a physiologically labile linker.

87. The conjugate compound of embodiment 86, wherein the physiologically labile linker is nuclease susceptible linker.

88. The oligonucleotide conjugate of embodiment 86 or 87, wherein the physiologically labile linker is composed of 2 to 5 consecutive phosphodiester linkages.

89. The conjugate compound of embodiment 86 to 88, wherein the antisense oligonucleotide has the formula D'-F-G-F' or F-G-F'-D", wherein F, F' and G are as defined in embodiments 46-56 and D' or D" comprises 1, 2 or 3 DNA nucleosides with phosphodiester internucleoside linkages.

90. The oligonucleotide conjugate of embodiment 88 or 89, wherein at least two consecutive phosphodiester internucleoside linkages are associated with a CA dinucleotide.

91. The conjugate compound of embodiment 76-90, which display improved cellular distribution between liver vs. kidney or improved cellular uptake into the liver of the conjugate compound as compared to an unconjugated nucleic acid molecule or antisense oligonucleotide.

92. The conjugate compound of embodiment 76-91, where in the conjugate compound is selected from the group consisting of CPM ID NO 20_12, 20_13, 20_14, 20_15, 20_16, 20_18, 20_20, 20_21, 20_22, 20_30, 20_35, 20_36, 21_2, 21_33 and 21_34.

93. A pharmaceutical composition comprising a nucleic acid molecule according to any one of embodiments 1 to 11, an antisense oligonucleotide of embodiment 12-73, a conjugate compound of embodiment 74-92 or acceptable salts thereof and a pharmaceutically acceptable diluent, carrier, salt and/or adjuvant.

94. A method for manufacturing the antisense oligonucleotide of embodiment 12-73, comprising reacting nucleotide units thereby forming covalently linked contiguous nucleotide units comprised in the antisense oligonucleotide.

95. The method of embodiment 94, further comprising reacting the contiguous nucleotide sequence with a non-nucleotide conjugation moiety as described in any one of claims 76-84.

96. A method for manufacturing the composition of embodiment 93, comprising mixing the antisense oligonucleotide with a pharmaceutically acceptable diluent, carrier, salt and/or adjuvant.

97. An in vivo or in vitro method for modulating PAPD5 and PAPD7 expression in a target cell which is expressing PAPD5 and PAPD7, said method comprising administering the nucleic acid molecule of any one of embodiments 1 to 11, the antisense oligonucleotide of any one of embodiments 12-73 or the conjugate compound of any one of embodiment 74-92 or the pharmaceutical composition of embodiment 93 in an effective amount to said cell.

98. The method of embodiments 97, wherein the PAPD5 and PAPD7 expression is reduced by at least 30%, or at least or at least 40%, or at least 50%, or at least 60%, or at least 70%, or at least 80%, or at least 90%, or at least 95% in the target cell compared to the level without any treatment.

99. A method for treating or preventing a disease comprising administering a therapeutically or prophylactically effective amount of the nucleic acid molecule any one of embodiments 1 to 11, the antisense oligonucleotide of any one of embodiments 12-73 or the conjugate compound of any one of embodiments 74-92 or the pharmaceutical composition of embodiment 93 to a subject suffering from or susceptible to the disease.

100. The nucleic acid molecule any one of embodiments 1 to 11, the antisense oligonucleotide of any one of embodiments 12-57 or the conjugate compound of any one of embodiments 74-92 or the pharmaceutical composition of embodiment 93, for use as a medicament for treatment or prevention of a disease in a subject.

101. Use of the nucleic acid molecule any one of embodiments 1 to 11, the antisense oligonucleotide of any one of embodiment 12-73 or the conjugate compound of any one of embodiment 74-92 for the preparation of a medicament for treatment or prevention of a disease in a subject.

102. The method, the nucleic acid molecule, or the use of embodiments 99-101, wherein the disease is HBV infection or chronic HBV infection.

103. The method, the nucleic acid molecule or the use of embodiments 102, wherein the secretion of HBsAg and/or HBeAg and/or intracellular HBV mRNA and/or HBV DNA is reduced.

104. The method, the nucleic acid molecule or the use of embodiments 102 or 103, wherein HBsAg is reduced by at least 30%, or at least or at least 40%, or at least 50%, or at least 60%, or at least 70%, or at least 80%, or at least 90%, or at least 95% compared to the level without any treatment.

105. The method, the antisense oligonucleotide or the use of embodiments 99-104 wherein the subject is a mammal.

106. The method, the antisense oligonucleotide or the use of embodiment 105, wherein the mammal is human.

EXAMPLES

The Examples illustrate the invention.
Material and Methods
Oligonucleotide Motif Sequences and Oligonucleotide Compounds

TABLE 4

List of oligonucleotide motif sequences targeting human and mouse transcripts Sequences are indicated by SEQ ID NO, the motif sequence and the position they target on the human PAPD5 transcript (SEQ ID NO: 1) and the human PAPD7 transcript (SEQ ID NO: 2).

| SEQ ID NO | Motif Sequence | Start ID NO: 1 | End ID NO: 1 | Start ID NO: 2 | End ID NO: 2 |
|---|---|---|---|---|---|
| 7 | AGATCTGCATCCACAG | 759 | 774 | 1032 | 1047 |
| 8 | CAGATCTGCATCCACAG | 759 | 775 | 1032 | 1048 |

TABLE 4-continued

List of oligonucleotide motif sequences targeting human and mouse transcripts Sequences are indicated by SEQ ID NO, the motif sequence and the position they target on the human PAPD5 transcript (SEQ ID NO: 1) and the human PAPD7 transcript (SEQ ID NO: 2).

| SEQ ID NO | Motif Sequence | Start ID NO: 1 | End ID NO: 1 | Start ID NO: 2 | End ID NO: 2 |
|---|---|---|---|---|---|
| 9 | CCAGATCTGCATCCACAG | 759 | 776 | 1032 | 1049 |
| 10 | CCAGATCTGCATCCACA | 760 | 776 | 1033 | 1049 |
| 11 | CCCAGATCTGCATCCAC | 761 | 777 | 1034 | 1050 |
| 12 | CCCAGATCTGCATCCA | 762 | 777 | 1035 | 1050 |
| 13 | TCCCAGATCTGCATCCA | 762 | 778 | 1035 | 1051 |
| 14 | GTCTCCCAGATCTGCAT | 765 | 781 | 1038 | 1054 |
| 15 | TCTCCCAGATCTGCAT | 765 | 780 | 1038 | 1053 |
| 16 | GTCTCCCAGATCTGCA | 766 | 781 | 1039 | 1054 |

Motif sequences represent the contiguous sequence of nucleobases present in the oligonucleotide.

TABLE 5

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 7 | 1-1-1-7-3-1-2 | AgAtctgcatCCAcAG | 7_1 | −23 |
| 7 | 1-9-3-1-2 | AgatctgcatCCAcAG | 7_2 | −22 |
| 7 | 1-9-2-1-3 | AgatctgcatCCaCAG | 7_3 | −23 |
| 7 | 1-1-2-6-2-2-2 | AgATctgcatCCacAG | 7_4 | −23 |
| 7 | 1-1-1-7-2-2-2 | AgAtctgcatCCacAG | 7_5 | −21 |
| 7 | 1-3-1-5-2-2-2 | AgatCtgcatCCacAG | 7_6 | −22 |
| 7 | 1-9-2-2-2 | AgatctgcatCCacAG | 7_7 | −21 |
| 7 | 2-8-1-1-4 | AGatctgcatCcACAG | 7_8 | −23 |
| 7 | 1-1-1-7-1-1-4 | AgAtctgcatCcACAG | 7_9 | −22 |
| 7 | 1-3-1-5-1-1-4 | AgatCtgcatCcACAG | 7_10 | −22 |
| 7 | 1-9-1-1-4 | AgatctgcatCcACAG | 7_11 | −21 |
| 7 | 3-7-1-1-1-1-2 | AGAtctgcatCcAcAG | 7_12 | −22 |
| 7 | 2-2-1-5-1-1-1-2 | AGatCtgcatCcAcAG | 7_13 | −21 |
| 7 | 2-8-1-1-1-1-2 | AGatctgcatCcAcAG | 7_14 | −20 |
| 7 | 1-1-3-5-1-1-1-2 | AgATCtgcatCcAcAG | 7_15 | −22 |
| 7 | 1-1-1-1-5-1-1-1-2 | AgAtCtgcatCcAcAG | 7_16 | −20 |
| 7 | 1-1-1-7-1-1-1-2 | AgAtctgcatCcAcAG | 7_17 | −19 |
| 7 | 1-2-2-5-1-1-1-2 | AgaTCtgcatCcAcAG | 7_18 | −21 |
| 7 | 1-3-1-5-1-1-1-2 | AgatCtgcatCcAcAG | 7_19 | −20 |
| 7 | 1-9-1-1-1-2 | AgatctgcatCcAcAG | 7_20 | −19 |

TABLE 5-continued

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 7 | 1-1-2-6-1-2-3 | AgATctgcatCcaCAG | 7_21 | −23 |
| 7 | 1-1-1-7-1-2-3 | AgAtctgcatCcaCAG | 7_22 | −21 |
| 7 | 1-3-1-5-1-2-3 | AgatCtgcatCcaCAG | 7_23 | −22 |
| 7 | 1-9-1-2-3 | AgatctgcatCcaCAG | 7_24 | −21 |
| 7 | 3-7-1-3-2 | AGAtctgcatCcacAG | 7_25 | −22 |
| 7 | 2-2-1-5-1-3-2 | AGatCtgcatCcacAG | 7_26 | −21 |
| 7 | 2-8-1-3-2 | AGatctgcatCcacAG | 7_27 | −20 |
| 7 | 1-1-3-5-1-3-2 | AgATctgcatCcacAG | 7_28 | −22 |
| 7 | 1-1-1-1-1-5-1-3-2 | AgAtCtgcatCcacAG | 7_29 | −20 |
| 7 | 1-1-1-7-1-3-2 | AgAtctgcatCcacAG | 7_30 | −19 |
| 7 | 1-2-2-5-1-3-2 | AgaTCtgcatCcacAG | 7_31 | −21 |
| 7 | 1-3-1-5-1-3-2 | AgatCtgcatCcacAG | 7_32 | −20 |
| 7 | 1-9-1-3-2 | AgatctgcatCcacAG | 7_33 | −19 |
| 7 | 1-1-1-8-5 | AgAtctgcatcCACAG | 7_34 | −23 |
| 7 | 1-10-5 | AgatctgcatcCACAG | 7_35 | −23 |
| 7 | 2-2-1-6-2-1-2 | AGatCtgcatcCAcAG | 7_36 | −22 |
| 7 | 2-9-2-1-2 | AGatctgcatcCAcAG | 7_37 | −21 |
| 7 | 1-1-2-7-2-1-2 | AgATctgcatcCAcAG | 7_38 | −22 |
| 7 | 1-1-1-1-1-6-2-1-2 | AgAtctgcatcCAcAG | 7_39 | −22 |
| 7 | 1-1-1-8-2-1-2 | AgAtctgcatcCAcAG | 7_40 | −21 |
| 7 | 1-3-1-6-2-1-2 | AgatCtgcatcCAcAG | 7_41 | −21 |
| 7 | 1-10-2-1-2 | AgatctgcatcCAcAG | 7_42 | −20 |
| 7 | 1-1-1-8-1-1-3 | AgAtctgcatcCaCAG | 7_43 | −21 |
| 7 | 1-3-1-6-1-1-3 | AgatCtgcatcCaCAG | 7_44 | −22 |
| 7 | 1-10-1-1-3 | AgatctgcatcCaCAG | 7_45 | −21 |
| 7 | 3-1-1-6-1-2-2 | AGAtCtgcatcCacAG | 7_46 | −22 |
| 7 | 2-2-1-6-1-2-2 | AGatCtgcatcCacAG | 7_47 | −21 |
| 7 | 1-1-3-6-1-2-2 | AgATCtgcatcCacAG | 7_48 | −22 |
| 7 | 1-1-1-1-1-6-1-2-2 | AgAtCtgcatcCacAG | 7_49 | −20 |
| 7 | 1-1-1-8-1-2-2 | AgAtctgcatcCacAG | 7_50 | −19 |
| 7 | 1-2-2-6-1-2-2 | AgaTCtgcatcCacAG | 7_51 | −21 |
| 7 | 1-3-1-6-1-2-2 | AgatCtgcatcCacAG | 7_52 | −20 |
| 7 | 1-10-1-2-2 | AgatctgcatcCacAG | 7_53 | −19 |
| 7 | 1-1-1-1-1-7-4 | AgAtCtgcatccACAG | 7_54 | −22 |
| 7 | 1-1-1-9-4 | AgAtctgcatccACAG | 7_55 | −21 |
| 7 | 1-2-2-7-4 | AgaTCtgcatccACAG | 7_56 | −23 |
| 7 | 1-3-1-7-4 | AgatCtgcatccACAG | 7_57 | −22 |

TABLE 5-continued

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 7 | 1-11-4 | AgatctgcatccACAG | 7_58 | -21 |
| 7 | 3-1-1-7-1-1-2 | AGAtCtgcatccAcAG | 7_59 | -22 |
| 7 | 3-9-1-1-2 | AGAtctgcatccAcAG | 7_60 | -21 |
| 7 | 2-2-1-7-1-1-2 | AGatCtgcatccAcAG | 7_61 | -20 |
| 7 | 1-1-3-7-1-1-2 | AgATCtgcatccAcAG | 7_62 | -22 |
| 7 | 1-1-1-1-1-7-1-1-2 | AgAtCtgcatccAcAG | 7_63 | -20 |
| 7 | 1-1-1-9-1-1-2 | AgAtctgcatccAcAG | 7_64 | -19 |
| 7 | 1-2-2-7-1-1-2 | AgaTCtgcatccAcAG | 7_65 | -20 |
| 7 | 1-3-1-7-1-1-2 | AgatCtgcatccAcAG | 7_66 | -19 |
| 7 | 1-11-1-1-2 | AgatctgcatccAcAG | 7_67 | -18 |
| 7 | 3-10-3 | AGAtctgcatccaCAG | 7_68 | -23 |
| 7 | 1-1-1-1-1-8-3 | AgAtCtgcatccaCAG | 7_69 | -22 |
| 7 | 1-1-1-10-3 | AgAtctgcatccaCAG | 7_70 | -21 |
| 7 | 1-2-2-8-3 | AgaTCtgcatccaCAG | 7_71 | -22 |
| 7 | 1-3-1-8-3 | AgatCtgcatccaCAG | 7_72 | -21 |
| 7 | 1-12-3 | AgatctgcatccaCAG | 7_73 | -20 |
| 7 | 3-1-1-9-2 | AGAtCtgcatccacAG | 7_74 | -22 |
| 7 | 3-11-2 | AGAtctgcatccacAG | 7_75 | -21 |
| 7 | 2-1-2-9-2 | AGaTCtgcatccacAG | 7_76 | -21 |
| 7 | 2-2-1-9-2 | AGatCtgcatccacAG | 7_77 | -20 |
| 7 | 1-1-3-9-2 | AgATCtgcatccacAG | 7_78 | -21 |
| 7 | 1-1-1-1-1-9-2 | AgAtCtgcatccacAG | 7_79 | -19 |
| 7 | 1-1-1-11-2 | AgAtctgcatccacAG | 7_80 | -18 |
| 7 | 1-2-2-9-2 | AgaTCtgcatccacAG | 7_81 | -20 |
| 7 | 1-3-1-9-2 | AgatCtgcatccacAG | 7_82 | -19 |
| 7 | 1-13-2 | AgatctgcatccacAG | 7_83 | -18 |
| 8 | 1-2-1-7-2-2-2 | CagAtctgcatCCacAG | 8_1 | -23 |
| 8 | 1-3-1-6-2-2-2 | CagaTctgcatCCacAG | 8_2 | -23 |
| 8 | 1-10-2-2-2 | CagatctgcatCCacAG | 8_3 | -22 |
| 8 | 1-2-1-7-1-1-4 | CagAtctgcatCcACAG | 8_4 | -23 |
| 8 | 1-10-1-1-4 | CagatctgcatCcACAG | 8_5 | -23 |
| 8 | 2-1-1-7-1-1-1-2 | CAgAtctgcatCcAcAG | 8_6 | -23 |
| 8 | 2-3-1-5-1-1-1-2 | CAgatCtgcatCcAcAG | 8_7 | -23 |
| 8 | 2-9-1-1-1-2 | CAgatctgcatCcAcAG | 8_8 | -22 |
| 8 | 1-1-2-7-1-1-1-2 | CaGAtctgcatCcAcAG | 8_9 | -23 |
| 8 | 1-1-1-2-1-5-1-1-1-2 | CaGatCtgcatCcAcAG | 8_10 | -22 |
| 8 | 1-1-1-8-1-1-1-2 | CaGatctgcatCcAcAG | 8_11 | -21 |

TABLE 5-continued

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 8 | 1-2-1-1-1-5-1-1-1-1-2 | CagAtCtgcatCcAcAG | 8_12 | -22 |
| 8 | 1-2-1-7-1-1-1-1-2 | CagAtctgcatCcAcAG | 8_13 | -21 |
| 8 | 1-3-2-5-1-1-1-1-2 | CagaTCtgcatCcAcAG | 8_14 | -22 |
| 8 | 1-4-1-5-1-1-1-1-2 | CagatCtgcatCcAcAG | 8_15 | -21 |
| 8 | 1-10-1-1-1-1-2 | CagatctgcatCcAcAG | 8_16 | -20 |
| 8 | 1-2-1-7-1-2-3 | CagAtctgcatCcaCAG | 8_17 | -23 |
| 8 | 1-10-1-2-3 | CagatctgcatCcaCAG | 8_18 | -22 |
| 8 | 2-1-1-7-1-3-2 | CAgAtctgcatCcacAG | 8_19 | -23 |
| 8 | 2-3-1-5-1-3-2 | CAgatCtgcatCcacAG | 8_20 | -23 |
| 8 | 2-9-1-3-2 | CAgatctgcatCcacAG | 8_21 | -22 |
| 8 | 1-1-2-7-1-3-2 | CaGAtctgcatCcacAG | 8_22 | -23 |
| 8 | 1-1-1-2-1-5-1-3-2 | CaGatCtgcatCcacAG | 8_23 | -22 |
| 8 | 1-1-1-8-1-3-2 | CaGatctgcatCcacAG | 8_24 | -21 |
| 8 | 1-2-1-1-1-5-1-3-2 | CagAtCtgcatCcacAG | 8_25 | -22 |
| 8 | 1-2-1-7-1-3-2 | CagAtctgcatCcacAG | 8_26 | -21 |
| 8 | 1-3-2-5-1-3-2 | CagaTCtgcatCcacAG | 8_27 | -22 |
| 8 | 1-4-1-5-1-3-2 | CagatCtgcatCcacAG | 8_28 | -21 |
| 8 | 1-10-1-3-2 | CagatctgcatCcacAG | 8_29 | -20 |
| 8 | 1-2-1-8-5 | CagAtctgcatcCACAG | 8_30 | -24 |
| 8 | 1-2-1-1-1-6-2-1-2 | CagAtCtgcatcCAcAG | 8_31 | -23 |
| 8 | 1-2-1-8-2-1-2 | CagAtctgcatcCAcAG | 8_32 | -22 |
| 8 | 1-4-1-6-2-1-2 | CagatCtgcatcCAcAG | 8_33 | -22 |
| 8 | 1-11-2-1-2 | CagatctgcatcCAcAG | 8_34 | -21 |
| 8 | 1-2-1-8-1-1-3 | CagAtctgcatcCaCAG | 8_35 | -22 |
| 8 | 1-4-1-6-1-1-3 | CagatCtgcatcCaCAG | 8_36 | -23 |
| 8 | 1-11-1-1-3 | CagatctgcatcCaCAG | 8_37 | -22 |
| 8 | 2-1-1-8-1-2-2 | CAgAtctgcatcCacAG | 8_38 | -22 |
| 8 | 2-3-1-6-1-2-2 | CAgatCtgcatcCacAG | 8_39 | -23 |
| 8 | 2-10-1-2-2 | CAgatctgcatcCacAG | 8_40 | -22 |
| 8 | 1-1-2-1-1-6-1-2-2 | CaGAtCtgcatcCacAG | 8_41 | -23 |
| 8 | 1-1-1-2-1-6-1-2-2 | CaGatCtgcatcCacAG | 8_42 | -22 |
| 8 | 1-2-3-6-1-2-2 | CagATCtgcatcCacAG | 8_43 | -23 |
| 8 | 1-2-1-1-1-6-1-2-2 | CagAtCtgcatcCacAG | 8_44 | -21 |
| 8 | 1-2-1-8-1-2-2 | CagAtctgcatcCacAG | 8_45 | -20 |
| 8 | 1-3-2-6-1-2-2 | CagaTCtgcatcCacAG | 8_46 | -22 |
| 8 | 1-4-1-6-1-2-2 | CagatCtgcatcCacAG | 8_47 | -21 |
| 8 | 1-11-1-2-2 | CagatctgcatcCacAG | 8_48 | -20 |

TABLE 5-continued

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 8 | 2-1-1-9-4 | CAgAtctgcatccACAG | 8_49 | −24 |
| 8 | 1-2-1-1-1-7-4 | CagAtCtgcatccACAG | 8_50 | −23 |
| 8 | 1-4-1-7-4 | CagatCtgcatccACAG | 8_51 | −23 |
| 8 | 1-12-4 | CagatctgcatccACAG | 8_52 | −22 |
| 8 | 2-1-1-1-1-7-1-1-2 | CAgAtCtgcatccAcAG | 8_53 | −23 |
| 8 | 2-1-1-9-1-1-2 | CAgAtctgcatccAcAG | 8_54 | −22 |
| 8 | 2-3-1-7-1-1-2 | CAgatCtgcatccAcAG | 8_55 | −22 |
| 8 | 2-11-1-1-2 | CAgatctgcatccAcAG | 8_56 | −21 |
| 8 | 1-1-2-1-1-7-1-1-2 | CaGAtCtgcatccAcAG | 8_57 | −23 |
| 8 | 1-1-1-2-1-7-1-1-2 | CaGatCtgcatccAcAG | 8_58 | −21 |
| 8 | 1-2-3-7-1-1-2 | CagATCtgcatccAcAG | 8_59 | −23 |
| 8 | 1-2-1-1-1-7-1-1-2 | CagAtCtgcatccAcAG | 8_60 | −21 |
| 8 | 1-2-1-9-1-1-2 | CagAtctgcatccAcAG | 8_61 | −20 |
| 8 | 1-3-2-7-1-1-2 | CagaTCtgcatccAcAG | 8_62 | −22 |
| 8 | 1-4-1-7-1-1-2 | CagatCtgcatccAcAG | 8_63 | −20 |
| 8 | 1-12-1-1-2 | CagatctgcatccAcAG | 8_64 | −19 |
| 8 | 2-1-1-10-3 | CAgAtctgcatccaCAG | 8_65 | −24 |
| 8 | 1-2-1-1-1-8-3 | CagAtCtgcatccaCAG | 8_66 | −23 |
| 8 | 1-2-1-10-3 | CagAtctgcatccaCAG | 8_67 | −22 |
| 8 | 1-4-1-8-3 | CagatCtgcatccaCAG | 8_68 | −22 |
| 8 | 1-13-3 | CagatctgcatccaCAG | 8_69 | −21 |
| 8 | 2-1-1-1-1-9-2 | CAgAtCtgcatccacAG | 8_70 | −23 |
| 8 | 2-1-1-11-2 | CAgAtctgcatccacAG | 8_71 | −22 |
| 8 | 2-2-2-9-2 | CAgaTCtgcatccacAG | 8_72 | −23 |
| 8 | 2-3-1-9-2 | CAgatCtgcatccacAG | 8_73 | −22 |
| 8 | 2-13-2 | CAgatctgcatccacAG | 8_74 | −21 |
| 8 | 1-1-2-1-1-9-2 | CaGAtCtgcatccacAG | 8_75 | −23 |
| 8 | 1-1-1-2-1-9-2 | CaGatCtgcatccacAG | 8_76 | −21 |
| 8 | 1-2-1-1-1-9-2 | CagAtCtgcatccacAG | 8_77 | −21 |
| 8 | 1-2-1-11-2 | CagAtctgcatccacAG | 8_78 | −20 |
| 8 | 1-3-2-9-2 | CagaTCtgcatccacAG | 8_79 | −21 |
| 8 | 1-4-1-9-2 | CagatCtgcatccacAG | 8_80 | −20 |
| 8 | 1-14-2 | CagatctgcatccacAG | 8_81 | −19 |
| 9 | 1-3-1-7-1-1-1-2 | CcagAtctgcatCcAcAG | 9_1 | −24 |
| 9 | 1-1-1-1-1-7-1-3-2 | CcAgAtctgcatCcacAG | 9_2 | −24 |
| 9 | 1-1-1-10-1-2-2 | CcAgatctgcatcCacAG | 9_3 | −23 |
| 9 | 1-12-1-2-2 | CcagatctgcatcCacAG | 9_4 | −23 |

TABLE 5-continued

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 9 | 1-1-1-1-1-9-1-1-2 | CcAgAtctgcatccAcAG | 9_5 | −23 |
| 9 | 1-1-1-11-1-1-2 | CcAgatctgcatccAcAG | 9_6 | −23 |
| 9 | 1-3-1-9-1-1-2 | CcagAtctgcatccAcAG | 9_7 | −23 |
| 9 | 1-13-1-1-2 | CcagatctgcatccAcAG | 9_8 | −22 |
| 9 | 1-3-1-10-3 | CcagAtctgcatccaCAG | 9_9 | −25 |
| 9 | 2-2-1-11-2 | CCagAtctgcatccacAG | 9_10 | −25 |
| 9 | 1-1-1-13-2 | CcAgatctgcatccacAG | 9_11 | −23 |
| 9 | 1-2-2-11-2 | CcaGAtctgcatccacAG | 9_12 | −25 |
| 10 | 1-3-1-6-1-3-2 | CcagAtctgcaTccaCA | 10_1 | −23 |
| 10 | 1-3-1-7-1-1-3 | CcagAtctgcatCcACA | 10_2 | −24 |
| 10 | 1-1-1-9-1-2-2 | CcAgatctgcatCcaCA | 10_3 | −23 |
| 10 | 1-3-1-7-1-2-2 | CcagAtctgcatCcaCA | 10_4 | −23 |
| 10 | 1-11-1-2-2 | CcagatctgcatCcaCA | 10_5 | −23 |
| 10 | 1-3-1-8-4 | CcagAtctgcatcCACA | 10_6 | −25 |
| 10 | 1-1-1-10-1-1-2 | CcAgatctgcatcCaCA | 10_7 | −23 |
| 10 | 1-3-1-8-1-1-2 | CcagAtctgcatCaCA | 10_8 | −23 |
| 10 | 1-12-1-1-2 | CcagatctgcatcCaCA | 10_9 | −22 |
| 10 | 1-1-1-1-1-9-3 | CcAgAtctgcatccACA | 10_10 | −23 |
| 10 | 1-1-1-11-3 | CcAgatctgcatccACA | 10_11 | −23 |
| 10 | 1-3-1-9-3 | CcagAtctgcatccACA | 10_12 | −23 |
| 10 | 1-13-3 | CcagatctgcatccACA | 10_13 | −22 |
| 10 | 1-1-1-1-1-10-2 | CcAgAtctgcatccaCA | 10_14 | −23 |
| 10 | 1-1-1-12-2 | CcAgatctgcatccaCA | 10_15 | −22 |
| 10 | 1-2-2-10-2 | CcaGAtctgcatccaCA | 10_16 | −24 |
| 10 | 1-3-1-10-2 | CcagAtctgcatccaCA | 10_17 | −22 |
| 10 | 1-14-2 | CcagatctgcatccaCA | 10_18 | −22 |
| 11 | 1-1-1-8-1-1-1-2 | CcCagatctgcAtCcAC | 11_1 | −23 |
| 11 | 1-2-1-7-1-1-1-2 | CccAgatctgcAtCcAC | 11_2 | −23 |
| 11 | 1-10-1-1-1-2 | CccagatctgcAtCcAC | 11_3 | −23 |
| 11 | 1-1-1-8-1-2-3 | CcCagatctgcAtcCAC | 11_4 | −25 |
| 11 | 1-2-1-7-1-2-3 | CccAgatctgcAtcCAC | 11_5 | −25 |
| 11 | 1-10-1-2-3 | CccagatctgcAtcCAC | 11_6 | −24 |
| 11 | 2-1-1-7-1-3-2 | CCcAgatctgcAtccAC | 11_7 | −25 |
| 11 | 2-9-1-3-2 | CCcagatctgcAtccAC | 11_8 | −24 |
| 11 | 1-1-2-7-1-3-2 | CcCAgatctgcAtccAC | 11_9 | −25 |
| 11 | 1-1-1-1-1-6-1-3-2 | CcCaGatctgcAtccAC | 11_10 | −23 |
| 11 | 1-1-1-8-1-3-2 | CcCagatctgcAtccAC | 11_11 | −23 |

TABLE 5-continued

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 11 | 1-2-2-6-1-3-2 | CccAGatctgcAtccAC | 11_12 | -24 |
| 11 | 1-2-1-1-1-5-1-3-2 | CccAgAtctgcAtccAC | 11_13 | -23 |
| 11 | 1-2-1-7-1-3-2 | CccAgatctgcAtccAC | 11_14 | -23 |
| 11 | 1-10-1-3-2 | CccagatctgcAtccAC | 11_15 | -22 |
| 11 | 1-2-1-1-1-7-1-1-2 | CccAgAtctgcatCcAC | 11_16 | -24 |
| 11 | 1-12-1-1-2 | CccagatctgcatCcAC | 11_17 | -23 |
| 11 | 1-2-1-1-1-8-3 | CccAgAtctgcatcCAC | 11_18 | -25 |
| 11 | 1-4-1-8-3 | CccagAtctgcatcCAC | 11_19 | -24 |
| 11 | 2-3-1-9-2 | CCcagAtctgcatccAC | 11_20 | -25 |
| 11 | 1-1-2-1-1-9-2 | CcCAgAtctgcatccAC | 11_21 | -25 |
| 11 | 1-1-1-1-2-9-2 | CcCaGAtctgcatccAC | 11_22 | -25 |
| 11 | 1-1-1-12-2 | CcCagatctgcatccAC | 11_23 | -23 |
| 11 | 1-2-1-1-1-9-2 | CccAgAtctgcatccAC | 11_24 | -23 |
| 11 | 1-2-1-11-2 | CccAgatctgcatccAC | 11_25 | -23 |
| 11 | 1-14-2 | CccagatctgcatccAC | 11_26 | -22 |
| 12 | 1-9-2-2-2 | CccagatctgCAtcCA | 12_1 | -24 |
| 12 | 1-1-1-7-1-3-2 | CcCagatctgCatcCA | 12_2 | -23 |
| 12 | 1-2-1-6-1-3-2 | CccAgatctgCatcCA | 12_3 | -23 |
| 12 | 1-9-1-3-2 | CccagatctgCatcCA | 12_4 | -23 |
| 12 | 1-2-1-7-1-1-3 | CccAgatctgcAtCCA | 12_5 | -25 |
| 12 | 1-10-1-1-3 | CccagatctgcAtCCA | 12_6 | -24 |
| 12 | 2-9-1-2-2 | CCcagatctgcAtcCA | 12_7 | -24 |
| 12 | 1-1-1-8-1-2-2 | CcCagatctgcAtcCA | 12_8 | -23 |
| 12 | 1-2-1-7-1-2-2 | CccAgatctgcAtcCA | 12_9 | -23 |
| 12 | 1-3-1-6-1-2-2 | CccaGatctgcAtcCA | 12_10 | -23 |
| 12 | 1-10-1-2-2 | CccagatctgcAtcCA | 12_11 | -22 |
| 12 | 2-1-1-10-2 | CCcAgatctgcatcCA | 12_12 | -25 |
| 12 | 1-1-1-11-2 | CcCagatctgcatcCA | 12_13 | -22 |
| 12 | 1-2-1-10-2 | CccAgatctgcatcCA | 12_14 | -22 |
| 12 | 1-13-2 | CccagatctgcatcCA | 12_15 | -22 |
| 13 | 2-10-1-2-2 | TCccagatctgcAtcCA | 13_1 | -24 |
| 13 | 2-2-1-10-2 | TCccAgatctgcatcCA | 13_2 | -25 |
| 14 | 1-3-1-6-1-1-1-2 | GtctCccagatCtGcAT | 14_1 | -24 |
| 14 | 1-4-1-5-1-3-2 | GtctcCcagatCtgcAT | 14_2 | -23 |
| 14 | 1-10-1-3-2 | GtctcccagatCtgcAT | 14_3 | -23 |

TABLE 5-continued

Lists oligonucleotides designs and specific antisense oligonucleotide compounds Compounds are indicated by CMP ID NO, and based on the on the motif sequence in table 4.

| SEQ ID NO | Design | Oligonucleotide Compound | CMP ID NO | dG |
|---|---|---|---|---|
| 14 | 1-1-1-2-1-6-1-2-2 | GtCtcCcagatcTgcAT | 14_4 | −24 |
| 14 | 1-4-1-6-1-2-2 | GtctcCcagatcTgcAT | 14_5 | −23 |
| 14 | 1-1-1-1-1-8-1-1-2 | GtCtCccagatctGcAT | 14_6 | −24 |
| 14 | 1-2-2-8-1-1-2 | GtcTCccagatctGcAT | 14_7 | −24 |
| 14 | 1-4-1-7-1-1-2 | GtctcCcagatctGcAT | 14_8 | −23 |
| 14 | 1-4-1-8-3 | GtctcCcagatctgCAT | 14_9 | −25 |
| 14 | 1-1-1-2-1-9-2 | GtCtcCcagatctgcAT | 14_10 | −23 |
| 14 | 1-1-1-12-2 | GtCtcccagatctgcAT | 14_11 | −23 |
| 14 | 1-3-1-10-2 | GtctCcagatctgcAT | 14_12 | −22 |
| 14 | 1-4-1-9-2 | GtctcCcagatctgcAT | 14_13 | −22 |
| 15 | 2-8-1-1-1-1-2 | TCtcccagatCtGcAT | 15_1 | −22 |
| 15 | 1-3-1-5-1-2-3 | TctcCcagatCtgCAT | 15_2 | −23 |
| 15 | 2-1-1-6-1-3-2 | TCtCccagatCtgcAT | 15_3 | −23 |
| 15 | 2-2-1-5-1-3-2 | TCtcCcagatCtgcAT | 15_4 | −23 |
| 15 | 2-8-1-3-2 | TCtcccagatCtgcAT | 15_5 | −22 |
| 15 | 1-3-1-5-1-3-2 | TctcCcagatCtgcAT | 15_6 | −21 |
| 15 | 2-9-2-1-2 | TCtcccagatcTGcAT | 15_7 | −23 |
| 15 | 2-1-1-7-1-2-2 | TCtCccagatcTgcAT | 15_8 | −23 |
| 15 | 2-2-1-6-1-2-2 | TCtcCcagatcTgcAT | 15_9 | −23 |
| 15 | 2-9-1-2-2 | TCtcccagatcTgcAT | 15_10 | −22 |
| 15 | 4-8-1-1-2 | TCTCccagatctGcAT | 15_11 | −24 |
| 15 | 3-9-1-1-2 | TCTcccagatctGcAT | 15_12 | −23 |
| 15 | 2-2-1-7-1-1-2 | TCtcCccagatctGcAT | 15_13 | −22 |
| 15 | 2-10-1-1-2 | TCtcccagatctGcAT | 15_14 | −21 |
| 15 | 2-2-1-8-3 | TCtcCcagatctgCAT | 15_15 | −24 |
| 15 | 1-3-1-8-3 | TctcCcagatctgCAT | 15_16 | −22 |
| 15 | 3-11-2 | TCtcccagatctgcAT | 15_17 | −22 |
| 15 | 2-1-1-10-2 | TCtCccagatctgcAT | 15_18 | −22 |
| 15 | 2-2-1-9-2 | TCtcCcagatctgcAT | 15_19 | −22 |
| 15 | 2-12-2 | TCtcccagatctgcAT | 15_20 | −21 |
| 15 | 1-2-2-9-2 | TctCCcagatctgcAT | 15_21 | −23 |
| 16 | 1-3-1-6-1-2-2 | GtctCccagatCtgCA | 16_1 | −24 |
| 16 | 1-10-1-2-2 | GtctcccagatCtgCA | 16_2 | −23 |
| 16 | 1-1-1-1-1-9-2 | GtCtCccagatctgCA | 16_3 | −24 |
| 16 | 1-1-1-11-2 | GtCtcccagatctgCA | 16_4 | −23 |
| 16 | 1-3-1-9-2 | GtctCccagatctgCA | 16_5 | −23 |

Designs refer to the gapmer design, F-G-F'. In classic gapmer design e.g. 3-10-3 all the nucleotides in the flanks (F and F') are constituted of the same 2'-sugar modified nucleoside, e.g. LNA, cET, or MOE, and a stretch of DNA in the middle forming the gap (G). In gapmers with alternating flank designs the flanks of oligonucleotide is annotated as a series of integers, representing a number of 2' sugar modified nucleosides (M) followed by a number of DNA nucleosides (D). For example a flank with a 2-2-1 motif represents 5' [M]2-[D]2-[M] 3' and a 1-1-1-1-1 motif represents 5' [M]-[D]-[M]-[D]-[M] 3'. Both flanks have a 2' sugar modified nucleoside at the 5' and 3' terminal. The gap region (G), which is constituted of a number of DNA nucleosides (typically between 5 and 16), is located between the flanks.

The heading "Oligonucleotide compound" in the table represents specific designs of a motif sequence. Capital letters represent beta-D-oxy LNA nucleosides, lowercase letters represent DNA nucleosides, all LNA C are 5-methyl cytosine, and 5-methyl cytosine DNA are presented by "e", all internucleoside linkages are phosphorothioate internucleoside linkages.

TABLE 6 list of oligonucleotide motif sequences targeting human and cyno Sequences are indicated by SEQ ID NO, the motif sequence (nucleobase sequence) and the position they target on the human PAPD5 transcript (SEQ ID NO: 1) and the human PAPD7 transcript (SEQ ID NO: 2).

| SEQ ID NO | Motif Sequence | Start ID NO: 1 | End ID NO: 1 | Start ID NO: 2 | End ID NO: 2 |
|---|---|---|---|---|---|
| 17 | TCAACTTTCACTTCAGT | 64669 | 64685 | 29514 | 29530 |
| 18 | TCAACTTTCACTTCAG | 64670 | 64685 | 29515 | 29530 |
| 19 | TGTTTCAATACTAAAA | 69414 | 69429 | 30731 | 30746 |

Motif sequences represent the contiguous sequence of nucleobases present in the oligonucleotide.

TABLE 7

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 17 | 2-12-3 | TCaactttcacttcAGT | 17_1 | −19 |
| 17 | 2-2-1-6-1-2-3 | TCaaCtttcacTtcAGT | 17_2 | −21 |
| 17 | 2-9-1-2-3 | TCaactttcacTtcAGT | 17_3 | −20 |
| 17 | 1-3-1-6-1-2-3 | TcaaCtttcacTtcAGT | 17_4 | −20 |
| 17 | 2-9-1-3-2 | TCaactttcacTtcaGT | 17_5 | −19 |
| 17 | 2-2-1-7-2-1-2 | TCaaCtttcactTCAGT | 17_6 | −21 |
| 17 | 1-1-1-9-1-1-3 | TcAactttcactTcAGT | 17_7 | −19 |
| 17 | 1-1-2-8-1-2-2 | TcAActttcactTcaGT | 17_8 | −18 |
| 17 | 5-8-1-1-2 | TCAACtttcacttCaGT | 17_9 | −23 |
| 17 | 4-9-1-1-2 | TCAActtttcacttCaGT | 17_10 | −21 |
| 17 | 2-2-1-8-1-1-2 | TCaaCtttcacttCaGT | 17_11 | −20 |
| 17 | 2-11-1-1-2 | TCaactttcacttCaGT | 17_12 | −19 |
| 17 | 1-1-2-9-1-1-2 | TcAActttcacttCaGT | 17_13 | −18 |
| 17 | 3-11-3 | TCAactttcacttcAGT | 17_14 | −21 |
| 17 | 2-2-1-9-3 | TCaaCtttcacttcAGT | 17_15 | −20 |
| 17 | 2-13-2 | TCaactttcacttcaGT | 17_16 | −18 |
| 17 | 3-1-1-6-6 | TCAaCtttcacTTCAGT | 17_17 | −26 |
| 17 | 2-1-2-6-6 | TCaACtttcacTTCAGT | 17_18 | −25 |
| 17 | 2-2-1-6-6 | TCaaCtttcacTTCAGT | 17_19 | −25 |
| 17 | 2-9-6 | TCaactttcacTTCAGT | 17_20 | −24 |
| 17 | 1-1-3-6-6 | TcAACtttcacTTCAGT | 17_21 | −24 |
| 17 | 1-1-2-1-1-5-6 | TcAAcTttcacTTCAGT | 17_22 | −23 |
| 17 | 1-3-1-6-6 | TcaaCtttcacTTCAGT | 17_23 | −23 |
| 17 | 5-6-3-1-2 | TCAACtttcacTTCaGT | 17_24 | −25 |

TABLE 7-continued

Lists oligonucleotides designs and specific antisense
oligonucleotide compounds Compounds are indicated
by CMP ID NO, and based on the on the motif sequence in table 6.

| SEQ ID NO | Design | Oligonucleotide Compound | CMP ID NO | dG |
|---|---|---|---|---|
| 17 | 4-7-3-1-2 | TCAActttcacTTCaGT | 17_25 | -23 |
| 17 | 3-1-1-6-3-1-2 | TCAaCtttcacTTCaGT | 17_26 | -24 |
| 17 | 3-2-1-5-3-1-2 | TCAacTttcacTTCaGT | 17_27 | -23 |
| 17 | 3-8-3-1-2 | TCAactttcacTTCaGT | 17_28 | -23 |
| 17 | 2-1-2-6-3-1-2 | TCaACtttcacTTCaGT | 17_29 | -23 |
| 17 | 2-1-1-1-5-3-1-2 | TCaAcTttcacTTCaGT | 17_30 | -22 |
| 17 | 2-1-1-7-3-1-2 | TCaActttcacTTCaGT | 17_31 | -21 |
| 17 | 2-2-1-6-3-1-2 | TCaaCtttcacTTCaGT | 17_32 | -22 |
| 17 | 2-3-1-5-3-1-2 | TCaacTttcacTTCaGT | 17_33 | -22 |
| 17 | 2-9-3-1-2 | TCaactttcacTTCaGT | 17_34 | -21 |
| 17 | 1-1-3-6-3-1-2 | TcAACtttcacTTCaGT | 17_35 | -22 |
| 17 | 5-6-2-1-3 | TCAACtttcacTTcAGT | 17_36 | -24 |
| 17 | 4-1-1-5-2-1-3 | TCAAcTttcacTTcAGT | 17_37 | -23 |
| 17 | 2-1-1-1-5-2-1-3 | TCaAcTttcacTTcAGT | 17_38 | -22 |
| 17 | 1-1-2-1-1-5-2-1-3 | TCAAcTttcacTTcAGT | 17_39 | -21 |
| 17 | 1-2-1-1-5-2-1-3 | TcaAcTttcacTTcAGT | 17_40 | -20 |
| 17 | 1-3-1-6-2-1-3 | TcaaCtttcacTTcAGT | 17_41 | -21 |
| 17 | 1-4-1-5-2-1-3 | TcaacTttcacTTcAGT | 17_42 | -20 |
| 17 | 1-1-3-6-2-2-2 | TcAACtttcacTTcaGT | 17_43 | -21 |
| 17 | 1-1-1-1-6-2-2-2 | TcAaCtttcacTTcaGT | 17_44 | -20 |
| 17 | 1-3-1-6-2-2-2 | TcaaCtttcacTTcaGT | 17_45 | -19 |
| 17 | 5-6-1-1-4 | TCAACtttcacTtCAGT | 17_46 | -26 |
| 17 | 3-1-1-6-1-1-4 | TCAaCtttcacTtCAGT | 17_47 | -25 |
| 17 | 2-1-1-7-1-1-4 | TCaActttcacTtCAGT | 17_48 | -22 |
| 17 | 2-2-1-6-1-1-4 | TCaaCtttcacTtCAGT | 17_49 | -23 |
| 17 | 2-3-1-5-1-1-4 | TCaacTttcacTtCAGT | 17_50 | -23 |
| 17 | 2-9-1-1-4 | TCaactttcacTtCAGT | 17_51 | -22 |
| 17 | 1-3-1-6-1-1-4 | TcaaCtttcacTtCAGT | 17_52 | -22 |
| 17 | 5-6-1-1-1-2 | TCAACtttcacTtCaGT | 17_53 | -23 |
| 17 | 4-1-1-5-1-1-1-2 | TCAAcTttcacTtCaGT | 17_54 | -22 |
| 17 | 4-7-1-1-1-2 | TCAActttcacTtCaGT | 17_55 | -22 |
| 17 | 3-1-1-6-1-1-1-2 | TCAaCtttcacTtCaGT | 17_56 | -22 |
| 17 | 3-8-1-1-1-2 | TCAactttcacTtCaGT | 17_57 | -21 |
| 17 | 2-1-2-6-1-1-1-2 | TCaACtttcacTtCaGT | 17_58 | -21 |
| 17 | 2-1-1-1-5-1-1-1-2 | TCaAcTttcacTtCaGT | 17_59 | -20 |
| 17 | 2-1-1-7-1-1-1-2 | TCaActttcacTtCaGT | 17_60 | -20 |
| 17 | 2-2-2-5-1-1-1-2 | TCaaCTttcacTtCaGT | 17_61 | -22 |

TABLE 7-continued

Lists oligonucleotides designs and specific antisense
oligonucleotide compounds Compounds are indicated
by CMP ID NO, and based on the on the motif sequence in table 6.

| SEQ ID NO | Design | Oligonucleotide Compound | CMP ID NO | dG |
|---|---|---|---|---|
| 17 | 2-2-1-6-1-1-1-1-2 | TCaaCtttcacTtCaGT | 17_62 | -21 |
| 17 | 2-3-1-5-1-1-1-1-2 | TCaacTttcacTtCaGT | 17_63 | -20 |
| 17 | 2-9-1-1-1-1-2 | TCaactttcacTtCaGT | 17_64 | -20 |
| 17 | 5-6-1-2-3 | TCAACtttcacTtcAGT | 17_65 | -23 |
| 17 | 4-1-1-5-1-2-3 | TCAAcTttcacTtcAGT | 17_66 | -23 |
| 17 | 4-7-1-2-3 | TCAActttcacTtcAGT | 17_67 | -22 |
| 17 | 3-1-1-6-1-2-3 | TCAaCtttcacTtcAGT | 17_68 | -22 |
| 17 | 3-2-1-5-1-2-3 | TCAacTttcacTtcAGT | 17_69 | -22 |
| 17 | 2-1-2-6-1-2-3 | TCaACtttcacTtcAGT | 17_70 | -22 |
| 17 | 2-1-1-1-1-5-1-2-3 | TCaAcTttcacTtcAGT | 17_71 | -21 |
| 17 | 1-1-2-1-1-5-1-2-3 | TcAAcTttcacTtcAGT | 17_72 | -20 |
| 17 | 5-6-1-3-2 | TCAACtttcacTtcaGT | 17_73 | -22 |
| 17 | 4-7-1-3-2 | TCAActttcacTtcaGT | 17_74 | -21 |
| 17 | 3-1-2-5-1-3-2 | TCAaCTttcacTtcaGT | 17_75 | -23 |
| 17 | 3-1-1-6-1-3-2 | TCAaCtttcacTtcaGT | 17_76 | -21 |
| 17 | 3-2-1-5-1-3-2 | TCAacTttcacTtcaGT | 17_77 | -21 |
| 17 | 2-1-2-6-1-3-2 | TCaACtttcacTtcaGT | 17_78 | -21 |
| 17 | 2-1-1-1-1-5-1-3-2 | TCaAcTttcacTtcaGT | 17_79 | -20 |
| 17 | 2-2-1-6-1-3-2 | TCaaCtttcacTtcaGT | 17_80 | -20 |
| 17 | 2-3-1-5-1-3-2 | TCaacTttcacTtcaGT | 17_81 | -19 |
| 17 | 1-1-3-6-1-3-2 | TcAACtttcacTtcaGT | 17_82 | -20 |
| 17 | 1-1-1-1-1-6-1-3-2 | TcAaCtttcacTtcaGT | 17_83 | -19 |
| 17 | 1-3-1-6-1-3-2 | TcaaCtttcacTtcaGT | 17_84 | -19 |
| 17 | 5-7-5 | TCAACtttcactTCAGT | 17_85 | -26 |
| 17 | 2-1-1-8-5 | TCaActttcactTCAGT | 17_86 | -23 |
| 17 | 2-2-1-7-5 | TCaaCtttcactTCAGT | 17_87 | -23 |
| 17 | 2-3-1-6-5 | TCaacTttcactTCAGT | 17_88 | -23 |
| 17 | 2-10-5 | TCaactttcactTCAGT | 17_89 | -23 |
| 17 | 1-1-2-8-5 | TcAActttcactTCAGT | 17_90 | -22 |
| 17 | 1-1-1-1-1-7-5 | TcAaCtttcactTCAGT | 17_91 | -22 |
| 17 | 1-3-1-7-5 | TcaaCtttcactTCAGT | 17_92 | -22 |
| 17 | 1-11-5 | TcaactttcactTCAGT | 17_93 | -21 |
| 17 | 5-7-2-1-2 | TCAACtttcactTCaGT | 17_94 | -24 |
| 17 | 4-1-1-6-2-1-2 | TCAAcTttcactTCaGT | 17_95 | -23 |
| 17 | 4-8-2-1-2 | TCAActttcactTCaGT | 17_96 | -22 |

TABLE 7-continued

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 17 | 3-1-1-7-2-1-2 | TCAaCtttcacTTCaGT | 17_97 | -22 |
| 17 | 3-2-1-6-2-1-2 | TCAacTttcactTCaGT | 17_98 | -22 |
| 17 | 3-9-2-1-2 | TCAactttcactTCaGT | 17_99 | -22 |
| 17 | 2-1-1-8-2-1-2 | TCaActttcactTCaGT | 17_100 | -20 |
| 17 | 2-10-2-1-2 | TCaactttcactTCaGT | 17_101 | -20 |
| 17 | 1-1-3-7-2-1-2 | TcAACtttcacTTCaGT | 17_102 | -21 |
| 17 | 1-1-2-8-2-1-2 | TcAActttcactTCaGT | 17_103 | -19 |
| 17 | 1-1-1-1-1-7-2-1-2 | TcAaCtttcacTTCaGT | 17_104 | -20 |
| 17 | 1-1-1-2-1-6-2-1-2 | TcAacTttcacTTCaGT | 17_105 | -19 |
| 17 | 1-1-1-9-2-1-2 | TcAactttcacTTCaGT | 17_106 | -19 |
| 17 | 1-3-1-7-2-1-2 | TcaaCtttcactTCaGT | 17_107 | -20 |
| 17 | 1-11-2-1-2 | TcaactttcacTTCaGT | 17_108 | -19 |
| 17 | 4-8-1-1-3 | TCAActttcacTTcAGT | 17_109 | -22 |
| 17 | 3-1-1-7-1-1-3 | TCAaCtttcacTTcAGT | 17_110 | -22 |
| 17 | 2-10-1-1-3 | TCaactttcacTTcAGT | 17_111 | -20 |
| 17 | 1-1-3-7-1-1-3 | TcAACtttcacTTcAGT | 17_112 | -21 |
| 17 | 1-1-2-8-1-1-3 | TcAActttcacTTcAGT | 17_113 | -19 |
| 17 | 1-1-1-1-1-7-1-1-3 | TcAaCtttcacTTcAGT | 17_114 | -20 |
| 17 | 1-2-1-8-1-1-3 | TcaActttcacTTcAGT | 17_115 | -19 |
| 17 | 1-3-1-7-1-1-3 | TcaaCtttcacTTcAGT | 17_116 | -20 |
| 17 | 1-11-1-1-3 | TcaactttcacTTcAGT | 17_117 | -19 |
| 17 | 5-7-1-2-2 | TCAACtttcacTTcaGT | 17_118 | -22 |
| 17 | 4-8-1-2-2 | TCAActttcacTTcaGT | 17_119 | -21 |
| 17 | 3-1-1-7-1-2-2 | TCAaCtttcacTTcaGT | 17_120 | -21 |
| 17 | 3-9-1-2-2 | TCAactttcacTTcaGT | 17_121 | -20 |
| 17 | 2-2-1-7-1-2-2 | TCaaCtttcacTTcaGT | 17_122 | -20 |
| 17 | 2-10-1-2-2 | TCaactttcacTTcaGT | 17_123 | -19 |
| 17 | 1-1-1-1-1-7-1-2-2 | TcAaCtttcacTTcaGT | 17_124 | -19 |
| 17 | 1-1-1-9-1-2-2 | TcAactttcacTTcaGT | 17_125 | -18 |
| 17 | 1-2-1-8-1-2-2 | TcaActttcacTTcaGT | 17_126 | -18 |
| 17 | 1-11-1-2-2 | TcaactttcacTTcaGT | 17_127 | -17 |
| 17 | 5-8-4 | TCAActttcacttCAGT | 17_128 | -25 |
| 17 | 3-10-4 | TCAactttcacttCAGT | 17_129 | -23 |
| 17 | 2-1-2-8-4 | TCaACtttcacttCAGT | 17_130 | -23 |
| 17 | 2-1-1-1-1-7-4 | TCaAcTttcacttCAGT | 17_131 | -22 |
| 17 | 2-1-1-9-4 | TCaActttcacttCAGT | 17_132 | -22 |
| 17 | 2-2-1-8-4 | TCaaCtttcacttCAGT | 17_133 | -23 |

TABLE 7-continued

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 17 | 2-3-1-7-4 | TCaacTttcacttCAGT | 17_134 | -22 |
| 17 | 2-11-4 | TCaactttcacttCAGT | 17_135 | -22 |
| 17 | 1-1-3-8-4 | TcAACtttcacttCAGT | 17_136 | -22 |
| 17 | 1-1-2-9-4 | TcAActttcacttCAGT | 17_137 | -21 |
| 17 | 1-1-1-1-1-8-4 | TcAaCtttcacttCAGT | 17_138 | -21 |
| 17 | 1-1-1-10-4 | TcAactttcacttCAGT | 17_139 | -20 |
| 17 | 4-1-1-7-1-1-2 | TCAAcTttcacttCaGT | 17_140 | -22 |
| 17 | 3-1-2-7-1-1-2 | TCAaCTttcacttCaGT | 17_141 | -23 |
| 17 | 3-1-1-8-1-1-2 | TCAaCtttcacttCaGT | 17_142 | -22 |
| 17 | 3-2-1-7-1-1-2 | TCAacTttcacttCaGT | 17_143 | -21 |
| 17 | 3-10-1-1-2 | TCAactttcacttCaGT | 17_144 | -21 |
| 17 | 2-1-3-7-1-1-2 | TCaACTttcacttCaGT | 17_145 | -22 |
| 17 | 2-1-2-8-1-1-2 | TCaACtttcacttCaGT | 17_146 | -21 |
| 17 | 2-1-1-1-1-7-1-1-2 | TCaAcTttcacttCaGT | 17_147 | -20 |
| 17 | 2-2-2-7-1-1-2 | TCaaCTttcacttCaGT | 17_148 | -21 |
| 17 | 2-3-1-7-1-1-2 | TCaacTttcacttCaGT | 17_149 | -20 |
| 17 | 1-1-3-8-1-1-2 | TcAACtttcacttCaGT | 17_150 | -20 |
| 17 | 1-1-1-1-1-8-1-1-2 | TcAaCtttcacttCaGT | 17_151 | -19 |
| 17 | 1-1-1-10-1-1-2 | TcAactttcacttCaGT | 17_152 | -18 |
| 17 | 1-2-1-9-1-1-2 | TcaActttcacttCaGT | 17_153 | -18 |
| 17 | 1-3-2-7-1-1-2 | TcaaCTttcacttCaGT | 17_154 | -20 |
| 17 | 1-12-1-1-2 | Tcaactttcacttcagt | 17_155 | -18 |
| 17 | 4-1-1-8-3 | TCAAcTttcacttcAGT | 17_156 | -22 |
| 17 | 4-10-3 | TCAActttcacttcAGT | 17_157 | -22 |
| 17 | 3-1-2-8-3 | TCAaCTttcacttcAGT | 17_158 | -23 |
| 17 | 3-1-1-9-3 | TCAaCtttcacttcAGT | 17_159 | -22 |
| 17 | 2-2-2-8-3 | TCaaCTttcacttcAGT | 17_160 | -22 |
| 17 | 2-3-1-8-3 | TCaacTttcacttcAGT | 17_161 | -20 |
| 17 | 1-1-1-1-1-9-3 | TcAaCtttcacttcAGT | 17_162 | -19 |
| 17 | 1-1-1-11-3 | TcAactttcacttcAGT | 17_163 | -18 |
| 17 | 1-2-1-10-3 | TcaActttcacttcAGT | 17_164 | -19 |
| 17 | 1-13-3 | TcaactttcacttcAGT | 17_165 | -18 |
| 17 | 6-9-2 | TCAACTttcacttcaGT | 17_166 | -23 |
| 17 | 5-10-2 | TCAACtttcacttcaGT | 17_167 | -22 |
| 17 | 4-1-1-9-2 | TCAAcTttcacttcaGT | 17_168 | -21 |
| 17 | 4-11-2 | TCAActttcacttcaGT | 17_169 | -20 |
| 17 | 3-1-2-9-2 | TCAaCTttcacttcaGT | 17_170 | -22 |

TABLE 7-continued

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 17 | 3-1-1-10-2 | TCAaCtttcacttcaGT | 17_171 | −21 |
| 17 | 3-12-2 | TCAactttcacttcaGT | 17_172 | −20 |
| 17 | 2-1-3-9-2 | TCaACTttcacttcaGT | 17_173 | −21 |
| 17 | 2-1-2-10-2 | TCaACtttcacttcaGT | 17_174 | −20 |
| 17 | 2-1-1-11-2 | TCaActttcacttcaGT | 17_175 | −19 |
| 17 | 2-2-1-10-2 | TCaaCtttcacttcaGT | 17_176 | −19 |
| 17 | 2-3-1-9-2 | TCaacTttcacttcaGT | 17_177 | −19 |
| 17 | 1-1-2-11-2 | TcAActttcacttcaGT | 17_178 | −18 |
| 17 | 1-1-1-1-1-10-2 | TcAaCtttcacttcaGT | 17_179 | −18 |
| 17 | 1-1-1-12-2 | TcAactttcacttcaGT | 17_180 | −17 |
| 17 | 1-2-1-11-2 | TcaActttcacttcaGT | 17_181 | −17 |
| 17 | 1-3-1-10-2 | TcaaCtttcacttcaGT | 17_182 | −18 |
| 17 | 1-14-2 | TcaactttcacttcaGT | 17_183 | −17 |
| 18 | 3-10-3 | TCAactttcacttCAG | 18_1 | −19 |
| 18 | 2-2-1-6-5 | TCaaCtttcacTTCAG | 18_2 | −21 |
| 18 | 1-1-3-6-2-1-2 | TcAACtttcacTTcAG | 18_3 | −18 |
| 18 | 5-6-1-1-3 | TCAActttcacTtCAG | 18_4 | −22 |
| 18 | 4-7-1-1-3 | TCAActttcacTtCAG | 18_5 | −20 |
| 18 | 2-9-1-1-3 | TCaactttcacTtCAG | 18_6 | −18 |
| 18 | 1-3-1-6-1-1-3 | TcaaCtttcacTtCAG | 18_7 | −18 |
| 18 | 2-1-1-7-1-2-2 | TCaActttcacTtcAG | 18_8 | −17 |
| 18 | 5-7-4 | TCAActttcactTCAG | 18_9 | −22 |
| 18 | 4-8-4 | TCAActttcactTCAG | 18_10 | −21 |
| 18 | 3-1-1-7-4 | TCAaCtttcactTCAG | 18_11 | −21 |
| 18 | 3-9-4 | TCAactttcactTCAG | 18_12 | −20 |
| 18 | 2-2-1-7-4 | TCaaCtttcactTCAG | 18_13 | −20 |
| 18 | 2-10-4 | TCaactttcactTCAG | 18_14 | −19 |
| 18 | 1-1-3-7-1-1-2 | TcAACtttcacTTcAG | 18_15 | −17 |
| 18 | 1-1-1-1-1-7-1-1-2 | TcAaCtttcacTTcAG | 18_16 | −16 |
| 18 | 1-3-1-7-1-1-2 | TcaaCtttcacTTcAG | 18_17 | −16 |
| 18 | 5-8-3 | TCAActttcacttCAG | 18_18 | −21 |
| 18 | 4-9-3 | TCAActttcacttCAG | 18_19 | −20 |
| 18 | 3-1-1-8-3 | TCAaCtttcacttCAG | 18_20 | −20 |
| 18 | 2-2-1-8-3 | TCaaCtttcacttCAG | 18_21 | −19 |
| 18 | 2-11-3 | TCaactttcacttCAG | 18_22 | −18 |
| 18 | 5-9-2 | TCAActttcacttcAG | 18_23 | −19 |
| 18 | 4-10-2 | TCAActttcacttcAG | 18_24 | −18 |

TABLE 7-continued

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 18 | 3-1-1-9-2 | TCAaCtttcacttcAG | 18_25 | −18 |
| 18 | 3-11-2 | TCAactttcacttcAG | 18_26 | −17 |
| 18 | 2-1-2-9-2 | TCaACtttcacttcAG | 18_27 | −17 |
| 18 | 2-2-1-9-2 | TCaaCtttcacttcAG | 18_28 | −17 |
| 18 | 2-12-2 | TCaactttcacttcAG | 18_29 | −16 |
| 18 | 1-1-3-9-2 | TcAACtttcacttcAG | 18_30 | −16 |
| 18 | 1-3-1-9-2 | TcaaCtttcacttcAG | 18_31 | −15 |
| 18 | 3-10-3 | TCAactttcacttCAG | 18_249 | −19 |
| 18 | 5-5-6 | TCAACtttcaCTTCAG | 18_250 | −25 |
| 18 | 4-6-6 | TCAActttcaCTTCAG | 18_251 | −24 |
| 18 | 3-1-1-5-6 | TCAACtttcaCTTCAG | 18_252 | −24 |
| 18 | 2-1-2-5-6 | TCaACtttcaCTTCAG | 18_253 | −23 |
| 18 | 2-2-1-5-6 | TCaaCtttcaCTTCAG | 18_254 | −22 |
| 18 | 1-3-1-5-6 | TcaaCtttcaCTTCAG | 18_255 | −21 |
| 18 | 1-9-6 | TcaactttcaCTTCAG | 18_256 | −20 |
| 18 | 1-1-1-1-1-5-3-1-2 | TcAaCtttcaCTTcAG | 18_257 | −19 |
| 18 | 1-3-1-5-3-1-2 | TcaaCtttcaCTTcAG | 18_258 | −18 |
| 18 | 1-9-3-1-2 | TcaactttcaCTTcAG | 18_259 | −17 |
| 18 | 3-1-1-5-2-1-3 | TCAACtttcaCTtCAG | 18_260 | −22 |
| 18 | 3-7-2-1-3 | TCAactttcaCTtCAG | 18_261 | −21 |
| 18 | 2-2-1-5-2-1-3 | TCaaCtttcaCTtCAG | 18_262 | −21 |
| 18 | 2-8-2-1-3 | TCaactttcaCTtCAG | 18_263 | −20 |
| 18 | 1-1-3-5-2-1-3 | TcAACtttcaCTtCAG | 18_264 | −21 |
| 18 | 1-3-1-5-2-1-3 | TcaaCtttcaCTtCAG | 18_265 | −20 |
| 18 | 1-9-2-1-3 | TcaactttcaCTtCAG | 18_266 | −19 |
| 18 | 5-5-2-2-2 | TCAACtttcaCTtcAG | 18_267 | −21 |
| 18 | 4-6-2-2-2 | TCAActttcaCTtcAG | 18_268 | −20 |
| 18 | 3-1-1-5-2-2-2 | TCAaCtttcaCTtcAG | 18_269 | −20 |
| 18 | 3-7-2-2-2 | TCAactttcaCTtcAG | 18_270 | −19 |
| 18 | 2-1-2-5-2-2-2 | TCaACtttcaCTtcAG | 18_271 | −20 |
| 18 | 2-1-1-6-2-2-2 | TCaActttcaCTtcAG | 18_272 | −18 |
| 18 | 1-1-1-1-1-5-2-2-2 | TcAaCtttcaCTtcAG | 18_273 | −18 |
| 18 | 1-3-1-5-2-2-2 | TcaaCtttcaCTtcAG | 18_274 | −18 |
| 18 | 5-5-1-1-4 | TCAACtttcaCtTCAG | 18_275 | −23 |
| 18 | 4-6-1-1-4 | TCAActttcaCtTCAG | 18_276 | −22 |
| 18 | 3-1-1-5-1-1-4 | TCAaCtttcaCtTCAG | 18_277 | −22 |
| 18 | 3-7-1-1-4 | TCAactttcaCtTCAG | 18_278 | −21 |

TABLE 7-continued

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 18 | 2-1-2-5-1-1-4 | TCaActttcaCtTCAG | 18_279 | -22 |
| 18 | 2-1-1-6-1-1-4 | TCaActttcaCtTCAG | 18_280 | -20 |
| 18 | 2-2-1-5-1-1-4 | TCaaCtttcaCtTCAG | 18_281 | -21 |
| 18 | 2-8-1-1-4 | TCaactttcaCtTCAG | 18_282 | -20 |
| 18 | 2-2-1-5-1-1-1-1-2 | TCaaCtttcaCtTcAG | 18_283 | -18 |
| 18 | 2-8-1-1-1-1-2 | TCaactttcaCtTcAG | 18_284 | -17 |
| 18 | 1-1-3-5-1-1-1-1-2 | TcAACtttcaCtTcAG | 18_285 | -18 |
| 18 | 1-1-2-6-1-1-1-1-2 | TcAActttcaCtTcAG | 18_286 | -16 |
| 18 | 1-1-1-1-1-5-1-1-1-1-2 | TcAaCtttcaCtTcAG | 18_287 | -17 |
| 18 | 1-1-1-7-1-1-1-2 | TcAactttcaCtTcAG | 18_288 | -16 |
| 18 | 1-2-1-6-1-1-1-2 | TcaActttcaCtTcAG | 18_289 | -16 |
| 18 | 1-3-1-5-1-1-1-2 | TcaaCtttcaCTTcAG | 18_290 | -17 |
| 18 | 1-9-1-1-1-2 | TcaactttcaCtTcAG | 18_291 | -16 |
| 18 | 5-5-1-2-3 | TCAACtttcaCttCAG | 18_292 | -22 |
| 18 | 4-6-1-2-3 | TCAActttcaCttCAG | 18_293 | -21 |
| 18 | 3-1-1-5-1-2-3 | TCAaCtttcaCttCAG | 18_294 | -21 |
| 18 | 3-7-1-2-3 | TCAactttcaCttCAG | 18_295 | -20 |
| 18 | 2-1-2-5-1-2-3 | TCaACtttcaCttCAG | 18_296 | -21 |
| 18 | 2-1-1-6-1-2-3 | TCaActttcaCttCAG | 18_297 | -19 |
| 18 | 2-2-1-5-1-2-3 | TCaaCtttcaCttCAG | 18_298 | -20 |
| 18 | 2-8-1-2-3 | TCaactttcaCttCAG | 18_299 | -19 |
| 18 | 1-1-3-5-1-2-3 | TcAACtttcaCttCAG | 18_300 | -20 |
| 18 | 1-2-2-5-1-2-3 | TcaACtttcaCttCAG | 18_301 | -19 |
| 18 | 1-2-1-6-1-2-3 | TcaActttcaCttCAG | 18_302 | -18 |
| 18 | 5-5-1-3-2 | TCAACtttcaCttcAG | 18_303 | -20 |
| 18 | 4-6-1-3-2 | TCAActttcaCttcAG | 18_304 | -19 |
| 18 | 3-1-1-5-1-3-2 | TCAaCtttcaCttcAG | 18_305 | -19 |
| 18 | 3-7-1-3-2 | TCAactttcaCttcAG | 18_306 | -18 |
| 18 | 2-1-2-5-1-3-2 | TCaACtttcaCttcAG | 18_307 | -18 |
| 18 | 2-1-1-6-1-3-2 | TCaActttcaCttcAG | 18_308 | -17 |
| 18 | 2-2-1-5-1-3-2 | TCaaCtttcaCttcAG | 18_309 | -18 |
| 18 | 2-8-1-3-2 | TCaactttcaCttcAG | 18_310 | -17 |
| 18 | 1-1-3-5-1-3-2 | TcAACtttcaCttcAG | 18_311 | -17 |
| 18 | 1-1-2-6-1-3-2 | TcAActttcaCttcAG | 18_312 | -16 |
| 18 | 1-1-1-1-1-5-1-3-2 | TcAaCtttcaCttcAG | 18_313 | -16 |
| 18 | 1-1-1-7-1-3-2 | TcAactttcaCttcAG | 18_314 | -15 |
| 18 | 1-2-2-5-1-3-2 | TcaACtttcaCttcAG | 18_315 | -17 |

TABLE 7-continued

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 18 | 1-3-1-5-1-3-2 | TcaaCtttcaCttcAG | 18_316 | −16 |
| 18 | 1-9-1-3-2 | TcaactttcaCttcAG | 18_317 | −15 |
| 18 | 4-7-5 | TCAActttcacTTCAG | 18_318 | −22 |
| 18 | 3-1-1-6-5 | TCAactttcacTTCAG | 18_319 | −22 |
| 18 | 2-1-2-6-5 | TCaACtttcacTTCAG | 18_320 | −22 |
| 18 | 1-1-3-6-5 | TcAActttcacTTCAG | 18_321 | −21 |
| 18 | 1-1-1-1-1-6-5 | TcAcTtttcacTTCAG | 18_322 | −20 |
| 18 | 1-3-1-6-5 | TcaaCtttcacTTCAG | 18_323 | −19 |
| 18 | 5-6-2-1-2 | TCAActttcacTTcAG | 18_324 | −21 |
| 18 | 3-1-1-6-2-1-2 | TCAactttcacTTcAG | 18_325 | −20 |
| 18 | 2-2-1-6-2-1-2 | TCaaCtttcacTTcAG | 18_326 | −18 |
| 18 | 1-1-2-7-2-1-2 | TcAActttcacTTcAG | 18_327 | −16 |
| 18 | 1-1-1-1-1-6-2-1-2 | TcAaCtttcacTTcAG | 18_328 | −17 |
| 18 | 1-1-1-8-2-1-2 | TcAactttcacTTcAG | 18_329 | −16 |
| 18 | 1-3-1-6-2-1-2 | TcaaCtttcacTTcAG | 18_330 | −17 |
| 18 | 1-10-2-1-2 | TcaactttcacTTcAG | 18_331 | −16 |
| 18 | 3-1-1-6-1-1-3 | TCAactttcacTtCAG | 18_332 | −21 |
| 18 | 2-1-1-7-1-1-3 | TCaActttcacTtCAG | 18_333 | −19 |
| 18 | 2-2-1-6-1-1-3 | TCaaCtttcacTtCAG | 18_334 | −19 |
| 18 | 1-1-2-7-1-1-3 | TcAActttcacTtCAG | 18_335 | −18 |
| 18 | 1-10-1-1-3 | TcaactttcacTtCAG | 18_336 | −17 |
| 18 | 5-6-1-2-2 | TCAActttcacTtcAG | 18_337 | −20 |
| 18 | 4-7-1-2-2 | TCAActttcacTtcAG | 18_338 | −18 |
| 18 | 3-1-1-6-1-2-2 | TCAactttcacTtcAG | 18_339 | −19 |
| 18 | 2-2-1-6-1-2-2 | TCaaCtttcacTtcAG | 18_340 | −17 |
| 18 | 2-9-1-2-2 | TCaactttcacTtcAG | 18_341 | −16 |
| 18 | 1-1-3-6-1-2-2 | TcAActttcacTtcAG | 18_342 | −17 |
| 18 | 1-1-1-1-1-6-1-2-2 | TcAaCtttcacTtcAG | 18_343 | −16 |
| 18 | 1-3-1-6-1-2-2 | TcaaCtttcacTtcAG | 18_344 | −16 |
| 18 | 2-1-2-7-4 | TCaACtttcactTCAG | 18_345 | −21 |
| 18 | 2-1-1-8-4 | TCaActttcactTCAG | 18_346 | −19 |
| 18 | 1-1-2-8-4 | TcAActttcactTCAG | 18_347 | −18 |
| 18 | 1-2-1-8-4 | TcaActttcactTCAG | 18_348 | −18 |
| 18 | 1-11-4 | TcaactttcactTCAG | 18_349 | −17 |
| 18 | 4-8-1-1-2 | TCAActttcacTTcAG | 18_350 | −18 |
| 18 | 2-2-1-7-1-1-2 | TCaaCtttcacTTcAG | 18_351 | −17 |

TABLE 7-continued

Lists oligonucleotides designs and specific antisense oligonucleotide compounds Compounds are indicated by CMP ID NO, and based on the on the motif sequence in table 6.

| SEQ ID NO | Design | Oligonucleotide Compound | CMP ID NO | dG |
|---|---|---|---|---|
| 18 | 2-10-1-1-2 | TCaactttcacTTcAG | 18_352 | -16 |
| 18 | 1-1-2-8-1-1-2 | TcAActtcacTTcAG | 18_353 | -15 |
| 18 | 1-2-2-7-1-1-2 | TcaACtttcacTTcAG | 18_354 | -17 |
| 18 | 1-2-1-8-1-1-2 | TcaActtcacTTcAG | 18_355 | -15 |
| 18 | 2-1-2-8-3 | TCaActtcacttCAG | 18_356 | -20 |
| 18 | 2-1-1-9-3 | TCaActtcacttCAG | 18_357 | -18 |
| 18 | 1-2-2-8-3 | TcaACtttcacttCAG | 18_358 | -18 |
| 18 | 1-2-1-9-3 | TcaActtcacttCAG | 18_359 | -17 |
| 18 | 1-12-3 | TcaactttcacttCAG | 18_360 | -16 |
| 18 | 1-1-1-1-1-9-2 | TcAaCtttcacttcAG | 18_361 | -15 |
| 19 | 5-6-5 | TGTTTcaatacTAAAA | 19_1 | -16 |
| 19 | 4-7-5 | TGTTtcaatacTAAAA | 19_2 | -15 |
| 19 | 5-6-2-1-2 | TGTTTcaatacTAaAA | 19_3 | -16 |
| 19 | 5-5-6 | TGTTTcaataCTAAAA | 19_4 | -18 |
| 19 | 4-6-6 | TGTTtcaataCTAAAA | 19_5 | -17 |
| 19 | 3-1-1-5-6 | TGTtTcaataCTAAAA | 19_6 | -17 |
| 19 | 3-7-6 | TGTttcaataCTAAAA | 19_7 | -16 |
| 19 | 2-1-2-5-6 | TGtTTcaataCTAAAA | 19_8 | -16 |
| 19 | 2-2-1-5-6 | TGttTcaataCTAAAA | 19_9 | -15 |
| 19 | 1-1-3-5-6 | TgTTTcaataCTAAAA | 19_10 | -16 |
| 19 | 5-5-3-1-2 | TGTTTcaataCTAaAA | 19_11 | -17 |
| 19 | 4-6-3-1-2 | TGTTtcaataCTAaAA | 19_12 | -16 |
| 19 | 3-1-1-5-3-1-2 | TGTtTcaataCTAaAA | 19_13 | -16 |
| 19 | 3-7-3-1-2 | TGTttcaataCTAaAA | 19_14 | -16 |
| 19 | 2-1-2-5-3-1-2 | TGtTTcaataCTAaAA | 19_15 | -15 |
| 19 | 1-1-3-5-3-1-2 | TgTTTcaataCTAaAA | 19_16 | -15 |
| 19 | 5-5-2-1-3 | TGTTTcaataCTaAAA | 19_17 | -17 |
| 19 | 4-6-2-1-3 | TGTTtcaataCTaAAA | 19_18 | -16 |
| 19 | 3-1-1-5-2-1-3 | TGTtTcaataCTaAAA | 19_19 | -15 |
| 19 | 5-5-2-2-2 | TGTTTcaataCTaaAA | 19_20 | -16 |
| 19 | 4-6-2-2-2 | TGTTtcaataCTaaAA | 19_21 | -15 |
| 19 | 5-5-1-1-4 | TGTTTcaataCtAAAA | 19_22 | -15 |

Designs refer to the gapmer design, F-G-F'. In classic gapmer design e.g. 3-10-3 all the nucleotides in the flanks (F and F') are constituted of the same 2'-sugar modified nucleoside, e.g. LNA, cET, or MOE, and a stretch of DNA in the middle forming the gap (G). In gapmers with alternating flank designs the flanks of oligonucleotide is annotated as a series of integers, representing a number of 2' sugar modified nucleosides (M) followed by a number of DNA nucleosides (D). For example a flank with a 2-2-1 motif represents 5' [M]$_2$-[D]$_2$-[M] 3' and a 1-1-1-1-1 motif represents 5' [M]-[D]-[M]-[D]-[M] 3'. Both flanks have a 2' sugar modified nucleoside at the 5' and 3' terminal. The gap region (G), which is constituted of a number of DNA nucleosides (typically between 5 and 16), is located between the flanks.

The heading "Oligonucleotide compound" in the table represents specific designs of a motif sequence. Capital letters represent beta-D-oxy LNA nucleosides, lowercase letters represent DNA nucleosides, all LNA C are 5-methyl cytosine, and 5-methyl cytosine DNA are presented by "e", all internucleoside linkages are phosphorothioate internucleoside linkages.

TABLE 8

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| SEQ ID NO | Design | CMP ID NO | Parent Compound/ stereodefinition |
|---|---|---|---|
| 18 | 3-10-3 | 18_1 | TCAactttcacttCAG XXXXXXXXXXXXXXXH |

| CMP ID NO | Stereodefined motif | CMP ID NO | Stereodefined motif |
|---|---|---|---|
| 18_32 | RSSRXXXXXXXXXXXH | 18_365 | SSSSSRSRRXXXXXXH |
| 18_33 | XRSSRXXXXXXXXXXH | 18_366 | SSSSSSRRRXXXXXXH |
| 18_34 | XXRSSRXXXXXXXXXH | 18_367 | SSSRSRRRXXXXXXXH |
| 18_35 | XXXRSSRXXXXXXXXH | 18_368 | SSRSSRRRXXXXXXXH |
| 18_36 | XXXXRSSRXXXXXXXH | 18_369 | SSRRSSRRXXXXXXXH |
| 18_37 | XXXXXRSSRXXXXXXH | 18_370 | SSRSRSRRXXXXXXXH |
| 18_38 | XXXXXXRSSRXXXXXH | 18_371 | SSRSSSRRXXXXXXXH |
| 18_39 | XXXXXXXRSSRXXXXH | 18_372 | SSSRSRSRRXXXXXXH |
| 18_40 | XXXXXXXXRSSRXXXH | 18_373 | SSSSRRRRXXXXXXXH |
| 18_41 | XXXXXXXXXRSSRXXH | 18_374 | SSRSSSRRRXXXXXXH |
| 18_42 | XXXXXXXXXXRSSRXH | 18_375 | SSRSSRSRRXXXXXXH |
| 18_43 | XXXXXXXXXXXRSSRH | 18_376 | SSSRSSRRRXXXXXXH |
| 18_44 | XXXXXXXXXXSSSSRH | 18_377 | SSRRSRRRXXXXXXXH |
| 18_45 | XXXXXXXXXRRRRRH | 18_378 | RSSRRSSSSRRRRSSH |
| 18_46 | XXXXXXXXXSSRRSRH | 18_379 | SRSRRSSSSRRRRSSH |
| 18_47 | XXXXXXXXXSSSRSRH | 18_380 | SSRRRSSSSRRRRSSH |
| 18_48 | XXXXXXXXXSSSRRSH | 18_381 | SSSSRSSSSRRRRSSH |
| 18_49 | XXXXXXXXXSRSSSH | 18_382 | SSSRSSSSRRRRSSH |
| 18_50 | XXXXXXXXXRSRSRSH | 18_383 | SSSRRRSSSRRRRSSH |
| 18_51 | XXXXXXXXXSSSSRSH | 18_384 | SSSRSRSSRRRRSSH |
| 18_52 | XXXXXXXXXSSRRSSH | 18_385 | SSSRRSSRSRRRRSSH |
| 18_53 | XXXXXXXXXRSSSSH | 18_386 | SSSRRSSSRRRRRSSH |
| 18_54 | XXXXXXXXXRSSRRH | 18_387 | SSSRSSSSRRRRSSH |
| 18_55 | XXXXXXXXXSRRRSH | 18_388 | SSSRRSSSSSRRSSH |

TABLE 8-continued

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| | | | |
|---|---|---|---|
| 18_56 | XXXXXXXXXSSRSRRH | 18_389 | SSSRRSSSSRRSRSSH |
| 18_57 | XXXXXXXXXRRRSRRH | 18_390 | SSSRRSSSSRRRSSSH |
| 18_58 | XXXXXXXXXRRSRSRH | 18_391 | SSSRRSSSSRRRRRSH |
| 18_59 | XXXXXXXXXSSRRRSH | 18_392 | SSSRRSSSSRRRRSRH |
| 18_60 | XXXXXXXXXSRRSSSH | 18_393 | SRSSRSSSSRRRRSSH |
| 18_61 | XXXXXXXXXRRRRRSH | 18_394 | SSRSSRSSSRRRRSSH |
| 18_62 | XXXXXXXXXRRSSRRH | 18_395 | SSSRSSRSSRRRRSSH |
| 18_63 | XXXXXXXXXRSRRRRH | 18_396 | SSSRRRSSRRRRRSSH |
| 18_64 | XXXXXXXXXSRRRSSH | 18_397 | SSSRRSSRSSRRRSSH |
| 18_65 | XXXXXXXXXSRSRSRH | 18_398 | SSSRRSSSRSSRRSSH |
| 18_66 | XXXXXXXXXRSSSSRH | 18_399 | SSSRRSSSSRSSRSSH |
| 18_67 | XXXXXXXXXSSSSRRH | 18_400 | SSSRRSSSSRRSSRSH |
| 18_68 | XXXXXXXXXRRSSSRH | 18_401 | SSSRRSSSSRRRSSRH |
| 18_69 | XXXXXXXXXRSSRRSH | 18_402 | RSSRRSSSSRRRSSRH |
| 18_70 | XXXXXXXXXRSSSRRH | 18_403 | SRSSRSSSSRRSSRSH |
| 18_71 | XXXXXXXXXSRRRRRH | 18_404 | SSRSSRSSSRSSSRSSH |
| 18_72 | XXXXXXXXXRRSRSSH | 18_405 | SSSRSSSRSSSRRSSH |
| 18_73 | XXXXXXXXXRSRSSRH | 18_406 | SSSRRSSRSSRRSSH |
| 18_74 | XXXXXXXXXRSRSRRH | 18_407 | RSSRRSSRRRRRSSRH |
| 18_75 | XXXXXXXXXSRRRSRH | 18_408 | SSSRSSSRRRRRXXXH |
| 18_76 | XXXXXXXXXRRSRRSH | 18_409 | SSSSSSSRRRRRXXXH |
| 18_77 | XXXXXXXXXSSSRRRH | 18_410 | SSSRSSSRRSRRXXXH |
| 18_78 | XXXXXXXXXRSRRSRH | 18_411 | SSSRSSSRRRSRXXXH |
| 18_79 | XXXXXXXXXSRRSRSH | 18_412 | SSSSSSSRRSSRXXXH |
| 18_80 | XXXXXXXXXRRSRRRH | 18_413 | SSSSSSSRRSRRXXXH |
| 18_81 | XXXXXXXXXSRRSSRH | 18_414 | SSSSSSSRRRSRXXXH |
| 18_82 | XXXXXXXXXSRSSSRH | 18_415 | SSSRSSSRRSSRXXXH |
| 18_83 | XXXXXXXXXRSRRRSH | 18_416 | SSRRSRRRRXXRXXXH |
| 18_84 | XXXXXXXXXSSSRSSH | 18_417 | SSSRSRRRRXXRXXXH |
| 18_85 | XXXXXXXXXSSRSSRH | 18_418 | SSRSSRRRRXXRXXXH |
| 18_86 | XXXXXXXXXRSSRSSH | 18_419 | SSRRSSRRRXXRXXXH |
| 18_87 | XXXXXXXXXSRSSRSH | 18_420 | SSRRSRSRRXXRXXXH |
| 18_88 | XXXXXXXXXSSSSSSH | 18_421 | SSSSSSSRRXXRXXXH |
| 18_89 | XXXXXXXXXRSRRSSH | 18_422 | SSRSSSSRRXXRXXXH |
| 18_90 | XXXXXXXXXRRRRSRH | 18_423 | SSSRSSSRRXXRXXXH |

TABLE 8-continued

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| | | | |
|---|---|---|---|
| 18_91  | XXXXXXXXXSSRSRSH   | 18_424 | SSSSSSRRRXXRXXXH |
| 18_92  | XXXXXXXXXRRRRSSH   | 18_425 | SSSSSRSRRXXRXXXH |
| 18_93  | XXXXXXXXXRSRSSSH   | 18_426 | SSRSSRSRRXXRXXXH |
| 18_94  | XXXXXXXXXRSSRSRH   | 18_427 | SSSRSRSRRXXRXXXH |
| 18_95  | XXXXXXXXXRRRSRSH   | 18_428 | SSSRSSRRRXXRXXXH |
| 18_96  | XXXXXXXXXRRSSRSH   | 18_429 | SSRSSSRRRXXRXXXH |
| 18_97  | XXXXXXXXXSRSSRRH   | 18_430 | SSRSSSRRRXXRXXXH |
| 18_98  | XXXXXXXXXSRRSRRH   | 18_431 | SSSSSRRRRXXRXXXH |
| 18_99  | XXXXXXXXXSRSRSSH   | 18_432 | SSSRRSSSSRSRRSSH |
| 18_100 | XXXXXXXXXSRSRRRH   | 18_433 | XXXXRSSRXSSSRXXH |
| 18_101 | XXXXXXXXXSSRSSSH   | 18_434 | XXXXRSSRXSSRRXXH |
| 18_102 | XXXXXXXXXRSSSSH    | 18_435 | XXXXRSSRXRSSRXXH |
| 18_103 | XXXXXXXXXRSSRSH    | 18_436 | XXXXRSSRXSRSSXXH |
| 18_104 | XXXXXXXXXRRRSSRH   | 18_437 | XXXXRSSRXRRRRXXH |
| 18_105 | XXXXXXXXXRRRSSSH   | 18_438 | XXXXRSSRXRRSRXXH |
| 18_106 | XXXXXXXXXSRSRRSH   | 18_439 | XXXXRSSRXSRRRXXH |
| 18_107 | XXXXXXXXXSSRRRRH   | 18_440 | XXXXRSSRXRRSSXXH |
| 18_108 | XXXXXXXXXXSSRSSH   | 18_441 | XXXXRSSRXSRRXXH |
| 18_109 | XXXXXXXXXXRRRSSH   | 18_442 | XXXXRSSRXRSSSXXH |
| 18_110 | XXXXXXXXXXRRSSRH   | 18_443 | XXXXRSSRXRRRSXXH |
| 18_111 | XXXXXXXXXXRSSSRH   | 18_444 | XXXXRSSRXRSRSXXH |
| 18_112 | XXXXXXXXXXRRSRRH   | 18_445 | XXXXRSSRXSRRSXXH |
| 18_113 | XXXXXXXXXXSSSSRH   | 18_446 | XXXXRSSRXSSSSXXH |
| 18_114 | XXXXXXXXXXRRRRH    | 18_447 | XXXXRSSRXSRSRXXH |
| 18_115 | XXXXXXXXXXSRSSSH   | 18_448 | XXXXRSSRXSSRSXXH |
| 18_116 | XXXXXXXXXXSSRSRH   | 18_449 | SSSRRSSSRRSSRSSH |
| 18_117 | XXXXXXXXXXRSSRSH   | 18_450 | RSSRRSSSRRRRRSSH |
| 18_118 | XXXXXXXXXXRSRRRH   | 18_451 | SRSRRSSSRRRRRSSH |
| 18_119 | XXXXXXXXXXSRRRRH   | 18_452 | SSRRRSSSRRRRRSSH |
| 18_120 | XXXXXXXXXXSRRRSH   | 18_453 | SSSSRSSSRRRRRSSH |
| 18_121 | XXXXXXXXXXSSSRSH   | 18_454 | SSSRSSSSRRRRRSSH |
| 18_122 | XXXXXXXXXXRSRSSH   | 18_455 | SSSRRSRSRRRRRSSH |
| 18_123 | XXXXXXXXXXSSSSSH   | 18_456 | SSSRRSSRRRRRRSSH |
| 18_124 | XXXXXXXXXXSRRSSH   | 18_457 | SSSRRSSSRSRRRSSH |
| 18_125 | XXXXXXXXXXRSRRSH   | 18_458 | SSSRRSSSRRSRRSSH |

TABLE 8-continued

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| | | | |
|---|---|---|---|
| 18_126 | XXXXXXXXXXSSRRSH | 18_459 | SSSRRSSSRRRSRSSH |
| 18_127 | XXXXXXXXXXRRRSRH | 18_460 | SSSRRSSSRRRRSSSH |
| 18_128 | XXXXXXXXXXSRSRRH | 18_461 | SSSRRSSSRRRRRRSH |
| 18_129 | XXXXXXXXXXRRSRSH | 18_462 | SSSRRSSSRRRRRSRH |
| 18_130 | XXXXXXXXXXRRSSSH | 18_463 | SSSRRSSSRRRSSSRH |
| 18_131 | XXXXXXXXXXRSSSSH | 18_464 | SSSRRSSSRRRSRRSH |
| 18_132 | XXXXXXXXXXRSSRRH | 18_465 | XXXXRSSRXRRSRRSH |
| 18_133 | XXXXXXXXXXSRRSRH | 18_466 | XXXXRSSRXXRSSSRH |
| 18_134 | XXXXXXXXXXSSRRRH | 18_467 | SSXXSXXRRRXXRXXXH |
| 18_135 | XXXXXXXXXXSRSSRH | 18_468 | SSXXSXXRRXXXXXXH |
| 18_136 | XXXXXXXXXXRRRRSH | 18_469 | SSSXSSSRRRXXRXXXH |
| 18_137 | XXXXXXXXXXRSRSRH | 18_470 | SXXXSXXXXXXXXXXH |
| 18_138 | XXXXXXXXXXSSSRRH | 18_497 | RRRSSRSSRSSRSRRH |
| 18_139 | XXXXXXXXXXSRSRSH | 18_498 | SSSRRSRRSRRSRSSH |
| 18_140 | SSRRRSSSSSRSSRH | 18_499 | SRRSRSRSRRRSRRRH |
| 18_141 | SSSSSRRRRRRSRRSH | 18_500 | SRRSSRRSSRSSSSH |
| 18_142 | SRSSRSSSRRRSRSRH | 18_501 | SRRSSRSSRSRSSSH |
| 18_143 | SRRSSSSRRSRRRRRH | 18_502 | RRRSSRSRSSSRRRRH |
| 18_144 | SSRRSRSRSSSRSRRH | 18_503 | SRRRSSSRRRSSSSH |
| 18_145 | SSSRRRRSRRRRSSRRH | 18_504 | RRSSRSRSRSSRRSSH |
| 18_146 | RRSRSRRSSSRRSSH | 18_505 | RRSRSRSRSSSRRSRH |
| 18_147 | RSSRRRSSSRSSSRSH | 18_506 | RSSSRRSSSRSRRSH |
| 18_148 | SSSSRRRSRSSSRRSH | 18_507 | SRRSRSSSSSRRRSH |
| 18_149 | SSSRSSSSSSRRRRH | 18_508 | RRSSRSRRSRSRRRRH |
| 18_150 | SSSSRSSSSSSSSSSH | 18_509 | RRRSRRRRSSSSRSH |
| 18_151 | RRSRRRRSSSSSSSSH | 18_510 | SSRRSRSRRSSSRRRH |
| 18_152 | RRRRSRSSRRRRSSSH | 18_511 | SSRRRSRSSSRRRRH |
| 18_153 | RRRRSSRRRSRSSRH | 18_512 | RRRRSSSRSRSSSSH |
| 18_154 | SSRRRSRSRSSRRSH | 18_513 | SRSRSSRRRSSSSSH |
| 18_155 | RSSSSSRSSRRSSSSH | 18_514 | RSRSRSSRSRRRRH |
| 18_156 | RRRSSSSSRSRSRRSH | 18_515 | SSRRSRSSSSRSSRH |
| 18_157 | RSSSRSRSRRRSRRRH | 18_516 | RSRRSRSSSRRSSSH |
| 18_158 | RRSRRSSSRRRRRRSH | 18_517 | RRSSRSRRRSRRRSRH |
| 18_159 | RRSSSSRSRSSSRSRH | 18_518 | SRSRSSSSSSSSSSSH |
| 18_160 | RSSRSRSRSRSRSRRH | 18_519 | RSSSSSRSRSSSRSSH |

TABLE 8-continued

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| | | | |
|---|---|---|---|
| 18_161 | SRRRSSSSRSRSRSRH | 18_520 | SRSSSSRSRSSSSRSH |
| 18_162 | SRSSSRRSRRRRSSRH | 18_521 | RRSRRSRRRSRRRSSH |
| 18_163 | RSSRRRSRRSRSSRRH | 18_522 | SRRSRSRSRSRSRRH |
| 18_164 | SSRRSSRSSRRRRSH | 18_523 | SRRRRSSSSRRSSRSH |
| 18_165 | RSRSSRRSRRRSSSRH | 18_524 | RSSSRRRRRSSSRRRH |
| 18_166 | RRRSRRRSSRSRRSH | 18_525 | RRSRRRRSSSSRRSH |
| 18_167 | SRRRSSSRSRSSRRRH | 18_526 | SSSSRSRRSRSSSRSH |
| 18_168 | SRSSRSSSSRSRSSH | 18_527 | RRRRSRRSSSSSRSSH |
| 18_169 | SSRRSRSSSSSRSSSH | 18_528 | SRRSRSRRRRSSRRSH |
| 18_170 | SSRRRRSRSRRSSSH | 18_529 | RSRSSRRRRRSSRSSH |
| 18_171 | SSSRRSSRSRRRRRSH | 18_530 | RRRSRSRSSRSRSSSH |
| 18_172 | RSSSSSSSRSRRRRRH | 18_531 | RRSSRSSSSSRSSSRH |
| 18_173 | SSRSRSSRSRRRSRRH | 18_532 | RRRSSSSSRSSSRSSH |
| 18_174 | SRSRSSSRRSRRRSH | 18_533 | RRSSSSSRRSSRSRRH |
| 18_175 | RRRRRRSSRRSSSRH | 18_534 | RSSRSRSRSSSSRRH |
| 18_176 | SSRSRRRRSRRSRSH | 18_535 | SSSRSSSSRRSRRSH |
| 18_177 | RRSRRRRRSSRRRSH | 18_536 | RRSSRRSSRSRRSSRH |
| 18_178 | SSSSRRRRRRRRRSRH | 18_537 | RRRSRRRSSSSRSSSH |
| 18_179 | SRRRSSRRRSSRRRSH | 18_538 | SSSRSSRRSRRRSSSH |
| 18_180 | SSRRRRRSRSSRRSRH | 18_539 | RSRRRRRRSSSSRRSH |
| 18_181 | RRSRRSSSSRRRSSRH | 18_540 | SSRSRSSSSRSRSRRH |
| 18_182 | SSRSRSSRRRSSSSH | 18_541 | SSSRSSSSRRRRSH |
| 18_183 | SSRSRRRRSSRSSSRH | 18_542 | SSRRSSSSSRSRRSSH |
| 18_184 | RRRSRRSRSRSRRRH | 18_543 | SSSRRRSRRRSSRSRH |
| 18_185 | RSRSSRSRSRRRSRH | 18_544 | SRSSSSSRSSRSRRSH |
| 18_186 | SSRRRRSSRRRSRRRH | 18_545 | SRSSSSSRRSSRRRH |
| 18_187 | RSSRRSRRRSRRRSH | 18_546 | SRRSSSSRRRRRSRH |
| 18_188 | SSSRRSSRSRSRSSSH | 18_547 | RSRSRRRSSSRSRRSH |
| 18_189 | RSRSSSSRSSRRRSSH | 18_548 | RRSRRSSSSSSRSSH |
| 18_190 | SSSRSSSRSRRSRSSH | 18_549 | RSSRRRSSRRSSSSH |
| 18_191 | RSSRSSSSRSSSSSRH | 18_550 | RSSRRSRSSRRSRSH |
| 18_192 | RSSRRSSRSSSSRRSH | 18_551 | RRSSRSRRRRRRRSH |
| 18_193 | RSSRRSRSRRSSSSRH | 18_552 | SRSSSRSRRRSSRSSH |
| 18_194 | RRSSSRRSRRRRSSSH | 18_553 | RSSRRRRSRSRRRRH |
| 18_195 | RRRRSSRSRSRRSSRH | 18_554 | RSRSSSSRRSSSSRH |

TABLE 8-continued

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| | | | |
|---|---|---|---|
| 18_196 | SSSSRSRRRSSRRRSH | 18_555 | RRRRSSRRRSSRSSRH |
| 18_197 | RSRRRRRRRSSRSRH | 18_556 | SSRSSRRSSSSRSRSH |
| 18_198 | RSRRSSSSRSSRSSRH | 18_557 | SRRRSSSSRRRSSRRH |
| 18_199 | SSRRSRSSRRRSSSRH | 18_558 | SRRSSSSRRSRRSRRH |
| 18_200 | RRRRSSSRRSRSRSSH | 18_559 | SSRRRSSRSSRSRRRH |
| 18_201 | RSRRRRRRSRRSSRSH | 18_560 | RSSRRRRSRSRRSRSH |
| 18_202 | SRRSRRRRRSRSSSSH | 18_561 | RSSRRRRSRRRRRRRH |
| 18_203 | SRRSRSSSRSSSSSH | 18_562 | RRRRRRSRSRSRSSRH |
| 18_204 | SSSRRRRSRSRRRSSH | 18_563 | SSSRSSSRRSSSRRH |
| 18_205 | SSRSRSRSSSRSRSRH | 18_564 | SRRSRSSSSSRSRRRH |
| 18_206 | SSSRRSRRRRRRSRSH | 18_565 | SSSSSRRSRSRSSRSH |
| 18_207 | SRSSRRSSSSSRRRH | 18_566 | SSRSRRRSRRSSSRH |
| 18_208 | RRSSRSSSSSSRSSRH | 18_567 | SSRSRSRRRSRSRRSH |
| 18_209 | SRSSRRSSRSRRSRRH | 18_568 | SRRSSRSRSRRRRSSH |
| 18_210 | RSRRSSRSRSSRRSSH | 18_569 | SRSRSRSRRSSSSRRH |
| 18_211 | RSSSRRSRSSSRSSSH | 18_570 | SRSSSRRRSRSSSSSH |
| 18_212 | SSSSSSSRSRRRSSH | 18_571 | SRRSRSSSSSRSRSSH |
| 18_213 | RRSSSSSSRSSSRRH | 18_572 | RSSRSRSRRSRSRRRH |
| 18_214 | SSSRSSSSRRRRSSH | 18_573 | SSRSRRRRRRSSSSH |
| 18_215 | SSSRRRRRSSSSRRH | 18_574 | RRSSRRSSSSSSSSH |
| 18_216 | RSRSRRRSSSRRRSRH | 18_575 | SRSSSRRRRSSRSRH |
| 18_217 | SSSSRRSRRRSSRRRH | 18_576 | SSSSRSRRSSRRSRH |
| 18_218 | RSSRRSSRSRRRSSSH | 18_577 | RSSSRSSRSRRRSSRH |
| 18_219 | RRSSSSSRRRRSRRSH | 18_578 | RRSRSRSRRRRSRRSH |
| 18_220 | RXXXXXXXXXXXXXH | 18_579 | SRSRSSRSSSSSRRSH |
| 18_221 | SXXXXXXXXXXXXXH | 18_580 | RRRSRRSSSSSSSRRH |
| 18_222 | XRXXXXXXXXXXXXH | 18_581 | RRRSRSRSSRRRSH |
| 18_223 | XSXXXXXXXXXXXXH | 18_582 | SSRSSRRRRSSRSRH |
| 18_224 | XXRXXXXXXXXXXXH | 18_583 | RSSSSSRRRRSSRSH |
| 18_225 | XXSXXXXXXXXXXXH | 18_584 | SRSSRRSRSSSRRSSH |
| 18_226 | XXXRXXXXXXXXXXH | 18_585 | RSSSSSSRRSSSSRRH |
| 18_227 | XXXSXXXXXXXXXXH | 18_586 | SRRRSSSRRRSSSSH |
| 18_228 | XXXXRXXXXXXXXXH | 18_587 | RRSRRRSRSSSSRSSH |
| 18_229 | XXXXSXXXXXXXXXH | 18_588 | SSSSRSSSRSRSSSSH |

TABLE 8-continued

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| | | | |
|---|---|---|---|
| 18_230 | XXXXXRXXXXXXXXH | 18_589 | RRSRRRRRSRSSRSRH |
| 18_231 | XXXXXSXXXXXXXXH | 18_590 | RRSSSRSRRRSRSSSH |
| 18_232 | XXXXXXRXXXXXXXH | 18_591 | RRSRSRSSSRSSSSSH |
| 18_233 | XXXXXXSXXXXXXXH | 18_592 | RRSSRSSSSRSRRSRH |
| 18_234 | XXXXXXXRXXXXXXH | 18_593 | RRRRSSRSRSRSRSRH |
| 18_235 | XXXXXXXSXXXXXXH | 18_594 | SRRSRSSRRSRSSSH |
| 18_236 | XXXXXXXXRXXXXXH | 18_595 | SRRSRRSRRRSSRSRH |
| 18_237 | XXXXXXXXSXXXXXH | 18_596 | SSSSRRRSSRRSSSH |
| 18_238 | XXXXXXXXXRXXXXH | 18_597 | RRSRRRSRSSRSRRRH |
| 18_239 | XXXXXXXXXSXXXXH | 18_598 | RSRSSRRSSRRSSRSH |
| 18_240 | XXXXXXXXXXRXXXH | 18_599 | SSSRRRRSSRSRSSSH |
| 18_241 | XXXXXXXXXXSXXXH | 18_600 | RRRRSSRSRRRSRSH |
| 18_242 | XXXXXXXXXXXRXXH | 18_601 | SSSRSSRSRSSRSRRH |
| 18_243 | XXXXXXXXXXXSXXH | 18_602 | RRRSRSRSSRSRRSH |
| 18_244 | XXXXXXXXXXXXRXH | 18_603 | SRSSSSSRRSSRSRSH |
| 18_245 | XXXXXXXXXXXXSXH | 18_604 | SSSRSSRSSSSSSSRH |
| 18_246 | XXXXXXXXXXXXXRH | 18_605 | SSRSRSSRSSSSRRH |
| 18_247 | XXXXXXXXXXXXXSH | 18_606 | SRSRRSRRSRSRRRRH |
| 18_248 | XXXXXXXXXXXXXRH | 18_607 | SRSRRRSRSRSSSH |
| 18_249 | XXXXXXXXXXXXXSH | 18_608 | SRSRRRRSSSRRSRH |
| 18_362 | SSSSSSSRRXXXXXXH | 18_609 | RRRSSSRSSRRSSRH |
| 18_363 | SSRSSSSRRXXXXXXH | 18_610 | RRRSSSSRRSRSRRH |
| 18_364 | SSSRSSSRRXXXXXXH | | |

| SEQ ID NO | Design | CMP ID NO | Parent Oligonucleotide Cmp/ stereodefinition |
|---|---|---|---|
| 18 | 1-1-2-8-4 | 18_347 | TcAActttcactTCAG XXXXXXXXXXXXXXH |

| CMP ID NO | Stereodefined motif | CMP ID NO | Stereodefined motif |
|---|---|---|---|
| 18_471 | SSSRRSSSRRRRRSSH | 18_478 | SSSRSSSRSRRSRSSH |
| 18_472 | XXXXRSSRXXXXXXXH | 18_479 | SRRSRSRSRRSRRRH |
| 18_473 | XXXXXXXXXRSSSRH | 18_480 | SRRRSSRRSSRSSSSH |
| 18_474 | XXXXXXXXXRRSRRSH | 18_481 | SRRRSSRSSSRSSSH |
| 18_475 | SSSSRSRRRSSRRRSH | 18_482 | RRRSRSRSSSRRRRH |
| 18_476 | RRSRSSRRSSSRRSSH | 18_483 | SRRRSSSRRRSSSSH |
| 18_477 | RSRSSSSRSSRRRSSH | | |

TABLE 8-continued

List of stereodefined variants.
The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347 and 18_12.

| SEQ ID NO | Design | CMP ID NO | Parent Oligonucleotide Cmp/ stereodefinition |
|---|---|---|---|
| 18 | 3-9-4 | 18_12 | TCAactttcactTCAG<br>XXXXXXXXXXXXXXH |

| CMP ID NO | Stereodefined motif | CMP ID NO | Stereodefined motif |
|---|---|---|---|
| 18_484 | SSSRRSSSRRRRRSSH | 18_491 | SSSSRSRRRSSRRRSH |
| 18_485 | XXXXRSSRXXXXXXXH | 18_492 | SRRSRSRSRRRSRRRH |
| 18_486 | XXXXXXXXXRSSSRH | 18_493 | SRRRSSRRSSRSSSSH |
| 18_487 | XXXXXXXXXRRSRRSH | 18_494 | SRRRSSRSSRSRSSSH |
| 18_488 | RRSRSSRRSSSRRSSH | 18_495 | RRRSRSRSSSRRRRH |
| 18_489 | RSRSSSSRSSRRRSSH | 18_496 | SRRRSSSRRRRSSSSH |
| 18_490 | SSSRSSSRSRRSRSSH | | |

In relation to the parent oligonucleotide CMP: Capital letters represent beta-D-oxy LNA nucleosides, lowercase letters represent DNA nucleosides, all LNA C are 5-methyl cytosine, all internucleoside linkages are phosphorothioate internucleoside linkages.

In relation to the stereodefinition/stereodefined motifs: X represent a stereorandom phosphorothioate internucleoside linkage, R represents one stereoisomeric form and S represents the other stereoisomeric form as defined in the a description, H represents the hydrogen atom at the 3' terminus of the oligonucleotide. The first letter (X, R or S) in the stereodefined motif correspond to the internucleoside linkage between nucleoside 1 and 2 from the 5' end of the oligonucleotide.

TABLE 9

Oligonucleotide motif sequences and antisense compounds with 5' ca biocleavable linker.

| SEQ ID NO | motif sequence | oligonucleotide compound with a C6 alkyl ca biocleavable linker | CMP ID NO |
|---|---|---|---|
| 20 | CATCAACTTTCACTTCAG | C6$_o$c$_o$a$_o$TCAactttcacttCAG | 20_1 |
| 20 | CATCAACTTTCACTTCAG | C6$_o$c$_o$a$_o$TCAActtttcactTCAG | 20_2 |
| 20 | CATCAACTTTCACTTCAG | C6$_o$c$_o$a$_o$TCAActttcacttCAG | 20_3 |
| 20 | CATCAACTTTCACTTCAG | C6$_o$c$_o$a$_o$TCAActtttcacTtCAG | 20_4 |
| 20 | CATCAACTTTCACTTCAG | C6$_o$c$_o$a$_o$TCAACtttcacttCAG | 20_5 |
| 20 | CATCAACTTTCACTTCAG | C6$_o$c$_o$a$_o$TCAACtttcacttcAG | 20_6 |
| 20 | CATCAACTTTCACTTCAG | C6$_o$c$_o$a$_o$TCAActttcacttcAG | 20_7 |
| 20 | CATCAACTTTCACTTCAG | C6$_o$c$_o$a$_o$TCAactttcactTCAG | 20_8 |
| 20 | CATCAACTTTCACTTCAG | C6$_o$c$_o$a$_o$TcAACtttcactTcAG | 20_9 |
| 20 | CATCAACTTTCACTTCAG | C6$_o$c$_o$a$_o$TcAACtttcacttcAG | 20_10 |
| 20 | CATCAACTTTCACTTCAG | C6$_o$c$_o$a$_o$TCaActttcacttcAG | 20_11 |
| 20 | CATCAACTTTCACTTCAG | C6$_o$c$_o$a$_o$TCaActttcacttCAG | 20_23 |
| 20 | CATCAACTTTCACTTCAG | C6$_o$c$_o$a$_o$TCaactttcactTCAG | 20_24 |

TABLE 9-continued

Oligonucleotide motif sequences and antisense compounds with 5' ca biocleavable linker.

| SEQ ID NO | motif sequence | oligonucleotide compound with a C6 alkyl ca biocleavable linker | CMP ID NO |
|---|---|---|---|
| 20 | CATCAACTTTCACTTCAG | $C6_o c_o a_o$ TCAaCtttcacttCAG | 20_25 |
| 20 | CATCAACTTTCACTTCAG | $C6_o c_o a_o$ TCaaCtttcacttCAG | 20_26 |
| 20 | CATCAACTTTCACTTCAG | $C6_o c_o a_o$ TCAaCtttcacttcAG | 20_27 |
| 20 | CATCAACTTTCACTTCAG | $C6_o c_o a_o$ TCaActttcactTCAG | 20_28 |
| 20 | CATCAACTTTCACTTCAG | $C6_o c_o a_o$ TcAActttcactTCAG | 20_29 |
| 20 | CATCAACTTTCACTTCAG | $C6_o c_o a_o$ TCAActttcactTcAG | 20_37 |
| 20 | CATCAACTTTCACTTCAG | $C6_o c_o a_o$ TcaACtttcacttCAG | 20_38 |
| 21 | CATCAACTTTCACTTCAGT | $C6_o c_o a_o$ TCAActttcacttCaGT | 21_1 |
| 21 | CATCAACTTTCACTTCAGT | $C6_o c_o a_o$ TcAactttcactTcAGT | 21_3 |
| 21 | CATCAACTTTCACTTCAGT | $C6_o c_o a_o$ TCAActttcacttCaGT | 21_4 |
| 21 | CATCAACTTTCACTTCAGT | $C6_o c_o a_o$ TCAactttcacttcAGT | 21_5 |
| 21 | CATCAACTTTCACTTCAGT | $C6_o c_o a_o$ TCaactttcacTtCAGT | 21_6 |
| 21 | CATCAACTTTCACTTCAGT | $C6_o c_o a_o$ TCAactttcacTtCaGT | 21_7 |
| 21 | CATCAACTTTCACTTCAGT | $C6_o c_o a_o$ TCaActttcactTCAGT | 21_8 |
| 21 | CATCAACTTTCACTTCAGT | $C6_o c_o a_o$ TCAActttcactTCAGT | 21_9 |
| 21 | CATCAACTTTCACTTCAGT | $C6_o c_o a_o$ TCAActttcactTCaGT | 21_10 |
| 21 | CATCAACTTTCACTTCAGT | $C6_o c_o a_o$ TCAactttcactTCaGT | 21_11 |
| 21 | CATCAACTTTCACTTCAGT | $C6_o c_o a_o$ TCAActttcactTCaGT | 21_12 |
| 21 | CATCAACTTTCACTTCAGT | $C6_o c_o a_o$ TCaactttcactTcAGT | 21_13 |
| 21 | CATCAACTTTCACTTCAGT | $C6_o c_o a_o$ TCAactttcacttCAGT | 21_14 |
| 21 | CATCAACTTTCACTTCAGT | $C6_o c_o a_o$ TCaactttcacttCAGT | 21_15 |
| 21 | CATCAACTTTCACTTCAGT | $C6_o c_o a_o$ TCAActttcacttCAGT | 21_16 |
| 21 | CATCAACTTTCACTTCAGT | $C6_o c_o a_o$ TCAactttcacttCAGT | 21_17 |
| 21 | CATCAACTTTCACTTCAGT | $C6_o c_o a_o$ TCAactttcacttCaGT | 21_18 |
| 21 | CATCAACTTTCACTTCAGT | $C6_o c_o a_o$ TCAActttcacttcAGT | 21_19 |
| 21 | CATCAACTTTCACTTCAGT | $C6_o c_o a_o$ TCaactttcactTCAGT | 21_37 |
| 21 | CATCAACTTTCACTTCAGT | $C6_o c_o a_o$ TCaActttcactTCaGT | 21_38 |
| 21 | CATCAACTTTCACTTCAGT | $C6_o c_o a_o$ TCAActttcactTcaGT | 21_39 |
| 21 | CATCAACTTTCACTTCAGT | $C6_o c_o a_o$ TCaActttcacttCAGT | 21_40 |

C6 represents an amino alkyl group with 6 carbons, capital letters represent beta-D-oxy LNA nucleosides, lowercase letters represent DNA nucleosides, all LNA C are 5-methyl cytosine, subscript o represent a phosphodiester internucleoside linkage and unless otherwise indicated other internucleoside linkages are phosphorothioate internucleoside linkages.

TABLE 10

GalNAc conjugated antisense oligonucleotide compounds.

| SEQ ID NO | CMP ID NO | antisense oligonucleotide conjugate | Corresponding CMP ID of naked compound |
|---|---|---|---|
| 20 | 20_12 | GN2-C6$_o$c$_o$a$_o$TCAactttcacttCAG | 18_1 |
| 20 | 20_13 | GN2-C6$_o$c$_o$a$_o$TCAActtttcactCAG | 10_10 |
| 20 | 20_14 | GN2-C6$_o$c$_o$a$_o$TCAActtttcacttCAG | 18_19 |
| 20 | 20_15 | GN2-C6$_o$c$_o$a$_o$TCAActtttcacTtCAG | 18_5 |
| 20 | 20_16 | GN2-C6$_o$c$_o$a$_o$TCAACtttcacttCAG | 18_18 |
| 20 | 20_17 | GN2-C6$_o$c$_o$a$_o$TCAACtttcacttcAG | 18_23 |
| 20 | 20_18 | GN2-C6$_o$c$_o$a$_o$TCAActtttcacttcAG | 18_24 |
| 20 | 20_19 | GN2-C6$_o$c$_o$a$_o$TCAActtttcactTCAG | 18_12 |
| 20 | 20_20 | GN2-C6$_o$c$_o$a$_o$TcAACtttcactTcAG | 18_15 |
| 20 | 20_21 | GN2-C6$_o$c$_o$a$_o$TcAACtttcacttCAG | 18_30 |
| 20 | 20_22 | GN2-C6$_o$c$_o$a$_o$TcAaCtttcacttCAG | 18_27 |
| 20 | 20_30 | GN2-C6$_o$c$_o$a$_o$TcAActttcacttCAG | 18_357 |
| 20 | 20_31 | GN2-C6$_o$c$_o$a$_o$TCaactttcactTCAG | 18_14 |
| 20 | 20_32 | GN2-C6$_o$c$_o$a$_o$TCAaCtttcacttCAG | 18_20 |
| 20 | 20_33 | GN2-C6$_o$c$_o$a$_o$TCaaCtttcacttCAG | 18_21 |
| 20 | 20_34 | GN2-C6$_o$c$_o$a$_o$TCAaCtttcacttCAG | 18_25 |
| 20 | 20_35 | GN2-C6$_o$c$_o$a$_o$TcAactttcactTCAG | 18_346 |
| 20 | 20_36 | GN2-C6$_o$c$_o$a$_o$TcAActtttcactTCAG | 18_347 |
| 20 | 20_39 | GN2-C6$_o$c$_o$a$_o$TCAActtttcactTcAG | 18_350 |
| 20 | 20_40 | GN2-C6$_o$c$_o$a$_o$TcaACtttcacttCAG | 18_358 |
| 21 | 21_2 | GN2-C6$_o$c$_o$a$_o$TCAActtttcacttCaGT | 17_10 |
| 21 | 21_20 | GN2-C6$_o$c$_o$a$_o$TcAactttcactTcAGT | 17_7 |
| 21 | 21_21 | GN2-C6$_o$c$_o$a$_o$TcAAcfficacttCaGT | 17_13 |
| 21 | 21_22 | GN2-C6$_o$c$_o$a$_o$TCAActtttcacttcAGT | 17_14 |
| 21 | 21_23 | GN2-C6$_o$c$_o$a$_o$TCaactttcacTtCAGT | 17_51 |
| 21 | 21_24 | GN2-C6$_o$c$_o$a$_o$TCAActtttcacTtCAGT | 17_57 |
| 21 | 21_25 | GN2-C6$_o$c$_o$a$_o$TCaActtttcactTCAGT | 17_86 |
| 21 | 21_26 | GN2-C6$_o$c$_o$a$_o$TcAActttcacttTCAGT | 17_90 |
| 21 | 21_27 | GN2-C6$_o$c$_o$a$_o$TcAActttcactTCaGT | 17_96 |
| 21 | 21_28 | GN2-C6$_o$c$_o$a$_o$TCAActtttcactTCaGT | 17_99 |
| 21 | 21_29 | GN2-C6$_o$c$_o$a$_o$TcAActtttcactTCaGT | 17_103 |

TABLE 10-continued

GalNAc conjugated antisense oligonucleotide compounds.

| SEQ ID NO | CMP ID NO | antisense oligonucleotide conjugate | Corresponding CMP ID of naked compound |
|---|---|---|---|
| 21 | 21_30 | GN2-C6$_o$c$_o$a$_o$TCaactttcactTcAGT | 17_111 |
| 21 | 21_31 | GN2-C6$_o$c$_o$a$_o$TCAactttcacttCAGT | 17_129 |
| 21 | 21_32 | GN2-C6$_o$c$_o$a$_o$TCaactttcacttCAGT | 17_135 |
| 21 | 21_33 | GN2-C6$_o$c$_o$a$_o$TcAActtttcacttCAGT | 17_137 |
| 21 | 21_34 | GN2-C6$_o$c$_o$a$_o$TcAactttcacttCAGT | 17_139 |
| 21 | 21_35 | GN2-C6$_o$c$_o$a$_o$TCAactttcacttCaGT | 17_144 |
| 21 | 21_36 | GN2-C6$_o$c$_o$a$_o$TCAActtttcacttcAGT | 17_157 |
| 21 | 21_41 | GN2-C6$_o$c$_o$a$_o$TCaactttcactTCAGT | 17_89 |
| 21 | 21_42 | GN2-C6$_o$c$_o$a$_o$TCaActtttcactTCaGT | 17_100 |
| 21 | 21_43 | GN2-C6$_o$c$_o$a$_o$TCAActtttcactTcaGT | 17_119 |
| 21 | 21_44 | GN2-C6$_o$c$_o$a$_o$TCaActtttcacttCAGT | 17_132 |

Figure 2:
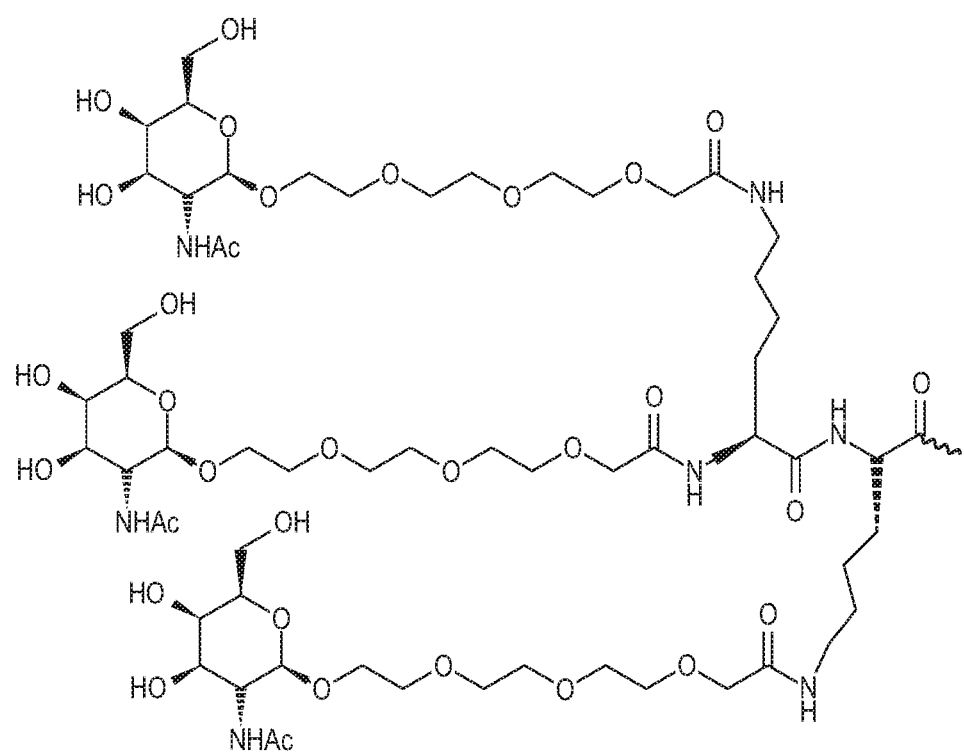

GN2 represents the trivalent GalNAc cluster shown in FIG. 2, C6 represents an amino alkyl group with 6 carbons, capital letters represent beta-D-oxy LNA nucleosides, lowercase letters represent DNA nucleosides, all LNA C are 5-methyl cytosine, subscript o represent a phosphodiester nucleoside linkage and unless otherwise indicated internucleoside linkages are phosphorothioate internucleoside linkages. Chemical drawings representing some of the molecules are shown in FIGS. 4 to 17.

AAV/HBV Mouse Models

In the AAV/HBV mouse model mice are infected with a recombinant adeno-associated virus (AAV) carrying the HBV genome (AAV/HBV) maintains stable viremia and antigenimia for more than 30 weeks (Dan Yang, et al. 2014 Cellular & Molecular Immunology 11, 71-78).

Male C57BL/6 mice (4-6 weeks old), specific pathogen free, are purchased from SLAC (Shanghai Laboratory Animal Center of Chinese Academy of Sciences) and housed in an animal care facility in individually ventilated cages. Guidelines are followed for the care and use of animals as indicated by WuXi IACUC (Institutional Animal Care and Use Committee, WUXI IACUC protocol number R20131126-Mouse). Mice are allowed to acclimate to the new environment for 3 days and are grouped according to the experimental design.

Recombinant AAV-HBV is diluted in PBS, 200 μL per injection. This recombinant virus carries 1.3 copies of the HBV genome (genotype D, serotype ayw).

On day 0, all mice are injected through tail vein with 200 μL AAV-HBV (1×10$^{11}$ vector genome). On Pre-dose Day 23 (23 days post AAV-HBV injection), animals were distributed to in groups based on serum levels of HBV markers and body weight. Each group was housed (up to 5/cage) in polycarbonate cages with corncob bedding. Low, medium, and high HBV titer values were spread, ensuring group means to be similar across groups. The animal groups can be treated with oligonucleotides which can be unconjugated or GalNAc conjugated. All serum collections (0.1 ml blood/ mouse) were performed by retro-orbital bleeding after animals were anesthetized with isoflurane inhalation.

HeLa Cell lines

HeLa cell line was purchased from European Collection of Authenticated Cell Cultures (ECACC, #93021013) and maintained as recommended by the supplier in a humidified incubator at 37° C. with 5% CO2. For assays, 2,500 cells/well were seeded in a 96 multi well plate in Eagle's Minimum Essential Medium (Sigma, M2279) with 10% fetal bovine serum (FBS), 2 mM Glutamin AQ, 1% NEAA, 25 µg/ml Gentamicin.

Differentiated HepaRG Cell Culture (No HBV Infection)

HepaRG cells (Biopredics International, Rennes, France, Cat# HPR101) were cultured at 37° C. in a humidified atmosphere with 5% CO2 in complete HepaRG growth medium consisting of William's E Medium (Sigma W4128), Growth Medium Supplement (Biopredics, Cat# ADD710) and 1% (v/v) GlutaMAX-I (Gibco #32551) for 2 weeks.

To initiate differentiation cells were grown in complete HepaRG growth medium for 2 weeks until they were fully confluent. Half of the medium was exchanged by HepaRG differentiation medium consisting of William's E Medium (Sigma W4128), Growth Medium Supplement (Biopredics, Cat# ADD720) and 1% (v/v) GlutaMAX-I (Gibco #32551), final concentration of DMSO was 0.9% (v/v)). After 3 days, medium was fully replaced by complete differentiation medium (final concentration of DMSO 1.8% (v/v)) in which cells were maintained for approximately 2 weeks with differentiation medium renewal every 7 days. Differentiated HepaRG cells (dHepaRG), displayed hepatocyte-like cell islands surrounded by monolayer of biliary-like cells. Prior to compound treatment, dHepaRG cells were seeded into collagen I coated 96-well plates (Corning BioCoat REF354407) at 80,000 cells per well in 100 µL of complete differentiation medium. Cells were allowed to recover their differentiated phenotype in 96-well plates for approximately 1 week after plating prior to oligonucleotide treatment. RNA was isolated 6 days after treatment.

HBV Infected dHepaRG Cells

HepaRG cells (Biopredics International, Rennes, France, Cat# HPR101) were cultured at 37° C. in a humidified atmosphere with 5% CO2 in complete HepaRG growth medium consisting of William's E Medium (GIBCO), Growth Medium Supplement (Biopredics, Cat# ADD711C) and 1% (v/v) GlutaMAX-I (Gibco #32551) and 1×Pen/Strep (Gibco, #15140) for 2 weeks.

To initiate differentiation, 0.9% (v/v) DMSO (Sigma-Aldrich, D2650) was added to the growth medium on confluent cells. After one week, medium was replaced by complete differentiation medium (HepaRG growth medium supplemented with 1.8% (v/v) DMSO) in which cells were maintained for approximately 4 weeks with differentiation medium renewal every 7 days. Differentiated HepaRG cells (dHepaRG), displayed hepatocyte-like cell islands surrounded by monolayer of biliary-like cells.

Prior to HBV infection and compound treatment, dHepaRG cells were seeded into collagen I coated 96-well plates (Gibco, Cat# A11428-03) at 60,000 cells per well in 100 µL of complete differentiation medium. Cells were allowed to recover their differentiated phenotype in 96-well plates for approximately 1 week after plating prior to HBV infection.

The dHepaRG cells were infected with HBV particles at an MOI of 30. The HBV particles were produced from HBV-producing HepG2.2.15 cells (Sells et al 1987 Proc Natl Acad Sci USA 84, 1005-1009). dHepaRG culture conditions, differentiation and HBV infection have been described previously (Hantz, 2009, J. Gen. Virol., 2009, 90: 127-135). In brief complete differentiation medium (HepaRG growth medium consisting of William's E Medium (GIBCO), Growth Medium Supplement (Biopredics, Cat# ADD711C) and 1% (v/v) GlutaMAX-I (Gibco #32551) and 1× Pen/Strep (Gibco, #15140), supplemented with 1.8% (v/v) DMSO), containing 4% PEG-8000 and virus stock (20 to 30 GE/cell) was added (120 µL/well). One day post-infection, the cells were washed four times with phosphate-buffered saline and medium (complete differentiation medium) was replaced on day 4 and day 7 during the experiment.

HBV Infected ASGPR-dHepaRG

From the HepaRG cell line (Biopredics International, Rennes, France, Cat# HPR101) a cell line stably overexpressing human ASGPR1 and ASGPR2 was generated using a lentiviral method. Proliferating HepaRG cells were transduced at MOI 300 with a lentivirus produced on demand by Sirion biotech (CLV-CMV-ASGPR1-T2a_ASGPR2-IRES-Puro) coding for Human ASGPR1 and 2 under the control of a CMV promoter and a puromycin resistance gene. Transduced cells were selected for 11 days with 1 µg/ml puromycin and then maintained in the same concentration of antibiotic to ensure stable expression of the transgenes. ASGPR1/2 overexpression was confirmed both at mRNA level by RT-qPCR (ASGPR1: 8560 fold vs non-transduced, ASGPR2: 2389 fold vs non-transduced), and at protein level by flow cytometry analysis. The differentiated cells are termed ASGPR-dHepaRG cells.

The ASGPR-HepaRG cells were differentiated using 1.8% DMSO for at least 2 weeks before infection. HBV infection was performed as for the dHepaRG cells described above.

Primary Mouse Hepatocytes (PMH)

Primary mouse hepatocytes were isolated from livers of C57BL/6J mice anesthetized with Pentobarbital after a 2 step perfusion protocol according to the literature (Berry and Friend, 1969, J. Cell Biol; Paterna et al., 1998, Toxicol. Appl. Pharmacol.). The first step was 5 min with HBSS+15 mM HEPES+0.4 mM EGTA followed by 12 min HBSS+20 mM NaHCO$_3$+0.04% BSA (Sigma #A7979)+4 mM CaCL$_2$ (Sigma #21115)+0.2 mg/ml Collagenase Type 2 (Worthington #4176). The Hepatocytes were captured in 5 ml cold Williams medium E (WME) (Sigma #W1878, complemented with 1× Pen/Strep/Glutamine, 10% (v/v) FBS (ATCC #30-2030)) on ice.

The crude cell suspension was filtered through a 70 µm followed by a 40 µm cell strainer (Falcon #352350 and #352340), filled up to 25 ml with WME and centrifuged at room temperature for 5 min at 50×g to pellet the hepatocytes. The supernatant was removed and the hepatocytes were resuspended in 25 ml WME. After adding 25 ml 90% Percoll solution (Sigma #P4937; pH=8.5-9.5) and centrifugation for 10 min at 25° C., 50×g the supernatant and floating cells were removed. To remove the remaining Percoll the pellet was resuspended again in 50 mL WME medium, centrifuged 3 min, 25° C. at 50×g and the supernatant discarded. The cell pellet was resuspended in 20 mL WME and cell number and viability determined (Invitrogen, Cellcount) and diluted to 250,000 cells/ml. 25,000 cells/well were seeded on collagen-coated 96-well plates (PD Biocoat Collagen I #356407) and incubated at 37° C., 5% CO$_2$. After 3-4 h, the cells were washed with WME to remove unattached cells and the medium was replaced. 24 h after seeding the oligonucleotides were added in the desired concentration and the cells were incubated at 37° C., 5% CO2 for 72 hours. RNA isolation (Qiagen, RNeasy 96) was followed by one-step RT-QPCR (Quanta Bioscience, qScript XLT 1-Step RT-qPCR ToughMix) using TaqMan assays for the target genes (PAPD5:Mm01244121_m1 FAM-MGB, PAPD7: Mm01349513_m1 FAM-MGB) and a house keeping gene (GusB Mm_01197698_m1, VIC-MGB) according to the manufacturer's protocols.

Primary Human Hepatocyte (PHH) Natural Infection Assay

Primary human hepatocytes (PHH) isolated by collagenase perfusion method from chimeric uPA/SCID mice with humanized livers were obtained from PhoenixBio (Hiroshima, Japan). The cells were plated on type I collagen coated 96-well plates at a concentration of 7×104 cells per well in culture media provided by Phoenix Bio (See Ishida et al 2015 Am J Pathol. Vol 185 page 1275-1285 for further details). HBV genotype D was derived from HepG2.2.15 cell culture supernatant and concentrated using PEG precipitation. PHHs were infected in PHH medium containing 4% PEG 8000 at MOI 10 for 20 h at 37° C. before cells were washed 4 times with PBS. One day 1 post-infection, oligonucleotide was delivered to the cells in a final volume of 125 µl of PHH medium. The cells were retreated on day 4 and 7 post-infection. At day 11 post-infection, supernatants and cells were harvested. HBsAg and HBeAg levels in the supernatants were assessed using the CLIA ELISA assay (see Materials and Method section; HBV antigen measurements). mRNA was extracted from the cells using a MagNA Pure robot and the MagNA Pure 96 Cellular RNA Large Volume Kit (Roche, #05467535001) according to the manufacturer's protocol. The relative PAPD5 and PAPD7 mRNA expression levels were analyzed using Real-time PCR as described in Materials and Methods section.

HBV Antigen Measurements

To evaluate the impact on HBV antigen expression and secretion, supernatants were collected on Day 11. The HBV propagation parameters, HBsAg and HBeAg levels, were measured using CLIA ELISA Kits (Autobio Diagnostic #CL0310-2, #CL0312-2), according to the manufacturer's protocol. Briefly, 25 µL of supernatant per well were transferred to the respective antibody coated microtiter plate and 25 µL of enzyme conjugate reagent were added. The plate was incubated for 60 min on a shaker at room temperature before the wells were washed five times with washing buffer using an automatic washer. 25 µL of substrate A and B were added to each well. The plates were incubated on a shaker for 10 min at room temperature before luminescence was measured using an Envision luminescence reader (Perkin Elmer).

Real-Time PCR for Intracellular HBV mRNA from HBV Infected Cells

HBV mRNA was quantified in technical duplicate by qPCR using a QuantStudio 12K Flex (Applied Biosystems), the TaqMan RNA-to-CT 1-Step Kit (Applied Biosystems, #4392938), Human ACTB endogenous control (Applied Biosystems, #4310881E). Taqman reagents were used together with the following commercial ThermoFisher Sceintific primers (HBV Pa03453406_s1, ACTB 4310881E). The mRNA expression was analyzed using the comparative cycle threshold 2-ΔΔCt method normalized to the reference gene ACTB and to PBS treated cells.

Real-Time PCR for PAPD5 and PAPD7 mRNA Expression

QPCR was conducted on RNA extracted from treated cells or homogenized tissue samples. After RNA/LNA duplex denaturation (90° C., 40 sec) Real-time PCR was done with a one-step protocol (gScript™ XLT One-Step RT-qPCR ToughMix®, Low ROX™ from Quanta Biosci-ence, #95134-500) in a duplex set up with the following TaqMan primer assays (ThermoFisher Scientific):
PAPD5 (Hs00223727_m1, FAM-MGB)
PAPD7 (Hs00173159_m1, FAM-MGB),
House keeping gene GUSB (Hu_4326320 E, VIC-MGB) following the recommendations of the provider.

HBV DNA Quantification Viral Particle Titer

HBV DNA extraction is performed using the QlAamp UltraSens Virus kit (Qiagen, #53704) according to the manufacturer's protocol with the following optimizations. 30 µL and 3 µL of the virus sample are diluted into 1 mL of PBS before adding buffer AC. The first centrifugation step is done for 45 min at full speed and 4° C. HBV DNA is quantified in duplicate by qPCR using a QuantStudio 12K Flex (Applied Biosystems), the TaqMan Gene Expression Master Mix (Applied Biosystems, #4369016) and a premix 1:1:0.5 of the primers indicated in Table 9 above and probe reconstituted at 100 µM. The qPCR is performed using the following settings: UDG incubation (2 min, 50° C.), enzyme activation (10 min, 95° C.) and qPCR (40 cycles with 15 sec, 95° C. for denaturation and 1 min, 60° C. for annealing and extension). Genomes equivalent calculation is based on a standard curve generated from HBV genotype D plasmid dilutions with known concentrations.

The HBV particle titer can be determined using HBV core-specific primer (Integrated DNA Technologies) (Table 11) in a QPCR on isolated intracellular mRNA from treated cells.

TABLE 11

HBV core specific TaqMan probes

| Name | Dye | Sequence | SEQ ID NO |
|---|---|---|---|
| HBV core Primer Forward (F3_HBVcore) | | CTG TGC CTT GGG TGG CTT T | 24 |
| Reverse (R3_HBVcore) | | AAG GAA AGA AGT CAG AAG GCA AAA | 25 |
| Probe (P3_HBVcore) | FAM-MGB | AGC TCC AAA/ZEN/TTC TTT ATA AGG GTC GAT GTC CAT G | 26 |

ZEN is an internal quencher

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 µmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle, a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THF/Pyridine/water 7:2:1. The rest of the reagents are the ones typically used for oligonucleotide synthesis.

For post solid phase synthesis conjugation a commercially available C6 aminolinker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10µ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography
$T_m$ Assay:

Oligonucleotide and RNA target (phosphate linked, PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Example 1: Screening for In Vitro Efficacy of Antisense Oligonucleotides Targeting PAPD5 and PAPD7 (Bispecific) in HeLa Cells An oligonucleotide screen was done using 16 to 18mer gapmers targeting SEQ ID NO: 17, 18 and 19. Efficacy testing was performed in an in vitro experiment in HeLa cells expressing both PAPD5 and PAPD7.

HeLa cells were cultured as described in the Materials and Method section. The cells were incubated for 24 hours before addition of oligonucleotides dissolved in PBS. Final concentration of oligonucleotides was 5 and 25 µM, the final culture volume was 100 µl/well. The cells were harvested 3 days after addition of oligonucleotide compounds and RNA was extracted using the PureLink Pro 96 RNA Purification kit (Ambion), according to the manufacturer's instructions.

PAPD5 and PAPD7 mRNA levels were analysed by Real-time PCR as described in the Materials and Method section.

The relative PAPD5 mRNA and PAPD7 mRNA expression levels are shown in table 12 as % of average control samples (PBS-treated cells) i.e. the lower the value the larger the inhibition.

TABLE 12 in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control | | | | % PAPD7 mRNA of control | | | | Compound (CMP) |
|---|---|---|---|---|---|---|---|---|---|
| | 25 µM | | 5 µM | | 25 µM | | 5 µM | | |
| | Avg | sd | Avg | sd | Avg | sd | Avg | sd | |
| 17_2 | 35.36 | 0.58 | 69.86 | 3.08 | 31.55 | 0.88 | 89.02 | 14.48 | TCaaCtttcacTtcAGT |
| 17_3 | 13.76 | 1.40 | 35.71 | 3.94 | 11.56 | 1.63 | 56.65 | 11.86 | TCaactttcacTtcAGT |
| 17_4 | 39.72 | 2.23 | 51.51 | 4.97 | 83.29 | 11.18 | 117.6 | 14.81 | TcaaCtttcacTtcAGT |
| 17_5 | 24.87 | 2.09 | 53.56 | 8.57 | 62.21 | 2.96 | 27.92 | 2.32 | TCaactttcacTtcaGT |
| 17_6 | 19.50 | 1.22 | 34.68 | 0.37 | 14.51 | 0.16 | 82.74 | 26.43 | TCaaCtttcactTCaGT |
| 17_7 | 6.17 | 1.04 | 22.09 | 0.01 | 13.47 | 3.64 | 20.41 | 3.12 | TcAactttcactTcAGT |
| 17_8 | 9.85 | 1.44 | 28.15 | 4.60 | 25.29 | 4.47 | 26.39 | 3.48 | TcAActtttcactTcaGT |
| 17_9 | 18.73 | 2.57 | 47.62 | 3.48 | 31.00 | 3.51 | 58.02 | 6.32 | TCAActtttcacttCaGT |
| 17_10 | 6.13 | 1.18 | 23.39 | 0.44 | 5.88 | 0.34 | 31.76 | 3.25 | TCAActtttcacttCaGT |
| 17_11 | 14.04 | 2.09 | 31.58 | 4.40 | 42.82 | 6.50 | 86.43 | 11.95 | TCaaCtttcacttCaGT |
| 17_12 | 15.33 | 0.62 | 29.82 | 1.07 | 34.94 | 5.35 | 51.77 | 3.89 | TCaactttcacttCaGT |
| 17_13 | 6.63 | 0.34 | 23.62 | 9.01 | 8.49 | 0.51 | 20.44 | NA | TcAActtttcacttCaGT |
| 17_14 | 4.61 | 1.98 | 22.51 | 5.00 | 6.19 | 0.36 | 44.27 | 6.69 | TCAacttttcacttcAGT |

TABLE 12-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control | | | | % PAPD7 mRNA of control | | | | Compound (CMP) |
|---|---|---|---|---|---|---|---|---|---|
| | 25 µM | | 5 µM | | 25 µM | | 5 µM | | |
| | Avg | sd | Avg | sd | Avg | sd | Avg | sd | |
| 17_15 | 17.99 | 2.70 | 32.73 | 4.67 | 26.59 | 2.61 | 38.30 | 4.15 | TCaaCtttcacttcAGT |
| 17_16 | 42.29 | 1.06 | 75.49 | 6.32 | 26.91 | 1.57 | 46.19 | 0.88 | TCaactttcacttcaGT |
| 18_2 | 41.16 | 0.15 | 65.30 | 5.51 | 48.83 | 6.29 | 63.37 | 10.84 | TCaaCtttcacTTCAG |
| 18_3 | 54.39 | 3.08 | 71.95 | 2.89 | 69.99 | 0.89 | 66.50 | 3.56 | TcAACtttcacTTcAG |
| 18_4 | 40.86 | 1.32 | 64.99 | 4.39 | 78.13 | 1.60 | 109.0 | 0.49 | TCAAtttcacTtCAG |
| 18_5 | 9.30 | 0.76 | 27.26 | 0.91 | 7.32 | 1.32 | 14.80 | 1.92 | TCAActttcacTtCAG |
| 18_6 | 7.49 | 0.75 | 21.64 | 2.49 | 10.32 | 0.39 | 14.16 | 0.82 | TCaactttcacTtCAG |
| 18_7 | 25.02 | 0.30 | 47.25 | 4.07 | 37.93 | 10.34 | 68.66 | 5.11 | TcaaCtttcacTtCAG |
| 18_8 | 22.93 | 8.09 | 44.18 | 1.59 | 33.95 | 7.34 | 39.70 | 5.06 | TCaActttcacTtCAG |
| 18_9 | 15.21 | 2.21 | 39.74 | 0.32 | 12.21 | 1.80 | 23.08 | 0.01 | TCAACtttcactTCAG |
| 18_10 | 3.99 | 0.67 | 20.53 | 4.40 | 7.81 | 0.52 | 23.89 | 2.49 | TCAActttcactTCAG |
| 18_11 | 13.84 | 3.93 | 35.46 | 1.52 | 28.39 | 1.96 | 56.56 | 11.43 | TCaaCtttcactTCAG |
| 18_12 | 5.13 | 0.14 | 20.21 | 0.24 | 3.40 | 0.29 | 41.51 | 7.20 | TCAactttcactTCAG |
| 18_13 | 11.90 | 1.05 | 26.20 | 0.47 | 26.51 | 0.82 | 20.79 | 5.61 | TCaaCtttcactTCAG |
| 18_14 | 5.42 | 0.33 | 20.05 | 2.62 | 8.85 | 1.46 | 66.72 | 8.16 | TCaactttcactTCAG |
| 18_15 | 7.16 | 0.03 | 20.84 | 1.94 | 6.17 | 0.05 | 46.67 | 1.26 | TcAACtttcactTcAG |
| 18_16 | 14.28 | 2.44 | 33.79 | 1.00 | 29.49 | 1.95 | 16.87 | 2.38 | TCAaCtttcactTcAG |
| 18_17 | 27.49 | 2.66 | 61.62 | 9.21 | 55.71 | 3.61 | 36.14 | 0.32 | TcaaCtttcactTcAG |
| 18_18 | 5.43 | 0.61 | 26.45 | 0.75 | 3.16 | 0.61 | 35.64 | 2.03 | TCAACtttcacttCAG |
| 18_19 | 4.85 | 1.04 | 17.24 | 1.69 | 12.48 | 0.60 | 13.12 | 0.88 | TCAActttcacttCAG |
| 18_20 | 5.51 | 0.05 | 20.28 | 1.07 | 12.76 | 1.24 | 14.83 | 0.13 | TCAaCtttcacttCAG |
| 18_21 | 10.64 | 0.32 | 23.88 | 1.67 | 12.61 | 0.50 | 14.50 | 1.05 | TCaaCtttcacttCAG |
| 18_22 | 10.66 | 1.95 | 34.29 | 7.33 | 16.22 | 1.84 | 25.81 | 7.43 | TCaactttcacttCAG |
| 18_23 | 5.50 | 1.99 | 24.63 | 0.61 | 10.97 | 0.12 | 27.22 | 1.51 | TCAACtttcacttcAG |
| 18_24 | 8.37 | 0.44 | NA | NA | 12.02 | 1.77 | NA | NA | TCAActttcacttcAG |
| 18_25 | 7.58 | 0.80 | 23.71 | 3.32 | 9.03 | 0.05 | 19.79 | 1.14 | TCAaCtttcacttcAG |
| 18_26 | 12.94 | 0.46 | 35.03 | 2.99 | 25.90 | 0.06 | 28.01 | 0.45 | TCAacttcacttcAG |
| 18_27 | 7.21 | 1.46 | 21.24 | 2.15 | 19.27 | 2.92 | 72.92 | 25.73 | TCaACtttcacttcAG |
| 18_28 | 15.47 | 4.10 | 39.98 | 4.60 | 14.80 | 0.36 | 43.25 | 5.37 | TCaaCtttcacttcAG |
| 18_29 | 32.76 | 9.68 | 43.53 | 4.96 | 21.47 | 5.16 | 34.84 | 0.17 | TCaactttcacttcAG |
| 18_30 | 4.45 | 0.12 | 20.61 | 5.21 | 10.94 | 1.63 | 24.09 | 0.58 | TcAACtttcacttcAG |
| 18_31 | 55.81 | 9.87 | 71.92 | 22.31 | 50.86 | 4.18 | 60.22 | 0.42 | TcaaCtttcacttcAG |
| 19_1 | 101.9 | 10.60 | 89.66 | 13.79 | 59.35 | 6.51 | 160.6 | 2.10 | TGTTTcaatacTAAAA |
| 19_2 | 90.94 | 1.54 | 68.65 | 6.91 | 59.66 | 1.75 | 60.33 | 1.98 | TGTTtcaatacTAAAA |
| 19_3 | 104.6 | 13.82 | 86.79 | 12.54 | 80.71 | 0.60 | 68.25 | 5.99 | TGTTTcaatacTAaAA |

Example 2: In Vitro EC50 and Efficacy in HBV Infected HepaRG Cells

All the oligonucleotides from Example 1 were tested for their effect on HBV propagation parameters in HBV infected dHepaRG cells.

For comparative purposes the antisense oligonucleotides of the invention were compared to antisense oligonucleotides targeting HBV mRNA directly. The HBV targeting oligonucleotides are shown in table 13.

TABLE 13

Comparative HBV targeting oligonucleotides

| Description | Compound | SEQ ID NO | Reference |
|---|---|---|---|
| HBV targeting 1 (HBV1) | AGCgaagtgcacaCGG | 27 | WO2015/173208 |
| HBV targeting 2 (HBV2) | GCGtaaagagaGG | 28 | WO2015/173208 |

HBV infected dHepaRG cells (described in the Materials and Methods section, HBV infected dHepaRG cells) were cultured in 96-well plates. One day post HBV infection the oligonucleotides were added to the cells in three-fold serial dilutions (20.00, 6.67, 2.22, 0.74, 0.25, 0.08, 0.03, 0.01 µM oligonucleotide) using unassisted uptake (gymnosis). A total of 49 oligonucleotides were tested. The experiment was conducted in triplicate, with PBS controls. The oligonucleotide treatment was repeated at day 4 and 7.

At day 11 post-infection, supernatants and cells were harvested.

HBsAg and HBeAg levels in the supernatants were assessed using the CLIA ELISA assay (see Materials and Methods, HBV antigen measurements).

EC 50, max KD (efficacy) of the HBV propagation parameters HBsAg and HBeAg was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in table 14 and are % of average control samples (PBS control and Non infected (NIF), calculated as follows [(Test Value−meanPBS)/(mean-NIF−meanPBS)]*100)).

TABLE 14

EC50 and Max KD of anti-PAPD5/PAPD7 compounds on HBsAg and HBeAg (average of 3) in HBV infected dHepaRG cells.

| CMP ID NO | HBsAg Max KD % of saline Avg | sd | EC50 µM Avg | sd | HBeAg Max KD % of saline Avg | sd | EC50 µM Avg | sd | Compound |
|---|---|---|---|---|---|---|---|---|---|
| 17_7 | 57.18 | 6.67 | 7.36 | 20.66 | 33.61 | 10.44 | 7.07 | 15.94 | TcAactttcactTcAGT |
| 17_8 | 28.29 | 13.46 | 4.75 | 1.59 | 23.75 | 11.32 | 5.14 | 1.69 | TcAActttcactTcaGT |
| 17_10 | 19.10 | 4.81 | 6.73 | 15.00 | 2.28 | 11.52 | 6.63 | 2.67 | TCAActttcacttCaGT |
| 17_13 | 22.07 | 8.55 | 5.74 | 1.01 | 4.09 | 15.51 | 4.40 | 1.52 | TcAActttcacttCaGT |
| 17_14 | 0.00 | 855.97 | 24.07 | 61.33 | 1.04 | NA | 21.37 | NA | TCAactttcacttcAGT |
| 18_1 | 5.42 | 9.05 | 4.67 | 0.71 | 5.88 | 14.10 | 4.12 | 1.22 | TCAactttcacttCAG |
| 18_5 | 4.70 | 9.40 | 6.67 | 1.20 | 0.30 | 7.04 | 4.86 | 0.80 | TCAActttcacTtCAG |
| 18_6 | 26.99 | 12.22 | 6.66 | 1.39 | 22.14 | 9.60 | 6.40 | 3.64 | TCaactttcacTtCAG |
| 18_10 | 0.00 | 10.01 | 4.94 | 0.88 | 2.68 | 10.92 | 4.40 | 1.09 | TCAActttcactTCAG |
| 18_12 | 14.01 | 8.21 | 6.52 | 0.60 | 3.86 | 14.96 | 6.12 | 1.14 | TCAActttcactTCAG |
| 18_15 | 15.87 | 25.90 | 6.22 | 3.82 | 32.23 | 7.88 | 2.10 | 4.75 | TcAACtttcactTcAG |
| 18_18 | 8.11 | 11.24 | 7.21 | 1.14 | 8.75 | 6.36 | 6.58 | 5.28 | TCAACtttcacttCAG |
| 18_19 | 3.43 | 3.49 | 2.32 | 0.18 | 3.75 | 5.69 | 2.16 | 3.09 | TCAActttcacttCAG |
| 18_20 | 36.72 | 4.45 | 7.05 | 17.16 | 0.00 | 74.91 | 8.07 | 9.71 | TCAaCtttcacttCAG |
| 18_21 | 26.03 | 51.79 | 9.16 | 9.36 | 0.00 | 92.94 | 10.13 | 14.18 | TCaaCtttcacttCAG |
| 18_23 | 11.13 | 7.74 | 5.53 | 0.76 | 6.33 | 9.42 | 4.82 | 0.99 | TCAACtttcacttcAG |
| 18_24 | 11.95 | 8.90 | 3.64 | 0.82 | 13.90 | 10.15 | 2.36 | 0.62 | TCActttcacttcAG |
| 18_25 | 25.93 | 17.79 | 7.90 | 2.60 | 19.84 | 10.18 | 6.78 | 4.08 | TCAaCtttcacttcAG |
| 18_30 | 16.85 | 5.93 | 2.51 | 0.38 | 12.47 | 8.12 | 2.22 | 0.27 | TcAACtttcacttcAG |
| 17_3 | 93.91 | 127.26 | 32.39 | 329.47 | 89.14 | 8.47 | 0.91 | 10.00 | TCaactttcacTtcAGT |

TABLE 14-continued

EC50 and Max KD of anti-PAPD5/PAPD7 compounds on HBsAg and HBeAg
(average of 3) in HBV infected dHepaRG cells.

| | HBsAg | | | | HBeAg | | | | |
|---|---|---|---|---|---|---|---|---|---|
| CMP ID NO | Max KD % of saline | | EC50 µM | | Max KD % of saline | | EC50 µM | | Compound |
| | Avg | sd | Avg | sd | Avg | sd | Avg | sd | |
| 17_5 | 90.80 | 7.82 | 1.31 | 10.00 | 95.11 | 10.13 | 0.10 | 10.00 | TCaactttcacTtcaGT |
| 17_6 | 92.43 | NA | 0.57 | NA | 89.80 | NA | 0.00 | NA | TCaaCtttcactTCaGT |
| 17_9 | 54.71 | 6.03 | 7.08 | 14.69 | 15.37 | 35.83 | 8.44 | 3.80 | TCAActttcacttCaGT |
| 17_11 | 83.26 | 7.52 | 3.61 | 10.00 | 62.66 | 9.37 | 0.58 | 10.00 | TCaaCtttcacttCaGT |
| 17_12 | 97.35 | 7.36 | 19.89 | 10.00 | 78.78 | 8.65 | 0.35 | 10.00 | TCaactttcacttCaGT |
| 17_15 | 91.43 | NA | 0.67 | NA | 78.81 | 8.76 | 0.46 | 10.00 | TCaaCtttcacttcAGT |
| 18_7 | 90.45 | NA | 11.53 | NA | 85.05 | 8.27 | 0.34 | 10.00 | TcaaCtttcacTtcAG |
| 18_8 | 63.76 | 12.80 | 5.22 | 1.98 | 52.50 | 9.20 | 4.77 | 1.14 | TCaActtttcacTtcAG |
| 18_9 | 23.40 | 156.35 | 12.06 | 23.00 | 26.07 | 11.37 | 7.57 | 16.01 | TCAActtttcactTCAG |
| 18_11 | 0.00 | 236.59 | 23.95 | 50.46 | 0.05 | NA | 18.25 | NA | TCAactttcactTCAG |
| 18_13 | 53.81 | 6.31 | 7.16 | 11.60 | 42.15 | 8.15 | 7.31 | 13.89 | TCaaCtttcactTCAG |
| 18_14 | 32.71 | 11.10 | 5.13 | 1.25 | 24.27 | 14.19 | 4.20 | 1.31 | TCaactttcactTCAG |
| 18_16 | 81.65 | 6.89 | 7.15 | 17.43 | 72.67 | 8.30 | 7.01 | 9.77 | TCaaCtttcactTcAG |
| 18_22 | 29.19 | 5.87 | 6.40 | 7.22 | 16.60 | 18.52 | 4.54 | 1.31 | TCaactttcacttCAG |
| 18_26 | 40.75 | 8.16 | 5.35 | 0.90 | 36.63 | 6.43 | 5.34 | 1.09 | TCAactttcacttcAG |
| 18_27 | 20.92 | 10.83 | 4.61 | 1.10 | 13.89 | 13.63 | 4.03 | 1.20 | TCaACtttcacttcAG |
| 18_28 | 67.96 | 9.83 | 8.11 | 77.37 | 47.21 | 2274.28 | 18.70 | 138.89 | TCaaCtttcacttcAG |
| 17_2 | 84.70 | 14.17 | 0.28 | 10.00 | 61.86 | 9.52 | 0.21 | 10.00 | TCaaCtttcacTtcAGT |
| 17_4 | 85.48 | 10.18 | 0.31 | 10.00 | 55.95 | 9.53 | 0.13 | 10.00 | TCaaCtttcacTtcAGT |
| 17_16 | 68.31 | 10.41 | 0.10 | 10.00 | 39.65 | 9.69 | 0.27 | 10.00 | TCaactttcacttcaGT |
| 18_2 | 94.41 | 8.20 | 0.47 | 10.00 | 61.03 | 9.43 | 0.28 | 10.00 | TCaaCtttcacTTCAG |
| 18_3 | 68.72 | 9.16 | 0.24 | 10.00 | 51.03 | 9.02 | 0.14 | 10.00 | TcAACtttcacTTcAG |
| 18_4 | 92.64 | 8.61 | 0.12 | 10.00 | 85.97 | 8.77 | 0.18 | 10.00 | TCAACtttcacTtCAG |
| 18_17 | 71.76 | 8.21 | 0.59 | 10.00 | 49.14 | 8.82 | 0.83 | 10.00 | TcaaCtttcactTcAG |
| 18_29 | 81.88 | 9.30 | 1.00 | 10.00 | 72.13 | 9.16 | 0.24 | 10.00 | TCaactttcacttcAG |
| 18_31 | 73.12 | 9.07 | 0.43 | 10.00 | 73.76 | 8.47 | 0.47 | 10.00 | TcaaCtttcacttcAG |
| 19_1 | 82.69 | 9.37 | 0.20 | 10.00 | 96.30 | 10.43 | 0.06 | 10.00 | TGTTTcaatacTAAAA |
| 19_2 | 85.50 | 16.76 | 0.27 | 10.00 | 83.38 | 8.96 | 0.24 | 10.00 | TGTTtcaatacTAAAA |
| 19_3 | 103.91 | NA | 0.30 | NA | 108.39 | 8.81 | 0.09 | 10.00 | TGTTTcaatacTAaAA |
| HBV1 | 0.00 | 16.32 | 2.44 | 1.22 | 0.00 | 23.37 | 1.33 | 1.09 | AGCgaagtgcacaCGG |
| HBV2 | 0.00 | 55.69 | 16.80 | 19.97 | 0.00 | NA | 20.73 | NA | GCGtaaagagaGG |

From these data it can be seen that a significant number of the compounds have a good effect on HBsAg and HBeAg. Compounds with the oligonucleotide motif of SEQ ID NO 17 and 18 seem more efficient than the compounds that have been made with the motif of SEQ ID NO: 19

Figure 3:
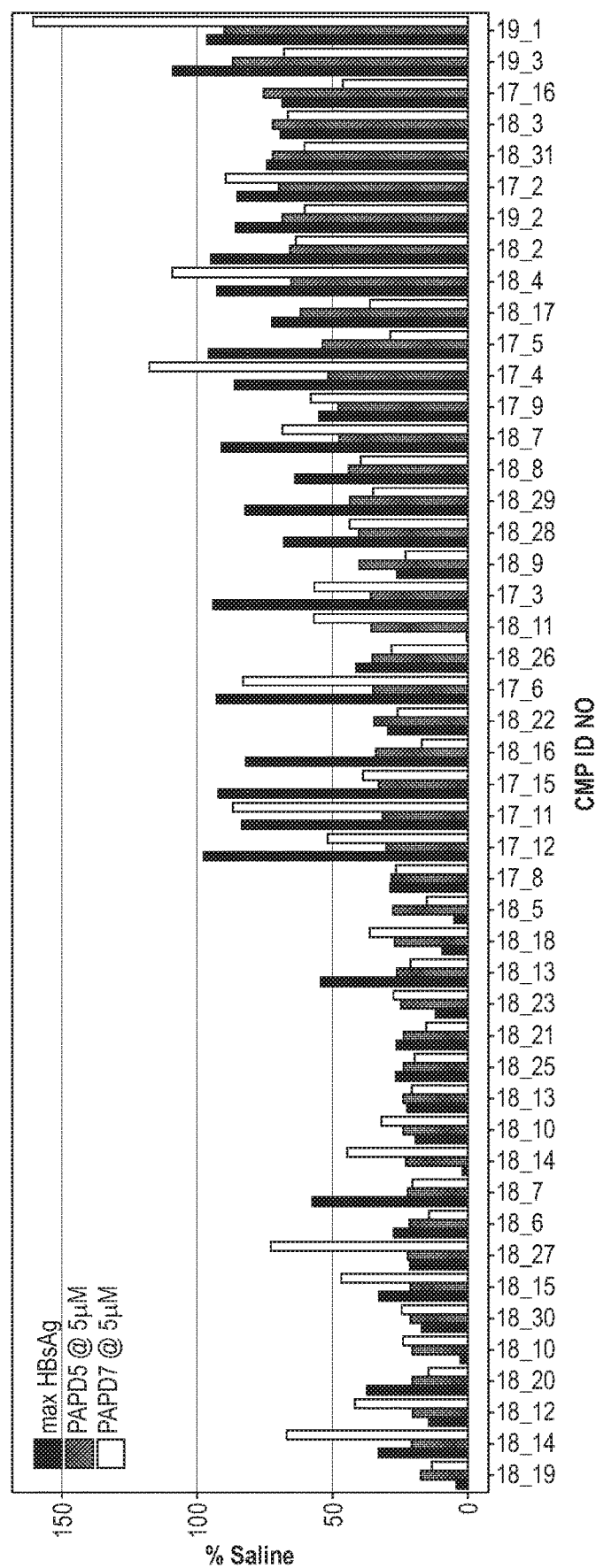
Figure 4:
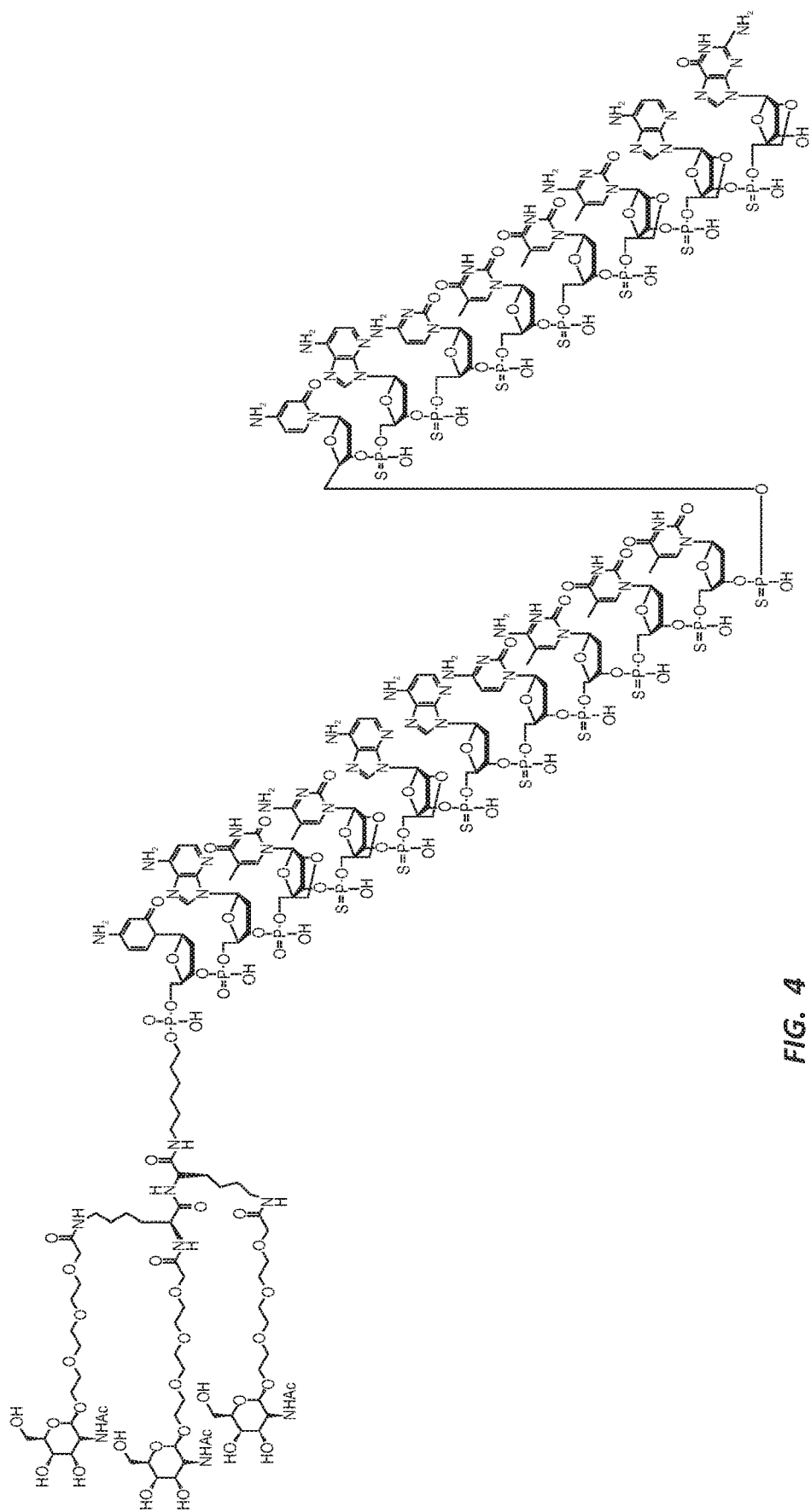
Figure 5:
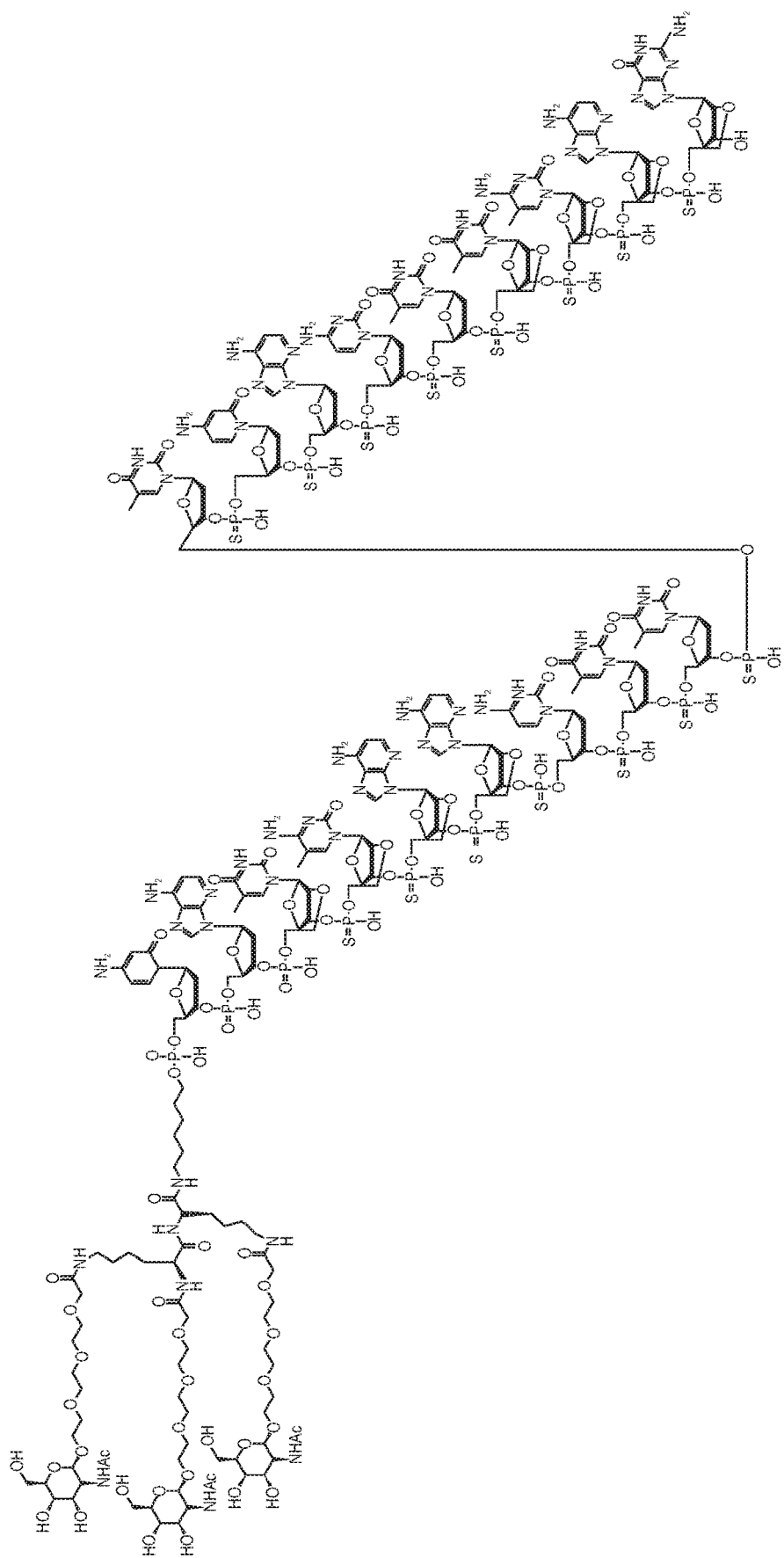
Figure 6:
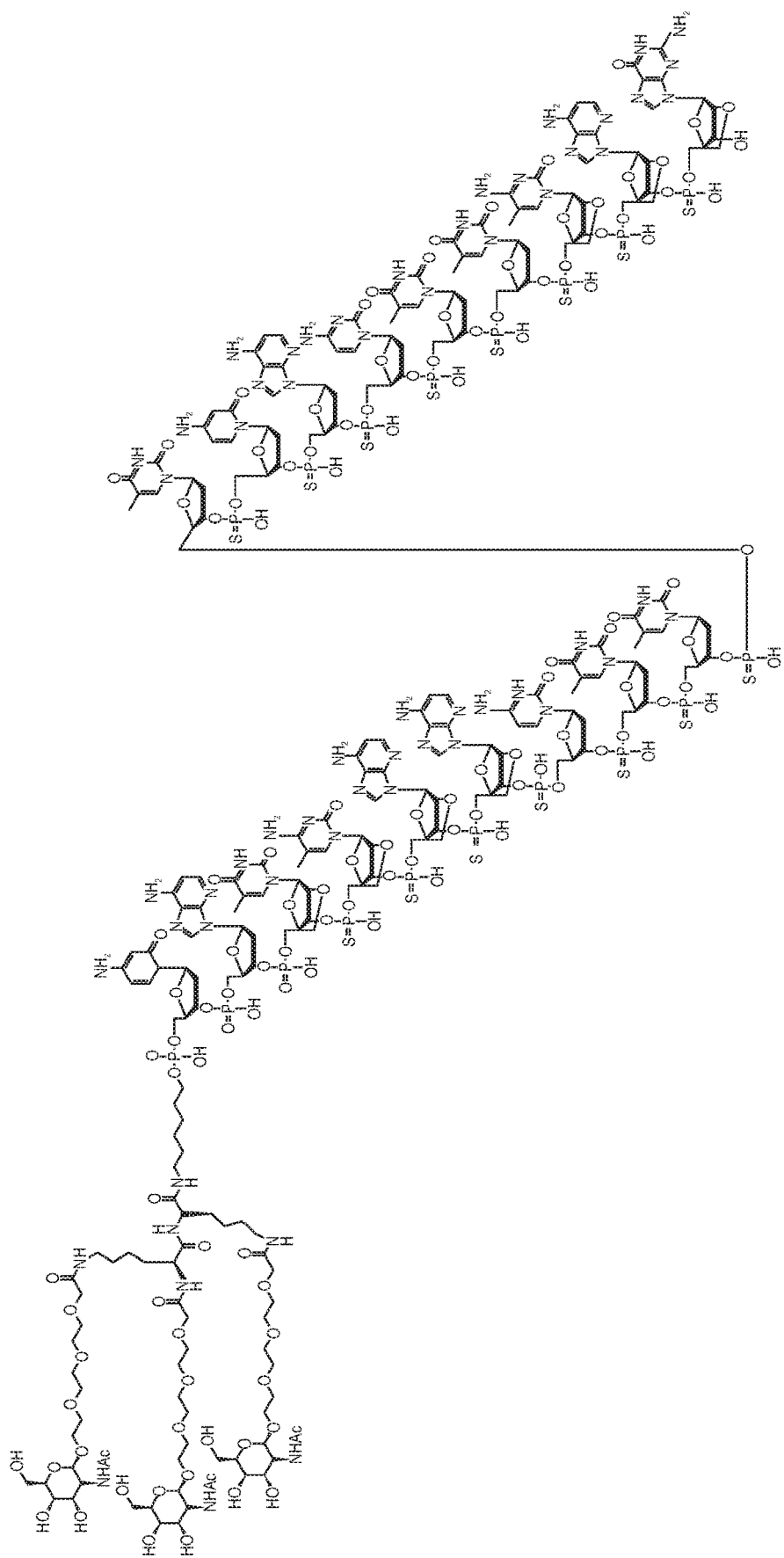
Figure 7:
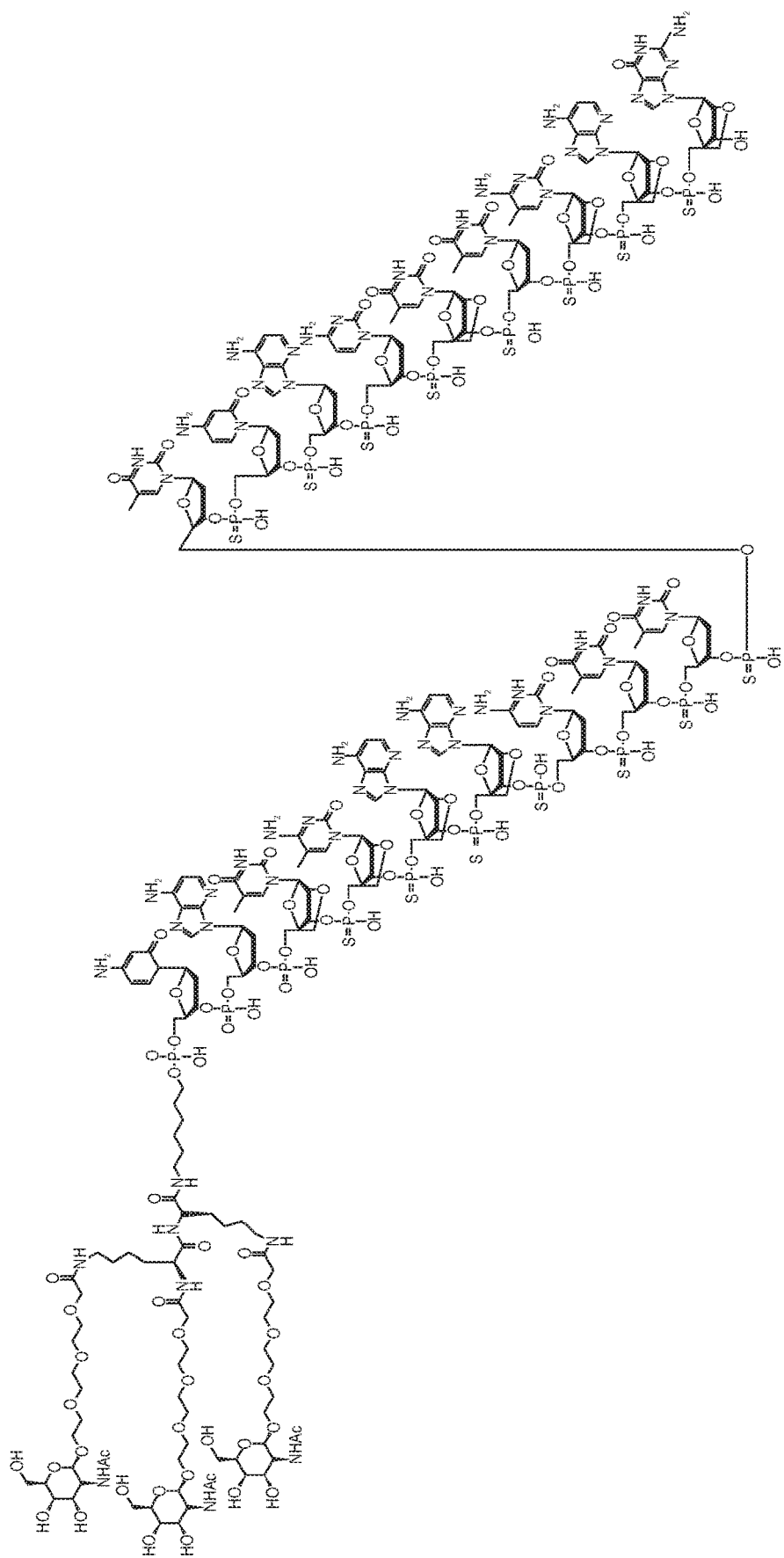
Figure 8:
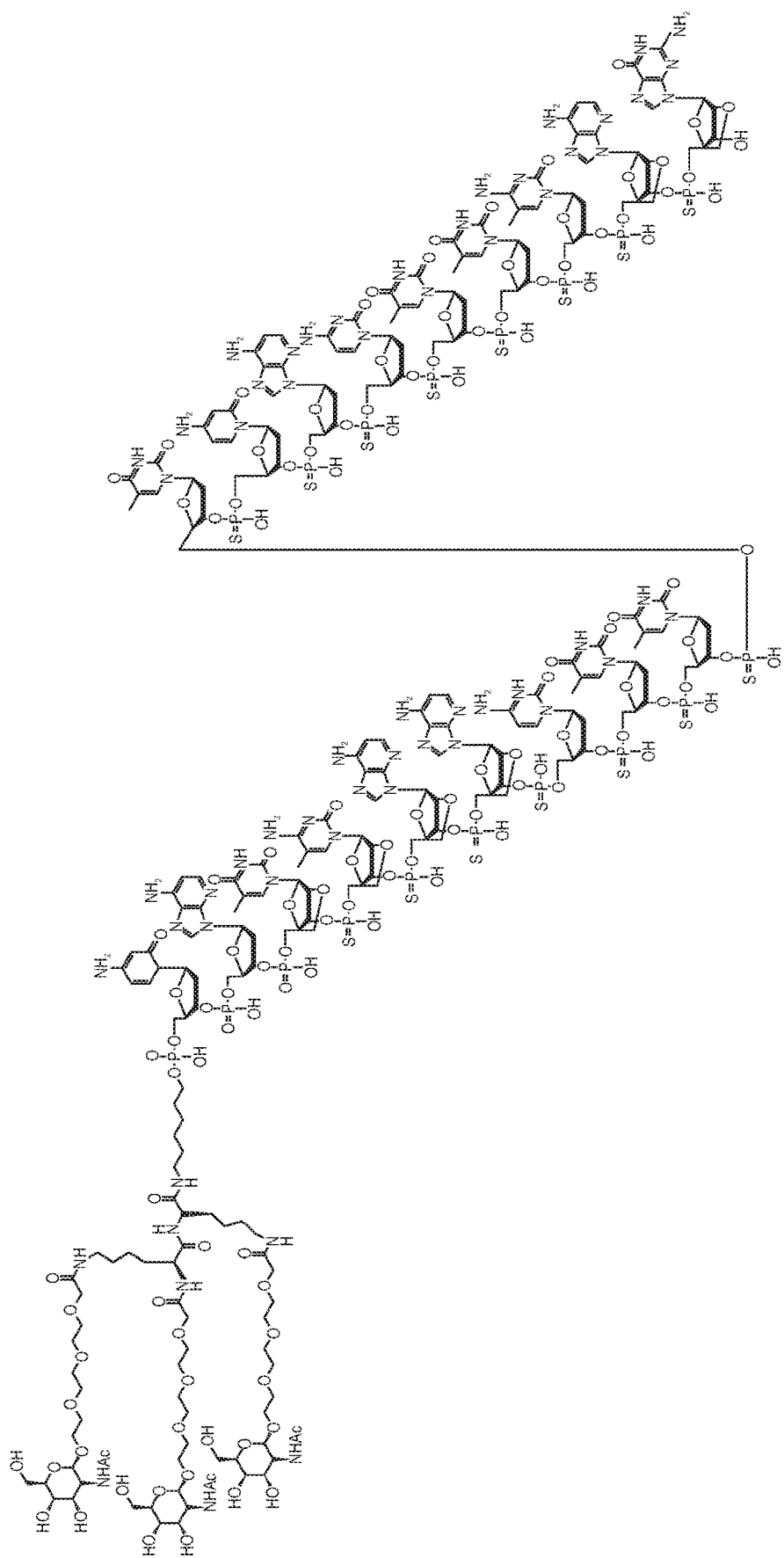
Figure 9:
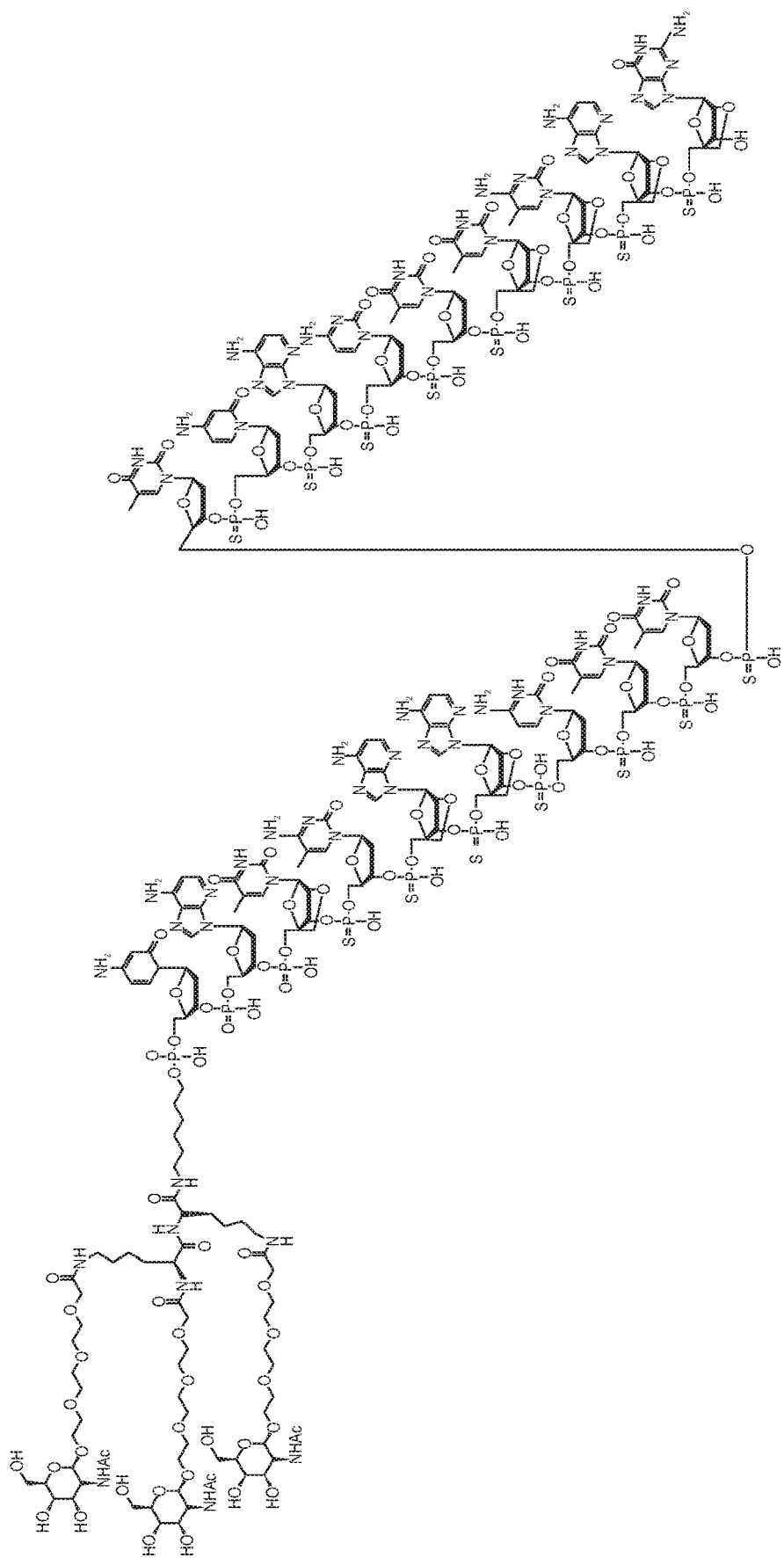
Figure 10:
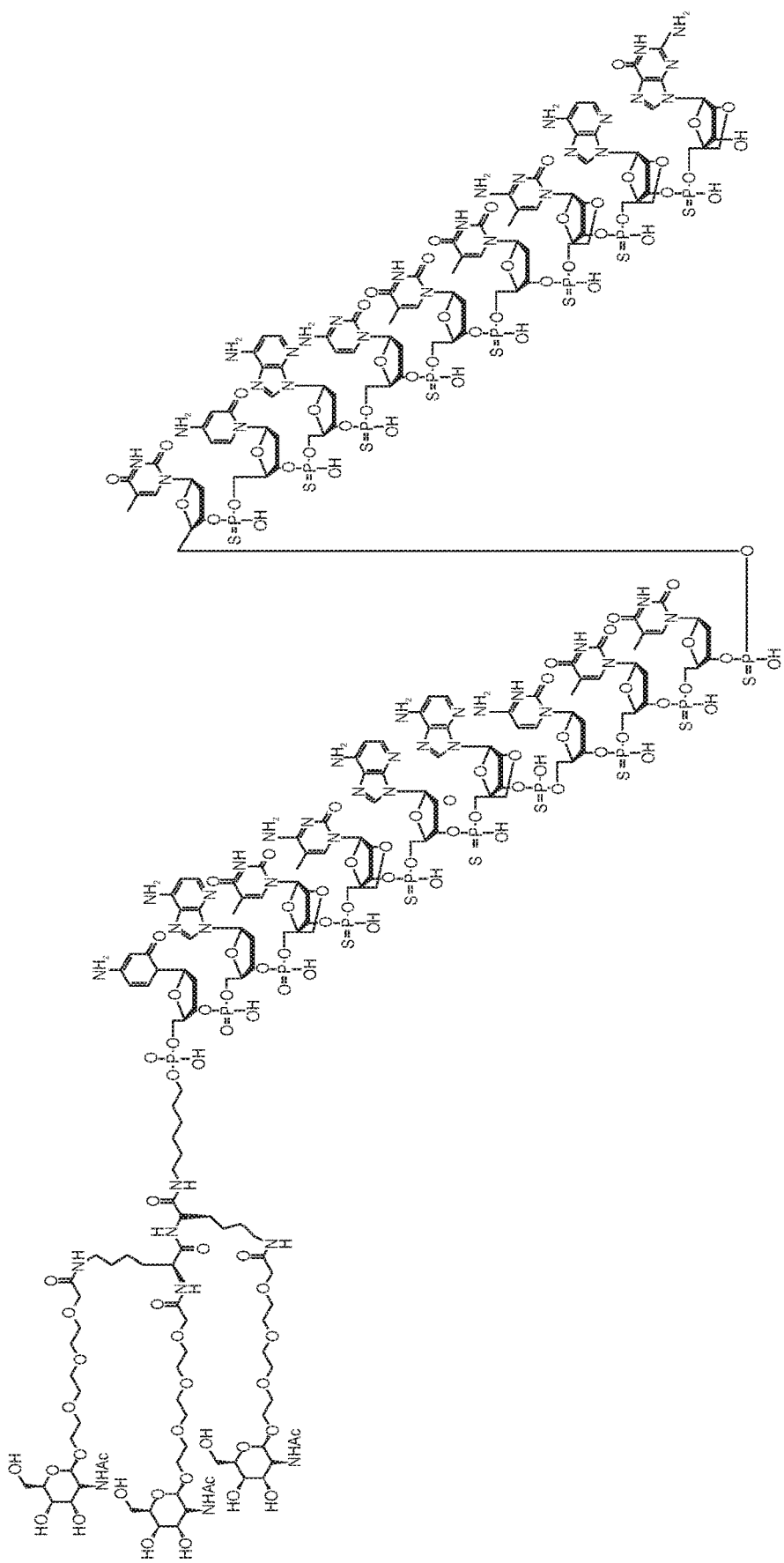

In FIG. 3, it can also be seen that for oligonucleotides that reduce PAPD5 and PAPD7 in HeLa cells with more than 70% there is a high correlation with respect to these oligonucleotides ability to reduce HBsAg in HBV infected dHepaRG cells.

Example 3 Screening for In Vitro Efficacy of Antisense Oligonucleotides Targeting PAPD5 and PAPD7 in HeLa Cells A further library of 298 oligonucleotides expanding the diversity of the oligonucleotide motifs of SEQ ID NO: 17, 18 and 19 using different designs was generated. Efficacy testing was performed in an in vitro experiment as described in Example 1, with the exception that the screening was only conducted at 5 µM.

The relative PAPD5 mRNA and PAPD7 mRNA expression levels are shown in table 15 as % of average control samples (PBS-treated cells) i.e. the lower the value the larger the inhibition.

TABLE 15 in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 5 µM Avg | sd | % PAPD7 mRNA of control 5 µM Avg | sd | Compound (CMP) |
|---|---|---|---|---|---|
| 17_17 | 97.74 | 7.10 | 88.55 | 3.38 | TCAaCtttcacTTCAGT |
| 17_18 | 86.48 | 5.52 | 81.81 | 1.73 | TcAACtttcacTTCAGT |
| 17_19 | 66.13 | 13.83 | 78.41 | 1.05 | TCaaCtttcacTTCAGT |
| 17_20 | 62.79 | 2.79 | 61.90 | 1.55 | TCaactttcacTTCAGT |
| 17_21 | 86.77 | 5.77 | 84.45 | 2.79 | TcAACtttcacTTCAGT |
| 17_22 | 83.56 | 9.69 | 76.97 | 2.27 | TcAAcTttcacTTCAGT |
| 17_23 | 75.81 | 5.73 | 73.23 | 5.44 | TcaaCtttcacTTCAGT |
| 17_24 | 97.11 | NA | 88.80 | 2.14 | TCAACtttcacTTCaGT |
| 17_25 | 62.02 | 5.46 | 64.52 | 2.73 | TCAActttcacTTCaGT |
| 17_26 | 90.95 | 11.41 | 92.31 | 2.78 | TCAaCtttcacTTCaGT |
| 17_27 | 75.23 | 6.15 | 75.70 | 3.92 | TCAacTttcacTTCaGT |
| 17_28 | 57.34 | 11.56 | 51.15 | 2.33 | TCAactttcacTTCaGT |
| 17_29 | 86.07 | 8.22 | 79.21 | 4.63 | TCaACtttcacTTCaGT |
| 17_30 | 82.66 | 3.99 | 82.55 | 7.92 | TCaAcTttcacTTCaGT |
| 17_31 | 63.66 | 7.08 | 58.10 | 6.16 | TCaActttcacTTCaGT |
| 17_32 | 70.24 | 8.96 | 74.38 | 4.15 | TCaaCtttcacTTCaGT |
| 17_33 | 62.01 | 4.54 | 66.85 | 2.18 | TCaacTttcacTTCaGT |
| 17_34 | 47.04 | 1.05 | 53.40 | 3.12 | TCaactttcacTTCaGT |
| 17_35 | 77.50 | 7.79 | 79.78 | 1.36 | TcAACtttcacTTCaGT |
| 17_36 | 100.06 | 11.65 | 81.00 | 3.56 | TCAACtttcacTTcAGT |
| 17_37 | 85.23 | 8.93 | 80.34 | 2.60 | TCAAcTttcacTTcAGT |
| 17_38 | 68.09 | 6.84 | 70.24 | 2.54 | TCAActttcacTTcAGT |
| 17_39 | 75.83 | 14.88 | 74.95 | 1.29 | TcAAcTttcacTTcAGT |
| 17_40 | 60.89 | 6.53 | 69.40 | 1.14 | TcaAcTttcacTTcAGT |
| 17_41 | 67.33 | 12.02 | 73.92 | 1.59 | TcaaCtttcacTTcAGT |
| 17_42 | 55.60 | 7.22 | 68.28 | 1.86 | TcaacTttcacTTcAGT |
| 17_43 | NA | NA | 73.73 | 6.69 | TcAACtttcacTTcaGT |
| 17_44 | 78.69 | 9.83 | 69.98 | 3.35 | TcAaCtttcacTTcaGT |
| 17_45 | 76.31 | 5.75 | 77.93 | 6.73 | TcaaCtttcacTTcaGT |
| 17_46 | 82.77 | 4.94 | 88.62 | 3.06 | TCAACtttcacTtCAGT |
| 17_47 | 75.09 | 3.28 | 75.56 | NA | TCAaCtttcacTtCAGT |
| 17_48 | 41.87 | 3.23 | 46.58 | 4.31 | TCaActtcacTtCAGT |
| 17_49 | 65.39 | 3.03 | 73.12 | 4.72 | TCaaCtttcacTtCAGT |
| 17_50 | 44.54 | 7.92 | 58.99 | 1.91 | TCaacTttcacTtCAGT |
| 17_51 | 38.28 | 4.62 | 49.61 | 11.12 | TCaactttcacTtCAGT |
| 17_52 | 72.04 | 11.74 | 67.18 | 1.56 | TcaaCtttcacTtCAGT |
| 17_53 | 77.11 | 6.61 | 80.39 | 4.87 | TCAACtttcacTtcAGT |
| 17_54 | 68.58 | 5.17 | 81.14 | 9.92 | TCAAcTttcacTtCaGT |
| 17_55 | 54.70 | NA | 55.71 | 7.63 | TCAactttcacTtcAGT |
| 17_56 | 73.62 | 8.99 | 77.13 | 4.24 | TCAaCtttcacTtcAGT |
| 17_57 | 37.11 | 4.10 | 45.26 | 2.67 | TCAactttcacTtCAGT |
| 17_58 | 75.70 | 7.51 | 79.77 | 3.37 | TCaACtttcacTtCaGT |
| 17_59 | 62.77 | 7.89 | 67.67 | 2.31 | TCaAcTttcacTtCaGT |
| 17_60 | 59.08 | 5.30 | 53.75 | 3.07 | TCaActtcacTtCaGT |
| 17_61 | 58.34 | 2.53 | 66.25 | 3.04 | TCaaCTttcacTtCaGT |
| 17_62 | 69.33 | 5.17 | 72.06 | 2.78 | TCaaCtttcacTtCaGT |
| 17_63 | 61.54 | NA | 64.88 | 2.78 | TCaacTttcacTtCaGT |
| 17_64 | 49.47 | 3.41 | 50.89 | 2.55 | TCaactttcacTtCaGT |
| 17_65 | 80.85 | 11.35 | 81.88 | 4.86 | TCAACtttcacTtcAGT |
| 17_66 | 65.22 | NA | 68.32 | 2.12 | TCAACtttcacTtcAGT |
| 17_67 | 54.53 | 4.81 | 53.80 | 1.98 | TCAActtcacTtcAGT |
| 17_68 | 74.51 | 6.00 | 76.56 | 0.65 | TCAaCtttcacTtcAGT |
| 17_69 | 56.83 | NA | 57.20 | 4.10 | TCAacTttcacTtcAGT |
| 17_70 | 76.86 | NA | 76.34 | 2.03 | TCaACtttcacTtcAGT |
| 17_71 | 63.44 | 10.55 | 64.68 | 5.87 | TCaAcTttcacTtcAGT |
| 17_72 | 62.56 | 5.79 | 61.72 | 1.34 | TCaAcTttcacTtcAGT |
| 17_73 | 60.51 | 6.25 | 67.89 | 3.45 | TCAACtttcacTtcAGT |
| 17_74 | 54.17 | NA | 56.84 | 3.66 | TCAactttcacTtcAGT |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 5 µM Avg | sd | % PAPD7 mRNA of control 5 µM Avg | sd | Compound (CMP) |
|---|---|---|---|---|---|
| 17_75 | 66.76 | 4.71 | 62.81 | 3.26 | TCAaCtttcacTtcaGT |
| 17_76 | 66.23 | 5.60 | 53.07 | 13.10 | TCAactttcacTtcaGT |
| 17_77 | 59.39 | 8.21 | 63.25 | 4.95 | TCAacTttcacTtcaGT |
| 17_78 | 56.02 | 5.00 | 64.25 | 3.27 | TCAACtttcacTtcaGT |
| 17_79 | 45.91 | 4.00 | 56.13 | 3.45 | TCaAcTttcacTtcaGT |
| 17_80 | 69.86 | 6.08 | 69.85 | 3.93 | TCaActttcacTtcaGT |
| 17_81 | 65.32 | 5.73 | 70.58 | 4.02 | TCaacTttcacTtcaGT |
| 17_82 | 63.33 | 8.83 | 70.99 | 4.18 | TcAACtttcacTtcaGT |
| 17_83 | 68.96 | 8.36 | 74.25 | 5.87 | TcAaCtttcacTtcaGT |
| 17_84 | 63.62 | 7.64 | 81.25 | 4.70 | TcaaCtttcacTtcaGT |
| 17_85 | 83.30 | 4.59 | 84.25 | 2.62 | TCAACtttcactTCAGT |
| 17_86 | 37.09 | 7.98 | 43.15 | 2.13 | TCaActttcactTCAGT |
| 17_87 | 50.48 | 4.81 | 60.27 | 6.81 | TCaaCtttcactTCAGT |
| 17_88 | 53.38 | 5.35 | 56.84 | 5.09 | TCaacTttcactTCAGT |
| 17_89 | NA | NA | 43.67 | 3.84 | TCaactttcactTCAGT |
| 17_90 | 29.17 | 3.73 | 37.06 | 3.81 | TcAActttcactTCAGT |
| 17_91 | 61.71 | 7.15 | 71.61 | 3.90 | TcAaCtttcactTCAGT |
| 17_92 | 56.04 | 3.53 | 65.82 | 5.45 | TcaACtttcactTCAGT |
| 17_93 | 45.09 | 4.71 | 56.40 | 2.59 | Tcaactttcact TCAGT |
| 17_94 | 69.38 | 7.28 | 70.95 | 4.84 | TCAACtttcactTCaGT |
| 17_95 | 64.57 | 3.46 | 70.96 | 2.87 | TCAAcTttcactTCaGT |
| 17_96 | 34.51 | 2.38 | 39.62 | 1.63 | TCAActttcactTCaGT |
| 17_97 | 55.05 | 10.06 | 57.09 | 1.62 | TCAaCtttcactTCaGT |
| 17_98 | 64.97 | 7.46 | 63.11 | 2.12 | TCAacTttcactTCaGT |
| 17_99 | 36.70 | 4.12 | 39.75 | 1.43 | TCAactttcactTCaGT |
| 17_100 | 39.06 | NA | 41.61 | 1.24 | TCaActttcactTCaGT |
| 17_101 | 41.26 | 2.45 | 49.05 | 3.40 | TCaactttcactTCaGT |
| 17_102 | 78.96 | 10.63 | 60.35 | 2.12 | TcAACtttcactTCaGT |
| 17_103 | 32.50 | 2.83 | 36.44 | 1.34 | TcActttcactTCaGT |
| 17_104 | 60.36 | 6.41 | 58.67 | 0.78 | TcAaCtttcactTCaGT |
| 17_105 | 58.78 | 3.01 | 65.37 | 2.47 | TcAacTttcactTCaGT |
| 17_106 | 41.78 | 7.71 | 45.57 | 2.93 | TcAactttcactTCaGT |
| 17_107 | 68.24 | 10.65 | 68.52 | 2.11 | TcaActttcactTCaGT |
| 17_108 | 63.66 | 6.15 | 69.87 | 1.49 | Tcaactttcact TCAGT |
| 17_109 | 43.39 | 6.06 | 44.03 | 1.22 | TCAActtttcactTcAGT |
| 17_110 | 67.71 | 3.99 | 68.24 | 2.49 | TCAaCtttcactTcAGT |
| 17_111 | 38.72 | 5.67 | 45.18 | 4.37 | TCAactttcactTcAGT |
| 17_112 | 74.81 | 8.54 | 82.12 | 2.07 | TCAACtttcactTcAGT |
| 17_113 | 45.61 | 3.48 | 49.46 | 3.00 | TCAActttcactTcAGT |
| 17_114 | 75.79 | 7.63 | 72.29 | 2.16 | TCAaCtttcactTcAGT |
| 17_115 | 75.42 | 15.41 | 74.41 | 3.07 | TcaActttcactTcAGT |
| 17_116 | 65.82 | 10.42 | 71.11 | 2.68 | TcaaCtttcactTcAGT |
| 17_117 | 59.41 | 10.07 | 62.29 | 5.94 | TcaactttcactTcAGT |
| 17_118 | 52.64 | NA | 52.72 | 2.61 | TCAACtttcactTcaGT |
| 17_119 | 39.63 | NA | 40.24 | 1.12 | TCAActttcactTcaGT |
| 17_120 | 59.98 | 2.92 | 50.20 | 0.85 | TCAaCtttcactTcaGT |
| 17_121 | 43.88 | 11.36 | 47.72 | 4.55 | TCAacTttcactTcaGT |
| 17_122 | 64.88 | 13.05 | 60.50 | 3.00 | TCaaCtttcactTcaGT |
| 17_123 | 63.11 | 5.97 | 66.33 | 6.52 | TCaactttcactTcaGT |
| 17_124 | 56.82 | 7.60 | 52.41 | 2.44 | TcAaCtttcactTcaGT |
| 17_125 | 53.85 | 8.06 | 61.73 | 4.31 | TcAactttcactTcaGT |
| 17_126 | 81.50 | 15.86 | 84.13 | 4.80 | TcaActttcactTcaGT |
| 17_127 | 78.91 | 10.65 | 82.69 | 2.51 | TcaactttcactTcaGT |
| 17_128 | 81.11 | 11.24 | 78.80 | 1.05 | TCAACtttcacttCAGT |
| 17_129 | 32.28 | 2.57 | 39.12 | 1.07 | TCAactttcacttCAGT |
| 17_130 | 70.27 | 8.13 | 72.06 | 1.44 | TCaActttcacttCAGT |
| 17_131 | 52.53 | 5.34 | 51.48 | 1.51 | TCaAcTttcacttCAGT |
| 17_132 | 39.54 | 5.34 | 40.49 | 2.90 | TCaActttcacttCAGT |
| 17_133 | 49.75 | 8.73 | 51.25 | 2.19 | TCaaCtttcacttCAGT |
| 17_134 | 40.11 | 4.72 | 46.40 | 3.25 | TCaacTttcacttCAGT |
| 17_135 | 32.68 | 5.78 | 44.12 | 1.28 | TCaactttcacttCAGT |
| 17_136 | 73.83 | 11.05 | 64.31 | 14.71 | TCAACtttcacttCAGT |
| 17_137 | 27.45 | 3.58 | 37.37 | 0.87 | TCAActttcacttCAGT |
| 17_138 | 52.94 | 2.36 | 52.33 | 6.75 | TCAaCtttcacttCAGT |
| 17_139 | 33.04 | 3.96 | 41.18 | 2.84 | TcAactttcacttCAGT |
| 17_140 | 51.65 | 1.57 | 52.29 | 3.62 | TCAAcTttcacttCaGT |
| 17_141 | 61.72 | 2.80 | 58.93 | 0.97 | TCAaCTttcacttCaGT |
| 17_142 | 46.19 | NA | 52.83 | 5.45 | TCAaCtttcacttCaGT |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 5 µM Avg | sd | % PAPD7 mRNA of control 5 µM Avg | sd | Compound (CMP) |
|---|---|---|---|---|---|
| 17_143 | 43.84 | 1.08 | 45.66 | 0.98 | TCAacTttcacttCaGT |
| 17_144 | 37.39 | 2.38 | 43.74 | 1.32 | TCAactttcacttCaGT |
| 17_145 | 67.26 | 7.35 | 74.40 | 4.87 | TCaACtttcacttCaGT |
| 17_146 | 56.45 | 2.94 | 56.68 | 0.48 | TCAACtttcacttCaGT |
| 17_147 | 47.22 | 1.68 | 54.43 | 1.21 | TCAAcTttcacttCaGT |
| 17_148 | 43.18 | 2.71 | 56.05 | 1.42 | TCaaCTttcacttCaGT |
| 17_149 | 45.97 | NA | 53.84 | 3.68 | TCaacTttcacttCaGT |
| 17_150 | 59.24 | 6.22 | 60.59 | 3.40 | TCAActttcacttCaGT |
| 17_151 | 51.93 | NA | 61.55 | 5.08 | TcAaCtttcacttCaGT |
| 17_152 | 47.41 | 5.67 | 52.89 | 3.10 | TcAactttcacttCaGT |
| 17_153 | 65.27 | 4.09 | 69.29 | 7.55 | TcaActttcacttCaGT |
| 17_154 | 53.74 | NA | 62.46 | 1.61 | TcaaCTttcacttCaGT |
| 17_155 | 66.62 | 5.23 | 74.14 | 3.90 | TcaactttcacttCaGT |
| 17_156 | 48.09 | 0.70 | 49.14 | 1.49 | TCAAcTttcacttcAGT |
| 17_157 | 38.49 | 2.92 | 43.72 | 1.30 | TCAActttcacttcAGT |
| 17_158 | 59.33 | 3.81 | 63.90 | 1.94 | TCAaCtttcacttcAGT |
| 17_159 | 56.79 | 9.47 | 55.56 | 2.69 | TCAaCtttcacttcAGT |
| 17_160 | 50.32 | 7.20 | 48.93 | 2.20 | TCAaCTttcacttcAGT |
| 17_161 | 40.36 | 4.00 | 45.81 | 1.30 | TCaaCtttcacttcAGT |
| 17_162 | 64.11 | 4.76 | 62.08 | 1.69 | TcAaCtttcacttcAGT |
| 17_163 | 58.28 | NA | 59.97 | 2.18 | TcAactttcacttcAGT |
| 17_164 | 76.29 | 13.13 | 77.15 | 3.83 | TcaActttcacttcAGT |
| 17_165 | 78.09 | 15.89 | 72.59 | 8.69 | TcaactttcacttcAGT |
| 17_166 | 62.49 | 3.63 | 64.37 | 5.16 | TCAACtttcacttcaGT |
| 17_167 | 50.03 | 8.03 | 54.73 | 1.30 | TCAActttcacttcaGT |
| 17_168 | 51.60 | 9.81 | 52.08 | 4.48 | TCAAcTttcacttcaGT |
| 17_169 | 46.17 | 5.15 | 51.40 | 2.49 | TCAActttcacttcaGT |
| 17_170 | 52.75 | 11.01 | 54.83 | 2.69 | TCAaCtttcacttcaGT |
| 17_171 | 53.33 | 9.21 | 54.36 | 2.78 | TCAaCtttcacttcaGT |
| 17_172 | 58.21 | 6.31 | 58.05 | 1.23 | TCAactttcacttcaGT |
| 17_173 | 53.76 | 2.90 | 58.61 | 1.13 | TCaACtttcacttcaGT |
| 17_174 | 50.25 | 5.79 | 50.99 | 7.67 | TCaACtttcacttcaGT |
| 17_175 | 51.82 | 4.61 | 54.72 | 1.85 | TCaActttcacttcaGT |
| 17_176 | 53.43 | NA | 58.36 | 6.34 | TCaaCtttcacttcaGT |
| 17_177 | 57.85 | 3.78 | 63.73 | 2.53 | TCaacTttcacttcaGT |
| 17_178 | 62.40 | 7.11 | 60.69 | 2.19 | TcAActttcacttcaGT |
| 17_179 | 58.09 | 9.19 | 57.23 | 4.50 | TcAaCtttcacttcaGT |
| 17_180 | 74.45 | 11.02 | 75.46 | 4.00 | TcAactttcacttcaGT |
| 17_181 | 90.80 | 14.30 | 82.83 | 2.65 | TcaActttcacttcaGT |
| 17_182 | 74.91 | NA | 75.31 | 4.39 | TcaaCtttcacttcaGT |
| 17_183 | 88.59 | 4.23 | 85.23 | 2.44 | TcaactttcacttcaGT |
| 18_1 | 32.92 | 3.39 | 35.69 | 3.82 | TCAactttcacttCAG |
| 18_250 | 100.08 | 10.66 | 88.51 | 4.20 | TCAACtttcaCTTCAG |
| 18_251 | 84.40 | 7.39 | 80.86 | 4.12 | TCAActttcaCTTCAG |
| 18_252 | 91.54 | 3.68 | 89.30 | 5.79 | TCAaCtttcaCTTCAG |
| 18_253 | 91.81 | 6.31 | 89.37 | 3.90 | TCAACtttcaCTTCAG |
| 18_254 | 85.25 | 10.05 | 84.67 | 2.91 | TCaaCtttcaCTTCAG |
| 18_255 | 86.24 | 2.27 | 87.98 | 0.91 | TcaaCtttcaCTTCAG |
| 18_256 | 78.51 | 4.22 | 82.48 | 9.24 | TcaactttcaCTTCAG |
| 18_257 | 89.59 | 11.37 | 90.01 | 5.75 | TcAaCtttcaCTTCAG |
| 18_258 | 95.95 | 14.37 | 92.27 | 12.06 | TcaaCtttcaCTTcAG |
| 18_259 | 81.62 | 8.01 | 75.93 | 5.23 | TcaactttcaCTTcAG |
| 18_260 | 89.34 | 4.48 | 92.90 | 6.69 | TCAaCtttcaCTtCAG |
| 18_261 | 54.74 | NA | 59.78 | 4.39 | TCAactttcaCTtCAG |
| 18_262 | 91.32 | 12.46 | 85.83 | 4.88 | TCaaCtttcaCTtCAG |
| 18_263 | 53.49 | 6.41 | 55.73 | 1.72 | TCaactttcaCTtCAG |
| 18_264 | 77.00 | 7.13 | 83.85 | 2.44 | TcAACtttcaCTtCAG |
| 18_265 | 82.71 | 2.41 | 80.20 | 3.21 | TcaaCtttcaCTtCAG |
| 18_266 | 65.50 | 14.42 | 63.32 | 7.76 | TcaactttcaCTtCAG |
| 18_267 | 88.30 | 14.79 | 88.12 | 2.67 | TCAACtttcaCTtcAG |
| 18_268 | 85.83 | 5.66 | 80.25 | 1.37 | TCAActttcaCTtcAG |
| 18_269 | 84.52 | 3.17 | 89.90 | 6.04 | TCAaCtttcaCTtcAG |
| 18_270 | 57.28 | 7.24 | 62.34 | NA | TCAactttcaCTtcAG |
| 18_271 | 84.49 | 8.06 | 91.51 | 3.02 | TCaaCtttcaCTtcAG |
| 18_272 | 76.13 | 4.46 | 79.90 | NA | TcAactttcaCTtcAG |
| 18_273 | 85.88 | 7.38 | 97.42 | 4.00 | TcAaCtttcaCTtcAG |
| 18_274 | 95.40 | 13.18 | 95.86 | 1.55 | TcaaCtttcaCTtcAG |
| 18_275 | 95.60 | 10.21 | 92.33 | 2.77 | TCAACtttcaCtTCAG |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 5 µM Avg | sd | % PAPD7 mRNA of control 5 µM Avg | sd | Compound (CMP) |
|---|---|---|---|---|---|
| 18_276 | 83.72 | 6.59 | 80.77 | 2.02 | TCActttcaCtTCAG |
| 18_277 | 90.13 | 10.30 | 96.27 | 13.83 | TCAaCtttcaCtTCAG |
| 18_278 | 55.67 | 8.13 | 62.46 | 6.54 | TCAactttcaCtTCAG |
| 18_279 | 87.22 | 13.33 | 88.16 | 8.73 | TCAACtttcaCtTCAG |
| 18_280 | 76.65 | 3.97 | 79.84 | 12.72 | TCAActttcaCtTCAG |
| 18_281 | 81.18 | 8.97 | 84.87 | 7.12 | TCaACtttcaCtTCAG |
| 18_282 | 61.04 | 7.74 | 61.76 | 1.66 | TCaactttcaCtTCAG |
| 18_283 | 84.65 | 3.34 | 80.88 | 2.96 | TCaaCtttcaCtTCAG |
| 18_284 | 61.02 | 6.86 | 62.10 | 2.82 | TCaactttcaCtTcAG |
| 18_285 | 86.61 | 3.69 | 95.03 | 18.61 | TcAACtttcaCtTcAG |
| 18_286 | 84.98 | 9.65 | 85.00 | 14.32 | TcAACtttcaCtTcAG |
| 18_287 | 86.45 | 4.35 | 88.69 | 7.72 | TcAaCtttcaCtTcAG |
| 18_288 | 57.67 | 1.82 | 61.38 | NA | TcAactttcaCtTcAG |
| 18_289 | 79.05 | 6.07 | 83.92 | 4.10 | TcaACtttcaCtTcAG |
| 18_290 | 87.52 | 9.96 | 91.14 | 2.20 | TcaaCtttcaCtTcAG |
| 18_291 | 73.29 | 5.03 | 69.25 | 5.43 | TcaactttcaCtTcAG |
| 18_292 | 72.78 | 7.03 | 68.16 | 1.00 | TCAACtttcaCttCAG |
| 18_293 | 59.43 | 5.50 | 58.08 | 2.89 | TCAActttcaCttCAG |
| 18_294 | 75.84 | 3.56 | 63.66 | 3.73 | TCAaCtttcaCttCAG |
| 18_295 | 46.89 | 3.57 | 49.06 | 2.63 | TCAactttcaCttCAG |
| 18_296 | 65.42 | 3.75 | 63.31 | 3.08 | TCaACtttcaCttCAG |
| 18_297 | 58.20 | 6.79 | 55.76 | 1.22 | TCaActttcaCttCAG |
| 18_298 | 66.88 | 4.87 | 66.09 | 3.03 | TCaaCtttcaCttCAG |
| 18_299 | 57.00 | 3.54 | 52.43 | 0.96 | TCaactttcaCttCAG |
| 18_300 | 67.40 | 4.43 | 64.15 | 3.50 | TcAACtttcaCttCAG |
| 18_301 | 76.29 | 2.94 | 66.61 | 0.93 | TcaACtttcaCttCAG |
| 18_302 | 79.40 | 6.94 | 75.09 | 2.40 | TcaActttcaCttCAG |
| 18_303 | 80.86 | 2.61 | 67.53 | 3.70 | TCAACtttcaCttcAG |
| 18_304 | 67.19 | 3.65 | 64.77 | 2.65 | TCAActttcaCttcAG |
| 18_305 | 79.81 | 7.90 | 76.61 | 4.75 | TCAaCtttcaCttcAG |
| 18_306 | 65.48 | 4.30 | 60.08 | 1.89 | TCActttcaCttcAG |
| 18_307 | 70.08 | 6.13 | 70.40 | 2.08 | TCaACtttcaCttcAG |
| 18_308 | 70.99 | 2.21 | 71.46 | 3.87 | TCaActttcaCttcAG |
| 18_309 | 69.43 | 6.30 | 81.14 | 12.38 | TCaaCtttcaCttcAG |
| 18_310 | 73.04 | 7.86 | 73.31 | 4.69 | TCaactttcaCttcAG |
| 18_311 | 72.32 | 9.45 | 78.61 | 8.91 | TcAACtttcaCttcAG |
| 18_312 | 67.82 | 11.23 | 78.05 | 7.27 | TcAActttcaCttcAG |
| 18_313 | 75.81 | 10.76 | 78.01 | 7.76 | TcAaCtttcaCttcAG |
| 18_314 | 66.04 | 5.65 | 75.33 | 8.56 | TcAactttcaCttcAG |
| 18_315 | 78.82 | 5.66 | 75.34 | 2.78 | TcaACtttcaCttcAG |
| 18_316 | 87.37 | 14.72 | 95.41 | 6.94 | TcaaCtttcaCttcAG |
| 18_317 | 79.19 | 4.27 | 94.13 | 12.76 | TcaactttcaCttcAG |
| 18_318 | 59.57 | 10.72 | 63.41 | 2.62 | TCAActttcacTTCAG |
| 18_319 | 84.55 | 4.72 | 81.60 | 3.53 | TCAaCtttcacTTCAG |
| 18_320 | 72.74 | 2.03 | 79.32 | 10.24 | TCaaCtttcacTTCAG |
| 18_321 | 72.73 | 6.17 | 74.90 | 3.78 | TcAACtttcacTTCAG |
| 18_322 | 70.71 | 12.19 | 72.65 | 3.47 | TcAaCtttcacTTCAG |
| 18_323 | 63.05 | 4.68 | 64.11 | 2.23 | TcaaCtttcacTTCAG |
| 18_324 | 90.00 | 7.49 | 79.94 | 4.07 | TCAACtttcacTTcAG |
| 18_325 | 79.21 | 4.73 | 75.34 | 2.42 | TCAaCtttcacTTcAG |
| 18_326 | 68.92 | NA | 67.74 | 4.83 | TCaaCtttcacTTcAG |
| 18_327 | 56.44 | 4.90 | 56.48 | 2.86 | TcAACtttcacTTcAG |
| 18_328 | 75.87 | 4.14 | 71.99 | 4.42 | TcAaCtttcacTTcAG |
| 18_329 | 61.35 | 2.64 | 57.83 | 2.46 | TcAactttcacTTcAG |
| 18_330 | 82.34 | 3.56 | 78.64 | 4.39 | TcaaCtttcacTTcAG |
| 18_331 | 75.40 | 6.43 | 72.02 | 3.95 | TcaactttcacTTcAG |
| 18_332 | 72.69 | 7.00 | 73.99 | 3.23 | TCAaCtttcacTtCAG |
| 18_333 | 47.08 | 4.26 | 45.64 | 2.17 | TCaActttcacTtCAG |
| 18_334 | 63.55 | 2.17 | 61.47 | 5.18 | TCaaCtttcacTtCAG |
| 18_335 | 45.43 | 2.17 | 43.67 | 0.51 | TcAActttcacTtCAG |
| 18_336 | 62.16 | 1.68 | 63.10 | 4.22 | TcaactttcacTtCAG |
| 18_337 | 68.12 | 1.83 | 69.62 | 5.48 | TCAaCtttcacTtcAG |
| 18_338 | 58.66 | 3.79 | 55.57 | 3.90 | TCAActttcacTtcAG |
| 18_339 | 64.78 | 3.20 | 67.31 | 4.73 | TCAaCtttcacTtcAG |
| 18_340 | 73.84 | 12.62 | 70.76 | 2.66 | TCaaCtttcacTtcAG |
| 18_341 | 63.86 | 1.31 | 62.80 | 2.97 | TcaactttcacTtcAG |
| 18_342 | 63.62 | 7.33 | 62.67 | 3.14 | TcAACtttcacTtcAG |
| 18_343 | 77.34 | 8.12 | 76.95 | 8.74 | TcAaCtttcacTtcAG |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 5 µM Avg | sd | % PAPD7 mRNA of control 5 µM Avg | sd | Compound (CMP) |
|---|---|---|---|---|---|
| 18_344 | 77.52 | 4.63 | 72.61 | 19.40 | TcaaCtttcacTtcAG |
| 18_345 | 44.88 | 5.16 | 44.48 | 2.03 | TCaACtttcactTCAG |
| 18_346 | 33.58 | 3.96 | 33.46 | 0.75 | TCaActttcactTCAG |
| 18_347 | 25.34 | 3.90 | 27.48 | 1.20 | TcAActttcactTCAG |
| 18_348 | 72.22 | 13.10 | 69.54 | 2.55 | TcaActttcactTCAG |
| 18_349 | 60.34 | 3.62 | 62.20 | 3.43 | TcaactttcactTCAG |
| 18_350 | 42.64 | 7.75 | 39.08 | 1.64 | TCAActttcactTcAG |
| 18_351 | 64.87 | 4.90 | 60.46 | 2.58 | TCaActttcactTcAG |
| 18_352 | 60.50 | 8.75 | 58.85 | NA | TCaactttcactTcAG |
| 18_353 | 46.91 | 7.66 | 48.41 | 2.35 | TcAActttcactTcAG |
| 18_354 | 56.92 | 5.54 | 55.90 | 3.41 | TcaActttcactTcAG |
| 18_355 | 83.71 | 14.79 | 81.27 | 2.26 | TcaActttcactTcAG |
| 18_356 | 39.74 | 8.56 | 46.46 | NA | TCaActttcacttCAG |
| 18_357 | 38.75 | 4.00 | 38.86 | 1.61 | TCaActttcacttCAG |
| 18_358 | 38.88 | 4.61 | 43.88 | 5.77 | TcaActttcacttCAG |
| 18_359 | 77.53 | 8.61 | 72.87 | 3.73 | TcaActttcacttCAG |
| 18_360 | 78.21 | NA | 75.73 | 4.38 | TcaactttcacttCAG |
| 18_361 | 57.41 | NA | 51.70 | 2.51 | TcAActttcacttCAG |
| 19_4 | 101.90 | 8.84 | 105.29 | 4.25 | TGTTTcaataCTAAAA |
| 19_5 | 105.24 | 11.89 | 100.23 | 3.22 | TGTTtcaataCTAAAA |
| 19_6 | 99.75 | 6.33 | 104.03 | 3.46 | TGTtTcaataCTAAAA |
| 19_7 | 91.29 | NA | 91.20 | 2.56 | TGTttcaataCTAAAA |
| 19_8 | 106.37 | NA | 100.46 | 3.70 | TGtTTcaataCTAAAA |
| 19_9 | 108.42 | 11.96 | 101.59 | 4.05 | TGttTcaataCTAAAA |
| 19_10 | 100.39 | 8.50 | 102.93 | 6.06 | TgTTTcaataCTAAAA |
| 19_11 | 90.83 | 3.68 | 92.38 | 3.27 | TGTTTcaataCTAaAA |
| 19_12 | 90.86 | 3.89 | 91.69 | 3.53 | TGTTtcaataCTAaAA |
| 19_13 | 89.85 | 3.87 | 91.34 | 2.59 | TGTtTcaataCTAaAA |
| 19_14 | 94.01 | 8.75 | 94.66 | 2.33 | TGTttcaataCTAaAA |
| 19_15 | 92.12 | 2.54 | 91.25 | 2.22 | TGtTTcaataCTAaAA |
| 19_16 | 97.86 | 5.30 | 93.85 | 1.92 | TgTTTcaataCTAaAA |
| 19_17 | 105.50 | 15.59 | 99.75 | 4.80 | TGTTTcaataCTaAAA |
| 19_18 | 102.61 | 5.30 | 96.26 | 2.40 | TGTTtcaataCTaAAA |
| 19_19 | 94.76 | 5.45 | 94.05 | 2.41 | TGTtTcaataCTaAAA |
| 19_20 | 97.80 | 9.88 | 102.61 | 9.09 | TGTTTcaataCTaaAA |
| 19_21 | 95.95 | 9.14 | 89.84 | 2.06 | TGTTtcaataCTaaAA |
| 19_22 | 101.79 | 7.29 | 95.45 | 3.90 | TGTTTcaataCtAAAA |

From these data it can be seen that the LNA-gapmer designs based on the motif sequence with SEQ ID NO: 19 have very low (between 0 and 10%) PAPD5 and PAPD7 knock down.

Example 4: In Vitro EC50 and Efficacy of Selected Antisense Oligonucleotides in HeLa Cells The EC50 and efficacy (KD) of the best performing oligonucleotides from Example 1 and 3 was determined using the same assay with the following oligonucleotide concentrations 50, 15.81, 5.00, 1.58, 0.50, 0.16, 0.05, and 0.016 µM.

EC 50, max KD (efficacy) of the PAPD5 and PAPD7 mRNA expression was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in Table 16.

TABLE 16

EC50 and Max KD of anti-PAPD5/PAPD7 compounds on PAPD5 and PAPD7 mRNA expression in HeLa cells.

| | PAPD5 | | | | PAPD7 | | | | |
|---|---|---|---|---|---|---|---|---|---|
| | Max KD % of saline | | EC50 µM | | Max KD % of saline | | EC50 µM | | |
| CMP ID NO | Avg | sd | Avg | sd | Avg | sd | Avg | sd | Compound |
| 17_7 | 1.45 | 7.29 | 2.40 | 0.55 | 8.00 | 6.58 | 3.13 | 0.65 | TcAactttcactTcAGT |
| 17_8 | 7.66 | 4.14 | 3.08 | 0.42 | 5.37 | 5.16 | 4.00 | 0.62 | TcAActttcactTcaGT |

TABLE 16-continued

EC50 and Max KD of anti-PAPD5/PAPD7 compounds on PAPD5 and PAPD7 mRNA expression in HeLa cells.

| CMP ID NO | PAPD5 Max KD % of saline | | PAPD5 EC50 µM | | PAPD7 Max KD % of saline | | PAPD7 EC50 µM | | Compound |
|---|---|---|---|---|---|---|---|---|---|
| | Avg | sd | Avg | sd | Avg | sd | Avg | sd | |
| 17_10 | 0.00 | 2.40 | 2.30 | 0.19 | 3.31 | 5.90 | 3.79 | 0.68 | TCActtttcacttCaGT |
| 17_12 | 6.52 | 3.37 | 2.72 | 0.31 | 11.14 | 4.37 | 3.32 | 0.49 | TCaactttcacttCaGT |
| 17_13 | 0.68 | 5.12 | 2.43 | 0.42 | 2.29 | 4.83 | 3.64 | 0.55 | TcAActtttcacttCaGT |
| 17_14 | 0.19 | 5.00 | 2.51 | 0.42 | 3.13 | 4.54 | 3.69 | 0.52 | TCAactttcacttcAGT |
| 17_51 | 3.29 | 3.89 | 1.41 | 0.21 | 5.81 | 1.20 | 1.78 | 0.08 | TCaactttcacTtCAGT |
| 17_57 | 2.61 | 7.96 | 1.54 | 0.47 | 3.07 | 3.45 | 1.76 | 0.21 | TCaactttcacTtCaGT |
| 17_86 | 0.00 | 3.77 | 1.19 | 0.17 | 0.00 | 3.32 | 2.01 | 0.22 | TCaActttcactTCAGT |
| 17_89 | 6.03 | 2.64 | 1.02 | 0.11 | 9.23 | 3.65 | 1.44 | 0.21 | TCaactttcactTCAGT |
| 17_90 | 2.43 | 5.44 | 1.38 | 0.29 | 1.87 | 5.63 | 1.95 | 0.40 | TcAActttcactTCAGT |
| 17_96 | 3.27 | 2.62 | 1.85 | 0.18 | 0.00 | 3.44 | 1.99 | 0.24 | TCActtttcactTCaGT |
| 17_99 | 0.00 | 3.61 | 1.42 | 0.18 | 0.55 | 5.03 | 1.57 | 0.28 | TCAactttcactTCaGT |
| 17_100 | 1.01 | 2.65 | 1.66 | 0.16 | 3.81 | 3.46 | 1.89 | 0.24 | TCaActttcactTCaGT |
| 17_103 | 0.00 | 2.69 | 1.09 | 0.12 | 0.00 | 3.70 | 1.46 | 0.21 | TcAActttcactTCaGT |
| 17_111 | 3.45 | 3.62 | 1.39 | 0.20 | 2.65 | 5.82 | 2.03 | 0.41 | TCaactttcactTcAGT |
| 17_119 | 0.00 | 6.24 | 1.75 | 0.39 | 0.30 | 3.81 | 1.86 | 0.25 | TCAActttcactTcaGT |
| 17_129 | 0.00 | 2.62 | 1.02 | 0.11 | 2.60 | 2.44 | 1.41 | 0.13 | TCaactttcacttCAGT |
| 17_132 | 1.71 | 2.02 | 1.27 | 0.10 | 0.00 | 4.17 | 1.74 | 0.26 | TCaActttcacttCAGT |
| 17_135 | 0.00 | 3.23 | 1.24 | 0.14 | 8.56 | 4.86 | 2.04 | 0.38 | TCaactttcacttCAGT |
| 17_137 | 0.00 | 2.80 | 1.07 | 0.12 | 1.34 | 3.94 | 1.64 | 0.23 | TcAActttcacttCAGT |
| 17_139 | 0.00 | 3.62 | 1.43 | 0.20 | 2.48 | 5.82 | 1.89 | 0.39 | TcAactttcacttCAGT |
| 17_144 | 0.91 | 2.35 | 1.40 | 0.12 | 1.53 | 1.58 | 1.95 | 0.11 | TCAactttcacttCaGT |
| 17_157 | 2.94 | 2.87 | 1.27 | 0.14 | 2.32 | 3.12 | 1.62 | 0.18 | TCAActttcacttcAGT |
| 18_1 | 2.74 | 1.41 | 1.82 | 0.09 | 5.06 | 2.24 | 2.03 | 0.16 | TCAactttcacttCAG |
| 18_5 | 4.25 | 6.93 | 4.08 | 0.82 | 6.91 | 4.42 | 3.35 | 0.47 | TCAActttcacTtCAG |
| 18_6 | 5.49 | 4.00 | 2.97 | 0.39 | 8.16 | 4.67 | 2.93 | 0.45 | TCaactttcacTtCAG |
| 18_10 | 0.00 | 6.55 | 1.60 | 0.38 | 0.00 | 3.59 | 2.17 | 0.26 | TCAactttcactTCAG |
| 18_12 | 1.34 | 3.34 | 1.69 | 0.20 | 0.84 | 4.01 | 2.37 | 0.32 | TCaactttcactTCAG |
| 18_15 | 5.89 | 2.84 | 2.92 | 0.28 | 6.85 | 3.64 | 3.10 | 0.39 | TcAACtttcactTcAG |
| 18_18 | 4.23 | 4.44 | 2.71 | 0.41 | 2.40 | 10.93 | 2.76 | 0.88 | TCAACtttcacttCAG |
| 18_19 | 2.22 | 3.25 | 2.04 | 0.23 | 1.66 | 5.12 | 2.53 | 0.44 | TCAActtttcacttCAG |
| 18_20 | 0.00 | 3.21 | 2.56 | 0.27 | 0.00 | 4.96 | 2.81 | 0.47 | TCaACtttcacttCAG |
| 18_21 | 2.13 | 3.08 | 2.52 | 0.25 | 5.72 | 2.45 | 2.73 | 0.23 | TCaaCtttcacttCAG |
| 18_23 | 0.49 | 4.56 | 2.65 | 0.39 | 0.53 | 3.28 | 3.02 | 0.31 | TCAACtttcacttcAG |
| 18_24 | 0.29 | 6.14 | 2.82 | 0.54 | 0.00 | 6.27 | 2.95 | 0.61 | TCAActtttcacttcAG |
| 18_25 | 2.22 | 5.75 | 2.55 | 0.49 | 0.00 | 3.68 | 3.13 | 0.36 | TCaACtttcacttcAG |

TABLE 16-continued

EC50 and Max KD of anti-PAPD5/PAPD7 compounds on PAPD5 and PAPD7 mRNA expression in HeLa cells.

| CMP ID NO | PAPD5 Max KD % of saline | | PAPD5 EC50 µM | | PAPD7 Max KD % of saline | | PAPD7 EC50 µM | | Compound |
|---|---|---|---|---|---|---|---|---|---|
| | Avg | sd | Avg | sd | Avg | sd | Avg | sd | |
| 18_27 | 0.00 | 4.13 | 2.30 | 0.30 | 1.21 | 2.04 | 2.87 | 0.19 | TCaACtttcacttcAG |
| 18_28 | 10.11 | 3.82 | 4.52 | 0.56 | 12.26 | 11.67 | 5.13 | 1.78 | TCaaCtttcacttcAG |
| 18_30 | 1.60 | 3.21 | 2.56 | 0.27 | 0.00 | 3.47 | 3.10 | 0.34 | TcAACtttcacttcAG |
| 18_346 | 0.56 | 3.27 | 1.27 | 0.17 | 1.43 | 1.58 | 1.49 | 0.09 | TCaActttcactTCAG |
| 18_347 | 0.16 | 3.81 | 0.87 | 0.14 | 0.00 | 1.55 | 1.17 | 0.07 | TCaActttcactTCAG |
| 18_350 | 0.00 | 3.12 | 1.54 | 0.17 | 1.43 | 1.29 | 2.10 | 0.09 | TCAActttcactTcAG |
| 18_357 | 0.00 | 2.87 | 1.61 | 0.18 | 0.00 | 1.97 | 2.18 | 0.15 | TCaActttcacttCAG |
| 18_358 | 0.00 | 2.30 | 1.54 | 0.13 | 0.15 | 1.91 | 2.31 | 0.14 | TcaActttcacttCAG |

Example 5: In Vitro Effect on HBV Infected ASGPR-dHepaRG Cells Using Selected Antisense Oligonucleotides Targeting PAPD5 and PAPD7

A selection of the oligonucleotides screened in example 3 was screened in ASGPR-dHepaRG essentially using the assay of example 2 with the following changes. The screening was conducted in HBV infected ASGPR-dHepaRG at the following concentrations 20, 6.67 and 2.22 µM of oligonucleotide and with the comparative molecules in table 17.

For comparative purposes combinations of a single targeting PAPD5 and a single targeting PAPD7 oligonucleotide in table 17 were tested together with the oligonucleotides of the invention.

TABLE 17

Combination of single targeting PAPD5 and PAPD7 oligonucleotide

| Description | Compound | SEQ ID NO | Reference |
|---|---|---|---|
| PAPD5 and PAPD7 single targeting combination 1 (combo1) | CAAaggttgttgtacTCT | 31 | PCT/EP2017/064980 |
| | CAGTtttatgctaatCA | 32 | PCT/EP2017/064980 |
| PAPD5 and PAPD7 single targeting combination 2 (combo2) | GTAttcttattcttgCT | 33 | PCT/EP2017/064980 |
| | CATTgcttttataatccTA | 34 | PCT/EP2017/064980 |

The reduction of HBsAg and HBeAg levels are shown in table 18 and 19, the larger the value the larger the inhibition.

TABLE 18 in vitro efficacy on HBsAg of anti-PAPD5/PAPD7 compounds in three concentrations (average of 3) in HBV infected ASGPR-dHepaRG cells.

| CMP ID NO | 20 µM | | 6.67 µM | | 2.22 µM | | Compound |
|---|---|---|---|---|---|---|---|
| | Avg | sd | Avg | sd | Avg | sd | |
| 17_51 | -9.61 | 19.93 | -30.60 | 9.19 | -33.16 | 6.96 | TCaactttcacTtCAGT |
| 17_57 | 9.44 | 6.27 | -18.18 | 8.10 | -33.24 | 6.19 | TCAactttcacTtCaGT |
| 17_86 | 20.58 | 5.80 | -5.34 | 4.43 | -8.03 | 5.54 | TCaActttcactTCAGT |
| 17_89 | 2.66 | 3.48 | -12.71 | 2.14 | -7.18 | 7.05 | TCaactttcactTCAGT |
| 17_90 | 40.07 | 6.93 | 3.05 | 14.90 | -11.67 | 7.22 | TcAActttcactTCAGT |
| 17_96 | 58.09 | 7.77 | 36.82 | 3.53 | 4.92 | 4.06 | TCAActttcactTCaGT |
| 17_99 | 25.54 | 6.97 | 5.75 | 8.72 | -7.25 | 5.93 | TCAactttcactTCaGT |
| 17_100 | 43.85 | 7.30 | 15.20 | 12.19 | -10.24 | 9.46 | TcAActttcactTCaGT |
| 17_103 | 41.44 | 9.31 | 25.07 | 2.93 | 9.98 | 3.98 | TcAActttcactTCaGT |

TABLE 18-continued in vitro efficacy on HBsAg of anti-PAPD5/PAPD7 compounds in three concentrations (average of 3) in HBV infected ASGPR-dHepaRG cells.

| CMP ID NO | 20 µM Avg | sd | 6.67 µM Avg | sd | 2.22 µM Avg | sd | Compound |
|---|---|---|---|---|---|---|---|
| 17_111 | -5.59 | 7.25 | -7.04 | 3.62 | -8.11 | 6.03 | TCaactttcactTcAGT |
| 17_119 | 73.06 | 2.91 | 51.21 | 3.44 | 13.11 | 9.33 | TCAActtttcactTcaGT |
| 17_129 | 37.17 | 10.95 | 9.73 | 10.63 | 2.19 | 14.92 | TCAactttcacttCAGT |
| 17_132 | 41.31 | 5.57 | 11.54 | 5.29 | -10.07 | 4.00 | TCaActtttcacttCAGT |
| 17_135 | 3.24 | 6.43 | 2.61 | 10.50 | -13.05 | 2.27 | TCaactttcacttCAGT |
| 17_137 | 60.37 | 4.60 | 44.00 | 4.51 | 13.77 | 1.76 | TcAActtttcacttCAGT |
| 17_139 | 51.89 | 6.99 | 25.28 | 5.62 | -9.98 | 3.81 | TcAactttcacttCAGT |
| 17_144 | 15.51 | 9.49 | 2.98 | 11.13 | -14.47 | 6.57 | TCAactttcacttCaGT |
| 17_157 | 60.44 | 2.21 | 43.72 | 7.14 | -0.43 | 5.64 | TCAActtttcacttcAGT |
| 18_1 | 90.68 | 1.23 | 75.99 | 2.96 | 17.58 | 8.44 | TCAactttcacttCAG |
| 18_346 | 87.27 | 1.42 | 51.65 | 5.99 | -0.36 | 6.52 | TCaActtttcactTCAG |
| 18_347 | 88.09 | 2.70 | 66.31 | 4.12 | 1.27 | 11.46 | TcAActtttcactTCAG |
| 18_350 | 82.82 | 2.94 | 68.17 | 3.68 | 25.39 | 3.40 | TCAactttcactTcAG |
| 18_357 | 91.46 | 1.63 | 77.08 | 2.24 | 35.54 | 3.18 | TCaActtttcacttCAG |
| 18_358 | 83.98 | 3.39 | 63.78 | 6.55 | 26.29 | 5.45 | TcaACtttcacttCAG |
| Combo1 | 72.08 | 0.75 | 58.03 | 2.25 | 21.27 | 8.25 | |
| Combo2 | 71.77 | 4.54 | 67.54 | 3.72 | 50.53 | 5.82 | |

TABLE 19 in vitro efficacy on HBeAg of anti-PAPD5/PAPD7 compounds in three concentrations (average of 3) in HBV infected ASGPR-dHepaRG cells.

| CMP ID NO | 20 µM Avg | sd | 6.67 µM Avg | sd | 2.22 µM Avg | sd | Compound |
|---|---|---|---|---|---|---|---|
| 17_51 | -39.37 | 39.73 | -71.52 | 24.98 | -89.89 | 24.95 | TCaactttcacTtCAGT |
| 17_57 | 2.88 | 4.42 | -38.92 | 11.07 | -76.67 | 6.90 | TCAactttcacTtCaGT |
| 17_86 | 22.69 | 5.54 | -20.63 | 5.70 | -42.45 | 4.40 | TCaActtttcactTCAGT |
| 17_89 | -11.41 | 3.45 | -36.53 | 9.77 | -34.92 | 9.69 | TCaactttcactTCAGT |
| 17_90 | 50.40 | 8.09 | -4.45 | 25.09 | -36.73 | 16.16 | TcAActtttcactTCAGT |
| 17_96 | 68.32 | 9.42 | 47.89 | 5.53 | 2.93 | 16.50 | TCAActtttcactTCaGT |
| 17_99 | 34.82 | 8.81 | 15.96 | 21.39 | -13.36 | 13.51 | TCAactttcactTCaGT |
| 17_100 | 55.17 | 5.99 | 20.03 | 20.34 | -25.12 | 18.75 | TCaActtttcactTCaGT |
| 17_103 | 48.08 | 14.67 | 28.80 | 9.35 | 7.18 | 12.00 | TcAActtttcactTCaGT |
| 17_111 | -5.24 | 15.62 | -10.26 | 3.22 | -18.78 | 9.24 | TCaactttcactTcAGT |
| 17_119 | 83.29 | 3.11 | 69.67 | 1.75 | 24.17 | 9.29 | TCAActtttcactTcaGT |
| 17_129 | 47.32 | 8.81 | 19.21 | 17.51 | -6.65 | 24.28 | TCAactttcacttCAGT |
| 17_132 | 59.04 | 4.63 | 21.83 | 1.86 | -14.91 | 0.44 | TCAActtttcacttCAGT |

TABLE 19-continued in vitro efficacy on HBeAg of anti-PAPD5/PAPD7 compounds in three concentrations (average of 3) in HBV infected ASGPR-dHepaRG cells.

| CMP ID NO | 20 µM Avg | sd | 6.67 µM Avg | sd | 2.22 µM Avg | sd | Compound |
|---|---|---|---|---|---|---|---|
| 17_135 | 8.35 | 11.28 | 2.09 | 13.51 | -25.60 | 9.12 | TCaactttcacttCAGT |
| 17_137 | 73.77 | 2.83 | 58.40 | 3.45 | 18.22 | 1.27 | TcAActtttcacttCAGT |
| 17_139 | 64.19 | 7.67 | 39.45 | 5.57 | -17.73 | 3.08 | TcAactttcacttCAGT |
| 17_144 | 24.74 | 7.77 | 12.21 | 16.40 | -31.19 | 11.36 | TCAactttcacttCaGT |
| 17_157 | 75.79 | 1.10 | 61.26 | 4.35 | 9.64 | 7.17 | TCAactttcacttcAGT |
| 18_1 | 97.88 | 1.00 | 89.38 | 2.73 | 39.44 | 12.14 | TCAactttcacttCAG |
| 18_346 | 90.95 | 3.99 | 61.25 | 4.11 | -4.13 | 6.95 | TCaActttcactTCAG |
| 18_347 | 91.45 | 3.48 | 78.72 | 2.03 | 9.18 | 8.96 | TcAActtttcactTCAG |
| 18_350 | 92.56 | 3.36 | 80.54 | 6.12 | 41.46 | 7.29 | TCAActtttcactTcAG |
| 18_357 | 96.37 | 1.27 | 87.86 | 2.94 | 51.94 | 2.98 | TcAActtttcacttCAG |
| 18_358 | 89.92 | 0.54 | 76.73 | 7.28 | 37.70 | 9.45 | TcaACtttcacttCAG |
| Combo 1 | 79.37 | 2.03 | 68.47 | 2.04 | 25.24 | 12.68 | |
| Combo 2 | 75.26 | 2.05 | 72.07 | 3.78 | 59.69 | 2.36 | |

From these data it can be seen that the best performing bispecific PAPD5/PAPD7 oligonucleotides have better effect in terms of HBsAg and HBeAg reduction with half the oligonucleotide concentration (20 µM) when compared to the combination treatments (2×20 µM).

Example 6 Screening for In Vitro Efficacy of Stereodefined Antisense Oligonucleotides Targeting PAPD5 and PAPD7 in HeLa Cells To expand the diversity around the motif sequences of SEQ ID NO: 18 even further, a library of stereodefined oligonucleotides was made based on the stereorandom parent compound with CMP ID NO 18_1.

Efficacy testing was performed in an in vitro experiment as described in Example 1, with the exception that the screening was conducted with 1 µM and some with 5 µM.

The relative PAPD5 mRNA and PAPD7 mRNA expression levels are shown in table 20 as % of the parent oligonucleotide i.e. the larger the value the better the inhibition.

TABLE 20 in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control | | | | % PAPD7 mRNA of control | | | | Stereodefinition |
|---|---|---|---|---|---|---|---|---|---|
| | 1 µM Avg | sd | 5 µM Avg | sd | 1 µM Avg | sd | 5 µM Avg | sd | |
| 18_1 | 100.0 | 6.3 | | | 100.0 | 3.4 | | | TCAactttcacttCAG XXXXXXXXXXXXXXH |
| 18_32 | 87.0 | 5.1 | | | 94.7 | 0.9 | | | RSSRXXXXXXXXXXXH |
| 18_33 | 76.4 | NA | | | 89.7 | 1.7 | | | XRSSRXXXXXXXXXXH |
| 18_34 | 79.8 | 6.7 | | | 91.5 | 2.3 | | | XXRSSRXXXXXXXXXH |
| 18_35 | 70.0 | 10.8 | | | 86.7 | 3.8 | | | XXXRSSRXXXXXXXXH |
| 18_36 | 102.5 | 7.8 | | | 107.4 | 3.1 | | | XXXXRSSRXXXXXXXH |
| 18_37 | 88.8 | 7.6 | | | 95.1 | 4.5 | | | XXXXXRSSRXXXXXXH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control | | | | % PAPD7 mRNA of control | | | | Stereodefinition |
|---|---|---|---|---|---|---|---|---|---|
| | 1 µM | | 5 µM | | 1 µM | | 5 µM | | |
| | Avg | sd | Avg | sd | Avg | sd | Avg | sd | |
| 18_38 | 68.3 | 6.5 | | | 82.0 | 3.6 | | | XXXXXXRSSRXXXXH |
| 18_39 | 87.2 | 5.7 | | | 93.8 | 5.0 | | | XXXXXXXRSSRXXXH |
| 18_40 | 92.2 | 3.5 | | | 96.3 | 5.5 | | | XXXXXXXXRSSRXXH |
| 18_41 | 81.1 | 1.3 | | | 95.2 | 7.6 | | | XXXXXXXXXRSSRXH |
| 18_42 | 78.0 | 3.8 | | | 92.0 | 9.4 | | | XXXXXXXXXXRSSRH |
| 18_43 | 80.4 | 3.4 | | | 92.7 | 3.6 | | | XXXXXXXXXXXRSSRH |
| 18_44 | 79.4 | 3.5 | | | 89.7 | 3.4 | | | XXXXXXXXXSSSSSRH |
| 18_45 | 75.2 | 8.2 | | | 88.7 | 2.4 | | | XXXXXXXXXRRRRRH |
| 18_46 | 86.2 | 6.5 | | | 91.0 | 6.7 | | | XXXXXXXXXSSRRSRH |
| 18_47 | 79.7 | 6.2 | | | 85.7 | 1.5 | | | XXXXXXXXXSSSRSRH |
| 18_48 | 80.6 | 1.6 | | | 87.5 | 1.5 | | | XXXXXXXXXSSSRRSH |
| 18_49 | 79.9 | 3.2 | | | 101.8 | 6.5 | | | XXXXXXXXXSRSSSSH |
| 18_50 | 82.7 | 3.1 | | | 88.9 | 2.2 | | | XXXXXXXXXRSRSRSH |
| 18_51 | 78.0 | 5.7 | | | 90.2 | 2.9 | | | XXXXXXXXXSSSSRSH |
| 18_52 | 90.1 | 6.0 | | | 93.7 | 1.1 | | | XXXXXXXXXSSRRSSH |
| 18_53 | 82.7 | 8.7 | | | 90.7 | 3.2 | | | XXXXXXXXXRSSSSH |
| 18_54 | 63.3 | 13.2 | | | 77.8 | 6.4 | | | XXXXXXXXXRSSRRH |
| 18_55 | 73.9 | 6.2 | | | 90.9 | 1.6 | | | XXXXXXXXXSRRRSH |
| 18_56 | 83.1 | 5.6 | | | 98.5 | 6.4 | | | XXXXXXXXXSSRSRRH |
| 18_57 | 73.4 | 6.8 | | | 89.6 | 8.2 | | | XXXXXXXXXRRRSRH |
| 18_58 | 89.1 | 2.2 | | | 98.7 | 2.8 | | | XXXXXXXXXRRSRSRH |
| 18_59 | 73.2 | 8.5 | | | 91.7 | 2.5 | | | XXXXXXXXXSSRRRSH |
| 18_60 | 88.8 | 4.2 | | | 93.3 | 3.4 | | | XXXXXXXXXSRRSSSH |
| 18_61 | 77.0 | 13.6 | | | 81.6 | 13.7 | | | XXXXXXXXXRRRRSH |
| 18_62 | 75.6 | 8.7 | | | 87.8 | 8.5 | | | XXXXXXXXXRSSRH |
| 18_63 | 74.8 | 5.0 | | | 85.5 | 1.4 | | | XXXXXXXXXRSRRRH |
| 18_64 | 86.9 | 7.3 | | | 92.2 | 2.5 | | | XXXXXXXXXSRRSSH |
| 18_65 | 77.8 | 10.3 | | | 89.0 | 7.4 | | | XXXXXXXXXSRSRSRH |
| 18_66 | 81.7 | 10.2 | | | 88.9 | 6.1 | | | XXXXXXXXXRSSSSRH |
| 18_67 | 77.6 | 7.4 | | | 81.1 | 4.7 | | | XXXXXXXXXSSSSRH |
| 18_68 | 88.9 | 9.2 | | | 91.3 | 2.7 | | | XXXXXXXXXRRSSSRH |
| 18_69 | 77.8 | 3.8 | | | 89.9 | 4.0 | | | XXXXXXXXXRSSRRSH |
| 18_70 | 75.9 | 11.7 | | | 83.9 | 7.8 | | | XXXXXXXXXRSSSRH |
| 18_71 | 84.2 | 6.7 | | | 88.7 | 1.4 | | | XXXXXXXXXSRRRRH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 1 µM | | 5 µM | | % PAPD7 mRNA of control 1 µM | | 5 µM | | Stereodefinition |
|---|---|---|---|---|---|---|---|---|---|
| | Avg | sd | Avg | sd | Avg | sd | Avg | sd | |
| 18_72 | 93.6 | 2.3 | | | 95.0 | 1.7 | | | XXXXXXXXXRRSRSSH |
| 18_73 | 90.5 | 4.3 | | | 92.4 | 2.9 | | | XXXXXXXXXRSRSSRH |
| 18_74 | 88.3 | 10.5 | | | 88.2 | 3.0 | | | XXXXXXXXXRSRSRRH |
| 18_75 | 85.2 | 7.1 | | | 89.0 | 3.1 | | | XXXXXXXXXSRRRSRH |
| 18_76 | 99.6 | 2.7 | | | 99.5 | 2.2 | | | XXXXXXXXXRRSRRSH |
| 18_77 | 87.4 | 1.5 | | | 87.2 | 1.8 | | | XXXXXXXXXSSSRRRH |
| 18_78 | 80.6 | 10.4 | | | 83.5 | 5.2 | | | XXXXXXXXXRSRRSRH |
| 18_79 | 89.3 | 6.8 | | | 98.7 | 3.4 | | | XXXXXXXXXSRRSRSH |
| 18_80 | 85.9 | 2.0 | | | 83.2 | 2.8 | | | XXXXXXXXXRRSRRRH |
| 18_81 | 92.4 | 5.0 | | | 84.1 | NA | | | XXXXXXXXXSRRSSRH |
| 18_82 | 86.8 | 3.4 | | | 89.8 | 3.0 | | | XXXXXXXXXSRSSSRH |
| 18_83 | 93.1 | 4.7 | | | 92.4 | 3.3 | | | XXXXXXXXXRSRRRSH |
| 18_84 | 91.1 | 4.9 | | | 93.4 | 5.2 | | | XXXXXXXXXSSSRSSH |
| 18_85 | 84.3 | 3.9 | | | 87.9 | 1.6 | | | XXXXXXXXXSSRSSRH |
| 18_86 | 86.2 | 8.1 | | | 84.6 | 2.2 | | | XXXXXXXXXRSRSSSH |
| 18_87 | 77.3 | 9.7 | | | 90.6 | 0.9 | | | XXXXXXXXXSRSSRSH |
| 18_88 | 85.8 | 5.4 | | | 92.4 | 3.0 | | | XXXXXXXXXSSSSSSH |
| 18_89 | 94.9 | 5.7 | | | 95.8 | 7.3 | | | XXXXXXXXXRSRRSSH |
| 18_90 | 91.2 | 6.3 | | | 92.9 | 2.3 | | | XXXXXXXXXRRRRSRH |
| 18_91 | 85.9 | 4.1 | | | 90.4 | 5.0 | | | XXXXXXXXXSSRSRSH |
| 18_92 | 84.7 | 6.5 | | | 90.1 | 9.3 | | | XXXXXXXXXRRRRSSH |
| 18_93 | 81.7 | 6.5 | | | 90.6 | 4.0 | | | XXXXXXXXXRSRSSSH |
| 18_94 | 82.2 | 7.7 | | | 82.9 | 8.0 | | | XXXXXXXXXRSSRSRH |
| 18_95 | 89.4 | 1.9 | | | 84.9 | 7.5 | | | XXXXXXXXXRRRSRSH |
| 18_96 | 80.1 | 3.7 | | | 85.0 | 5.9 | | | XXXXXXXXXRRSSRSH |
| 18_97 | 68.9 | 7.5 | | | 82.3 | 4.8 | | | XXXXXXXXXSRSSRRH |
| 18_98 | 81.7 | 4.1 | | | 93.9 | 6.9 | | | XXXXXXXXXSRRSRRH |
| 18_99 | 97.7 | 5.4 | | | 97.7 | 8.7 | | | XXXXXXXXXSRSRSSH |
| 18_100 | 77.5 | 3.7 | | | 85.4 | 4.1 | | | XXXXXXXXXSRSRRRH |
| 18_101 | 77.9 | 7.1 | | | 88.3 | 4.3 | | | XXXXXXXXXSSRSSSH |
| 18_102 | 77.3 | 6.3 | | | 93.0 | 2.8 | | | XXXXXXXXXRSSSSSH |
| 18_103 | 74.8 | 3.7 | | | 86.4 | 1.2 | | | XXXXXXXXXRSSSRSH |
| 18_104 | 90.3 | 6.1 | | | 91.5 | 2.3 | | | XXXXXXXXXRRRSSRH |
| 18_105 | 95.7 | 7.2 | | | 102.9 | 1.7 | | | XXXXXXXXXRRRSSSH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 1 µM | | 5 µM | | % PAPD7 mRNA of control 1 µM | | 5 µM | | Stereodefinition |
|---|---|---|---|---|---|---|---|---|---|
| | Avg | sd | Avg | sd | Avg | sd | Avg | sd | |
| 18_106 | 79.7 | 5.4 | | | 85.7 | 1.2 | | | XXXXXXXXXXSRSRRSH |
| 18_107 | 87.6 | 4.4 | | | 89.0 | 2.2 | | | XXXXXXXXXXSSRRRRH |
| 18_108 | 86.4 | 10.6 | | | 95.3 | 4.0 | | | XXXXXXXXXXSSRSSH |
| 18_109 | 99.1 | 2.5 | | | 99.0 | 6.6 | | | XXXXXXXXXXRRRSSH |
| 18_110 | 91.1 | 5.4 | | | 93.1 | 3.5 | | | XXXXXXXXXXRRSSRH |
| 18_111 | 103.1 | 2.9 | | | 99.1 | 6.2 | | | XXXXXXXXXXRSSSRH |
| 18_112 | 96.5 | 2.7 | | | 90.7 | 2.5 | | | XXXXXXXXXXRRSRRH |
| 18_113 | 76.0 | 17.5 | | | 90.4 | 3.7 | | | XXXXXXXXXXSSSSRH |
| 18_114 | 86.9 | 3.4 | | | 88.8 | 4.5 | | | XXXXXXXXXXRRRRRH |
| 18_115 | 94.7 | 8.1 | | | 94.1 | 3.8 | | | XXXXXXXXXXSRSSSH |
| 18_116 | 79.8 | 4.1 | | | 83.7 | 2.6 | | | XXXXXXXXXXSSRSRH |
| 18_117 | 88.3 | 6.6 | | | 95.6 | 4.1 | | | XXXXXXXXXXRSSRH |
| 18_118 | 83.6 | 7.9 | | | 86.8 | 2.1 | | | XXXXXXXXXXRSRRH |
| 18_119 | 85.2 | 2.3 | | | 88.7 | 2.5 | | | XXXXXXXXXXSRRRRH |
| 18_120 | 86.2 | 6.8 | | | 91.9 | 0.7 | | | XXXXXXXXXXSRRRSH |
| 18_121 | 90.4 | 5.9 | | | 86.9 | 0.7 | | | XXXXXXXXXXSSSRSH |
| 18_122 | 74.2 | 8.8 | | | 79.5 | 7.8 | | | XXXXXXXXXXRSSSH |
| 18_123 | 82.2 | 1.0 | | | 87.6 | 1.5 | | | XXXXXXXXXXSSSSSH |
| 18_124 | 91.0 | 12.7 | | | 111.4 | 11.9 | | | XXXXXXXXXXSRRSSH |
| 18_125 | 87.6 | 6.7 | | | 85.7 | 4.4 | | | XXXXXXXXXXRSRRSH |
| 18_126 | 81.5 | 7.1 | | | 85.5 | 1.9 | | | XXXXXXXXXXSSRRSH |
| 18_127 | 82.9 | 3.7 | | | 96.0 | 2.3 | | | XXXXXXXXXXRRRSRH |
| 18_128 | 79.0 | 3.7 | | | 83.5 | 4.3 | | | XXXXXXXXXXSRSRRH |
| 18_129 | 98.4 | NA | | | 91.7 | 6.2 | | | XXXXXXXXXXRRSRSH |
| 18_130 | 90.7 | 5.4 | | | 89.8 | 2.3 | | | XXXXXXXXXXRRSSSH |
| 18_131 | 82.2 | 6.1 | | | 89.6 | 1.0 | | | XXXXXXXXXXRSSSSH |
| 18_132 | 81.6 | 6.9 | | | 84.2 | 2.3 | | | XXXXXXXXXXRSRRH |
| 18_133 | 88.9 | 4.1 | | | 94.5 | 4.0 | | | XXXXXXXXXXSRRSRH |
| 18_134 | 73.6 | 7.5 | | | 83.3 | 4.3 | | | XXXXXXXXXXSSRRRH |
| 18_135 | 86.6 | 10.3 | | | 91.0 | 7.1 | | | XXXXXXXXXXSRSSRH |
| 18_136 | 93.8 | 4.5 | | | 85.0 | 8.1 | | | XXXXXXXXXXRRRRSH |
| 18_137 | 100.6 | 6.4 | | | 83.2 | 7.2 | | | XXXXXXXXXXRSRSRH |
| 18_138 | 83.1 | 9.5 | | | 86.5 | 4.0 | | | XXXXXXXXXXSSSRRH |
| 18_139 | 82.4 | 10.8 | | | 87.3 | 2.9 | | | XXXXXXXXXXSRSRSH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control | | | | % PAPD7 mRNA of control | | | | Stereodefinition |
|---|---|---|---|---|---|---|---|---|---|
| | 1 µM | | 5 µM | | 1 µM | | 5 µM | | |
| | Avg | sd | Avg | sd | Avg | sd | Avg | sd | |
| 18_140 | 83.9 | 5.6 | | | 78.9 | 5.1 | | | SSRRRSSSSRSSRH |
| 18_141 | 96.7 | 9.9 | | | 89.2 | 13.8 | | | SSSSSRRRRRSRRSH |
| 18_142 | 81.7 | 13.0 | | | 83.7 | 7.7 | | | SRSSRSSSRRRSRSRH |
| 18_143 | 86.4 | 11.5 | | | 80.3 | 11.7 | | | SRRSSSSRRSRRRRH |
| 18_144 | 88.5 | 7.1 | | | 78.6 | 8.5 | | | SSRRSRSRSSSRSRRH |
| 18_145 | 75.2 | 12.2 | | | 78.4 | 3.9 | | | SSSRRRSRRRSSRRH |
| 18_146 | 109.4 | 6.8 | | | 105.6 | 8.1 | | | RRSRSSRRSSSRRSSH |
| 18_147 | 82.8 | 7.1 | | | 80.3 | 2.9 | | | RSSRRRSSSRSSSRSH |
| 18_148 | 78.2 | 7.1 | | | 73.3 | 9.6 | | | SSSSRRRSRSSSRRSH |
| 18_149 | 78.5 | 3.9 | | | 77.1 | 14.5 | | | SSSRSSSSSSSRRRRH |
| 18_150 | 80.2 | 5.3 | | | 75.0 | 8.5 | | | SSSSRSSSSSSSSSH |
| 18_151 | 65.6 | 21.5 | | | 73.0 | 9.1 | | | RRSRRRRRSSSSSSSH |
| 18_152 | 98.9 | 5.4 | | | 92.9 | 3.3 | | | RRRSRSSSRRRRSSSH |
| 18_153 | 92.1 | 9.5 | | | 93.2 | 3.1 | | | RRRRSSSRRRSRSSRH |
| 18_154 | 98.3 | 4.0 | | | 92.3 | 2.7 | | | SSRRRRSRSRSRRSH |
| 18_155 | 77.4 | 8.1 | | | 82.0 | 3.8 | | | RSSSSRSSSRRSSSSH |
| 18_156 | 79.9 | 7.8 | | | 81.6 | 5.9 | | | RRRSSSSRSRSRRSH |
| 18_157 | 76.8 | 4.3 | | | 82.6 | 3.5 | | | RSSSRSRSRRRSRRRH |
| 18_158 | 81.8 | 12.8 | | | 86.8 | 4.1 | | | RRSRRSSSRRRRRSH |
| 18_159 | 76.4 | 12.4 | | | 77.9 | 2.8 | | | RRSSSSRSRSSSRSRH |
| 18_160 | 82.2 | 16.3 | | | 88.8 | 4.2 | | | RSSRSRSRSRSRSRRH |
| 18_161 | 76.4 | 14.9 | | | 77.9 | 4.9 | | | SRRRSSSSRSRSRSRH |
| 18_162 | 66.6 | 15.9 | | | 80.4 | 4.1 | | | SRSSSRRSRRRRSSRH |
| 18_163 | 76.8 | 14.0 | | | 85.3 | 2.9 | | | RSRRRSRRSRSSRRH |
| 18_164 | 88.4 | 9.4 | | | 97.5 | 5.2 | | | SSRRRSSRSSRRRSH |
| 18_165 | 75.1 | 14.9 | | | 85.2 | 3.0 | | | RSRSSRRSRRRSSSRH |
| 18_166 | 81.6 | 6.7 | | | 83.9 | 5.8 | | | RRRSRRRSSRSRRSH |
| 18_167 | 74.4 | 11.7 | | | 77.5 | 4.5 | | | SRRSSSRSRSSRRRH |
| 18_168 | 73.9 | 9.7 | | | 77.3 | 1.9 | | | SRSSRSSSSRSRSSH |
| 18_169 | 73.7 | 15.1 | | | 86.2 | 1.1 | | | SSRSRSSSSSRSSSH |
| 18_170 | 75.8 | 7.0 | | | 82.4 | 2.0 | | | SSRRRRSRSRRSSH |
| 18_171 | 97.4 | 2.3 | | | 98.5 | 3.3 | | | SSSRRSRSRRRRRSH |
| 18_172 | 85.3 | 10.9 | | | 81.0 | 2.0 | | | RSSSSSSSRSRRRRH |
| 18_173 | 88.5 | 10.0 | | | 92.5 | 1.4 | | | SSRSRSSRSSRRSRRH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control 1 µM | | 5 µM | | % PAPD7 mRNA of control 1 µM | | 5 µM | | Stereodefinition |
|---|---|---|---|---|---|---|---|---|---|
| | Avg | sd | Avg | sd | Avg | sd | Avg | sd | |
| 18_174 | 84.1 | 11.1 | | | 81.5 | 17.2 | | | SRSRSSSRRRSRRRSH |
| 18_175 | 72.7 | 6.6 | | | 79.1 | 1.1 | | | RRRRRRSSRRSSSRH |
| 18_176 | 77.0 | 14.4 | | | 81.9 | 4.8 | | | SSRSRRRRSRRSRSH |
| 18_177 | 81.9 | 5.6 | | | 79.9 | 10.1 | | | RRSRRRRRSRRRSH |
| 18_178 | 88.9 | 3.9 | | | 94.4 | 3.1 | | | SSSSRRRRRRRRSH |
| 18_179 | 87.6 | 11.8 | | | 81.5 | 8.6 | | | SRRRSRRRSSRRRSH |
| 18_180 | 75.9 | 2.9 | | | 72.9 | 11.0 | | | SSSRRRRSRRSSRRH |
| 18_181 | 85.3 | 11.1 | | | 86.7 | 1.9 | | | RRSRRSSSRRRSSRH |
| 18_182 | 93.0 | 9.2 | | | 95.4 | 7.3 | | | SSRRSRSSRRRSSSSH |
| 18_183 | 83.6 | 12.3 | | | 80.6 | 5.2 | | | SSRSRRRRSSRSSRH |
| 18_184 | 87.0 | 15.0 | | | 79.3 | 4.5 | | | RRRSRRSRSSRSRRRH |
| 18_185 | 98.7 | 4.6 | | | 96.8 | 1.7 | | | RSRSSRSRSRRSRSH |
| 18_186 | 87.9 | 3.7 | | | 87.7 | 5.2 | | | SSSRRRRSSRRSRRRH |
| 18_187 | 99.1 | 3.5 | | | 99.8 | 2.3 | | | RSSRRSRRRRSRRRSH |
| 18_188 | 101.1 | 5.9 | | | 92.8 | 6.6 | | | SSSRRSSRSRSRSSSH |
| 18_189 | 106.9 | 4.2 | | | 105.0 | 3.1 | | | RSRSSSSRSSRRRSSH |
| 18_190 | 104.8 | 3.5 | | | 96.7 | 2.2 | | | SSSRSSSRSRRSRSSH |
| 18_191 | 87.7 | 10.4 | | | 84.9 | 7.8 | | | RSSRSSSSRSSSSSRH |
| 18_192 | 86.5 | 7.9 | | | 96.1 | 1.6 | | | RSSRRSSRSSSSRRSH |
| 18_193 | 76.5 | 8.0 | | | 80.4 | 3.2 | | | RSSRRSRSRRSSSSRH |
| 18_194 | 80.0 | 4.8 | | | 86.4 | 3.3 | | | RRSSSRRSRRRSSSH |
| 18_195 | 100.4 | 8.3 | | | 99.3 | 1.6 | | | RRRRRSSRSRRSSSRH |
| 18_196 | 109.5 | 2.6 | | | 113.5 | 4.2 | | | SSSSRSRRRSSRRRSH |
| 18_197 | 82.6 | 1.9 | | | 81.0 | 4.8 | | | RSRRRRRRRSSRSRH |
| 18_198 | 87.2 | 4.6 | | | 87.4 | 6.4 | | | RSRRSSSSRSSRSSRH |
| 18_199 | 80.9 | 2.8 | | | 91.5 | 1.0 | | | SSRRSRSSRRSSSRH |
| 18_200 | 74.7 | 11.4 | | | 84.8 | 2.1 | | | RRRSSSRRSRSRSSH |
| 18_201 | 73.5 | 13.7 | | | 82.0 | 1.3 | | | RSRRRRRRSRRSRSH |
| 18_202 | 70.6 | 8.6 | | | 81.4 | 1.4 | | | SRRSRRRRSRSSSSH |
| 18_203 | 69.8 | 9.5 | | | 73.8 | 1.4 | | | SRRSRSSSRSSSSSH |
| 18_204 | 77.8 | 6.8 | | | 86.3 | 2.7 | | | SSSRRRRSRSRRRSSH |
| 18_205 | 73.4 | 4.2 | | | 77.8 | 2.6 | | | SSRSRSSSRSRSRH |
| 18_206 | 80.6 | 12.7 | | | 90.4 | 3.6 | | | SSSRRSRRSRRRSRSH |
| 18_207 | 67.8 | 7.5 | | | 74.3 | 2.6 | | | SRSSRRRSSSSSRRRH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control | | | | % PAPD7 mRNA of control | | | | Stereodefinition |
|---|---|---|---|---|---|---|---|---|---|
| | 1 µM | | 5 µM | | 1 µM | | 5 µM | | |
| | Avg | sd | Avg | sd | Avg | sd | Avg | sd | |
| 18_208 | 71.9 | 12.0 | | | 83.0 | 4.9 | | | RRSSRSSSSSSRSSRH |
| 18_209 | 74.0 | 5.5 | | | 83.7 | 3.4 | | | SRSSRRSSRSRRSRRH |
| 18_210 | 55.6 | 14.6 | 48.5 | 5.4 | 84.2 | 7.2 | 66.2 | 4.5 | RSRRSSRSRSSRRSSH |
| 18_211 | 60.5 | 11.1 | 52.4 | 6.7 | 84.4 | 6.7 | 76.4 | 6.8 | RSSSRRSRSSSRSSSH |
| 18_212 | 53.3 | 3.3 | 47.3 | 3.5 | 93.4 | 8.0 | 60.5 | 5.6 | SSSSSSSSRSRRRSSH |
| 18_213 | 43.0 | 8.3 | 26.1 | 6.0 | 72.4 | 10.7 | 38.3 | 8.4 | RRSSSSSSSRSSSRRH |
| 18_214 | 66.6 | 8.9 | 97.1 | 4.2 | 108.3 | 7.0 | 106.6 | 7.8 | SSSRSSSSRRRRSSH |
| 18_215 | 61.0 | 11.2 | 59.9 | 8.2 | 98.3 | 10.7 | 76.0 | 11.9 | SSSRRRRRSSSSRRH |
| 18_216 | 35.6 | 9.3 | 42.2 | 5.4 | 56.2 | 6.8 | 53.1 | 12.8 | RSRSRRSSSSRRRSRH |
| 18_217 | 37.6 | 8.9 | 73.8 | 8.8 | 65.0 | 6.4 | 79.6 | 8.0 | SSSSRRSRRRSSRRRH |
| 18_218 | 101.7 | 11.6 | 90.1 | 1.6 | 162.0 | 9.8 | 100.5 | 2.4 | RSSRRSSRSRRRSSSH |
| 18_219 | 70.9 | 10.8 | 75.5 | 3.7 | 97.0 | 9.1 | 93.3 | 4.9 | RRSSSSSRRRRSRRSH |
| 18_220 | 58.0 | 11.3 | 62.5 | 4.0 | 92.0 | 8.6 | 79.5 | 6.3 | RXXXXXXXXXXXXXXH |
| 18_221 | 66.8 | 8.8 | 89.8 | 4.1 | 101.2 | 11.1 | 109.1 | 6.9 | SXXXXXXXXXXXXXXH |
| 18_222 | 73.2 | 6.2 | 79.4 | 3.4 | 108.4 | 8.8 | 95.1 | 4.2 | XRXXXXXXXXXXXXXH |
| 18_223 | 84.1 | 9.0 | 98.4 | 4.9 | 134.3 | 6.6 | 134.7 | 5.5 | XSXXXXXXXXXXXXXH |
| 18_224 | 73.3 | 7.0 | 91.9 | 4.7 | 117.0 | 6.4 | 131.4 | 5.2 | XXRXXXXXXXXXXXXH |
| 18_225 | 76.5 | 9.3 | 94.3 | 7.7 | 110.1 | 6.0 | 108.4 | 7.6 | XXSXXXXXXXXXXXXH |
| 18_226 | 74.4 | 11.6 | 92.4 | 6.7 | 102.3 | 7.6 | 108.8 | 6.3 | XXXRXXXXXXXXXXXH |
| 18_227 | 83.1 | 11.6 | 109.9 | 8.4 | 99.1 | 14.1 | 111.2 | 6.9 | XXSXXXXXXXXXXXH |
| 18_228 | 56.4 | 7.2 | 55.0 | 5.5 | 87.4 | 3.7 | 74.5 | 7.5 | XXXXRXXXXXXXXXXH |
| 18_229 | 69.4 | 6.2 | 81.4 | 4.4 | 113.1 | 4.6 | 104.9 | 7.4 | XXXXSXXXXXXXXXXH |
| 18_230 | 66.6 | 5.8 | 84.6 | 3.3 | 109.3 | 6.6 | 106.4 | 6.7 | XXXXXRXXXXXXXXXH |
| 18_231 | 80.7 | 2.7 | 109.0 | 1.1 | 114.1 | 5.6 | 120.8 | 4.9 | XXXXXSXXXXXXXXXH |
| 18_232 | 63.4 | 4.4 | 66.6 | 6.3 | 101.7 | 5.2 | 88.0 | 8.2 | XXXXXXRXXXXXXXXH |
| 18_233 | 68.3 | 3.1 | 96.4 | 8.0 | 102.4 | 6.5 | 120.3 | 6.6 | XXXXXXSXXXXXXXXH |
| 18_234 | 69.9 | 10.7 | 98.7 | 8.9 | 113.0 | 5.2 | 124.2 | 7.1 | XXXXXXXRXXXXXXXH |
| 18_235 | 68.6 | 16.7 | 82.3 | 7.5 | 91.1 | 12.4 | 90.3 | 9.2 | XXXXXXXSXXXXXXXH |
| 18_236 | 114.6 | 7.6 | 90.5 | 2.8 | 187.8 | 9.9 | 113.0 | 4.6 | XXXXXXXXRXXXXXXH |
| 18_237 | 66.4 | 13.5 | 66.6 | 7.3 | 117.3 | 12.3 | 93.2 | 7.3 | XXXXXXXXSXXXXXXH |
| 18_238 | 72.5 | 5.3 | 90.1 | 3.9 | 122.5 | 6.6 | 126.8 | 4.3 | XXXXXXXXXRXXXXXH |
| 18_239 | 39.8 | 3.0 | 20.9 | 5.7 | 67.2 | 6.4 | 29.2 | 2.1 | XXXXXXXXXSXXXXXH |
| 18_240 | 63.0 | 12.0 | 92.7 | 2.0 | 116.2 | 7.9 | 117.7 | 1.6 | XXXXXXXXXXRXXXXH |
| 18_241 | 65.1 | 15.1 | 75.4 | 4.4 | 105.9 | 19.9 | 104.8 | 5.0 | XXXXXXXXXXSXXXXH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID NO | % PAPD5 mRNA of control | | | | % PAPD7 mRNA of control | | | | Stereodefinition |
|---|---|---|---|---|---|---|---|---|---|
| | 1 µM | | 5 µM | | 1 µM | | 5 µM | | |
| | Avg | sd | Avg | sd | Avg | sd | Avg | sd | |
| 18_242 | 65.0 | 12.7 | 85.0 | 3.2 | 106.0 | 12.5 | 114.3 | 2.4 | XXXXXXXXXXXXRXXXH |
| 18_243 | 145.2 | 7.8 | 112.0 | 6.0 | 180.8 | 6.4 | 118.8 | 6.5 | XXXXXXXXXXXXSXXXH |
| 18_244 | 75.3 | 9.9 | 87.8 | 2.8 | 110.4 | 8.1 | 91.2 | 4.8 | XXXXXXXXXXXXXRXXH |
| 18_245 | 81.7 | 8.6 | 63.6 | 5.6 | 100.3 | 5.9 | 79.2 | 1.9 | XXXXXXXXXXXXXSXXH |
| 18_246 | 60.3 | 7.4 | 71.7 | 6.2 | 90.4 | 8.0 | 80.8 | 8.1 | XXXXXXXXXXXXXXRXH |
| 18_247 | 70.3 | 8.0 | 90.4 | 6.4 | 108.4 | 7.5 | 94.4 | 8.1 | XXXXXXXXXXXXXXSXH |
| 18_248 | 74.0 | 7.7 | 77.4 | 5.1 | 87.4 | 19.5 | 86.7 | 7.3 | XXXXXXXXXXXXXXXRH |
| 18_249 | 74.8 | 4.9 | 88.2 | 5.4 | 114.8 | 5.6 | 109.7 | 6.4 | XXXXXXXXXXXXXXXSH |

Example 7: In Vitro EC50 and Efficacy of Selected Stereodefined Antisense Oligonucleotides in HeLa Cells The EC50 and efficacy (KD) of the best performing oligonucleotides from Example 6 was determined using the same assay with the following oligonucleotide concentrations 33, 10.44, 3.33, 1.044, 0.33, 0.104, 0.033 and 0.01 µM.

EC 50, max KD (efficacy) of the PAPD5 and PAPD7 mRNA expression was calculated using R-function drm( ) from the drc package (v3.0-1) a four-parameter log-logistic function is fitted to the expression of the gene of interest as a function of oligonucleotide concentration to obtain a value for EC50 and maximum knock-down. The results are shown in Table 21.

TABLE 21

EC50 and Max KD of anti-PAPD5/PAPD7 compounds on PAPD5 and PAPD7 mRNA expression in HeLa cells. CMP ID NO 18_1 is the stereorandom parent compound.

| CMP ID NO | PAPD5 | | | | PAPD7 | | | | Stereodefined motif |
|---|---|---|---|---|---|---|---|---|---|
| | Max KD % of saline | | EC50 µM | | Max KD % of saline | | EC50 µM | | |
| | Avg | sd | Avg | sd | Avg | sd | Avg | sd | |
| 18_1 | 2.74 | 1.41 | 1.82 | 0.09 | 5.06 | 2.24 | 2.03 | 0.16 | TCAactttcacttCAG XXXXXXXXXXXXXXXXH |
| 18_36 | 0.49 | 2.00 | 1.19 | 0.08 | 0.00 | 2.77 | 1.57 | 0.14 | XXXXRSSRXXXXXXXH |
| 18_76 | 1.83 | 5.88 | 3.18 | 0.54 | 1.12 | 7.32 | 3.38 | 0.69 | XXXXXXXXXRRSRRSH |
| 18_99 | 0.12 | 7.43 | 2.87 | 0.63 | 4.53 | 13.63 | 3.39 | 1.30 | XXXXXXXXXSRSRSSH |
| 18_109 | 2.46 | 3.84 | 1.59 | 0.20 | 2.66 | 4.77 | 2.04 | 0.32 | XXXXXXXXXXRRRSSH |
| 18_111 | 0.36 | 8.02 | 2.41 | 0.59 | 5.64 | 3.86 | 2.88 | 0.34 | XXXXXXXXXXRSSSRH |
| 18_124 | 0.00 | 8.02 | 1.76 | 0.45 | 0.00 | 4.30 | 2.27 | 0.28 | XXXXXXXXXXSRSSH |
| 18_146 | 0.00 | 4.37 | 1.59 | 0.22 | 0.00 | 5.67 | 2.27 | 0.40 | RRSRSSRRSSSRRSSH |
| 18_171 | 0.00 | 3.47 | 1.44 | 0.17 | 0.00 | 5.90 | 2.24 | 0.41 | SSSRRSSRSRRRRRSH |
| 18_185 | 2.94 | 4.54 | 1.57 | 0.23 | 2.34 | 5.97 | 2.10 | 0.40 | RSRSSRSRSRRSRSRH |
| 18_187 | 0.00 | 2.50 | 1.73 | 0.14 | 0.00 | 6.11 | 2.27 | 0.40 | RSRRSRRRRSRRRSH |
| 18_188 | 0.00 | 3.88 | 1.66 | 0.21 | 3.63 | 6.56 | 1.94 | 0.38 | SSRRSSSRSRSRSSSH |
| 18_190 | 3.56 | 5.01 | 2.59 | 0.41 | 7.41 | 6.38 | 3.11 | 0.62 | SSSRSSSRSRRSRSSH |

TABLE 21-continued

EC50 and Max KD of anti-PAPD5/PAPD7 compounds on PAPD5 and PAPD7 mRNA expression in HeLa cells. CMP ID NO 18_1 is the stereorandom parent compound.

| | PAPD5 | | | | PAPD7 | | | | |
|---|---|---|---|---|---|---|---|---|---|
| CMP | Max KD % of saline | | EC50 µM | | Max KD % of saline | | EC50 µM | | |
| ID NO | Avg | sd | Avg | sd | Avg | sd | Avg | sd | Stereodefined motif |
| 18_196 | 0.00 | 2.00 | 1.31 | 0.09 | 1.40 | 5.30 | 1.71 | 0.28 | SSSSRSRRRSSRRRSH |
| 18_223 | 0.00 | 3.36 | 1.40 | 0.16 | 1.15 | 4.84 | 1.83 | 0.28 | XSXXXXXXXXXXXXXH |
| 18_227 | 0.00 | 6.48 | 1.75 | 0.37 | 0.45 | 6.48 | 2.20 | 0.39 | XXXSXXXXXXXXXXXH |
| 18_231 | 0.00 | 3.57 | 1.37 | 0.17 | 0.00 | 4.34 | 2.13 | 0.28 | XXXXXSXXXXXXXXXH |
| 18_236 | 2.37 | 3.44 | 1.82 | 0.21 | 4.69 | 3.90 | 2.22 | 0.27 | XXXXXXXXRXXXXXXH |
| 18_243 | 0.15 | 5.38 | 2.38 | 0.37 | 5.18 | 8.67 | 2.52 | 0.66 | XXXXXXXXXXXSXXXH |

From these data it can be seen that improvements in EC50 and efficacy in relation to PAPD5 and PAPD7 knock down can be achieved both with stereodefined sub-libraries and with fully stereodefined compounds.

Example 8: In Vitro Effect on HBV Infected ASGPR-dHepaRG Cells Using Selected Stereodefined Antisense Oligonucleotides Targeting PAPD5 and PAPD7

A selection of the most efficacious oligonucleotides from example 6 was tested for their effect on HBV propagation parameters in HBV infected dHepaRG-ASGPR cells.

The experiment was conducted as described in example 5.

The reduction of HBsAg and HBeAg levels are shown in table 22 and 23, the larger the value the larger the inhibition.

TABLE 22 in vitro efficacy on HBsAg of anti-PAPD5/PAPD7 compounds in three concentrations (average of 3) in HBV infected ASGPR-dHepaRG cells. CMP ID NO 18_1 is the stereorandom parent compound

| CMP ID | 20 µM | | 6.67 µM | | 2.22 µM | | |
|---|---|---|---|---|---|---|---|
| NO | Avg | sd | Avg | sd | Avg | sd | Stereodefined motif |
| 18_1 | 97.88 | 1.00 | 89.38 | 2.73 | 39.44 | 12.14 | TCAactttcacttCAG XXXXXXXXXXXXXXXH |
| 18_36 | 72.64 | 1.45 | 37.85 | 8.05 | 10.98 | 8.04 | XXXXRSSRXXXXXXXH |
| 18_76 | 40.85 | 34.07 | 2.07 | 19.39 | -15.02 | 23.15 | XXXXXXXXXRRSRRSH |
| 18_99 | 34.94 | 6.39 | -13.21 | 12.32 | -42.74 | 12.83 | XXXXXXXXXSRSRSSH |
| 18_105 | 82.12 | 2.60 | 74.93 | 3.30 | 19.30 | 7.25 | XXXXXXXXXRRRSSSH |
| 18_109 | 57.43 | 14.41 | 18.19 | 9.25 | 7.15 | 16.09 | XXXXXXXXXXRRRSSH |
| 18_111 | 28.98 | 6.10 | -10.71 | 7.93 | -30.92 | 15.15 | XXXXXXXXXXRSSSRH |
| 18_124 | 59.86 | 4.12 | 27.17 | 15.97 | -3.69 | 18.85 | XXXXXXXXXXSRRSSH |
| 18_146 | 62.69 | 6.93 | 44.31 | 4.08 | -19.52 | 12.39 | RRSRSSRRSSSRRSSH |
| 18_171 | 38.32 | 2.10 | -11.53 | 3.85 | -28.30 | 10.51 | SSSRRSSRSRRRRRSH |
| 18_185 | -20.73 | 17.60 | -19.59 | 14.46 | -4.32 | 7.01 | RSRSSRSRSRRRSRSH |
| 18_187 | 56.84 | 6.44 | 17.42 | 10.77 | -49.55 | 11.42 | RSSRRSRRRRSRRRSH |

TABLE 22-continued in vitro efficacy on HBsAg of anti-PAPD5/PAPD7 compounds in three concentrations (average of 3) in HBV infected ASGPR-dHepaRG cells. CMP ID NO 18_1 is the stereorandom parent compound

| CMP ID NO | 20 µM Avg | sd | 6.67 µM Avg | sd | 2.22 µM Avg | sd | Stereodefined motif |
|---|---|---|---|---|---|---|---|
| 18_188 | 59.41 | 12.82 | 25.09 | 16.54 | 6.76 | 20.56 | SSSRRSSRSRSRSSSH |
| 18_189 | 32.87 | 6.69 | -3.52 | 16.56 | -50.76 | 34.50 | RSRSSSSRSSRRRSSH |
| 18_190 | -53.00 | 16.64 | -57.27 | 12.78 | -69.75 | 14.40 | SSSRSSSRSRRSRSSH |
| 18_195 | 32.58 | 3.42 | -12.74 | 45.18 | -16.33 | 18.72 | RRRRRSSRSRRSSSRH |
| 18_196 | -17.72 | 3.29 | -36.50 | 9.00 | -49.29 | 11.33 | SSSSRSRRRSSRRRSH |
| 18_218 | 53.86 | 6.46 | 42.40 | 3.88 | 9.55 | 20.41 | RSSRRSSRSRRRSSSH |
| 18_223 | 83.06 | 2.73 | 62.17 | 11.58 | 15.29 | 11.02 | XSXXXXXXXXXXXXXH |
| 18_227 | 79.92 | 1.95 | 49.95 | 6.87 | -11.69 | 7.50 | XXXSXXXXXXXXXXXH |
| 18_231 | 83.13 | 1.45 | 69.70 | 3.35 | 37.16 | 11.77 | XXXXXSXXXXXXXXXH |
| 18_236 | 64.19 | 2.58 | 38.47 | 5.37 | -19.29 | 5.10 | XXXXXXXXRXXXXXXH |
| 18_243 | 82.96 | 1.85 | 67.55 | 3.06 | 26.96 | 10.36 | XXXXXXXXXXXSXXXH |
| Combo 1 | 79.37 | 2.03 | 68.47 | 2.04 | 25.24 | 12.68 | |
| Combo 2 | 75.26 | 2.05 | 72.07 | 3.78 | 59.69 | 2.36 | |

TABLE 23 in vitro efficacy on HBeAg of anti-PAPD5/PAPD7 compounds in three concentrations (average of 3) in HBV infected ASGPR-dHepaRG cells. CMP ID NO 18_1 is the stereorandom parent compound

| CMP ID NO | 20 µM Avg | sd | 6.67 µM Avg | sd | 2.22 µM Avg | sd | Compound |
|---|---|---|---|---|---|---|---|
| 18_1 | 90.68 | 1.23 | 75.99 | 2.96 | 17.58 | 8.44 | TCAactttcacttCAG XXXXXXXXXXXXXXXH |
| 18_36 | 61.56 | 2.27 | 32.88 | 7.00 | 13.90 | 2.63 | XXXXRSSRXXXXXXXH |
| 18_76 | 42.45 | 24.97 | 12.44 | 4.58 | 5.05 | 11.65 | XXXXXXXXXRRSRRSH |
| 18_99 | 29.44 | 4.44 | -5.01 | 7.61 | -15.22 | 8.54 | XXXXXXXXXSRSRSSH |
| 18_105 | 77.20 | 2.93 | 63.83 | 3.75 | 17.89 | 6.08 | XXXXXXXXXRRRSSSH |
| 18_109 | 50.97 | 12.79 | 18.65 | 7.96 | 18.34 | 10.47 | XXXXXXXXXXRRRSSH |
| 18_111 | 26.62 | 5.65 | 5.57 | 6.76 | -5.32 | 8.48 | XXXXXXXXXXRSSSRH |
| 18_124 | 52.84 | 6.90 | 26.44 | 13.62 | 8.76 | 13.32 | XXXXXXXXXXSRRSSH |
| 18_146 | 57.25 | 5.51 | 32.84 | 4.19 | -5.83 | 9.16 | RRSRSSRRSSSRRSSH |
| 18_171 | 31.41 | 2.24 | -0.52 | 0.38 | -5.55 | 4.51 | SSSRRSSRSRRRRRSH |
| 18_185 | 3.01 | 9.20 | 0.38 | 6.33 | 6.86 | 2.17 | RSRSSRSRSRRSRSRH |
| 18_187 | 45.26 | 5.54 | 14.19 | 7.61 | -7.36 | 5.03 | RSSRRSRRRSRRRSH |
| 18_188 | 51.94 | 10.97 | 26.12 | 10.92 | 15.12 | 17.90 | SSSRRSSRSRSRSSSH |
| 18_189 | 32.71 | 4.45 | 3.59 | 7.73 | -20.18 | 13.54 | RSRSSSSRSSRRRSSH |
| 18_190 | -8.26 | 5.56 | -19.34 | 5.60 | -23.56 | 3.06 | SSSRSSSRSRRSRSSH |
| 18_195 | 33.37 | 4.40 | 6.47 | 23.36 | -3.00 | 7.15 | RRRRRSSRSRRSSSRH |

TABLE 23-continued in vitro efficacy on HBeAg of anti-PAPD5/PAPD7 compounds in three concentrations (average of 3) in HBV infected ASGPR-dHepaRG cells. CMP ID NO 18_1 is the stereorandom parent compound

| CMP ID NO | 20 µM Avg | sd | 6.67 µM Avg | sd | 2.22 µM Avg | sd | Compound |
|---|---|---|---|---|---|---|---|
| 18_196 | 8.16 | 3.13 | -5.42 | 9.08 | -16.04 | 9.21 | SSSSRSRRRSSRRRSH |
| 18_218 | 52.20 | 7.32 | 38.24 | 6.77 | 9.85 | 11.45 | RSSRRSSRSRRRSSSH |
| 18_223 | 79.06 | 3.79 | 53.28 | 3.42 | 15.60 | 12.30 | XSXXXXXXXXXXXXXH |
| 18_227 | 76.98 | 5.26 | 39.75 | 9.09 | -0.96 | 3.34 | XXXSXXXXXXXXXXXH |
| 18_231 | 72.79 | 4.62 | 54.88 | 2.74 | 25.58 | 8.29 | XXXXXSXXXXXXXXXH |
| 18_236 | 59.69 | 3.81 | 33.06 | 7.16 | -0.33 | 4.37 | XXXXXXXXRXXXXXXH |
| 18_243 | 79.05 | 1.15 | 53.54 | 2.97 | 21.12 | 7.39 | XXXXXXXXXXXXSXXXH |
| Combo 1 | 72.08 | 0.75 | 58.03 | 2.25 | 21.27 | 8.25 |  |
| Combo 2 | 71.77 | 4.54 | 67.54 | 3.72 | 50.53 | 5.82 |  |

Example 9: In Vitro Effect on HBV Infected ASGPR-dHepaRG Cells Using Selected GalNAc Conjugated Antisense Oligonucleotides Targeting PAPD5 and PAPD7

A selection of the most efficacious oligonucleotides from Example 1 were conjugated to a GalNAc conjugate moiety and tested for their effect on HBV propagation parameters in HBV infected ASGPR-dHepaRG cells.

The assessment of the EC50 and efficacy (KD) on HBsAg and HBeAg of the GalNAc conjugated oligonucleotides was performed as described in Example 2 using HBV infected ASGPR-dHepaRG cells and without comparative oligonucleotides. The results are shown in Table 24.

In addition to the procedure in example 2 the harvested cells were washed once in PBS and lysed in MagNA Pure lysis buffer (Roche #05467535001) and stored at −80° C. RNA was extracted using MagNA Pure "96 Cellular RNA Large Volume Kit" (Roche #05467535001) and PAPD5 and PAPD7 mRNA expression levels were determined as described in Materials and Methods section, Real-time PCR for PAPD5 and PAPD7. EC50 and efficacy (KD) was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in Table 24A

TABLE 24

EC50 and Max KD of anti-PAPD5/PAPD7 compounds on HBsAg and HBeAg (average of 3) in HBV infected ASGPR-dHepaRG cells.

| CMP ID NO | HBeAg Max KD % of saline Avg | sd | EC50 nM Avg | sd | HBsAg Max KD % of saline Avg | sd | EC50 nM Avg | sd | Compound |
|---|---|---|---|---|---|---|---|---|---|
| 20_12 | 6.1 | 1.0 | 127.7 | 10.1 | 7.7 | 1.6 | 87.0 | 17.4 | GN2-C6$_o$c$_o$a$_o$TCAactttcacttCAG |
| 20_13 | 0.8 | 0.3 | 65.1 | 1.3 | 2.5 | 1.0 | 72.4 | 3.5 | GN2-C6$_o$c$_o$a$_o$TCAActtcactTCAG |
| 20_14 | 0.3 | 1.1 | 43.2 | 3.4 | 1.2 | 1.3 | 58.5 | 5.1 | GN2-C6$_o$c$_o$a$_o$TCAActtcacttCAG |
| 20_15 | 0.0 | 0.7 | 45.3 | 6.1 | 0.4 | 1.7 | 37.8 | 11.2 | GN2-C6$_o$c$_o$a$_o$TCAActtcacTtCAG |
| 20_16 | 3.9 | 2.9 | 58.2 | 6.6 | 1.9 | 2.4 | 84.2 | 11.6 | GN2-C6$_o$c$_o$a$_o$TCAActtcacttCAG |
| 20_17 | 5.9 | 1.9 | 83.8 | 11.8 | 11.2 | 1.7 | 110.4 | 14.3 | GN2-C6$_o$c$_o$a$_o$TCAActtcacttcAG |
| 20_18 | 6.5 | 2.1 | 75.6 | 34.3 | 13.9 | 2.4 | 77.8 | 33.2 | GN2-C6$_o$c$_o$a$_o$TCAActttcacttcAG |
| 20_19 | 0.0 | 7.3 | 76.3 | 81.9 | 11.4 | 4.2 | 106.9 | 26.9 | GN2-C6$_o$c$_o$a$_o$TCAactttcactTCAG |
| 20_20 | 0.0 | 6.1 | 79.6 | 59.4 | 9.2 | 2.4 | 135.0 | 16.2 | GN2-C6$_o$c$_o$a$_o$TcAACtttcacttcAG |
| 20_21 | 1.8 | 2.4 | 41.5 | 8.7 | 7.8 | 2.6 | 74.9 | 17.6 | GN2-C6$_o$c$_o$a$_o$TcAACtttcacttcAG |

TABLE 24-continued

EC50 and Max KD of anti-PAPD5/PAPD7 compounds on HBsAg and HBeAg (average of 3) in HBV infected ASGPR-dHepaRG cells.

| | HBeAg | | | | HBsAg | | | | |
|---|---|---|---|---|---|---|---|---|---|
| CMP ID NO | Max KD % of saline | | EC50 nM | | Max KD % of saline | | EC50 nM | | Compound |
| | Avg | sd | Avg | sd | Avg | sd | Avg | sd | |
| 20_22 | 7.2 | 1.2 | 60.6 | 6.8 | 10.7 | 0.7 | 126.7 | 6.9 | GN2-C6$_o$c$_o$a$_o$TCaActttcacttcAG |
| 21_2 | 14.6 | 55 | 79.2 | 40.8 | 18.8 | 3.3 | 125.9 | 23.6 | GN2-C6$_o$c$_o$a$_o$TCAActtcacttCaGT |

From these data it can be seen that by conjugating a GalNAc moiety to the oligonucleotide the EC50 values are improved at least 40 fold (note the current table is in nM whereas table 14 is in μM). For example is the HBsAg reduction of compound 20_15 (GalNAc conjugated) improved 176 fold over compound 18_05 (naked version of 20_15).

TABLE 24A in vitro efficacy and potency (EC50) of GalNAc conjugated anti-PAPD5/PAPD7 compounds. PAPD5 and PAPD7 mRNA levels are normalized to GUSB in ASGPR-dHepaRG cells and shown as % of control (PBS treated cells).

| | PAPD5 | | | | PAPD7 | | | |
|---|---|---|---|---|---|---|---|---|
| CMP ID NO | Max KD % of saline | | EC50 μM | | Max KD % of saline | | EC50 μM | |
| | Avg | sd | Avg | sd | Avg | sd | Avg | sd |
| 20_12 | 1.9 | 0.95 | 0.032 | 0.002 | 1.6 | 1.59 | 0.030 | 0.003 |
| 20_13 | 17 | 1.93 | 0.045 | 0.009 | 17 | 1.57 | 0.038 | 0.006 |
| 20_14 | 5.2 | 1.24 | 0.024 | 0.008 | 2.9 | 1.47 | 0.003 | 0.002 |
| 20_15 | 11 | 1.45 | 0.002 | 0.002 | 8.5 | 0.99 | 0.001 | 0.001 |
| 20_16 | 10 | 1.20 | 0.046 | 0.006 | 11 | 1.18 | 0.041 | 0.005 |
| 20_17 | 5.2 | 2.29 | 0.022 | 0.012 | 4.3 | 2.05 | 0.037 | 0.013 |
| 20_18 | 5.4 | 1.14 | 0.047 | 0.006 | 2 | 1.27 | 0.014 | 0.007 |
| 20_19 | 4.7 | 1.68 | 0.048 | 0.009 | 6.5 | 1.54 | 0.041 | 0.009 |
| 20_20 | 9.3 | 1.33 | 0.047 | 0.005 | 4.7 | 2.17 | 0.019 | 0.012 |
| 20_21 | 6.2 | 1.30 | 0.043 | 0.006 | 4.4 | 2.78 | 0.020 | 0.008 |
| 20_22 | 4.7 | 1.29 | 0.044 | 0.008 | 5.4 | 2.68 | 0.048 | 0.010 |
| 21_2 | 12 | 1.12 | 0.075 | 0.005 | 12 | 3.41 | 0.052 | 0.013 |

From these data it can be seen that the majority of the selected GalNAc conjugated oligonucleotides targeting PAPD5 and PAPD7 are capable of reducing the mRNA levels to below 10%.

Example 10: Screening for In Vitro Efficacy of Antisense Oligonucleotides Targeting PAPD5 and PAPD7 in dHepaRG Cells The oligonucleotides screened for PAPD5 and PAPD7 knock down in HeLa cells (Example 1 and 3) were screened in dHepaRG cells to demonstrate efficient knock down in a liver cell line.

dHepaRG cells were cultured as described in the Materials and Method section. The following oligonucleotide concentrations 50, 15.81, 5.00, 1.58, 0.50, 0.16, 0.05, and 0.016 μM were used in a final culture volume of 100 μl/well. The cells were harvested 6 days after addition of oligonucleotide compounds and RNA was extracted using the PureLink Pro 96 RNA Purification kit (Ambion) according to the manufacturer's instructions.

PAPD5 and PAPD7 mRNA levels were analysed by Real-time PCR as described in the Materials and Method section. EC 50, max KD (efficacy) of the PAPD5 and PAPD7 mRNA expression was calculated using the R-function drm( ) from the drc package (v3.0-1) a four-parameter log-logistic function is fitted to the expression of the gene of interest as a function of oligonucleotide concentration to obtain a value for EC50 and maximum knock-down.

The results are shown in table 25.

TABLE 25

EC50 and Max KD of anti-PAPD5/PAPD7 compounds on PAPD5 and PAPD7 mRNA expression in dHepaRG cells.

| | PAPD5 | | | | PAPD7 | | | | |
|---|---|---|---|---|---|---|---|---|---|
| CMP ID NO | Max KD % of saline | | EC50 μM | | Max KD % of saline | | EC50 μM | | Compound |
| | Avg | sd | Avg | sd | Avg | sd | Avg | sd | |
| 17_103 | 11.0 | 6.1 | 1.7 | 0.4 | 2.2 | 39.9 | 7.6 | 13.3 | TcAActtcacttTCaGT |
| 17_111 | 7.5 | 8.7 | 2.2 | 0.8 | 0.0 | 38.7 | 6.4 | 11.7 | TCaactttcacttTcAGT |
| 17_119 | 5.3 | 16.1 | 1.8 | 1.1 | 2.1 | 15.7 | 3.8 | 2.2 | TCAActttcacttTcaGT |
| 17_129 | 11.5 | 5.5 | 1.5 | 0.4 | 0.0 | 31.2 | 5.0 | 6.2 | TCAacttcacttCAGT |

TABLE 25-continued

EC50 and Max KD of anti-PAPD5/PAPD7 compounds on PAPD5 and PAPD7 mRNA expression in dHepaRG cells.

| | PAPD5 | | | | PAPD7 | | | | |
|---|---|---|---|---|---|---|---|---|---|
| | Max KD % of saline | | EC50 µM | | Max KD % of saline | | EC50 µM | | |
| CMP ID NO | Avg | sd | Avg | sd | Avg | sd | Avg | sd | Compound |
| 17_132 | 9.8 | 10.0 | 3.2 | 1.3 | 13.2 | 13.2 | 6.6 | 3.5 | TCaActttcacttCAGT |
| 17_135 | 4.1 | 3.6 | 1.1 | 0.1 | 0.0 | 32.7 | 4.0 | 4.3 | TCaactttcacttCAGT |
| 17_137 | 0.0 | 7.5 | 3.5 | 0.9 | 16.6 | 8.2 | 5.0 | 1.5 | TcAActttcacttCAGT |
| 17_139 | 5.3 | 8.3 | 2.3 | 0.7 | 5.7 | 19.1 | 7.7 | 4.9 | TcAactttcacttCAGT |
| 17_144 | 6.0 | 8.0 | 1.4 | 0.4 | 0.0 | 12.7 | 2.8 | 1.3 | TCAactttcacttCaGT |
| 17_157 | 8.2 | 4.6 | 3.1 | 0.5 | 0.0 | 16.2 | 8.8 | 4.9 | TCAActttcacttcAGT |
| 18_1 | 0.0 | 7.8 | 1.6 | 0.4 | 0.0 | 8.7 | 3.8 | 1.2 | TCAactttcacttCAG |
| 18_6 | 10.1 | 9.2 | 2.5 | 0.9 | 0.0 | 19.8 | 5.8 | 4.2 | TCaactttcacTtCAG |
| 18_10 | 13.4 | 15.6 | 1.5 | 1.0 | 10.1 | 15.1 | 4.1 | 2.3 | TCAActttcactTCAG |
| 18_12 | 8.8 | 7.4 | 1.9 | 0.6 | 13.3 | 8.9 | 4.6 | 1.6 | TCaactttcactTCAG |
| 18_15 | 0.0 | 35.4 | 4.7 | 6.0 | 34.8 | 11.8 | 4.8 | 2.3 | TcAACtttcactTcAG |
| 18_18 | 0.0 | 27.1 | 2.6 | 2.7 | 25.0 | 7.3 | 5.4 | 1.5 | TCAACtttcacttCAG |
| 18_19 | 0.0 | 7.0 | 2.8 | 0.7 | 0.0 | 18.1 | 1.2 | 1.0 | TCAActttcacttCAG |
| 18_20 | 11.9 | 10.6 | 4.2 | 1.8 | 0.0 | 64.2 | 9.3 | 22.5 | TCAaCtttcacttCAG |
| 18_21 | 21.9 | 7.0 | 4.4 | 1.3 | 0.0 | 40.5 | 16.0 | 25.6 | TCaaCtttcacttCAG |
| 18_23 | 8.8 | 10.8 | 3.0 | 1.2 | 0.0 | 32.5 | 3.5 | 4.1 | TCAACtttcacttcAG |
| 18_24 | 13.5 | 5.9 | 3.3 | 0.8 | 23.3 | 6.2 | 3.4 | 1.0 | TCAACtttcacttcAG |
| 18_25 | 13.0 | 11.4 | 3.0 | 1.3 | 9.4 | 18.7 | 5.0 | 3.3 | TCaACtttcacttcAG |
| 18_27 | 7.9 | 9.2 | 2.7 | 0.9 | 19.2 | 7.5 | 3.3 | 1.0 | TCAACtttcacttcAG |
| 18_28 | 13.4 | 11.3 | 4.7 | 2.1 | 19.1 | 5.8 | 4.6 | 1.1 | TCaaCtttcacttcAG |
| 18_30 | 9.9 | 7.4 | 5.1 | 1.2 | 0.0 | 14.4 | 7.1 | 3.5 | TcAACtttcacttcAG |
| 18_346 | 8.1 | 8.9 | 1.5 | 0.6 | 0.0 | 19.1 | 3.9 | 2.5 | TCaActttcactTCAG |
| 18_347 | 9.2 | 15.0 | 1.6 | 1.0 | 0.0 | 24.0 | 4.3 | 3.6 | TcAActttcactTCAG |
| 18_350 | 8.5 | 6.3 | 1.8 | 0.5 | 0.0 | 24.4 | 3.4 | 2.6 | TCAActttcactTcAG |
| 18_357 | 0.0 | 10.0 | 4.5 | 1.6 | 0.0 | 25.5 | 8.1 | 6.5 | TCaActttcacttCAG |
| 18_358 | 0.0 | 19.3 | 3.9 | 2.5 | 29.9 | 9.2 | 4.3 | 1.8 | TcaACtttcacttCAG |

From these data it can be seen that an effective target reduction can also be archived in a hepatocyte derived cell line.

Example 11: Screening for In Vitro Efficacy of Stereodefined Antisense Oligonucleotides Targeting PAPD5 and PAPD7 in dHepaRG Cells The stereodefined oligonucleotides screened for PAPD5 and PAPD7 knock down in HeLa cells (Example 7) were screened in dHepaRG cells to demonstrate efficient knock down in a liver cell line.

The screening was conducted as described in example 10 with the following oligonucleotide concentrations 33, 10.44, 3.33, 1.044, 0.33, 0.104, 0.033 and 0.01 µM.

PAPD5 and PAPD7 mRNA levels were analysed by Real-time PCR as described in the Materials and Method section. EC 50, max KD (efficacy) of the PAPD5 and PAPD7 mRNA expression was calculated using the R-function drm( ) from the drc package (v3.0-1) a four-parameter log-logistic function is fitted to the expression of the gene of interest as a function of oligonucleotide concentration to obtain a value for EC50 and maximum knock-down.

The results are shown in table 26.

TABLE 26

EC50 and Max KD of anti-PAPD5/PAPD7 stereodefined compounds on PAPD5 and PAPD7 mRNA expression in dHepaRG cells

| | PAPD5 | | | | PAPD7 | | | | |
|---|---|---|---|---|---|---|---|---|---|
| | Max KD % of saline | | EC50 µM | | Max KD % of saline | | EC50 µM | | |
| CMP ID NO | Avg | sd | Avg | sd | Avg | sd | Avg | sd | Stereodefined motif |
| 18_1 | 0.0 | 7.75 | 1.6 | 0.43 | 0.0 | 8.71 | 3.8 | 1.16 | TCAactttcacttCAG XXXXXXXXXXXXXXXH |
| 18_36 | 3.6 | 2.33 | 1.3 | 0.11 | 0.0 | 7.23 | 1.6 | 0.34 | XXXXRSSRXXXXXXXH |
| 18_76 | 0.0 | 18.65 | 6.3 | 3.60 | 11.6 | 11.23 | 6.5 | 2.36 | XXXXXXXXXRRSRRSH |
| 18_99 | 9.4 | 6.99 | 5.7 | 1.40 | 13.7 | 18.67 | 7.2 | 4.94 | XXXXXXXXXSRSRSSH |
| 18_109 | 4.0 | 9.74 | 2.3 | 0.75 | 6.4 | 15.14 | 3.4 | 1.73 | XXXXXXXXXXRRRSSH |
| 18_111 | 7.4 | 16.00 | 3.0 | 1.61 | 12.6 | 14.95 | 4.4 | 2.12 | XXXXXXXXXXRSSSRH |
| 18_124 | 7.0 | 29.13 | 1.7 | 1.81 | 6.3 | 14.24 | 3.7 | 1.55 | XXXXXXXXXXSRRSSH |
| 18_146 | 1.7 | 19.93 | 1.8 | 1.19 | 12.3 | 20.51 | 4.9 | 3.39 | RRSRSSRRSSSRRSSH |
| 18_171 | 3.9 | 6.86 | 1.7 | 0.40 | 0.0 | 16.12 | 3.0 | 1.52 | SSSRRSSRSRRRRRSH |
| 18_185 | 0.0 | 14.48 | 2.6 | 1.19 | 10.4 | 9.76 | 4.1 | 1.28 | RSRSSRSRSRRSRSRH |
| 18_187 | 5.2 | 8.79 | 1.5 | 0.45 | 2.9 | 5.11 | 2.0 | 0.35 | RSSRRSRRRRSRRRSH |
| 18_188 | 7.5 | 4.82 | 1.5 | 0.28 | 12.2 | 10.13 | 1.7 | 0.63 | SSSRRSSRSRSRSSSH |
| 18_190 | 0.0 | 27.66 | 8.1 | 8.27 | 30.4 | 10.66 | 4.1 | 1.95 | SSSRSSSRSRRSRSSH |
| 18_196 | 9.0 | 8.92 | 1.8 | 0.62 | 19.7 | 8.01 | 1.5 | 0.51 | SSSSRSRRRSSRRRSH |
| 18_223 | 11.2 | 10.00 | 1.4 | 0.62 | 19.9 | 6.90 | 2.5 | 0.75 | XSXXXXXXXXXXXXXH |
| 18_227 | 6.4 | 20.21 | 1.7 | 1.19 | 10.8 | 10.55 | 3.2 | 1.15 | XXXSXXXXXXXXXXXH |
| 18_231 | 10.2 | 5.89 | 1.3 | 0.30 | 9.9 | 6.10 | 2.1 | 0.44 | XXXXXSXXXXXXXXXH |
| 18_236 | 10.8 | 6.26 | 3.1 | 0.59 | 15.3 | 6.47 | 3.3 | 0.64 | XXXXXXXXRXXXXXXH |
| 18_243 | 6.0 | 9.15 | 1.8 | 0.52 | 26.9 | 3.26 | 1.9 | 0.24 | XXXXXXXXXXXSXXXH |

From these data it can be seen that stereo defined oligonucleotides also are effective in target reduction in a hepatocyte derived cell line.

Example 12: In Vitro Effect on HBV Infected ASGPR-dHepaRG Cells Using Selected GalNAc Conjugated Antisense Oligonucleotides Targeting PAPD5 and PAPD7

A selection of the most efficacious oligonucleotides from example 5 were conjugated to a GalNAc conjugate moiety and tested for their effect on HBV propagation parameters in HBV infected ASGPR-dHepaRG cells.

For comparative purposes the antisense oligonucleotides of the invention were compared to GalNAc conjugated versions of the he HBV targeting oligonucleotides shown in table 13, the GalNAc conjugated versions are shown in Table 13A.

TABLE 13A

Comparative HBV targeting oligonucleotides

| Description | Compound | SEQ ID NO | Reference |
|---|---|---|---|
| HBV targeting 1 | GN2$_o$c$_o$a$_o$AGCgaagtgcacaCGG | 29 | WO2015/173208 |
| HBV targeting 2 | GN2$_o$c$_o$a$_o$GCGtaaagagaGG | 30 | WO2015/173208 |

The assessment of the EC50 and efficacy (KD) on HBsAg and HBeAg of the GalNAc conjugated oligonucleotides was performed as described in Example 2 using HBV infected ASGPR-dHepaRG cells. The results are shown in Table 27.

In addition to the procedure in example 2 the harvested cells were washed once in PBS and lysed in MagNA Pure lysis buffer (Roche #05467535001) and stored at −80° C. RNA was extracted using MagNA Pure "96 Cellular RNA Large Volume Kit" (Roche #05467535001) and PAPD5 and PAPD7 mRNA expression levels were determined as described in Materials and Methods section, Real-time PCR for PAPD5 and PAPD7. EC50 and efficacy (KD) was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in Table 27A.

The compounds indicated in the the table have phosphodiester linkages in the ca dinucleotide following the C6 linker as it is indicated in table 10.

TABLE 27A in vitro efficacy and potency (EC50) of GalNAc conjugated anti-PAPD5/PAPD7 compounds. PAPD5 and PAPD7 mRNA levels are normalized to GUSB in ASGPR-dHepaRG cells and shown as % of control (PBS treated cells).

| | PAPD5 | | | | PAPD7 | | | |
|---|---|---|---|---|---|---|---|---|
| CMP | Max KD | | EC50 | | Max KD | | EC50 | |
| ID | % of saline | | μM | | % of saline | | μM | |
| NO | Avg | sd | Avg | sd | Avg | sd | Avg | sd |
| HBV1 | 58 | 9.26 | Inf | 10.00 | 76 | 11.5 | 0.780 | 10.000 |
| HBV2 | 59 | 43.5 | Inf | 24000 | 82 | 7.47 | Inf | 10.000 |
| 21_26 | 11 | 2.01 | 0.080 | 0.010 | 14 | 2.01 | 0.059 | 0.010 |
| 21_27 | 7.8 | 1.04 | 0.056 | 0.004 | 14 | 3.4 | 0.076 | 0.018 |

TABLE 27

EC50 and Max KD of anti-PAPD5/PAPD7 compounds on HBsAg and HBeAg (average of 3) in HBV infected ASGPR-dHepaRG cells.

| | HBeAg | | | | HBsAg | | | | |
|---|---|---|---|---|---|---|---|---|---|
| CMP | Max KD | | EC50 | | Max KD | | EC50 | | |
| ID | % of saline | | μM | | % of saline | | μM | | |
| NO | Avg | sd | Avg | sd | Avg | sd | Avg | sd | Compound |
| HBV1 | 26.4 | 3.6 | 0.124 | 0.026 | 39.6 | 7.3 | 0.220 | 0.104 | GN2-C6caAGCgaagtgcacaCGG |
| HBV2 | 31.3 | 4.2 | 0.233 | 0.373 | 33.2 | 4.8 | 0.391 | 0.119 | GN2-C6caGCGtaaagagaGG |
| 21_26 | 11.4 | 15.7 | 0.175 | 0.113 | 18.1 | 8.9 | 0.201 | 0.070 | GN2-C6caTcAActttcactTCAGT |
| 21_27 | 18.5 | 6.2 | 0.128 | 0.041 | 23.3 | 8.1 | 0.192 | 0.068 | GN2-C6caTCAActttcactTCaGT |
| 21_33 | 28.4 | 19.3 | 0.247 | 0.133 | 33.2 | 10.5 | 0.242 | 0.106 | GN2-C6caTcAActttcacttCAGT |
| 21_34 | 17.6 | 5.5 | 0.083 | 0.037 | 27.3 | 3.7 | 0.085 | 0.091 | GN2-C6caTcAacttttcacttCAGT |
| 21_36 | 13.8 | 6.0 | 0.086 | 0.156 | 20.6 | 9.6 | 0.193 | 0.086 | GN2-C6caTCAActttcacttcAGT |
| 20_12 | 0.0 | 2.6 | 0.073 | 0.088 | 9.9 | 1.9 | 0.057 | 0.005 | GN2-C6caTCAactttcacttCAG |
| 20_35 | 3.2 | 10.4 | 0.080 | 0.166 | 9.7 | 6.6 | 0.085 | 0.143 | GN2-C6caTCaActttcactTCAG |
| 20_36 | 3.7 | 4.0 | 0.082 | 0.001 | 3.9 | 3.1 | 0.082 | 0.014 | GN2-C6caTcAActttcactTCAG |
| 20_30 | 4.8 | 5.6 | 0.107 | 0.031 | 2.3 | 4.2 | 0.137 | 0.032 | GN2-C6caTCaActtcacttCAG |

TABLE 27A-continued in vitro efficacy and potency (EC50) of GalNAc conjugated anti-PAPD5/PAPD7 compounds. PAPD5 and PAPD7 mRNA levels are normalized to GUSB in ASGPR-dHepaRG cells and shown as % of control (PBS treated cells).

| CMP ID NO | PAPD5 Max KD % of saline | | PAPD5 EC50 µM | | PAPD7 Max KD % of saline | | PAPD7 EC50 µM | |
|---|---|---|---|---|---|---|---|---|
| | Avg | sd | Avg | sd | Avg | sd | Avg | sd |
| 21_33 | 8.4 | 1.2 | 0.050 | 0.005 | 14 | 2.16 | 0.075 | 0.009 |
| 21_34 | 4.8 | 1.05 | 0.065 | 0.004 | 9.4 | 1.75 | 0.047 | 0.006 |
| 21_36 | 3.9 | 1.04 | 0.087 | 0.005 | 2.4 | 5.85 | 0.033 | 0.025 |
| 20_12 | 1.6 | 1.05 | 0.034 | 0.004 | 3.6 | 1.79 | 0.040 | 0.006 |
| 20_35 | 6.7 | 1.51 | 0.038 | 0.006 | 8.4 | 1.81 | 0.054 | 0.008 |
| 20_36 | 3.4 | 1.48 | 0.037 | 0.004 | 6.9 | 4.35 | 0.082 | 0.018 |
| 20_30 | 1.9 | 1.06 | 0.035 | 0.003 | 4.9 | 5.8 | 0.040 | 0.019 |

Inf = EC50 could not be calculated due to lack in dose response.

As expected the two HBV targeting molecules had very insignificant effect on PAPD5 and PAPD7, their HBsAg and HBeAg effects are therefore not connected to their ability to reduce PAPD5 or PAPD7. The reminder of the tested compound show target reduction below 85% and EC50 values below 0.09 µM, which correlate well with the effects seen on HBsAg and HBeAg in table 27.

Example 13 In Vitro Effect on HBV Infected PHH Cells Using Selected GalNAc Conjugated Antisense Oligonucleotides Targeting PAPD5 and PAPD7

A selection of GalNAc conjugated oligonucleotides were further tested in HBV infected primary human hepatocytes (see materials and method section; PHH natural infection assay) to illustrate efficacy in an in vitro system with a natural ASGPR expression. The oligonucleotide concentrations used were three-fold serial dilutions (20.00, 6.67, 2.22, 0.74, 0.25, 0.08, 0.03, 0.01 µM oligonucleotide).

EC 50, max KD (efficacy) of the HBV propagation parameters HBsAg and HBeAg was calculated using the R-function drm( ) from the drc package (v3.0-1) a four-parameter log-logistic function is fitted to the expression of the gene of interest as a function of oligonucleotide concentration to obtain a value for EC50 and maximum reduction. The results are shown in Table 28.

EC 50, max KD (efficacy) of the PAPD5 and PAPD7 mRNA expression was calculated using the same algorithm. The results are shown in Table 28A.

TABLE 28

EC50 and Max KD of anti-PAPD5/PAPD7 compounds on HBsAg and HBeAg (average of 3) in HBV infected PHH cells.

| CMP ID NO | HBsAg Max KD % of saline | | HBsAg EC50 µM | | HBeAg Max KD % of saline | | HBeAg EC50 µM | | Compound |
|---|---|---|---|---|---|---|---|---|---|
| | Avg | sd | Avg | sd | Avg | sd | Avg | sd | |
| 20_13 | 11.8 | 4.1 | 0.078 | 0.179 | 9.0 | 2.3 | 0.078 | 0.010 | GN2-C6caTCAActtttcactTCAG |
| 20_14 | 11.9 | 1.9 | 0.062 | 0.006 | 13.1 | 1.8 | 0.063 | 0.006 | GN2-C6caTCAActtttcacttCAG |
| 20_12 | 17.0 | 2.1 | 0.054 | 0.006 | 24.4 | 1.3 | 0.075 | 0.005 | GN2-C6caTCAactttcacttCAG |
| 20_15 | 9.5 | 1.4 | 0.017 | 0.003 | 11.2 | 2.4 | 0.029 | 0.006 | GN2-C6caTCAActtttcacTtCAG |
| 20_16 | 16.7 | 1.9 | 0.098 | 0.010 | 19.5 | 3.4 | 0.180 | 0.031 | GN2-C6caTCAACtttcacttCAG |
| 20_17 | 16.9 | 2.1 | 0.068 | 0.011 | 26.0 | 3.0 | 0.119 | 0.024 | GN2-C6caTCAACtttcacttcAG |
| 20_18 | 13.2 | 1.9 | 0.066 | 0.008 | 19.2 | 1.0 | 0.070 | 0.004 | GN2-C6caTCAActtttcacttcAG |
| 20_20 | 14.8 | 5.0 | 0.087 | 0.022 | 18.8 | 4.3 | 0.168 | 0.043 | GN2-C6caTcAACtttcactTcAG |

The compounds indicated in the the table have phosphodiester linkages in the ca dinucleotide following the C6 linker as it is indicated in table 10.

From these data it can be seen that the selected GalNAc conjugated oligonucleotides targeting PAPD5 and PAPD7 are capable of reducing HBV antigen secretion in infected primary human hepatocytes.

TABLE 28A in vitro efficacy and potency (EC50) of GalNAc conjugated anti-PAPD5/PAPD7 compounds. PAPD5 and PAPD7 mRNA levels are normalized to GUSB in PPH cells and shown as % of control (PBS treated cells).

| CMP ID NO | PAPD5 | | | | PAPD7 | | | |
|---|---|---|---|---|---|---|---|---|
| | Max KD % of saline | | EC50 µM | | Max KD % of saline | | EC50 µM | |
| | Avg | sd | Avg | sd | Avg | sd | Avg | sd |
| 20_13 | 0 | 6.28 | 0.030 | 0.028 | 0 | 10.4 | 0.018 | 0.034 |
| 20_14 | 3.6 | 1.92 | 0.026 | 0.007 | 0 | 8.63 | 0.011 | 0.020 |
| 20_12 | 4.2 | 3.41 | 0.033 | 0.009 | 2.9 | 5.31 | 0.007 | 0.012 |
| 20_15 | 0 | 6.37 | 0.001 | 0.001 | 0 | 8.93 | 0.033 | 0.061 |
| 20_16 | 11 | 2.67 | 0.094 | 0.016 | 1.8 | 6.2 | 0.016 | 0.016 |
| 20_17 | 91 | 4.6 | 4.200 | 0.270 | 13 | 6.05 | 0.039 | 0.022 |
| 20_18 | NA | NA | NA | NA | 6.7 | 7.11 | 0.015 | 0.016 |
| 20_20 | 11 | 3.19 | 0.045 | 0.012 | 13 | 7.9 | 0.004 | 0.015 |

NA = not assessed due to technical error

From these data it can be seen that the selected GalNAc conjugated oligonucleotides targeting PAPD5 and PAPD7 are capable of reducing their targets to 11% or lower, with the exception of compound 20_17 that appears to have very little effect on PAPD5 mRNA, while maintain the effect on PAPD7 mRNA.

Example 14 Screening for In Vitro Efficacy of Antisense Oligonucleotides Targeting Human and Mouse PAPD5 and PAPD7 (Bispecific) in HeLa Cells and PMH Cells An oligonucleotide screen was performed using gapmer oligonucleotides targeting the human and mouse transcripts of PAPD5 and PAPD7 (table 5) in the human HeLa cell line and in primary mouse hepatocytes (PMH).

The screening in HeLa cells was conducted as described in Example 1 with a 25 µM concentration.

The screening in PMH cells was conducted as described in the "Materials and methods" section under "Primary mouse Hepatocytes" using 5 µM oligonucleotide.

Figure 11A:
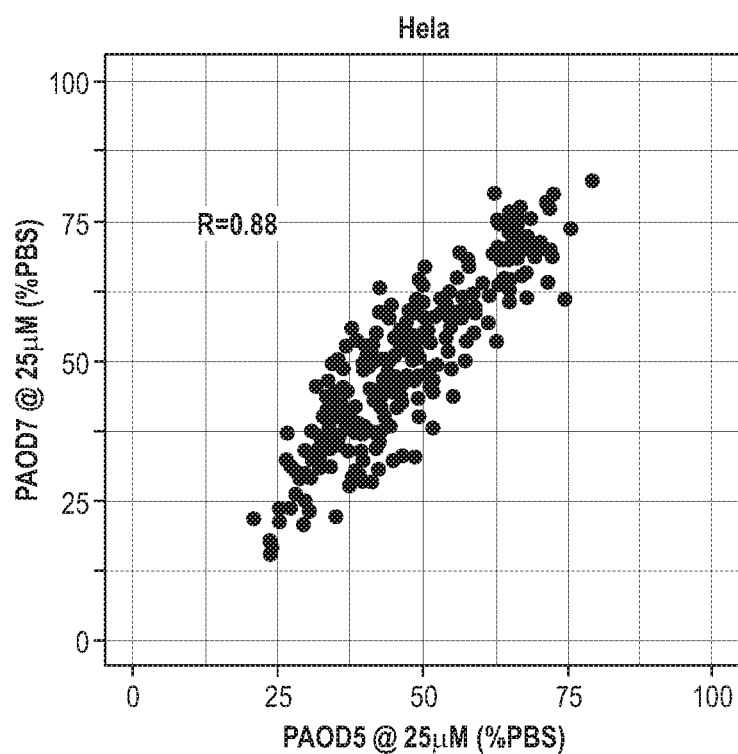

FIG. 11 shows the results of the screen, each dot represents a compound from table 5 and it's ability to reduce PAPD7 mRNA (Y axis) and PAPD5 mRNA (X axis). In the HeLa cells (human) there is a good correlation between PAPD5 and PAPD7 mRNA reduction, whereas in the PMH (mouse) cells it appears that the reduction of PAPD7 mRNA is not very efficient compared to the PAPD5 mRNA reduction.

A plausible explanation of the modest inhibition of PAPD7 mRNA in the mouse hepatocytes is that the primary spliced mRNA transcript of PAPD7 expressed in primary mouse hepatocytes has a transcription start site downstream of the binding site of the oligonucleotides. This was not identified until a whole transcriptome shotgun sequencing (RNAseq) was performed on the primary mouse hepatocytes.

Example 15: In Vitro Effect on HBV Infected ASGPR-dHepaRG Cells Using Selected GalNAc Conjugated Antisense Oligonucleotides Targeting PAPD5 and PAPD7

A further selection of oligonucleotides from example 2 and 5 were conjugated to a GalNAc conjugate moiety and tested for their effect on HBV propagation parameters in HBV infected ASGPR-dHepaRG cells.

The assessment of the EC50 and efficacy (KD) on HBsAg and HBeAg of the GalNAc conjugated oligonucleotides was performed as described in Example 2 using HBV infected ASGPR-dHepaRG cells. The results are shown in Table 29.

In addition to the procedure in example 2 the harvested cells were washed once in PBS and lysed in MagNA Pure lysis buffer (Roche #05467535001) and stored at −80° C. RNA was extracted using MagNA Pure "96 Cellular RNA Large Volume Kit" (Roche #05467535001) and PAPD5 and PAPD7 mRNA expression levels were determined as described in Materials and Methods section, Real-time PCR for PAPD5 and PAPD7. EC50 and efficacy (KD) was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in Table 29A.

TABLE 29

EC50 and Max KD of anti-PAPD5/PAPD7 compounds on HBsAg and HBeAg (average of 3) in HBV infected ASGPR-dHepaRG cells.

| | HBeAg | | HBsAg | | |
|---|---|---|---|---|---|
| CMP ID NO | Max KD % of saline Avg | EC50 µM Avg | Max KD % of saline Avg | EC50 µM Avg | Compound |
| 20_12 | 8.12 | 0.05 | 9.59 | 0.05 | GN2-C6ocoaoTCAactttcacttCAG |
| 21_20 | 26.60 | 0.32 | 27.25 | 0.32 | GN2-C6ocoaoTcAactttcactTcAGT |
| 21_21 | 21.08 | 0.12 | 24.20 | 0.17 | GN2-C6ocoaoTcAActttcacttCaGT |
| 21_22 | 42.22 | 0.52 | 40.26 | 1.43 | GN2-C6ocoaoTCAactttcacttcAGT |
| 20_31 | 17.80 | 0.18 | 17.19 | 0.29 | GN2-C6ocoaoTCaactttcactTCAG |

TABLE 29-continued

EC50 and Max KD of anti-PAPD5/PAPD7 compounds on HBsAg and
HBeAg (average of 3) in HBV infected ASGPR-dHepaRG cells.

| | HBeAg | | HBsAg | | |
|---|---|---|---|---|---|
| CMP ID NO | Max KD % of saline Avg | EC50 µM Avg | Max KD % of saline Avg | EC50 µM Avg | Compound |
| 20_32 | 1.20 | 0.07 | 10.25 | 0.08 | GN2-C6ocoaoTCAaCtttcacttCAG |
| 20_33 | 15.30 | 0.13 | 22.90 | 0.17 | GN2-C6ocoaoTCaaCtttcacttCAG |
| 20_34 | 12.51 | 0.07 | 14.65 | 0.07 | GN2-C6ocoaoTCAaCtttcacttcAG |
| 21_41 | 26.52 | 4.25 | 37.88 | 4.84 | GN2-C6ocoaoTCaactttcactTCAGT |
| 21_44 | 35.05 | 0.11 | 37.69 | 0.23 | GN2-C6ocoaoTCaActttcacttCAGT |
| 20_40 | 0.00 | 0.06 | 6.26 | 0.09 | GN2-C6ocoaoTcaACtttcacttCAG |
| 20_39 | 0.00 | 0.05 | 16.47 | 0.07 | GN2-C6ocoaoTCAActttcactTcAG |
| 21_42 | 23.75 | 0.13 | 26.69 | 0.17 | GN2-C6ocoaoTCaActttcactTCaGT |
| 21_43 | 8.92 | 0.08 | 16.60 | 0.16 | GN2-C6ocoaoTCAActttcactTcaGT |

TABLE 29A in vitro efficacy and potency (EC50) of GalNAc conjugated
anti-PAPD5/PAPD7 compounds. PAPD5 and PAPD7 mRNA levels
are normalized to GUSB in ASGPR-dHepaRG cells and shown
as % of control (PBS treated cells).

| | PAPD5 | | | | PAPD7 | | | |
|---|---|---|---|---|---|---|---|---|
| CMP ID NO | Max KD % of saline | | EC50 µM | | Max KD % of saline | | EC50 µM | |
| | Avg | sd | Avg | sd | Avg | sd | Avg | sd |
| 20_12 | 1.8 | 1.31 | 0.043 | 0.005 | 1.5 | 1.42 | 0.027 | 0.005 |
| 21_20 | 6.8 | 1.48 | 0.076 | 0.009 | 12 | 3.21 | 0.096 | 0.018 |
| 21_21 | 12 | 1.38 | 0.035 | 0.007 | 16 | 4.3 | 0.009 | 0.019 |
| 21_22 | 4.7 | 0.723 | 0.044 | 0.003 | 5.1 | 2.2 | 0.044 | 0.009 |
| 20_31 | 5.9 | 1.55 | 0.056 | 0.009 | 6.3 | 1.57 | 0.048 | 0.008 |
| 20_32 | 8 | 1.37 | 0.058 | 0.007 | 6.2 | 2.09 | 0.027 | 0.020 |
| 20_33 | 11 | 1.28 | 0.084 | 0.008 | 5.4 | 3.57 | 0.001 | 0.002 |
| 20_34 | 6.8 | 1.87 | 0.046 | 0.011 | 8.2 | 2.2 | 0.044 | 0.007 |
| 21_41 | 35 | 4.51 | 0.097 | 0.045 | 37 | 5.74 | 0.220 | 0.096 |
| 21_44 | 10 | 1.79 | 0.120 | 0.016 | 21 | 2.2 | 0.140 | 0.024 |
| 20_40 | 4.2 | 1.38 | 0.041 | 0.006 | 7.3 | 1.11 | 0.047 | 0.004 |
| 20_39 | 5.4 | 1.98 | 0.026 | 0.011 | 8 | 3.15 | 0.025 | 0.014 |
| 21_42 | 16 | 1.8 | 0.098 | 0.011 | 16 | 2.46 | 0.063 | 0.010 |
| 21_43 | 5.8 | 1.31 | 0.059 | 0.008 | 11 | 2.31 | 0.044 | 0.010 |

Example 16 Effect on HBsAg Expression from
Chromosomally Integrated HBV DNA Using
Selected Bispecific PAPD5 and PAPD7 Targeting
Oligonucleotides In the current experiment it was tested whether a selcection of GalNAc conjugated anti-PAPD5/7 oligonucleotides with good potency towards PAPD5 and PAPD7 were capable of reducing HBs antigen and mRNA expression from the human hepatocellular carcinoma cell line Hep3B which secrete HBs antigen from chromasomally integrated HBV DNA.

Hep3B cells (Knowles et al. 1980. Science 209 pp. 497-499) were purchased from ATCC (ATCC HB-8064) and cultured in Eagle's minimum essential medium (EMEM) supplemented with 10% FBS. The cells were plated on collagen coated 96-well plates at a concentration of $1.5 \times 10^5$ cells per well and cultured at 37° C. in a humidified atmosphere with 5% $CO_2$. One day after seeding the cells oligonucleotide was added to the cells using concentrations starting at 20 µM and three-fold serial dilutions thereof (20.00, 6.67, 2.22, 0.74, 0.25, 0.08, 0.03, 0.01 µM oligonucleotide). The treatment was repeated with a medium change on day 4 and day 7. At day 11 the supernatants were harvested for HBsAg measurement (performed as described in the Materials and Method section under HBV antigen measurements) and the cells were washed once with PBS and 200 µl MagNA Pure lysis buffer was added to each well and plates were stored at −80° C. for RNA extraction.

Intracellular mRNA was extracted from lysed Hep3B cells using a MagNA Pure robot and the MagNA Pure 96 Cellular RNA Large Volume Kit (Roche, #05467535001) according to the manufacturer's protocol. PAPD5 and PAPD7 mRNA was quantified in technical duplicate by separate RT-qPCRs using a QuantStudio 12K Flex (Applied Biosystems), the TaqMan RNA-to-CT 1-Step Kit (Applied Biosystems, #4392938), Human ACTB endogenous control (Applied Biosystems, #4310881E), and PAPD5 and PAPD7 mRNA Taqman primers and reagents (Life Technologies, assay ID Hs00900790_m1 (PAPD5) and Hs00173159_m1 (PAPD7) and custom assay ID APMFW4G (Small HBs)). The qPCR was performed using the following settings: UDG incubation (15 min, 48° C.), enzyme activation (10 min, 95° C.) and qPCR (40 cycles with 15 sec, 95° C. for denaturation and 1 min, 60° C. for annealing and extension).

EC 50 and max KD (Max efficacy in % of saline) of the HBsAg, HBs mRNA, PAPD5 and PAPD7 reductions was calculated using using GraphPad Prism 7.02 non line fit. The results are shown in Table 30 and 31.

TABLE 30

EC50 and Max KD of anti-PAPD5/PAPD7 compounds on chromosomal integrated HBs mRNA and HBsAg expressed from the chromosomal integrant (average of 3 biological replicates and 2 technical duplicates) in Hep3B cells.

| CMP ID NO | HBsAg Max KD % of saline Avg | HBsAg EC50 µM Avg | HBs mRNA Max KD % of saline Avg | HBs mRNA EC50 µM Avg | Compound |
|---|---|---|---|---|---|
| 20_12 | 26.51 | 0.37 | 49.94 | 0.33 | GN2-C6ocoaoTCAactttcacttCAG |
| 20_21 | 45.17 | 1.55 | 52.85 | 0.27 | GN2-C6ocoaoTcAACtttcacttcAG |
| 20_20 | NA | >20 | 67.68 | 0.13 | GN2-C6ocoaoTcAACtttcactTcAG |
| 21_34 | 82.3 | NA | 86.73 | NA | GN2-C6ocoaoTcAactttcacttCAGT |
| 20_13 | 14.25 | 0.43 | 27.67 | 0.19 | GN2-C6ocoaoTCAActtttcactTCAG |
| 20_14 | 19.60 | 0.39 | 35.97 | 0.15 | GN2-C6ocoaoTCAActtttcacttCAG |
| 21_33 | 56.68 | 5.33 | 68.22 | 0.02 | GN2-C6ocoaoTcAActtttcacttCAGT |

NA = not applicable

TABLE 31

EC50 and Max KD of anti-PAPD5/PAPD7 compounds on on PAPD5 and PAPD7 mRNA expression (average of 3 biological replicates and 2 technical duplicates) in Hep3B cells.

| CMP ID NO | PAPD5 mRNA Max KD % of saline Avg | PAPD5 mRNA EC50 µM Avg | PAPD7 mRNA Max KD % of saline Avg | PAPD7 mRNA EC50 µM Avg | Compound |
|---|---|---|---|---|---|
| 20_12 | 10.83 | 0.16 | 14.08 | 0.18 | GN2-C6ocoaoTCAactttcacttCAG |
| 20_21 | 15.57 | 0.33 | 15.72 | 0.35 | GN2-C6ocoaoTcAACtttcacttcAG |
| 20_20 | 27.34 | 0.17 | 33.46 | 0.22 | GN2-C6ocoaoTcAACtttcactTcAG |
| 21_34 | 21.51 | 0.43 | 33.83 | 0.46 | GN2-C6ocoaoTcAactttcacttCAGT |
| 20_13 | 9.76 | 0.11 | 12.31 | 0.17 | GN2-C6ocoaoTCAActtttcactTCAG |
| 20_14 | 5.17 | 0.15 | 7.78 | 0.17 | GN2-C6ocoaoTCAActtttcacttCAG |
| 21_33 | 21.19 | 0.16 | 30.13 | 0.31 | GN2-C6ocoaoTcAActtttcacttCAGT |

From these data it can be seen that 4 out of the 7 tested oligonucleotides are capable of reducing HBsAg and HBs mRNA expression from an intergrated HBs fragment to less than 55% of the saline control.

Example 17 Effect of a Selected Bispecific PAPD5 and PAPD7 Targeting Oligonucleotide in Non-Human Primates Inhibition of PAPD5 and PAPD7 mRNA expression in the liver of cynomolgus macaques was quantified by RNA-sequencing. The animals were treated once-weekly with either saline or 1, 3, or 10 mg/kg/week with compound ID NO 20_12 for 4 weeks (6 animals per group, 5 doses total at days 1, 8, 15, 22 and 29) and sacrificed on day 29 (4 weeks post dosing). In parallel, animals were treated once-weekly with either saline or 10 mg/kg/week of compound ID NO 20_12), again for 4 weeks, for a total of 5 doses, but with a 4 week recovery period and sacrificed at day 56 (4 week dosing+4 weeks recovery).

Liver samples were collected in RNA-Later (Qiagen cat. 76104) within 20 min after exsanguination. Approximately 10 mg of tissue were lysed in 800 microL Magnapure lysis buffer (Roche) using the Tissue Lyser II (Qiagen). 350 microL aliquots of lysates were then transferred into the Magnapure 96 Deep Well Plate and processed automatically. RNA was quantified by absorption spectroscopy (Nanodrop, ThermoFischer) and RNA integrity (as per RNA integrity number, RIN) was controlled by microfluidic capillary array electrophoresis using the Agilent Bioanalyzer 2100 with RNA 6000 Nanochips (Agilent cat. 5067-1511).

For the construction of barcoded cDNA libraries, 400 ng total RNA aliquots were used as input for the TruSeq™ Stranded Total RNA kit (Illumina cat. 20020598) in conjunction with the Ribo-Zero™ Gold rRNA Removal Kit (Illumina cat. MRZG12324). The size distribution of the libraries was estimated by electrophoresis using the Agilent High Sensitivity DNA kit (cat. 5067-4627). The libraries were quantified using the KAPA Library Quantification qRT-PCR kit (Kapa Biosystems cat. KK4824). The libraries were pooled at equimolar concentrations and diluted to 11 µM prior to loading onto a flow cell of the Illumina HiSeq 4000 sequencer as follows The libraries were extended using the HiSeq PE Rapid Cluster Kit v2 (Illumina cat. PE-402-4002). The flow cells carrying amplified clusters were sequenced using paired-end reads (50-base pairs) with the TruSeq Rapid SBS Kit—HS (Illumina cat. FC-402-4001). Real time image analysis and base calling were performed using the HiSeq Sequencing Control Software (HCS). CASAVA software version 1.8 was used for production of FASTQ files of sequence read pairs.

The lowest library size obtained was 17 million read pairs and the highest was 114 million read pairs. On average there were 50 million read pairs per sample and the median was at 47 million read pairs per sample. Read pairs of each library were aligned to the Cynomolgus transcripts from the RefSeq/NCBI database using the GSNAP program to generate gene-level raw counts. These were normalized to the respective library size (for inter-samples comparisons) and for each transcript the data were further normalized to the respective transcript length (for inter-transcript comparisons). For all samples this generated transcript-level expression in normalized units RPKMs (Reads Per Kilobase of transcript, per Million mapped reads). The values for PAPD5 and PAPD7 in the treated animals were normalized to the saline-treated animals, at the corresponding timepoint the results are shown in table 32.

TABLE 32

PAPD5 and PAPD7 mRNA expression in liver of cynomolgus monkeys treated with CMP ID NO 20_12.

| CMP ID NO 20_12 | Dose | PAPD5 mRNA % of saline*, geo-metric mean | PAPD5 mRNA geo-metric SD factor | PAPD7 mRNA % of saline*, geo-metric mean | PAPD7 mRNA geo-metric SD factor |
|---|---|---|---|---|---|
| After 4 wk dosing | Saline | 100 | 1.35 | 100 | 1.24 |
|  | 1 mg/kg | 24.2 | 1.31 | 46.4 | 1.30 |
|  | 3 mg/kg | 18.2 | 1.23 | 37.1 | 1.40 |
|  | 10 mg/kg | 19.3 | 1.34 | 33.8 | 1.22 |
| After 4 wk dosing + 4 wk follow up | Saline | 100 | 1.13 | 100 | 1.26 |
|  | 10 mg/kg | 21.8 | 1.65 | 45.5 | 1.31 |

*normalized to control animals for same time-point

Relatively to the respective vehicle control group, the results show down-regulation of PAPD5 and PAPD7 mRNAs in liver, both in the main group animals and in recovery animals, at all tested dose levels of CMP ID NO 20_12. The down-regulation of PAPD5 mRNA appeared saturated in the liver with around 80% at 3 and 10 mg/kg. The down-regulation of PAPD7 mRNA was dose-related, reaching 66% reduction of mRNA at 10 mg/kg. In the recovery animals dosed with 10 mg/kg/week, the down-regulation of PAPD5 mRNA was 78%. For PAPD7 mRNA, the down-regulation reached 55%. The latter data indicates that the PAPD5 and PAPD7 mRNA inhibition persisted in the liver at least for 4 weeks after last dose.

Example 18 Effect on HBsAg and HBeAg in HBV Infected Mice Following Administration of PAPD5 and PAPD7 Targeting Oligonucleotides The present study sets out to show an in vivo effect on the HBV propagation parameters when reducing the PAPD5 and PAPD7 transcripts in the AAV/HBV mouse model.

Figure 11B:
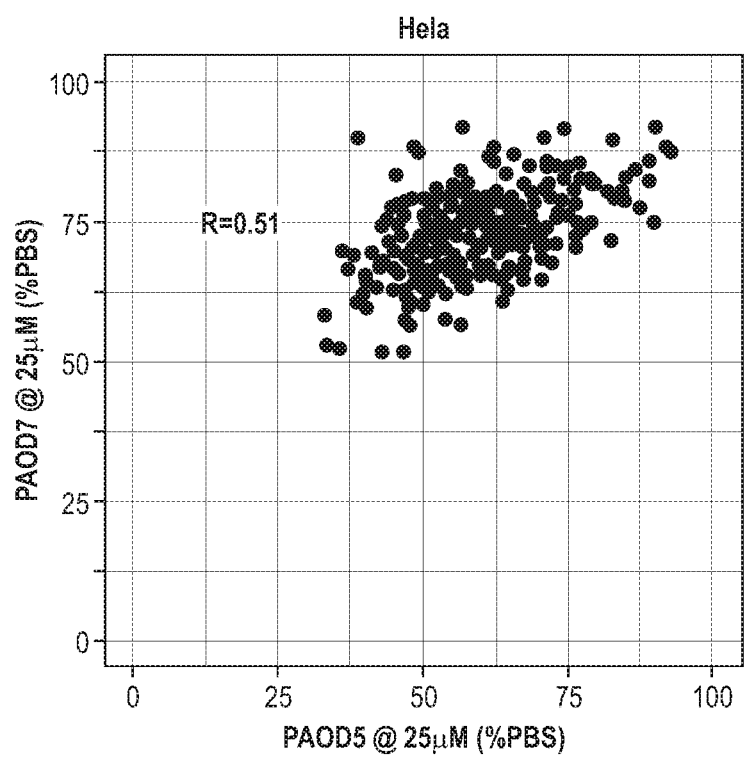
Figure 12:
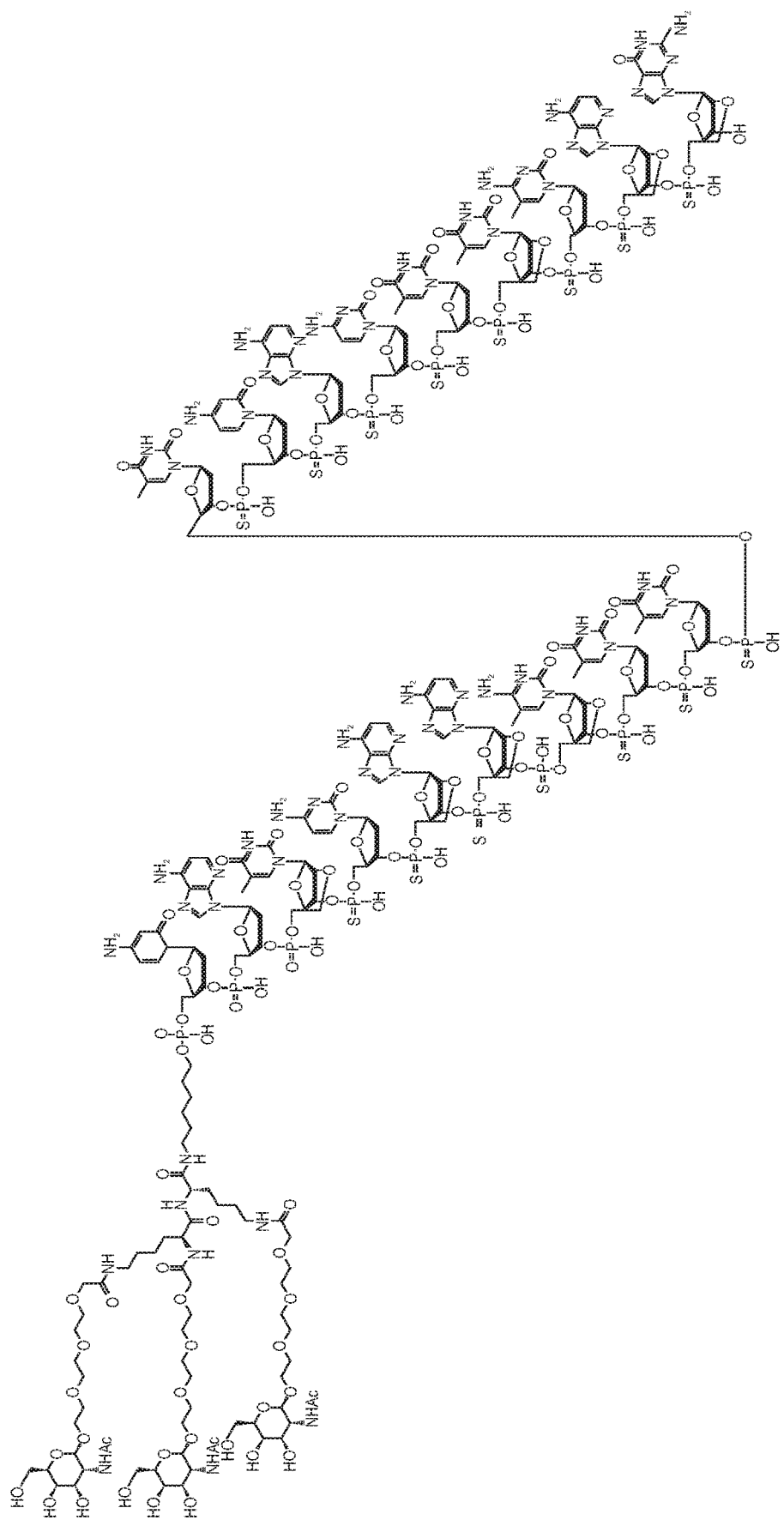
Figure 13:
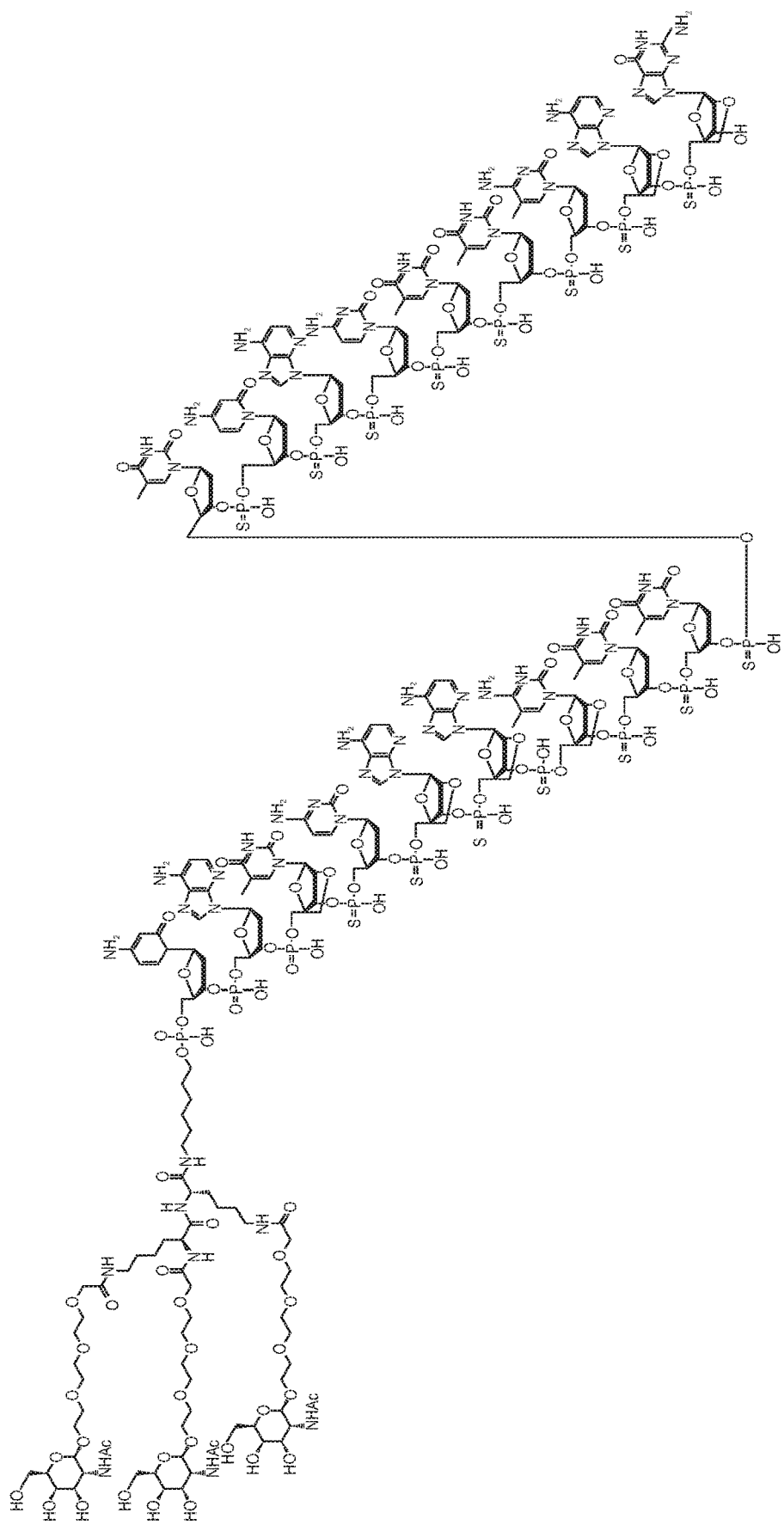
Figure 14:
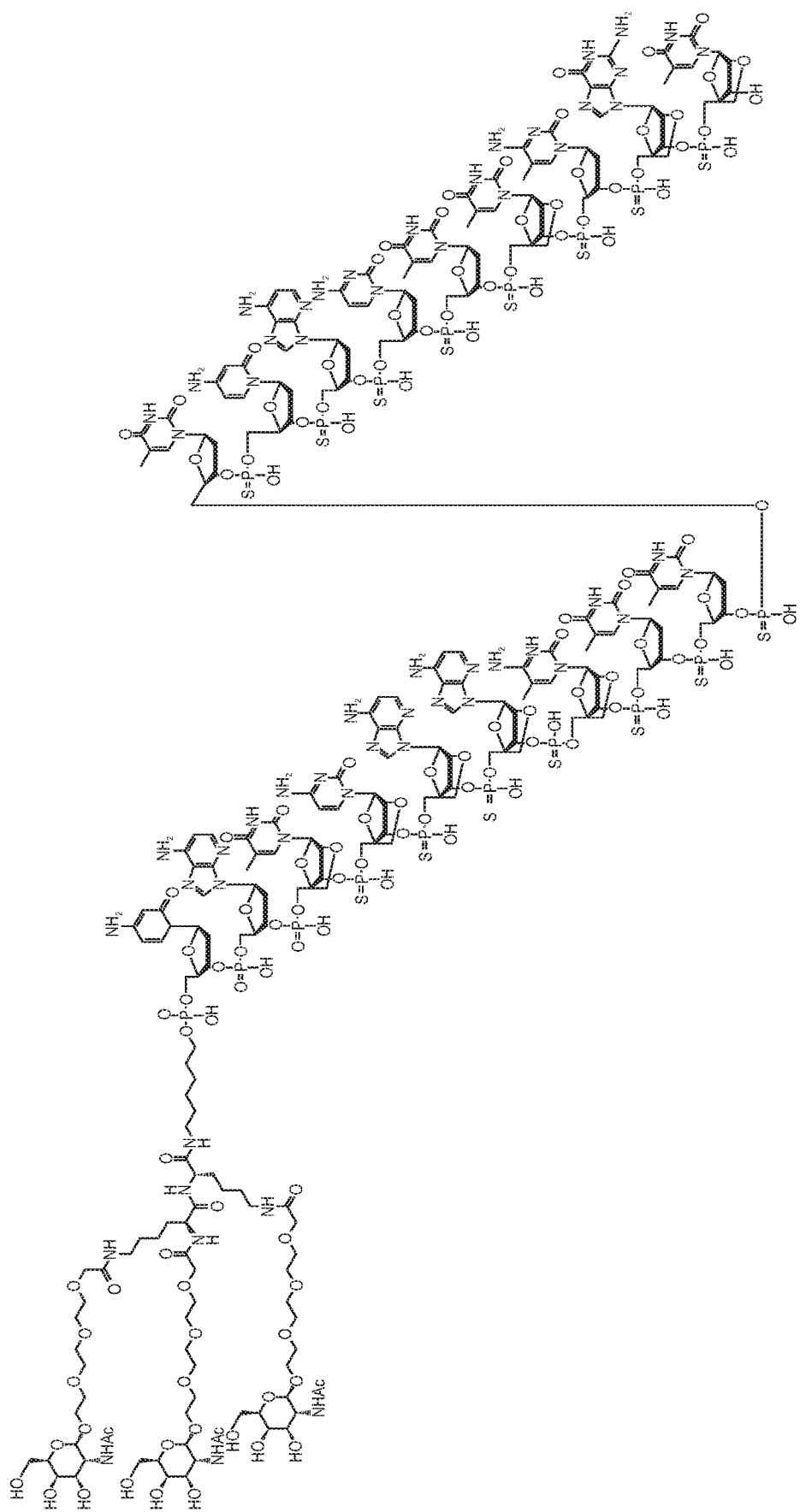
Figure 15:
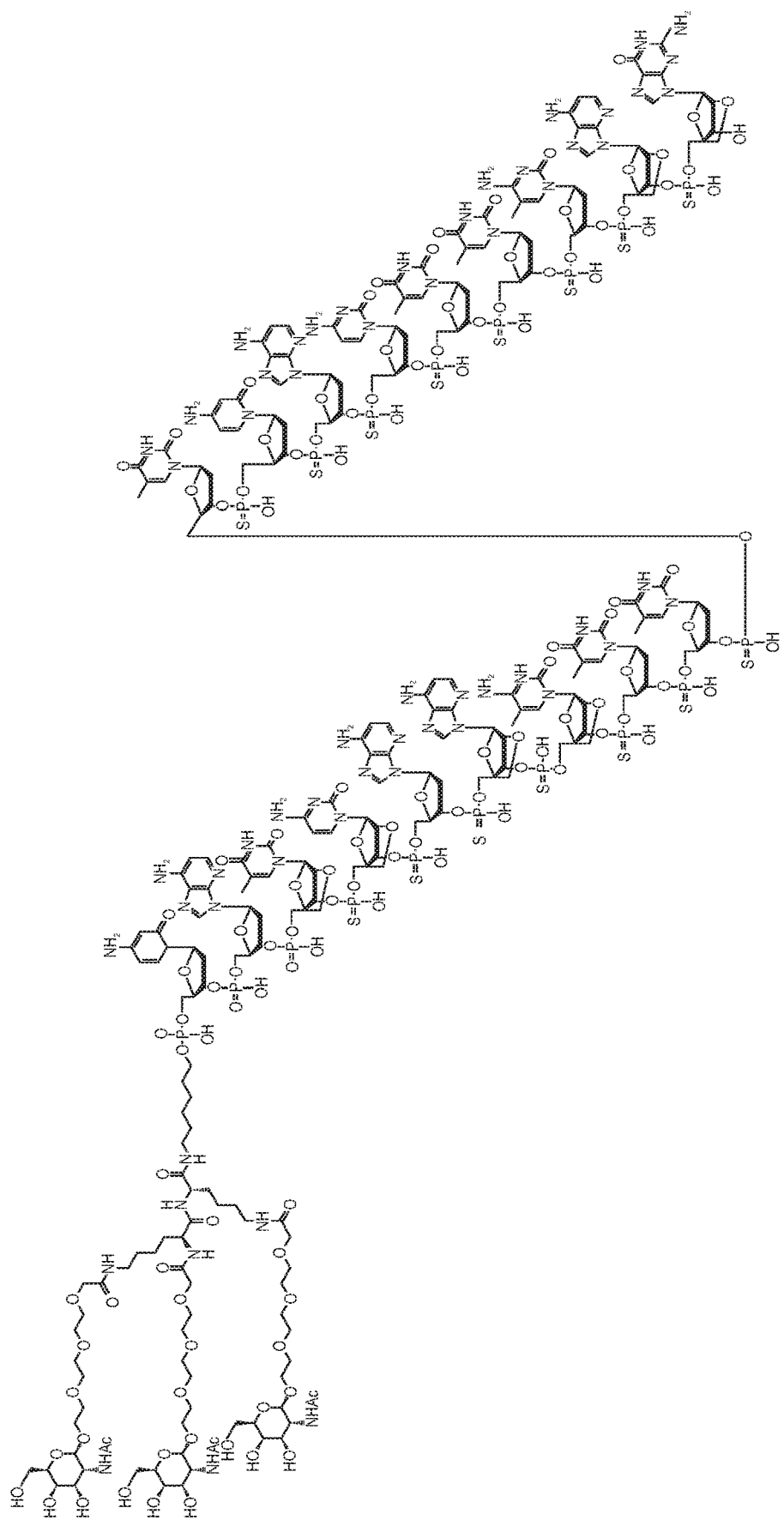
Figure 16:
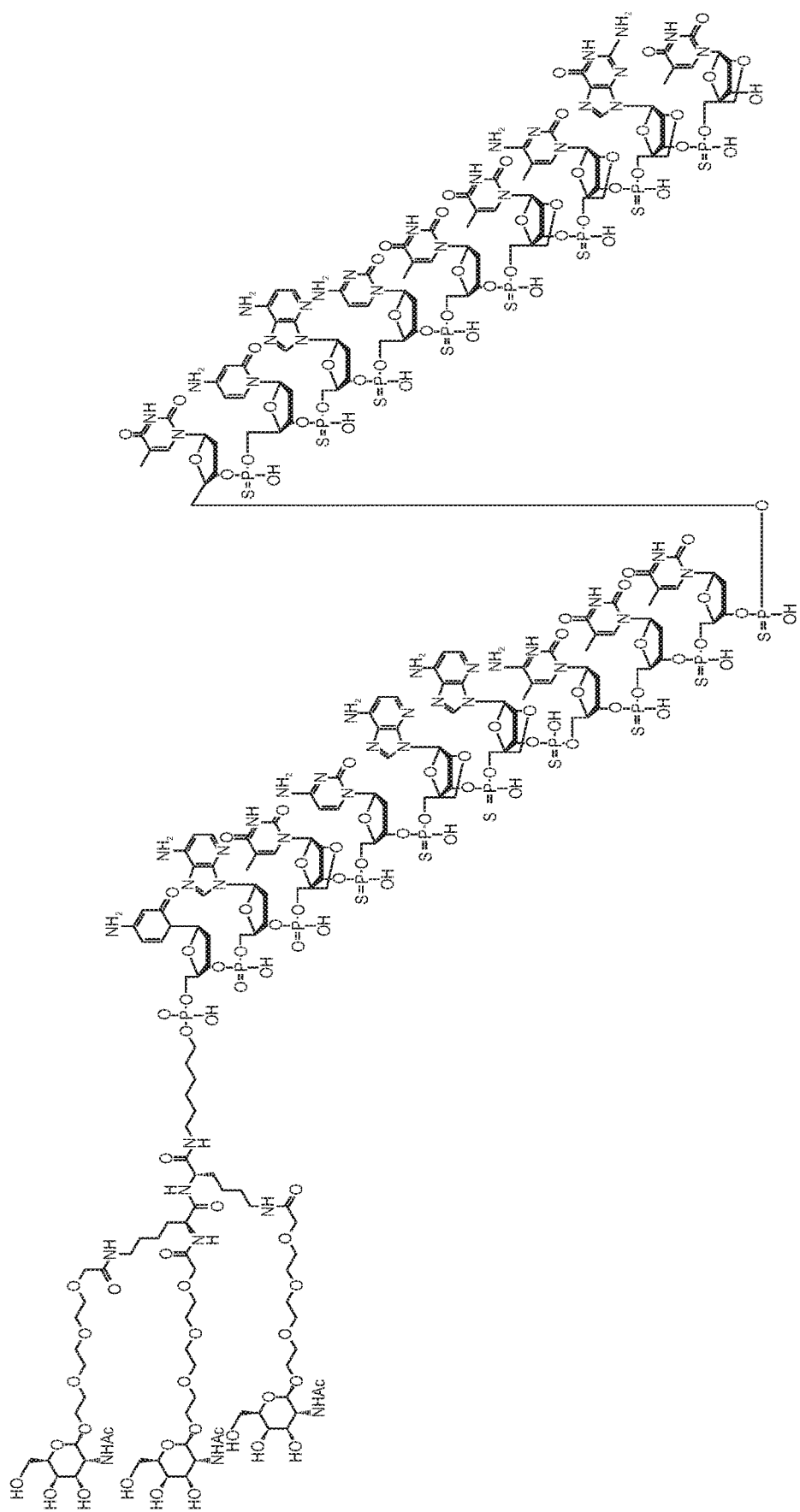
Figure 17:
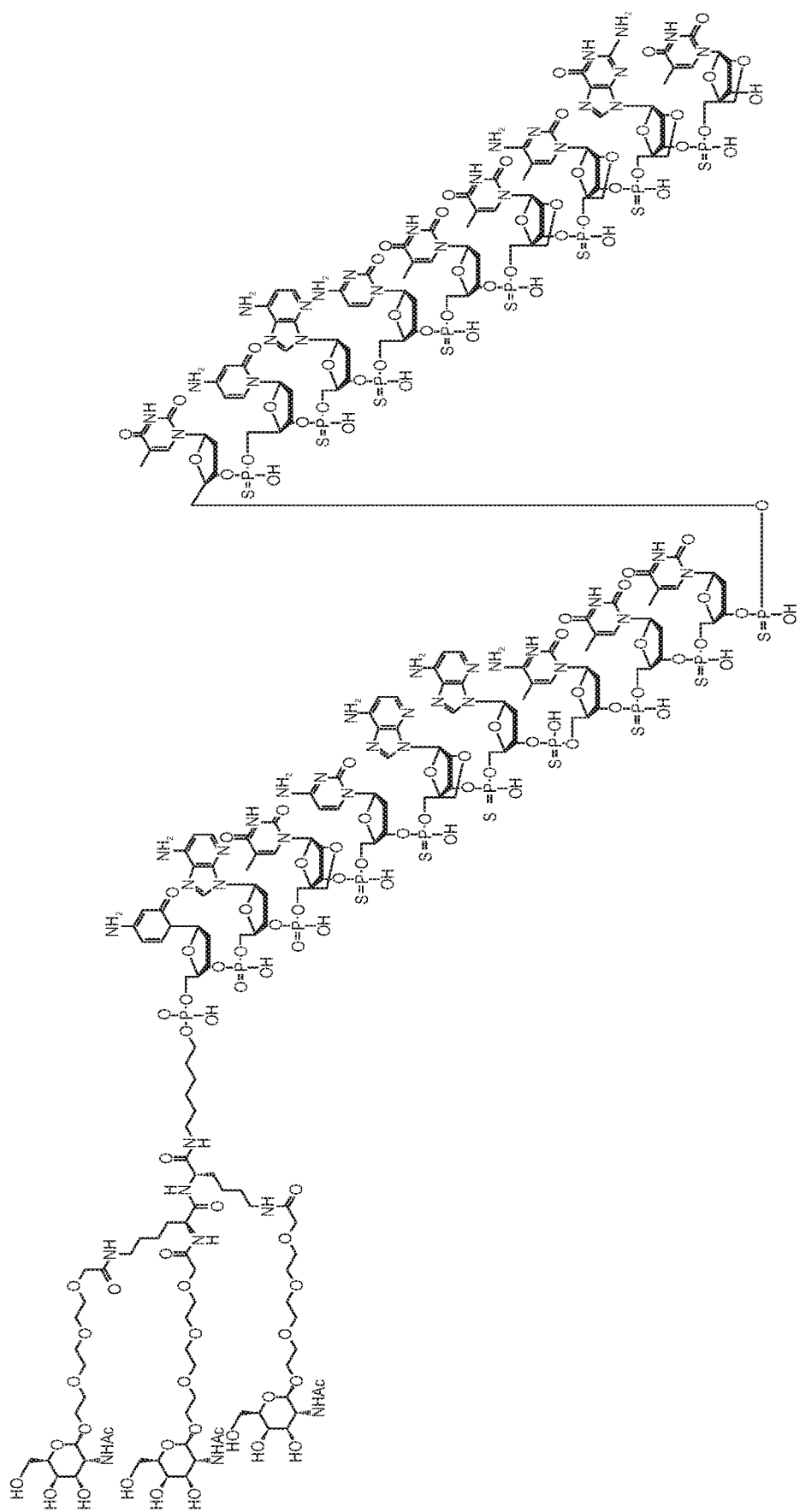

Example 14 and FIG. 11B showed that it was challenging to target both PAPD5 and PAPD7 in a mouse cell line using a single oligonucleotide. In the present study a combination of two oligonucleotides, one targeting mouse PAPD5 (CMP ID NO: 22_1) and one targeting mouse PAPD7 CMP ID NO: 22_1) listed in table 33, has therefore been used.

TABLE 33

Oligonucleotides targeting mouse PAPD5 (SEQ ID NO: 5) or mouse PAPD7 (SEQ ID NO: 6)

| SEQ ID NO | Motif sequence | Start | End | CMP ID NO | Compound |
|---|---|---|---|---|---|
| 22 | caacataagtctacacatcc | SEQ ID NO: 5 60034 | 60051 | 22_1 | 5'-GN2-C6$_o$c$_o$a$_o$ACataagtctacacATCC |
| 23 | cagttttaccgattcatca | SEQ ID NO: 6 10684 | 10700 | 23_1 | 5'-GN2-C6$_o$c$_o$a$_o$GTtttaccgattcATCA |

GN2 represents the trivalent GalNAc cluster shown in FIG. 2, C6 represents an amino alkyl group with 6 carbons, capital letters represent beta-D-oxy LNA nucleosides, lowercase letters represent DNA nucleosides, all LNA C are 5-methyl cytosine, subscript o represent a phosphodiester nucleoside linkage and unless otherwise indicated internucleoside linkages are phosphorothioate internucleoside linkages.

The AAV/HBV mouse model described in the Materials and Method section was used. Mice (3 pr. group) were dosed subcutaneously with a single dose of 10 mg/kg of each of compounds 22_1 and 23_1 (two separate injections 6 hours apart) or with 5 ml/kg saline (control) on day 0. HBsAg and HBeAg in serum was measured every 3 days using the methods described in the "Materials and Methods" section. To measure target knockdown two intermediate groups of mice were sacrificed on day 3 and day 14 and the remaining mice were sacrificed on day 27. After scarification their liver was removed following PBS perfusion. The perfused liver was cut in smaller pieces and directly frozen.

mRNA was extracted from the frozen liver pieces by adding them to 2 ml tubes containing ceramic beads and 1 ml MagNA Pure lysis buffer (Roche #05467535001). The liver pieces were homogenized using the TissueLyser (Qiagen). RNA was isolated from the tissue homogenates using MagNA Pure "96 Cellular RNA Large Volume Kit" (Roche #05467535001). The lysates may be stored at −80° C. PAPD5 and PAPD7 mRNA was measured essentially using qPCR as described in the Materials and Method section, with the following change in the TadMan primer assay, which was performed with the following two assay (ThermoFisher Scientific):

| Mouse GUSB | Mm1197698_m1 |
| Mouse PAPD5 | Mm1244121_m1 |
| Mouse PAPD7 | Mm1349513_m1 |
| Mouse TBP | Mm00446971_m1 |
| Mouse PAPD5 | Mm_011244125m1 |
| Mouse PAPD7 | Mm1349513_m1 |

GUSB and TBP are housekeeping genes used for normalization of the PAPD5 and PAPD7 mRNA measured with the primer assay indicated below the housekeeping gene.

The results are shown in the table 34, 35 and 36 below. The data in table 34 are furthermore presented in FIGS. 18 A and B.

TABLE 34

HBsAg (Log10 IU/mL serum) in AAV/HBV mice treated with PAPD5 and PAPD7 targeting oligonucleotides

| | Control (5 ml/kg saline) | | | PAPD5 and PAPD7 oligonucleotide (10 mg/kg each) | | |
|---|---|---|---|---|---|---|
| Day | HBsAg Mean (Log10 IU/mL) | SD | No of animals | HBsAg Mean (Log10 IU/mL) | SD | No of animals |
| 0 | 4.21 | 0.19 | 10 | 4.23 | 0.31 | 11 |
| 3 | 4.30 | 0.19 | 10 | 3.50 | 0.43 | 11 |
| 6 | 4.05 | 0.29 | 7 | 3.08 | 0.36 | 8 |
| 9 | 4.12 | 0.29 | 7 | 3.17 | 0.35 | 8 |
| 12 | 4.15 | 0.32 | 7 | 2.89 | 0.44 | 8 |
| 15 | 4.39 | 0.12 | 4 | 2.67 | 0.75 | 5 |
| 18 | 4.45 | 0.23 | 4 | 2.59 | 0.80 | 5 |
| 21 | 4.36 | 0.14 | 4 | 2.51 | 0.73 | 5 |
| 24 | 4.27 | 0.11 | 4 | 2.50 | 0.77 | 5 |
| 27 | 4.37 | 0.06 | 4 | 2.41 | 0.90 | 5 |

The data show that targeting PAPD5 and PAPD7 in the AAV/HBV mouse model with a single treatment resulted in a sustained 2 log reduction in HBsAg up to 27 days after treatment.

TABLE 35

HBeAg (Log10 IU/mL serum) in AAV/HBV mice treated with PAPD5 and PAPD7 targeting oligonucleotides

| | Control (5 ml/kg saline) | | | PAPD5 and PAPD7 oligonucleotide (10 mg/kg each) | | |
|---|---|---|---|---|---|---|
| Day | HBeAg Mean (Log10 IU/mL) | SD | No of animals | HBeAg Mean (Log10 IU/mL) | SD | No of animals |
| 0 | 3.39 | 0.06 | 10 | 3.40 | 0.05 | 11 |
| 3 | 3.31 | 0.06 | 10 | 2.75 | 0.07 | 11 |
| 6 | 3.39 | 0.05 | 7 | 2.83 | 0.03 | 8 |
| 9 | 3.29 | 0.05 | 7 | 2.77 | 0.04 | 8 |
| 12 | 3.33 | 0.03 | 7 | 2.75 | 0.05 | 8 |
| 15 | 3.32 | 0.06 | 4 | 2.74 | 0.05 | 5 |
| 18 | 3.28 | 0.04 | 4 | 2.67 | 0.02 | 5 |
| 21 | 3.22 | 0.03 | 4 | 2.63 | 0.01 | 5 |
| 24 | 3.24 | 0.04 | 4 | 2.70 | 0.03 | 5 |
| 27 | 3.32 | 0.05 | 4 | 2.80 | 0.04 | 5 |

As for HBsAg the targeting of PAPD5 and PAPD7 leads to reduction in HBeAg levels in the serum, although not as significant as for HBsAg.

TABLE 36

PAPD5 and PAPD7 mRNA in AAV/HBV mice (3 animals on day 3 and 14 and 5 on day 27) and ALT levels (11 animals day 0, 8 on day 14 and 5 on day 27) following a single dose treatment with PAPD5 and PAPD7 targeting oligonucleotides (10 mg/kg of each).

| | % PAPD5 mRNA of control | | % PAPD7 mRNA of control | | ALT (U/L) | | | |
|---|---|---|---|---|---|---|---|---|
| | | | | | Control | | Treated | |
| Day | Avg | sd | Avg | sd | Avg | sd | Avg | sd |
| 0 | NA | NA | NA | NA | 30.91 | 6.95 | 27.27 | 7.55 |
| 3 | 14.47 | 4.20 | 24.82 | 3.43 | NA | NA | NA | NA |
| 14 | 21.995 | 5.13 | 20.37 | 1.75 | 37.50 | 14.49 | 47.00 | 26.51 |
| 27 | 37.543 | 7.65 | 27.52 | 8.08 | 28.80 | 9.55 | 28.00 | 18.97 |

From these data it can be seen that the PAPD5 and PAPD7 targeting oligonucleotides leads to reduction in PAPD5 and PAPD7 mRNA levels, respectively, and are well tolerated in the AAV/HBV mouse model.

The invention claimed is:

1. An antisense oligonucleotide conjugate of the formula GN2-C6$_{ocoao}$TCAactttcacttCAG (SEQ ID NO: 20) or pharmaceutically acceptable salt thereof; wherein capital letters represent beta-D-oxy LNA nucleosides; all cytosine LNA nucleosides are 5-methyl cytosine; lowercase letters represent DNA nucleosides; subscript o represents a phosphodiester nucleoside linkage; and all other internucleoside linkages are phosphorothioate internucleoside linkages;
   wherein C6 represents an amino alkyl group with 6 carbons; and
   wherein GN2 represents a trivalent GalNAc cluster shown in FIG. 2;
   wherein the wavy bond line in FIG. 2 indicates the site of conjugation of the trivalent GalNAc cluster to the C6 amino alkyl group.

2. A pharmaceutically acceptable sodium salt of the antisense oligonucleotide conjugate of claim 1.

3. A pharmaceutical composition comprising the oligonucleotide conjugate or pharmaceutically acceptable salt thereof of claim 1 and a pharmaceutically acceptable diluent, solvent, carrier, salt and/or adjuvant.

4. A method for modulating PAPD$_5$ and PAPD7 expression in a target cell which is expressing PAPD5 and PAPD7, the method comprising administering the oligonucleotide conjugate according to claim 1 or a pharmaceutically acceptable salt thereof to said cell in an effective amount.

5. A method for treating HBV infection in a subject suffering from HBV infection, the method comprising administering a therapeutically effective amount of the oligonucleotide conjugate of claim 1 or a pharmaceutically acceptable salt thereof to the subject suffering from HBV infection.

6. A method for treating chronic HBV infection in a subject suffering from chronic HBV infection, the method comprising administering a therapeutically effective amount of the oligonucleotide conjugate of claim 1 or a pharmaceutically acceptable salt thereof to the subject suffering from chronic HBV infection.

7. A method for reduction of the infectiousness of a HBV-infected subject, the method comprising administering a therapeutically effective amount of the oligonucleotide conjugate of claim 1 or a pharmaceutically acceptable salt thereof to the HBV-infected subject.

8. An antisense oligonucleotide with a design and motif sequence of TCAactttcacttCAG (SEQ ID NO: 18) or a pharmaceutically acceptable salt thereof; wherein capital letters represent beta-D-oxy LNA nucleosides; lowercase letters represent DNA nucleosides; all cytosine LNA nucleosides are 5-methyl cytosine; and all internucleoside linkages are phosphorothioate internucleoside linkages.

9. A pharmaceutically acceptable sodium salt of the antisense oligonucleotide of claim 8.

10. A pharmaceutical composition comprising the antisense oligonucleotide of claim 8 and a pharmaceutically acceptable diluent, solvent, carrier, salt and/or adjuvant.

11. A method for modulating PAPD5 and PAPD7 expression in a target cell which is expressing PAPD5 and PAPD7, the method comprising administering the antisense oligonucleotide according to claim 8 or a pharmaceutically acceptable salt thereof to said cell in an effective amount.

12. A method for treating HBV infection in a subject suffering from HBV infection, the method comprising administering a therapeutically effective amount of the antisense oligonucleotide of claim 8 or a pharmaceutically acceptable salt thereof to the subject suffering from HBV infection.

13. A method for treating chronic HBV infection in a subject suffering from chronic HBV infection, the method comprising administering a therapeutically effective amount of the antisense oligonucleotide of claim 8 or a pharmaceutically acceptable salt thereof to the subject suffering from chronic HBV infection.

14. A method for reduction of the infectiousness of a HBV-infected subject, the method comprising administering a therapeutically effective amount of the antisense oligonucleotide of claim 8 or a pharmaceutically acceptable salt thereof to the HBV-infected subject.

15. A conjugate compound comprising the antisense oligonucleotide of claim 8 or a pharmaceutically acceptable salt thereof and a conjugate moiety attached to said antisense oligonucleotide or pharmaceutically acceptable salt thereof.

16. The conjugate compound of claim 15, wherein the conjugate moiety is a trivalent N-acetyl-galactosamine (GalNAc) moiety capable of binding to an asialoglycoprotein receptor.

17. The conjugate compound of claim 15, wherein the conjugate moiety is covalently attached to said antisense oligonucleotide or pharmaceutically acceptable salt thereof.

18. The conjugate compound of claim 15, wherein the conjugate moiety is covalently attached to said antisense oligonucleotide or pharmaceutically acceptable salt thereof; and
   wherein a linker is positioned between the antisense oligonucleotide or pharmaceutically acceptable salt thereof and the conjugate moiety.

19. The conjugate compound of claim 18, wherein the linker is a physiologically labile linker.

20. The conjugate of claim 19, wherein the physiologically labile linker is a nuclease susceptible linker.

21. The pharmaceutical composition of claim 10 wherein the pharmaceutically acceptable diluent is sterile phosphate buffered saline.

22. A pharmaceutically acceptable potassium salt of the antisense oligonucleotide conjugate of claim 1.

23. A pharmaceutically acceptable potassium salt of the antisense oligonucleotide of claim 8.

24. The pharmaceutical composition of claim 3 wherein the pharmaceutically acceptable diluent is sterile phosphate buffered saline.

* * * * *

SEQUENCE LISTING

```
<160> NUMBER OF SEQ ID NOS: 35

<210> SEQ ID NO 1
<211> LENGTH: 82393
<212> TYPE: DNA
<213> ORGANISM: Homo sapiens

<400> SEQUENCE: 1
acaacgcgct ccctgcgggg cgggcggcaa cctccatgcg gcctcgtcca cgctcagcac        60
cggggaagcc gaggcggaga agccgcgcgc gcctcagaag ctcccggacg cccaggtacg       120
tgggagcact ccacagatgg cgcaagtacg gttgggccag gcggttgcgg ccccgtcgcg       180
ccgcggcctc tgtgacgcac ggcgaggcct cccgggctgc tgcgcggcgc agcggggcg        240 gggcgagcgc gtgagggcgg ggcggtgggg gggggggcg gagcgagagg ggcggagccg        300
gcagaggccc cgccccgggg ccggaggagc gaggacgcta cggagcaggc gcgtctcgct       360
gccgccgctg ccgccgccgc cgctcgctct tctgtggagc cgccgccgcc gccgccgcca       420
```

```
tttgcacggg gaccccagtg acaggggctc ggcggagggg cggaggggcg gagggagggg      480
gggagggccc gcggagcccc cgagggcggg agcgacgccg ccggcgccgg ccgggctccc      540
tgcgcgaccg cgccgcccgc ggcgggcccc gagcagcagc agcagcagca gcggcagcag      600
cggcagcagc agcagcagcc gaggccgggc gtgcgcctga ggcggcggcg gcggcggccc      660
tgcgggcggc cgggaggggc gggggcagcg gccgccgccg tttgatggat ccgaggatcg      720
cctggtttca gccagagcag ctcggaccgt ccaacagtct gtggatgcag atctgggaga      780
cgacccaggg gctgaggaac ctctacttca accaccactg tcacagcagc ggcggcgcga      840
gcggcggcgg cggcagcagc agcagcagca gcacggccac cggcgggagc ggcagcagca      900
ccggcagccc cggcggcgcg gcctcggccc cggccccggc cccggccggc atgtatcgct      960
ccggggagcg cctgctgggc agccacgcgc tgcccgcgga gcagcgggac ttcctgcccc     1020
tagagacgac caacaacaac aacaaccacc accagcccgg ggcctgggcc cgccgggcgg     1080
gctcctcggc gtcctcgcct ccctcggcgt cctcgtcccc gcacccttcg gccgccgtcc     1140
ccgccgccga tccagccgat tcggcctcgg gcagcagcaa caagaggaag cgcgacaaca     1200
aggccagcac gtatggactc aactacagcc tgctgcagcc cagcggaggg cgggccgcgg     1260
ggggcggccg agcagacggc ggcggggtcg tgtacagcgg gaccccgtgg aaacggagga     1320
actacaacca gggagtcgtg gggtgagtgc tggctctgcg gcccgatggc ctggccggtg     1380
cgaatgcgca gcccgcacag gccacagaga ggggggttgt gagggtctag gagcggccac     1440
ccccacggcc tgccttcgct gctgttgcac gggggtgctg ctggccatcc caacccccc     1500 agtcgttcac acctttcccc aagcctcctt agccgtccac accctccgtc tcctgtcctc     1560
ccttagtcgt ccacaccttc ctcccctccc tcttaaccgt ccacaccttc cccaggcccc     1620
cccctttatc cattcactct cctcccatcc cccttagtta aacacatcta cccttgacca     1680
ccaccccgcc tccagccctc cacaccttt tccccatcat cacaactcaa gatgagaccg     1740
cttagcacgg gcctatcatt cattccctga gaacattggt gtgtgagtgt ttttgatgg     1800 tgcaggaccc ggaggtgctt tccttgccaa gaatagaaac atccagaatg ctcctcccca     1860 tccccaatc ccagacagca attatgtcag ccctgtaagg cattgcctgc tcttgaccct     1920
ttggcccatc ttttattt aaaaaatc ccatgtcaca gatgccctgt ctatgcagag     1980
ggtggcgtgg gatgggtgac cactaagttt aggctggtga aggtggtgag cccttctgag     2040
gccctgatag aactttccag gagttcatgg tccgcggctc cagcttctca ctgtaaagtt     2100
gtcatcctgg cagaggcagc caatgctttt cattctaggg ggtagagatt tatgctaatg     2160
agtgaatatt gcaccactag tgactttctg tttaaagttc agctcttaga aaatggaatc     2220
ttacctgacc cctagtgaat tatgtacata agcagggaat gtttccaact agatctccct     2280
tcagaagagt ccctgtgctg gaataggtca ctgaatctta tttgttttgt aaaacaaagc     2340
ttttgggtct cgtgggtgtg tgtgtgtgtg tgtgtgtgtg tgtgtagctt     2400
gagtatggag aaccggcttt caaattgctt ttcatttttc aggttgtgtt ttacattgag     2460
ggctttagca tgcaaatgaa attaccaatt agtaatccca tgtgaacctt ttcctggatt     2520
tattcattca gatctgccct gctttggctg agagagagag ttctgtgtac cttttgaag     2580 gtctggataa aatgagttgg tgggttccat ctgcttccag tgggctggtg tctgctctat     2640
gctactatta caactcctac cttttgtgga aaatgcagtc aagcgttcta ggactggtgc     2700
tgtggtacat gtcaaacctg ccctcacatt ccagaaaggg aacccctttta gggttgagtc     2760 ctctgttgct aagcttcaag ggtgctctcc atggtcatca cgttttatta aaggcttgtg     2820
```

```
gttccatcct gttagcattt ccaagtctac gcgtaaacct gtggtttagt gacaagcaaa    2880
ttgatgttga gggtttctgg tagtttcatt tcacaggagt aagctccagt taggtaatca    2940
ctgtcaacga aaaccttgaa gttccttaat tgcattttac tgaagcctct ttgcatgtgt    3000
ctagcaaaag atataagtcc aagatgctta ttttttttt gataaattag aaattgtcct     3060
ctcctctact tgctatttaa tgcagaagat actctaaaag gttcatattt atacttagaa    3120
gcaagatgtt cttgttcctg attcaaatat attgccctca aagggattag agaggaatt     3180 ttcatttccc ggagggatta ctgtttaaaa actggttgta aacctcttta aaaactgctt    3240
atcacttcac cagattttcc attcttttgc ctcctccctt agaggatgtc agcagttaat    3300 tttttttta aattaaaaaa agttcaattc tgagacctcc tagtttcaaa aaatacatta    3360
aacaattccc aagagtgtta agagtgtctg ggtgcttaga aattcttgct ttgattcatg    3420
tattctgatt ttttttttt ttttgagacg gagtttcgct cttgttgccc aggctggagt    3480
gcagtggctc gatctcagct caccgcaacc tctgcctccc aggttcaagc gattctgctg    3540
cctcagcctc ccgagtagct gggattacag gcgcttgcca ccacgcctgg ctaatttttt    3600
atttttagta gagacggggt ttcttcatgt tggtcaggct ggtctcgaac tcctgacctc    3660
aggtgatctg cccgtcttgg cctcccaaag gactgggatt acaggcatga gccaccgtgc    3720
ccggcctcat tatcctgatt tcttttttt cttttgagac tgggtctcac tctgctgcct    3780
aggctggagt ggagtgacgt gatcatagct cactgtatcc tctaactctt gggctcaagt    3840
gatcctcctg cctagcttc ctggagtagc tgggactaca ggcacatgtc accacacctg     3900 cctaatttt ttatttttac ttttgtaga gatggggcct ccatttgttg cctaggctgg      3960
tcttcaaccg gcctcaagca gtcctccac cttggcctca cagagtgctg ggattatagg     4020
catgagccac cattctcgcc agtatcctta tttcttaact ttagaaagtt tttctatttt    4080
taatataggt atttaaaaaa atctgaattc agagtgcacc tcgatgttat gctgttctga    4140
gattaaatat actaaaactg ttaccattgt tttctgaatt cttaagatgt gactgatagt    4200
tagctaatag gttaacacat tgtggtggtt cttggcctct gaactgatag tccagatggg    4260
gagaggagac cagaaagcat gtgaaaatgg actagaacca tgggacagct atatagtctc    4320
tcgcagctgt cttttgtgtt ctctgcttcc accaaattgg ttgatttatt tagaatgctg    4380
acctcttgca ttgcctaagt ccttgatgtt tttggtttct cctctgaact ctcaaaggta    4440
ctcacttcat gctcttggta tagcccactt atgtttaact ttccttttat tatgtgttcc    4500
ctcttacaca tgacatggac atttctttaa tatgtagagt aagatattgg atttcatcct    4560
aaagtcttca aaataaaact cttgagctca tcatctcaga cttcttcatg tacccacaga    4620
ccagggattt tgtttgcttt ttaaaacatt ttttattt tgtttttatt atttttaaat      4680
tttaatttaa ttttatggag acagggtctc gctctgttgc ccaggctgga gtgcagtggt    4740
gtgatctcgg ctcactgcag cctttgcctg ggctcaagcc atccacatgc cttggcctcc    4800
cagtgtgctg ggattacagg tgtgagccac tgtgcctggc ctaaatttat ttttttaatt    4860 tttttgaga cagggtcttg ctctgtcgct caggctggag tgcagtgtca taatcatggg    4920
tcacagcagc cttggcctcc caggctgaag tgaacttccc acctcagcct cctgagtagt    4980
tgggactaca ggcgagtgcc accatgcctg gctcattttg gtttttttg taaagatggg     5040 gtcttgtcat gttgcccatg aaggtctcca actcctggtc caagtgatcc tcccgcctcc    5100
gcctagcaaa atgttgggat tacaggtgtg agccaccatg cctggcctta tttatttatt    5160
```

```
taattatgaa tgaatgaatg aattaatgag agggagtctt gctctcttgc ccaggctgga    5220
gtgtggtggc acaatcttgg cccactgcaa cctccgtctc ccaggttcga gcaattctcc    5280
tgcctcagcc tcccgagtaa ctgggattac aggcgcccgc caccatgccc aggtaatttt    5340
tgtattttta gtagagatgg ggtctcacca tgttggccag actggtttcg aacttctgac    5400
ctcaagtgat ctgcccacct tggcttccca aagtgtcagg attacaggca tgagccacca    5460
tgcctggcct ggccttttat gttttaagtt gcttccactg attctcttgg gctttgctcc    5520
cctccagaac tggccatggt ttaggatgct gtccacctgc tgctgcttgt ccatgaaaac    5580
gagccataaa ccctttcctt ttgaaagact taattgttta tcactatgga gaaagagggg    5640
atggcaagaa gtagcaaata cagggaattt gcagaacttg gtcttgagcc ctgggtccag    5700
aaacttcttc tggaaggtgc ttggtgtttg tccaagctca tgataggttt ctgttggctg    5760
tactgccaga tctgtagatg cttttttaag gcttggatga cttgttcaaa acaatgtttt    5820
ggagtacaaa tttggctgtg gggacatcaa gaccttgttg ggaaacttgg gtttaaggta    5880
caatttctta aactaggatg gtgggaatgg ggatgtgaag ggagaatgaa tgtgagaggt    5940
attacagggt aaggatggag atgattcaga ttccttaagt ggatttaata atcacactgt    6000
agctttgaac ttgagtgact ggggaaatat ttgtggtgtt tttggaaata agggccagaa    6060
ggactattgg tttgggtaag aagatagtag ggggatgtat aggtggacct gctagtgggg    6120
agctgagatt tggagggctg agatgtagtg ctcttcactg ccgtagggca gtatcctctt    6180
gtatgtgcca tcctctagtg cccattgttc atcatgtcat agtaagccca agatgttcat    6240
gccttttttc agcactgcat tagggcttat atctgcttct cttctctctct ctctctcgct    6300 ctcgctccct ccctctctct ctcttttctgt ttttttttt ttttagacg gagtttcact    6360 tgtgttgccc aggttggagt gcagtggcgc gatcttggct cattgcaacc tctgactccc    6420
gggttcaagc aattctcctg cctcagcctc ccaagtagct gggattacag gcatgtgcca    6480
ccatgcctaa ttttgtatct ttagtagaga tggggtttct ccatgttggt caggctggtg    6540
tcaaactccc aacatcaggt gatctacctg cctcggccgc ccaaagtgct gggattacag    6600
gcatgagcca ccgcgcccgg cctctctctg cttatttcta cacagtgtta ccaatgagat    6660
tggtgttact gctgggctcc aaagcaatca gacagattaa agtagattga atatgaaaga    6720
atttagaggc ctttttccaa gtgatttgtg ctctatttaa tttctgtgca tttgcagata    6780
tagcccacag taattcttag tgaactagaa ccttcaggtt attgaatttt actgatttgg    6840
gtactgacat gcgcttttaa gaagacatta ggttttctat agtgtagatt gtacactaac    6900
aatataattc atatttaaga atgtctcaaa atttagtata ctgtgttcaa ctaacttaac    6960 tttcttgtt tttttgttt tgttttgttt ttgtttttttg agacggagtc ttgctatgcc    7020
acccaggctg gagtgcagtg gcgtgatctt ggcttactgc aacttcaaca ctcctgggtt    7080
caagtgattt tcctgcctca gcctcctgag tagctgggat tacaggcacc cgccaccaca    7140
ccggctaatt tttgtatttt tagtagagac ggggtttcgc cgtgttggcc aggctggtct    7200
tggactcctg actcaaatga tctgcctgcc ttggcctccc acagtgctag gattacagac    7260
atgagccact gcgcccggcc gctaacttaa ctttcattcc acaacttcca tcttttatcc    7320
aaaatctgtg atcattgaat actgtcacca ttaatcattg gcatttcagt gtttggactt    7380 ttttttttccc ccttcgtctt tgtggactct tttttaacac tcataaagtt ttaactattg    7440
aaaagcaaag gaaacggtga gtgacttttt ggagtctgtc tacccagtgg tcacacaaaa    7500
ggcttactac attacaggaa agataggatg ggaaagggat actagaaaat tctaagtcag    7560
```

```
gaacggggt gtgtattaga aaaattctga tcctggcatg ccagatggcc ttacatctca    7620
atttcttccg tgaaattcct gccaacaaat catagtgtta gaagtacaga agggtccatg    7680
ggaacagaat ttaagggctc cgttggtgat acggaactga tcagatggtt ctcacttgtt    7740
ctcagataac ctgtatactg aatatcacag aagggtata gacgtcatgg cagtggttag     7800
atattcttgc acctgctgaa gctgagaaaa ttaaagtaat ttttttttcct gtggaaagta   7860 gaaaatcaag cttttgtatg atttcacaca gctttctatt ctctcttttg ttgactctgt    7920
taagagtaac atttagtggt ggaaactatt tcaggatcac acccacaaca ctagagactg    7980
tattaatcac ttacacacac ataggtatag agtaatcttg aagggctgt aggccaaaga     8040 taatgctttt ttgaagaatt agagactagt taccagcacc tggtatttgc tgtttcctac    8100
agagctgact ggacagccta gagtctgctg aggaattcag aggatggcca gtagaatgtt    8160
ctttccaccc cagaatattt ggtagggact cagctgctgt ggaatgccaa aaaggctttg    8220
agtttgtttc actattctta agattacacg taattgtttt tttgtaagag attatatata    8280
ttcaagttga ggatggcttt gagttagact ttccttaatt tggaatcaca cagcagatga    8340
tacatttatt tccatctgat aagttacttg atgatgtaaa aagacatttg agttaaagat    8400
ttttgggaaa aaagctgaat gttgagccat ttatgttgtg tactggttcc ctattcactt    8460
ggacaatttt aagtcttaaa acaatcttaa ccatgtgcac aagagatttc acatagtatt    8520
tggtaattaa attaaggaat tctagctcaa gtcatgcttt ttgctgaaat agttgtatat    8580
atttagtgcg gaaacctgtg ttttcaaatt aatgtaataa aagtttcaat aaaatggaag    8640
cctttattac cgtgtttcaa atgctatgct aaaccttttc catttgttat tatattaacc    8700
tcctcataca tagccctact aattttttta ctttctattt tgaaataatt acagatttat    8760
aggaagttgt gaaaaatagt acagagccca tgttcccttc accaagtttc acctaatggt    8820
agtagctcac ataacgataa tttaatgtca agaaccagga aattgtcatc gttgcaatcc    8880
ataagccttt tttagatttc accagtttca catgtatttg tgtgtgtgtg tatatatata    8940
attgtatgca attttatcat gtgtagatct ggatagccac tgtaacagtc tatagttcta    9000
tatacagagc tactccatca cctcagggct ccctatgcta ccactttata gccgcacgca    9060
cccttccagc aaccactaat ctgtttgcat ctctgtaatt ttgccatttt gagaatgtta    9120
tataaatgga atcatacaga atgtaacttt ggctttttt cttttaccat acttcctttg     9180
agagccatcc aaattgctgc atgtatcagt agttcatttc tttttactat tgagtagtag    9240
tccatagtat ggctgaacca cacaatttgt ttaaccattt acttattgaa ggacatacca    9300
gaagggtggt ttccagtttt ttggctattg caaataaagc tgctataaac attcatgtat    9360
ataaatattt ttatgtgaat ataaagtttt cattttgggg gaataaatgc ccaaatgttt    9420
ggattgtatg gtaagtgcat gtttggtttt tagagaaact gctgaactat ttattttcta    9480
gaatgactat atcctcttat attcctatca acaatatatg agatatccag tttctctgca    9540
tccttgctag catttagtgt taccactttt ttatttgagc ggttctaata tgtgtagtga    9600
tagcctgttt tgccttatat taatcaataa aaatagcctc atctaatctt aactttttt    9660 atttaaaac atcttggcag tattgaactt tctcaatgaa aaatctctaa aattgtgact    9720
tgaaaggctt taattttcca gttttttcttt ggttttactc ttagcagtaa catttaact    9780 ttttttttgtc tttgaagtaa ttttcagtgt ttcctttaca tgttgctttt tcttagaaac   9840
tagttactag catgaagtag atctttagcc tcgtttttcta aaaacataaa aaagtaaaac   9900
```

```
tgtgggttt atttcaaaat tgagagtcct gtcttttcat atgaggatat tttatagtct    9960
gttggcttgg ctatatttta gggagtaaac ctgtggttag tggtttgttg ttggtggtgg   10020
taaagttttc ttacagtatt tttatacctg aataatacct ttagactcta tagaatagat   10080
acttgatctt caaatctatc ctagaataaa ttgttttatc taaacagctt tgtgacctga   10140
gaattgggac ttagtccctt agttttccct tactggccct ttgtagtcac tgttttgatt   10200
ttgtgaaagt aacttaactc ttagcactgt caggtattgt acattcctgc caaagcaaga   10260
ataagaatac ataggattgt gttttaattc tataattagg tgacttttgg ctaatttcca   10320
ggaacttgga cttaataaag tactagtgat aagtttggaa attttagtgt ccttgttctt   10380
tgaagttatt caccctttac tttcttgttt gtttggggtg tttatactac tgtccctaaa   10440
tatagctgaa ataaggaag aaaaataacc cctgtaatat cactaccagg ataatttc   10500 tttttttttt tttttttga gatggagtct cgctctgtcg cccaccatct cggctcactg   10560
caagctctgc ctcctgggtt cacgccattc tcctgcctca tcctcccgag tagctgggac   10620
tacaggcgcc cgccaccaca cccggcttat tttttgtatt tttagtagag acggggtttc   10680
actgtgttag ccaggatggt cttgatctcc tgatcttgtg atccacctgc ctcggcctcc   10740
caaagtactg ggattacagg catgagccac cgcgcccggc ctgatataat ttctgttaac   10800
agtttgatgt aaatatttt tgacttttta gtgtttttat atatatatat attttatgtt   10860 tttctttat caatacgcac tcttactgtg ggaataattt taatgttttt aaagagttgg   10920
gttttatttg tttatttat tttatagaaa tggggtctcg ccgggtgcga tggctcacgc   10980
ctgtaatccc agtactttgg gaggccaagg caggagcatc acctgaggtc gggagttcga   11040
gaccagcctg accaacatgg ataaaccgcc tctctactaa aaatacaaaa ttagccgggc   11100
gtggtggcac gtgcctgtaa ttccagctac ttgggaggct gaggcaggag aatcacttga   11160
acccggccgg tggaggttgc agtgagcaaa gattgtgcca ttgcactcca tcctgggcag   11220
caagagtgaa acttcatctc aaaaaaaata aaaataaaa agaaagaaa gaaagaaatg   11280 ggatctcacc attttggctg gttttgaact tgtggtctca agcagtcttc ctacctcagc   11340
atcccaaagt attgggatta caggtgtgag cccatcctgt tgttgttgt tcttttgttg   11400 ttgttgtttt tagatgaagt ctccctctgt cacccaggct ggagtgcagt ggcgctatct   11460
tggctcactg caagcccgc cacccaagtt caagcaattt tctgcctcag cctcccgagt   11520
agctgggatt acaggcgccc accaccatac ctggctaatt tttgtatttt tagtggagac   11580
gaggtttcac catattggcc aggctagtct tgagctcctg acctcgtgat ccacctgcct   11640
cggcctccca agtgctggg attacaggtg tgagccactg cgcctggcct gttgttgttt   11700
aaataaaaga aatttattct cttacagtcg aggccagaac ttagaactgg ttttcaatct   11760 aaatttttt tcttctttgg gagaagggca tcagaatatt gtggatatac ttttttgact   11820 taaaaaaaa ggttttactg ggctgggcat ggtggctcac ctgggattaa ctgcctgtaa   11880
ccttggcact ttgggaggct gaggcaggtg gatcgcttga gtccaggagt tcaagagcag   11940
cttgggtgac atggtgaaac tccgtctcta ccaaaaaaaa aaaattagcc aggcatggtg   12000
atggcgtgcc cttgaagtcc cagctacttg ggaggcttag ctgggaggat cgcttgagac   12060
caagaggcag aggttgcagt gagctaagtt catgccactg cactccagcc tgggtgacag   12120
agcgagacct cgtctgaaaa attttttttt ttttttacta atatgacaaa catcttttca   12180
tttcaaatat atttctatac cattttaat atctcattgc cttagaatg accttgtatt   12240 catagtacat atgtatgtga tattccattt atttatttt ttctttgt cttttttgg   12300
```

```
ttatattcca ttgatttaat gtaccttaat ttatcttacc aatttcttgt tgaccatttt   12360
gtttccagtc ttttgttttt ttaccagaca tggattaagc tgagcctttg ccccagacga   12420
cattatttct tttttatcag caaaatatgc gtgtaatgaa attagaatta aaaggcaaaa   12480
aaggttatcc tttattttc tacttatttt tattgagata gtaattcaca taccataaat    12540
ttaacccttt taaagtgtac agttcagtgg ttttcatata ttagaaggtt gtacaaccat   12600
cgcaactaat tccagaacat tttcatcacc ccagaaagaa actctgaacc cattatcact   12660
ccccactccc tcacacaccc taaccctggc agtcacatat agactctctg tctctgtgga   12720
tttgtttact ctggaccttt catataagtg gaatcataac agtttgtggc cttttgtgct   12780
tggcttctca aacttatctg tttccaaagg ttatctgtgt cgtagcatgt gtcagtactt   12840
cattcctttt tatggctgaa tattttattg catgtatatg ccacattttg tttatccatt   12900
cacctgtaga aggacattta ggttgtttcc attttttggc tgttatgaat attactgctg   12960
tagacgttca tgtacaagtt tttatgtgaa cgtgttttca tttttcttgg gtatatactt   13020
aagtgaggaa ttcctgggtc ttaagttaac tctctgttta acattttgag gaactgccaa   13080
attatttttt aaagtggctg tgacatttta tattctacca gcagtgaatg aaatttccaa   13140
tttctccaca tacttgacag cacttttttt ttttttttt  tttgaggtga agtcttgctt   13200
tattgcccag gctggagtgc agtagcatga tcttggctca ctgcaacctc cacctcccag   13260
gttcaagcaa ttcttgtatc tctcagcctc ccgagtagct gggattacag gcgcatgtca   13320
ccatgcctgg ctaattttg  tatttttat  agagacaggg ttttgccatg ttggtcaggc   13380
tggtcttgaa ctcctgattt caagtgatcc acctgcctta gcctcccaga gttctgggat   13440
tacaggcgtg agccactgca cccagtctgc actttcttta ttatctgtct tctttattat   13500
agccaatcta gtgggtatga agtaagtgtg tcatttgtga ttttgattgt tagtggtgac   13560
taaaaatgtt gaatatcttt acatgagctt gttggccatg tgcacatctt tgttggagaa   13620
atatctattc aaatcttttg actatttaa  aattgggtta tttatctttt tattgttgag   13680
ctataggagt tctttatttt atttactga gacagggtct tgctctgtca cctaggctgg    13740
agtgtagtga tgccatcttg actcactgca acctctgccc ccaccccagg ctcaagtgat   13800
cctcccacct cagtcagcat cccacagctg ggaccacagg cgcatgccac catgcctggc   13860
taattttttt ttttttttt ttttgtatt ttagtataga cagagtctca ccttattgcc    13920
caggctggtc tcaaactcct gagctgaagc aatccgccca tctcagcttc ccaaagtgct   13980
ggaattagag gcatgagcca ctgtgcctgg cctatttat  tttaaagatg aggcctcact   14040
ttgtcaccca ggttggagtg cagtggcgtg atcatagttc actgccattt tgccctcctg   14100
ggctcaaaca gtactcacga ctcatcttcc tgagtagcta ggactgcagg catgtcgcta   14160
gcatgcccag ctaaaacagt tctttatatt ctagatcggg gtgtccaatc ttttgacttc   14220
cctgggccac attagaagaa gaagaattgt cttgggccac acataaaata cactaacagt   14280
aatgacagct gatgagctaa aaaagaatt  accaaaacat ctcataatgt tttaagaaag   14340
tttacaagtt tatgttgggc cacattcaaa gccatcgtgg gcctctggcc gtgggttgga   14400
tgagcttgtt ctaaatgcta gacccttatc agatggatgt tttgtagata tttatcgcat   14460
gctgtgggtt tttttttttt actttctttt aggttttttt ttttcttaaa taattaaact   14520
gattaaaagc tttaatcttt tcattttctt gataatgtct tttaaagcac aaagttttgt   14580
ttcaatgatg tctaatttgt ctattttttt ttctttggtt gcttgtcata cgtaagaaac   14640
```

```
tgttgctaaa tccagaatgc tgaagattta cttgtgaact ttgtttcctt ctatgagttt    14700 tatagttttta gctcttgtat ttaggtcttt gatacatttt gaggttttt tgttgttgtt     14760 gagacagtct tgctctgtcg cccaggctgg agtgcagtgg tgtgatcttg gcttactgca    14820
ccctctgcct cctcggttca agcaattctc atgcttcagc acccgagtag ctcggattac    14880
aggcgtgcac caccaagcct ggctaatttt tgtatttta gtaaagaggg ggcttcacca     14940
tgtttgtcag gttggtcttg aactcctggg ctcaagcaat cctctcatct cggcctcccc    15000
aagtgctggg attacaggca tgagccacca cgcccagcct gttttgagtt catttttaaa    15060
atatggtgtg aggtagaggt cccatttcat tcctttgcct gtgggtatcc agttgtccca    15120
gaaccatttg ttgaaatgac tcttgttccc tcattgagca atgtcgtgag accctatctc    15180
cataaaaaat aattaaaaaa aaaaagaat gcagaaggaa acagttttgc caatttttgta    15240 gtatttactg acaatttgca tatgtcttta cattctttag ctatttattt ttcttttgaa    15300
ttactgcctt tgttcatttt tcttttggag ttgtttgtct ttttcttatt aatttgtaag    15360
agattttgca aatatataca atttcttttc tctttttttt gagatggagt tttgctcttc    15420
ttgcccaggc tggagtgcag tggcatgatc ttggcttact gcagcctctg cctcctggtt    15480
tcaagagatt cttctgcctc agcttcctga gtagctggga ttacaggtgc ccaccaccac    15540
acccagctaa tttttttttt tttttttgt attttagta gagactcggt ttcatcatgt     15600
tggccagact ggtctcaaac tcctcacctc agttgatcca cccaccttgg cctcccaaag    15660
tgctgggatt acagttgtga gccaccgtgc ctggacctcc acattattt tgaaacaaat     15720 tccatatcac ataatttctt ttttttgaga cagagtctcg ctctgtcacc caggctggaa    15780
tgctgtggcg tgacctgtgc ttactgtacc ttctgcctcc taggttcaag cgattctcct    15840
gcctcagtct cctgagtagc tgggattaca ggcacgcacc accacacctg gctagttttt    15900 gtattttag tagagatggg gtttcaacat gttggccagg ctggtcttga actcctggcc      15960
tcaggtggtc cgtccacttc ggcctcccaa agtgctggga ttacaggctt gagccactgc    16020
acccagccaa tatcatataa tttcatataa atagttcttt gtgtatcttt agataaggac    16080
ttaaaagaag gcataatcgt aacaccatta ttaataccta aaagaagtga gcaataaata    16140
attcatttgc cgtatcaaat atccaatgtt catatttcct ccattgtccc ataataattt    16200
ttaaaagttt gctcaaatca aaatccaaac aagattattt caaagcattg tttgaggtac    16260 atttttaaatc ttaatttata gatttctctg ctgtctcttt tcccccatat ttatttgttg    16320
aagaaaccaa gcgttgtttc ctgtggactt tcctactctc tggattttgc tggttatatt    16380
cctctggtat cagtttacta tgatcccttt ttccctgta ttttctgtaa atttgtaact      16440
agatctagag atttgtttag attttgtggg tttttttttt tttttttttt tttttgcaa      16500 aaatgcatca taaatggtgg tgtgtacatc tctcagaaga cacatatctt aatgtctttt    16560
tgtggtatta gttattaatg attactgcct atatttatta attcattatt tggattgtaa    16620
gtttatgata gtctcttgat gcttttttctg ttgttagctg gaatgcttct aaaaggagaa    16680
ggctttcctc ttcaagctac ttggttgtct tgagggtttg cttcttatag ggaaagcagg    16740
ctaagggtga aaaaggaaat agtttctaac tgggtctgtt aatgagctgt caccccaggc    16800
aaagagaagc aaggcaggtc acaggaaagt gaagtgggct tgggatgatt ggtgccccat    16860
gcgtgcatgc atgaagggaa gttaatcctc cctgtagtga actctactgg gcttttggtc    16920
agtagccaag actgtcaagg aagacctttg tcagaagcca tacctggcct ttgctttag     16980 ctgttggtag ctgaaggaaa ccagaacaga cctatgacct gtgaacttct gctcagtaga    17040
```

```
caaagttctc tcagcctaaa ttcagtaagc aggagtaaga tgcttgcttt cccttgaagt   17100
gaaacgtgaa ttatatgttt cttcaacttg tgctaatatt cttttttttt ttgagatgga   17160
gtctcacact gtctcccagg ctggagtgca gtggtgcaat ctccgctcac tgcaacctca   17220
gcctcccgag tagctgggat tacaggcgcc tgccaccacg cctggctaat tttttgtatt   17280
tttagcagag atggggtttc actatgttgg ccaggctgga cttgaactcc tgacctcacg   17340
atctgcctgc ctcggtctcc caaagtgctg ggattacagg cgtgagccac cacacctggg   17400
caacttgtgc taatattctt aaccttcatg tgaatcattc ctgccctcag gctagcataa   17460
cccatacagc cttccttata ggaagatttc ctactgggag tgaatttgtc cagtgattcc   17520
cccaagatat cccccaatca aatattttaa aagtcatcat ttacatgtaa aaactatgta   17580
acaagcatgg tagcagcagc gttaaagaaa tggcagtatg gccctgtaa ggaaggctc   17640 cagaagatga gccgcactca gcctctaggt cacagctacc ttaggagttt gcagttgttc   17700
ctggggaagt cagtagacaa agctatctct caggcctggg caagataggg attttttttt   17760
tttctttgag atggagtctc accctgtcat ccaggctgga gtgcagcagc atgatctcgg   17820
ttcaccacaa cctccacctc ctgggttcaa gtgattttac tgcctcagcc tcctgagtag   17880
ctgggactac aggtgcgggc catcatgcct ggctcatttt tgtattttta gtagagatgg   17940
ggtttcacca tgttggctag gctagtctca aactcctgac ctcaggtgat ccacctgcct   18000
cccagagtgc tgggattata ggcatgagcc actgtgccca gtgtttttttt tttttaatt   18060 gtagtgacag gatctcactt tgtttcctgg gctattccca aactccaggc tcaagccgt   18120 cctcctacct tagcctccca gagtgctggg gttacaggtt tgacccactg tgcctagtct   18180
cagaattcat gttttaaaa gtcactctgt gccaggctca tgcctgtaat cctaatactt   18240
tgggaggctg aggcaggagg gttgcttgag cccaggagtt tgagaccagc ctggaaacca   18300
tagcaaaatc ctaactctac aaaaaataca aaaatagcc aggtgtggtg gcatgcacct   18360
gtagtcccgg ttacttggga ggctgaagtg caaggatcgc ttgagcctag gaagttgagg   18420
ctgcagtgag ctgtgatcat gccactgcac aacagcctgg gcaacagagt gagaagtaac   18480
tctggctgtg gtggggaaag tggattagtg gagaatggaa gctgggaaac atggtggttc   18540
ttgctaagtc agtatcaagg gatcacagat gaggggcta tttcgtccta ataagggcct   18600
tggtctccca gatagtcatg gatttttcta tttagaagct ccttctcagt ttttcttgcc   18660
caaggcatat acggttgata tttgtacaac acaggctgga tctgtatggg tccacttata   18720
tgtggatttt ttttcaacca aacttggatt aaaaatatag ttgtaggcca ggcacagtga   18780
cttatgcctg taagcctagc actttgggag cccaaggcag gcggatcagc tgaggtcagg   18840
agtttgagac cagcctggcc aatgtggtga accatgtgc ctactaaaaa tacaaaaaat   18900
agctgggtgt ggtggtgtgc acttgtaatc ccagctactc aggaggctga agccagagaa   18960
ttgcttgaac ccgggaggtg gaggttgcag tgagctaacg cagcagaggt tgcagtgagc   19020
taacgcagca gaggttgcag tgagccaacg gggtggaggt tgcagtgagc caagattgca   19080
ccaccacact ctagcctgtg tgacagagca agactctgtc tcaaaaataa ataataaaa   19140 atacagtgta ggccaggtat agtggctcat gcctataatc ccagaacttt gagaggccaa   19200
ggcaggcaga tcagttgaag ccaggagttt gagaccaacc tggctaacat ggtagaaccc   19260
cacctctact aaacagaagt acagaaatta ccaggcata ggtggtgcat gcctgtaatc   19320
ccagctgctt gctaaactga ggcaggagaa ttggaggca gaggttgcag tgagctacga   19380
```

```
ttgtgccact ggactccaga ctgggtgaca gagcgagact ctgtctccaa gagaaaaaaa    19440
aaaattgtac ttacaggaca tgaaacccac ctgtacggtg tgctgactgg gagactggag    19500
tatgcatagt tcttggtaaa caaggggatt cctgaaacca atcccctgag tatatggagg    19560
gttgactata tattttaata gaatttatta ctttttttt ttttttagc agttttaggt    19620 ttatggaaaa attgagcagg agtacatagt ttctctatct ccctcacatt tccccattac    19680
tagcatcttg aaatagtgtg gtacatttgt tacaactgaa gagccaaata ttgatacatt    19740
actgttaact aaggtccgta atttacttta gagttcactc ttggtgttgc agtttctatg    19800
agtgttggca aatatatcat gacatgtatc tagcattata gtatcatatt gagtagtttc    19860
actgccctaa aaatccccctt tgttccacct tttcatccct ccatctacct gaacccctga    19920
taaccactga tccttttaca gtctctatag ttttaccttt tacagaatgt catatagttg    19980
gaatcataca gattggcttc tttccatgtt ccttcctggc ttgatagctc ttttcttttt    20040
tttgagatgg agtctcgctc tcgcccaggc tggagtgcag tggcgcaatc ttggctcact    20100
gcaaactctc cgcctcctgg gttcaagcaa ttctcctgtc tcagcctccc aagtagcttg    20160
gactacaggc gcatacctcc cctgcctggc taatgtttgt attttggta aaggtggggt    20220 tttaccatat tggtcaggct ggtctcaaac acctgtcctc aggtgatcca cccacctcgg    20280
cctcccaaag tgctgggatt acaggcgtga gccaccctgc cctgccagct cttttttttg    20340
tactgctgaa taatactcca ttgtataggt gtatgagttt atctattcac cttctgaagg    20400
acattttggt tgctcctaag ttttggcaat tatgcatgaa gttactataa acatctgtgt    20460
gtaggttttt gtgtggtcat gtttttagct catttggata ataccaagg agcacgattg    20520 ttggatcgta tggtaagagt atgtttagtt ttgtaagaaa ctgccaaaact gtctttcagg    20580 gtgactgtac cattttgcat tcccaccagc aatgaatcaa gttcctgtcg ctccacatcc    20640
tcgttagcat ttggtgttgt cagtgttttg cttttcacc attctaatag atatgtagtg    20700
atatcttgtc ttactttgca gttctctaat gacgtatgat gttgagcatc ttttcatctg    20760
cttatttgtt gttgttgttg ttgtgttgtt cattgaaatg gaatctcgct ctattgccca    20820
ggctggagtg caatggtaca atcttggctc actgcaacct ctgcctcctg ggttcaagtg    20880
attctcctgc ctcagctccc caggtagctg ggattacagg cgcccgccac catgcccggc    20940 tagttttttgt attttagta gagacaggat ttcaccatgt tggccaggct ggtcttgaac    21000
tcctgacctt aggtgatctg cccgcctcgg cctcccaaag tgctgggatt acaggcgtga    21060
gccactgcgc ctggctttca tctgcttatt tgatatgtgt atatgttatt tggcaaagta    21120
tctgttctga tcttttgccc attttttaat cagattgttc tttattgct tctggggttc    21180 tttttgtttg cttttttga gacagagtct tgctctgtcg cccagtctgg aatgcagtgg    21240
catgatctca gctcactgcg acctctgctt cctgggttca gtgattctt gtgccttagc    21300 ctcccaaata gctgggatta caagcatgtg ccactgcacc tggctaattt ttgtattat    21360 agtagggaca gggttttgcc atgttggcca ggctggtctt ggactcctgg tcttcagtga    21420
tccacccacc tttgcctccc aaagtaatga gattacaggc gtgagccacc atgcccggct    21480
tattgttaag tttaagagt tctttgtata tgtgtatttt ttgattcttt taaaattaat    21540
acttaataaa ataattgtac atatttatgg gatgcatgtg atattttgat acatgcatac    21600
aatgtggatc aaatcaaggt aattagagta ttacctcaaa catttgtcat ttctttatgt    21660
tgggaacatt tcaaaatgtc tagctatttt gaaatataca ataaattatt atctataagt    21720
cacctcattg tgctgtcaaa cattagaact tattctttct acctggcttt attttttta    21780
```

-continued

```
ccccttaacc aaccattctt catcagctcc ccgtctcccc tactcttttt tttttttttt   21840 tttttttgata cggagtcgct ctgttaccca ggctagagta cagtggcaca atctcgactc   21900
actgcagctt ccgcctccca ggtttaagca attctctgcc tcagcctccc gagtagctgg   21960
gattacaggc gaatgctacc acacccgact aattttttata tttttagtag agatgggggtt   22020 tcaccatctt agccagactg gtcttgaact cttgacctcc tgatccaccc gcctcagcct   22080
cccaaagtgc cgggattaca ggggtgagcc accatgcctg gcccctctta ctcttttctt   22140
agcctctggt atctatcatt ctactctcta cttctatgag atcaactttt ttttagctcc   22200
cacatatgag taagaacatg taatatttct ctttctgggt ctggcttctt tgtatatttt   22260
ggataataag tcttttatta gatacgtgtt ttgcaaatat ttttttccgag tccgtgactt   22320 atcttttcat tctcttaaat agtgtctttt gcagagcaca cattatacat tttagtgcag   22380
tccagtttac caattctttc tttgatggat tttgcttttg gtattgtgtc tagaaagtct   22440
tcgccaaacc acagtcatct agagttcccc ttatattatc ttacaggagt tttatagttt   22500
ttgttttaca tttaggtctg tgatctattt taagttaatt tttatgtgaa agatataaga   22560
tctatgtctg gattctctct tttttttgaga tggagtctcg ctttgtcgcc aggctgaagt   22620
gcagtggcgc gatctcggct cactgcaacc tctgactccc tggttcaagg gattctcctg   22680
cctcagcctc ccgagtagca catgacacca cgcccagcta atttttgtat tttgagtaga   22740
gacggggttg caccatgttg gccaggatgg tcttgatctc ttgacctcgt gatccgcccg   22800
cctcagcctc ccaaagtgct gagattacag gcatgagcca ccacgtccgg ccagttttttt   22860 tgttttattt atttatttat ttgaaacagg gtcttgttct gttgcccagg ctgcagtata   22920
gtgacaccat caaggcttcg ttgcagcctt gacctcctag ggtcaagtta tcttcttgct   22980
tcagcctcct gagtagctgg gactacaggt gagcaccact ctgaccaggt actttttaaa   23040
tttattttag agacagggtt ttaccatgtt gcccaggctg gtcttgaact cctgggctga   23100
aatgcccctc ctaccttggc ctcccaaagt gttgggatta cagacatgag gcactcagcc   23160
cagccaatat aattctttttt ttttttttttg agacagtctt actctgttgc ccaggctgga   23220
gtgcagtggc atgatcacag ctcactgcaa cctctgcctc ctggactcaa gctgtcctcc   23280
cacctcagcc tcccaagcag ctgggattat gggtgcccat gaccacaccc agctaagttt   23340
ttaaattttt ttagagattg aatctttctt tttctcagcc tggtctcaaa ctcctgagct   23400
catatgatct gcccgcctcc gtctcccaaa gtgctgcgat tacaggcatg aaccactacg   23460
cccagcctac aatttatttg taatccaagt tttattgaaa aaaaaatcca catataagtg   23520
gacatatgta gatccaacct gtgttgttcc agtgtcaacc atatatacca ataattcttt   23580
tttttttttt tttttttttt tttttttgag atggagtctt gctctgtcgc ccaggctgga   23640
gtgcagcggt gcaatctcat ctcactgcaa cctctgcctc ccgggttcaa gtaattctcc   23700
tgcctcagcc tcctgagcag ctgggactac aggcatgcac caccacgccc agataatttt   23760
tgtattttta gtagagatgg ggtttcacca tattggccag gctggtctca aactcctgac   23820
ctcaagtgat ccacccgcct tggcctccca agtgttggg attacaggag tgagccactg   23880
tgcctggcct ataattcttt acgtatattg ttagattcag tttgctagta ttttatttag   23940
catttgtgta tctgtgttca tgagaggtat tgttctgtag ttttctttgg tttcttttct   24000
gtctggttta gggtaatgct ggcctcatag aataggttag gaaatatttc ctctgcttct   24060
gtttctgaaa gagaattgag gtaatatcta tttttttttt tttgagatgg aatcttgctc   24120
```

```
tgtcgcctag gctggagtgt agtggcgcaa tcttggttca ctgcaacctc tgcctcccag   24180
gttcaagtga ttctcctgcc tcagtctcct gagtagctag aattacaggc atgcaccacc   24240
atgcctggct aattttttgta ttttttagtag agatggggtt tcactatgtg ggccaggctg   24300
gtcttgaact tctgatctca ggtgatccac ctgtcttgtc ctcccaatgt gctgggatta   24360
caggcgtgag tcactgtgcc tggcccgaga taatatctaa tttaacagtt tggtagaatt   24420
caccagtgaa cccatctggg cctggtgcct tttgctttag aaggttattg attattgatt   24480
caatttcctt aatagataaa ggtgcattga gattgtcttt tcttcttggg taagttttaa   24540
tacattgtgt ctttcaagaa attgttccat ttcatctagg ttatcaaatt tgtgggatta   24600
gagtccttca taatatttct ttgttttgct tttggtgtcc ataggttcag aagtgatggc   24660 ccttttttcat ttttttctatt agtaatttgt gtctttgccc tttttttttct ttgttaatct   24720 ggctagaagc ttatcaattt tgttgatctt ttcaaagaac cagttttttgg tttcactgat   24780 ttttctctat taattttgtt ttcaatttaa ttgatttctg ctctaattgg ttttcttctg   24840
ctcactttgg atttaatttt ttttagtttt tctagaaaac taagttttta agtgaaaact   24900
gagattattg attttttagat ctttttttcta atgtttacag ttaacactgt acaatttcct   24960
gtaagcactg ctttctctat atcttacaaa ttttgatgtc atattttcat tttcatttag   25020
ttagaaatat ctcttgagac ttctttgacc catctgttat ttagaagtgt attgtttaat   25080
ctccaagtat gtatttttggg attttttctgg ctatctttct gctgttgatt tctagtttaa   25140
ttacatgtgg tctgagagca taccttgtat gctttctatt cttttcaatt tgttaaggtg   25200
ctctttgtgt ctcaaggtgg tctactttttt tttttttttt tttttttaaag aaaagctggc   25260 caggtgcagt ggcttatgcc tgtactccag cactttggga ggcgtaagtg ggaggatcac   25320
ttgaggtcag gagtttgaga ccagcctggg caacatatag agacttcact tgcacaacaa   25380
atttttaaaa tattagttgg gtatggtggc atatacctgt atatggctga agtgggagga   25440
ttgcttgagc cctggaggtt gaggctacat gagccatgat cgcaccactg tactccagcc   25500
tgggcaacag agtgaaattt tgttctctct tgaaagaaa aaaaagttg atgacataaa   25560 gttcattcat ctttttttgta tgtgacttca aataactac tgatggttaa aaaaaaaatc   25620
agaatgatgc aacccaagtg tccatcaatg gatgaataga taatatgtgg tgtatgaata   25680
caatgggcta ctattattca gccttttaaa ataagaaaat gctgacactg ctgtaacatg   25740
gatgaacgtt cagatcatta tgctaaatga gaaaagccag acacaaaagg acaaatattg   25800
catgattgca cttatatgag gtatctggaa tataagagtc atagaaacag taattcagta   25860
attagaataa tgcttgccag ggcctgtggg gaggagggaa tgaggaattc atgtttaatg   25920
ggtacagagt ttcatttgga aaagattaaa aagttatgga ggtggatggt ggtgaggatt   25980
gcacaacagt gtgaatgtac ttaataccac tgaactgtac acctaaaaat gattaaaatg   26040 gtacattttta tgttacatat gttttacaac aattttttaca gatggaaaaa aattataaaa   26100
aacatcagga tggtgttgac agtgaaaagg ttaaagagtt actttaaaaa tttactttat   26160
tccagccggg tgcggtggct cacacctgta atcccagcac tttgggagac cgaggcgggt   26220
ggatcacctg aggtcaggag tttgagacca gcctgaccaa catggagaaa ccccgtctct   26280
actaaaaata caaaattagc caggtgtggt ggcgcatgcc tgtaatccca gctacttggg   26340
aggctgaggc aggagaatcg cttgaacccg ggtggtggag gttgcagtga gccgagatct   26400
tgccattgca ctccagcctg gcaacaaag cgcaactccg tctcaaaaga aaattttttt   26460
tttttacttt atcccaaatg tttatattta ctttggggct tatgtgacca gtttaatttt   26520
```

```
catttgtaat tgacttgata gaacacacta atgttcagtt aagatttctt atggtgtggt    26580
gaggagtagg atttttatgt aaataagccc aaaattgtat atatgaggtt aatctgatat    26640
ttgcagaaga tattcatgca ttactgtaag gaccactctg cttattcatt tgaccgattt    26700
gttacaacat ggttagaaat catcaaggtg tttgagatca aaggatcttc agaggtgatt    26760
tactccaatc cttttttaaa aaattaataa cttgagcctc agagaagtta agtgacatta    26820
ccaagttctg ctgttagtat agtgacttta tctttacctg aatccagggt tcttagccc    26880 tagtctgtaa tgtgtcctag tgtgcctcta gaatctggtc ctgtcagccc aagtctgtta    26940
aatcaaataa aaccagggct tggtgcttca ccttgtcttc tgccataccg ttgggtttcc    27000
tgtggaccat gcagataatg atgatgggct cagtgggctt gatagtgata actcctaaag    27060
cagctccttc taagtgcggt tctcaatctg aggaagttaa aaaaaaaatt agtgactaga    27120
acccacttct caggtactct gataaaatac atttgtaggg gagtgatagt tttcactttc    27180 ttttttctt tttctttttt ttttgagatg gcgtctcgct cttttgccca ggctggagtg    27240
caatggtgcg atctcagctt actgcaacct ctgcctccca gtttcaagtg attcttctgc    27300
cttagcttcc tgagtagctg agattacagg tgtgtgccac catgcctggc taattttgt    27360 attttattta gagacgggat ttcaccatgg ttggtcaggt tggtctcgaa ctcctaacct    27420
tgtgatctgc ctgcctcagc ctcccagagt gctgggatta caggcatgag ccactgtgcc    27480
cagccttcac atattttttg aaataatagg ccagttgcgg tggttcatgc ctgtaatctc    27540
acactttggg aggccgaggt gggcagatca cttgaggcca ggagttcaag gccaccctgg    27600
ccaacatggc gaaaccctgt ttctactaaa aatacaaaaa aattagccgg gtatgatggc    27660
atgtgcctgt ggtcccagct actctggaag ttgaggcatg agaatcgctt taacttagga    27720
ggtggaggtt gcagtgaggc aagatcgtgc ccctgcactc cagcctgggt gacagagcga    27780
gactccatct caaaaaaaaa aaaaaaaatc gtatgcagta aaggttgaaa actgctgccc    27840
aaaggcgcta ttaaactata ggttcccaaa cctggccaat tgtcaaaatc cctcaagaag    27900
gggcagtggg gtctaaggga ccccattgct gtagaggaga ttagtagtcc aagagtgaga    27960
tgaactgttg gaagtcctca aacttccaaa ctattaaaat agaatagttt tgcttcctta    28020
aaatagaata gttttcttcc tcactgattt ttctgtattg attagaacca taacaagtga    28080
attaaacaac tacaaaatag ttatgtgggc cacagacatt attgtaatga agtgaagttt    28140
ggctcaggcc ttgtaacaca attgcttttt ggattaaaag taaaaatatt aaattgtgaa    28200
attatgtgta agttttaaaa aattggtctt gtacaaaagt gttgggtttt tctttgtttt    28260
taactggatt tgttttaag caagacagaa tatttatatt gttggagagt cacaaggag    28320 gtgtgtttgt ggatttaaat gtggagacag tgtgccttga aatgcccttt atcagtctga    28380
ttcaagccac ctgcaatcat ggatttgaac tttttttttt ttttcccctg agatagggtt    28440
gcctaggctg gggtgcagtg gtgtgatctt ggctcactgc aacctctggc tcagcctctt    28500
ggagtacctg ggactatagg cacacaacat catatccagc tattgtattt tttttttttt    28560
ttttttttat agagacagag tttcaccatg ttgtccaggc tggtcttgaa ctcctgagct    28620
caagcaactc acctgcctcg gccttccaga gtgctgagat tataggtgtg agccaccatg    28680
cccagccttc actttatttta aaaaccatag ttttttaaaag ccacattcct actgatgaac    28740
acagaggttg tttccagtgt tttcatttgc agggctgtag tgattgtttt tgcacatgcc    28800
tctttatgta catgtgctgt gtcttctggg acagagagtg gacattttaa gtgttttatt    28860
```

```
ggtcctgcta aattgtcttt cagccaaact gctgcagagg tgatggagat gaggtgggta    28920
ctcaggagaa ttatgctcag tgcttgtgtg ctagtcactg acctggaaac attttattaa    28980
aaatgctaga ttaggttagt gatgtaaata ccaggtgata gtaaccagaa taattgtgtc    29040
aaaacatcaa gaatcatcaa gagatgccag gcatggtggc tcatgcctgt aatctcagcc    29100
ctttagtagg aggccgaggt gggcagattg cttgagctca ggagttcaag accagcctag    29160
gcaacatggt gaaaccctgt ctctaccaaa aatacaaaaa tttgctggat gcagtggtac    29220
gtgcatgtgg tcccagctac tcagtaggct gaggcgggag gatcgcttga gcctgggagg    29280
cagaggttgc agtgagccaa gactacacta cagcccgggc aacagagtga aaccctgcca    29340
taaaaaaagg agaaaaagaa tcatcaagag aaaacttaat ttgatgtgct ctgcgttttc    29400
tttggtgctt catgtcagtg ttagaaacta taggttgtat attattaat ttttctccta     29460 catttgttca acttgactaa atattaact ccaaatgcct agaatttcaa ataacctctt      29520
cgttataaag tatcaactat ttcttagtcc ccttaagctg atagtattgt gtcattgtaa    29580
aagatccctt gtgaaaaata attttgtca acatgaaagg tcttaatgtg tctcctagtt     29640 tacatttac atggtctttt ccatgtattt atatagttga catatatagc ttttttgta      29700 aatacacttt cctatgtgaa catgccaagg tttacttaag cattctctta ttcttggaca   29760
tctaaattgc ttcttatttt ctattgtaaa taaagtgcta gaagcttctt tcctgaaaag   29820
ttatttactt ttcacctagt atttccatct gtgttcctca aaataagatt gctgagattc    29880
atgtatgttg ccagaaagat tgtgaggttt aacagtgaat gaggaaaact tttaacactc   29940
aaggtctacc aagtacagca agttttattt tacctttttt tttttttttt tttttttttt   30000
tttttgagtt aggccaagtt gcctaggctg ggctcaagca atccttctgc ctcagcctcc    30060
ggagtagctg ggattatagg tgtgcagcac cacacccggc tttcttgtat ttttttttta    30120
tttttattta tttatttatt tttgagatgg agtttcactc ttgtcaccca ggctggagtg    30180
caatggccca atctcgactc accgcaacct ctgcctccca ggttcaagcg attcttctgc    30240
ctcagcctcc caagtagctg ggattacagg catgtgccac cacacccggc taattttttct   30300 attttttagta gagacggggt tcctccatgt tggtcaggct ggtctcaaac tcccgacctc    30360
aggtgatcca cccacctgag cctcccaaag tgctgggatt acaggtgtga gccaccgtgc   30420
ctggctgctt tcttgtatttt tatcttgctg tagcggttgt gggatttttg cctggtgtgt   30480
tcattggagt gtgtgtgtgt gttttgagat gtatgactgt gttggttgtg ttgtcatact   30540
ttgaaggttc attaatgtgc tggtcttctct atttttcttg ttatacttag tcacttaaaa    30600 acccttttt ttttttttt ggaattctta tttttacagt actttgaatt cctgttttat      30660
taatcacctt cttatctgaa agtgaagtaa tagtgtactt ggcaccattg aattagaaaa    30720
ttgtgtgtcc ttggccagaa gatcacatac acaggaactc gataagttga gagatttagc   30780
cgtttcagaa atgggcattt tgtgtcttcca gtggagaagc atctgcaaaa gaattgggca   30840
gatttggcca ggcgcggtag ctcatgcctg taatcccagc actttgggag gccgaggtgg   30900
gcagatcacc tgaggtcagg agtttgagac cagcctggcc aacatggtga aaccccgtct   30960
ctactaaaaa tacaaaatta gccaggcgtg gtggctaacc catttaaagt gggtgaatta    31020
tatcttttat gttttaatgt attcctagag ttgtgcaacc atcaccagaa taagttgtag    31080
aacattttca tcaacccaaa aagaaacttt gtattcatta gtcgttcctc ctcatttctc    31140
ccctaacctc ccagcactag gcaaccatca gaatactttt tgtctccacg gatttgactg    31200
ttttggacat ttcatattaa tggaatgcac aatacagtag tataatacat taattttgga   31260
```

```
aggccaaaat taatggcttt tgatgtctgc cttttttcac ttagaataat gtcttccagg   31320
tccatctgtg ttatagcatg tatcattact ttatccttta tgtggctggg taatattcca   31380
ttgtatggtt ataccatgtt ttgtttatct attcatcagt tgatggacat ttaggttgtt   31440
ttccattgac tattaagagt aatgctgccg gccgggcgcg gtggctcacg cctgtaatcc   31500
cagcactttg ggaggctgag gcgggtggat acgagggtca ggagatcgag accatcctgg   31560
ctaacacggt gaaaccccgt ctctactaaa aacaaaaaa ttagccgggc gtggtggcgg   31620
gcgcctatag tcccagctac gcaggaggct gaggcaggag aatggcgtaa acccgggagg   31680
cggagctggc agtgagccga gatggcgcca ctgcactcca gcctgggcga cagagcgaga   31740
ctccatctca aaagaaaaa aaaagagaa taatgctgcc atcatgcttg agggtttttt   31800
tttattttgt tttgttttgt ttgtggggggg agcggagggc acagtctcac tctgttacgc   31860
aggctggagt gtagtaggct tactgcagcc tcctccgccc cctggttcta gtgattcttg   31920
tgcctcaggc tcctgagtat catgctgcaa ttttttgtgtg agcatacatt tttcatttct   31980
cttgggtcaa tatctaggag tatccccact tttggttctg agtgttaatt gagcctgttg   32040
tgttctcaca ttccctgtac ttagatgaa atagtgcttt gcctaaaaag aaaataaaag   32100
acctgattgt gcaggcgagt gagaaagaga gagaggcgct agggttattt ccaccctgat   32160
actctttggg tagtcttggt atgactagca aagaagcaag ctccaagttg tagtttgctt   32220
ccaagtttct ggcttctgtg ggaatttctg catctaagta atgacaattt tcagttactt   32280
gcagtaagta aattatcaac caatcttact gtgtattact agcctagtag gaatttactt   32340
gtatatcgag aggaatgctg cagctttcac cttacttcta atggggatta atgcttactt   32400
aacttgcagt tttggaggca agtacaaagt acaggaccaa ttatggtcat gaagtgagag   32460
agaagtctgg ctagtgaatg gtgattggca actccagttg actgttcatg gcatcttaga   32520
tctgtgagga gggaggaggg aaggaaagtt caagctggtc tttatggtaa gttctggaac   32580
atttccctgt gtcaatgggt catctgttca ttcactgtgt aaaatggttg agggaagttt   32640
taatttacat gcttccttat tgtgtaaacc tttgattttt agtgatttca gagttttgttt   32700 ttataattac ttaacacgtg aagaggatgc agagtaacgt atcgaagctc tggttacctt   32760
ccactgggat ttgacacatt tgatttcctt tattccctcc ttccttccct tcctccctct   32820
ctcttttctt aaggaatgca actactcaga ttcacctgca cacccttggc atacctctca   32880 ctcccccttta ccccccacttc ctcagaggtg acctgtcctc agaggcaaat gtgtgccctt   32940
tccatccgta cttttatgct ctcatctatg tttacatcta ttagtacact attgtctgta   33000
tttttaaaca ttacataaat ggtgtaattt ttactttta ttctgtagtg gtgtttctca   33060
aattaagttc tgcacaaaac attttatag atatccagtg ttagcttaac gttttcttta   33120
ttgtggtaaa atatacataa gataaaattt accattttag ccattttaa gtttacaagt   33180 cagtggcatt aagtacattc acagtgttgt ataaccatca ccattgtcca ttgccagaac   33240
ttttcatcat cctaaacaga aactctgtac tcattaaaca atagtttatc actccttccc   33300
tgcaactaga tgctggcaat caccattcta ctttctatct ctatcaattt gcctcttcca   33360
tctaagtgga atcctacata tttgtcgctt tgttctggc tttttttttct tcttgtgatg   33420 ctttgtttta attatgttcc tggctttcat catctagcag gctgattcca aggtttgtcc   33480
atgtggtagc ttgtatcact ttaatgtttt tagagatagt taatattaca ttgttttatat   33540 ataccacatt ttgttttttc attcaacctt gatggacatt tgaattgttt ccccctttac   33600
```

```
ctgttgtgaa taatgctgcc gtgaacattg ataaccaaat atttgtttga atctctgatt    33660
tcagttcttt tggttccata cctaggagtg gaattgctgg atcatatgat aattctatgt    33720
ttaactcttt gagggatggc cagactttc caccatagct aaatcatttt accttcccac    33780
aagcaaagtt caagggctcc agtctctccc cataaggtcc tttgcacttt ttttttttgag   33840
acggaatctc actctgttgc ccaggctgga gaacagtggc accatcttgc ctgacctcaa    33900
gtggcacctg ccttggcctc ccaaagtgct aggattgtag gcgtgggcca ctgcactctg    33960
ccaattttt aatttttatt ttcatttatt tttctttttt taatttttaa tttttttatt    34020
ttttgaaggg ataaggtctc actttgttgc ccaggctggt cttgaactcc tggcttcaag    34080
caatcctcct acctcggctt ctcagagtgc tgagattata ggtgtaagcc cctgcacatg    34140
gcctttactc tcttgatagt gtcctttgat gcacaaaagc tttcaatttt gatgaagttt    34200
attttttatc ttgttacctg tacatttggt gtcatatatc taagagacca ttgccaaatg    34260
cagtgtcatg aagcttccc tcagtgtttt ctttctgcag ttttatgatt ttagctccta    34320
agtttaggtc tttgatccat tttgagttaa ttttgtata cagtttgaga gtcacacttg     34380
aggctctggg cgcagtggct cacgcctgta atcccactac ttggggaggc cgaggcggat    34440
ggatcacctg aggtcaggag tttgagacca gcctggccaa catgccgaaa ccctgtctct    34500
actaaaaata caaaaattag ccaggcatgg tgatgcatac ctgtggtccc agctacttgg    34560
gaggctgagc aggagaatt gcttgaacac aggaggcgga ggttgcagtg agccgagatt     34620
gtgccactgc actccagcct gggcgacaga gcgagactcc atcgtgcggg tgggggta     34680
aaagtcaaac ttgagtcttt tgcctgtgga tatccagttt tcccatcact atttgttgaa    34740
aagactatcc tttctcaact gtgaatggtc ttggtaccct agctgaagtt attttatta    34800
ttatgttact taggaatgca cataaggcct ggcacggtgg ctcatgcttg taattgcagc    34860
actttgagag gtcaaggtgg gaggattcct tgagccgagg agtttgagac cagcctgggc    34920
aatatagcag caagaccccca tctctatatt ttaaaaaaag aagaaaaaaa aacctctgat   34980
gcataaaata tttaaacttg tatgcattct tttctttctt tattttttaa aaattgagac    35040
agcagcttac tctgttgtcc aggctggtct tgaactcctg gctcaagca gttcctctca     35100
ccttggcctg cagtgctgag atgacaggtg tgaaccacta cacctggcct gcttacagat    35160
tataaaaga aaataagttt acaagttaaa gacagataaa atgacaaaat cagtaaaatt    35220
aaaattactt ttatggagcc gatgatgttt attccagttg ctcctctcat tgtgaatatg    35280
gtattgttgc tgtggcagat ttggaggccg tggcagattt ggaggctttg gcaatggctt    35340
ctgttacctt gccatgaggt aactcagttc cctcatcact tttctctgag aactataaaa    35400
ccttggaggg gtgccttctg cccttcgctt ggcatgtata ttatgcaggg atcaggtctt    35460
actccgttct tgattgttag tacaaattag ttaaaattgt attgtttggc cttagcctga    35520
tggtaaacac aacagcacac gtgggctgtg aaatctctgg gcagctctgt gtttctaggg    35580
aagcatctcg atgatccaga acaggcttat actaatgttt tagtgtaatt ttgaaatgaa    35640
aacacagcat ttaaaaattc ttatagagaa tgtatagacc ttgagaagtg ttagcagacc    35700
cagtttacga catgtctcaa tattatgaaa cattgcttta ttccctatcc tgcttgtaca    35760
tttaattttt tcatccagtt ttaaacaact tgggtactgt ggcctgtgcc tgtattccca    35820
gctactaggg aggctgaggc aggaggattg cttgagcaca ggactttgag ggctgtagtg    35880
agctgtgatt gtgcctgtga atagccattg tgctccagcc tgggcaacat agcaagaccc    35940
tgataccttg ggttttaaa aaacaaaaca agatacatgc tgacatttct ggtttggcag    36000
```

```
gcagagcttg ttctgctccc caccctccct tttcccatag taaccattta taggacatct    36060
cactgttgtc tactctgtgt tgcctctgct tccctgcgtg gtagatctag gaatcttagg    36120
atttcttagt tttagctggt gatccgtatc tttttcttaa ttccattgta acttcagctt    36180
ttcttattgc ttgtaggaag gctgtttcca ttgaatacaa acaaaataaa gcttttatt     36240 cttaatctta gagataggat gtttgtattt aaaaataatt gtgctgtcaa aattctgtca    36300
agttggcttt taccacatta gttttttta atgtggttta tatgaccctg gagtaccttg    36360
tcttctcact gttaaattct caactgagtt gtccctattt aaagtgtgag actgtgccag    36420
tttgatttta aaatattgca agtgcgttat ggcaagataa aactgcaaag aaagaacctt    36480
catgtccctt tgattataaa tgcttttggc acttgtttct actttttcct aatgtttttt    36540
gaggaaagaa cctccaactc tccagacagg tctgggggca aatgactaaa acatgaactg    36600
aggccctggg ctgtctctgt gaggatatcc cctctattct ctctgaaatg tcccagcatg    36660
tggtgcattt cttgttagtg tggactcctc tgtatataac acatcttatt tatcttctgt    36720
gcataacatg aagtagtgcc ctaatgcaat tccaggatgt aattcagcat ttctataaaa    36780
atacagtgtt tttctacatt tgcatcaaaa aataaccaga taattatatt tattaagaaa    36840
atagcatttt tggctgggtg tggtagctca cgtaatccca gcactttggg aggccgaggc    36900
aggcagatca cttgaggtca ggagtgaggc aggcagatca cttgagatca ggagttcgag    36960
accagcctgg ccaacatggt gaaaccccat ctctactaaa aatgcaaaat tagcctggcg    37020
tagtggtgca tgcctgtaat cctagctact caggagactg aggcaggaga atcacttgaa    37080
cttgggaagg ggagattgca gtgagctgag attgtgccac tgcactccag cctaggcaac    37140
agagtgagac tctgtttcaa aaaaaaaaaa aaaaacaaa gaaagaaaa gaaagaaaga    37200 aatgtatttt tggtatttgt tttcacaaac tagagcattt atgtgaaata acattgctag    37260
tattgatatt ataccatagt ataatactta gttcttcagc gatgtatctc tgctgatcag    37320
ctacatgata tctacttgag ctgttggatt tttttaaga acagtgcatt tttgaatgct    37380
tttgaaaaat tgtagtaaaa tacataaaac aacatttacc ttgtaagcat tttaattggt    37440
acaattcagt gacattaagt acagtcccag tttagtgcaa ccactgttac tgtctagttt    37500
cagaacgttt ttgccccaga tggatactct gtacctgttg aacattcagt cctcatggcc    37560
caataatctt tatgtctgta tagatttgcc tattctgcat attttatata aatgaaatca    37620
tgtcttttgt gtctggcttc ttttacctag catagtattt tcaaggttca tccatgttgc    37680
agcatgtttc aatactttgt tccttttat gtccattgta tggatatgcc acatttcgtt    37740
aatgacaatt cttttgggta gctacatttt aaaacattat agtagaatac atatagcata    37800
caatttacta tcttaaccat ttaagcctgc agttcagtgg cattaaatac attcacgtta    37860
ctgtgcaatt atcaccacca tctgtttgca gaaactttc atctcctcca tttgaaactc    37920
tgtatacatt aaacatgaac tctcccttct ccccttcctc cagccctggc agccaccgtt    37980 ctacatttt atctttctga cagagatttt actactctag gtacctcaca taagtgaaat    38040
caaccagtat ttatccttt gtgaccagct tatttcatta gcttaatgtc ctcaaggttc    38100
atccatgttg tagcatatgt caacatgact ttccttttaa ggttgaataa tattccattg    38160
tatgtatatg tcacaatttg tttctccatt tatccatcac tggacatttg ggttgctttt    38220
acctatcggc tgtcttgaat catgttgcta tagctgtaca agtatctatt tgagtttctg    38280
ctatcaattc tttaagtata tgcccagaag tggaattgct ggatcatatg gtaattccgt    38340
```

```
gtctggtttt ttttttgagg aagtgccatg ctgttttcca cacagctgta ccattgtaca    38400 ttcccccag caatgtacga gggctctgat ttcttcacat ccttgctaac acttagtatt    38460 tttttgata gaatagccat cctaatggct acttttaaag tatgtttaac attatttatt    38520
tatttttaat tttttttgta gagatggcat cttactgtgt tgcccaggct ggtcatgaac    38580
tcctgggctc aagcagtcct cctgcttcag cctcccaaag tgttcggatt ataggcgtga    38640
gccaccatgc ccagcccaaa tttaaatata taactaaaca catagcagct aacaccaagc    38700
ctttaaaaat atcattaata ggccaggcgc agtggctcat gcctgtaatc ccagcacttt    38760
gggaggccga ggcgggcaga tcacctgagg tcgcgagttc gagaccagcc tgaccaacat    38820
ggagaaaccc tgtctctact aaaaatacaa aattagccgg gcatggtggc acatgcctgt    38880
aatcccagct actggggagg ctgaggcagg agaatcactt gaacctggga ggcggaggtt    38940
gcggtgagtc gagatcgcac cattgccctc cagcctgggc aacaagagca aaactccatc    39000
tcaaaaaaac aaacaaacaa acaaatatat tatatcatta ataggccggg catggtgtct    39060
cacgcttgta atcccagtgc tttgagaggc cgaggtgggc agatcactgg ggtcaggagt    39120
tcgataccag cctgggcaac atggtgaaac cctgtctctg ctaaaaatac aaaaattagc    39180
cacgcatggt ggtaagcacc tgtaatccca gctactcagg aggctgaggc tggagaatgc    39240
ttggacctgg gaggtggagg ctacagtgag ctgagatcac actccagcct gggtgacaga    39300
gcaagactct gtctcaaaaa aaaaaaaaaa aatcattaat aaatgtgatc ttttttcttc    39360
ctatacaaca agttgtcaag caagtatgac cttcttaatt gacccttga catgaactgg    39420 gatgagatcg tggaggatgt tgaggagaca gttgttacca tagtgcactt ctaaaaactt    39480
taattctata gatttcttta aaatttttt taaaattatt atgagtacac aataggtgca    39540
tctatagatt tcattaccct caaataaatg tacaaggcaa tgcagagaaa tgcacagtgt    39600
aacttggtag acttgaccta tcaagttact gttgaatata ttatggagcc tgtgtattac    39660
caggggcagc agacttttcc tgtaaagata gttgttttca gctttgttga atctgtggtc    39720
tctgtcttaa ctacaactga gaaagccatt gacaatatat agatgaatgt acatgactat    39780
tctaataaaa ctgtgtacac tgtaatttga attgcacata attttcatgt gtctcctgta    39840
taattcttct tttgacttct tttcaaccat taaaaaatgt aaaaacaggc caggcgtggt    39900
ggctcatgct tgtaatccca gcactttggg aggctgggtg gattgctgga gcccaggagc    39960
ttgagatcag cctgagcaat gtgatgaaac cctgtctcta caaaaaatta gctgggcatg    40020
gtgttatgtg cctgtggtcc cagctacttg ggaggctgag gtaggaggat tgcctgaacc    40080
cgaggaagtc aaggctacag tggtttgtgc cactgcactc tagcctaggt gacagagtga    40140
gaccctgtct cagtgaatga atgaatacat tattagcttg tggactatac aaaaatcaga    40200
ggctggaggt gagctgggta tggccattgg gtgtggtttg ctgacttctg gtagagagga    40260
attaggagat gttaaaggtg gtggaactgt cagatacttg cattcttta gaaatacttt    40320 ggagttagct ttttggttca ggcaaaggac caaagggtta ggagagtcag gccggtaaag    40380
aggagtggtg ggcccatagc agcagttcct ggagttttt tttttttttt tttttgtga    40440 gacggagttt tgctctgtcg cccaggctgg agtgcagtgg cacgatctcg gctcactgca    40500
acctctgcct cctgggctca agcaattctc ctgcctcagc ctcccgagta gctgggacta    40560
caggtgccca ccgccacgcc cggccaattt ttttctattt ttagtagaga tgggatttca    40620
ccgtgtttgc taggatggtc tcgatctcct gacctcgtga tccacctgcc tcggcctccc    40680
aaagtgttgg gattacaggt gtgagtcacc gcgcctggcc aggtcctgga gtctttaaga    40740
```

```
ggaggtttgt ctgatggttg gttggacaaa agcctgggca tgttgtcacc ttccataagt    40800
gtttgtggga atgtaggtaa tgaggaggag taaaggattc ctgaaggatg aggaggaggg    40860
ctggtggctg ccataggaag tgatcactgt tttggcagac ctgtcttaga gtaatgaccg    40920
tcatactctc tcattgccct tgtgaactca tgaaatccca tggctgctaa agctgaaggt    40980
caagtgggga cttcccggcc actgggctta gcaccccaca gagctgtgga gtgggcatta    41040
atgtcccttt tttatagatg cggagactga gaatgaggac tgttggtaac ttttgaaagg    41100
gcactcagct agaaaagtct gagccaggat ttcaagtccc atggctttac ctctgtggtc    41160
ctaatatttg gtgtgttcaa gtgagatctg ttttttttcct atttcatttt gattattgat    41220
tttcataaat ttttttctct tttgagatag tatcttctct ctcttttctt ttttctgttc    41280
tttctttctc ttttctttct ttttttttt tctctgaga cggagtcttg ctctgtcgcc    41340
caggctggag tgcaatggtg caatctcagt tcactgcaac ctctgcctct cgggttcaag    41400
cgattctccc atctcagcct cctgagttgc tgagattaca ggcacctgcc atcttgcctg    41460
gctagttttt gtattttttgt agagacgggg tttcatcacg ttggccaggc tggtcttgaa    41520
cttctgacct caggcgatcc acccgcctct gcctcccaaa gcgctgtgat tatatgcatg    41580
agccaccatg cctggccatt atttctttct ttctttcttt ttctttttttt caggttcatt    41640 gaatttgctt tgagacaggg tcttgctctg ttgcccaggc tgaagcgcag tggtgcagtc    41700
atggctcact ggagcatcaa tttcctgggc tcaagcgata cttgcacttc agcacccctc    41760 caccccacc cgctccttttc ccccacagta gctggaacta caggcgctag ccaccgtgct    41820
tggctaattt tttttttttt ttttttttttg agacggagtc tcgctctgtc acccaggctg    41880
gagtgcagtg gcgcgatctc ggctcactgc aagctctgcc tcccaggttc acatcattct    41940
cctgcctcag cctcccaagt agctgggact acaggcgccc gccaccatgc ccggctaatt    42000
ttttgtattt tttagtagag acggggtttc accgtgttag ccaggatggt ctcgatctcc    42060
tgaccttgtg atccgcctgc ctcggcctcc caaagtgctg ggattacagg catgagccac    42120
tgcacccggc ctggctaatt tttaaatttt tttttgtaga ctgcccaggc ttgtttaatt    42180
gattttctat gtgatcttag ggaaatcgat tatttcccat aaacattttt ttaattagaa    42240
gttaaattct gcctagtttg attcacagga ttattgtgga tgactgaaac agagaatagg    42300
taagagcttc tttgaaaaat atgaggtacc atacagaagt tagatgcttt gtcctggtga    42360 tacccctcc aaagcacagc taaggaaatg tggaaggcac tcttatctca tcatatagct    42420
ttgaaagcct agcattgaaa gtacgaactt gattcttttg gagaaatcct ttggctctca    42480
gtgagtttac tttctattaa tgactgtgtt aagcggaatg aaaactgaaa gaggaaaggg    42540
gaggaagtca gaattaagca ggaagagtga gcccatagca gagtccagat ttagacccca    42600
agctacttgg aatgatactg gacaattatg ggtgtgttta atgatggtcc tgagtcatga    42660
aaacaaaagg aggcttttaaa ttatgtctgg cttagtgtac agcatatttt tgtcattatt    42720
caagttttag catgtaaaga ggaaagtgtg cagtacttat gcatatcatt ttcattaatg    42780
aaactaaatg aggcctcttt aaaattatca gtgttcacag tatcttccaa aagacatgta    42840
aatgtataaa ggtataaaaaa atatacatat aaattttaca attttgtgag ctatatagta    42900
gatctcttat tttgtccata ggtcttaaag atcttatact gtattcagga ataaagataa    42960
cttcagtggg aggcctttac agggctaatg agtaagcatt attttgataa agttctgtgt    43020
tgtctacaat agatatagta gaaatactct tggaatggta atcatcccag gccctgcttt    43080
```

```
ggagcggaag aaatagtcaa tgtagaactt tacagtatat tgtacacaga tgtgcctgct    43140
aataacttct gtagacagca aagtttaaga gaaattaggt ggtaaatgca acatatgtat    43200
ctaaataaat ttggtctgag ggatttgata agatgaaaca gtacatagtc cagaaaattt    43260
ttatactcaa agaattatag aaaatatctg aaatgttttc agttttgtgc atatccagaa    43320
aatgtcatcc tgtgatctgc tggttggcag cccaatggca gtattagatg tattgttttt    43380
attttgtttt gtttgctatt tatttggtta agagagttac ctaattagga gtgtgaaaaa    43440
aaagatttat tatagtagtg ggcttttgtt tgacttaaaa cattttttgtt gttaccacag    43500 tatgagtgcc ttgtttgtga aatttgttta ccgggaagcc atatacttag agtagctttt    43560
agtttatcat tatcatcatc atcatcatca tcatcatcat catcatcatc tccttcatca    43620
tgaaaggaag aagctaccaa tgttgcttta ttctgcaaaa aatacaatag atgcttgttg    43680
aaagtatgga gtgaaatctt aaatatgtct gttaaaaaga gtacaactgg ccaggggtag    43740
tgcctcatgc ctgtaatccc agcactttgg gaggccaagg cgggcagatc gcttgagcca    43800
ggagtttgag accagcctgg gcaacatggt gaaatcctgt ctctacaaaa aaaaaaaaaa    43860
tagacaaaaa ttagctgggt gtgatggcat gcagctgtag tcccagctac agtgggctg     43920 aggcaggggg attgcttgag cccaggaagt aaaggctgca gtgagctatg gttgtgccac    43980
tgcattccag tgtgggtaac agaacgaaac cctgtctcaa aaaaaaaaaa atagtacaac    44040
tttaagcagg atgtgggcac atgcctgtag tctcagctac ttgggaggct aagtcaggag    44100
agtcacttga gcccaggagc ttgatgctgc agtgagatgt gattgtgcca ctgccttcca    44160
gcctggggat gatagcaaga ccccatctct aaaaaaaaa caaaaaacaa aaaaaaaca     44220 gagtacaaca acctttggta aacttggaat ataaaggtgt ttccttaacc tgttaaagag    44280
ctgataaaga gtggtacttt caaaccagta cacattatgt gaaacactag agacacttcc    44340
catttgttaa aagaaaaacc ttagccaaat taaatttaag tttttttttgg agacagagtc    44400 ttgctttgtc acccaggctg gagtgcagtg gtgcaagcac agctcactgc aacctccgcc    44460
ttctgggttc aagtgatttt cctgcctcag cctcctgcgt agctgggact acaggtgtgc    44520
accaccacgc ctgggtgatt tttgtatttt ttgtagacat ggggttttgc catgttgccc    44580
agtctggtct tgaactcctg ggctcaagca atctgcctgc ctgggcctct gaaagtgctg    44640
ggattacagg cgtgagccac catgccattt aatggtttaa ttgagcaaag aatgatttgc    44700
aaattgggca gcctcccgag ccagagtagg ttcagagact ccagcacagc catgtcgtgg    44760
aaaaagattt atgaatggaa agaggaaagt gatgtaccga aaacggaagt gaggtacaga    44820
aacagccgga ttggttacag ctctgaattt gccttatttg aacacaagtt gaggtttgta    44880
cagttggcca ccttttgattg gccaaaactc ggtgattggc acaagagcag gttatagtct    44940
gtttacatct ccattttggt tatagttcat tatggacaga aaaacctgta ggtcaaactt    45000
aaaatatgta aggagacagt tttaggctaa acttgattta acacattaaa tccgtaacaa    45060
gacaggatgc ctgccctcac catgttattt gatcttattt tagtaattct agccaatgta    45120
gtagggcaag aaaactgcct gcttggctac aaaataaaca cacaaaagtc agtatctgta    45180
atatgtgaca gaaaatataa ttaaaaaaaa aaaaaaagc cgggcacagt ggcccatgac    45240
tgtaatccta gcactttggg aggccaacgt gggtggatct cttgagctca ggagttcaag    45300
accatcctag gcaacatggc aaaaccccgt ctctacaaaa aatacaaaaa aattagccac    45360
gtgtggtggt gagctcctat agtcccagct actttggagg ctgaggttgg aggatcattt    45420
gaacctgaga agcacaggtt atagtgagct gagatcacgc cactgcactc cagcctgggt    45480
```

```
gacaaagtga gactctgtct aaaaaaaaaa aaaaagaag aaaggaaag gaaagtaaaa      45540 gaaaaaataa tttcacttac tagagcatca atccctaag ataatttaga gcaaagccag      45600
aaaagtgaag aaaatataaa aatctttaca gtgggttgca ttttaaaaaa aaacttgaag      45660
atatcagatc aactcactaa tgtattaatt aatataattt aaattaaaat cccactgatt      45720
tttttgtggg gagggtggga gagtcatttg ttaaaatgat tctaaagagc atctggaaga      45780
ataagcaggc aagaatagcc aagaacattt tgaaaactaa agatgagttt ggaagacgat      45840
tggttttgta ctgtcaacta cttatagatt ttacatgaat tttaaagggt aatctgagcc      45900
ctcgaataga cagaaatagc catagatctg aaagaacact taagacctga tccagctatc      45960
catgagagta tatataatca aagtctttgt gtgtgaatca ggagtctttc aggtgcaagg      46020
taaataaact cataattgct tacgcaaagg tggtatttgc tttagtgact ccagagaaag      46080
ctcaagtgcc tatctctccc ctgactttga ttcttttgg ggttggctcc attctctcct      46140
gttgctaatg gcttcctttg tgcagccaga ggaaggagg tgtggtttt tgatacttcc      46200 aggcttctat ttttatagct tgagatcaaa gagggaagtg accttcctta gagtcagtgt      46260
gtaaagtcct aaggaagata ccacgtgggg tgctggggcc atgtgcccat ccctggccca      46320
tgaccatggg gatgctacac taactggggg ccacgcatgg ctgttcctgc cctgaactgc      46380
cagctggctt tgcagtgcag cctcaccaga atcacatgga atagtaggga tatgaattgt      46440
ttcccaaaga aagtgtgtgg ggtggtagaa ttactagtgg gggagtaagg ggacaggcca      46500
ttgggcatac tggagcagca tttactcagt cattgagaaa aggatggaac attcaataaa      46560
gggtgctgga cacatttgtg ctctaaaaat tttgtgtttc acctattaat ttatccctcc      46620
ccttagcccc tggcaaacac tgatctgttt actgtctcca tagttttgcc tttcccagaa      46680
tgtcacaccc ttggaatcat acagcatgta aaccttttcag attggcttct tttacgtagt      46740
aatatgcatt taggattcct tcatgccttt tcctggattg atagctcatt tcttttagt      46800 cctgaataat attccattct atggatatac cacaattgat ccattcacct actgaaggtc      46860
attttgattg cttccaagtt ttgataattt aaaaaatttt ttaagacagg gtgtcattgt      46920
gttttccata ctggtctcct gaacacctgg gctgatgtga accctctcc tcagcctcct      46980 gggtaactgg gattacagct atacaccact gtgcccagtg tgacaattat gaataaggct      47040
gctgtaaact tctgtgtagg ttttttttgtg tgtggacatt ggttttcagt tcattatggt      47100
aaataccaag gagtgcagtt gctggattgt atggtaaaag tatgtttagt ttgctaagga      47160
actgccagct gggtgtggtg gctcatgcct gtaatcctag cataatggga ggctgagaca      47220
ggaggatccc ttgaagccag gagttcgaga ctagcctggg caacatagtg agacctcatc      47280
tctacaaaaa atttaaaaat tagctgggcg tggtcttatg tgcctatagt cctaactgct      47340
tgggagactg aggtgggagg atcacttgag cccaggagct ggaggtggca gtaaactgtg      47400
atcataccac tgcactgctg cctgggtgac aaagcaagac cctgacttaa aaaaaaaag      47460 agaaagaaa aaagatgag tcagagggta aggaagcaaa aataagtaaa taaataaata      47520
gaagagaaaa gaaaaaagaa aaaactgtct ttcaaagtgg ctgcgccatt ttgcattcct      47580
accagcaatg aatgagagtc tgttgttgca catcctcacc agcatttggt gttgtcagtg      47640
ttctggattt tgaatattct attaggtata taatgctgtc tcacttgttt taatcaatga      47700
tatatgcact tgagcatctt tttaatatgt ttacttctca tctatgtatc ttctttagtg      47760
aggcctttgt ttaggtcttc tgcccatttt aaaaaatggg ttcattttct tattgttgaa      47820
```

```
tatcatgagt tctttgtcta ttttgaatac ctgccttttg ctttattttt gtgtttttta    47880
ttttttttt ttattgagac aagttctcac tctgttgccc aggctagagt gcagtggcat    47940
gaacatggct cactgcagcc tcaacttctc ccagcctcaa gcaatcctct tgcctcagcc    48000
ttccgagtag ctgggactat aggcacacac caccatgccc tgctaattta aaagagtttt    48060
tttttgtaga ggtgggatct cgccatgtta cccaggtggt cttgaactcc tggcctcagg    48120
caatcttcca gccctcagcc tcccaaagtg ctgattatag gcctgagcca cttagcctag    48180
ctcagaattt attttttatt tgttaatttt gaaaaaatat aggacctcat aaaagtcagt    48240
ctacatttgt acacattatg tttttggtga atatgtaaat ggattctttg tgaatcaatt    48300
tggttttgtt ttttgctttt taaaaatacc agccctgggc tggatgcggt ggctcacgcc    48360
tgtaatccta gcactttggg aggctgaggc aggtggatct cctgaggtca ggagtttgag    48420
accagcctgg ccaacatggt gaaacgctgt ctctactaaa aatacaaaaa ttagctgggc    48480
gtggtggcgc atgtcagtaa tcccagctac ttaggaggct gaggcatgag aatcgattga    48540
acctgggagg cagaggttgc agtgagccga gatcgcgcca ctgcactcca accttggcga    48600
tagagcaaga ctctgtctca agaaaaaaaa aaatgccagc agtggctggc tgaggtggct    48660
cacacctata atcccagcac tttgggaagc caaggcaggc agatctcttg tggtcaggag    48720
ttcaagacca gcctggcgaa catggcgaaa ccccatctct accaaaaata caaaaattag    48780
ctggatgtgg tagtgcgcac ctgtaatttc agctgctggg gaggctgaga catgagaatc    48840
acttggaccc tggaggcaga ggttggagtg agccactgta ttccagcctg ggtgaaagag    48900
ggatactcta tttaaaaaaa aaaaaaaaaa agcgggctg gatacagtgg tgcacacctg    48960
taaccctagc actttgggag gctgaggtgc tcagattgct tgagctcagg agtttgagac    49020
cagcctagac aacatagtga gacatcgtcc ctaaagaaaa aaaaaaaata ccagcactta    49080
gccaaaagat ttcaacagtg cagaaaaaga aagttgtgat atcttttctc caaattagtc    49140
ttgttttcag tttcattatc caagtaacca ctactaatag ttaaaacatt tgaaatacgt    49200
gtgggagctt gtcctattta atataaatta tttattgagc aaataatcac cactagtatg    49260
ttttggatac tggaattttc atatgtagga gtccttgaat gtaaggtgcc cctttggtag    49320
ttctgtgctt cttttaccctg tactgtaaca tagggaaaga tgttacaaat ggttgtattt    49380
ttaacagagc agtatctatt cttaaacacc agcccttcca ctaaaggtaa acaacaaatg    49440
aatacataaa tgaagttttg gtattgggat tatgtgggtt aaacacatcc atatttcatt    49500
attaatattt aagaatataa caaacttttt attggcattt ggaccttgta gctaaggaaa    49560
gattaaactt tgtttatttg tgctttgttt ttttcttca ctcagatatt tgaggatttc    49620
ccatttgagg aatacattta ttaatcaagc tttagtttca agatccttga tcttagggaa    49680
taccatcaac cgttcttctt taagcttcct aactttgccc aaatttggtt agaactactc    49740
aagagtagtt tgggtaattc agaaatttta ttggaagggg aaagaatttt tgacccaaat    49800
tagataaagc aactcttggg taatgatttc ttttcttgtt ctctctttat aatcaattga    49860
aagtagtagt aaggctgggt ggcaaaagaa agaggcctgg ggagaatcgc gtggttttca    49920
ttatctcttt tcatagcagc aaagtgggaa gggaccaaga ggaaatcaac tgaaaaacca    49980
tccttctgaa acattggcct aaaaaactgt agtccagaaa ttgagtgcaa ctggcagtgg    50040
catttaaaag gaatgctcta atttctagga aagcaggcac gagtacctct aaaagaaga    50100
aaaaaatgaa aactgtaatt taggacacat agacgagtat ccattccctg tacttttact    50160
ctcatgtcct aaccaaggaa gggttgccat agcaaatatg gcattcctta gccatgattc    50220
```

```
actgttgtaa atgcctgcag cattcataaa agtaagatat atgggctctt cttttccctt    50280
ttaaatcttt atttctgtat ttaaatctgt atgtcatcat ctgtattttc tctcttgttt    50340
tttttaaatc ttgggagatg gtacaaatta tttaggggag ggaatgagtt tcttgtccac    50400
aaatagagga gagagagggc ttttgtctt tctgctttgg aactggagag cttcctattt     50460
aggcatggcc ttttcaagt gaccttgtat tgttatcagt actgtagaag gtaggcacgt     50520
tgtgtaaact ttaaaattga aagccattag gcattccact tgtaaacctt ggcttttaa     50580
agaaaattac atgttcattg tgaatatttt cttatcgacc tatctctgtg cacatgcaga    50640
cttcctttgc ctacattctg aaaggtgtaa ttgccttctt taaggacagc ggacatctat    50700
agttcttggg tcaaattgtc ctccttctgg ttttgtcagt tctcagccac actgtgtgag    50760
catccatttt cttggattct ggttcggagc tcattttaag gaacatcatg tccctttga    50820
gactctgtgg acattggggt gggtagatgt cccctgtga acagaaggtc cctccctaag    50880
gaggtgcttc tctgtgttga gtcctgcatc tgggcacaca gagcccgaag caggaagagt    50940
tgagtctgaa tagggaggcc tgtaagcctg actgctctgc cacgggtagg cctggtctgc    51000
catgctccag gagcccccag gaggctctga agtcattctg cctctgggaa ttttacagag    51060
gagctaatat ttgagctgag tgagaaggtg attcttgaaa aagcaaggcg tgccctggtc    51120
cagttctgtg gggctgtcgt agaagagggc tcggaagctc ttgggagtga ggctagaaag    51180
gtaggcagtg ttaccataag gaggttggaa gtgacacaga taggctaagg aaggggactt    51240
cagtaatcat gcagcaatgg cctggaaaag ggagaggctc atagtaggga gaccagtttg    51300
gaggctgcca tagtgttcta ctgagagaga aaaagacttg aactcagagc acggtcaggg    51360
aaggtggagg ggcagggtct gatttggaag tgttttgttt tttggttttg ggaacaagga    51420
tttggaaacc tcttggctcc gtagatgaag aaaggtgaac caaggaagac tgaagtttcc    51480
actcaaggaa acagtaactc agggaagaaa acacaggagt aggaataggt ttaagagaat    51540
gacaagcagt tgtgttttgg acttgtttag ttcgaggtga catctttgta gggatgtcta    51600
gctggtagct gcaagtatag gaggaggctg gatgtgtgca tgagtttctt ggtaaagatc    51660
catctgcagt ctcctgaaga tgtcacccag attgccctgc catcacccca gggccttgag    51720
tcactcgctt ctcttggtgt ctaggcaggc ttgaagaaaa tcaaacagta caaaatcatg    51780
caaattcaga cctctattcc accccagagg aaagtcctgc tagcagtttt tgtgtattct    51840
tccagaaatt tgccttgcaa cgcgtttgag tatataaata atcccagaaa ggatgggcca    51900
gacactagca gaaactcacc acacacactg cactgggcat gcagaaactt tgcaaaatgt    51960
actggtgtgt gctgtcactg cattcctggg tttggaggtc ttctgtgtcc ccagctgtca    52020
gtattgccca caggctgacc actgagctcc ttccacagcc ggcccatatc accctctttc    52080
gaagtgtgtc tgcaaggcta gattattaga gtaatttaag tgtttctgct ttgtgttttc    52140
tttaatgaat ttttttatga tgaagttctt gttttaaaaa tatacagtgg taattaacat    52200
gtatgcattt ttcttaaaat gaccccccca gtccctcttc ggatgtgatc actgttaaca    52260
gtatcgtata tagaccctgt tctgtgtggg gcgggcagag ggctggttag tgggtggaac    52320
atgcatactc acaaccatat ttttcacatg ggaaaatata aaggtgacaa caaatctcct    52380
ggactataat ctcatcaagc agacaataat ctctgtttca aaagtggaca aatacatgct    52440
gattttttaa aaaaaattat aatagtacag aaagatacaa aaataagtta aagtcttcct    52500
aactctcctg cctgtgccct ccactgggca aaagtccctg tccctaaggt aatatctgtt    52560
```

```
aacagttctc cttccagaaa acttgcaatg caaataggaa cattttgtgt gtctgcctct   52620
gtgtgtatgt gtttacatgt ctttttttt tttttttttt tttttttttt tttttttttt   52680
tttttttttt tgagacagag tcttgctctg ttatccaggc tggagtgcag tggcatgatc   52740
tcagcttgct gtgatctctg cctcctgggt tcaagtgatt ctcatgcctc agcctcccga   52800
gtagctggaa ttacaggcgc ctgccaccac acccagctaa ttttttgtatt tttagtagag   52860
atggggtttc gccatgttgg ccaggctggt ctgaaactcc tgacatcaag tgatctaccc   52920
gcctcagcct cccaaagtgc tgggattaca ggtgtgagcc actgcttctg cccctgcaca   52980
tgtctaacgc acacaaaaga gattctgctg aacacatttt ttatgctttt tctttccaat   53040
ttaacatatt tgacatcttt atcagcttat atagctttat tttttttaaga ggttattggc   53100
tataaaggga aagtgcttta tgggtgcttc tgttgttatt taattggatc ctgttgatgg   53160
acattgatat catttctaaa tttttttagta tcctaattaa tcctgtggtg agcatcctta   53220
tacagatatc cttgttccct catgaaaata tttctggagg atggaaagaa gggaaatttt   53280
aaaaattatt tgtgtaaaca ttatcgtttg ttagtagaat gacctcagga gagattgtag   53340
taatttatac ttccccacat gcatatgaat gccttttcaa tatattgttt caaaattgga   53400
tatcatgaac cttaagagat aaatatatat gtatgtattt tttttttttt ttttttttttg   53460
gtgggggcat gtcctgttat tgacagtttg ttttggtgga gggatgtcct gttattgaca   53520
gttatcgaat agaactttgt cagttccttc atgtaaggga tgaatttggt aataaaacag   53580
gtctgacttc agttatggaa ctgggaaagc tggaccttga tgtggaggtg ggctcagaca   53640
tgctgtgtct gggcaggtat ctcttgggaa gcagtgtcat ccctgaacag aaacatggat   53700
gagccgcagg ggacggtgct gagcagaggg gctggccgtg ggtcatctgc ctcccttggc   53760
ctagaaggca caagggagct ttccaccttg cctttggttt tgagaatgca gaagctacta   53820
agcaactcac agtgtgccca gggtggtcca gctgaaggat gcgaaatggt tcttcctttt   53880
ccagccaaag atcttgaacc tcccacccca tgacaagcat tataaaattc acataatttt   53940
gataggctgg attccttttc tgtagcagat ctttcctcag aacagaagtt tgtttttttt   54000
ttttaaccta aattacctgt gagttttatt ttttaaatat ggaatctgtt ttttggacac   54060
ctccttgtca tattaaatgt tctgttatta attttgagat tttaatgtaa attttacccc   54120
agcaaattaa ttttgtttct cttgctctct cttttttttt ttttggcatc ctttcccgtt   54180
gtatagtggt gctcatttta tcatactgct tttatatgac ttttcttttg tgaacaggga   54240
tcttgttcac ttttccttt ttaaaaattt ttttatttt ttgagacgga gtcttgctct   54300
gttgcccagg ctggagaaca gaggcacaat ctcagcccac tgcaagtttt gtcttccggg   54360
ctcaagcgat tctcccacct tagcctcttg agtagctggg attacaggcg tgcaccatca   54420
cgcctggcta atttttttgt attttttgtag agatggggtt tcactatgtc atccaggctg   54480
gtctcgaact cctggactca agcgatccac ccgcctcagc ctcacaaaat gctagggtta   54540
caggcgtgag ccactgtgcc cgagccactt ttccttttaa cataaaaaca ttgatatcct   54600
agagagggca ctgtattttg ggtacataca ggttcagatc acggaagagt tgtattctat   54660
acttttttc atcattctta gttcagtatg atgtattta taatttcata tgagaaactg   54720
taacaatggg catgtgtcat ccagcaatac ctactcataa atcatattaa attttgatcc   54780
aaacatggga gaaactgaag ttttctctgt gtacttggat gctttcagag gcataaaatt   54840
atattaccat gtgaaagcaa gcctacaaaa ttcctcaggt ggtccactct gccactcaaa   54900
tgagagccag acttacagtg cacactctac aaacggactt ccagctcgtc agggtatttt   54960
```

```
aagtgcctga atatgcaagg cactgtgcca gtaaaattac tcagtcctga ggatagagcc   55020
tgttagaatt attttaaaat ctgtacttga agtttatttc ctcagtattc caagatattt   55080
tatctggttg ttctctgagt atttcacacg tagctagtta catataggtg agatggtgat   55140
gcttgtgcct ggtgtggatg agaaactgag cctggcagac ccgagattgg atttcctctt   55200
ctgactttgc aagtgtggct ttgctttaat aatagccctc ctcttttttct gtattcctct   55260 tttctccttc cagtgtggca aatatgcatc aatcaaaata caataacctg tggaaccatt   55320
ttttctaaaa taggaaggtg gtgccatggg ctattgattg ttgagggtag tcttcagagc   55380
ctgtcttata aatctataat aattccccccc aaattaatgt gctagttaga accctagaat   55440
tgcagcactg aaagtgaatt ttagaatctt ttccaacttt ttaccaagct cagaaagccc   55500
ttttattgga cctttgtttg cctcatggtc atctggtttc tttatgctgg tagtaacagg   55560
aaccttacta acctacaagg tgacccagtc catcctgggc agctgtgatc attggaaagc   55620
tctgaatcat tcatctggaa gctgcctgtg gcagaatagt acagaacata tgcattgcac   55680
acactacaaa actgctttaa ataagtgttc cttttcattg ttagatggaa gtgacccagg   55740
gcaaggatca tgttttatga gccagttttc tcctagtgcc ttgaacatag gcacttggta   55800
gtgtttagag aatgaattgt cttttttttt tttgagacaa agtctcactc cattgcccag   55860
gctggattgc agtggcacgg tgtcagctca ctgcagcctc cacctcccaa gttgaagtga   55920 ttttttgtgcc tcatcctccc gaggagctgg aattacaggc atgcgccacc acacccagct   55980 aattttttata tttttagtag agatggggtt ttgcgtgttg gccagatggt ctccaactcc   56040
tggcctcagg cgatctgcct gcctcagcct cccaaagtgc tgggattaca ggcgtgagcc   56100
actgcgcctg gccagagaat gaattcttaa taagtttctt atgacttcag attgactggc   56160
agttgtgcta aatattttttt gcctttattt gaattagaaa attcgtaagg gggccttgag   56220
agtagatgca gtcacatttta ggagattttt ccccccccatt ggttaaaatg cagttttttct   56280 atggatctgc tttagaacta caaataaact ccgatcactc acagcagact acgcaatgag   56340
ataagaagca gtccatttgt tctgtcgttt attcatggcc ctcatctttg ccagccaacc   56400
tgtgcagaag agcacagcaa agcataagct tcctaacagc tattcccatt cagctgctgt   56460
cttcaagaag cagaagggtt tagataacct tagagaacat aatcaaacct gggaaactca   56520
aatcaaaaca aaacttcgaa acggaagttg aaggtcctga ggtacccaga ggcatagcaa   56580
ggaaaacgtc cccactggga tatcttctgg attcacctac agacctctct ggagttttaa   56640
gatccacgtt ttatgacata ttgcatagca aacaggccga acgctgttgt aaatcatcct   56700
ctacgaaagg cccaggtttt gaaactgaag gcctgaaaag gctcctgctt accagctgtg   56760
tgctgtacct gacacactga agcctgagag tgccagtcac ctgtcagagg aacacagct   56820 gccctcaggc agaacctgag tctagaactc aaggtttttg actcttaggc taaaaataaa   56880
aaatcagaag gaggaactat ggattgctta atcagtcaca ttttcacttt ctaaggtttc   56940
ttgtagcaaa agttatagtc tttggggatt gggatgtaga cactttttttt tccttcccta   57000 aaacaatttt tggcctgcca gttttttcgag cttcctgctc tggaccctga agttgccatg   57060
cagttgcaga catgctcctc cttcaaggct ctgttaagct gtggctgccc ttccttacca   57120
ctgctgtgcc ccaggccaaa cccctgccc ctccttcccc taaggcactt tgcacctgtt   57180
gctccgagcc ttctggtcta tcccagttgg tagagtccct gtgcttacct ctgtggctca   57240
gtcctcgtgg gtggtcagtg ctctagggaa ggtgagctga ccacttcact ttcccttccc   57300
```

```
agccatagct cttcacagcc tcaccaactt agaaaggaat gctgcttttc tctctgtccc    57360
ccgtcctgac tatgttcaag tcattgctca gcccagtgag tttgtccttt cttccagacc    57420
agtagttttc ccccagtccc tcaggcttca gcccttgaag gcatccttag ccccccacca    57480
ccatgatagt caggcgctgc gcctatccgc agggtgtggg tatgtgtgtg tcttttgttt    57540
ctggagccca ttcctttcct tccaccagcc tctaggcctt catccaatcc ttttgcaact    57600
cagtgattca tgacttttcc ctgcatccag tctagtctct ttgctggtcc attgtttcca    57660
tagttgccag tttaatcttc ttaaaatgct gcattttga agtcagtctc ttttggtccc    57720
tctcagaaac atttaaatag ctatctgttg ccacaggggg aaagcttgaa cctcttagcc    57780
agtcattcag agcctgccct ctgctgggc ctgctttcct ctacagatgc ttctcccact    57840
ctgcctgcca cagcccttgt agctggctga ttgccctgta cctcgcaggc tctggaagtc    57900
ttcagctcct tcatggagcc tttgccagcc attctttcca agactttgct gttgttcact    57960
gcctgatttg ttcatttgac acttaattca ctgagcaaac attatgaaag atgtactgtt    58020
tgctactgtg aggaatggat ccccaagaga taagagggtc agtccctact gccaggaaac    58080
ttgcctgtgt cacctgggtt cagtatcttg tgtctattag atcagaagtg gaaaggcaga    58140
ggccagcccg tatgcttgtt ttattttatt taaatcacca gcaccccagc aagtgttttg    58200
cacaggaaat ttctcattat ttaattattt tgggttttt gattaaattc tgtacattcc    58260
cattttagct tatcttgagt tataacatta aaattaaggt agtcatcagc tgaattataa    58320
gacttaatta gataagatta tttaagatag tgatttctca ttagattggc cctgttcata    58380
ttaacttttc tgtttttttc ttcagtctgc atgaagaaat cagtgatttt tatgaataca    58440
tgtctccaag acctgaggag gagaagatgc ggatggaggt ggtgaacagg atcgagagtg    58500
taattaagga gctctggccc agcgctgacg tgagtcccctt cctgggtagc ttatgcttcg    58560
gacagtcctt gtccacgggc tagaagccta tctgctggta tctcatgcta gtcctcacat    58620
gcaagtagaa gtgctctgta gagttgtggt ctaattaaat tttaaaggca aacaattttc    58680
tgcagtcttt agaattgagg cttcctaact attttcattg gattggatga ctaacaacta    58740
tttttttttt gtagtgctaa tagcaactac taaaggcaag ctatccttag aaattattag    58800
tgtaaagaga agaaagacaa atcaaacctc attgttgtag tggtctgtta ttggatatga    58860
tatatcaaaa cctcattact acttagttcc agcctgccag ggtaaacatt atataattgt    58920
ttacagctaa atgaaaatgt caagtaagaa cttttgtcac ttgaagttca tttcctttgg    58980
ctaatgcacg cataagtctt ttcttatttc tttcctgaaa ttgccatttt tcatctctct    59040
cagaccagct aattgccttt tagacagctc ccagtcagtg aacaaaatga ttactcagga    59100
tttcttcttg gcttatttgt cgttttgtt actggtacta agtctttgt ttttgtttt    59160 tgagatgggg tctcactctg ttgctgaggc tggagtgcaa tagtgcgatc acgacttact    59220
gcagcctcga tttcctgggc tcaggtgatc cacctcagca tcccgagtag ctgggactgc    59280
aggtgcacgc caccacactt agctaatttt tgtattttt tgtagagact gagtctcact    59340
atgttgccca ggttggtctt gaactcctgg gttcaagcaa tgtgcccgcc ttggcctccc    59400
aaagtgctag gattacaggt gtgagccacc acacttggcc tgttactggt actaagttaa    59460
tacgtcactt tttagggcac tttgagggcc tgttctacaa ttttgtgtat gcaaagaagt    59520
acacaaaata atactaataa aatccattac tttgtgtttg tagcttttct tcaggcactg    59580
tcctgggtgg tggtgggaag ctagggaagg ttttttttcca attggcaaaa caagaagtt    59640 tcattgtatg taaaacttgc aagtatatga cagtatgtat atgacactgt aggtaaaggg    59700
```

```
aaaaggcaag ggtactaatg ttttatgagc aatgaccata catcgcattc tttctcctat   59760
gtgatccaaa tcagtggttc tcagctagtg gctattttgt tctccagggg gcatttggca   59820
atgtccgaga catatttgat tgtcctgact gggtacgcac tgctagtacc tagtgggtag   59880
aggccatgga tgccatcagc cattctatga tgaacagtat aggcccttac aacaaagaat   59940
tatccacccc caaatgccaa tgttgagaag ccgtgatcta acttaaccct tatctttctt   60000
aggtggaggt tgattatcta tctatctctt tctctccagc cagccaggca gccatcatct   60060
gtctacctac agatgaggaa catgagcttg tggttaggtt cccaggtcca tctcgcctca   60120
gaggttgaac tggtttcact gtttatcatt ttttcccccc gagatggagt ctcgctctgt   60180
cgcccaggct ggagtgcagt gacatgatct cagctcactg cagcctttgc ctcccaggtt   60240
caagaaattt tcctgtctca gcctcccaag tagctgggt tcaggcgccc gtcaccacac   60300
ctggctgatt tttgtaattt tagtagaggt gggatttcat catgttggcc aggctggtct   60360
tgaactcctg acatcaggtg acccacctgc cttggcctcc caaagtgctg ggattacagg   60420
cgtgagccac tgtgcccggc ctatcctttt tttattacaa ttacctgcat acatatttct   60480
gcctgagttc caccgttctc catgggttga gatggaatgc atcccagttt tatgccacag   60540
catgatgtta cctgatgttc tttgtggaat tgacctaaag gccctcactt gccctacagt   60600
taaagtagtc tgatcccaat ttagtaatct attcgaagac tcctgcttag agaacaaaaa   60660
tgaaggattt gtgattgtgt ctctggataa tgagggaaca ttagtgatct gaactgcttc   60720
tgaaagtttc ctgtggttgg ctttctgtat ccacaggtac cacacctcca tattaaacca   60780
acaatggatt gaaaatattc agaaaaaact ataaaaataa caatgtacca ataaaaacaa   60840
tacaaattat tttaaaaata cagtataaca actatttagg tagcatttac atcatacttg   60900
gtattatagg tattataagt aatctaaaga tgatgtaaag tacatgggag gactagcata   60960
ggttgcatgc aaatactcta ccattttata gcagggactc aagcatcttc agattttggc   61020
atggtgggac tggaaccaat ctcctgccga taccaaggga caactgtatt ttggtctatg   61080
tgtttcatat tgaaccagat aagtttaaat tatattcaga atgtctgctt gtgaaacaga   61140
atccccgctt catgaagctt gggggttagaa aaaaatgctc ttgtcatacc aaaaagtacc   61200
agtagagggt agcaaaaact gacatttctc catatcttgg tgactcaata tgataacaac   61260
ttctgataac tcaatataat aacaacttct ttttctgttt caggtccaga tatttggaag   61320
ttttaaaact ggactttatt tacctactag gttagtacac tcatgaatct ttcaaaggac   61380
ttttcttaga gtgtattcat tttggctgtc aaatttgtaa ggagtagaaa caaaacaaat   61440
ttataaaaca aaatggggct gggcatggtg gctcatgcct gtaatcctag cacttcggga   61500
ggccaaggag ggtggatcat ttgaggtcag gagttcaaga ccagcctggc caacatggta   61560 aaacccccatc tctactagaa atacaagaat tagccaggcg tagcagtgcg cacctgtaat   61620
cccagctact caggaggctg aggcaggaga attgcttgaa cccgggaggt gaaggttgca   61680
gtgagccgag atcgcgccac tgcactccag cctgggcgac agagcaagac tctgtctcaa   61740
aaaataagta agtaaataaa taaggattt accagcattt aatttgattt accttgaagt   61800
agaatatcac ttcacatcat cttaccaaga catagatggt acagagagat ggaaaaggga   61860
tcatgttgca atggaatcaa ttagttacta attttagaaa ttgactgcct ggcagagtat   61920
tgctcagtcc cataacttaa cccactgaca cagatgttaa tgtagtatca tgataaaatg   61980
tctgattata tatcctcttg aatgtgagtt cccgctgtct tgctcactca ctcttacact   62040
```

```
caccctcgct ttcaaattaa gaactcattc tactagttat ggctccagca tcctgatcca   62100
gaaattcagg gtacagatct cttctctgag aaagatcttg cctttcagg actgttgttc    62160 agtttcagtc ttctcaaatg agacctcttg tgacgcacag ccttggaggc tctcttttgg   62220
gaaatgataa tgtttctcca aagggtgaat acttgctctc taagaattga aattgtttga   62280
acattccatc atggttatta ttattattac cttaaatttt aatctctcca gaataaagtc   62340
agcatcatgt ttttccattt gagcttgatt tggtatactt taccccaact taaagtgtgc   62400
tgaagtggat ggaccctggc aatttccgtt cttctcatag atgcccttgg cctgcaaaag   62460
tcataaaata ctcaacttcg agttaatatt tcttatttag gttgtcagca tcagtaaaac   62520
atgaaaaatc acctttctta aaaaatttaa ttaaatttta tgaataggta gtacattcac   62580
atagttcaca tttggaaaag gcacaaaaat caatacaggg aaaagtctca gtcccacctc   62640 tgcccctgg ttctccttgg aacagccgct tttaccagtt tctcacatat cctttcagag    62700
atatctgtgc ataaaaagg acatgtgtgt atattaacac aaatggtagc atgctggata    62760
cctgttctgc atccagctta aagcacttca taatatttct gagttgcaat taatctcatc   62820
cggataggaa aatcattatg tctagtacca caagcgttta ttaaagaaaa tacatgaagt   62880 gcttttgtt tttttttctt tgaggtttta cttctttcaa aatcaccata tttcctgagg    62940
cctgaattct gtgaaatgac tgagaggagg agtttgttaa aatcaacaac tactatttcc   63000
cttctccaca aaaccattat caccaacaca tttagtcttc gttggccagg gtgggaaata   63060
ggttttaatt gtactaatga agtctataag catgagtgtc agttaaaaca gtttccaac    63120 ttcttccgac cctcttgtat atgtattctg tgttcagtga catcgaccta gtggtgtttg   63180
ggaagtggga gaacctaccc ctctggactc tggaagaagc tcttcggaaa cacaaagtcg   63240
cagatgagga ttcggtgaaa gttttagaca aagcaactgt aagttctgca gcatttcata   63300
ttaaaatcct tagttatttta cctatgaaac ttgaattaaa attaaagttt ggtgagcaca   63360
gttgcattgc aagtgagtga ttctttcatt ttgttaatgt caccgtgctt gcacataaaa   63420
agttttctgg ttgtccacac tggagtgtga ccatacaatc tcggctcact acaacctgtg   63480
cctcctcggc tcaagtgatc cttctacctc agcctcttgg ggagctgtac tacaaacaca   63540
acctgccatg cctggctaat tttgttgtat tttttgtaga cacggggttt caccgtgtta   63600
cccagactga tctccaactc ctgggctcaa gtgatccacc cacctctgcc tcccaaaatg   63660
ctgggattac aggcgtgagc cactgcacct ggtctgcatt tcttttcaca gcagcaaaat   63720
atgcaatttt attatacaca gtactcactg tagagatttt tgtttgtttt attcatttt    63780 tttagagaga tacagtctca ctatgttgcc caggctggtc tctaactcct ggactcaagt   63840
gatcctccca cctcagcctt atgtgtatct gggactaagg cgcaccctac cacgccctgc   63900
ttatttaaaa aattttttt tgtagagata gggtctccct gtgttgccca gttaggcca    63960 ttttttgaaa agaactgctg atagctcatg taaataatcc tgtcagcttt ttagaataat   64020
ttttatattt tatcttgtca ggttgttttt tgggctattt gcaaaactga ccagtaatgc   64080
aagtgggttg tagtgtacac cttaagaatc cagcaatttt cttattagaa acagtttgat   64140
gatacaaaac atttaatacc tggcattcct agttcttcat cttatactca gaaagtgttc   64200
tccaaattat tgaggaaggt ttttgttcat tttaaaatta tcattataac tatatgtcaa   64260
ctaataaatg agatgatggg catattaatt tatttaactg tagtaatcac ttcagtatgt   64320
atatcaagat aagtatatca aaacatgtac accttaaata taaacaataa aaataaataa   64380
taaaaaattg gacaccaaac aaaattctcg gttgatagaa attatactgt aatatactgt   64440
```

```
atgggaccca gtgctaaata tgcagcatat agtatttgta gcagaccagg tttactgggg   64500
tgtgccatat ttagaatact cagtgttctt atgctctcat gagatgatgg agacctcatg   64560
tctagtaggc ttccatcccc tgattttatc atttaatctg gttaaagcat ttacatttta   64620
cctttcttct cttataggt acctattatt aaattaacag attcttttac tgaagtgaaa    64680
gttgatatca gctttaatgt acagaatggc gtgagagcag ctgacctcat caaagatttt   64740
accaaggtca gagaatttag cgtttataca acaaaactat tagaaacgta attttaagat   64800
tctgttgtgg tggtgttcta atattttat atgcatgttg ctgtctctct ctctctcttt    64860
taaatagagc tagggtctca ctctgtcacc taggctggag tgcagtggct ggatcatggc   64920
ccgctgcagc ctcaaactcc tgggttcaag tggtcatctc acctcagcct cccaagtagc   64980
tgggactaca gacgtgagcc actacacctg gctattttt gtatttttt ttttttttta    65040 gtgttgggt ctcgctgtgt tggccaggct ggtctcttaa ctcctggcct tagcctccca    65100
aagcactggg attacaggca tgagccacca tgctcagcct gcaccttact tttgtatgca   65160
acggttttgc tttctttgaa tctgcttgta atgatcagtg attaacttat aatgtgacct   65220
caagtaagaa ttaaaagttg agaaagcttt tgaagaaatt gtctgctcta gatccttcct   65280
tgtagagaca gaagagatgg aattctacta cacagttgat tccatctgtt tttaaccttc   65340
aggagttcag attaagaacc tttcctttaa cccatttccc atatgcccca agaatactgt   65400
gcgggcagtg agctgcactt ttttttttc ttttttcgag gcagagtctc tctctgtcac    65460
ccgggctgga gtgcagtggc acgatcttgg ttcactgcca cctccgcctc ccgggttcaa   65520
gcaattcttc tgcctcagtc tcatgagtac ctgggactcg tgcctgggac gagtaccagg   65580
cacctgccac catgcctggc taattttgt attttatta gagatggggt ttcaccatat    65640
tggccaggct ggtctcgaac tcctgacctt gtgatccgcc tacctcggcc tcccaaagtg   65700
cccggattac aggcgtgagc caccgtgccc agctgtactt ttttttttcc taaacaggaa   65760
ataggttaag agttttaaga gccttttcta gatttcaatc cctaaattac ctttaaggtg   65820
tttcctacag gcttccttac ttctgttttg aaattattta agtttatttc tattctgttt   65880
tcttccaaga tagagaataa tttgtcacca tcatctgtgg aacattttac atacttaggt   65940
agttgtcagc tttctcacct ctaacctaag ccattaactc ctttggcttc tgttagaata   66000
ttcacaattt ttttttctg tagcagctct aaagtttcta tttcttcttt tttgtttttt    66060
aagaaaaaaa tgttaactac ttgatgttac aagcattatc atcttgcata aatgtatgga   66120
agacagaaaa gcagaaaaat aaaagaaaga ttatccataa tcgcactata ttgggggtgt   66180
gtgtgtgtgt gtctgtctaa tattttcttt ttctggaaaa aacttttaaa aattgaaatt   66240
catatgcatg ataacattca tcagtataaa gagacagtgt aaagtgagtc acccttacac   66300
catagatact tagatcattt ttacagaatt tctccattgcc aattattgtt ttttgcgttg   66360
cttttttatg ttcttttaaaa ttataagcaa aaggagtagc acattataca cacattgtct   66420
tataacttca taaaaactta atgttttgga ggtttcttcc atattagcac atacaggctt   66480
gctttattct ttttgttggt tacacaggca gtagtctttt ataaggctgt gactgcttga   66540
tttagcagtt cttcagtatt gttccagttt tcttttgcta ttagaaaaag ggattgatga   66600
atatacttcc atacatgcat cttgctttac acatgcaaaa tgtttgtaga aagattccca   66660
aaagcaaaat tttgaggtcg aagggtatat ccagataaaa ttctgttgga tatttcccta   66720
attatttatt ctttcatatt ctcattttct ctctctcct ccccctttc ttctccctcc     66780
```

```
ccctcttcct ctatccctcc cttctccttt tctctcttt tctttccctc ccttttcttt   66840
tctcttttct cttcttcctt tttcttcctt ccccttcc ttttccttcc ttctgcttcc   66900 ttttttcct ttctttcatt ttttgacacc gagtctcact ctgttaccca ggctagagcg   66960
cagtgatcat ggctcactgc agcctcggct tcttgggctc aagtgatcct cccaccttgg   67020
cctgagtatc tgggatcaca ggcttgccca ccacacctgg ctaactttt ttttaatttt   67080 ttttttttg agatggagtc tcactctgtt gcccaggctg gagtgcagtg gcgcgatctt   67140
ggctcactgc aacctccgtc tcccaggttc aagcgattct cctgccttag cctcctgagt   67200
agctgggatt agaggcgcac accaccacgc tcagctaatt tttgtatttg tagtagagat   67260
gtggttgcac catgttggcc agggtggtct caaaccctga cctcaggtga tccgccctcc   67320
tcagcctccc gcagtgctgg gattacaggc gtgagccact gagcccggcc actttttat   67380 tttatttttt aagtagagat gaggtcttgc tatgtggcca ctttttttt tcttttttt   67440 taagtagaga taaggtcttg ctatgttgcc caagctgttc ttaaactcct gggctcaagc   67500
agtcctcctt ccttgacctc ccaaagtgtt gggattacag gcatgaacca ccacacctga   67560
cccctaattg ttctttgaaa gggaactgta tctagactga cttaaccacc atgttttgtt   67620 ttgtttttg agacagagtc ttgctctgtc actcaggctg gagtgcaatg gtgcgatcat   67680
ggctcattgt accctccgcc tcctgagttc aaacgattct tgtgcctcag cctccagaat   67740
agctgggact acatatgtgt gccaccacgc tgggctaatt tttgtatttt tagtagagat   67800
ggggtttctc catgttggcc aggctggtct tgaactcctg acctcaagag atccacccgc   67860
ctcagcctcc cagagtgctg ggattacaga tatgagccac cgtgcccagc ccacaatgtt   67920 taaaatact tatttctcca tatttttgtt ctttcctatg cttgcttagt ttgatacaat   67980
ttgcaaaagt ataagctttt ttttcttt tatagaagcc atgcgtgttc attgtaggac   68040
atctagaaaa cagagataag agtaaagaaa aaaaaatgga aatcaccggc caggtgctat   68100
gtttcacacc tgtaatccca acactttggg aggcccagac aggcagatca tttgagctta   68160
ggagttcaag accagcccgg gcaatgtggt gaaaccctgt ctctacaaaa atacaaaaat   68220
tagctgggca tggtgggctg aggtcggagg atcacttgag cccaggagct ggagattgca   68280
atgagccaag attgtgctac tgtactccag cctgggtgac agaatgaggg ggaaaaaaat   68340
ggaaatcact agtaattta ccaccctaag taataatagc tgttaagact tctttgaaga   68400
tgttgtgcct gctttgtttc cctccgtggc cccagcctat ggcatggttt acagaggagt   68460
gaatgaatat gtgcacagca aaaggtggac tcattctgta catacttgcc cactcaggtg   68520
ttctctcggg tagccctgcc tcattccctg tgaagcgtgg aagggagggg tggtctgtgt   68580
gtagtcatca gcccatgtgc aagtcagcag gcaggactct tgtttgcccc agggctgtgg   68640
cagaataatc taaaggtcgc tagtctacag tggtacatca ccaagaaaag tgattcttaa   68700
aaatctcact gatttagtgc tttaagatgt tggttacttt gtccttgtac tctttctatt   68760
ctctgtttac aaatgaatat tagagggtca tggtcacaaa tgagcatcat cagttacatg   68820
ctgttagtgt ttctatccta tagcaagtac tttttttt ttttgagatg gagtcttgct   68880
ctgtcaccca ggctggggtg caatggcacg atctcgcctc actacatcct ctgcctcccg   68940
ggttcaagtg attctcctgc ctcagcctcc caagtagctg ggattacagg ctcccaccac   69000
cactcctggc tatttttgt attttagta gagataggcg tttcaccatg ttggccaggc   69060
tggtctcgaa ctcctgacct caggtgatct gcccgccttg gtctcccaaa gtgctaggat   69120
tacaggcatg agccaccatg cccagccctg tagcaagtac ttagatacta ttattcattt   69180
```

```
gtacatgtct tacaatttaa gtataagggg agaaccattc attacctata gtttacttt    69240 ttttaatagc ttactcttaa aatagaaaat taagtatgtt gtatatctct accaaatttt    69300
ataatgtaag gaccaattta tgcccctctt aatgcttaga tctgttgctg atacaggaat    69360
tcattgaaaa tacaatttc ttttcagaa atatcctgta ttgccatact tggtttagt      69420 attgaaacaa ttcctattgc agagggacct taatgaagta tttacaggtg gaattggttc    69480
ttatagtctc ttttaatgg cagtcagttt ccttcaggta agtcatatgg gtatagcatg    69540
ctagtgcaca ctaaaagcaa aagtgatcaa tcagctggga acatttggg aaaaaatcga    69600 aatcaacctg taattgcatt gcttcctg attacttaac ggcttttccc tttaaactgg     69660 gtacattta tcatttagca aatatgtatt tttaaattcc tatgaaagaa tattttggt     69720 tttaaatccc atacattcta gtattttga gacttttcac tgcaaattt aacatgcaaa    69780 atgtacggcc tggtttccat aagcataaat agtataaatg ccaacaataa gaatgtcttc   69840
taagcagcta aatcttgtaa gtttagttgg aattgagacc agctatttgg gtaagcgaat    69900
tagagtctta gtattgtaag tgggtatgtt tatgtggcac agggttgcca actgcctgag    69960
tctattcgtg agtcagaacg actttgctga tgtgttgggc caagccagcc ctggttggca    70020
gcctggtgca gccgtaaaat tcagccttac aaacagtctc ccgccattcc cgcaccatgg    70080
gactttagtt ttgtgtgtaa caacagtata acctgctgtt agcccattat caactgactg    70140
ctatgctaaa ccaaaattat aataatattg cttgtagaag ttagaatata atttattccc    70200
cctctccttg ataatttagc aaaaatccaa tataatttct tctttctgc tttagttac     70260 atcccaggga agatgcttgc atccccaata caaactatgg tgttctctta atagaattt     70320 ttgaattata tggacgacac ttcaattatt taaagactgg catccggata aaggatggtg    70380
gttcatatgt ggccaaagat gaagtacaga aaaatatgct agatggctac aggccatcaa    70440
tgctttatat cgaagatcct ttacaaccag gtattgaaat taggtaaatt tgtgggcatt    70500
caaagagagg gcactgtcag tcaccttatt atactttaaa ttctctttag atgaaaaatg    70560
aaggaacaac ttctaattgt tattctttt tcatcgaaat atttcatgag caaacatact    70620
aaaataaaca gacacagaca atagaaaaac accttggaga cttccagata agtagggagt    70680
agaatctgtt taaccctaaa agcatagtag aaaaggcatt cacttatttg gatgggttca    70740
tgtttggtgg ctgtttctcc ttcttgggtc cttattgcct tgattacaac caattgtcag    70800
caattaatga ggctttaatg agatgattct gaagtcctga gaggcagcaa gcatagtaat    70860
atatctttga attcatgagc agaagggtgc aaggagacaa tgtattttct ttttgaattt    70920
ctcctttcct gtttgatttt gcatgtctct ttgtgctttt tccagcttca tgtgggcttg    70980
aaagtaagca gaaagtaaat tccttccatg ctttttctgaa gttctgtttg cttgcttgtg    71040
tcctgatttt tgtgagcaat atttttcctt gatataattg taaaatagat tctgcgttat    71100
tggacttcag tggaagtgct tttagtcatt tgctttaatg tgtaaacttt gaaaatgagt    71160
aaggaaaggg ggtgaagaga tagagtagtt gcctaggaac cattttctgg cttattgagc    71220
tgccttataa acattaatag ttctatgtgt ttattcattg aggaaacatt acattgattg    71280
ggagcctgct ctgttcaaaa gtattgggcc aaaggacacg aagactttc agcaagacga    71340 tccttgcttt ttaggggctc ataatttaga gtgagaaata gatatatagc taatataaac    71400
ccaaaaaata tagaagtatt tctgatgtaa cttggggttt cactcttagg agtgaacagg    71460
gcactatttc ttttgtttgc ataactgttt atgtatggaa tgggataatt cttgatgggc    71520
```

```
cagaatacat tccggcaact gatacaccat aatgaagtac caactgcatg attcacatat    71580
tcagagactg gggagctttg gggacagctc acagctcagc ttccaggcac aactctggtg    71640
ggataactat ggcccttgct ctcctggaag agagtcatca acatttagtg catattaagc    71700
acagtcaggc ttactatgtt acgtatattt cttttaaagg taacgatgtt ggaaggagtt    71760
catatggggc catgcaagtg aagcaggcct ttgattatgc ctacgttgtt ttgagtcatg    71820
ctgtatcacc aatagcaaag tactatccca acaatgaaac agaaaggtaa aagttcatct    71880
ataaccagcc cattgtgtca aaattagttg tggcttctta tcttcaaatt aatgttattc    71940
cctccctctc cctttctttt taaacacatg cagcatacta ggtagaataa ttagagtaac    72000
agatgaagtt gccacatata gagattggat atcaaagcag tggggcttga agaatagacc    72060
tgagccttca tgcaatggta agatattttc cttggtcgat tgactgagta ttagaggctt    72120
ttctgtgttg tgtgcgttta atgggaagaa acgttttcca atcttttgcc actctttcag    72180
gaaatggtgt taccttgata gtagatactc agcagttaga taaatgtaat aataatctat    72240
ctgaagaaaa tgaagccctt ggaaaatgta gaagtaaaac ctcggaatct cttagtaaac    72300
actcttcaaa ctcttcatca ggtccagtgt cgtcctcttc tgccacacag tccagctcta    72360
gtgatgtagt aagtatgaaa gcctcggctc ttctgaactc agatgcatgc acgttctctt    72420
gctggggtta acactgtctc gaaggctaag gctacttcct ttgcttacat gttactggga    72480 tatttaata  actttcatgc ttgtacattt tctcaacatt ttgttatgaa aaagttcaag    72540
catatagtaa aagtgaacaa attttagtga gcattcatgt actcaccagt agattctgct    72600 attaacctt  tacttgctta tgtcatacct gtctatccat cactctatcc attaattcat    72660
cttattcttt gatccatttc aaagtagatt acagacatca gttcccctag agtactgtag    72720
cttgtgcatc cttgtagcca gactccagta tttgtttatt gtttttttcct ttttttttt    72780 tttgagacgg gatctccctc tgtcacccag gctggagtgc agtggtatga tctcggctca    72840
ctgcaacctc cgcctcccat gttcaaacga ttctcctgcc tcaacctcct gagtagctgg    72900
gattacaggt gcgtaccacc atacccagct aattttttgt attttagta  gagacggggt    72960 ttcaccatgt tggtcaggct ggtcctgaac tcctgatctt gtgatccacc cgcctcaacc    73020
tcctaaattg ctgggattac aggcatgagc caccacacct ggcctttaac gttttttcttt    73080 tcttttcttt tcttttttt  gagacggagt cttgctctgt cacccaggct ggaatgtaat    73140
ggcatgatct tcactcacct caaccttcgc ctcctgggtt caagcgattc tcctgcctca    73200
gcctcctgag tatctaggat tacaggcatg tgccaccaca cccagctaat ttttttgtatt    73260 tttagtagag atggggtttc accatgttgg ccaggctggt ctcgaattcc tgacctcaag    73320
agatccaccc gcctcagcct cccaaagtgc tgggattaca ggcgtgagcc cagctgttat    73380
gactttttaa caccatagtt agttttgcct gtttcagaat tcatacaaa  tggaaccaca    73440 tagaatatag tcttgtgtaa ggcttctttc actcaatttt ttttcagctt tctggttgaa    73500
ttttttgttg ttgttgtttt gttttgtttt ttgagacgga gtctcgctct gtcgcccagg    73560
ctggagtgca gtggcgcgat cttggctcac tgcaagctcc gcctcccggg ttcatgccat    73620
tctgcctcag cctcccaagt agctgggact acaggtgccc gccaccacac ccggctaatt    73680 ttttgtatt  ttagtagagc agggtttca  ccgtggtctt gatcgcctga cctcatgatc    73740
cgactgcctc ggcctcccaa agtgctggga ttacaggcgt gagccaccac gcctggccaa    73800
attttttttt agttgagata tagttaacat aaaattcagc attaaaaatg tacaattcag    73860 tggttttag  aacatattca caatgttgtg cagccatctc cagtaattct agaacatttc    73920
```

```
catcacccca agaagaaacc ctgcatttag cagtagtttc ttctaattct tccttccctc    73980
ccttaacctc tggtaacctc taatctactt tctctttcta tcctgataga atttttttg    74040 ttcccccatc ctgatagaat ttatgtgtca attataatgt aagttacctt ttaaaatcaa    74100
agtgaatttg tagtgtactg atttgagatc taaagcaggc ttacctgttt gagtttaact    74160
ttattaagtg taggacatga aaagtaatct aaatattgta tgttgttgat gatgaccatg    74220
tgtcaatatg gaatcataaa tcctcctgtg cagaatctcc ctgtgtgctt ttttggttcc    74280
tagagcagta tgctttggag gacagaagcc aagctagatg tcacagacac agggagatgg    74340
agtgttgggg actgagagaa tgtgactctg acatgctggg tagagtgcca gggccagggt    74400
ggagacctgc agagagacgt agcattgtca tggcccatgc agcccagaaa taggtggagc    74460
tcagcccact gtcgcgggaa gtccacccc acccacacca gtatgtttgg ttagaatgat    74520
cactgatttg tcatcacaga ctctcagaga ttgaacccct aaacccatc atcttgtgtc    74580 tggctgaagc cagggactag gacctaggtt cctcactctt taccatactc tttcattttc    74640
tataaataaa aaaacaaata aacttagacc tctgtgagct ccttcaaggt cagatgtggg    74700
cagtggattt aacaatgaac agaagctctc tgataaaatc agtcattta aatgtttgga    74760 ggaaaattta aacaaacagt taatttttg tgtgcttctt ttaactccca aatgtttaaa    74820
tttagtccag agagtacttt aaccaaaatt gttttctttt ctgaatattg agtatctaaa    74880
ttactaatat gtcacattat aactcacgtg acttgtgtta ggattccgat gcaacaccat    74940 gcaaaaccc gaaacagctg ctttgccgtc cgtccactgg gaaccgagta gggtcgcaag    75000
atgtatcctt ggagtcctct caggcagttg ggaaaatgca aagcacccaa accactaaca    75060
catccaacag caccaacaaa tctcaggtgt gtggaacgtg ggttttaat tgttagtatt    75120 tgatacaaaa tatttagaat ttcccacatg taaataatat gcagcatggg tttgaagaaa    75180
acgctagatt gaagaacaaa cttattttat tctaagaggt tccaacacat gacagtgctt    75240
ctaggaacag gatgtcctaa ggatccttgt gagacaccat tgtaacataa atctcttcag    75300
gaatctattg actggtcctt ataagatgtt ccagccaaac taccatataa aaagtgtctc    75360
agttgtacat gaaataagct ggcatgaagg ttttgtgagg cctcatggca gtgtgcatat    75420
ctgggaataa tgtatccttt tctaatattt taatgttcaa taccttgttg ctggtgttga    75480
aatgatcagc tggctgtcag gcgtggtcag ttgattaaca ttagcttgga cttaaaaggc    75540
cacagagata ctctagttta agttttttg ttgcctagaa ttgtcattaa ctgagtaatg    75600
actcagagtg aggggaggaa gccattgata tgggctctg gcctaaggct gggtcactcc    75660
tcactatagc tgggaacctg ggaataggcc tcttggctgt aaccttgtgt ctgatttgac    75720
tcactgagtt cactttacct acgcggcctt agcatgtat gccagacaca gacttatcac    75780
aaaataccag ttcaagtgac agggttgaca gaagggactg aggtcacgag aaagccacag    75840
gccatgagta gcaggaaggg agtagccacc tgtgctgacc aaacctacc agtgtgcctg    75900 tcatgcccaa gagcctcttc ccgctctgtc acttatgatg tggtgtttgg gttggtaagt    75960
ttcttaagaa aacctttgca tcccacacac tgttaagaag gcgggcgagt ggtctatgct    76020
tttcattatt tccattaaaa taagtaagg gtttagagc taaaagaac ccctgtaaca    76080 gcttttctg cccactagat aagtcagtga tcagtaaggt aacaatctag ccagcatatt    76140
cctagttttg aaagcttccc caaatccagg tgtttgagaa cactctgctt ttctgcaata    76200
ctgatgtctt tgtggtcgtt ttctgtttct gcagcatgga tcagcaaggc tctttcgttc    76260
```

```
ttccagcaaa ggcttccaag gtacaactca aacaagccat ggttccttga tgacaaacaa    76320
acaacatcaa ggcaaatcca ataatcagta ttaccatggc aaaagagga aacacaagag    76380 ggacgcgccc ctctcagacc tctgtagata gtcagcgctg cgcggtggac tgtcttctct    76440
gtgcaatgat ctcatgctca ggacagttgc gcagggactc ctgggagata ttcaggagcc    76500
tcacactgtt cagacgttga cttagcaact gcgttttttc ccagctcgcc acagaatgga    76560
tcatgaagac tgacaactgc aaaaaaaaca aacaaaaaca aaaaaaaaag caagcaaaaa    76620
agagggaaaa aaaaggctgc ttatttgata agtcatatgc tacaacaggg tcattttaag    76680
atttaaagct tgaatgtaaa ataaatatat ttctcattgg cttttatgcag agttataggg   76740 aatagtattc agtgttggta gggtgataga aacaaaaaac agtatcagag gatgaggtgg    76800
ggaaggaaaa caaggtatc tgataggaag tccagattcc aaaggggaaa gtgatctgtg     76860
catgtttttt ttttaaatat ttttgcatat atttaccatt ttattgtgtg tatatataga    76920
agaccatata ggagattgat atttgtaata gtggatttgt taataatact ttttacataa    76980
cattactgtt taaattgtaa acagattttt tctcaggatt agtttgaaaa ataatctaaa    77040
ttgtcatctt aacatccata tatagggaag tgattagttc tattactcaa tttgtttttc    77100
tcagcattga aatgacttaa tagaacccct tgtgtcctgct gcaaaatttt ttcctctcta   77160
aagaaaaggt ttatggtggc aaatgatgtt tatttttattt tgtaaaaaaa aaaaaatgta   77220
ctatgtactt ttgtgtaaac actgaaaaat ctctggtcat ctccgagaat taacttgcaa   77280 ctgtttttcta tagtgctgtc gtcttgggca atgggcaatt acatgacttt gtgtttgctt   77340
cctttgcagt cttttttttt tccccccatt tcttcctaat aggaaaaaaa aaaaaaaaaa    77400
ggtcacccat gtctggtctc attcctgttg cagtgaaact tcgagttcca cagactttgc    77460
atgctggctt ctctaaccct gtgtgctgcg tgtgcctgtt tctcatctct tattcttttt    77520
aaaattcatg cttaactact gtgggagaat aactgtaaac agctttaatt aaatcatact   77580
tataaaaaac tattttctta tattccactc tatgcttttg gtattgttga tctttacaaa    77640
ttaaatggtc tttgataatg gatctatttt gtattgcctt attaagacca aatacttctt    77700
gtcatcccat tctttatcct cttctttcat ggaattgtta tcgttaatta aaactttttt    77760
aaacattggc ttgtttcaat catactgtaa attttggttg tagtcagctt tgagtgcaat    77820
gagatgtata attctgttat cattaccgtgt gagtttgaa actcagttgg gaatatttaa    77880
tataatagaa tgtaagtgac atttctgaaa atgctttctt tcagggtgaa agctcttatg    77940
tttagcatca atgtgtatgg ctctgttaaa tgcagccatt tctgagacga gattctttta    78000
tatatatata catataaagt actattggct tttaggagtt tcttttatat acatttatga    78060
aatactgaag accaatcaga ccattaatgg acacttagtg taactttta taaagaaaat     78120 aatgctaaag taagaccaaa actgatgtca tcactgaaat taacaatttt caatatgttc   78180
atattttaat tcacaatgga aaatgtgtt ccaaaactgg aaactcatag tactcgtgta    78240
aactgtggaa gatttcaaat gtgatgttat tttgacaatg ttttaaattt tagagtcaca    78300
ttttattctg atcagaattt ttattgagat gttgagcttt tgttttgaa actagtttgt    78360 cataacattg tgcataatca cagtatttat tttctaggac aattgtgaat gtgtagactt    78420
atgtttactg ctaagggaac aattattttat aaaataatat taaatccagt attagctgcc   78480
tatttcagac acttaatact tgcagagatc tatgttacat ttaccacact gaagtttttt    78540
ttgttgtttt ttgtttgttt ttaaagaatc accctcattg ttgaaagtaa atgtactctt    78600
agggtgcgaa tattagtgtt ccaataagca tgtgattata ttaaggtggt ggtagcggga    78660
```

```
agataattct gattccattg ggaatcttag gttttcgtaa atttattggg aaaatagttt   78720
ttcctgtact gctgaagttt cttttttggta aacagtatct ttctaaaaga aaaaagcatg   78780
aaggagaaat tgaggtgtgt atacatttcc tcaaatgacc agcattgtat tcgtgaatac   78840
tgtgtatctt gcagtgaaca gtgtggaagc tgttcatttt tcaatctgaa gtaaaatact   78900
ttcaagaact tttagtttgc ctgctcattt gttttataca tttcatctat ttgactccta   78960
tcttatttct tttttgagtt ttaatacttc ctatattttg tgaatatatc agaaatgtgt   79020
catttatata ttagagtcca ttcatatcca tgaatcataa ccttcctttg ctaatacttg   79080
ttgaatggga ttttacaaat tctccctcac tctggtgaca tttctcaggc agtcatgtat   79140
gtgtacctgg ccattagaaa tattaatatt taaagactgt tttttagagg agctgatggg   79200
ttggtgaggt gtcagcacaa aatcttactg gttatgtttt gatgataaaa gtatatccat   79260 ttttttccctc cagctttaag gtgactgtga aggtgcctgg ttttgaatgt ctttgtttgg   79320
tttggagatg tcgcactcag ttttcaaatc tagcttggat ctgtaggacc tatgttttt   79380 acaagtaatt gccctccagt cttcaacagt tgattctgtt ttattttttat cctgtttttga   79440 gtgtacttta cctttacttg cattttgagc ctcattaata tttaggttat ttgatttggc   79500
tccagatatt cctagatctg cacagggcaa acatgggct ataggggtgag cattttttaat   79560 tgtcttttc tgctggaacc ttatatctct ccatgtgttt tctgctcctt ccctccccca   79620
tgaaatggta agtgtgactt gtgtttgcct gaacctgtgg actagtgttt ggggtttctg   79680
gaaacactag agggtcagaa aagagtaatg accaccgtga cgtgcaggat tctcttgctg   79740
tgacatgttc attgcaaagc cctctccagt gactaggagg tgtagttatt aaggttgatc   79800
tgttagaaat caccattatt aggtattagt ggtagatgtt gctgatactt ttattggtca   79860
tgactacatc tcagttttac tttaatattg atctatagtt tgatcagttc cttgaattct   79920
aatatgttga tttctcagtg tttctgtcac taaccaagaa tgtttctagg cagttggttg   79980
cttcacagtc aaaactaaat ggtaaactat caaaaataca ttcccaattt tgctgtgata   80040
aatattgaaa tgttaaaatt aatgaacaga agaatttatt cttacccatc tattcttgtt   80100
ctcctagttc attaaacttt cagttattgg aaaggcacat tctcaaagta ttttatgagc   80160
aaaatattct ataatgcgt ctaacaaacc taattgaata taaaagttat atttagtagt   80220
tactgttgat agtaattttc atcagggtca tagttcatct agtaaaatat ttagagaatg   80280
atgttaacat tccagcatta aagtgggaac aaagatttat atatgaaatt ccttaaaaga   80340
gttcatcttg ccttggtttc tgaccctcaa gactctagct acctgccatc ttgtcaaaac   80400
atttgtgggt agaataagtg ttaaagatca aattttaata tgcttctcga tatttaacat   80460
agctaagaag ccagattta ctgtagaagt tatttcatg atttgaaaac ttgacctaac   80520
tggaagcctt tttctcagtc atcttgttct aagccatctt gacttcacac ccttagcgac   80580 ttttctttt tttttggtca aagataatga gctaaatata tatagacgtt gaatgttgac   80640
aaaattatta accagaaaaa ttgcttataa aggctgctga tctatttgat acctagaatt   80700
aaatatttga ggacagtttt tagttaataa actgctaatg tttatttac tgtctctcag   80760 gttttttggtt tttttaaaaa aaatgtgttt ggcctttaca ttttctactt aagtgtgtac   80820
tttattgagt ttaaccttgt ctgtagccta gtagcctgaa agaaaggag acagaaccag   80880 agagatggat gtagtgcatt ccctttggtt attacacatt tgtggtagct cctggattta   80940
ctgagagata ttttagctat gtcaataaga acagctaatg atgtggaaat caggtgttct   81000
```

```
cttgtgtatt tcagtgaaca tttttattag tagttgcata tcatctctag ttccacattt    81060
taacttaacg tctttgtggc ttccactg agctacctt cactacacca gcttctgtgt        81120
ggcctggtaa catggaaggt ctctcctaag gacagtctgg acgtattttg ggggaatgtt    81180
atttatctta aagatgccta gaaacaaaac gcatatagta ccagtgagaa actatgaagt    81240
aaacaagttg ctcaggccgg gcatggtggc tcacgcctgt aatcccagca ctttgggagg    81300
ccgaagcggg aggatggctt gaggctggga gtttgagacc ttcatctctt aaaaaaacaa    81360
acaaaaacct gaatggtgag gtgtggtgga attgggtagg ggagggaaag gaggacttgg    81420
aaaagcattc tccaaagcca gcaacttggt gaagttcagt acttgcctct tagaggttag    81480
gccatgcctt tcaaagagag tgaaatgatg ggttatcagc cacattcttg gagttaatat    81540
ttttcttcat ctttcagttt gggttctgtg ctattcatag ttcttcccta agaccatttc    81600
attattacct tttatattta gttgcaattt attataatat gttgttttgt ccctgaactt    81660
aatctcctaa ttttaagatc ctctctgatt tttgcatatt gaaacttaca gaagtcactt    81720
taaaaagtc ttttgaaagt cctacaatcc taaaataaat cacaagcttg tttgttagac     81780
gtgtcaagag tctccagtct ttactactaa aaagcagcac tgccttaaca cacattgtta    81840
tgggtgaaaa gtgagggacg accagtgtag tttctggata taaagtgtga aggactgttg    81900
agttaaacat ttttagtgga atatacatag ataacgtgta tttagaaact ttggtgaagc    81960
cagtatttgt ttttagtaac cttttttatgt atttccttct ttgattagca ttgtcttcag   82020
tgttaagaaa tgtggactcc tgtgaggtgc tggaggtttg aatcatcttg aaaactttcc    82080
aatcttgtct agttaccact gcagagacac taaggaattt accagaaaaa gatatttgat    82140
acaagtgatt taagaaatct caacattcc tgaggccgta tcactgggca accagtgatg     82200
aaaactatga atgaattgca cacctggaag attttttaag ctaatgacag tttcttcaaa    82260
gatgtcaatt atttgccttg gaaatttat aaattgcatt tctatgcaca tcggcctcta    82320
gtgcttacca ctcggtttat tattcataat ctgcaattca ataaaggctt tgtgttttca    82380
tttatcttca aaa                                                        82393

<210> SEQ ID NO 2
<211> LENGTH: 44042
<212> TYPE: DNA
<213> ORGANISM: Homo sapiens

<400> SEQUENCE: 2
ccacgctgcc ctgcgcacgc gcagcgcggc tcaggcggca gcccggtgac accggcccta    60
gcgcgcatgt ctgcacgccg gggtctgcgc gccgcggcgg gccgagggcg gcgtgcgggc    120
cttccagccg ctgcctattc cacccaacgc cggcctagtc agtaatggct caacgccacc    180
gcctctccct ccagcccctc ccagtcgcgt agcttctgac gccgtcctca cccgcccgc     240
ggccgacggg gccccaacgc gcaggcgcgg taaccacggc ggcagtgtct agtgaggatt    300
tgaaatcggt cgcgcgtgcg caccggcgac acggcccggc gaccgaggcc gcgcttcctc    360
ctgccgcccc cgtccccgcc ccctcccccg cccctcattg gagcggacgc ggcggcggcc    420
ccctccttcc cccgcgctgt cgccgccgag agtgtctttt caccgccgcc gccgccgccg    480
ccgcaggagc gccgagccag cggcgcgagc gtgactgagg gctagccgca cgggcggcgg    540
cgcctcccgc gggtccttca gcgctcggc gcctgggccc gccccctcgg ccccgccgcc     600
cgccttctc cgatgcctc tccccgcggc ccgagtggaa cgccgccgcc gcgcggccc       660
ccgcgcccgc cccgcgccgc gtgaagcggg agcccggaga ccgcagccgc ccgctgggac    720
```

-continued

```
gcgccaagcg ccggagccgc ccgccgcggc ctgccggggc ccatcaccgc cgccgccgcc    780
ccacgccgga gcccgacggg agcgcggcta gagcaggagg ccggggctcg gcccgcccgc    840
cgccgccgcc gccgccgccg ccaccggccc aggcccgtcc gtccgtccgt gcgcgcgcgg    900
ccgggcctcg gggcgcggcg ggggcggggc gcgtcgggg cgggcgggcg cgcgggcccc     960 gcggggggcgg cgcgtggatg gatccgcgcg tggcctggat ccagcccgag cagaagggggc   1020 cggccaatgc cctgtggatg cagatctggg agacctcgca gggcgtgggc cgcggcggct   1080
cgggcttcgc gtcctatttc tgcctcaact cgccggcgct ggacacggcg gccgcggcgg   1140
gggcggccgg gcggggcagt ggcggcctgg gccccgcgct gccgccgcg tcgccccgc     1200 cgcccggccc caccgcgccc gccgcgctgc ccccgcgct gctgacggcg ctggggcccg    1260
cggccgaggg cgcgcggcgc ttgcacaagt cgccgtcgct gtcgtcctcg tcgtcgtcct   1320
cctcgtccaa cgcggagtcg ggcaccgaga gccccggctg ctcgtcgtcg tcctccagca   1380
gcgcctcgct gggccggccg ggcggcggcc gcggcggcgc cttcttcaac ttcgccgacg   1440
gcgcgcccag cgcccctggc acagccaacg ggcaccccgg gccgcgcggc cccgcgcccg   1500
ccggctcccc gtcgcagcac cagttccacc cgggtcgccg gaaacgcgag aacaaggcca   1560
gcacctacgg cctcaactac ctgctgtccg gcagccgcgc ggccgctctc agcggagggg   1620
gcggccccgg ggcccaggcg ccgccggccccg gcacccgtg gaaagagccgc gcgtacagcc   1680 cgggcatcca ggggtgagtg cgcggggagg ccgcggggc ggggcgggg cccatggtcc    1740 tggccggcgc ccgcggtgca gacacccgtc ccaggcgccc gggcttttgg aggatggatg   1800
ttgaaggcta aggccaaggc ccgactctgc actgaaagtt ttttttttaa acatcagact   1860
catttatcgt ggagtgactt gcccagatcc tacaagtaac agtccaagaa aaggggctgc   1920
tgggtaggac ctgcaggtat ttgtcttttt tactcttgag attggaacgg gaaatcgact   1980
ctctacccct ccaccccgcc tccgggcaag tgaggaaccc cttgtcaaag tggggcgtag   2040
ataagtgtgg agtttcacgt aagttaagtt gcagaataat ttagcattgc caggaactcg   2100
aatcacgtcg aaggtaaata ttaacctttt taatttcatt ttttaaaaaa atttaactgt   2160
caacttagag gtgattcatt ttttggggggg tgttgtgtcc tttaattttg tgctgcaatt   2220
accataagca tcgcctatgg tttataaaca ttggcttaat tcaaagaaaa aaccagattt   2280
gtcatatatg tctattcttt ggaaggtgcc attttttattt taaatatttc tacatccgcc   2340
tagagggaat tagaggctct acttaaattt agtgcactta cagacggcaa ggaatgaaac   2400
gaaaggtggt gtgtgtttcg gggttggaat tgtcccaggt gaggctgttc aggtgtgatg   2460
ctgttgacgc agccccttg ccatttggg cttttctgag cgtctggaag caatttatgt     2520
gtaggttgta tgtcagtatt ttaagactta aatgataatt tttccttgca caattttcc    2580 ccccaattta aaaaacaatt aaggattgc tggggtatga gggttgttgc atgcagtaga    2640
gtcctacaaa taaccacaat tgctaggtgt tgggagttct tatagtaaac ttttgcttgt    2700
aactcttttt ctcatttgaa gtatgttggg aaacacgagt tgatacttct ttaaagcgtg   2760
tgatacactg taatagctgc atgttctgta acttatttca cctggcttgg gctacaagcg   2820
ataccttcta aatttcccga agtgtaaaca tgcagtgcag acgccggcag gagcgcagac   2880
tcctcttctc tccctccagt tcttacctgt agaactttct gagagcaggt ggttgggagc   2940
agtttcttct tgatgaatag caatatatac ctaagggctc gcttggggag gacctttagg   3000
tttccagcct gttatgtaac tggaatggac tccgtttctc ttagcactag aaaaaacagg   3060
```

```
aagacacgtg gtctctgcca gtcttgggtt gtacctctgc tcttagaaag tggtagcgca    3120
tcaggtccca tgcacctcac ttgggctccc cgagctgttt cctccaggta actctagtca    3180
ggctcagtag gtggtgttgc ttttgttagt gaatgagccc actaggatca ggtgctgtgc    3240
taggatctgg ggatctgggg cagggacggc atgggagaca cagtctcatg atcttgaccc    3300
accctgaaac ctgcctgcaa gtgcccctg cctagagcac aagagtaccc tgctcagttg     3360
tgcaggtccc ctctcacgct cttcgtcacc cacgtccagt ctctcatcac atgctgttcg    3420
tttggccctt ttaatctctc cacacctcat cctccctcat gcaggctctt gttacttctg    3480
tggagattgc tcaagcagcc ggaggtgcct ttgatgcact ctggtcctgc ttgagtcctt    3540
tcccatcaca ggtaatgggg caatcttctc tgccagcagg tctggtcaga ttccccttca    3600
ccctgtgatg tcacctcccc catctccaat cccccacatt aaagactaaa gcctaaaact    3660
cagcaacacc tccagggctc tgctgctcag atgcccctag gtcctggctc ctggcccac    3720 cccttgccaa cccgttagaa cctagctgta aggcagtatg gtgtagggca tgagagggct    3780
ctgaagccca ccaggaggtc tggtttgata ctgcagtcat gctcttggaa cttcctttt    3840 cccctttgct ggagacctct ccttgcctgt ctctgggtgg tgtgtaccat gcctccagta    3900
tggccttggg tgcatccgct tcctgccgtc tctgcccaaa ggggcctgtg aggaccacct    3960
gctctgtgcc cagaagggca cggtgacctc tgcttgggct gctattccag ctactctttc    4020
agaagcaaac ctaagctgtg gtagagttgg gcctgtggct agaggaggta aggtccccc     4080 tgtgatcatt tccacatggc ctgttggtcc tatataaact aaccttttttg tatcaataaa   4140 tagttctgtc tagaacttgc ttctggccat cagcttaccc agagtgttga gaaaggccac    4200 caaaagtct ttcggttgtg gcttagctaa ggaaataact gagttttaaa ggctcacctg     4260
ggctggccaa tagtaaagga ccttgttgct gagaagctgc ttggggttgt gatatagtcc    4320
caggacatgc acttctgaaa atgcagtgtg tattcctcat gggaggatga gcctgctgtg    4380
gagcattggc tgaacccagt tgggtctttg cctggtagcc catgtggcaa ccctcactgt    4440
ttgtcctttt ctggggagga gttttctgcc cttggacact ttgcctggtg gcttggcctt    4500
gtgagactgc cagtctgcct tctgcttcaa gtaggatgaa gaaaaagcag gtgaaagagg    4560
acagggattg gtgcaagaac cttcagagga gaggaggtga aatgcttctt ttggctctgg    4620
ttcttgaatc attgtttgat tgaaatctca agcctttgtt ttgggagtgg tgtgcttagc    4680
gtgagctgtg ctatctacct gggcttctga cctagagatg ttgggcaggt gtttggacag    4740
gccctgggcc ctttgcatcc cagcctctgg ctgctgtcac ttgcaagtgc tctcatcccc    4800
tgacccagca gggctttggg ctgttgttac tttgtcatgg tcgttctagc agctttggaa    4860
acctcttcag gttaagagtc ttgcataagt gagagtggga gcatggccct cagatatttg    4920
gccacatcct tactggtgtg ttacagagac ccaggaagaa tgtagttgaa cgaggacaca    4980
tgcaggtgtc ccgggccctg aacagcttct attcagagtt tggcctttcg aaggctgtgc    5040
catctcaggt gtgcctgcag tgtgcagcag gtgtatgcag cttcctcttt gcaggtttct    5100
tggtatttaa tctcatcctt taatatcttc tattaactca aggaaattc tgttcttagt     5160 ttgaagtctg agagagaccg acgactgtcg gcataggaca tggtcagcca tgccccgcaa    5220
ggcgtctggt gagagtcgtt tccaacttgg tgcatgtttt tctcaattct ttcttgcgaa    5280
ggagtcacag cttggaggcg caaccaggat ccccctctc cctctagcct gacctcactg     5340
acataaagta gagcaggtgt gacctgtccg gaacatcctt gtgatgctca gcagggcctg    5400
ctgcagagca cggaggcat cactctaggg gccttccct cccatacttt cctgtgagtg      5460
```

```
tccaggatgc atgagagagg ttgttgtgag acctgcctta aagggtggcg gtggcacgtg    5520
tggaccttgc tttctgagtt tcactctccg agtcccagag gtataagctt gtgaagagaa    5580
gcgtgtatgt atgatcacac taagcagata cttgctcctg cactgttgga ggaggaagag    5640
gagttaattt catcaattaa ctcttccaac actccttcca tttagtaata gcatcacttg    5700
ttcctgtctt tgttccatg gccaagctcc acaaggtgaa attgaaaatc gagtgcaaga    5760
cactggctgt gctggagttg aggaaagttt tgctggagac ctgcttgcac catatgtctg    5820
gtcactgata gatgaggact ggccaggtca ggacagctga cacttggaga aggggctgcc    5880
caggagggca tgacagactc tggaaaagga gggtcggagt attaaactgg ctgggaatga    5940
gaggcctcca atcttttcgc aggaaaaaaa aaaaaggct taatgctcgt gctgtggaag    6000
tcagaatgga gcaaagtggg ttctgtctgt cttgctgctg tgagcgtgtg atggaacaac    6060
agtgtcattt gcttttctc agaaatattt aatgcatgtt tgtgacataa ttttcaaag    6120 taattttaag taaatatttt aaagtaaaaa gttctaagat ttgtgtctca aggtaaagtc    6180
tcaaacgttc tttggtcact atttaatatg agattttgtc ctcatttaa atggattcat    6240 gtaagcgtcc tgtggaagaa gagttaatag ttatccttgg aaaataagaa ctttttatgc    6300
ctcagttagg tcatatggtt taggatctga ttttgtagtt gtggagtaaa ggttaagaaa    6360
aaaaaacagc aaaccttgat attcaaattc agaaacttga tttttgagga tgcaaccaga    6420
atttggacta aaggtacaga ggggtggcag agtcagacca cccagacttg cagaagattg    6480
aagaagccgc agtgctgcca tgaagaggcc ctttctagga ggtgtggctg gcttgtcagt    6540
gctttgtctt ctctgcagtg aattggatgg caagcctcgc cctcttcgaa agctgccact    6600
ctgaacctgc cttgagaagc acctcaggga gggcaggcag gtggtctcag tcagcgctga    6660
caggtgtcca agttacctga cctgttggga acatgtgcct gagtgaggtg gccaggatgc    6720
cttttctccc aacactgggg atgcacactc gtcagcatcc tattttgag atttctatgt    6780 tgtggtagtt ctctgttgct gtgtagcaaa ttaacataaa ctcagaggct tagaagaaca    6840
ctcacttatg gtcttaagga ttttgtgtgt cagatcaggg atggcggggc tgggttctct    6900
gcttaggctt ttgcaaggct gaagtcaagg tgttggccag ctgtgttctc agctggcact    6960
cagggtcctc ttaccagcac attcctgtta ttgtcagaat tcagttcctt gcaggatgga    7020
agtccttgat tgcttgctag ctgccagcag gggaattggg tagggcgctg tcagcttctt    7080
aaggccacct gcattccatc tgcaaagcaa ggtactttga atttctctga tgttttccgc    7140
cagctggagg aagcccctg tttctatggg cttgtgttat tgagtcaggc tcctgcagat    7200
aacctgccta cctgaaggtc atgtagtagt acaacatgat catggtgtga taacctcatc    7260
agagccacag gttccaagga gtagggtgta ggaccttgag gggaggaggt tcttctgtgg    7320
gtagacttcc cctggcatag aatccgttga tgagcaggtt gtggttcttc ttgtccaaca    7380 cttttccccct gactgactc cagcccatcg caatgactct tgcagattgc cagttccgtc    7440
ctctggcttg gtggttacta ctgaactcag gcagccacta taaccaggag aacctttctg    7500
tgctgcactc agatgaacat tctttaaaat atgtcattta agaaaagttt gcaggactac    7560
tcgggaggca gaggcaggag aatcctttga actggagagt tggaggttgc agtgagccga    7620
gatcgcacca cagcactcta gcctggtgac agagcgagac tctgtctcaa aataaataaa    7680
taaataaata aataaataaa taaataaata aataaaagtt tgcaggaaag ccgtgtgaat    7740
atatgaaaat acagtgattg aaaagtcctg ttcacgaggt gtcctgcatt ggctagttta    7800
```

```
ggaaaggggt ctttcctatg caggtggggg ttgatgactt acccaagagt cacctctgga    7860
acccagttct cttaagttga tagcagtcta tctttgcttt gcagaagatg tggggaacac    7920
ttgtcctgca agcccaggtt cgtagcaatg ttggcttccc cagaaccttg gcttcagagc    7980
actgtgcctc ctttaggagg cacaagaaaa ctcccacacg gttcttccct ctgtcccttc    8040
ctgagccccc tgagtgtttg gctcttgtgg agttgctgct attactaagt tgatcccact    8100
gccctcctga gtctcctcag ggaaggaggg gctgtattgt agcccgcatt cttagtgcca    8160
agcacacggt agccactaag taagtatctc ccaagaaaga gagcaggag gaggatctgc     8220
caactcagga gagcaggtgg gggatggcaa gtcttcggag tattcataaa ccaaatgcta    8280
agggaaactt ttgttgtttg tcttagaatt ttaaaaaata aagtctgttg cagtttatct    8340
gctttccttc ctggagagtg gctaaactag tgttctgttt tacaatgtag aatgcaaaag    8400
cagaaaacat tcaagaaaat tctatactgt atttgaaaaa catcaccatt tagttttaac    8460
tgctctttgt ttcttattat aaaaattaat acctaactat gaaaagttag aaagcctgga    8520
gaagtatgga ggtgagttgt ccaccattgg gccactagag agtgccctat gagcctgtcc    8580
ctggtgtcct ggactctggt ggtgtgcact gcatttgctg gcagtgagcc aggggtggg    8640
ccacatctgg gcccgggcgg ggtggatctc tgcagaagtt tatccatctc ttggctgaca   8700
gggtgggcga gatgggagca gctctgaggg tccctgttgg cagagaatgt ctttgattat    8760
caacaacatg cctttttgtt gtgggcttgt gatccttttc tttcctaaat cagctgccgt    8820
gcataaccag ttaggctctc ctgtggcttc agattggagt tagtttccca agtgctagga    8880
tgtgggtgtt aggtgatttc tgtctttccg tttgaaagag atttcagatc attgtaacat    8940
ttctggaatc ctgtcgatct gaaggaatgg ctaggatgta gtagtttaag ggaaatgaaa    9000
agtcgaatgt attttgatgt ttctgcatca gacctgctcg gtggagtcca tttctcagct    9060
tcgggagcca cgtgcttggc tcttgagagc ctagctccat cagcccatgt cacacactca    9120
caggtctggc tttagctggt ttcgccatgg tttctaactt gagcctcagt ttccccccct    9180
gtgaagcaga gcctgtggca cccacctcag agagtacatg aaagacttgg aagcactctg    9240
tgagttgtca tgcgagagat taaaaaggcc accgctgccc ttttctcctc tctttaagga    9300
aattgaaacc aaaaattaag tccttcttgc cagctggaca ggaaaagcct ttttcttggt    9360
ttttgaaaat acaacttcca ctttcagacc aaagtgaaaa ctgctaaaga ctgaatattc    9420
tgagtcttgg gagtgggggg ctagagggt gttgtgaatt gaaagatacc tttctatttt    9480
taaaacattt taacaatgcc ttaatgatga ataatgtctg ttctagtttt gcatttgtta    9540
gttttttttt ttttttttt ttaactgttc tgaaggtaca tcagcactgt tctacagctt    9600
taaataagaa tctcatctcc ccagaggcaa gggtactctt gatgtatttg ctcagggctg    9660
tatgtgctgc tccgtgtaac tcatttaaag ttggttaagg ttttttttatt tcttgcacat   9720
agtagaagga gtggatgaag tgttttctga actctttgca gcttctaaca tagtgttctg    9780
tgtatagtga aggaaaacaa aattaagggc cagggaacat taagtaggca actagaacag    9840
cactgtccag tagaacttcc tgtggagatg gaataattct atttttgcac taatacagta    9900
gccactggcc atatgtgact tttgagcact tgaaatgtga caaatgcaac tgaggagctg    9960
aatttttaatt ttatttactt ttaattaaaa tttaaatggc catgtattta gacagctctg   10020
aactgcagta actttaggct ctatttgaaa cagtgtttga ttcagtaact gttgctgaaa   10080
taaattgaaa ctcatacaac agtaaaagct gtgttactca gcaagttatc actgtgaaag   10140
ctctagaaat tgtttgagtt tccaatgcaa atcctttca aaaagccgct gttttaatag    10200
```

```
cacatgaagc ataaaatagg ttcatagcag agcgcagcac agagcaacat ggagcaactg   10260
ttatgacctg gagtgtctcc agtccagcat gcaggtgata ggtctcagca tttttgcacg   10320
caggttaatg atggtgcaga cggtcacttc cttctctcaa cagtcttcct ggtcacgagc   10380
accattgtgg ctcgtgtgtg gggctctttt ggcttagctc tctgcacgag tttgctcctt   10440
tagttcccag agctgaccct tgaaatgagt gatattactc ctgttttgta gacagaaaac   10500
tgaagccttg acagtctgac gtgacctggc aagaggtgct gcagttggaa atgtgaattc   10560
acggctgaca tctgggcact ttactcctaa cagtgttcag tgaacaagac gtcgctaaca   10620
tgcgggggat ggaacctagc aactcattct acaaacatgg ttcaaatatg ttggtgcagg   10680
gccttttgct ttgttttcct aaagagatta gattcagatg tggtggggtg ctttgacagc   10740
caccgcagga caaagttgat agctgtgggg ttgcggagtg ttaggatttt catagggaag   10800
ccagtcctgc gcagtagtac gctcaggttc gtgctttctt gaggtgttcc agaactggcc   10860
tggagggagg ctgcagtgtg gaagcgggat ttctgtcacc tggagtattc ttagaagttg   10920
cattctatga agagtggagc atctgatgag ctgtttactc gctgtttcat ctgacggcag   10980
ttgaaagaca aggcaggact ggcagcgcag ctgcctcagt cagcactgct gcactggggg   11040
cttgacctgc agtctcgcaa tcctggacta taactcattt tgaagagaga aaaattaagc   11100
attaagtgat tcaagcgtct tgcccaaggc gctactagaa aataaaggca ctggtgccca   11160
gatgcaggtc tgcatggtat gcaagcctgg gcttcttccc acctccccca cagagagggc   11220
actggtatgt tggagtgaag agccacgcaa gacctctgtg aatgggcaga gatgggccag   11280
tgacgcaaca cagtaaagtg tattttggtt ataggcatcg tctctaaact tatgtaaaac   11340
attattaaaa aatggaagga caacgatgaa atgatggcca aaaatataga aaaggatacc   11400
ttgcatgtcc tgtgaaatgc aaaggaattc taaagtgtca ttatgagtta cctcatggaa   11460
gaaagcaaaa ggtgaatcta tctagagttt gtggttctga ctcacaagag actgatgttc   11520
atgctgaagg acgagtgtga caggtggaag gatagagcac cgagaccaca ctctaaaggg   11580
taggaatcta tgggaactat tcagggagat gaaagcatgg aatgaactga agcttgcaga   11640
ctcgttgagt aaaaagcgcg ttttaggatt ggttttagaa taaaataaca aggcctgtgg   11700
ttggggaaga tgacttgctg ttcacagagc ctcccttaat aggtggggac ctcagctttt   11760
cctctgctgc catcaggtga gtggtgtaca gtcctagcca cagtagtaat caccactggc   11820
ctgactgagc cctcacccct tatacagtgt ctcctgccac cctcctggga gaggctgttc   11880
tcggcacagc tggcctgggg tcacacagct ggtaggtgta aagcaggcat ggagtccag    11940 gtagtctcac tccgtagcct gtctcttag ccactggaaa tgtagagcaa agcgagaatt    12000
gtccaaagag ataagctaat aaagaggaaa acaggctggg tgcaatggct cacgcctgta   12060
atcccagcac tttgggaggc caaggagggc ggatcacaag ttcaggagat cgagaccatc   12120
ctggctaaca cagtaaaacc ccatctctac taaaaataca aaaaattatc cgggcgtgat   12180
ggcacgcacc tgtagtccca gctacttggg aggctgaggc aggagaatct cttgaatcca   12240
ggaggcggag gttgcagtga gccgagatca cactactgca ctccagcctg cgtgacagag   12300
cgagactccg tctcaaaaaa agaaaaaaaa agaaaacaa ttatgctgag ttccagaaa    12360 gtgatgtctg tcttctcagg agagatgccg atgctgtctg agggcctgcc cagtctccac   12420
atgattcaga gactccagag atggacagct agtgccctga ttttcccaag aggattctga   12480
gggtgacttc tgtcaaccaa acaggaggac ctggtgctgt catcaccagt tgtagagagg   12540
```

```
ctgcggacca cctgctgtgt gtgccatctt acactgccat ttgctgattg cttcaaagct    12600
agaggttgtt tctaagagtg cttcgtgcta actaactaaa acataatgac attgtttttg    12660
taaaactgat ccgtggtttg ttttttaaag cagaaagctc taaagtcact cagtcccacc    12720
acccagaagc acaagcaggt ggctgccact gtaggacctc tctctctagg ctcgtgtaga    12780
tggacacatg gattggtcag tagaaatact tttattaaaa gtcttatctt tacataaatt    12840
tgccaaatta ttaattttgc ttgaaaggga aaggtgtcca acttcagttg gaaatactag    12900
tttctaagag atactgctga gactaagagc ataaaacatg atgaaaacct taagtggcta    12960
agtgcagcaa cgtcagagta aaagctttga tgaagtcttg gtttgcttgg gctgtgtagg    13020
ttggaggctc agcctttgtt tctccctcct ctggtgccca gtggtggtgt ttgtgtccgt    13080
gaattttcaa cctctgtagt ttgtttgtag ttatgaccac tgttgcaccg aacccttacc    13140
gagggccagg ccctgtgcta agcacttgcc agtgtggatt tattaagtct tcatgacagc    13200
accatgtagg gggagctgcg tccctgtgtt gtacttggga cgcgatctga cctcaggcac    13260
ttcaggctcc tgaagggtct gcagtctcgt ctctgcctgg gaaaccacga tttgcagcat    13320
attccacaga cctcatgctc atcatcagga ggcttcccgg gactgctgcc tgagatttct    13380
aagttcctaa tgtggttcat gcttctggtg agtttctttg aggcgacgcc ccctgcgttg    13440
cctctggtca gctcagtcct gtggtcctgc agggcatcct acagtgtcct ctgtctgtga    13500
cttgtgccgt gccaccttga cctggcatcc actgtcctct accgcgtttg cagataggag    13560
ccactgttgg tgccttttg tcgtgtgtgt tgaatggtca gggtcccaaa tagctgattg    13620
ggagcactct ccttgaatct gccatgtgcc tgggtctcag gtgactgggc ccctccttgc    13680
ttcagaaccc acgtgcgttg cctgtcctct ctggcttgga gggttgtgtg gaatcagagg    13740
tgagacccag tccccaggga tgggcagttg cctttgattg cccagctgtc ctcagcgccc    13800
tccctcctgc gcccaactgc tgtctcagtt gcttgcttga ggatccggat atagactgag    13860
gtcggcctta gcgtggcggg gggttttctc ttgagtcttg gatactttgt taccggtccc    13920
atcttcctgt gggtgggagt gtctgtcttg cttggcccag cctcccagag accttagctc    13980
tcttagtaca tgggctctgc ctaccttgat ccccagctca ccaccctagt gcagttgctt    14040
cttcgctctt gttccactcc ttgtcgccat ccaccctgtg ctttctcgat gtgtccttac    14100
tcggtgtttc tgtggagcag ggcatcctgg gcttcctttc tgatccctgg ctcctgtgat    14160
cttccgtgct gggctccctc ttcccttccc ttttccactg tgttgccctc acacagctgg    14220
catgccatgg atgtcgctca cccaagccct tcctaatgtt gctcaccaaa accctctccca   14280 ccttgcccct gggaccttct cccttccag gctgcatgca ggccgagggc ctggcgtctc    14340
agcaggaggc agtggggcct ttgctggcac ctgggctctg catcctgacc ttctgagggc    14400
ttggtccttt aggtccatct tgaatctcct ccaggcttcg gactctctgc tctgtagctg    14460
gcccatggag acgggtacac tcaggcctgg tcttagactc cgctgcttgg gctgtgctgg    14520
tgcctttggt gccctcttag tccatcccac ctgggggccc tgtcctgctg tccattgtgc    14580
cagagtgctg tccccttgtc tttccgtaac tggctgctcg ttacctttcc catctcagcc    14640
tcagtaccag ccacttggta tcagggaggc tctccctgac caacctaaag ttcacagccg    14700
tggttgccag tttaaatttc tgcatagcaa cttttttggtt tattttggct acttatcttc    14760
cccatcatgc cccctgtccc tcccatataa actcagtgag agtaggggcc acatctcatc    14820
atcctgccca cagctctgct gtctgtatca gccagggtat gctgtgcaga ggctcacggt    14880
aaatagctgc agaccacgaa tcccatctgc ttgctgtgct ttaatattgg cttacatctt    14940
```

```
tggatccagt gagttctttt ctctgtctcc ctctctctca ctcgctcata cttactttgt   15000
gtaattggtg atttccagcc ttttgtatag tcctttctcg aatagttgtt ttctgtcatc   15060
ttggcggggg cctcaagggg ttgactgtac ggagggcagg ggctgcagag ctgcagctgc   15120
tgcctggggt ctcacggcgc ccgtgaggtg taggcaggtg cttttgcctct gagctgtctg  15180 tagaatgggg tgacggcggt ttcatcagac tcagtgaagc atgtcataca gtgagtgtct   15240
ggtcacagca ggaagatggt gaatgtcagc taatgagtat tcatcaccaa tgaatagtaa   15300
cagttttttt tactaaggct atgtaatgta gcctcagaat tccactcagc acagcccct   15360 ggcagcggtg cctctgagag ctggcatgat ggagagagcc tggttggcct tactggtgtg   15420
gttggggcac ttgggagaac gccttcctca caaagctcat ctggagggtt ttcggacttg   15480
taggatagct ttttcagggg ccttgccttt ggcaggcag ggacgtgtac tgctgcagtc     15540
tagggtatgg gataactttc taaaccagac ccagaacttc atggccgcag gggccttta    15600 gccatgcggg gctaggagct gacacagcgt cagcagcatg agggcctgtg gtgctgggcg   15660
gcagagccca gagggagccc ctgctggtgt gactttagtg taaaggctgg gggataccag   15720
attcttacag aagacttaag acgggcacag tgatgtctgc tctttgaccc ttgcagtatg   15780
aattagtaaa actgaaatta ttacatttcc tttattagga ttataaaagc aatgatgact   15840
tattgaagaa aatttggaaa atacagaaac tacctataat ttttccattg ttaacatttg   15900
agcatatttc ttgtcacttt taatggtgct ttaaatatgt agcaaatgta tcatttcgta   15960
ttttaaaaaa atgctaggta agcatttcct cctgtcctta aaaagctctt ttaaacaact   16020
ttaaaatatt gtatagatag atgtacacaa ttttctgaat aattggagtt atatttacat   16080
cttttcactc tttaggaaag gactggcctg tttctgtgtt gggttccttc ctgagtgtgg   16140
cttccagctc agtggctcag acttcaagat gaagacttca gtcctggttg tgtatggtct   16200
tgggccagtt accatatgtc taatgaatac ttagttttgt catctacaaa atgaaaatag   16260
taatatttgc ctcaaagact attatttggg aggatctagt gcaaatgtta gtaatgtgga   16320
tattgtgtag tgtcccagga tattaatgtt tttagcctct tggctttat tctgtattgt    16380 tgccccaaaa gatgatgctc acttatcttt catccagtgt aaggatatct ggaaagacaa   16440
cagaaagtat agctgttttc atttcaaaag tgatcagctg cttgagctag caagcaaggc   16500
ttgcactagc ttccaggcgc agtcacgcag tttcacagca ggcgcggttc cctcggagca   16560
cccagagctg ccctgcggta gtcagcagtt gtgctgtggc tgcactgcca ggctgggtgg   16620
caggtggatc ggagccagca gatgtggctc aggaagtgcc ttcttggcct ctccttaatc   16680
tctttcagag tctgtgggcc cttgattgca ctgtgggttg tttcagactc cagtattagg   16740
agactgaacc ccttggtggt ttttttgtgt gtgtgtgctg agctgggttg aggacatgtt   16800
aagcaggtgg ggtgcctccc ctgggtttgc tccgggtggt acctgtggtg tggggtggtt   16860
ctgagtagtt ctgccccac tgctggagta tctgcccact cagttgtga gatgcaggg      16920 cttcatcctg gtctggtgcc tcatttttctt ctttagcagt gggcttagaa ccaatgcaga   16980
ttcccaagtt aagtattttt tctgtagctt aattattaca ggcttctggt acctaagccc   17040
tttcttactt tctgttctga ggggaagaga agataatgtt gtttctccgc ccccccccgg    17100
agtggcccca ggaccttgca tggcatttgc agcatttgca gcgtgcttgg gtttgcttta   17160
ctagggtgaa agtgttgcac cccccagcac ccacaaaggc acctctgctc acactccggt   17220
gaggttctga ctggccctgg gacatcacct gctccaggat cctatgtggc tcatcccagg   17280
```

```
agagatgtgg gagggaaggg gaaaaaaggc ttacatttgc tgagtggaat tcatgtagat    17340
ctgagttccg cattgattcc taagctgcag agcccttatg ccttggctgt tttgtgaatg    17400
ttagtcggtc ttaacctttt tcaccgagtt agcattggct gtctcaggag gctcacagct    17460
cctgctcctc ctccagggga gtgcgccctc ctcctctgtc ggtagctgtc aggtgcccct    17520
ttcctctgca gcagactgtc ctgggtcctt gcctggcctt ccccttacac gtgagcctgc    17580
agcttcattc acagccctg tgtagaaaga taggcacatc gataggtccc tccctgccca    17640
gagtgggcgg aactgaggca ggcactaaaa gcagctgact ggcagcccta gaaacatgaa    17700
gggtttcatt tatagtttca gtcctttttcc ttctttcgag ccttaattta aaaaaaaaaa    17760
aaaaaaagc cttgaagtcc tgcttctgag ttttctaatt tgtgcaggta ttagttgcct    17820
tgtaacataa tcaaaaataa ataaaaatga tttataatta gcttattaac tgtatcagta    17880
aatggatact ttaaagagga tcattgatcc ctcaaaatag aagcaatgca gtcattccct    17940
cattatgctt tacttgtgat ttgcttacaa cccactcttc ctagttaaag ttaaatatta    18000
atccagaccc tatcagtgcg atgtagtagt gtctgaatca gttgttgttt tggtgtaatc    18060
gtatcaaagc atgttataaa atctacaaaa ttgcagggtt aactccaaat attttcacta    18120
aggtattgtt tttttgggca aaaatgcata gtgaacattg tggagctgaa gtgagggaac    18180
ttcgatttct gagaaaccac tagttttaag ggttttgaag gaagagttgg aggaggagag    18240
gaagagaata aattcacagt taatgagttt ccagtatttt ctgtcgcatt ttacgttgta    18300
atggaaaaga ctgggaactg aactcacatg cagtttgtca aatcactttt tccctagaat    18360
tcaggattga tgagattaac ggggtgttaa aggtaaactg aggcacataa ttaacatgga    18420
cagaactgta gacctgagtg ttgagagttg ggaaatttca gtgagttggg aagactggaa    18480
gcacctgttc ttcagagtgc aggtcctcat attcagtggg tttaaggtgc tgaaactttt    18540
tttttttttt tgagatgggg tcttgcactg ttgcccagac tagagtgcag tggtgtaatc    18600
accactcact gtagcttcga atcctgggct gtcagcctat cctcccacat cagcctcctg    18660
actagctgga ctgcaggcct gggccaaaac tcctggcttg aaacttcttg taaccagatt    18720
ggaggaggag ggcatgttca ttttcgtgac gtttcctttc ccttaaacat ccagtgaaat    18780
ctgacctttg accatcactt tgcttaaaag aagctactgg atttaaagtc taggagaatg    18840
tcctagacaa gcccatagta tgttcctgta tgttccccac ccagagacct gcgttatgaa    18900
gtgtttggtg tgcttcttcc agccccactg ttctttctaa agtgttttat tttacatacg    18960
ctgtcctggc ttctgggcta tgaccttgc cttttttgcc ctttagttcc tttgcccttt    19020
acctactgca gtgcagctgc ctgtccttgg gttgactaca aagaagtcac ctttgaacaa    19080
cttagaaatt gtgacttttg gggaaggcag ggcagagcct tggggctgag atgggggagg    19140
agccagctct gccctgggag agatacaaag cgcctgcctg ggtgaggcag tgcacgggtg    19200
ggcttgcttc acctctttgg ccccagcttc aaaaccagcc agtcctccct ggctttggct    19260
ttaattcaca tttacaagct tgaaaaccag ttaatcccat tagctcagct tctaaagctg    19320
aaaatcgtcc cctaaatggg tcacctgttg tcatcaatag ctttattagc tatggaataa    19380
tatagttttg ttctctaact gtaggatcct tcttttgctc ttaaaatagc tcagtaagtt    19440
gggtctcata aatacataca gcaagcatat accagatact aaaatacaaa acattgctg    19500
atcttgcttt tcagtactaa aagcagaaaa tcgggaattt actaaattga gaagtcagtc    19560
attacctttc gatgggtttg gactcttgca aggcagtgat tgtaaacgag agtgatcttt    19620
tgttgttttt caatgaactt tattctctaa tttttagtaa agcacactag gaaataatgc    19680
```

```
ttcagaattc tgttttcgag tagtttcctg actaaaataa aaattcacta aaaaaaacct  19740
ctgctgtcac catttccttt tttcttaaga taactaggaa atgaatcatt aagagtttgc  19800
tccgtggcaa tggatcggga agctgaccct gctctctgtg gggctggagc cttgctaatg  19860
tcccaggatt tcacttcaca gagacaagca tcagaggctt gcttcattta tagatcctac  19920
ttcttttcta caccacagcc aactcaaaat ggtgacagaa tctaagacga ggctagaagt  19980
caccacggag cagttggaag ctctgcttcc ggttctgggg gcagtgttcc tggcgttgtg  20040
tcctttggcc ccacctcagt ttgtccgttt agctcctcag ctgagaatga gatgtgtatc  20100
atataggagt ttcctgggcc actcacagcc ccaagctgga gagtgccagc ctaatgtgtc  20160
aggagtaggg ggtgaggcca gagggctgtg tgccaactcc tccctaagaa gcctcctggg  20220
aaagccctcc caggcacttc ccaggtctca ctggccgcct gaggctgcag gggaggatgg  20280
tcaggccgcc tcttggctgg cactgcttcc cggcgtgccg ccagcctttc tcatggggag  20340
gggaatgatg gcatgcctgg ggggcagcag ggccccaggg ctgcctaggg ctctcactgt  20400
gtcctcctgg ttctgagatg ccacctttgt gatccactgt agagggattt attctattat  20460
gatcaatgca tagaaatttc ttcgatttgg agactgaaca ctagtgagca gaactgaaat  20520
tgagctttaa aagatattga tgacgggtct gtggataggg actttagtg tggtttttat  20580
gcagacgtcc tgccagctgt aaattccctg gaggtttggt atgtgagaac ataagactaa  20640
acttatttct attttgttga ggagaaatga ttaaaacttt tcattgatgt acttctgtgg  20700
cagacttttt ggagaattga accagcgggc atattcagta tttgaagtca tagatgagta  20760
aaggaggtat gttgtagttt cgctggcgg cgtggcctgt ggtcggcagg cttatctgt  20820
gaaggtatgt gcacagcttc ctaaggcagt gaaaagtcct ggcagtgtta gtattgaatg  20880
agataatcca aaaaatgtaa aaatgtttac atttttaaag ggatagttgg cgatttaaat  20940
ggtttctgct aacaaatcaa attattcatt gcagaggtaa aatattttca gaatgttaat  21000
tttagatgtc gtagagagtg tacatcagca atgacaaggt cagcaaaata tcttagcaaa  21060
acttgattga ttgattccat gcacaggcaa gcgctgttct gggcaccgga gacggagcag  21120
tgcgctgttg cgtccatcca cagatggcct ccagagtcat gcggttgcag ggaggccgaa  21180
gggccaggga ggccgctggg tgggcacggc tgggcggtgc cctcacgtgg gttttgttgg  21240
gctactctta ctgtgcactt tttctcagtt tggtcagtgt tccgccttgc tgcctggccc  21300
ccaaccctcg ccctctgagg gcctcacaaa gagccaagca gaaggcaggc tgggggcttt  21360
tcaggccagc ccagaggatg taatgatgat ggttggcact gtcccacggc cgccaccagt  21420
ctcacactgc ctcgtgggca gtcctggagt cgtgcggcac cttgctggtc cctgctctcc  21480
ttgaagaagg gccagtgggg cacttcgcca gagccttctt gtctgactcc gtcatccaag  21540
aggcatggat ggccgggccc ccggcagttt ccattctatt ctgagaaggc aaaacaaaat  21600
tattcctgtc tcttattatc taatatttgt tacagcagtt gctcacttt aggtgcattt  21660
tattacagat ttcagacagg tgtggttatt agtgcagctt actgtttgga cacaatgcca  21720
aggtcaggag gacagtgttc ccctgagcac cacttctgct aggagcatgg gcaggccatg  21780
cctcgccatt aatctctcct gatttagggg aggaatacca ggccaccccc tcttctccct  21840
gtgcaaggga acagacattt gacaaaaacg gatgccatgt tacgctgatt ttgtgtgtct  21900
aaggcagact gcagcaggtg ttatctccgt gctcttcctt tcctggagtg ttgagcatct  21960
cttgatagta ggggatgccc ctgagggtgg tgaatgtggc tgcacaggtc ctgaaagcta  22020
```

```
tttgatgttg ccgttacttc aggtagaact taaagttgac agtacattct actctgcagg   22080
tggaaatgtg gagtgccatt ttgacaaatt ggaatgccct gtttacaata tgctttaatg   22140
agttaaatct gggggatgtg gatagaattt tagtatccta gctttggcat tcttccatga   22200
ctttgggcca attatttaat aattccaagc ctgcatcttt gttagaatct ctaaatttct   22260
ctactcctgt tattatcctc agaacaggac tgtgaggtgc agtaggccac atggtgtagt   22320
ggtttaggtg gacagacttg ccagtgctgt tctcatggat agcctaggac tgtccctagc   22380
tctctgcagt gacagtgata gtgactggtg aaggtgaagg gatccaccca gacgttcttc   22440
ctgatggaga gaggctggcc tgtggctctt ccctggggtg gatgttaacc tgctaacgtg   22500
acatatctag tcctgcttac attactaagt ggtaggaaat tttaggtaac acctcagact   22560
ttaaagtggc ctactgagct ggtagaaaag tgtgtagttg gtgctcagta attgttgaaa   22620
agatagaagc tttacttcaa agctcttgta gtttgatcag tttggaaaaa atattttaat   22680
gttgggctct gttaacagct ggactggtgg ctgtctgaat tgggaccatg cttggggtga   22740
ggttttttct tactttttt ttttttttg gtgagacaga gtcttgctct gtcgcccagg   22800
ctggagtaca gtggtgcaat ctcggcccac tgcagcctct gcctcctggg ttcaagcgat   22860
tctcctgcct cagttttctg agtagctggg actacaagca tgtgccacca cgcctggcta   22920
atttttttct attttagca gagatggggt ttcaccattt tagtcaggat ggtcttgatc   22980
tcctgaactt gtgatccatc cacctcagcc tcccaaagtg ctgggattac aggcgtgagc   23040
caccgcatct ggccacatat ttttttaaat taaatgtgat acataaaatt aggctgcagg   23100
catggcctga tttgcaggtg cttcatgagc aagcgtgcac agcatttatt tgctgctcct   23160
ggagtctctc gtgtgtgctt gtagcctagc cttaagccct ctgtggacgg cttggaatgc   23220
gtactccaaa tgactctttt ggcggggtgg gaagtggcaa tactttaggt gactgacagt   23280
tgaaattaac cttacacaag agccaaactg taggctgatg cagggccact cacctttgta   23340
ctcacccctg gcaggtcctg taagaggtgc tacttgcttc cactttgcca gctgttcgtt   23400
ggccctgttt tgtcttctgc tgtttgcctt atttatgaaa cagaatggaa acaggcgagt   23460
ttgatttgtt ataattccta ggagtcatag aatggaagca ggtgagtttg atttgttata   23520
attcctagga ttgataatt tgccttcccc tctctccatc tttaattaat cccttaaagg   23580
aaaagaggac gacagcactt ttcctgcagt catctgtgta ggcctcagcc ttaactcatg   23640
acataggctg gtgccactgg ccacagggct gacctcagct cttggagccc atgggtgac   23700 aggagatcag cacctttgag gtggcggcgt gaggcgtctt ccaggccttg ctcatggtgc   23760
ttgaaaacac tgctttagag ctttgttaag agagagaggc cctacttact cctgtcccac   23820
aggcatttgg gtgttgacct ccttgttggc ctcttaagga gagaatactt gagtattgaa   23880
ttcgatcagc ttttctgcct ccagggaccc tgtttctctc tgctgagact gtggcggatg   23940
aaaccaggat ttagtggatg gtcaccaggt agcttgggca gacctgggcc gcggggcccc   24000
tgaggactca tacgtctttt tcctgttcac atgttccttc cccacacctt ggcccattct   24060
cagtccctcc catgctcctt agcgtgaggc actcagggag gtgcccatgg ggccttgggg   24120
cctgtgctag agctggttcc cagcctcaga agtgtgccta actgtgccac attcattgga   24180
aagctgcttt cacacttcct ggatggaatt ctctcatttt ttcaatataa agtcactgag   24240 atgattttt tggagaagtc tttaaaggcc agttatacat ttattgatac ttggtattga   24300
caaagttcag ttgtttagtg ttgctaagtc atactgtgta agtttgttga gcacagagtt   24360
ttcattttat actttcagag gagaaatgaa actgaatttc gtggccagaa atatgtttga   24420
```

```
gcgtcatcct gatgtaagaa cagaacagaa aatgtggtga catttcattg taactctagt    24480
atgttttctt ttttgtccat tagactacat gaggaaataa ttgactttta taacttcatg    24540
tccccttgtc ctgaagaagc agctatgaga agagaggtgg tgaaacggat cgaaactgtg    24600
gtgaaagacc tttggccgac ggctgatgtg agtatgttct ttggagttct gtgtcgcacg    24660
tcacgtgcga gtaaatttaa ataccctgtg atgatgatgt gtcggctaga tccacacaga    24720
ccttttctcg ttggcccgag gcagcagttc tccaagtgtg ctttgagaag gcctccgttg    24780
cctggaatgc atggcccccg gcgcacctgc acctgctgtc ttagacacct gcggtggccg    24840
cacatcttcg tgatgctggc gcgcactcaa gtgcgaagac catcggctga gggatttgtt    24900
gggttttttt ttttttttttt tggaaggggg agaatggtgt gattgtttct cttaagttca    24960
ccttaaaatt tagaaatttc accctgtcac ccacccctgc ttccccacca ccacacatag    25020
tagcatataa tgtgctcatt tttgtaaaac ttggaagtgt tccctcatca cacaccactc    25080
ttgcagtgaa ggaacaagtg tttttgaca tgtggagtgg ggccttctgg aatgcttggt    25140
gcaggtggcg tgaagcctgc ccctggccgg ctctattcag cagccttccc tactgctgac    25200
tgggctcagt ggaccagcag ggctggccgt gccccagctg tgaggggcat gtgtgctctt    25260
ggtgggcaag ggcaacccag ttttctgcgc ctcttttaaa atgatacaga ttttttggctt    25320 taaacttcag agtcctagga caaagccctg ccccagtgcc ttagctgtgg gtttaagaag    25380
aggttgaagg gtttgaagct agctctgaaa agtcctcagc tttgaagggt tatagggtga    25440
ggacaaaact tgtttcacct cttaattttg agttttaaa cattccttt ttgggcatgt    25500 cttaactta aagggaattt tctggttgat tgttatacgg tcccctccat cagtttccaa    25560
ggtagtttta ttttttaccc aagggtatag tgagggcttt cttttagtaa gaaataatgg    25620
tagtgtgact gcttggttg tggtatacat tttaaggcaa ccactcttc tttcaggtac    25680 agatatttgg cagctttagt acaggtcttt atcttccaac taggtgagta ccagactgca    25740
tggcatgggc tagtgggggg ctgggatggt gtctatgcaa tattaagggc tacaaataga    25800
ttctttgtaa ttgagtctaa ggcgagaaat gccagctaaa ggaaaagact gtggttacag    25860
agggaaattg gcagaaagat ttaatttagt gttatgatga attcattgct ttgcattttt    25920
cctctcacac ttaatttgtt ggggtgcaaa aatgcttcat gctggaaata tgaagaagac    25980
aggtgggagg actgtgggaa gtaaacgcaa tagaagacat tctgctgata ttttaggaca    26040
tgtgtttgaa aaattgatct tatgttttga tgaagattca agcaaaattc tctttaaata    26100
gtattttcta agtattttta cctgatagga aaatgtcaaa caagtttgca ttctaaaata    26160
caaactagta ttttctcatt aaggattctt gatagccaaa taaatttcct gtgcactgtc    26220
tcattaaaag cttaccttct attaacccac tgctagttag catttggagg ccgaagaggc    26280
tataatctca ggatttgggg gttgacatta gcagggccag tgggtaattg aacaggtttg    26340
ggtatccagg aatctctggg tccgcaggag tgatccagcg taggcagtgc cggagtaggt    26400
gctgggagag cggggcctca gcctggtttg ggggcaggca ttttcatttg aatcccctca    26460
catacctagt gctgttggga gaatgattta accttcttgc tttccatctt atgctacaaa    26520
tatggaagtc ttcccttaag ttcagcgagg acttgctgta gttcatgaac tgcacttcac    26580
ctccttaggg gccataggct agtgggattg tgtcttggcc tttgtgggag acacaggcac    26640
atgtgccttg gtgcttatcc tccccacacg agtgtgtagg ctgtggcgag gggagcagtg    26700
gctgacgtgc gttttcttct gtcagcgaca tagacctggt ggtcttcggg aaatgggagc    26760
```

```
gtcctcctttt acagctgctg gagcaagccc tgcggaagca caacgtggct gagccgtgtt    26820
ccatcaaagt ccttgacaag gctacggtga gtgcctggct ttggcccctc tgaccgggca    26880
ggagccttgt cacatcccag gtggtcacag gatacgcctg cgtcacgagc ttgtggtatt    26940
ttacacagtt attggctaca gttttgaaga ttaatctgct tctggtatag acatgtgttt    27000
tatgtttttg tttcatagtc gtgatcacca actgagaaca tgtttagtga cagtctgaac    27060
ttttgggact tgtgagccca ttaaactgtt cttggaatga aaatatatga ttgtgtctac    27120
ttgtgttagg atgaatagga aaggagagtc atctgaaacc ggacactgac attcaggtgc    27180
tgcccattat ggagagtgtg gctcaatgat taaaccatgg ttttatgat taccatttgc     27240 tatgttatgt taaagaggaa caacttagct gttcctttcg tggttccaaa aaatatacat    27300
atatgaaaag cctttatct ttgggggaag tttgaagatg agactgtttc tggtgtgtac     27360
ttgctaaggt ttatgtcagt tcaagattat aagcccccca gggactatga ggtacttgcc    27420
tgttgtatga cagttcttag ctcacctgtg cgaccggcta gcatttcatt tttaaatttg    27480
tgtgtcaact tgtgtgtgat tcacatcctt atagtgttta gcagaatgta agttaaggca    27540
ggagcttcct cctgcctgtg tggtgatagg ggaggggggca ttcacatgtt tctcattgtc    27600
aggtgctttt gattgaggct gggggcaagt tttaaaacat gatatatgca ctgaaaagtg    27660
cacatgtacc aggtgcacct cttggtgaga gttaacgaag tgcacatgct catgtcactg    27720
tcatgtggac cagagcgagc aggcagcacc agaggttccc tccaggccca ggttccagaa    27780
ggggctgttg gctcttctca ttagcacgag acaagccctg gccggccact ttctcaaatg    27840
cttacgggcc ttattgcact tagctctccc agccactctc atcagcagat gctgttgctg    27900
ttcacatttt acaggtgagg aaactgagat gcggagaggt gaggtcatta gcccaaggtg    27960
ggtcagcgga atagtccagg ccgctgttgt ctgctgctcc tctgtgtgtg ccaaggggca    28020
gcggggaggt gggtgggaat cctgaccagg cgaccacctt tggagtagag gaactaaggc    28080
gcggctgtcc tgaggccaca cagtaggttg agcagttaca gtaactgctt agtcccagtg    28140
acctcgttac tgtcgcatat tggctactaa gtatcttttc ctctgttacc tgagggccag    28200
tgtagactgt agggagagcc tggagcctgc cactgctcat ttctggggag cactgtgcag    28260
ccggccagtc atgggcacaa gagacccagg gcgagggctg agtttaaggt gaaatcttgt    28320
ctatttggaa caacaaccca aaactgtgtt acagtgttaa ctcctcacct ccaggatttg    28380
gggttcctgc cgtgagtgag tgtgtgcaag agtagggcag gagagtgcca ggagtgattg    28440
tgggaaggag tctatgagat ggaaaggaag ctgcttccta aactgtgggt gtcagggagg    28500
catagccatt gagtgttggc ttcttccaaa gcagtttctg atgagttctt tgggaaagta    28560
tttctttctc tgccttctta agaacatact ggcctcaggg cttaccctgc ctggtggtcg    28620
cagtggtgtc caggtgactc tggccccact ggcatgtcct cacacgctga gtccttggtt    28680
ggttgccctc aagtgtagac attaaagccc agaataggtg tgtactgaat gcactgtccc    28740
tacgttgcct atcactggca tttgaacttt tcgttagaca ctgattgttt tggttaaagg    28800
aattcctttt tttaatcctt caaggctgaa ggaaacaaaa cattgccttt tcttctggaa    28860
gaattcagtt ttactggtgg ggtggagggt ggggcatgag tgtggtctgg acagttgctc    28920
aggcagattt tgaatgccat tcggtgacag ttcttgttgg tgagaatatt tctaaaatag    28980
ccttttattt gctgaatttt ttaggggaaa aatttttttta gtaaagttgt cttaaagagt    29040
gaaaacccaa agtagagaaa caatatcagt ataacataca atttaaaaaa tggcttcgaa    29100
gttacattaa atgatttcaa aaattctgcc aaataaaagt ctggggccaa gcacctctct    29160
```

```
ccatcccagc acatagggtg ggcgtggcag agactaactc ctgttccctg ttggctccct   29220
cccctcacgt ctctttgatg cttggtcacc tctggtgctg atccagggct acaggggctg   29280
ggcagaatgt gggtcctgct gtgaggggct ggggcctggg agtcgtcctg ggttcaggga   29340
ctactgatgc tgacagtgtt ctctgacccc ctttcattac taagaaaaaa caccaaacct   29400
ctgtacagct ttggcagcat tttgatgcct ggctgtggag agtcctgcat gttaaagcag   29460
tttttaaaat gaaatcttta caggtaccaa taataaagct cacagatcag gagactgaag   29520
tgaaagttga catcagcttt aacatggaga cgggcgtccg ggcagcggag ttcatcaaga   29580
attacatgaa ggtactgtgc ttggtgaccc agcgcggcga gagtgcagga ctggagtgct   29640
tgtgcttggt ggcatcctac gatgtttaca gctgtcagct gcacacacaa gtctttcgta   29700
acacagacta cacttacatt atttctccta caatattatt tctagagata ctttgaaatt   29760
acatagctgt ttttaaaatt tgcttttcct gagtaaccat tttataaagt tgacaattat   29820
tttagagagc tttgttaaaa tgttctttct agttattaca gactttgctt ctagctcagt   29880
gtgcctcatt cgcaggtttt acccaggtgg aagttgataa atcatgaggt gccttaaata   29940
tactcacttt ggaggtctc agtgcctgag gatgggcaga gagacttggt tgagctgaca   30000
tgtttgggac tctgaccatg tgcctggtct aaacgggtg gtcatgacct cctgttacag   30060
tagaggccgt gcagtcctta gcaggggcag acgcacctcc gggtggtcgt gacctcctgt   30120
tgcagtagag gctgttgcaa tccttagcag gggcaaatcc accctgcaa tctggtccca   30180 tcttgttcca ttttcaaggg ccttgctctt caggttcccc cttccccctt gtcatctggt   30240
ctgagggagc atgtccaccc caagcgcaac acgaacagca gcagccaggc tttccctccc   30300
tcctgccatc tcctgccgct ctgccttcct tgccagcctc actctgctct cctgctccgg   30360
aggcccccac tgtcctcatg gcctgtgtag caagcacata aacactccag tgaacgcgct   30420
ggtctcttcc tgagttcctt tgtgcctgtg gactcgtcat ggtaggggtg caccctgct   30480 gagtcgtaac ccagggagag ctccacagtc tcgattttca caagcccctc aggaaattaa   30540
ttcttagcgt cccccaacca aagtttgaga cttaatgact gagagccttc agatgggcaa   30600
gaggatcgag gaaactttcc tttctgtctt gtgtgatttg ctatgtgaaa tctctttgaa   30660
agtatggtaa ttactcagta aatcttttc ttttggaatt tacagaaata ttcattgctg   30720
ccttacttga ttttagtatt gaaacagttc cttctgcaga gggacctgaa tgaagttttt   30780
acaggtggaa ttagctcata cagcctaatt ttaatggcca ttagcttttct acaggtatgt   30840 atgctttctt gagactgttt ctgttgagac atgtgtaaga gtagactctt ccaaccagtt   30900
gcctagtggg ttccagcagc ctttgctctc cttttactgt attgtttcaa tttggtagag   30960
gctgatttct gattccttaca atcaaaccct cttgattaat gcacctttct ggatgctcat   31020
tttgtactgg gtgtaactgt tggtgcaggg gtgcccgtct ggttctgtga gtccagtgca   31080
catcagtcca agctcaggga attctctgta ttcagaaatg tccatttcat ggtaaacaat   31140
aaacatttct tggtgcttgt ctgtgattta tattgaaaaa aatttgtctc agaataaagt   31200
tgagtaccac atatgagaaa aggatttaca agagagcttt ctcagactga tgaaacatca   31260
ttattttgtc ttaaattata tgtggtcctt attttgctga gtaacatgga aaatctatca   31320
atagaaaacc tacgtgtttt aaaaagtatt gttaaatgct gtgatgtatt gataaactgt   31380
aattatactt tttaaacata taaatcatc tctaattgga acagtaatta ttccgttat   31440 attttcttga gtgaagaatt ctgtcccttta caaaatcttg cctatataat ttagccgcac   31500
```

```
ggctgtattt ctccagtgtt taccattaat ttggtctttg tgattgtgct gagattaccg    31560
aatctgtcca tgatttggta atgttctcac tgtcatgaat gctatgatag tagaatcact    31620
gggtaactac ctgtgatgat cgcagcttcc ttggtctgtc tctgccaaga tgctttaaaa    31680
gtagtgaaaa tggaattcca tgtctgtttt cttacagttc tagtcacact gtcctgtctt    31740
cactttcccc tctgagatgt ggcccttata tatagccttt cttccatagt ttttggacat    31800
tattttgaat taaacatggg cctctgttct ttactgatat actcctgact tgcactattt    31860
tcatggcctt gtagtaacaa cagctactta atactttgat catgcatgtg ccatgtgcca    31920
ggcctgggtc cagggcctcc tccaccccct caggggtcc tttcagtgat cctgtgaccc     31980
cacaggaggc caccacagca tgagtgggat tcctgtgttc actgccacat ccctgtgcct    32040
tgtccagtgc ccagagcttg tcctgcctca gcggtgtgac tgtggcagca tctgagtttc    32100
ttgactaagt gaggggagga ggcccaccct ggcaccggcc aggctcttgg atatgtgatt    32160
ttggctaaaa gacaaggaat aaggaaggga ataaaggtca ggccagaatc ggaatcctcc    32220
tcttgtgtgg tggaaatatg cagagaactc cggaattctt ctgaacccta aaaacatttg    32280
tatgctttct agctgcagct cctcctggca ctctgtgtta taaatagttt caagcaccgt    32340
gcttctctga gggcttctc tcatgtgccc tcgtccatcc ctttcgagtt ggcactgtcc      32400
gatagaattc tgtgatggtg atggccactt ctgcatggtc cggcaagggg caggcgcca    32460 catgtggcta ctgagtattg cagtgtggct ggtgagagca caagctgga ttttaatta      32520 atttgtttta attcatttaa atagacatgt gggcaatgca ggtctggaca gctgagaatt    32580
atgaccctca ggaggtgtgg tggacagtgg tttacttccg aacaagccca gtgcctgctt    32640
ttgaagacga tatggcactg aactgagagt ggtgctcatc tgtgtgacaa gcaggatgga    32700
agcttgctat aaatattgtg atataatgct aatgaccttt acacagctaa atcaatcct     32760 ttcactttc cggttttatg tgatactgcc atactagtca gtctaacact gacccctgtt      32820
ggttgtgctt cagcataacg aaattaggat gacgagaatc tgaaattaca tctaccatcc    32880
aggtgactaa gttatgcaga atatagtcca acttatttgc ccatatttgg ttaatcagat    32940
atctgtgttt gcaggaagtt tgctgtatgg attaccaatt tcaaaaatca aactacacta    33000
aaattcagat gagtccgttg tgttccttt gaacactcct cgttgaagag gctgctgttc     33060
aggcttcctc gtggtgctgg tgagtgagcg agtgccactc actggtattg ccttgaagag    33120
gctgctggac agcagacttc gtcgcgtgct attttctta gaacatgcca tgaatccata     33180
caaattgtgg gtgcattgct tttacagttg catccaagaa ttgatgcccg gagagctgat    33240 gaaaccttg gaatgcttct tgtagaattt tttgaactct atgggagaaa ttttaattac     33300
ttgaaaaccg gtattagaat caagaagga ggtgcctata tcgccaaaga ggagatcatg      33360
aaagccatga ccagcgggta cagaccgtcg atgctgtgca ttgaggaccc cctgctgcca    33420
ggtaagggcg ccctgatctc cactgctgag agctgggcca gcctcgggga cgtgctggtg    33480
acagggcctg tgttggggct ctgagagccc cgggcagttc atttgctctt gatgcaggtt    33540
tctcttatac taaccagtta ataatcacac tttgagaaat ccttatttaa tgcttctaat    33600 taactttgt ctttctaact gtttacattc tataataaag aagaattaag gaaaatctttt    33660 tcttttctg attattgaag tataacatat ccaccctaaa ccatttgttt ctctgaagta     33720
tgtaatatag aaaaaccatg gatgccataa tcccctttta tttggacatg tatttctcca    33780
cttttcccct atatggatat taatgtttat tattgttatc ttgttgaaca catcccсacaa    33840 cgcaaacacg tttgtcactt ggcttttgac ttaacgctta cccttgaccc tttcctatgt    33900
```

```
gtgtaggttg tgttttgtcg tgaggattgc cgcattgaag agtctaaggc tgggctagag   33960
gtttcccggt tttattccca ttggcgtatt cagggggtatt tatgtcctca ttcctttggt   34020 gacagtctttt taaaatcttt gccaatctga taaaaccatg tgttaacgct tttaaattta   34080
tatttcttta atgattagtg gggttaaaca cattgctatt tatgaattcc acaaattttg   34140
attgagcgtc tgttaggtga gataccattc ttactgttgg tgataaaatc gttggcggac   34200
gggtgacaga acaggtggtg gagagcccag ctccaggcgc gtgtccctgg gccttctcct   34260
ctgtgtggct ctgtgtgctg tccgcccggt tgctggctgc cctcctctgc tgtgtgcaag   34320
gcctgtgtgt gtcggggaag cctttcttgt cacacatgtc atactttttc caatttgttt   34380
tttgcatttg tattttttta ttcagctcct atacatttaa aaaacaccct cagatttaat   34440
ggttgttttt gttttatggc ttctgggatg tgagctttat ttatttccta agatcgtct   34500 caaggaaaac acattggctg atgtgttttg ttgttgttta tagatggcat gatttgtgca   34560
ggctcttgag tggttttctt ggtagcacgg tatggcagtg tatcatccat ttttgtccgt   34620
tggatgagtc acattggaga cattggcatt gtcttcaagt gtctgctgaa atgtactcaa   34680
aaaacaaaga cccacataat cgttgagtta taatataaat ctagaaaaga taaaactcca   34740
gtacttagaa catatatcct ttaaaagaaa tccacactta acctgattgt gaagaatgag   34800 ttgttttgtag attaaaatta gaaacagtgc ttttcttatg aaaattaagc ttctcctgac   34860
tggcttcctt ggtgactgct gtgacagatt cctttgattt gctgtcccag ttttccacac   34920
gtgagaattc acattccatt ctaaaggatt tacttcctgt aggttccatt agcgttgact   34980
gagttgtgat gcacttgggg tgagctgccc ttctacctgc cctgttgggg cactgtgagg   35040
cctcctgatt gtcagatcag cgatcacagt gggtcggtgc tgctggtctg cacaatggta   35100
gtctttggct tcctcatgtt tctgccacct ggagaggtgg cttttttgtgg gctgtcactc   35160 cgtctgtgaa tggcagccgc ctccgtgagg tgggccatga gcacaggggc actgatgatg   35220
cagaccagtc ctctcggcac tcacagactg tgccctgtgc atggtgattg acagggcctt   35280
tgccagtgcc aagtgccacc cgtgcccatt gtgttcgcct gtctgggctt tgctggtagg   35340
gtctggaaga gtttcagtgg tgagggcctg cttcagagtc acttgtatga gaagatccaa   35400
aacatgtgga cgatggtgtg catgtgggga gggtctgaca tagcctttt gctgcaggga   35460 atgacgttgg ccggagctcc tatggcgcca tgcaggtgaa gcaggtcttc gattatgcct   35520
acatagtgct cagccatgct gtgtcaccgc tggccaggtc ctatccaaac agagacgccg   35580
aaaggtaatg ggttgtgtgt ctgcgtctgg gctcagcgtg cctgtgggat ggtacttatc   35640
cctttcctgt gtcatttacc tccatgaaat ttatgaaggg atgttctgcc gtatttcagt   35700
agaatctaga tatgttggtg aaggaaggcc ttctaggaat atgggatggc tgtgtgggat   35760
tcatccatgg ttgagagttg aaaatttctt tcttggagat ttgacatttt cttcagggtc   35820 tttttgttttg gggaggtgat ttctggcttt taaaattcag tccctaccat cttctcttat   35880
gtacactcgt cccttgttct acatttttggg gcattttttac agtcccaaaa tgtagtcaga   35940
agtatttact tctcacccag atcattctgt ggtagtggaa agggtggtat ttgaagggg   36000 gggagatgag ataggaatgg gaaggaagag taacgtggtc gtcaagagtg gaattcgaaa   36060
cagtttgata gatctgttct gtggtggatg atggaataaa caggtttcga ggcctggctc   36120
agcagccgct gcaggtgctg gtggtgctgg agctctgtgt gttcctgagc cgctgtctgc   36180
tcggtgtttt caggcggagc tctgggcccc atgtagggca ctcgtctcgg taccgtctcc   36240
```

```
attctcgtcc gtgcagtggg aagtgaaatg tcagcactgt atgatcatcg tgggtgggaa    36300
ggccccgctc ccctacttgg agctgcattt cacagtggtc ttctgtaggt agatgtactg    36360
cgatcccagg gtatgcttga gctgaatcat taaaagtcag agatatttgt caacgtattt    36420
tagctccttt cctactgtcc ttcacctagc gagatgatct gttaggggta taaggtagct    36480
gttcgagagg ggttctcagc tccctgacac ctgttgtact ctgttgatct ccaacaatgt    36540 cccttttgcag tactttagga agaatcatca aagtaactca ggaggtgatt gactaccgga    36600
ggtggatcaa agagaagtgg ggcagcaaag cccacccgtc gccaggcatg ggtgagagat    36660
taattcattt gtgttcatcc taaccactgg ctggcatgtt catgcagaag tgtctctatt    36720
cctttgtggt aaattggtca aattaagaaa atagctagtt tttctgatga gcattaatta    36780
agaagacaat aagatctaga gcagcactgt ccagtagaag caatataatg catgccacac    36840
atagaatttc aaagtttcta ggctgtgtca aatgtgaaaa gaaacaggtg aaataatttt    36900
gatagatttt attccactca agtcaaaata ttaacatttc aacatgtaat caacataaaa    36960
ataattaaga tattttatag ctgtttcttg tactgtctga atccggtgt gtatttattc    37020 gtacttatag tacatcctaa ttaggatgct aaattttcgt aaaaaatact tgatctatat    37080
ttagatttta gaaagttcac agttgaagat gatttgcata cccaagttat tacaaacatg    37140
tttaatgttt tccaacaact aattgaatgt aatttttaaa attaaattag gcaaaaccta    37200
atgttgggtt tgttagtcac attagcagcg ttcccggctc agcagagccc gtgactgatg    37260
ctgccggggc ggctccacgc cgcagttctc aggagttatt aaccaaggct ttttccctcc    37320
acagacagca ggatcaagat caaagagcga atagccacat gcaatgggga gcagacgcag    37380
aaccgagagc ccgagtctcc ctatggccag cgcttgactt tgtcgctgtc cagccccag    37440 ctcctgtctt caggctcctc ggcctcttct gtgtcttcac tttctgggag tgacgttgta    37500
agtgccctcc cctcctccgt gtgtctgttg acagtttgt gtctctggta aatgtccata    37560
gccgcgagct taaaatctcc cccttggttt tgctcaggtt ttgtttcctt gtatgtgtgt    37620
ggaggtgggt gggggggcagc cccgtgatgt gggcaccagg cttcctttcc cctgccgtga    37680
accttcagaa cctgtctgtg cgactcatgc ggctgtcgag ggcagtaatc ctctaaatgg    37740
ttgaactaca gtggacttcc ttgagtagtt tttaaaaatt tatttgaaga ttaaaaaaa    37800 aattaaatcc aagtatctct tctgtatttc ctttaacatt ctttttcagt tgtgatgaaa    37860
ttacttgaag gaagcctggg taggtttggg ctgcctgttc agaagttaga cttaatttga    37920
ataacctttc atagccagcc tggatgcagg cgtttctttt catagcttta aggaagtagt    37980
agtgcacctt tgtggtacag ctgtcctttt tgttttttgt accgggttca aggattcaga    38040
cacaccgccc tgcacaacgc ccagtgttta ccagttcagt ctgcaagcgc cagctcctct    38100
catggccggc ttacccaccg ccttgccaat gcccagtggc aaacctcagc ccaccacttc    38160
cagaacactg atcatgacaa ccaacaatca ggtacgtggc cctctggcac ccttcccgct    38220
ggtggcccct gggaacagca tccgagctgt gatatgcact agaggagatt gatggtcctt    38280
tgaattagaa gagtaacttt ttgagtattt ggccattggt gtgttgttct aggaaatcct    38340
ctcttttttg tggtgttgag gtcccccatg tatagtttca gcagcgagga cactgtggtt    38400
cttgagtgct gccgtggctt ttcacggggg ccaggttgac tgccttcctg caagtttcct    38460
cactgcccca gcatgagact gctgtcgagg gtcatcttga gagagcgact cagtcacgac    38520
ccacttagct gggcgccaag ccgtgccaga cacttgtccc tacttcctct cagaatctca    38580
atgaaagttt taatgtgaac ttattagact tttttcatgt ttgaaattag gcataatttc    38640
```

```
taaggctttt tctgttggaa tatactgttt ttaaaattta gataaaatta gaaatctaaa    38700
ggataatttt ataaatacta aattttgtat ctacttgcga ttatacatca cttgaatatg    38760
tgtgggtata aaacccaaca tgttaattga cttaaaacca ttttctgaaa tgtggggtat    38820
aatttgagca taaagctatg taggtacatg caaaagtgtt ttgactcatt tcttggagtt    38880
ttgcactctg ctctggggaa gacattctca caggatccac cgtgattctg gcggagcttc    38940
tgggatgctg gctctgtaat gacccacaga gctgatgagc agagccatgg cccagccgga    39000
caccgtaacg tgtctaattg cagcataagt gtaaaattca gggcaatta tttacactct     39060 taaaatgaat tataccacag ataaacttgg tcgcctttt atggtcatca cagtggccct     39120
gacgtcctgg ccatgtgtca caaaggtgtt tgttttaacc acccacaagc cttggggccc    39180
ttgagagccc agtgcggctg ctgagctaca gagccacact ctgcggctgc ttgtgtggtt    39240
cgagtgtgaa gtccagggac gctgagggtt tataggtttt tatctaagaa gactcttggc    39300
cacagtcaat ctccagaggt tgttggggta aatgcacggg atgccaagat gcaaccaggt    39360
cagtattgca agtctgagaa aaggggttct cgttagcgca cttctgctgc tgacagtaac    39420
gggtgatgct gacatagaag cagcctggga cctggacagc aggcaaggaa ggaactgcca    39480
gccgtcccac ggcctctcag gccaccagtt gggccagcct tgggctgtga cccctgagtt    39540
cagcgtgtga gtaggggggtt caccacgggg gtgacggttg ttcttctgat gactctaatg    39600
tcttgatcgt ttgatcttca atgagtttca aactttatga cttggattac tgggcatact    39660
ttatatgcca gttgctgttt tagaatacga agtatttcca attcaaagca caatattgtt    39720
aggtaatagt aaaacagact gctctatgga gcccacatgc aactgtgcca tttatcagct    39780 gcccttggt ggtgctgagc ttagaagccg gatggttttc ctctgattgc tttggtaccc      39840
atggccgtct ctcattttgt tcctagacca ggtttactat acctccaccg accctagggg    39900
ttgctcctgt tccttgcaga caagctggtg tagaaggaac tgcgtctttg aaagccgtcc    39960
accacatgtc ttccccggcc attccctcag cgtcccccaa cccgctctcg agccctcatc    40020
tgtatcataa ggtatagctc tgtcctggtg cattcaccta cctgttcaag ctgccatgtg    40080
agaggcggtg ctaaatgttt tctcctccag agagaattcc agagagatca tttgaaaacg    40140
gaatttgctt tgttgtcatt cagcctgttt gcttgtcttt ccaaacaaaa cttaaaaaag    40200
ttaaattatt ttaagatgta atatatagtt taattggttg ccacaaacat ctcttaattc    40260
ctctgttgaa ctgattagca taaaactgaa gtttgaaata aggctcaaaa tgaagacttt    40320
tcccatttac ataattcatt tatatgctaa ataccttggt tttcaagaag caaatgataa    40380
aaccaagagc agatcttgcc atgatgtccc gtgtatgctg ctgtcattcc cacgttgcct    40440
gatccccgcc tggggcagga gcaagcgtca gggctggcag agctgtgtgc tgggcctcag    40500
cagggccctg gcatgcgtgc ccttgtggct cctctcaagt ccagctgtgt gcatggagga    40560
aacaggtcac gttaagtctc tatattcttg aagtacctga atgattggga gagccatggc    40620
gaggatcttc caggtcagcc cccgtcgtgt gtgatgttcc ttgggctctg cggatgctcg    40680
gtgctttcat cggtgtccac acctctttat tccgctcctc cttttgcttgt ctaatcctat    40740 tttgccagta agttttttat tcttgaggct ttgttggccc tgtgttgtat gatgattgtt    40800
tttaggagtt aagtaataga acatttcctc ttggatttat ccatcccga tagacacatt      40860 cagggtgaaa gaacaacttc gcacaccggc ctcttctttg catttggct ttgctttccc      40920 agtctcctcc tgctgttttt cttgctctga gactttcctg aagccggcgt gtgttccctc    40980
```

```
tcagtctgct tggccgcgac tttgcagtgc agggaatgtg ctttgggtgt agcccaagca   41040
caggctgctg catgctggga tcgacaggct gctgagggcg agagcgccag gtcctggcac   41100
gtgtgacttg cttggttctt tctagaaggt cacagctggg ggaagaacat gacagggacc   41160
ttcttacttc tgttttttg gagacagaat ctcactccat cacccaggct ggagtgcagt    41220
ggtgtgatct cagctcactg caacctccgc ctcccgggtt caagcaattc ttgtgcctca   41280
gcttcttgag tagctggaat tacaggtgtg tgccaccaca cccagccaat ttttgtattt   41340
ttagtagaga cggggtttca ccatgttggt caggctggtc tcaagctcct gacctcaagt   41400
gacatgcctg cctcggcctc ccaaagtggt ggaattacag gtgcaagcca ttggcacctg   41460
gctagggacc ttcttatttc tatggataag tggaacaagt tagaagtgag gttctgctga   41520
atttgtgtgg tttgatcctg gtacatggtt cttgccttta gtcattcacg gaatgggaag   41580
aatgcttttc tctcagatgg aggagttggg aagtcccaga gggcaggtgt ccatccctgc   41640
tctctatgta acatcacgtc ggtgcttagt gtggtcactg cccgaggacg tgggcattgt   41700
gcctgctgtc tggctccaac actgctgtct ctctcttttct ccagcagcac aacggcatga   41760
aactgtccat gaagggctct cacggccaca cccaaggcgg cggctacagc tctgtgggta   41820
gcggaggtgt gcggccccct gtgggcaaca ggggacacca ccagtataac cgcaccggct   41880
ggaggaggaa aaacacaca cacacacggg acagtctgcc cgtgagcctc agcagataat    41940
ggctcctggc tgcgtcagcc tcccccaccc ctctgcagac tgccccgcgg cctcggccac   42000
cggcagggga accgagacca gcaccccgca cgtcagccgg gctcgcggca cgcccgccgc   42060
tgatcactct gcatgtttct tcgtgtggtg gtcgcgtcca tcttcaagaa cagctcgttg   42120
tgctcatctg tgaagcctta ttaaacgtgg acgttgtttt ctgccttccc aggattcttc   42180
cttcagtgct gaggcaggtc gggctcagga actgcaggga cgtgaacatg cgcttgcggt   42240
ttgaggtagc cgtgtctgtt ccttcgcggt ttgctatttt catttcctgt tcgtcaaagc   42300
agcagaggag atcaaacccc gttcgtgtgt ctttcctcca cggataagct tgggaggtca   42360
ttgttttact gccctcacat tttgtttgaa atttcagaac tgttttcta tgtaaatatt    42420 gaaaacttat gatttgtgca ataactcaga tattttttat ttaatttcct attttcacat   42480
aagttatatt taagggagga gggaattttt tttaaacaag cttaggtcct ttcccgagct   42540
gcatttccta agtgggtca tcgtgtcggc tggttgtctg acgagcatcg ttacaaacac    42600
catgatgagg ggtttggggt tttattttga tgtcttttct tttggtcgga agtgagtgaa   42660
ggagccaggt cgccctgaag gttttccaaa gggcttggct ccagagccac ctggcagact   42720
gcccgtggcc ctgctgtcgg gccccaggcc gttgtcctgc tctgaccaca gagttttaat   42780
gttttggttt tcacttcttt taaactggac aacaaatcca gcatttcaag tgccagaagt   42840
ataactttct aaggagagaa gggttgtcac attataaaat ctttaggaaa atgtgaactg   42900
gaaaacgctt cggtcagttt tagtgacata gcctgtgatg atgggtctgg tgactattat   42960
tgcggaccgt ggtacccagt tttaggaatg tggagaaagg aattctgttg attccgttga   43020
ggaatctgta gcgtatgcat tcgttctgtt aagagcaaat ctaggagaag tgcttcagct   43080
gcccagtgcg ccgtggggag tgttttaacg gatcgtgtcg caggagagca cagcccagcg   43140
ttggggccgg gaccgctggc gcccgacgtc ggaagcatac aggtatacta tgcaagtgta   43200
ttctgccaca caaccactg tctttgttac cttttttga acaagaatat atccatcctg     43260
cctaaccctg agttttgga gcaccacagt tgtcctggga gttggttgca tcttgtaggc    43320
catctgactt cctgtttta aaacgggggt ctggtcttgc taaacactac aggtaggttg    43380
```

```
gtctttgaag tccactagtg gagaatgtca agacaagata cttattacca tgacatctga    43440
tgcatgtgca gcagtgggga gttctagatt gatctctgaa tgtgatcgac gcccagcaag    43500
gacaagcttt aaaatgtctg cggtctgccc ttttgaagca ggactggctc actctgtcat    43560
tgggagctgt cagctgcgac tgcaggttct ctaggaggca ttccagaata gagtagcaca    43620
ctgtgtctgc agttctcgat gaccgaaagt tatcaaaaat atttaaaata tttaaattgt    43680
gaacctattg ataaagaata tttataaaaa ctgatctgta ggcctgtact aatctctacg    43740
cattagcaat attgactgta aacccacatt aaggaaacca ctacgggtct ggcagtgcgt    43800
gtcccgtggg gtgtgcattt taaaactcga ttcatagaca caggtaccat gttccatttc    43860
cgtcatggtg aagcaaatga attggcctgg ctaccactgt ggtcgcgtgc tacaggtttg    43920
acaaaaagat atcatgtttc gattttttg tgtgtggaca acaatatgga agctaaaatt    43980
gacatatttt tatgtaaagt ttttctattc tttgattttt aataaacttt ggaaaccagt    44040
tt                                                                  44042

<210> SEQ ID NO 3
<211> LENGTH: 86750
<212> TYPE: DNA
<213> ORGANISM: macaca fascicularis
<220> FEATURE:
<221> NAME/KEY: misc_feature
<222> LOCATION: (23430)..(24809)
<223> OTHER INFORMATION: n is a, c, g, or t
<220> FEATURE:
<221> NAME/KEY: misc_feature
<222> LOCATION: (70678)..(70758)
<223> OTHER INFORMATION: n is a, c, g, or t
<220> FEATURE:
<221> NAME/KEY: misc_feature
<222> LOCATION: (71318)..(71417)
<223> OTHER INFORMATION: n is a, c, g, or t

<400> SEQUENCE: 3
ggcggcgcgg cctcggcccc ggcccccggcc ccggcccccgg ccggcatgta ccgctccggg       60
gagcgcctgc tgggcagcca cgcgctgccc gcggagcagc gggacttcct gcccctagag      120
acgaccaaca acaacaacaa ccaccaccag cccggggcct gggcccgccg ggcgggctcc      180
tcggcgtcct cgtcccccctc ggcgtcctcg tccccgcacc cttcggccgc cgtgcccgcc      240
gccgatcccg ccgactcggc ctcaggcagc agcaacaaga ggaagcgcga caacaaggcc      300
agcacgtatg gactcaacta cagcctgctg cagcccagcg gagggcgggc cgcggggggc      360
ggccgagcag acggcggcgg ggtcgtgtac agcggtaccc cgtggaaacg gaggaactac      420
aaccagggag tcgtggggtg agtgctggcc ctgcggcccg atggcctggc cggtgcgaaa      480
gcgcagccga gcacacgccc acagtggggg gttgtgaggg tctgggagcg gccacccca     540 cggcctgcct ttgcttctgg tgcacggggg tgctgctggc catcccacc cccctagtcg     600 tccacacctt tccccagcct ccttaaccgt cccacccctc cgctctcctg tcctcccttta     660 gtcgtccaca ccttcctccc ctccctctta accgtccaca ccttccccag gtccccccttt     720 tatccattca ctctcctccc atccccctta gtcaaacaca tctacccctg accaccaccc     780
cgcctccagc cctccacacc ttttcccccg tcatcacaac tcaagatgag accgcttaac     840
acgggcatat cattcattcc ctgagaacat tggtgtgtga gtgttttttg atggtgcagg     900
acccggaggt gctttccttg ccaagaatag aaacatccag aatgtcctc cccctcccc      960 agtcccagac agcaatcatg tcagccctgt aaggcattgc ctgctcttga cccttggcc     1020
```

-continued

```
aatctttta ttttttaaaa attcgcatat cacagatgcc ctgtctgtgg agagggtggc    1080
gtgggatggg tgaccgctaa gtttaggctg gcgaaggtgg tgagctcttc tgaggccctg    1140
atagaacttt ccaggagttc atggtccgcg gctccagctt ctcactgtaa agttgtcatc    1200
ctggcagagg cagccaatgc ttttcattct aggggtaga gatttatgct aatgagtgaa    1260
tattgcacca ctagtgactg tttaaagttc agctgttaga aaatggaatc ttacctgacc    1320
cctagtgaat tatgtacata agcagggaat gtttccagct agatcaccct tcagaagagt    1380
ccctgtgttg aataggtta ctgagtctta tttgttttgc aaaacaaagc ttttggtctc    1440
gtgtgtgtgt gtgtgtgtgt gtgtgtgtgt gtgtgtgtgt gtgtgtagct tgagtatgga    1500
gaacgggctt tcaaattgct tttcatttt caggttctgt tttacactga gggctttggc    1560
atgcaaatga aattaccaat tagtaatctc atgtgaacct tttcctggat ttattcattc    1620
agatctgtcc tgctttggct gagagagaga gttctgtgta ccttttgaa ggtctggata    1680 aaatgagttg gtgggttcca tctgcttcca gtgggctggt gtctgctcta tgctactatt    1740
acaactccta ccttttgtgg aaaatgcagt caagcgtttt aggactggtg ctgtggtaca    1800
tgtcaaacct gccctcacat tccagaaagg gaacccttt agggttgagt cctctgttgc    1860
taagcttcaa gggcgctctc catggtcatc acgttttatt aaaggcttgt ggttccatcc    1920
tgttagcatt tccaagtcta agcgtaaacc tgtggttag tgacaagcaa attgatgttg    1980
agggtttctg gtagtttcat ttcacaggag taagctccag ttaagtaatc actgtcaacg    2040
aaaaccttga agttccttaa ttgcatttta ttgaagcctc cttgcatgtg tctagcaaaa    2100
gatataagtc caagatgctt atttttttt gataaattag aaattgtcct ttcctctgct    2160
tgctatttaa tgcagaagat actctaaaag gttcatattt gtacctagta aagcaagat    2220 gttcttgttc ctaattcaaa tatattgccc tcaaagggat taggagagga attttcattt    2280
cccagaggga ttactgtttt aaaactgatt gtaaacctct ttaaaaactg cttatcactt    2340
caccagtttt tccattcttt tgcctcctcc cttagaggat gtcagcagtt aattttttaa    2400
aaaaaaaatt gaaaaagaa tttcaattct gagtcctcct agtttcaaaa aatacgttaa    2460
acaattccca ggagtgttaa gagtgtcggg gtgcttagaa attcttgctt tgattcatgt    2520 atcctgatt cttttttttt tttttttttt tgagatgaag tttcactctt gttgcccagg    2580
gtggagtgca gtagcacaat ctcagctcgc acaacctct gcctcccagg ttcaagcgat    2640
tctgctacct cagcctcctg agtagctggg attacaggtg cttgccacca tgcctggcta    2700
cttttttatt tgtagtagag acggggtttc tccatgttgg tcaggctggt ctcgaactcc    2760
cgatctcagg tgatctgccc gccttggcct cccagagtac tgggattata ggcatgagcc    2820
accgtgcccg gcctcattat cctgatttct tttttttttt tttttttttt ttttttttt    2880 ttttgagac tgggtctcac tctgctgcct aggctggagt ggagtgatgt gatcatagct    2940
catggtatcc tctaactctt aggctcaagt gatcctcctg cctcagcttc ctggagtacg    3000
tgggactaca ggcacatgtc accacacctg cctaattttt ttattttac ttttttgtaga    3060 gatgggcct ccatttgttg cccgggctgg tcttcaactg gcctcaagca ctcctcctgc    3120
cttggcctca cagagtactg ggattatagg catgagccac cattcttgcc agtgtcctta    3180
tttcttaagg aagttttct gttttgata caggtatttc aaaatatctg aattcagagt    3240
gcacctcgat gttttgctgt tctgagattt aatatactaa aactattacc attgttgtct    3300
gaattcttaa gatgtgactg atagttagct aataggttaa cacgttgtgt tggttcttgg    3360
cctctgaact gatagtccag atagggagag gacaccagaa agcatgtgaa aaatggacta    3420
```

```
gaactatgga acagctatat agtctctcac agctgtcttt tgtgttctct gcttcaacca    3480
aactggttga cttatttaga attctgacct cttgcattgc ctaagtcctt gatgttttttg   3540
gtttcttctc tgaactctca aaggtactca cttcatgctc ttggtatagc ccacttatgt    3600
ttaactttcc ttttattatg tcttccctct tacacatgac atggacattt cttttaatat    3660
gtagagtaag atattggatt tcatctaaag tcttcaaaat aaaactcttg ggctcaccat    3720
ctcagacttc ttcatgtatt tacagaccag ggattttgtc tgcttttaa aaaaatttta    3780
tattttttat tatttttaaa ttttaattta attttatgga gacagggtct cgctctcttg    3840
cccaggctgg agtgcagtgg tgtgatcttg actcactgca acctttgcct gggctcaacc    3900
catccacatg ccttggcctc ccagagtgct gggattacag gtgtgagcca ctgtgcctgg    3960
cctaaattta ttttttttaat tttttttgag acagggtctt gctctgtcac tcaggctgga   4020
gtgcagtggc atgatcatgg gtctcagcag ccttggcctc ccaagctgaa gtgatcttcc    4080
cacctcagcc tcctgagtag ttgggattac aggtgagtac caccacgcct ggctcatttt    4140
ggtatttttt gtaaagatgg ggtcttgcca tgttgcccat gcaggtctcc aactcctggc    4200
ccaagtgatc ctcccacctc accctcgcaa aatgttggga ttacaggtgt gagccactgt    4260
gcctggcctt atgtatttat ttaattatga atgaatgaat gagagggagt cttgctctct    4320
cgcccaggct ggagtgcggt ggcacaatct tggctcactg caacctctgc ctcccaggtt    4380
caagcagttc tcctgcctca gcctcccgag taactgggat tataggcgcc tgccaccatg    4440
cccagctaat ttttgtattt ttagtggaga tggggtctca ctatgttggc cacactggtt    4500
ttgaacttct gacctgccca cctcggcttc ttaaagtgtc aggattacag gcatgagcca    4560
ccgcgcctgg cctggccttt tatgttttaa gttgcttcca ctgattctct ttcttgggct    4620
tgctgccct ccagaactgg ctatggtgta ggatgctgtc cacctgctgc tgcttgtcca    4680
tgaaaacgag ccataaaccc ttttatttgg aaagacttag ttgttgatcg ctatggagaa    4740
agaggggatg gcaagaagta gcaactacag agaatttgca gaacttggtc ttgagccctg    4800
ggtccagaaa cttcttgtgg aaggtgcttg gtgtttgtcc aagctcatga ggataggttt    4860
ctgttggctg tactgccaga tctgtagatg cttttttaag gcttggatga cttgttcaaa    4920
acaacgtttt ggagtacaaa tttggcttgg ggacatcaag accttgttgg gaaacttggg    4980
tttaagatat aatttcttaa actaggatgg tgggaatggg gatgtgaagg gagaatgaat    5040
gtgagaggca ttacagggta aggatggaga ggattcagat tccttaagtg gatttaataa    5100
tcacactgta gctttgaact tcagtgactg ggaaatgtt tgtggtgttt ttggaaataa    5160
gggccagaag gactattggt ttggggaaga agatagtagg gggatatata ggtagacccg    5220
ctagtggggt gctgagattt ggagggcaga gatgtagtgc tcttcactgc tgtagggcag    5280
tatcgtcctg tatgtgccat cctctagtgc ccttttttca ccatattgta gtaagcccga    5340
gatgttcatt ccttttcttca gtactgcatt aaggcttatc tctgcttgtt tctttgtttc    5400
tgtgttttt tttttttttt aagatggagt tttgcttttg gtgcccaggt tggagtgcaa    5460
tggcgcgatc ttggctcacc gcaacctctg cctcccggtt tcaagcgatt cccctgcctc    5520
agcctcccac gtagctggga ttacgggcat gcgccaccat gcccgactaa ttttgtatct    5580
ttggtagaga tggggtttct ccttgttggt caggctggtc tcaaactcct gacatcaggt    5640
gatctacccg cctcggccgc ccaaagtgct gggattacag gcatgagcca ccacgcccgg    5700
cctatctctg cttatttctg cacagtatta tcagtgagat tggtgttact gctgggctcc    5760
```

```
aaagcaatca gacatagtaa agtagattga atatgaaata atttagaggc cttgttccaa    5820
gtgatttgtg ctttgtttaa tttctgtgca tttgtaaata tagcccacag taattcttag    5880
tgaactggaa ccttcaggtt attgcatttt actgatttgg gtactgaaat gtgcttttaa    5940
gaagacatta ggttttctat agtgtagatt gtacactaac aatataattc atatttaaga    6000
atgtctcaaa atttagtatg ctgtgttcag ctaacttaac tttatttgtt ttttttgtttt    6060 gttttgtttt tttctttgag atggagtctt gctgtgccac ccaggctgga gtgcagtggc    6120
atgatcttgg ctcactgcaa cttcaacact cctgggttca agtgattctc ctgcctcagc    6180
ctcctgagta gctgggatta caggcacccg ccaccacacc agctaatttt tgtattttta    6240
gtagagatgg agttttgcca cgttggccag gctggtctcg gactcctgag tcaaatgatc    6300
tgcccgcctt ggcctcccac agggctagga ttacagacat gagccactgc gcccggccac    6360
taacttaact ttcattccac aacttccatc ttttatccaa aatctgtgat cagtgaacac    6420
tgtcaccatt aaccattgac atttcagtgt ttggactttt tttttttcttt tcccctttg    6480 tctttgtgga ctctttttta acactcataa agttttaact attgaaaagc acaagaaac    6540 agtgagtgac ttttggaat tgtttaccc agtgttcaca taaaaggctt actacattac    6600
aggaaagata ggatgagaaa gggatactag aaaattctaa gtcagggacg ggggtgtgta    6660
ttagaaaaat tctgatcctg gcatgccaga tggccttaca tctcaacttc ttctgtgaaa    6720
ttcctgccaa caaatcatag tgttggaagt acagaagggt ccatgggaac agaatttaag    6780
ggctcccttg gtgatactga actgatcaga tggttctcac ttgttctcag ataacctgca    6840
tactgaatat cacaggaagg gtatagacat catggctatg gttagatatt cttgcacctg    6900
ctgaagctga gaaaattaaa gtcatttttt tttctgtgga aagtagaaaa tcaagctttt    6960
atatgatttc acacagcttt ctattctctc ttctgttgac tctgttaaga gtaacattta    7020
gtggtggaaa ctatttcagg atcacaccca caacactaga gactgtatta atcactcaca    7080
cacacatagg tatagagtaa tcttgaaggg gctgtaggcc agagataatg ctttttttgaa    7140 gaattagaga ctagttacca gcacctggta tttgctgttt cctacagacc tgactggaca    7200
gcttagagtc tgctgaggaa ttcagaggat ggccagtaga atgttctttc tacccccagag    7260 tatttggtag ggactcagct gctatggaat gccaaaaagg ctttaagttt ctttcactat    7320
tcttaagatt acatgtaatt gttttttttgt aagagattat atatattcaa attgaggatg    7380
gctttgagct agacttttcc ttaatttgga accacacagc agatgataca tttatttcca    7440
tctgataagt tacttgatga tgtaaaagac atttgagtta aagattttg ggaaaaaagc    7500 tgaatgttga gccatttatg ttgtgtactg gttccctatt cacttagaca attttaagtc    7560
tgaaaacaat cttatcatat gcacaagaga tttcatgtag tatttggtaa ttaagttgag    7620
gaattctagc tcaagtcatg cttttttgctg aaataggtgt atatatttag tgcaaaaacc    7680
tgtgttttca aaaaaatta atgtaataaa agtttcaaca aaatgaaagc ctttataacc    7740
atgtttcaaa tgctatacta aaccttttcc atttgttatt atattaacct cctcatacat    7800
agccctacta tttttttttt ttttttacttt ctattttgaa ataattgtag atttatggga    7860
agttgtgaaa aatagtacag agcccatgtt cccttcacca agtttcacct ggtggtgata    7920
gctcacataa ctatagttta atgtcaagaa ccaggaaatt gtcattgtta caatccataa    7980
ggctttttta gatttcacca gtttcacatg tatttgtgtg tatgtgtgta tataatagta    8040 tgcaattttta tcatgtgtag atctgggtag ccactctaac agtctatagt tctatataca    8100
gaactactcc atcacctcag ggctccccat gctaccgctt tgtagccgca tgcacccttc    8160
```

```
caacaaccac taatctgttc tgcatctctg taattttgcc attttgagaa tgttatataa    8220
atggaatcat acagaatgta actttggctt ttttctttta ccataattcc tttgagagcc    8280
atccaaattg ctgcatgcat cagtagttca tttctttttta ctattgagta gtagtccata    8340
gtatggctga accacacaat ttgtttaacc atttacttgt tgaaggacat accagaaggg    8400
tggtttccag ttttttgact attacagata aagctgctat aaacattcat gtatataaat    8460
atttttatat gaattaaagt tttcattttg ggggaataaa tgcccaaatg tttggatcat    8520
ctggtaaatg catgtttggt tttagagaa actgctgaac tatttatttt ctagaatgac    8580
tatatcctct tgtattccta tcaacaacgt atgagatatc cagtttctct gcatccttgc    8640
tagcatttag tgttaccatt tttttatttg agcggttcta atatgtgtag taatagcctg    8700
ttttgcgtta tattaatcaa taaaatagc ctcatctaat tttaactttt taattttaaa    8760
atatcttggt ggtattgaac tttctcagtg agaaatatct aaaattgtga cttgaaaggc    8820
tttaattttc aagttttttct ttggttttac tcttagcagt aacatttaa ttttttttgt    8880 ctttgaagta attttcagtg tttcctttac atgttgcttt ttcttagaaa ctagttatta    8940
gcatgaagta gatctttagt ctcgttttct aaaaacataa aaaagtaaaa ctgcgggatt    9000
tatttcaaaa ttgagagtct tgtcttttca tatgaggata ttttatagtc tgttggcttg    9060
gctatatttt agggagtaaa cctgtggcta gtggtttgtt ggtgatggtg gtggtaaagt    9120
tttcttacag aattttttatt ttttttttta tttttttattt tttatttatt tattttttt    9180 gagacggagt ctcgctctgt cacccaggct ggagtgcagt ggccggatct cagctcactg    9240
caagctccgc ctcccgggtt catgccattc tcctgcctca gcctcccgag tagctgggac    9300
tacaggcgcc tgccacctcg cccggctaag ttttttgtatt tttagtagag acggggtttc    9360
actgtgttac ccaggatggt ctcgatctcc tgacctcgtg atccgcccgt ctcagcctcc    9420
caaagtgctg ggattacagg cttgagccac cgcgcccggc caagaatttt tatacctgaa    9480 tgatacctttt agactctata gaatagatac ttgatttcaa atctatccta gaataaattg    9540
tttcatctaa acagctttgt gacctgagaa ttgggactta gtgccttagt tttcccttac    9600
tggcccttgg tagtcactgt tttgatttag tcaaagtaac ctaactctta gcactgtcag    9660
gtattgtaca ttcctgccaa agcaagaata ataatacata ggattgtgtt ttaattctat    9720
aattaggtga cttagctaat ttccaggaac ttggacttaa tacagtacta gtgataaggc    9780
ttgaaatttt agtgcctttg ttctttgaag ttattcaccc tttagtttcg tgtttgtttg    9840
gggtgtttat accactgtcc ctaaatatag ctgaaataac ggaggaaaac ccctgtaatg    9900
tcactagcag gatataattt ctgttaatag tttgatgtaa atattttttg actttttaat    9960
ttttttatat atatatatat tttctttcat caatatggac tcttactgtg agcataattt    10020
taatgtcttt aaagagttgg gttttgttta tttgtttatt ttattttata gaaatgggat    10080
ctcactgggt gcggtggctc acgcctgtaa tcccagtact tgggaggcc aaggcaggcg    10140 catcacctca ggtcagtgag gttggtcacc agcctgacca acatggagaa accccgtctc    10200
taccaaaaac acaaaattag ctggacgtgg tgacatgcgc ctgtaattcc agctacttgg    10260
gagcctgagg caggagaatc acttgaaccc aggaggtgga ggttgcggtg agtcaagatt    10320
gcaccattgc attccagcct gggcaacaag agtgaaactt tgtctcaaaa aaaaaaaaa    10380 aaaaagaaag aaagaaagaa agaaagaaat ggggtctcac cattttgatg ggttttgaac    10440
ttgtggtctc aagcagtctt cccacttcag catcccaaag tattgggatt acaggtgtga    10500
```

```
gcccatcctg gttttttgtt gttgtcgttg tttgcttgtt ttttgtttgc caccgtaccc   10560
ggctaatttt tgtattttta gtagagacag ggtttcacca tattggccag gctggtcttg   10620
agctcctcac ctcgtgatct tcccacctcg gcctcccaaa gtgctgggat tacaggcgtg   10680
agccactgtg cccagcctat tgttgtttaa ataaaagaat gttgtttaaa taaaataaat   10740
ttattctctt atagtctgga ggccagaact tagaactggt tttcagtcta attttttttt   10800
tcttctttgg gagaagggca tcagaatatt gtgaatatac ttttttgact aaaaaaagtt   10860
ttctctgggc atggtggctc acctggaatt gcctgtaatc ctggtacttt ggaggaggct   10920
gaggcaggtg gatcgcttga gtccaggagt tggagagcag cttgggtgac atggtgaaac   10980
ccagtctcta ccaaaaaaaa aaaaaaaaat tagccaggca tgatggtggc gtgcccttgt   11040
agtcccagct acttgggagg cttagctggg aggatcactt gagaccaaga ggcagaggtt   11100
gcagtgagct aaattcatac cactgcactc cagcctggat gacagagcaa gacctcgtct   11160
gaaaaaaaaa ttttttttttt tactagcatg acaaacatct tttcatttca aatatatttc   11220
tttttttttt tttttttgag acggagtctc gctctgtcgc ccaggctgga gtgcagtggc   11280
cggatctcgg ctcactagtt tttttgtattt tttagtagag acggggtttc accgtgttag   11340
ccaggatggt ctcgatctcc tgacctcgtg atccgcccac ctcggcctcc caaagtgctg   11400
ggattacagg cttgagccac cgcgcccggc ctcatttcaa atatattct ataccatttt   11460 taatatctca ttgcctttag aatgaccttg tattcatagt acatatgtat gtgatattcg   11520
atttatttat ttttcgtttg tcttattttt ggttatattc cattgattta atgtaccata   11580
atttatctta ccaatttctt gctgaccatt ttgtttccag tctttttgttt ttttatcaga   11640 catggattaa gctgaggctt tgtcccagac aacattattt cttttttatc agcaaaatat   11700
gcatgtaatg aaattaaaat taaaaggcaa aaaacgttat cctttatttt cttcttattt   11760
ttgttgagat aataattcac ataccataaa tttaaccctt ttaaagtgta caattcagtg   11820
gttttgtata ttagaaggtt gtaccatcac aactaattcc agaacagttt caagaaactc   11880
tgaacccatt atcactcccc actccctcac acgccctaat cctggcagcc acatagagac   11940
tgtctgtctc tgtgtatttg tctattctgg acctttcata taagtggaat cataacaatt   12000
tgtggccttt tgtgcttggc ttctcaaact tagcacaatg tttgcaaagg ttatctgtgt   12060
cgtagcatgt gtcatacttc attccttttt gtgactgaat attttattgc atatatatgt   12120
cacattttgt ttatccattc acctgtagaa ggattttttag gttgtttcca ttttttagct   12180
gttatgaata ttactgctgt agacgttcat gtacaagttt ttatgtgaat gtgttttcat   12240
ttttcttggg tatatactta ggtaagaaat tctgggtctt atgttaactc tctgtttaac   12300
attttgagga actgtcaact tgttttttaa agtggctgtg acatttata ttctaccagc   12360 agtgaattaa atttccaatt tctccacata cttgacagca ttttttgttt tgtttttttt   12420
tttgttttgt tttttttgag acgaagtctc gctttatcgc ccaggctgga gtgcagtcgc   12480
acgatcttgg ctcactgcaa cctccgcctc ctgggttcaa gtgattcttg tgcctctcag   12540
cctcccaagt agctgagatt acaggcacgt gtcaccacac ctggctaatt tttgtatttt   12600
tttttttttt tgagacggag tctcactctg tcgcccaggc tagagtgcag tggcatgatc   12660
tcaggtcact gcaagctccg cctcccggga tcacaccatt ctcctgcctc agcctcccga   12720
gtagctggga ctacaggcgc ccgccaccac cccgggttaa ttttttttat atatttttag   12780
tagagacggg attttaccgt gttagccagg atggtctcga tctcctgacc tcgtgatctg   12840
cctgccttgg cctcccaaag tgctgggatt acaggcgtga gccactgtac ccggcctaat   12900
```

```
ttttgtattt ttttttagag acaggatttt gccatgttgg tcaggctggt cttgaactac    12960
tgacttcaag tgatccacct gccttagcct cccaaagtgc tgggattata ggcgtgagcc    13020
actgtgcccg gcctacactt tttaaattat ctgtcttctt tattatagcc aacctagtga    13080
gtatgaagta agtgtctcat ttgtgatttt gattgttagt ggtgactaac aatattgaat    13140
atctttacat gagcttgttg gccatgtaca catctttgga gaaatatcta ttcaaatctt    13200
ttgaccattt taaaattggg ttatttatct ttttattgtt gagctatagg agttctattt    13260
tattttattt tattttattt tattttattt tactgagaca gggtcttgct tgtcaccca    13320 ggctggagtg tagtgatgcc atcttgactc actgcagcct ctgccccac cccaggctca    13380 agcaatcctc ccacctcagc atcccacagc tgggaccaca ggcgcatgcc actgtgcctg    13440
gctaattttt tttttttgt atttagtat agacggagcc tcaccatatt gcccaggctg    13500
gtctcaaact actaagctga agcagtctgc ccatctcagc ttcccaaagt gctggaatta    13560
gaggcatgag ccactgtgcc tgtctattt tattttaag atgagacttt actttgtcac    13620
ccaggttgga gtgcagtagc atgatcatag ttcactgcca ttttgccctc ctgggctcaa    13680
atgatcctcc cggcttatct tactgagtag gtaggactgc aggcatgtcg ctaccacgcc    13740
cagctaaaag agttctttat attctagatc ggggtatcca atcttttgac ttccatgggc    13800
cacattggaa gaaaaattgt cttgggccac acataaaata cactaacagt aatgacagct    13860
gatgagctaa aaagaatta ccaaaaaatc tcataatgtt ataagaaagt ttacaagttt    13920
gtgttgggcc acattcaaag ccatcgtggg cctcatggct gtgggttgga tgagcttgtt    13980
ctaaatgcta gacccttatc agatggatgg tttgtagcta tttatctcat gctgtggatt    14040 tttttttactt tctttttttt cttttaggtt ttttttttctt aaataattca actgattata    14100
agctttaatc gttttgtttt cttgatagtg tcttttaaag cacaaagttt tatttcgatg    14160
gtgtctaatt tgtctgcttt ttctttggtt gcttgtcata tgtaagaaac tgttgctaaa    14220
tccagaatgc tgaagattta cttgtgaact ttgtttcctt ctatgtgttt tatagtttta    14280
gctcttacat ttaggtcttt gatcattttg ggggttttt tttttttttt tttttttttt    14340
gacagagtcc tgttctgtat cccaggctgg agtgcagtgg tgtgatcttg gctcactgca    14400
ccctctgcct cctcggttca agcaattctc atgcttcagc acccgagtag ctgggattac    14460
aggcatgtac caccaagcct ggctaagttt tgcattttta gtaaagagag agttccacca    14520
tgtttgtcag gctggtctcg aactcctggg ctcaagcagt cctctaacct tgacctctgc    14580
aagtgctagg attacagggt gtgagctacc gcgcccagtc catttggagt tcattttaa    14640 aatacggtgt gaggtagagg tcccatttca ttcctttgcc tgtgggtatc cagttgtccc    14700
agaaccattt gttgaaaaga ctgttgtttc tccattgagc aatgttgtga ggccctatct    14760
ccataaaaaa aaaaaaaaa aaaaagaatg cagaaggaag cagttttgc caattttgta    14820 gtatttactg acaatttgca tatatctgta cattctttag ctatttattt ttcttttgag    14880
ttattgcctt tgttcatttt tcttttggag gtgtttgtct tttcttatt aatttgtaag    14940 agattttgca aatgtataca atttcttttt tttttttttt tttttttttt tttgagacgg    15000
agtctcgctc tgtcacccag gctggagtgc agtggcgcaa tctcggctca ctgcaagctc    15060
cgcctcctgg gttcacgcca ttctccggcc tcagcctccc gagtagctgg gactacaggc    15120 gcccgccccct gcgcccggct aatttttttct atttttagta gagacggggt ttcaccatgt    15180
tctcgatctc ctgaccttgt gatccgccca cctcggcctc ccaaagtgct gggattacag    15240
```

```
gcgtgagcca ccacgcccgg ctaatttctt tcttgtttg ttttgagata gagttttgct    15300
cttgttgcct aggctggagt gcaatggcat gaccttggct cactgcagcc tctgcctcct    15360
ggtttcaaga gattctcctg cctcgacctt ccgagtagct gggattacag gtgcccacca    15420
ccacacccag ctaattttttt ttttttttttt ttttgtatt tttagtagag attcgtttca    15480
tcatgttggc caggctggtc tcaaactcct cacctcaggc gatccaccca ctttggcctc    15540
ccaaagtgct ggaattacag gtgtgagcca ccgtgcctgg acctcccacc ttatttgaa    15600 acaaatttct ttcttttttt ttcttctttt tttgttttga gaccaagtct cgctctgtca    15660
cccaggctgg agtgcagtgg catgatctgt gcttgctgta ccttctgcct cccaggttca    15720
agtgattctc ctgcctcagt ctcctgagta gctgggattg caggcatgta ccaccacacc    15780
tggctaattt ttatattttt agtagagacg gggtttcaac atgttggcca ggctggtctt    15840
gaactcctgg cctcaggtga tccacccgct ttggcctccc aaagtgctgg gattacagac    15900
ttgagccatt gcgcctggcc agtatcacat aatttcatat aaatatttct ttgtgtatct    15960
ttagataagg acttaaaaga aggcataatc ataacaccat tattaatacc taaaagaaat    16020
gaataataaa taattcattt gttgtatcaa atatccaatg ttcatatttc ctcaattgtc    16080
ccataataat ttttaaaagt ttgcttaaat caaaatcgaa acaagattct ttcattgcta    16140
ttgtttgaga tacatttgaa atcttaattt atagatttct ctgccatttc ttttccccca    16200
tatttatttg ttgaagaaat caagtgttgt ttcctatgga cttttcttact atctggattt    16260 tgctggttat attcttctgg cgtcagttta ctatgatccc ttttcccctg tattttctat    16320
aaatttgtaa ttaggtctag agatttgtta agattttgtg gtgtttttttt ttttttttt    16380 ccaaaaatgc atcataaatg gtggtgtgta gatatcgcag aagacacgta tcttaatgtc    16440
tttttgtggt attagtagtt attaatgatt actacctata tttattaatt cattatttgg    16500
actataagtt tataatattc tcattctctt gatccttttt ctgttgttag ctgtaatgct    16560
tctaaaagga gaaacctttc ctcttcaagc tacttggttg tcttaagggt tcacttctaa    16620
tagggaaaac gggctaaggg tgaaaaagga aatagttttt aactgaatct gttaatgagc    16680
tgtcacccca ggcaaagaga agcaaggcag gccctaggaa actgaagtgg gtttgggatg    16740
attggtgccc catgcgtgca tgcatgaagg gaagttaatc ctccctgtag tgaactctac    16800
ttggcttttt gtcagtggcc aggactgtca aggaagacct tgtccaaag tcatacctgg    16860 cctttgcttt tagctcttgg tagctgaagg aaaccaaaac agacctatga cctgcaaact    16920
tctgcttagt agacaaagtt ctcacagcct caattcagta agcaggagta agatgcttgc    16980
tttcccttga agtgaaatgt gaattacatg tttcttcaac ttgtgctaat attctctttt    17040
ttaatattta tttatttatt tatttattga gatggagtct cacactgtcg ccgaggctgg    17100
agtgcagtgg tgcaatctcc gctcactgca acctcagtct cccgagtagc tgggattaca    17160
ggtgcctgcc atcatgcccg ctaattttt tgtattttta gtagagatgg ggtttcacta    17220
tgttggccag gctggaattg aactcctgac ttcgtgatcc gcctgcctca gtctcccaaa    17280
gtgctgggat tacaggcgtg agccaccaca cccgggcaac ttgtgctaat attcttaaca    17340
gggtgtgaat cattcctgcc ctcaggctaa cataacccat acagccttcc ttataggaag    17400
atttcctact gggagtgaat tgtccagtg attcccccaa aatgtccccc aatcaaatat    17460
tttaaaactc agcatttaca tgtaaaaact aacaagcatg gtagcagcag tataagaaa    17520 cagcagtatg gcccttgtaa gggaaggctc cggaagatga gctgcactca gcctctaggt    17580
cacagctacc ttaggagttt gcagtagttc ctggggaagt cagtagacag gccatctctc    17640
```

```
aggcctgggc aagatagggt cttttttttt tttttcttttt gagatagagt ctcaccctgt   17700
cgtccaggct gaagtgcagt ggcatgatct cggttcacca caacctccac ctcctgggtt   17760
caagtgattc tcctgcctca gcctcctgag tagctgggac tacaggcgcg acaaccatg   17820
cctggcccat ttttgtagag atggggtttc atcatgttgg ccaagctggt ctcaaactcc   17880
tgacctcagg tgatccaccc ccctcccaaa gtgctgggat tacaggcatg agccactatg   17940
cccagtgttg tttttttttt ttttgaattg tagtgatagg atctcacttt gtttgatggg   18000
ctattcccaa actccaggcc tcaagccgtc ctcccgcctt ggcctccag aatgctgggg    18060
ttacaggttt gacccactgt gcctggtccc agaattcatg ttttttaaaag tcactctgtg   18120
ccaggctcat gcctgtaatc ctaatacttt gggaggctga agcaggagga ttgcttgagc   18180
ccgggagttt gagaccagcc tggacaacat agcaaaaccc taactctaca aaaatacaaa   18240
aactagccag gtgtggtggc atgtgcctgt agtcccggtt gctttggagg ctgaagtgga   18300
aagatcgctt gagtctagga agttgaggtt tcagtgagct gtgattgtgc ctgggcaaca   18360
gagtgagaaa agtcactctg attgtggtgg ggaaagtgga ttaatggaga atggaagctg   18420
ggaaacatgg tggttcttgc taagtcagta tcaagggttc acagatgagg gggctgtttc   18480
ttcctagtaa gggccttggc caaatagtca tggatctttc tctttggaag aagctcctca   18540
attttttcttc cccaaggcat atatggttga tgcttgaaca acacaggctg ggtctgtatg   18600
ggttcactta tatgtggatt tttttttcaac caaacttgga ttaaaaatat agttgtaggc   18660
cagggtcagt gactcatgcc tgtaagccta gcactttggg agcccaaggc aggtggatca   18720
cctgaggtcg ggagtttgag acgagcctgg ccaacatagt gaaaccatgt gcctactaaa   18780
aatacaaaaa atagctgggc ttggtggcgt gcgcttgtaa tcccagctac tcaggaggct   18840
gcagctggag aattgcttga acctgggagg tggaggttgc agtgagccaa cggggtggag   18900
gttgcagtga gctgagattg caccaccaca ctctagcctg tgtgacagag caagactctg   18960
tctcaaaaat aaataaataa aaatacagtg taggccaggt acagtggctc atgcctataa   19020
tcccagaact ttgagaggcc aaggcaggca gatcagttga agccaggagt ttaagaccaa   19080
tctggctaac atggtagaac cccacttcta ctaaacagaa gtacagaaat taaccaggca   19140
tggtggtaca cgcctgtaat cccagctact tgctaaactg aggcaggaga attgtaatcc   19200
cagctgcttg ggaagcttga ggcaggggaa ttggagggcg gaggttacag tgagctgtga   19260
tggtgccact ggactccaga ctgggtgaca gagcgagact ctctctccaa gagaaaaaaa   19320
aaaaattgta tttacaggac atgaaacctg cctgtatgat gtgctgactg ggagactaga   19380
gtatgcacag attttggtaa acaaggggat tcctgaaacc aatcccctga gtatatggag   19440
gattgactat atattttaat agaatttatt tattattatt tttagcagtt ttaggtttgt   19500
ggaaaaattg agcaggagta catagttttct ctctctcct cacatttccc cgttactaac   19560
gtcttgaaat agtgtggtac atttgttaaa actgaagagc caagtattga tacatcactg   19620
ttaaccaagg tccatagttt agagttcatt cttggtgttg ccgtttctat gagtgttggc   19680
aaatatataa tgcacatgtat ctaccattat agtatcatat tgagtagttt cactgcccta   19740
aaaatccccc tcgttctacc ttttcatccc tccctctatc tacctgaacc cctggcatcc   19800
attgatcctt ttactgtctc catagtttta ccttttacag aatgtcaaat agttggaatc   19860
atatagattg gcttctttcc atgttccttc tggcttgata gctcttttct tttcttttt   19920
tttgagacag agtctcgctc tcgcccaggc tggagtgcag tggtgcaatc tcagctcact   19980
```

```
gcaaactctc tgcctcctgg gttcaagcaa ttctcctgtc tcagcctccc aagtagcttg    20040
gactacaggt gcctacctcc ctgcctggct aatgtttgta ttttggtag agacggggtt     20100
ttaccatatt ggtcaggctg gtctcaaact cctgtcttca ggtgatccac ccacctcagc    20160
ctcccaaagt gctgcgatta caggtgtgag ccaccctgcc ctgccagctc ttttctctgt    20220
actgctgact aatactctat tgtataggtg tatgagttta ttcaccttct gaaggacatt    20280
ttggttgctc ctaagttttg gcaattatgc atgaagttac tataaacgtc tgtgtgtagg    20340
tttttgtgtg gtcatgtttt tagctcattt ggataaacac caaggagcac gattgctgga    20400
ttgtatggta agagtatgtt tagttctgta agaaactgcc aaactgtctt tcagggtgac    20460
tgtaccattt tacattccca ccagcaatga atgaagttcc tgtcgctcca catcctcgtt    20520
agcatttggt gttgtcagtg tttttggcttt tcaccattct aatagatgtg tagtgatatc   20580
ttgttttagt ttgcaattct ctagtgatgt atgatgttga gcatcttttc atctgcttat    20640
ttgttgttgt tgttgttgtt gttttttatt gagatggagt ctcgctctat tgcccaggct    20700
ggagtgcagt ggtacaatct tggctcactg caacctctgc ctcccgggtt caagtgattc    20760
tcctgcctca gctccccaag gagctgggtt tacaggcgcc cgccgccatg cccagctaat    20820
ttttgtatt ttagtagaga tggggtttca ccatgttgcc caggctggtc ttgaacttct     20880
gacctcgtga tctgcctgag ctcaagcaat ccgcctgcct cagcctcaca aagtgctggg    20940
tttacaggcg tgagccaccg cgccctgtct tcatctgctt atttgatatg tgtatatgtt    21000
atttggtgga gtgtctgttc tgatcttttg cccatttta aatcagattg tttattgtt     21060
tctgcggttc ttttagtttg ttttttttgag acaaactctc gctctgtcac ccagtctgga   21120
gtgcagtggc gtgatctcag ctcattgcga cctctgcttc ctgggttcaa gcgattctcg    21180
tgcgttagcc tcccaaatag ctgggattac aagcatgtgc cactgcacct ggctaattttt   21240
tgtatttata gtagggacag ggttttgcca tgctggccag gctggtcttg gactcctggc    21300
cttcagtgat ccacccactt tgcctcccaa agtaatgag attacaggtg tgagccacta     21360
tgcccggctt attgttaagt tttaagagtt ctttgtatgt gtgtattttt tgtgattctt    21420
ttaaagttaa tgcttaataa aataattgta catatttatg ggatgcatgt gatatttga     21480
tacatgcata caatgtggat caaatcaagg taattagagt atcacctcaa acattttca    21540
tttcttatg ttggaaacat ttcaaatctt ctagctattt tgaaatatat agtaaattat     21600
taactataag tcacctcatt gtgctatcaa acattagaac ttattctttc tacctgactt    21660
tatttttttt acccattaac caaccattct tcatcagctc cccatctccc ctactctttt    21720
tttttttttg agatggagtc gctctgtcac ccaggcggga gtgcagtggc gcgatctggg   21780
ctcactgcaa cttccgcctc ccgggtttaa gcagttctct gcctcagcct cctgagtagc    21840
tgggattaca ggcgaatgcc accatacctg gctaattttt gtattttag tagagatggg    21900
gtttcaccat cttgtccagg ctggtcttga actcctgacc tcctgatcac ctgcttcggc    21960
ctcccgaagt gctgggatta cagggtgag ccaccacgcc tggcccctct tactctttgc     22020
ttagcctccg atatctatca ttctattctc tacttctatg agatcaactt tttttttagc    22080
tcccacatat gagtaagaca tgtaatattc ctctttccgt gtctgatttc tttgtatatt    22140
ttggataata gtctttatt agatacgtgt tttgcaaata ttttttccca gtccctgact     22200
tatcttttca ttctcttaag tagtgtcttt tgcagagcac acatttttaca ttttagcaca   22260
gtccagttta ccaattcctt ctttcatgga ttttgctttt ggtattgtgt ctaaaaagtc    22320
tttgccaaac cacagtcagc tagagttccc cttaccttac aggattttta agttttttgtt  22380
```

```
ttacatttat gtctgtgatt cattttaagt taacttttat gtgaaagatg taagatctat   22440
gtctggaatt tctcttttt tttgagatgc agtctcgctc tgtcgccagg ctagagtgca    22500
gtggcgtgtg atctcggctc actgcaacct ctgactccct ggttcaaatg attctcctgc   22560
ctcagcctcc tgagtagcac acgccaccat gcccagctaa gttttgtttt ttagtagaga   22620
cgggatttca ccatgttgac ctggatggtc ttgatctcct gacctcgtga tccgcccgcc   22680
tcagcctccc aaagtgctgg gattacaggc atgagccacc acgccctgcc gggcttaacc   22740
atttttaagt gtacagttca gtagtgttaa gcacattcac attgcaaaca atctctacaa   22800
gtttttcaaa aaaactgaaa aacttgcaaa actgaaactt tatacccact aagtggtaac   22860
tccccattct agtggttacc ctagcccctg gtaaccacca ttctcctttc tgtttctatg   22920
aatttgacta ctctgggaac cttagataag ggaaatcata cagttcttgt ttttttgtgg   22980
ctagcttctt tcacagcatg atgtctaagg ttcatcccca tagtaccatg tgatcctaat   23040 gttttaaac ctccacagca acactttcaa gttagatttc acattttaca ggtgagaaaa     23100
tggagactca aaagaaaaa gcaattgtcc ataggtagtg tcatgggttg acactagctt    23160
tgaaggttgg tccccacctc caaagacatg cccaagtccc aagtcccagt accgtgaatg    23220
tggtgttatg tggaaatagg tctttgcaga tgtaattaag ttatggatct cgatatgaaa   23280
tcttcctgag tttggggtgg actctaaatt ttacgactga tgtcctcata agagaaggga   23340
gggggaggtc aggcgcagtg gctcacacct gtaatcccag cactttggga ggctgaggcg   23400
ggcagatcac ctgaggtcgg gagtttgagn nnnnnnnnnn nnnnnnnnnn nnnnnnnnnn   23460
nnnnnnnnnn nnnnnnnnnn nnnnnnnnnn nnnnnnnnnn nnnnnnnnnn nnnnnnnnnn   23520
nnnnnnnnnn nnnnnnnnnn nnnnnnnnnn nnnnnnnnnn nnnnnnnnnn nnnnnnnnnn   23580
nnnnnnnnnn nnnnnnnnnn nnnnnnnnnn nnnnnnnnnn nnnnnnnnnn nnnnnnnnnn   23640
nnnnnnnnnn nnnnnnnnnn nnnnnnnnnn nnnnnnnnnn nnnnnnnnnn nnnnnnnnnn   23700
nnnnnnnnnn nnnnnnnnnn nnnnnnnnnn nnnnnnnnnn nnnnnnnnnn nnnnnnnnnn   23760
nnnnnnnnnn nnnnnnnnnn nnnnnnnnnn nnnnnnnnnn nnnnnnnnnn nnnnnnnnnn   23820
nnnnnnnnnn nnnnnnnnnn nnnnnnnnnn nnnnnnnnnn nnnnnnnnnn nnnnnnnnnn   23880
nnnnnnnnnn nnnnnnnnnn nnnnnnnnnn nnnnnnnnnn nnnnnnnnnn nnnnnnnnnn   23940
nnnnnnnnnn nnnnnnnnnn nnnnnnnnnn nnnnnnnnnn nnnnnnnnnn nnnnnnnnnn   24000
nnnnnnnnnn nnnnnnnnnn nnnnnnnnnn nnnnnnnnnn nnnnnnnnnn nnnnnnnnnn   24060
nnnnnnnnnn nnnnnnnnnn nnnnnnnnnn nnnnnnnnnn nnnnnnnnnn nnnnnnnnnn   24120
nnnnnnnnnn nnnnnnnnnn nnnnnnnnnn nnnnnnnnnn nnnnnnnnnn nnnnnnnnnn   24180
nnnnnnnnnn nnnnnnnnnn nnnnnnnnnn nnnnnnnnnn nnnnnnnnnn nnnnnnnnnn   24240
nnnnnnnnnn nnnnnnnnnn nnnnnnnnnn nnnnnnnnnn nnnnnnnnnn nnnnnnnnnn   24300
nnnnnnnnnn nnnnnnnnnn nnnnnnnnnn nnnnnnnnnn nnnnnnnnnn nnnnnnnnnn   24360
nnnnnnnnnn nnnnnnnnnn nnnnnnnnnn nnnnnnnnnn nnnnnnnnnn nnnnnnnnnn   24420
nnnnnnnnnn nnnnnnnnnn nnnnnnnnnn nnnnnnnnnn nnnnnnnnnn nnnnnnnnnn   24480
nnnnnnnnnn nnnnnnnnnn nnnnnnnnnn nnnnnnnnnn nnnnnnnnnn nnnnnnnnnn   24540
nnnnnnnnnn nnnnnnnnnn nnnnnnnnnn nnnnnnnnnn nnnnnnnnnn nnnnnnnnnn   24600
nnnnnnnnnn nnnnnnnnnn nnnnnnnnnn nnnnnnnnnn nnnnnnnnnn nnnnnnnnnn   24660
nnnnnnnnnn nnnnnnnnnn nnnnnnnnnn nnnnnnnnnn nnnnnnnnnn nnnnnnnnnn   24720
```

```
nnnnnnnnnn nnnnnnnnnn nnnnnnnnnn nnnnnnnnnn nnnnnnnnnn nnnnnnnnnn    24780
nnnnnnnnnn nnnnnnnnnn nnnnnnnnng atggagtctt gctctgtcac ccaggctgga    24840
gtgcagtggt gcaatctcat ctcactgcaa cctccacctc ctgggttcaa gcgattcttc    24900
tccctcagcc tcctgagcag ctggagctac aggcatgcgc caccacgctc agctaatttt    24960 tgtattttt gtagagatgg agtttcacca tattggccag gctggtctca aactcctgac    25020
ctcaagtgat ccacccacct tggcctccct aagtgttggg attacatcca tgagccgctg    25080
cgcccggcct ataattcttt atgtacattg ttagattcag tttgctagta ttttatttag    25140
catttgtctg tgttcatgag aggtattgtt ctgtagtttt ctttggtttc ttttctgtct    25200
agtttagggt aatgctggcc tcatagaata ggttaggaag tacttcctct gcttctgttt    25260
ctgaaagaga attgagataa tatctttttt tttgagatgg aatcttgctc tgtcatctag    25320
gctggagtat agtggtgcca tcttggctca ctgcaacctc tgcctcccag gttcaagtgc    25380
ttctcctgcc tcagtctcct gagtaggtgg aattacaggc atgcaccacc atgcctggct    25440
aatttttgta ttttagtag atgggggtt tcactgtgtg ggccaggctg gccttgaact    25500
tctgatctca ggtgatccgc ctgccttgtc ctcccaatgt gctaggatta caggcatgag    25560
tcactgcgcc tggcctgaga taatatctaa aacagtttgg tagaattcac cagtgaaccc    25620
atctgggcct ggtgccttt gcttagaag attattgatt attgattcaa tttccttaat    25680
agataaaggt acattgagat tgtcttttct tcttgggtaa gttttaatac attgtgtctt    25740
tcaagaaatt gttccatttc atctaggtta tcaaatttgt ggattagagt ccttcataat    25800
atttctttgt tttgcttttg atgtccacag gtttagaagt gatggccctt tttcatttt    25860 tctattagca atttgtgtct ttgccttttt ttttctttc ttaatctggc tagaagctta    25920 tcaatttgt tgatctttc aaagaaccag ttttggtttt cactgatttt tctctgttaa    25980
ttttgttttc agtttaattg atttctgttg taattggttt tcttctgctc actttggatt    26040
tttttttagt tttcctagaa aactaagttt ttaagtgaaa actgagatta ttgatttta    26100 gatctttttt gtaatgttta tagttaatgc tatacaattt cctgtaagca ctgctttctc    26160
tgtatcttac aaattttgat aagtcatatt ttcattttca tttagttaga catatctctt    26220
gagacttctt tgatccatct gttatttaga agtgtggtgt ttaatctcca agtatgtatt    26280
ttgggatttt ctggctatct ttctgctatt gatttctagt ttaattacat gtggtcttag    26340
agcataccct gttgctttc tattctttc aatttgttaa ggtgttcttt gtggctcaga    26400
agttggtcta cttttttttt tttttttttt tttttaaaga aaaactggct agatgcagtg    26460
gcttatgcct gtactcccag cactttggga ggcctaaatg gaggatcac ttgaggtcag    26520 gagtttgaga ccagcctggg caaaattttt aaaagattag ttgggtatgg tggcatatac    26580
ctgtgtatgg ctgaagtggg aggattgctt gagccctgga ggttgagact acattgaact    26640
atgatcacat cactgtactt cagcctgggc aacagagtga aactttgttc tctcttgaaa    26700
agaaaaaaat agttgatgac ataaagttca ttcatctttt ttgtatgtga cttcaaaata    26760
actactgatg gttaaaaaaa aaatcagaat gatgcagccc aagtgtccat caatggatga    26820
atagataaac aatatgtggt gtgtgaatac aatggactac tattattcag ccttaaaaaa    26880
taagaaaatt ctgacactgc tgtaacatgg atgaaccttc agctcgttat gctaaatgaa    26940
aaaaaccaga cgcaaaagga caaatattgc atgattgcac ttatatgagg tgtctggagt    27000
ataaaagtca tagaaacagt aattcaataa ttagaataat gattgccagg ggctctgggg    27060
aggagggaat gaggaattca tgtttaatgc atacagagtt tcatttggaa aagattaaaa    27120
```

```
agttacggag gtggatggtg gtgagggttg cacaacagtg tgaatgtact taataccact    27180
gaattgtaca cttaaaaatg attaaaatgg tacattttat gttacatata ttttacaaca    27240
acttttacag atggaaaaaa tttattaaaa aacatcagga tggtgttgac agtgaaaagg    27300
ttaaagagtt actttaaaaa tttactttat tccggccagg tgccgtgact cacacctgta    27360
atcccagcat tttgggaggc cgaggtggac agatcacctg aggtcgggag ttcgagacca    27420
gcctgaccaa catggagaaa ccccatctct actaaaaata caaaattagc cgggcgtggt    27480
ggtgcatgcc tgcagtccca gctactcggg aggctgaggc aggagaattg cttgaactcg    27540
agtggcggag gttgcagtga gccaagatct cgccattaca ctccagcctg gcaacaaga    27600 gcgcaactcc atctcaaaaa aaaaaatttt tttaattttt attccaaata tttatattta    27660 ctttgggct tatgtgacca gtttaatttt catttgtaat tgacttgata gaatacacta    27720
tgttcagtta agattcctta tggtgtgatg aggaatagga attttatgta agtaagccca    27780
aaattgtatc agattaatct gatatttgca gaagatattc atgcattaat gtaaggacca    27840
ctctgcttat tcatttgact gatttgtagc aacatggtta gaaatcatca aggtgtttga    27900
gatcaaagga tcatcagagg tcatttactc taatcctttc tttaaaaaat taataacttg    27960
agcctcagag aagttaaatg atattaccaa gttctgctgt tagtatagtg actttatctt    28020
tacctgaagc cagggcttct tagccctagt ctgtaatgtg tcctagtatg cctgtggaat    28080
ctggtcctat cagcccaagt ctgttaaatc aaataaaacc agggcttggt gcttcacctt    28140
gtcttctacc ataccactgg gtttcctgtg gaccatgcag ataacgatga tgggctcagt    28200
tggcttgata gtgataactc ctaaagcagc tgcttctaag tgtggttctc aatctgagga    28260
agttaaaaaa aatttagtg actagaaccc acttctcagc tactcttact aaataaatct    28320
gtaggggagt gatagttttc aattttttt tttttttttt tttttttgag atggagtctc    28380
actctgttgc ccaggctgga gtgcaatggt gcgatctcag ctccctgcaa cctctgcctc    28440
ccagcctcaa gcgattcttc tgcctcaacc tcctgagtag ctgggattac aggtgcgtgc    28500
caccatgcct ggctaatttt tgtattttta gtagagatgg ggtttcaccg tgttggtcag    28560
gctggtctcg agctcctaac cttgtgatct gcctgcctca gcctcccaaa gtgctgggat    28620
tacaggcatg agccactgcg cccggccttc acatattttt tgaaataata ggccagttgc    28680
ggtggttcgt gcctgtaatc tcagcacttt gggaggccga ggtgggtggg tcacttgagg    28740
ccaagaattc aaggccactc tggccaacgt ggtgaaaccc tgtttctact gaaaatacaa    28800
aaaattagcc gggtatgatg gcatgtgctt gtggtcccag ctactctgga agctgaagcg    28860
tgagaatcgc tttaacttag gaggcagagg ttgcagtgag gcgagattgc gccctgcgc    28920 tccagcctgg gtgacagagc aagactccat ctcatttaaa aaaaaaaaa aaaatcata    28980 ggcagtaaag gttgagaact gctgcccaaa ggacctatta aactatagat tcccaaacct    29040
ggccaattat caaaatccct caagaagggg caatggggtc taaggaccc cactggaaga    29100 gattagtagt ccaagagtga gatgaactgt tggaagtcct cagacttcca aactattaga    29160
atagttttgc ttcctcaaaa tagagtagtt ttgcttcctc actaattttt ctgtattgat    29220
tagaaccgta acaagtgaat taaacaacta caaaatagtt atgtgggcaa cagacattat    29280
tgtaatgaag tgaagtttgg ctcaggcctt ggaacacaat tgcgttttgg attaaaagta    29340
aaaatattta ttaaatcatg tgagattatg tgtaagtttt aaaaaattgg tcttatacaa    29400
aagtgttggg ggttttttt ttttttttg gctgaatttg ttttaagca agacagaata    29460
```

```
tttatattgt tggagagtca cagaggaggt gtgtttgtgg atttaaatgt ggagacagtg   29520
tgccttgagt gcccttatc agtctgattc gagccactga taatcatgga tttgaactac    29580 cgcccccccac cccctgcgcc tagatagggt ctccctctgt tgcctaggct gcggtgcagt  29640
ggtgggatct cggctcgctg caacctctgg cttagcctct tggagtagct gggactacag   29700
gcacacaaca ccatacccag ctattgtttt ttttgtttgt tttctttgtt tttttttttt   29760 ttttttttt atagagacag ggtttcacca tgttgctcag gctggtcttg aactcctgag    29820
ctcaagcaac ccacctgtct cggccttcca gagtgctggg attacaaggc ctgagctacc   29880
atgcccagct ttcacttcat ttaaaaacca tagtttttaa aatccacagt cctactgacg   29940
aacacagagg ttgtttccag tgttttcatt tgcagtattg cagtgattgt ttttgcacat   30000
gcctccttat gcacatgtgc tgtggcttct gggacagaga atggacatat taagtgtttt   30060
attgatcctg ctaaattgtc cttcagccaa actgctgcag aggtgataga gatgaggtgg   30120
gtactcagga gaattgtgcc cagtgcttgt gtgctggttg ctgacctgga aacattttat   30180
taaaaatgct cgattaggtt agtgatgtaa agatgattac caggtgatag taaccagaat   30240
aattgtgtca aaacatcaag aattatcaag agatgccagg catggtggct cacgcctgta   30300
atcgcagcac tttaggaggc caaggtgggc agattgcttg agctcaggag ttcaagacca   30360
gcctgggcaa catggtgaaa ccctgtctct accaaaaata caaaaatttg ctggatgcag   30420
tggtatgtgc atgtggtctc agctattcag taggctgaga cgggatgatc acttgagcct   30480
ggaaggcaga ggttgcagtg agccgagaca atactgcagc ccgggcaaca gagtgaaacc   30540
ctgccttaaa aaaaaagag aaaaagaatc atcaagagaa aacttaattt gatgtgttct    30600
gtgttttctt tggtgcttcc tgtcagtgtt agaaactgta ggttatatat ttaataattt   30660
ttctcctgta tttgttcaac ttgactataa aatattaact ccaaatgcct agaatttcaa   30720
aacacctctt cattataaag tatcagctat ttctgagtcc ccttaagctc atagtattgt   30780
gtcattgtaa aagatctgtt gtgaaaaata atttttgtca acatgaaagg tcttaatgtg   30840
tctcccagtt tacattttac atggtctttt ccgtgtattt ttatagttga catatatagc   30900
tttttttgta aatatacttt cctatatgaa catgccaagg tttacttaag cattctctta   30960
ttcttggaca tctaaattgc ttcttatttt ctattgtaaa taaagtgcta gaagcttcct   31020
tcctgaaaag ttatttactg ttcagctagt atttccatct gtgttcctca aaataagatt   31080
actgagattc atgtatgttg ccagaaagat tgtgaggttt aacagtgaat gaggaaaact   31140
tttaacactt aaggtctctc aagtacagca agttttatca tttttacttt tttttgagat   31200
aaggtcttgc taagttgcct aggccagtct caaactgctg ggctcaagca atccttctgc   31260
ttcagactcc ggagtagctg ggattatagg tgtgcagcac cacacccggc tttcttgtat   31320
tattattatt attatttatt tatttatttt tgaggtggag tttcactctt gtcacccagg   31380
ctgtagtgca atgacccgat gtcggctcac tgcagcctcc atctcccagg ttcaaatgat   31440
tctcctgcct cagcctccca gtagctggg attataggca tgcgccacca cacccaccta    31500 attttctat ttttagtaga cagggttc ctccatgttg gtcaggctgg tctcgaactc      31560
ccgacctcaa gtgatatacc cgcctgagcc tcccaaagtg ctgggattac aggtgtgtgc   31620
caccgcgcct gtccgctttc ttgtattatt tttatcttgc tgtagtggtt gtaggatttt   31680
tgcctggtgt gttcattgga gtgtgtgtgt gtgtgtgtgt gtgtgtgtgt gtgtgtgtgt   31740
gtgttttgag atgtatgact gtgttggttg tgttgtcatg ctttgaaggt tcattcatgt   31800
gctcatctat ttttctcatt atacttagtc acttaaaaac ctctttattt tggatttcta  31860
```

```
attttttacag ttcctgtttt attaatcacc ttcttatctg aaagtgaagt attgaattag   31920
aaatttgtgt gtccctgatc agaagatcac gtacacagga acaagataag ttgagggatt   31980
tagcagttcc agaaatgggc atttgtgtct tccagtggag aagcatctgc aaaagaattg   32040
tgcagatttg gccgggcacg gtagctcatg cctgtaatcc cagcactttg ggaggccgag   32100
gcgggcagat cacctgacgt caggagtttg agaccagcct ggccaacatg gtgaaacccc   32160
gtctccacta aaaatacaaa attagccagg cgtggtggcg ggcgcctgta atcccagctg   32220
cttgggagga tgaggcagga aaatcacttg aacccatgat gcggtggttg cagtgagcca   32280
agatcgcacc attgcacacc attgcactcc agcctgggca acagagtgag actccatctc   32340
aaaagaaaaa aaaaaaaaat catgcagatc tatttaactt tccataaagt gagacagaac   32400
tccgtaagtt agggtaaatt taaggacatg taatgtgctc attatgttat taggaaatta   32460
atggtgaaaa gggtgttttg gcctcgtgtg gcttcttgaa gatgacctgt gaaaacagca   32520
aggcctggaa gggaactgaa ttgggcagat gcagatttgt ggactctagt gaactatgga   32580
gaaacaatta ggactccagg atgagatctt cttaggttgg tgcagaagta attacagttt   32640
tggactgtga attttaaatc attataacta ggcttaaaca catctttatt aatcaaaata   32700
ggaaccatta cagtcaacac attttcacca acaagaaata agtttgtttc ttcctgcagc   32760
acaaaaatcc gtgcttcagg attcaacaaa ctgttggaaa gcattttctg catcctgctg   32820
gttgtggaaa tgttttccct gcaaaaagtt gttgagatgc ttcaagaagt ggtagttggt   32880
tggcaagagg tcagatgagt atggtgaatg aagcaaaatt ttgtagccca attcattcaa   32940
cttttgaaac gttgtgtgac gtgaggccaa acgttgtcat ggagaagaat tgggcccttt   33000
ctgttgacca atgccggctg caggtgtagc agtttccgga gcatctcatt gatttgctaa   33060
gcatacttct cagaggtaat ggttttgcca ggattcagaa agccgtactg gatcagacca   33120
gcagcagacc agcagcagac caccaaacag tgaccatgac cttttttttt tttggtgcaa   33180
atttggcttt gggaagtgtt ttagagctgc ttcttggtcc agccactgaa ctggtcatcg   33240
ccagttgttg tataaaatct acttttttgtc gcacatcaca atccaattga gaaatggttc   33300
gttgttgtgt agaataagag aagacaacac ttcaaagtga tgattttttt ttttaaattt   33360
ttgctcagct cctgaggcac ctacttttca agctttaaat aagtagtgac cctgggattc   33420
ctagatccct tgtgggtcct gatgtaatgt ggtctgcaga tgttttcagt attcataaag   33480
gtgaacaatt tgcctgttaa ctaaaatatg aagttgtgtt ttgggtttgt gtgggtcatc   33540
cattatcata acgtctgagt cttctttta ttgacttaga gtcttccagt cctcttattt   33600
tgcttggtgg tagcatgtac aagatagaag tttaggcaca ataatctatt cagtggctgt   33660
aatagcagct tgtcctgcct ggttttttt gtttttgttt ttttgtaata gcattgagga   33720
gatataattc acccatttaa agcaggtgaa ttatatattt tatgttttaa tgtattccta   33780
gagttgtgca accatcacca gagtaagtta tagaacattt tcatcaaccc aaaaagaaac   33840
tttgttttca ttaatcgttc ctcctcattt ctcccctaaa ctcccagcac taggcaacca   33900
tcagaatact ttttgtctcc acagatttga ctgttttgga catttcatat taatggaatg   33960
tacgatacag tagtataata cattaatttt ggaaggccaa agttaatggc cttcgatgtc   34020 tcccttttt cacttagagt aatgtcttcc aggtccatct gtgttgtagc ctgtatcatt   34080
actttatcct ttatgtggct gagtaatatt ccattgtatg gttgtaccat gttttgttta   34140
ttcatcagct gatggacatt taggttgttt tccattgact attaagaata atgctgccat   34200
```

```
catgcttgag ttttttttttt tttattttag gggtgggtgg tgggcagagg gcacagtctc    34260
gctctgttac gcaggctggc gtgcagtggt gcgatctcgg ctcaccgcag cctcctctac    34320
cccctgggtt ctagtgattc ttgtgcctca ggctcctgag tattatgctg cagtttttat    34380
gcgagcatac attttcagtt cttttgggtc aatatctagg agtatcccca cttttggatc    34440
tgagtgttaa ttgagcctgt tgtgttctca cattccctgt acttacatgg aaatagtgct    34500
ttgcctaaaa agaaaaacaa aagacctaat tgcgcaggcg agtgagagag aaagagagag    34560
agagagaaag agagagagag agagagagag agagagagag agagacacgc tagggttatt    34620
tccaccctga tactctttgt gtagtcttgg tatgactagc aaagaagcaa gctccaagtt    34680
gtaatttgct tccaagtttc tggcttctgt gggaatttct gcatcttagt aatgacaatt    34740
ttcagttact tgcagtaagt aaattatcag ccagtcttac tctgtattac tagtctagga    34800
ggagtttact tgtatattga gagaaatgct gcagctttta ccttacttct aatggggatt    34860
aatgcttact taacttaccg tttcggaggc aaataaaaag tgtaggacca attatggtct    34920
tgaagtgaga gagaagtctg gctagtgaat ggtgattggc aactccagtt gactgttcat    34980
ggcatcttag atctgtgagg agagaggagg aaggaaagt tcaagctggt ctttatggta    35040
agttctggaa catttccctg tgtcagtggg tcatctgttc attcactgtg taaaatggct    35100
gaggaaagtt ttcattttca tacttcttca ttgtgtaaac ctttgatttt tagtgatttc    35160
agagtttgtt tttataatta tttaaacatg tgaagaggat acagagtaac atatcgaacc    35220
tctggttatc ttccactggg atttgacata tttgagttcc ttttcttcct tcttccttcc    35280
ctccctccct ctctctttttc ttaaggaatg caactactca gattcacctg cataccgttg    35340
gcatacctct cacttcctca gaggtgacca gtcctcagag caaatgtgtg ccctttccat    35400
ccgcgctttt atgctctcat ctatgtttac atctattagt acactattgt ctatattttt    35460
aaacattaca taaatggtgt aattttttact tttaattctg tagtggtatt tctcaaatta    35520
agttctgcat aaaacatttt tatagatatc cagtgttagc ttaacgtttt tcttattgtg    35580
gtaaaatata cataagataa aatttaccat ttttgccatt tttaagtata caagtcagca    35640
gcattaagta cattcacagt gtagtataac catcaccatt gtccattgct ggaactttc    35700 ctcatcctaa acagaaactc tatactcatt aaacaatagt ttatcactcc ttccctgcaa    35760
ctagatgctg gcagtcacca ttctactttc tgtctctatc aatttgcctg ttccatctaa    35820
gtggaatcct acatatttgt cgctttgttt ctggctttt ttttcttctt gtgatgcttt    35880
gttttaatta tgtttctggc tttcttcatc tagcaggctg attccaaggt tcgtccatgt    35940
ggtagcttgt atcactttaa ttcttttaga gataattaat attatgttgt ctgtatatgc    36000 cacatttgt ttttcattc aaccttgatg gacatttgga ttgtttcccc cctttaacta    36060
ttgtgaataa tactgctatg aacattgatg gccaaatatt tgtttgaatc tctgatttca    36120
gttcttttgg ttctataccct aggagtggaa ttgctggatc atatgataat tctatgttta    36180
actctttgag ggatggccag acttttccac catagctaaa tcattttacc ttcccacaag    36240
caaagttcaa gggctctagt ctctccccat catgtccttt gcacttttt tttttttttt    36300 ttgaggcaga gtctcactct gttgcccagg ctggagagta gtggcacgat ctttcctgac    36360
ctcaagtggc ccctgctttg gcctcccaaa gtgctaggat tataggtgtg ggccactgca    36420
ctctgccaat tttaaattt taattttcat ttatttttcg tttttcatt tttagttttt    36480 tttattttt gaagggataa ggtctcattt tgttgcccag gctggtcttg aactcctgac    36540
ttcaagcaat cctcctacct cggcctctca gagtgctgag attgtaggtg taagcccctg    36600
```

```
cacctggcct ttactctctt gatagtgtcc tttgatgcac aaaagctttc aattttgatg   36660
aagtctattt tttctcttgt tacctgtaca tttggtgtca tatatctaag agaccattgc   36720
caaatgcaat gtcgtgaagc tttccctcag tgttttcttt ccatagtttt atgattttag   36780
ctcctaagtt taggtctttg atccattttg agttaatttt tgtatacagt ttaagagtca   36840
gacttgagac tctgggcgca gtggctcact tctgtaatcc cagtactttg ggaggccgag   36900
gtgggtggat cacctgaggt caggagtttg agaccagcct ggccaacatg ccaaaacccc   36960
gtctctagta aaatacaat aattagccag gcatggtgat gcatacctgt ggtcccagct   37020
actcgggagg ctgggcagga gaatcgcttg aacccgggag gtggtggttg cagtgagctg   37080
agattgtgcc actgcactct agcctgggcg acaaaagcga gtctccatct ggggaaaaaa   37140
caaaaaaaaa gtcaaacttg agtcttttgc ctatggatat ccagttttcc catcactatt   37200
tgttgaaaag actatccttt ctcaactgtg aatggtcttg gtatcctagc tgaagttatt   37260
tttattacta tgttacttag gaatgcacat aaggccgggc acagtggctc atgcttgtaa   37320
ttgcagcact ttaggaggtc aaggtgggag gattccctga gccgaggagt ttgagaccag   37380
cctgggcaat atagcagcaa gaccccatct ctatatttta aaaaagaag aagaaaaaaa   37440 aaacccactc tgacacataa ttatttaaac ttgtatgcat tcttttcttt ctttattttt   37500
aaaaaattga gatagcagct tactctgttg cccaggctgg tctcgaactc ctgggctcaa   37560
gcagttcctc ttaccttggc ctgaagtgct gagatgacag gtgtgagcca ctacatctgg   37620
cctgcttaca gattataaaa agaaaataag tttacaaatt aaagacagat aaaatgacag   37680
aatcagtaaa attaaaattt cttttatgga gctgatgatg tttatcccaa ttggtcctct   37740
cattgtgaat atggtattgt tgctgtggca gatttggagg cttggcaat ggcttctatt   37800 accttgccat gaggtaactc agttccctca ttactttct ctgagaactg taaaaccttg   37860
gaggggtgcc ctctgccctt cgcttggcat gtgtattatg cggggatcag gtcttactct   37920
gttcttgatt gttagtacaa acgagttaaa atcctgttgt ttggccttag cctgatggta   37980
aacacaacag cacacatggg ctgtgaaatc cctgggcagc tctgtgtttc tagggaagca   38040
tctcgatgat ccagaacagg cttatactga tgttttagtg taattttgaa atgaaaacac   38100
tgcatttaaa aaattctcat agagaatgta tagacctgga gaagtgttag cagacccagt   38160
ttaagacatg tctcaatatt acggaacatt gctttattcc ctgtcctgct tgtacattta   38220
attttttcac ccacttttaa acaacttggg tactgtggcc tgtgcctgta ttcccagcta   38280
ctagggaggc tgaggcagga agattgcttg agcacaggac ttcgagggct atagtgagct   38340
gtgtttgtgc ctgtgaatag ccattgtgct ccagcctggg caacatagca agaccctgat   38400
accctgggtt tttaaaaaac aaaacaagat acatgctgac atttctagtt tggcaggcag   38460
agcttgttct gctccccacc ctcccttttc ctatagtaac catttatagg acatctcact   38520
gttgtctact ctgtgttgcc tctgcttccc tacgtggtag atctaggaat cttaggattt   38580
cttagtttta gctggtgatc catatatttt tcttaattcc attgtaactt cagcttttct   38640
tattgcttgt aagaaggctg tttccattga atacaaacaa ataaaagct tttatttgta   38700 atcttagaga taggatgttt gtatttaaaa ataattgtgc tgtcaaaatt ctgtcaagtt   38760
ggcttctacc atattagttt tttttttttt ttatgtgatt tatatgaccc tggagtacct   38820
tgtcttctca ctgttaaatt ctcaactgag ttgtccctat ttaaagtgtg agactgtgcc   38880
agtttgattt taaaatattg caagtgcgtt atggcaagat aaagctgcaa agaaagaacc   38940
```

```
ttcatgttcc tttgattata aatgcttttg gcacttgttt ctactggaag ataactttt    39000
cctgatgtgt ttttgaggaa agaacctcca acgctctaga caggtctggg ggcaaatgac   39060
taaaacatca actgaggccc tgggctgtct ccatgaggat atccctcta ttgtctctga    39120
aatgtcccag catgtggtgc atttcttgtt agtgtggact cctctgtata taacacccat   39180
tatttatgtt ctgtgcataa catgaaatag tgccctaatg caattccagg atgtaattca   39240
acatttctat aaaaatacaa tgtttttgta catttgcatc aaacaataac cagataatta   39300
tatttgttaa gaaaatagta ttttggctg ggtttgatag ctcacgtaat cccagcactt    39360
tgggaggctg aggcgggtgg atcacttgag gtcaggagtt caagaccagc ctggccaaca   39420
tggtgaaacc ccatctctac taaaaatgca aaattagcca ggcatagtgg tgcatgcctg   39480
taatcctggc tgctcaggag actgaggcag gagaattgct tgaactcagg aagggagat    39540
tgcagtgagc tgagattgtg ccactgctct gtagcctagg caacagagtg agactctgtt   39600
tcaaaaaaaa gaaaaagaa agaaagaaag aaaatagtat ttttggtatt tgttttcaca    39660
aactagagca tttatgtgaa ataacattgc tagtattgat attataccat agtataatac   39720
ttagttcttc aaatgatgta tctctgctga tcagctacat gatatctacg tgagttgttg   39780
cgtgtttttt ctcttttttt aaagagcagt gcatttttga atgcttttga aaaattgcag   39840
taaaatacat aaacgtaaca tttaccttgt aaccatttta attggtacaa ttcagtgaca   39900
ttaagtacag tcccagtgtt gtgcaaccac tgttactgtc tagtttcaga atgttttagc   39960
tccaaatggg taccctgtac ctgttgaaca ttcagtccta gtggcccaat aatcttcttt   40020
atgtctgtat agatttgcct gttctgcatg tttatataa atggaatcat gtcttttttg    40080
tctggcttct tttacttagc atagtatttt caaggttcat ctacgttgca gcatgtttca   40140
atacttcgtt ccttttatg tccattatga atataccaca tttcgttaat gacagttctt    40200
tggggtagct acatttaaa acattatagt aaaatacaca tggcatacga tttactatct    40260
taaccacgta agcctgcagt tcagtggcat taaatacatt cacattattg tacaattatc   40320
accaccatct gtttccagaa attttcatc tcctccaatt gaaactctgt atacattaaa    40380
catgaactct ccattctccc cttcctccag cccttagcag ccaccattct acatttctat   40440
ctttctgaca gattttacta ctctaggtac ctgacataag ttaaatcaac cagtatttat   40500
cctttttgtga ccagcttatt tcattagctt aatgtcctca agattcatcc atgttgtagc  40560
atatatcaga attactttcc ttttaaggtt gaataatatt ccattgtatg tatatgtcac   40620
aattcgtttc tccattatc catcactgga catttgggtt gcttccacgt atcgcctatc    40680
ttgagtcatg ttgctatagc tgtacgagta tctatttgag tccccgctat caattctttg   40740
agtatatgcc cagaagtgga attgctggat catatggtaa ttccgtgtct ggtgtttttg   40800
aggaactgcc atgctgtttt ccacacagct gtatcattat atgttccctc cggcaatgta   40860
tgagggctct aagttcttca catctttgct aacacttagt atttttttt ttatggaata    40920
gccatcctaa tggctacttt aaaaatatat ttaactttat ttatttattt ttaaatttt    40980
ttatagagat gccatcttac tatgttgccc aggctggtca tgaactcctg ggctcaagca   41040
atcctcctgc ctcagcctcc caaagtgttc agattacagg aatgagccac catgcccagc   41100
ccaaatttaa atatgtaact aaacacatag cagctaacac caagccttta aaaatatcat   41160
taataggctg ggtgcagtgg ctcatgcctg taatcccagc actttgggag gccgaggtgg   41220
gcagatcacc tgaggttggg agttcaagac cagcctgacc aacatggaga aaccctgtct   41280
ctactactaa aagtacaaaa ttagctgggc atggtggcac atgcctgtaa tcccagctac   41340
```

```
tagggaggct gaggcaggag aattgcttga acctgggagg cagaggttgt ggtgagccga    41400
gattgcgcca ttgcactcta gcctgggcaa caagagcaaa actccatctc gcaaaataaa    41460
tatctgtatc tatatctata tatcgaactt cttaccccag tgatccaccc acctcggcct    41520
cccaaagcac tggaattaca ggcatgagcc accacacccg gcctattaat tatatatgca    41580
cctataatcc caactactcg ggaagctgag gctggagagt ggcttgaacc tgggaggtgg    41640
aggctacagt gagctgagct cacactccag cctgggtgac agagcaagac tctgtctcag    41700
aaaaaaaagt cattaataaa tgtgatcttt ttttttcctg tacaagttgt caaggaagta    41760
tgaccttctt aattgaccct ttgacatgaa ctgggatgag atcgtggagg atgttgagga    41820
gacagttgtt accatagtgc gcttctaaaa actaattcta tagatttctt tacaaaaatt    41880
tgtttaaatt attatgagta cacaataggt gcatctatag atttcattac cctcaaataa    41940
atgtacaagg caatgcagag aaatacatag tgtaacttgg tagacttgac ctatcaagtt    42000
actcttgaat atgttatgaa gcctgtgtat tactgggggc agcaaacttc tcctgttatg    42060
atagttgttt tcagctttgt tgaatctgtg gtctctgtct taactacaac tgagaaagca    42120
gccatcgaca atatgtagat gaatgtacat gactctattg taataaaact gtgtacactg    42180
taatttgaat tgcacataat tttcatgtgt cccctgtata attcttcttt tgacttcttt    42240
tcaaccatta aaaatgtaa aaacaggcat ggtggctcat gcttgtaatc ccagcacttt    42300
gggaggctgg gtggattgct tgagcccagg agcttgagat cagctttagc aatgtgacga    42360
aaccctgtct ctacaaaaaa ttagctgggc atggtggcat gtgcctgtgg tcgcacctac    42420
tcgggaggct gaggtgggag gattgcctga gcccgagaaa gtcaaggcta cagtgatttg    42480
tgccactgca ctctagccta ggtgacagag tgagaccctg tctcagtgaa tgaatgaata    42540
cattattagc ttgtggacta tacaaaaatt agaggctgga ggtgagctgg gtatggccat    42600
tgggcatggt ttactgacct ctggtagaga ggaattagta tatgttaaag gtggtggaac    42660
tgtctgatac ttgcgttctt ttagaaatac tttggagtta gcttttggt tcaggcaaag    42720 gaccaaagag ttaggagagt caggctggta aagaggagtg gtgggcccat agcaacaggt    42780
cctggagtct ttaagaggag gtgtgtctca tgtgacattg gttggttgga caaaagcctg    42840
gcatgttgtc accttccata ataagtgttt gtgggaatgt aggtaatgag aaggaggagt    42900
aaagggttcc tgaaggatga ggaggagggc tggtggctgc cataggaagt gatcaccatt    42960
ttggcggacc tgtcttagag taatgaccat catactctct cactccttgt gaactcatga    43020
agtcccatgg ctgctaaagc taaggtcaa gtggggactg ctctgggcac tgggcttggc    43080
accccacaga gctgtggagt gggcattaat gtccctgtta tatagatgca gagactgaga    43140
atgaggactg ttggtaactt ttgagagggc actcagctag aaaagtctga gccaggatgt    43200
caagtcccat ggctttacct ctgtggtcct aatggttggt gtgttcaagt gagatccgtt    43260
ttttcatatt tggttttgat tattgatttt catgcatttt ttttcttttt tgagttagta    43320
tattctctct cttttctttt tttctttttct ttctttcttt cttttcttct ttcttttct    43380 ttctttcttt ctttctttct ttctttcttt ctttctttct ttcttctttt cttttctttc    43440
ttttctttct tttctttctt tctttttttt ttttttttt gtgagacaga atctcgctct    43500
gtcacccaga ctggagtgtg cagtggtaca atctcagttc actgcaacct ccacctctcg    43560
ggttcaagtg attctcccat ctcagcctcc gaagttgctg agattacagg cacctgccat    43620
catgcctggc tagttttat attttgtag agacagggtt tcaccgcgtt ggccaggctg    43680
```

```
gtcttgaact cctgacctca ggtgaaccac ctgcctctgc ctcccaaagt gctgtgattt    43740
ataggcatga gccactgtgc ctagccagta ttttttttctt tctttctttt tcttttttttc    43800 aggttcattg aatttgcttt gagacaggat cttgctctgt tgcgcaggct gaagcacagt    43860
ggtgcaatca tggctcactg gagcctcaat ttcctgggct caagcaatcc ttgcacctca    43920
gcacccctcc accccacct actccttttcc cccaccagta gctggaacta caggcgccag    43980
ctaccgtgct tggctaattt tttaaatgtt tttatagact gggtttccct atgctgccca    44040
ggcttattaa ttgattttct gtgtgatctt agggaaatcg attatttccc ataaacatttt    44100 tttaaattag aagttaaatt ctgcctagtt tgcctcacat gattattgtg gatgactgaa    44160
tcagagaaga ggtaagagct cttttgaaaaa tatgaagtac catacagaag ttagatgctt    44220
tgtcctggtg agacccctcc aaagcacagc taaggaagtg tggaaggcac tcttatcaca    44280
tcatatagct ttgaaagcct agcattgaaa gtatgaactt gattcttttg gagaaatcct    44340
ttggctctca gtgagtttac tttctattaa tgactatatt aagcggaatg gaaactgaaa    44400
gaggaaagag gaggaagtca gaattaaata ggaagagtaa gcccatagca gagtccagat    44460
ttagacccca agctacttgg aatgatactg gacaattatg ggtgtgttta atgattgccc    44520
tgagtcatga aaacaaaagg aggctttaaa ttatgtctgg cttagtaata tagcatattt    44580
tatcattatt caagttttag catgtaaaga ggaaaagtgt gcagtactta cacataccat    44640
tttctattag cgaaactaaa tgaggccgct ttaaaattat cagtgttcac agtatcttcc    44700
aaaagacatg taaatgtata aatgtataaa aaatatacat ataaatttta cagtttggtg    44760
agctatatag tagatctctt attttgtcca taggtcgtaa agatcttata ctgtatttag    44820
gaacaaatat aacttaagtg gggagtccttt acagggctaa taagtaagca ttattttgat    44880
aaagtgctgt gttgtctaca ctaggtatag tagaaatact cttggaatag taatcatccc    44940
aggccctact ttggagtgga agaaatagtc aatgtagaac tttatagtac attgtacgta    45000
gatgtgcctg ctaataactt ctgtagacag caaagtttaa gagaaattag gtggtaaata    45060
caacatatgt atctaaataa atttggtctg agagatttga taagatgaaa cagtacatag    45120
tccagaaaat ttttatactc aaagaattgt agaaaatatc ttaaatgttt tcagttttgt    45180
gtatatccag agaatatcat cctgtaatct gctggttggc aacccaatgg cagtattaga    45240
tgtatgtttt tattttgttt cgtttgctat ttgtttggtt aagagagtta cctaattagg    45300
agtgtggaaa aaaaaaaaag atttattata gtagtgggct tttgtttgac ttcagacatt    45360
tttgttgtta caacaatatt agtgtcttgt ttgtgaaatt tgtttaccgg gaagccaaat    45420
acttagaata acttttagtt tatcattatc atcatcatca tcatcatcat ctccatcatg    45480
aaaggaagaa gctaccaatg ttgctttatt ctgcaaacaa tataatagat gcttgttgaa    45540
agtatggagt gaaatcttaa atatatctgt taaaagagt acaactggcc aggtgtggtg    45600
cctcatgcct gtaatccaag cactttggga ggccaaggcg ggcgaattgc ttgagccagg    45660
agtttgagac cagcctgggc aacatagtga aaccctgtct ctacaaaaaa aatagacaaa    45720
aattagctgg gtgtgatggc atacacctgt agtcccagct acagtggggc tgaggcaggg    45780
ggtattgcat gagcccagga agtaaaggct gcagtgagct atggtcgtgc cactgcactc    45840
cagtgtgggt aacagaatga gaccctgtct caaaaaaaaa aaaaaaatag tacaacttta    45900
agcaggatgt gggtacatga ctgtagtctc agctacttgg gaggctaagg caagagggtt    45960
acttgagccc agaagcttga tgctgcagtg agatgtgatt gtgccactgc cctccagcct    46020
ggggaccata gaaagatccc atctcttaaa gaaaaaaaaa acagagtaca acaactttgg    46080
```

```
taaacttgga atataaagat atttccttaa cctattaaag agctgataaa gagtggtact    46140
ttcaaaccag tacacattat gtgaaacact agaggcactt cccatttgtt aaagaaaaa     46200 ccttagccaa attaaattta agttttgttt tttttttttt tgttttttg tttttttgtt     46260 tcttgagaca gagtcttgct tgtcaccca ggctggagtg cagtggtgca agcacagctc     46320
actgcaacct ccgccttctg ggttcaagtg attttcttgc ctcagcctcc tgagtagttg     46380
ggactacagg tgtgcaccac cacgcctggc taattttgt attttttgta gacacgtggt     46440
tttgccatgt tgcccaggct ggtcttgaac tcctgggctc aaggaatctg cctgcctggg     46500
cctctgaaag tgctgggatt acagatgtga gccactatgc catttaacgg tttaattgag     46560
caaagaatga tttgcaaatt gggcagcctc ccgagccaga gtaggttcag agagactcca     46620
gcacagccat gtggtggaag aagatttatg gatggaaaaa ggaaagtgat gtatagaaaa     46680
gagaagtgag gtacagaaac agccggattg gttacagctc agaatttgcc ttttagaac      46740 acaagtagag gtttgaacag ttggccacct ttgattggcc aaaacccggt gattggcaca     46800
agagcaggtt ccagtctctt tacatctcca tttaggttat agttcactat ggatggaaaa     46860
acctgtagat caaacttaaa atacgtaagg agacagtttt aggctaaact tgatttaaca     46920
cattaaatcc ataacaagac aggatgcctg ccctcaccat gttatttgat cttattttag     46980
taattctagc caatgtagta gggcaagaaa actgcctgct tggttacaaa ataaacatgc     47040
aaaagtcaat atttgtaata tgtgacagaa aatataattt aaaaaagaag aagccgggca     47100
cggtggcccg tggctgtaat cctagcactt tgggaggcca acacaggtgg atctcttgaa     47160
ctcaggagtt caagaccatc ctaggcaaca tggaaaaccc cgtctccaca aaaaaattag     47220
ccaggtgcgg tggtgcgcgc ctgtagttcc agctgctttg gaggctgagg ttggaggatt     47280
gtttgagcct aggaagcaca ggttgtagtg agctgagatc atgccactgc actccagcct     47340
gggtgacaaa gtaagactct atctaaaaaa aaaaaaaga aagaaagaaa aggaaagaaa     47400
aagaaaaaag aatttcactt actagagcat caaatcccta agataattta gaacaaagcc     47460
agaaaagtga agaaaataca aaatctttta cagtgagttg cataaaaaaa aacaacttga     47520
agatgtcaga tcaactcatt aatgtgttga ttaatgtaat taaaatccca ctgttttttt     47580 tgtgggagg gtgggagagt cacttgttaa aatgattcta aagagcatct ggaagaataa     47640
acaggcaaga atagccaaga acattttgaa aactaaagat gagtttggaa gacgattggt     47700
tttgtactat caactactta tagatttta atgaattta aagggtaatc tgagtcctcg       47760
aatagacaga aatagccata gatctgaaag aacacttaag acctgatcta gctatccgtg     47820
agagtatgta taatcaaagt ctttgtgtgt gaatcaggag tctttcaggt gcaaggtaaa     47880
taagctcata attgcttaag caaggtggt atttgcttta gtgactccag agaaagctca      47940
agtgcctgtc tcccctgac tttgattctt tttgggttg gctccattct ctcctgttgc       48000
taatggcttc cttgtgcag ccagaggaaa ggaggtgtgg ttttttgata cttccagtct      48060
tctattttta tagcttgaga tcaaagaggg aagtgacctt ccttagagtc agtgtgtaaa     48120
gtcctaagga agataccacg tggggtgctg gggccatgtg cccatccctg gcccatgacg     48180
atggggatgc tacactaact gggggccacc catggctgtt cctgccttga actgccaact     48240
ggctttgcag tgcagcttca ccagaatcac atggaatagt agggatagga attgtttccc     48300
aaagagagtg tgtggggtgg taaaattact agtgggggag taaggggaca ggccattggg     48360
cagactggag cagcatttac ttactcagtc attgagaaaa ggatggaaca ttcaataaag     48420
```

```
ggtgctggac acagtttgtg ctctaaaaat tttgtgtttc acctattaat ttatccctcc   48480
ccttagcccc tggcaaacac tggtctgttt actgtctcca tagttttgcc tttcccagaa   48540
cgtcatgccc ttggaatcat acagcaggta accttttcca gttggcttct tttatctagt   48600
aatgtgcatt taagattcct tcatgtcttt tcctggattg ataacccatt tcttttagt    48660 cctgaataat attccattgt atggttgtac cacagttgat ccattcacct actgaaggtc   48720
attttggctg cttccaagtt ttgataattt gaaaaaaaaa ttttgagaca gggtgtgatt   48780
gtgtttaaga tactggtctc ctgaacaact gagctcacgt gaacccctct cctcagcctc   48840
ctgggtaact gggattacag ctatacacca ccgtgcccag tgtgacaatt atgaataaag   48900
ctgctataaa cttctatgta ggttttttttg tgtttggaca ttggttttca gttcattatg   48960
gtgaatacca aggagtgcaa ttgctggatt atatggtaaa agtatgttta gtttgctaag   49020
aaactgccag ctgggtgtgg tggctcacgc ctgtaatcct agcataatgg gaggctgaga   49080
caggaggatc ccttgaagcc aggagtttga gactagcctg gcaacatag tgagacctca    49140 tctctacaga aaatttaaaa attagctggt cgtggtctta tgtgtctata gtcctaactg   49200
cttgggaaac tgaggtggga ggatcacttg agcccaggag ctggaggtgg cagtaaactg   49260
tgatcatacc actgcactgc agcctgggtg acaaagcaag accctgactt taaaaaaaaa   49320
aaaaaaaaaa aatgagtcag agggtaagga agcaaaaata agtaaataaa taaatagaag   49380 ataaagaaa atctatctt tcaaagtggc cgtgccattt tgcattccta ccagcaatga     49440
atgagagtct ctgttgttgc acatcctcac cagcatttgg tggtgtcagt gttctggatt   49500
ttgaatattc tattaagtat ataatgctgt ctcacttgtt ttaatttcca attcttagt    49560 gatgtatgtc attaagcgtc tttttaatat gtttacttat catatatgta tcttctttag   49620
tgaggccttt gtttaggtct tctgcccatt tttaaaaatg ggtttatttt cttattgttg   49680
aatagtatga gttctttgtc tattttgaat acttgtcttt tgctttattt ttgtgttttt   49740
tttttatttt tatcttttttg agacaagttc tcactctgtt gcccaggctg gagtgcagtg   49800
gcatgaacat ggctcactgc agcctcaact tcttccaggc tcaagcaatc ctcttgcctc   49860
agccttccga gtagctggga ccataggcgc acaccaccac accctgctaa tttgaaaaaa   49920
ttttttgcag aggcggggtc tcaccatatt acccaggctg gtcttgaact cctggcctca   49980
gtcaatcttc cagccctcag cctcccaaag tgctgattat aggcctgagc cacttagcct   50040
agcccagaat ttatttttttt atttcttagt tttgaaaaaa tataggacct cataaaagtc   50100
agtctagatt tgtacacatt atgttttttgg tgtatatgta aatggattct ttgtgaatca   50160
atttggtttt gttttttttgc ttttaaaaat accagcactg ggctgggtgc tgttgctcat   50220
acctgtaatc ccagcacttt gggaggctga ggcaggtgga tcacctgagg tcaggagttt   50280
gagatcagcc tggccgacat ggtgaaacgc tgtctctact aaaaatacaa aaattagctg   50340
ggcgtggtgg cacatgtcag taatcccagc tactcaggag gctgaggcag gagaattgat   50400
tgaacttggg aggcggaggt tgcagtgctc caagattgcg ccactgcact ccagccttgg   50460
cgatagagca agactttgtc tcaaaaaaaa aaaaaagaa aaaaccgca gcagtggctg      50520 gccaaggtgg ctcacacctg taatcccagc actttgggag gccaaggcag gtagatctct   50580
tgcggtcagg aattcaagac cagcctagcg aacatggcga acccccatct ctaccaaaaa   50640
tactaaaatt agccagatgt ggtagtgcac acctgtaatt ccagctgcct gggagactga   50700
ggcatgagaa tcacttgaac cctggaggca gaggttggag tgagccactg tattccagcc   50760
tgggtgacag agggagactc tatttaaaaa aaaagaaaa aaaaggctgg atacagtggt   50820
```

```
gcacgcctgt aaccccagca ctttgggagg ctgaggtgct cagattgctt gagctcagga    50880
gtttgagacc agcctggaca acatagtgag acatcatctc ttaaaaaaaa aaaaaaatac    50940
ctgcacttgg tcaaaagatt tcaacagtgc agaaaaagaa agttgctata tcttttctcc    51000
aaattagtct tgtttctagt ttcattatcc aaataatcac tactaatagt taaaacattt    51060
taaatacaca ttgggagttt gtcctattta atataaatta tttattgagc aaataatcac    51120
tgctagtata ttttggatac tggaatttte atatgtaggg gtccttgaat gtaaggtgcc    51180
cctttggtag ttctgtgctt cttttacctg tactgtaaca tagggaaaga tgttacaaat    51240
ggttagtatc tattcttaaa caccagccct tccactaaag gtaaacaaca aataaatata    51300
taaatgaagt tttggtattg ggattacacg ggttaaacac atccatattt cattattaat    51360
atttaagaat ataacaaact tcttattggc atttggacct tgtagctagg gaaagattaa    51420
gctttgttta tttgtgcttt gttttttttc ttcactcaga tatttgaggg tttcccattt    51480
gaggaataca tttattaatc aagctttagt tgcaagatat ttgatcttag agaataccat    51540
caaccattct tctttaagct tcctaacttt acccaaatgt ggttggatct actcaagagt    51600
agtttgggta gttcagaaat tttattggaa ggggaaataa ttttttgaccc aaatttgata    51660 aagcaactct tgagtaatga tttctttttct tgttctctct ttataatcag ttgaaagtag    51720
tagtaaggct gggtggcaaa agaaagaggc ctggggagaa tcgggtggtt ttcattatct    51780
cttttcatag cagctaagtg ggaagggacc aagaggaaat caactgaaaa accatccttc    51840
tgaaacattg gcctaaaaaa gtgtagtcca gaaattgagt gcaactggca gtggcattta    51900
aaaggaatgc tctaatttct aggaaagcag gcacgagtac ctcttaaaag aagaaaaaaa    51960
tgaaaactgt aatttaggac acacagacga gtatccattc cctgtacttt tttactctcg    52020
tgtcctaacc aaggaagggt taccatagca aatatggcat tccttagcca tgattcactg    52080
ttgtaaatgc ctgcagcatt cataaaagta agatatatgg gctctttctt tttccttttg    52140
aatccgtatt tctgtattta aatctgtatg tcaacatctg tattttctgt ctctcttgtt    52200
tttttaaatc ttgggagatg gtacaaatta tttaggggag tgaataagtt tcttgtctac    52260
aaatagagga gagagaaggc ttttttgtctt tctgctttgg aactggagag cttcctattt    52320
aggcacggcc ttttttcaagt gaccttgtat tgttatcagt actgtagaag gtaggcacat    52380
tgtacagact ttaaaatgta aagcttttag gcattccact tgtaaaccctt ggcttttttaa    52440 agaaaattac atgttcattg tgaatatttt cttatcgccc tatctctgtg cacatgcaga    52500
cttcctttgg ctacattctg aaaggtgtaa ttgtcttctt taaggacagt ggacatctat    52560
agttcttagg tcaaattgtc ctccttctgg ttttgtcagt tctcagccac actgtgtgag    52620
catccatttt cttggatcct ggtttggagc tcattttaag gaacatcacg tcccttttga    52680
gactatgtgg acatcagggg gggtagatgt tcccctgtga acagaaggtt cctccctaag    52740
gaggtgcttc tctgtgttga gtcttgcatc tgggcacaca gagcccaaag caggaagagt    52800
tgagtctgaa tagggaggcc tgtaagcctc actgctctgc cacggctagg cctggttggc    52860
catgctctag gagccctcag gaggctctga agtgattctg cctctgggaa ttttacagag    52920
gagctaatat ttgagatctc caaagctgag tgagagggtc attcttgaaa aggcaaggca    52980
tgcctcggtc cagttctgtg gggctgtcat agaagagggc tcggaagctc ttgtaagtga    53040
ggctggaaag gtaggcagtg ttaccataag gaggatggaa atgacacaga taggctaagg    53100
aaggggacct ctgtaatcat gcagcgatgg cctagaaaag ggacaggctc atggcaggga    53160
```

```
gaccagtttg gaggctgcca cagtgttcta ctgagagaga aaaagaatta aactcaaagc  53220
acggtcaggg aaggtggagg ggcaggatct gatttggaag tgttttgttt tttggtttcg  53280
ggtacaagga tttggaaacc tcttgactcc gtagatgaaa gaatatgaac caaggaagac  53340
tgaagtttcc actcagggaa gaaaacacag gagtaggaat cgatttaaga gaatggcagg  53400
cagttgtgtt ttgaacttgt ttagtgtgag gtgacatctt tgtagggatg tctagctggt  53460
agctgcaagt acaggaggct agatgtgtgc atgagtttct tggtaaagat ccatctgcag  53520
tctcctgaag atgtcactca gattgcactg ccatcacccc agggcccaag agaagacact  53580
cgcttctctt ggtgtctagg cgggtttgaa aaaaatcaaa cagtacaaaa tcatgcaaat  53640
tcagacctct actccacccc agaggaaagt cctgctagca gttttttgtgt attcttccag  53700 aaatctgcct tgcaacatgt ttgagtatat aaataatccc agaaaggatg ggccagacac  53760
tagcagaaac tcaccacaca cactgcgctg ggcatgcaga aacttcgcga aatatactgg  53820
tgtgtgctgt cactgcattc ctggatttgg gggtcttctg tgtccccagg tatcagtatt  53880
gcccacaggc tgaccactga gctccttcca cagccgactc acgtcaccct ctttcgaagt  53940
gtgtctgcaa agctagatta ttagattgtt tctgcttttgt gttttctttta atgaattttt  54000 taatgatgaa gttcttgttt taaaaatata cagtggtaat taacatgtat gcattttttct  54060 taaaatgacc cccccagtcc ctcttcagat gtaatcactg ttaacagtat cgtatataga  54120
ccctgttctg tgtggggtgg gcagagggcc ggttagcggg tggaacatgc atactcacaa  54180
ccatattttt cacatgggaa aatataaagg tgacaacaaa tctcctggtc tgtaatctca  54240
tcaagcagac aataatcact atttgaaaag cggacaaata catgctgatt tttaaaaaaa  54300
attatagtag tacagaaaga tacaaaaaaa aaacaaagtt aaagtcttcc taactctcct  54360
gcctgtaccc tccactgggc aaaagtccct gtccctaagg taatatctgt tgacagttct  54420
ccttgcaata cagataggag catgttgtgt atctgcctct gtgtgtatgt gtttacatgt  54480
cttttttttt tttttttttt tgagacggag tcttgctctg tcatccaggc tggagtgcag  54540
tggcgtgatt tcagcatgct gtgacctccg cctcccgggt tcaagtgatt ctcatgcctc  54600
agcctcccga gtagctggga ttacaggcaa ccaccaccac acccagctaa ttttttgtatt  54660 ttttgtagag atggggtttc accatgttgg ccaggctggt ctgaagctcc tgacgtcaag  54720
taatccaccc gcctcagcct cccaaagtgc tgggattaca ggcatgagcc acaactcctg  54780
cccctgcaca tgtctaacgc acacaaaggg gattctgctg aacacatttt tttgtgctttt  54840 ttcttttccaa cttaacatat ttgacatctt tatcagctta tatagcttta cttcattctt  54900
ttaaagaggt tattggctat aaagagaaag tcagagaaag tcagtcaatg ggtgcttcta  54960
tgattattta attagatcct gttgatggac attgatacaa tttctaaatt ttttagtatc  55020
ctaaataatc ctgtggtaaa catccttata cagatgtcct tgttcgctca tgaaaatatt  55080
tctggaggat ggtgagaagg gaaattttaa aaattattta tataaacatt atcatttgtt  55140
agtagaatga cctcgggaga ggttgtagta atttatgctt ccccacatgc atatgaacgc  55200
cttttcaata tattgtttca aaattggata tcatgaacct aaagatatat atatatgtat  55260 gtatttttttt ttttttttttg ggggtggggg gatgtcctgt tattttcagt tatcgaatag  55320
aactttgtta gttccttcat gtaaggatga agttggtaat tattattttt tttgtgtgtg  55380
tgtgttactt tcttttttttt tttttttgaa gttggtaatt aaagggatct gacttcagtt  55440
atggaactgg gaaaacagga ccttgatgtg gaggtgggct tagacatgct atgtctgggc  55500
aggtatctct tgggaagcag tgtcacccct gaacagaagc atggatgagc cgcagggac   55560
```

```
ggtgctgagc agaggggctg gccgtgggtc atctgcggct gttgacctgg aaggcacaag    55620
ggagttttcc acctttcctt tggttttgag agtgcagaag ctactaagca actcacaacg    55680
tgcccagggt ggtggtccaa ctgaaggatg tgaaacggtt cttcctttcc cagccaaaga    55740
acttgaacct cccaccctgt gacaagcatt ataaaattca cataattttg ataggctgga    55800
ttcccttcct gtagcagatc tttcctcaga acagaagtgg ttttttgttt tttggttttt    55860
ttttaaccta aattacctgt gagttttatt ttttaaatat ggaatatgtt ttttggacac    55920
ctccttgtca tattaaatgt tgttattaaa tttgagattt taatataaat tttaccccag    55980
caaattaatt ttgtttctct tactctcttg tttttggcat cttttcccgt tatatagtgg    56040
tgctcatgtc atcatattgc tcttatgtga cttttccttt gtgaacaggg atcttgttca    56100
cttttccttt tttaactttt tttttgtttt tcgagacgg agtcttgctc tgttgcccag    56160
gctggagaac agaggcacag tctcagccca ctgcaacctt tgtctcccgg gctcaagcga    56220
ttctcccacc ttagcctctt gagtagctgg gattacaggc atgcaccatc acgcctggct    56280
aattttttgt attttttgtag agatgggggtt tcaccatgtc atcgaggctg gtctcgaact    56340
cctggactca agcgatccac ctgcctcagc ctcccaaaat gctagggtta caggcatgag    56400
ccactatgcc tgagtcactt ttccttttaa cataaaaaca ctggtatcct agagagggca    56460
ctatattttg ggtacatatg agttcagatc acagaagagt tgtattctat acttcttttt    56520
tcatcattct tacttcagta tgatgtattt tataatttta tatgagaaac tataacactg    56580
ggcatgtgtc atcaagcagt acctactcat aaatcatatt aaattttgat ccaaacatgg    56640
gacaaactga agttttctct gtgtacttga atgctttcag aggcataaaa ttatattacc    56700
atgtgaaagc aagcctacaa aattcctcag gcgtccactc tgccactcaa atgagagcca    56760
gacttacagt gcacactcta caaacaaact tccagcccgt cagggtattt taagtgcctg    56820
aatatgcaag gcactgtgcc agtaaaatta ctcagtccca aggatagagc ctgttagaat    56880
tattttaaaa tctgtacttg aagtttattt cctcagtgtt ccaagatatt ttatctggtt    56940
gttctctgag tatttcacat gtagctagtt acatataggt gagatagtga tgcttgtgcc    57000
tggtgtggat gagaaactga gcctggcaga cctgagattg gatttccttt tctgactttg    57060
caagtgtggc ttggctttaa tagccctcct ctttttccgt attcctcttt cccccttcca    57120
ttttgcaaat atgcatcaat caaaatacaa attgattgca aatatgtgtc aatcaaattg    57180
tattgtattt tgattgtgca catatgcact gatagttaca catatgcatc aatcaaaata    57240
caataacctg tggaaccatt ttttctgaa ataggaaggt ggtgccatgg ctattgatt     57300
gttgaaggta gtcttcagag cttgtcttac aaatctataa taattttccc ccaaattaat    57360
gtgctagtta gaacactaga ttgcatcact gaaagtgaat tttagaatct tttccaactt    57420
tttaccaagt tcagaaaacc gttttattgg acctttattt gcctcatggt catctggttt    57480
ctttatgctg ataatgacag ggaccttact aacctacaag gcaacccagt ccatcctggg    57540
cagctatgat cattggaaag ctctgaatca ttcatctgga agctgcctat ggcagaatag    57600
tgcagaacat atgcattgca ctatgttcta caaaactaca ttaaataagt gttccttttc    57660
attgttagat ggaagtgacc cagggcaagg atcatgtttg atgagccagt tttctcctag    57720
tgccttgaac ataggcactt ggtaatgttt aaagaatgaa ttcttttttt ttggagacaa    57780
aatctcactc caccacccag gctggagtgc agtggcacgg tgtcagctca ctgcaacctc    57840
tacctcccaa gttcaagtga ttttttgtgcc tcagcctcct aaggaactgg aattacaggc    57900
```

```
atacgccacc acgcccagct aattttttata tttttagtag agaagggggtt tcgccatgtt    57960 ggccagatgg tctccaactc ctggcctcag gcagtctgcc tgcctcagcc tcccaaagtg    58020
ctgggattac aggcatgagc catttgcctg gccagagaat gaattcttaa tcagtttctt    58080
atgacttcat attgactgac agttgtgcta aatacttttt gcctttattt gaattagaaa    58140
atttgtaagg gggccttcag aatagatgca gtcacattta ggagttttct tcccccatt    58200 agttaaaatg cagttttct atggatctgt tttagaacta cgaataaact ctgatcagtc    58260
actgcagact acgcagtaag ataagaagca gtccatttgt tctgtcgttt attcatggcc    58320
ctcatctttg ccagctgact tgtgcagaag agcacagcaa actgtaagct tcctaacagc    58380
tattcccatt cagctgctgt cttcaagaag cagaagagga tagatagacc ttagagaaca    58440
taatcaaacc tgggaaactc aaatcaaaac aaaacacaac ttcaaaacag aagttgaagg    58500
tcctgaaggt acccagaggc atagcaagga aaatggcccc actgggatat cttttggatt    58560
cacctacaga cctctctgga gttttaagat ccactttttg tgacatattg catagcaaac    58620
aggccgaacg ctgttgtaaa tcatcctctg cgaaaggccc aggttttgaa actgaaggcc    58680
tgaaaaggct cctgcttacc agctgtgtgc tgtacctgac acactgaagc ctgagagtgc    58740
cagtcacctg tcagagggaa cacagctgcc ctcaggcaga acctgagtct agaactcaag    58800 gttttttgact cttaggctaa aaataaaaaa tcagaaggag gaactatgga ttgcttaatc    58860
agtcacattt tcacttttcca gagtttcttg tagcacaagt tatagccttt ggggattagg    58920
atgtaaacac ttttttttcc ttccctaaag cgattttttgg tctgtcagtt tttccagctt    58980
cctgctctgg gccctgaagg tgccacacag ttgcaggcat gctcctactt caaggctctg    59040
ttaagctgtg gctgcccttc cttcccactg ctgtgcccca ggccaacccc tctgcccctt    59100
ccttcccctg aggcgctttg cacctgttgc tccgagcctc ctggtctatc ccagttagta    59160
gagtccctgt gcttacctcc gtggctcagt cctcatgggt ggtcagtgct ctagggaagg    59220
tgagctgacc tcttcacttt cccttcccag ccatttatag ctcttcatag cctcaccaac    59280
ttagaaaggg atgctgcttt tctctctgtc ccccatcctg actacattca agtcattgct    59340
cagcccagtg agtttgtcct ttcttccaga ccagtagttt tcccccaggc cctcaggctt    59400
cagcccttga aggcatcctt agccccccc ccacactatg atagccaggc gctgtgcctg    59460
gccatggggt gtgggtatgt gtgtgtgttt tgtttctgga gcccattcct ttccttccac    59520
catcttctag gccttcatcc aatcctcctg caacttgatt catgactttt ccctgcatct    59580
agtctagtct ctttgctggt ctgttgtttg catagttgcc agtttaatct tcttaaaatg    59640 ctgcatttt gaagtcagtc tctctctagt ccctgtcaga aacatttaaa tagctctgtt    59700
gccacagggg gaaagcttga acctcttagc cagtcagtca ttcagagcct gccctctact    59760
ggggcctgct ttcctctcca gatgcttctc ccactctgcc tgccacagcc cttgtagctg    59820
gctgattgcc ctgtacctcg caggctctgg aagtcttcag ctccttcatg gagcctttgt    59880
ctaccagcca ttcttttcaa gactttgctg ttgttcactg cctgatttgt tcatttgaca    59940
cttaattcac tgagcaaaca ttatgaaaga tgtactgttt gctactgtga ggaatggatc    60000
cccaagaggt aagagggtca gtccctactg ccaggaaatt tgcctggatt cagtatcttc    60060
ttgtgtctat tagatcagaa gtggaaaggc agaggccagg ctgtatgctt tttaaatttt    60120
attttatttt atttaaatca ccagcacctc agcaagtgtt ttgcacagga aatttcttaa    60180
tgttatttaa ttattttggt tttttgatt aaattctgta cattcccatt ttagcttatc    60240
ttgagttata acattaaaat taaggtagtc atcaactgaa ttataagacc taattaaata    60300
```

```
agattattta agatagtgat ttctcattag attggcccta ttcatattaa cttttctgct    60360
tttttcttca gtctgcatga agaaatcagt gatttttatg aatacatgtc tccaagacct    60420
gaggaagaga agatgcggat ggaggtggtg aacaggatcg agagtgtaat taaggagctc    60480
tggcccagcg ctgacgtgag tcccttcctg ggtagcctat gcttgggaca gtccttgtcc    60540
acgggccaga ggcctatctg ctagtatctc atgctagtcc tcacatgcaa gtagaagtgc    60600
actgtagagt tgtggtctaa ttaaatttta aaggcaaaga attttctgca gtctttagaa    60660
tttgaggctt actaattatt ttcattggat tggatgacta acaaccttt ttttttttt     60720 tttgtagtgc taatagcaac tactaaaggc aagctattgt tagaaattat tagtgtaaag    60780
agaagaaaga caaatcaaac ctcattgttg tagtggtctg ttattggata tgatatatca    60840
aaacctcatt actacttagt tccagcctgc cagagtaaac attatataat tgtttacagc    60900
tgaatgaaaa tgtcaagtac gaaattttgt cacttgtggc taatgcaggc ataagtcttt    60960
tcttatttct ttcctgaaat tgccatttc atctctctca gaccagctaa ttgcctttta    61020
gacagctccc agtcagtgaa caaaatgatt gcttgggatt tcttcttggc ttatttgttg    61080
tttttgttac tggtaccaag tcttttgttt ttttttttt tttttttga gatagggtc      61140 tcactctgtt gctgaggctg gagtgcagta gtgcgatcac gactcattgc agccttgatt    61200
tcctgggctc aagtgatcca tctcagcatc ccgagtagct gggaccgcag gtgcacgtca    61260
ccacacctag ctgattttcg tatttttttg tagagactga gtctcactgt gttgcccagg    61320
ctggtcttga actcctgggc tcaagcagtc tgcccgcctt ggcctcccaa agtgctagga    61380
ttataggcgt gagccaccac acttggcctg ttactggtac taagttaata cttcactttt    61440
tagggcactt tgagggcctg ttttatgatt ttgtgtatgc aaagaagtaa caaataata    61500 gaatccatta ctttgtgttc tgtaacttt ctttaggcac tgtcctgggt ggtgtttttg    61560
tccaattggc aaaacaagga agtttcactg tatgtaaaac ttgcatgtat atgacagtat    61620
atatatgacg ctgtaggtaa agggaaaagg ggaggatact aatatttat gaacagtgac     61680 catatgtcac attctttctc ctatgtgatc caaatcagtg gttcttagct ggtggttatt    61740
ttgctctcca gggggcgtt tggcaatgtc cgagacattt ttgattgtcc tggctgggta    61800
tgcactgcta gtacctagtg ggtagaggcc atggatgccg ccagccattc tgtgatgagc    61860
agtataggcc cttacaacaa agaattatcc actcccaaat gccaatgttg agaagccctg    61920
gtctaattta acccttatct ttcttaggtg gaggttgact ctctctctct ctctctctcc    61980
agccagccag ccagccatca tctgtctacc tacagatgag gaacatgagc ttgtggttag    62040
gttcccaggt ccatctcgcc tcagaggttg aacttgtttc actgtttatc ctttttcccc    62100
gccctgagat ggagtcttgc tctgttgccc aggctggagt gcagtgacac agtgacatga    62160
tctcagctca ctgcagcctc tgcctcccag gttcaagcaa ttctcctgtc tcagcctcct    62220
gagtagctgg gattacaggt acccgtcacc acacctggct gatttttgtg ttttagtag     62280 agatgggtt tcatcatgtt ggccaggctg gtcgtgaact cctgacctca ggtgatccac     62340
ctgcctcggc ctcccaaagt gctgggatta aaggcgtgag ccactgtgcc cggcctatcc    62400
ttttttatta caattacctg catacgtatt tctgcctgag ttcccctgtt ctccatgggt    62460
tgaggtggaa tgcatcccag ttttatgcca cagcacgatg ttataaaatg atggtgcctg    62520
gtgttctctg tggaattgac ctgaaggccc acacttgccc tacagttagt ctgatcccaa    62580
tttagtaatc tattcgaaga ctcctgctca gagaacaaaa attaaggatt tgtgattgtg    62640
```

```
tctctggata atgagggaac attattgatc tgaactactt ctggaagttt cctgtggttg    62700
gctttctgta tccttaagta ccatacctcc atattaaacc aacagtggat tgaaaatatt    62760
cagaaaaaaa ctattaaaat aacaatgcac taataaaaac aatacaaatt attttttaaaa   62820 tatagtataa tgactatttta gatagcattt acattgtact aggtattata agtaatctaa   62880
agatgatgta aagtatatgg gaggactcgc atagttatat gcaaatactc caccattta    62940 tagcagtgac tcgaacatct tcagattttg gcatagtggg actggaacca gtctcctgcc    63000
gataccaagg gacaactgta ttttggtctc tgtgtttcat atttgaacca ggtaagttga    63060
aattatattc agaatgtctg cttgtgaaac agaatgccca cttcatgaag aatgggggtta  63120 gaaaaaaaaa tactcttgtc atactgaaaa gtaccagtag agggtagcaa aaactgacat    63180
ttctccatat cttggtgact ttatctgata cctcaatata ataacttctt tttctgtttc    63240
aggtccagat atttggaagt tttaaaactg gactatattt acctactagg ttagtacact    63300
catgaatctt ttaaaggact gtaccttttc ctagagtgta ttcgttttgg ctgtcaaatt    63360
tgtaaggagt agaaacaaaa caaatttata aaacaaaaat gggactgggc atggtggctc    63420
acgcctgtaa tcctagcaat tcaggaggcc gaggagggcg gatcacttga agtcaggagt    63480
tcaagaccag cctggccaac atggtgaaac tccatctcta ctaaaaatac aagaattagc    63540
tgggtgtagc ggcacgcgcc tataatccca gctactccgg aggttgaggc aggagaattg    63600
cttaaactcg ggaggtggag gttgcagtga gctgagattg tactccaggc tgggcaacag    63660
agcgagactc tgtctcaaaa aaataaataa ataaaaataa aaaataaaaa agtaaaggat    63720
ttaccagcat ttaatttgat ttaccttgaa gtagaatatc acttcacatc tccaagacgt    63780
agatggtaca gagagatgga aaagggatca tgttgcagtg gaatcagtta gttactaatt    63840
ttagaaattg actacctggc agagtattgc tcagtcccat aacttaaccc actgacacag    63900
atgttaatgt agtctcatga taaaatgtct gattgtatat cctctagaat gtgagttccc    63960
actgtctcac tcactcactc actctctctc tcactctcac tttcaaatta agaactcatt    64020
ctactagtta tggctccagc atcctgatcc agaaattcag gtacagatct cttctctgag    64080
aaagatcttg gcctttcagg actcttgttc agtttcagtc ttctcaaatg agacctctct    64140
tgatgcacag ccttggaggc tttcttttgg aaatgatgtt tctctgaagg gtgaatactt    64200
gctctctaag aattgaaatt gtttgaacat tccgtcatgg ttattactat tattacttaa    64260
tctctccaga ataaagtcag cgtcatgttt ttccatttga gcttgatttg gtacacttta    64320
gcccaactta aagtgtgctg aagtgggtgg accctggcaa tttccattct tcccatagat    64380
gtccttggcc tgcaaaagtc ataaaatact caacttcgag ttcatatttc ttacttaggt    64440
tctcagcctc agtaaaacat gaaaaatcac tctttcttaa aaaatttaat taaatttttat   64500 gaataggtag tacattcaca tagttcacat ttggaaaagg cacaaaaatc aatacaggga    64560
aaagtctcag tcccacctct gccccctggt tctccgtgga acagccactt gttttttgt     64620 tttgttttgt tttgttttttg agatggagtc tggctctgtc gcccaggctg gagtgcagtg    64680
gcgcgatctc ggctcactgc aagctccgcc tcccgggttc acggcgttct cctgcctcag    64740
cctcctgagt agctgggact acaggcgcct gccattgtgc ccggctaatt ttttttgtatt    64800 ttttagtaga tagggtttt caccgtgtta gccaggatgg tctcaatttc ctgacctcgt     64860
gatctgccca cctcggcctc ccaaagcgct gggattacag gtgtgagcca ccacgcccag    64920
ccagaacagc cactttttacc agtttctcac atatcctttc agagatacct gtgcatataa   64980
aaggacatgt gtgtgtatta acacaaatgg tagcatgctg gatacttgtt ctgcatccag    65040
```

```
tttaaagtac ttcataatat ttctgagttg caattaatct catccagata ggaaaatcat   65100
tatgtctagt accggaagcc tttattaagg aaaggacgtt aagtgccttt ttttttttc    65160 tttttttttt ttttgaggtt ttacttcttt caaaattacc ctatttcctg agacctgaat   65220
tctgtgaaat gactgggagg aggagtttgt taaaatcaac aactactatt tccctctcc    65280 acaaaaccat tatcactaac acatttagtc tttgttggcc agggtggaaa ataggtttta   65340
attgtactaa tgaagtctgt aagcatgagt gtcagttaaa acaagtttcc agcttcttca   65400
gaccctcttg tatatgtatt ctgtgttcag tgacatcgac ctagtggtgt ttgggaagtg   65460
ggagaaccta cccctctgga ctctggaaga agctcttcgg aaacacaaag tcgcagatga   65520
ggattcggtg aaagttttag acaaagcaac tgtaagttct gcagcatttc atattaaacc   65580
ttggttattt acctatgaaa cttgaattaa aattaaagtt tggtgagcac agttacattg   65640
caagtgagtg attctttcat tttgttaatg tcaccgtgct tgcacataaa aagttttctg   65700
gttgtccacg ctggattgtg accacacaat cttgggtcac tgcaacctgt acctcctcgg   65760
ctcaagtgat ccttctactt cagcatctcg aggagctgga ctacagacac agcctgccat   65820
gcctggctaa ttttttttgta aattttgtag agacgggtt tcaccgtgtt gcccagactg    65880
atctccaact cctgggttca agtgatccac ccacctctgc ctcccaaagt gctgggatta   65940
caggtgtgag cctctgcacc tggcctgcat ttcttttaac aacagcagaa tacccaattt   66000
tatcacacac agtactcact gtagagatgt tgttttatt catttgcatt attattttt    66060 ttttgagaca gagtcttgct ctgtcaccca ggctggagtg catggcgcga tctcggctca   66120
ctgcaagctc cgcctcccgg gttcacacca ttctcctgcc tcagcctcct gagtagctgg   66180
gactacaggc gcctgccacc actcccggct catgttttgt attttaata gagacggggt    66240 ttcactgtgt taggcaggat ggtctcaatc tcctgacctc gtaagccgcc ccgcctcagc   66300
ctcccaaagt gctgggatta caggcgtgag ccactgcgcc cagcaatatt ttattcattt   66360
ttttagagag agatacagtc tcactatgtt gcccaggctg ttccctaact cctggactca   66420
agtgatcccc ccacctcagc cttatgtgta gctgggacta caggctcacc ctaccacgcc   66480
ttgtttattt aaaaaaaaat tttttttgta gagatagggt ctccctgtgt tgcccaagtt   66540
ggagcatttt ttgaaaagaa ctcctgatag ctcatgtaaa taatcatgtc agttttgag    66600 aataatttt atatcttatc ttgtcaggtc gcttttggg ctatttgcaa aactgaccag     66660
taatgcaagg gggttgtagt gtataccttta agaatccagc aatttctctt tttttttttt   66720
tttttttttt tttttttttt tttttttttt tttttttttt tttgagacgg agtctcgctc   66780
tgtcgcccgg gctggagtgc agtggccgga tctcggctca ctgcaagctc cgcctcccgg   66840
gttcacgcca ttctcctgcc tcagcctccc gagtagctgg gactacaggc gcccgccacc   66900
tcgcccggct agttttttgt attttttag tagagacggg gtttcaccgt gttagccagg    66960
atggtcttga tctcctgacc tcgtgatccg cccgtctcgg cctcccaaag tgctgggatt   67020
acaggcgtga gccactgcgc ccagcaatat tttattcatt tcttagaga gatacagt      67080 ctcactatgt tgcccaggct gttccctaac tcctggactc aagtgatccc ccacctcag    67140 ccttatgtgt agctgggact acaggctcac cctaccacgc cttgtttatt taaaaaaaaa   67200
ttttttttgt agagataggg tctccctgtg ttgcccaagt tggagcattt tttgaaaaga   67260
actcctgata gctcatgtaa ataatcatgt cagttttga gaataatttt tatatcttat    67320
cttgtcaggt tgcttttttgg gctatttgca aaactgacca gtaatgcgag ggggttgtag   67380
```

```
tgtatacctt aagaatccag caattttctt attagaaaca gtttgatgat acaaaacatt   67440
taatacctag tattcattgt tcttcatctt atactcagaa agtgttctcc aaagtattga   67500
ggaaggtttt tgttagataa tttaaaaatt attataacta tatgtcaact aataaacgag   67560
atgatgggca tattaattta cttaactgtg gtaatcactt cagtatgtat atcaagataa   67620
gtatatcaaa acatgtatgc cttaaatata aacaataaaa ataaataatc aaaaattgga   67680
caccaaacaa aattctcaat ttatagaaat tacaaaatat attgtatggg gcccaatgct   67740
aaatatgcaa catgatattt gtagcagtcc agggttactg gggtgtgcca tatttagaat   67800
actcagtgtt cttatgctcg catgagatga tggagacctc atgtctagta accctccatc   67860
ccctgatttt gtcatttaat ctggttaaag catttacatt ttacctttct tctctttata   67920
ggtacctatt attaaactaa cagattcttt tactgaagtg aaagttgata tcagctttaa   67980
tgtacagaat ggcgtgagag cagctgacct catcaaagat tttaccaagg tcagagaatt   68040
tagtgtttat acaataaaac tattagaaac gtaattttaa gattctgttg tggtggtggt   68100
ctaatatttt tatatgcgtg ttgctgacaa acacctctct ctctctctct ctctttctct   68160 cttttttaaaa tggagctagg gtctcactct gtcacctaag ctggagttca gtggctggat   68220
catgacccac tacagcctca aactcctggg ttcaagtgat catctcacct cagcctccca   68280
agtagctggg actacaggcg tgagccacta cacctggctt tttttttttt ttttttttt   68340 tgagacgag tcttgctctg tcacccaggc tggagtgcag tggccggatc tcagctcact   68400
gcaagctccg cctcccgggt ttacgccgtt ctcctgcctc agcctccga gtagctggga   68460 ctacaggcgc ccgccacctc gcccggctag ttttttttgta ttttttagta gagacggggt   68520
ttcaccgtgt tagccaggat cgtctcttga tctcctggcc tcgtgatccg cccgtctcgg   68580
cctcccaaag tgctgggatt acaggcttga gccactgcgc ccagcctttt tttttttttt   68640
ttttaagtgt tggggatctc gctgtgttgg ccaggctggt ctctaactcc tagcctcaag   68700
caatcctcct gcctcagcct cccaaagcac tgggattata ggcatgagcc accatgctca   68760
gcctgcacct tacttttgta tgcaatggtt ttgctttctt tgaatctgct tgtaatgatc   68820
agtgattaac ttataatgtg acctcaagta agaattaaaa gttgagaaag cttttgaaga   68880
aattgtctgc tctagatcct tccttgtaga gacagaagag atggaattct gctacacagt   68940
tgattccatc tgttttaac cttcaggagt tcagattaag aacctttcct ttaacccatt   69000
tcctgtttgc cccaagaata ctgcgtgggc agtgagctgc actttctttt ttttcttttt   69060
ttgaggcaga gtctcgctct gtcacccagg ctggagtgca gtggtgcgat cttggttcac   69120
tgccacctcc acctcccagg ttcaagcaat tcttctgcct cgatctcaca gtacctggg   69180 actacaggca cccgccgcca tgcctggcta attttgtat ttttagtaga tgggggttt   69240 caccgtattg gccaggctgg tcctgaactc ctgaccttgc aatctgctca cctcagcctc   69300
ccaaactgct gggattacag gcgtgagcca ccgtgcccgg ctgtactttt tttttctaa   69360 acgggaaata ggttaagagt tttaagagca ttttctagat ttcaatccct aaattacctt   69420
taaggtgttt cctacaggct tccttacttc tattttgaaa tgatttaagt ttatttctat   69480
tctattttct tccaagatag agaagaattt gtcaccatta tctgtggaac attttacata   69540
cttagatagt tgtcagcttt ctcctctcta acctaaacca ttaactcctt tggcttctgt   69600
tagaatattc acaattttt tttctcaagc agctctaaag tttctatttc ttctttgttt   69660
tttaagaaaa aatgttaact acttgatgtt gcaagcatta tcatcttgca taaatatatg   69720
gaagacagaa aagcagaaaa ttaaagaaat attatccata atctcactat attgggtgtg   69780
```

```
tgtatgtgtg tgtgcatgtg cgcctgtcta atattttct ggaaaaaagc ttttaaaaat   69840
tgaaattcgt atgcatgata acattcatca gtatgaagag atggtgtaaa gtgagtcacc   69900
cttacaccat agatacttag atcatttta tagaatttct cattgccagt tattatttt    69960
tgtgttgctt tttatgttc tttaaaatta taagcaaagg agtagcacat tgtacacaca   70020
ttgtctcata cctttgtaaa aacttaatgt tttggaggtt tcttccatat tgacgcatag   70080
aggcttgctt tattctttt gttggttaca caggcagtag tcttttgtaa gactgtggct   70140
gcttgattta gcagttcttc agtgttgttc cagtttttct tttgctgtta gaaaaggga    70200
ttgacgaata tacttccatg catgcatctt gctttacacg tgcaaaatgt ttgtaggaag   70260
agtcccagaa gcaaaatttt gaggtcgaag ggtatatcca ggtaaaactg cgttagatat   70320
ttccctaatt atttattctt tcacattctc attttctctc tctccctccc ccttttcttc   70380
tccctctccc tatccctctc tctcttcctc tgtccctccc tttctctttt ctctctttt    70440
ctttcccttc ctcttcttt cttttctttt tccttttct tccttccct ttcccttttc     70500
cttccttctt ccttttcttc ctttctttca ttttttgaca ccgggtctca ctctggtacc   70560
caggctagag tgcagtgatc atggctcact gcagcctcag cctcttgggc tcaagtgatc   70620
ctcccacctt agcatgagta tctgggatca caggcgggcc taccacacct ggctaccnnn   70680
nnnnnnnnn nnnnnnnnnn nnnnnnnnnn nnnnnnnnn nnnnnnnnnn nnnnnnnnnn     70740
nnnnnnnnn nnnnnnnntt ttttttttt tttttttaat ggagtctcac tctgttgccc    70800
aggctagata gagtgcaggg gcgtgatctc ggctcactgc aacctccgcc tcctgggttc   70860
aagcgatttt cctgcctcat cctcctgagt agttgggatt acaggtgctc accaccacgc   70920
tcagctaatt tttgtatttt tagtagagat gtagtttcat catgttggcc agggtggtct   70980
caaacgccga cctcaggtga tccgccctcc tcagcctctc gaagtgctgg gattataggc   71040
gtgagccacc aagcccggcc actttttttt ttttcaaagt agagatgagg tcttgctatg   71100
tggcccccc ctttttttt tccttttttt taaatagaga tgaggtcttg ctatgttgcc    71160
caggctgttc ttaaactcct gggctcaagc agtcctcctt gcttgacctc ccaaaatgtt   71220
gggattacag gcatgagcca ccaaacctga ccccttattg ttctttggaa gggaactgta   71280
tctagactga cttaactaca atgttttttt tttttttnnn nnnnnnnnn nnnnnnnnnn    71340
nnnnnnnnn nnnnnnnnnn nnnnnnnnnn nnnnnnnnn nnnnnnnnnn nnnnnnnnnn     71400
nnnnnnnnn nnnnnntga gacagagtct tgctctgtca ctcaggctgg agtgcagtgg    71460
tgcgatcttg gctcattgta ccctccacct cccgagttca aatgattctt gtgcctcagc   71520
ctctagaata gctggatcta catacgtgtg ccaccacgcc cggctaattt ttgtattttt   71580
agtagagatg ggtttttcc atgttggcca ggctggtctc gaactcccta cctcaagtga   71640
tctgcccacc tcggcctccc aaagtgctga gattacaggc gtgagccacc atgcccagcc   71700
cacaatgttt aaaaatactt acttctccat atttttgttc tttcctatgc ttgcttagtt   71760
tgatacaatt tgcaaaagta taagcttttt tttttttc ttttttatag aagccatgcg    71820
tgttcactgt aggacatcta gaaaacagag ataagagtaa agaaaaaaat agaaatcact   71880
ggccaggtgc tatggttcac acctgtaatc ccaacacttt gggaggccca ggcaggcaga   71940
tcacttgagc tcaggagttc aagaccagtg gtaaaaccct gtctctacaa aaatacaaaa   72000
attagctggg tgtcgtgggc tgaggtggga gaatcacttg agcccaggag ctggagattg   72060
cagtgagcca agattgtgct actgtactcc agcctgggtg acagagtgag ggggagaaaa   72120
```

```
atggaaataa ctagtaattt taccaccsta agtaataata gctgttaaga cttctttgaa    72180
gatgttgtgc ctgctttgtt ttcctcagtg gcctcagcct atggcatggc ttacagagag    72240
gagtgaatga atatgtgcac agcaaaaggt ggactcattc tgtacatact tgtccgttca    72300
ggtgttctct aggatagccc tgcctcattc cctgtaaagc atggaaggga ggggtggtct    72360
gtttgtagtc atcagcccat gtgtaagtca gcaggccgga ttcttgtttg ccccaggact    72420
gtggcagaat aatctaaagg tccctagtct acagtggcgc gccaccaaga aaagtgattc    72480
ttaaaaatct cactgattta gtgctttaag atgttggtga ctttgtcctt gtactctttc    72540
tattatctgt ttacaaatga atattagagg gtcatggtca caaatgagca tcatcagtta    72600
catgctgttt gtgtttctat cctatagcaa gtactctttt tttttttttt tttttgaga    72660
tggattcttg ctctgtcgcc caggctggag tgcaatggca cgatctcgcc tcactacatc    72720
ctctgcctcc cgggttcaag tgattctcct gcctcagcct cccaagtagc tgggattaca    72780
ggctcctgcc accactcctg ctgtttttt gtattttag tagacacagg gtttcatcat    72840
gttggccagg ctggtctctg actcctgacc tcaggtaatc tgcctgcctt ggtctcccaa    72900
agtgctggga ttacaggcat gagccaccat gcccagccct gtagcaaata cttagatgct    72960
attattcctg tgtacatgtc ttacatttta gatataaggg gagaaccatt cattacctat    73020
agtttacttt ttttaatag cttactctta gaatggaaaa ttaagtatgt tgtatatcgc    73080
taccaaattt tataatgtaa ggaccaattt atgcccctct taatgcttag atctgttgct    73140
gatacaggaa ttcattgaaa atacaatttt cttttcaga aatatcctgt attgccatac    73200
ttggtttag tattgaaaca attcctattg cagagggacc ttaatgaagt atttacaggt    73260
ggaattggtt cttatagtct cttttaatg gcagtcagtt tccttcaggt aagtcatatg    73320
ggtataccat gctagtgcac actaaaagca aaagtgatca atcagctggg aaacattttg    73380
gaaaaaatca aaatcaacct gtaattgcat tgctttcctt gattccttac ggttttcc    73440
tttaaactgg gtacattttt atcatttagc aaatacatat ttttaaattc ctgtgaagaa    73500
atatttttgg ttttaaatcc catatattct agtattttg agacttttca ctgcaaattt    73560
taacatgcag aatgtacggc ctggtttcca taagcgtaaa tagtataagt gccagcaata    73620
agaatgtctt ctaagcagct aaatcttgta agtttagttg gaattgagat ttgctatttg    73680
gatgagcaaa ttcgagtctt agtattgtaa atgggtgtgt ttatgtggcg cagggttgcc    73740
aactgcctga gtctattcgt gagtcagaac gactttgctg atgtcttggg ccaagccagc    73800
cctggtcggc agcctggtgc acctgtaaaa ttcagcctta caaacagtct cccaccattc    73860
ccgcaccatg ggactttagt gttgtgtgta acagcggtat aggctgctgt tatcccatta    73920
tcaattgact gctatgctaa accaaaatta taataatatt gcttgtagaa gttagaatat    73980
aatttattcc ccctctcctt gataatttag caaaaatcca atataatttc ttcttttctg    74040
cttttagtta catcccaggg aagatgcttg catccccaat acaaactatg gtgttctctt    74100
aatagaattt tttgaattat atggacgaca cttcaattat ttaaagactg gcatccggat    74160
aaaggatggt ggttcatatg tggccaaaga tgaagtacag aaaaatatgc tagatggcta    74220
caggccatca atgctttata tcgaagatcc tttacaacca ggtattgaaa ttaggtaaat    74280
ttttgggcat tcaaagagag ggcactgtca gtcacttat tatactttaa attctcttta    74340
gatgaaaaat gaaggaacaa cttctaattg ttactctttt ttcatcaaaa tatttcatga    74400
gcaaacatac taaaataaac agacacagac aatagaaaaa cacttggag acttccagat    74460
aagtagggag tagaatctgt ttaaccctaa aagcatagta gaaaaggcat tacttatttg    74520
```

```
gatggattca tgtttggtgg ctgcttctcc tttttcttgg gtccttattg ccttgattat    74580
aaccagttgt cagcaattaa tgaggcttta atgagatgat tctgaagtcc ttagaggcag    74640
caagcacagt aatatatctt tgaattcatg agcagaagga tgcaaggaga caatgtattt    74700 tcttttttgaa tttctccttt cctctttgat tttgcatgtc tctttgtgct ttttccagct    74760
tcgtgtgggc ttgaaagtaa gcagaaagta aattccttcc atgctttttt gaagttctgt    74820
ttgcttgctt gtgtcctgat ttttctgagc aatattttt cttgatataa ttgtaaaata    74880
tttagattca gcgttgttgg acttcagtgg aagtgctttt agtcatttgc tttaatgtgt    74940
aaactttgaa aatgagtaag gaaagggagt gaaaagatac agtagttgcc taggaaccat    75000
ttctggctta ttgagctgcc ttataaacat taatagttct atgtgtttat tcactgagaa    75060
aacattacat tgattgggag cctgctgtgt tcaaaagcat tgggccaaag gacacgaaga    75120
cttttcagca agatgatcct tgcttttttag gggctcataa tttagagtga taaatagata    75180
tatagctaat ataaaccccca aaaatataga agtatttcta atgtaacttg gggttcact    75240 cttaggagtg aacagggcgc tatttctttt gtttgcataa ctgtttatgt atggaatggg    75300
atagttcttg atgggccaga atacatttcg acaactgata caccataatg aagtaccaac    75360
tgcatgatgc acatattcag agactgggga gctttgggaa cagctcacag ctcagcttcc    75420
aggcacaact ctggtgggat agctatggcc cttgctctcc tggaagaggg tcgtcaacat    75480
ttagtgcaca ttaagcacag tcaagcttac tatgttacct atatttcttt taaaggtaat    75540
gatgttggaa ggagttcata tggggccatg caagtgaagc aggcctttga ttatgcctac    75600
gttgttttga gtcatgctgt atcaccaata gcaaagtact atcccaacaa tgaaacagaa    75660
aggtaaaagt tcatgtgtaa ccagcccatt gtgtcaaaat tggttgtggc ttcttatctt    75720
caaattaatg ttattccctc cctctccctt tctttttaaa cacgtgcagc atactaggta    75780
gaataattag agtaacagat gaagtcgcca catacagaga ttggatatca aagcagtggg    75840
gcttgaagaa tagacctgag ccttcatgca atggtaagat attttccttg gtcgattgac    75900
tgagtattag aggcttttct gtgttgtgtg cgtttaatgg gaagaaacgt tttccaatct    75960
tttgccactc tttcaggaaa tggtgttacc ttgatagtag atactcagca gttagataaa    76020
tgtaataata atctatctga agaaaatgaa gcccttggaa aatgtagaag taaaacctcg    76080
gaatctctta gtaaacactc ttcaaactct tcatcaggtc cagtgtcgtc ctcttctgcc    76140
acacagtcca gctctagcga tgtagtaagt atgatagcct cagcccttct gaactcagac    76200
gcatgcacgt tctcttgctg gggttaacgc tgtcttgaag gctaaggcta cttcctttgc    76260
ttacatttta ctgggatatt ttaataactt ccatgcttgt acttttctc aacattttat    76320 tatgaaaaat ttcaagcata cagcaaaagt gaacaaattt tagtgagcat tcatgtactc    76380
accaatagat tctgccatta acctttact tgcttatctc ataccctgtct atccatcact    76440 ctatccatta attcatctta ttctttgatc tatttcaaag tagattacag acatcagttc    76500
ccctagagta ctgtagcttg tgcatccttg tagccagact ccaatatttg tttattgttt    76560 tttcccttttt tttctttttg agacggggtc tccctctgtc gcccaggctg gagtgcagtg    76620
gtatgatctc agctcactgc aacctccgcc tcccatgttc aaacgattct cctgtctcag    76680
cctcctgggt agctgggatt acaggcgcct gctaccacac aggactaatt ttttgtatt    76740 tttagtagag acggggtta accttgttgg ccaggctggt ctcaaactcc tgaactcaag    76800
tgatccacct gccacccctcc caaagtgctg ggattacagg cgtgagccac cgtgcccagc    76860
```

```
ctatttttc cttttgatat gaaattgaca tataaggaaa tcttaattgt acatttacta    76920
aatttttttt tttaatttcc ctaattgttt tactttcagg gtctaggtta cttgctcata    76980
tgttcactaa attttatcaa atacatacat acacatgtat agcccaaaat cctaataagg    77040
tacaaatatt accgtcaacc caaagagcaa gctcatgatt ctttcatcaa tccctaaccc    77100
caccctcaga gggaaccact gttacgattt tttttttttt ttttgagatg gagtctcgcc    77160
ctgtcgccaa ggctggagtg cagtggtgtg atcttggctc actgcagcct ctgcctcccg    77220
ggttcaagcg attctcctgc ctcagcctcc tgagtagctg ggattacagg tgcacaccac    77280
cgtgcctggc taattttttt tatttttagt agagacgggg tttcactatg ttggtcaggc    77340
tggtcttgaa ctcctgatct cgtgatccac ccgcctcaac tcctaagtt gctgggatta    77400 caagcatgag ccaccccacc tggcctttaa cattttctt tctttctttt tttttttttt    77460
tttgagacgg agtcttgctg tgtcacccag gctggaatgt aatggcatga tcttcgctca    77520
ccacaagctc cacctcctgg gttcaagcaa ttctcctgcc tcagcctcct gagtatctga    77580
gattacaggc acgtgccacc acaccgagct aattttttct attttagta gagatggggt    77640 ttcaccatgt tggccaggct ggtcgcgagc tcctgacctt gtgatctgcc caccttggcc    77700
tcccaaagtg ctgggattac aggtgtgagc ccagctgtta tgacttttg acaccatagt    77760 tagttttgcc tgtttcagaa tttcatatat atggaaccac atagaatata cttttgtgta    77820
aggcttcttt cactcaattt ttttcagctt cctggttgaa ttttgtttgt tttttgtttt    77880
tttttgtttt ttgagacgga gtctcgctct gttgcccagg ctggagtgca gtggcgtgat    77940
cttggcccac tgcaagctcc accacccggg ttcccgccat tctcctgtct cagcctcccg    78000
agtagctggg actacaggtg cccgccaccg cacctggcta attttttgta tttttagtag    78060
agacggggtt tcaccatgat ctcgatctcc tgacctcgtg atccacccgc ctaggcctcc    78120
caaagtgctg ggattagagg tgtgagccac tgtacccagc caaatttttt ttaattgagg    78180
tataattaac ataaaattca gcattaaaaa tgtacaattc agtggttttt agaacatatt    78240
cacaatgttg tgcagccgtc tccagtaatt ctagaacatt tccataccc aagaagaaac    78300 cctgcattta gtagtagttt ctcctaattc ttccttccct cccttatcct ctggtaatt    78360 ctaatctact ttctctttct accctgatag aattttttt cttcccccat cctgatagaa    78420
tttatgtgtc aattataacg taagttacct tttaaaatca aggttaattt gtagtttact    78480
gatttgatat ctaaagcagg cttacctgtt tgattttaac tttattaagt gtaggtcatg    78540
aaaagtaatc taaatattgt atgttgttga tgaccgtgtg tcaatatgga atcataaatc    78600
ctcctgtgca aaatctcccc gtgtgccttt ttggttccta gagcagtatg ctctggagga    78660
cagaatgcca agctagatgt cacagacaca gggagatgga gtcttgggaa gtgagagact    78720
gcgactctga gatactgggt aaagtgccag ggccagggtg gagacctgca gagagacgta    78780
gcattgtcat ggcccaagca gcccagaaac aggtggggct cagcccactg tcgctgggaa    78840
gtctgcaccc acccacacca gtatgtttgg ttggaatgat cattgatttg tcattacaga    78900
caaatgacat cttgtgtctg gctgaagcca gggactagga cctaggttcc tcactcttta    78960
ccatactctt tcattttcta taaataaaaa aacaaataaa ctcagacctc tgtgagctcc    79020
ttcaaggtaa gatgtgggca gtggatttaa caatgaacag aagctctctg ataaaatcag    79080
tcactttaaa tgtttagagg aaaatttaaa caaacaatta attttgtaaa ttcctcagtg    79140
tgcttctttt aactcccaaa tgtttaaatt tagtctagag agtactttaa ccaaaattgt    79200
ttttctttct gaatattgag tatctaaatt actaatatgt cacattataa ctcatgtgac    79260
```

```
ttgtgttagg attccgatgc aacaccatgc aaaaccccga aacagctgct ttgccgtccg   79320
tccactggga accgagtagg gtcgcaagat gtatccctgg agtcctctca ggcagttggc   79380
aaaatgcaaa atacccaaac cactaacaca tccaacagca ccaacaaatc tcaggtatgt   79440
ggaacgtggg ttttaattg ttagtgttg atacaaaata tttagagttt cctacatgtg   79500
aataatatgc agcatgggtt tgaagaaaac gctagattga agaacaaact tactttattc   79560
taagagattc caacacatga cagtgcttct aggaacagga tgtcctaagg atctttgtga   79620
gacaccattg taacataaac ctcttcagaa atctattgac tggtccttat aagatgttcc   79680
agccaaacta ccatataaaa aatgtttcaa ttgtacatga aataagctgg catgaaggtg   79740
ttgtgaggcc tcatggcagt gtgcatgtct gggaataatg tatccttttc taatatttta   79800
atgttcaata gcttgttgcc cgtgttgaaa tgatcagctg gctgtcaggc atggtcagtt   79860
gattaacatt agcctggact taaaaggcca cagagatact ctagtttaag tttttttgtt   79920
gcctagaatt gtcattaact gagtaatgac tcagagtgag gggaggaagc cattgatatg   79980
gggctctggc ctgaggctgg gtcactccta actataactg ggaacctggg aagaggcctc   80040
ttggctgtta ccttgtgtct gatttgactc actgagttca ttttacctcc gtggcttttta  80100 gccatgtatg ccagacacag actcaaaata ccagttcaag tgacagggtt gacagaaggg   80160 actgggtca tgagaaagcc acaggccatg aatagcagga agggagcggc cacctgtgct   80220
gaccccaacc tacccgtgtg cctgtcatgt ccaagagcct cttcccgcta tgtgacttat   80280
gatgtggtat ttgggttggt aggtttctta agaaaaccctt tacatcccac acacactgtt   80340
aagaaggtaa gcgagtggtc tatgcttttc aatatttcca ttaaaataaa gtaagggttt   80400
cagagctaaa aagagttaac ccctgtaaca gcttttttctg cccactagat aagtcagtgg   80460
tcagtaaggt aactctctag ccagcatatt cctagttttg aaagctgccc caaatccaga   80520
tgcttttctg caatactgat gtctttgtgg tcgtttttctg tttctgcagc atggatcagc   80580
aaggctcttt cgttcttcca gcaaaggctt ccaaggtaca actcaaacaa gccatggttc   80640
cttgatgaca aacaaacaac atcaaggcaa atccaataat cagtattacc atggcaaaaa   80700
gaggaaacac aagagggacg cgcccctctc agacctctgt agatagtcgg cgctgcgcgg   80760
tggactgtct tctctgtgca atgatctcat gctcaggaca gttgcgcagg gactcctggg   80820
agacattcag gagcctcaca ctgttcagac gttgatttag caactgcgtt ttttcccagc   80880
tcgccacaga atggatcatg aagactgaca actgcaaaaa aaaaaaaaaa aaaaaaaaa   80940 aaaaaaaaaa aaaaaaaaa aggggggaaaa aaggctgct tatttgataa gtcatatgct   81000
acaacagggt cattttaaga tttaaagctt gaatgtaaaa taaatatatt tctcattggc   81060
tttatgcaga gttataggga atagtattca gtgttggtag ggtgatagaa acaatatcag   81120 aggatgggt ggggaaggaa aacaaaggta tctgatagga agtccagatt ccaaagggga   81180
aagtgatctg tgcatgtttt gtttttttt tttttaatat tttgcatat atttaccatt   81240 ttattgtgtg tatgtataga agaccatata ggaaattgat atttgtaata gtggatttgt   81300
taataatact ttttacataa cattactgtt taaattgtaa acagattttt tctcaggatt   81360
agtttgaaaa ataatctaaa ttgtcatctt aacatccata tatagggaag tgattagttc   81420
tattactcaa tttgttttc tcagcattga aatgacttaa tagaaccctt gtgtcctgct   81480
gcaaaaattt ctcctctcta aagaaaaggt ttatggtggc aaatgatgtt tatttttattt   81540 tgtaaaaaaa aaaaaaaaa aaatactatg tactttgtgt aaacactgaa aaatctctgg   81600
```

```
tcatctctga gaattaactt gcaactgttt tctatagtgc tgtcgtcttg ggcaatgggc    81660
aattacatga ctttgtgttt gctgcctttg cagtcttttt ttttccccc catttcttcc    81720 taataggaaa aaaaccccc aaaaaacaaa accaaaaaaa aaaacggcca cccatgtctg    81780
gtctcattcc tgttgcagtg aaacttcgag ttccacagac tttgcatgct ggcttctcta    81840
accctgtgtg ctgcgtgtgc ctgtttctca tctcttattc tttttaaaat tcatgcttaa    81900
ctactgtggg agaataactg taaacagctt taattaaatc atacttataa aaaactatttt   81960 tcttatattc cactttatgc ttttggtatt gttgatcttt ccaaattaaa tggtctttga    82020
taatggatct attttgtatt gccttattaa gaccaaatac ttcttgtcat cccattcttt    82080
atcctcttct ttcatggaat tgttatcatt aattaaaact tttttaagca ttggcttgtt    82140
tcaatcatac tgtaaatttt ggttgtagtc agctttgagt gcaatgagat gtataattct    82200
gttatcatta cctgttgagt ttgaaactca gttgggaata tttaatataa tagaatgtaa    82260
gtgacatttc tgaaaatgct ttctttcagg gtgaaagctc ttatgtttag catcagtgtg    82320
tatggctctg ttaaatacag ccattctga gacaagattc ttttatatat atatacatat    82380
aaagtactat tggcttttag gagtttcttt tatatacatt tatgaaatac tgaagaccaa    82440
tcagaccatt aatggacact tagtgtaact ttttataaag aaaataatgc taaagtaaga    82500
ccaaaactga tgtcatcact gaaattaaca attttcaata tgttcatatt ttaattcaca    82560
atggaaaaat gtgttccgaa actgaaaact catagtactc gtgtaaactg tggaagattt    82620
taaatgtgat gttatttga caatgtttta aattttgag tcacattctg atcagaattt    82680
ttatcgagat gttgagcttt tgtttttgaa actagtttgt cataacattg tgcataatca    82740
cagtatttat tttctaggac aattgtgaat gtgtagactt atgtttactg ctaagggaac    82800
aattatttat aaaataatat taaatccagt attagctgcc tatttcagac acttaatact    82860
tgcagagatc tatgttacat ttaccacact gaagttttt tgttgtttt ttgtttgttt    82920 gtttttaaag aatcaccctc attgttgaaa gtaaatgtac tcttagggtg cgaatattag    82980
tgttccaata agcatgtgat tatattaagg tggtggtagc gggaagataa tcttgattcc    83040
attgggaatc ttaggttttc gtaaatttat tgggaaaata gttttcctg tactgctgaa    83100 gtttctttt ggtaaacagt atctttctaa aagaaaaaag catgaaggag aaattgaggt    83160
gtgtatacat ttcctcaaat gaccagcatt gtattcgtga atactgtgta tcttgcagtg    83220
aacagtgtgg aagctgttca ttttcaatc tgaagtaaaa tactttcaat aacttttagt    83280
ttgcctgctc atttgtttta tacatttcat ctctctattt gactcctatc ttacttcttt    83340 tttgagttt aatactttct ataaagattt tgtgaatata tcagaaatgt gtcatttata    83400
tattatagtc cattcatatc catgaatcat aaccttcctt tgctaatact tgtagaatgg    83460
gattttacaa attctgcctc actctggtga catttctctg gcagtcatgt atgtgtacct    83520
ggccattaga aatattaata tttaaatact gttttttaga ggtgctgatg ggttggtgag    83580
gtgtcagcac aaaatcttat gggttatgtt ttatgataaa agtatatcca ttttttccct    83640
ccagctttaa ggtgactgtg aaggtgcctg gttttgaacg tctttgtttg gtttggagat    83700
gttgcactca gttttcaaat ctagcttgga tctgtaggac ctatgttttt tataagtaat    83760
tgccctccag tcttcaacag ttgattctgt tatattttg gcctgttttg agtgtacttt    83820
acttgcattt tgagccttat taatatttag cttatttgat ttggctccag tattcctaga    83880
tgaaatctgc acagggcaaa acatgggcaa tagggtgagc attttaatt gtcttttcc    83940 actggaacct tatatatctc catgtgtttt ctgctcattc cctcccccat gaaatggtaa    84000
```

```
gtgtacttgt gtttgcctga acctatggac tagtgtttgg ggtttctgga aacactagag   84060
ggtcagaaaa gagtaataac cacgtgaagt gcaggattct cttgctgtga cgtgttcgtt   84120
gcaaagccct ctccagcgac tgggaggtgt agttgttaag gttgatctgt tagaaatcac   84180
cattatgagg tattagtggt aaatgttgct gatatttta ttggtcatga ctacatctca    84240
gttttacttt aatattgatc tatagtttga tcagttcctt gaattctaac atgttgattt   84300
ctcaatgttt ctgtcactaa ccaagaatgt ttctagacag ttggttgctt cacagtcaaa   84360
attaaatggt aaactatcaa aaagacattc ccaattttgc tgtgataaat attgaaacat   84420
taaaattaat gaacagaaga atttattctt acccatctat tcttcttctc ctagttcatt   84480 acacttttc agttactgga aaggcacatt ctctaagtat ttggtgagca aaatattcta    84540
taaatgcctc taacaaacct aattgaatat aaaagttaca tttagtagtt actgttgata   84600
gtaattttca tcagggtcat agttcatcta gtaaatatt tagagaatga cgttaacatt    84660
ccagcattaa agtgggaaca agatttgta tgtgaaattc cttgaaagag ttcatcttgc    84720
cttggtttct gaccctcaag actagctacc tgccatcttg tcagaacatt tgtgggtaga   84780
ataagtgtta aagatcaaat tttaatgtgc tccttgatat ttaacatagc taagaagcca   84840
gattttactg cagaagttat ttacatgatt tgaaaactcg acctaactgg aagcctttt    84900 ctcagtcatc ttgttctgag ccatcttgac ttcacaccat tagcaacttt tcttttttt    84960 tggtcaaaga taatgagcta aatatatgta gatattgaat gttgacaaaa ttattaacca   85020
gaaaaattgc ttataaagtc tgctgatcta tttgatatct agaattaaat atttgaggac   85080 agttttagt tagtaaactg ctaatgttta ttttactgtc tctcaggttt ttggtttttt    85140 aaaaaaatg tttggccttt acatttctta tttaagtgtg tactttattg agtttaacct    85200
tgtccatagc ctagtagcct gaaagaaaag gaggcggaac cagagagatg gatgtagtgc   85260
attcactttg gttattataa atttgtggta gctcctggat ttactgagag atattttagt   85320
tatgtcaata agaacagcta atgatgtgga aatcaggtgt tctcttgtgt atttcagtga   85380
acgtttttat tagtatttgc atatcatctc tagttctacg ttttaactta acgtccttgt   85440
ggcttcacca ctgaggtacc tttcactaca ccagcttctg tgtggcctgg taacatggaa   85500
ggtctctcct aaggacagtc tggacatatt ttgggggaat gttatttatc ttaaagatgc   85560
ctagaaacaa cgcatatagt accagtgaga agtatgaag taaacaagtt gctcaggctg    85620
ggcatggtgg ctcacgcctg taatcccagc actttgggag gctgcagtgg gaggattgct   85680
tgaggccagg agttcaagac ctttgtctct taaaaacaaa caaaacctg aatggtgagg    85740 tggggtagaa ttgggtaggg gagggaaagg gggacttgga aaagcattcc ccaaagccag   85800
tgacttggtg aagttcagta cttgcctctt agaagttagc ccatgccttt caaagagagt   85860
gaaatgatgg gttatcagcc acattcttgg agttaatatg tttcttcatc tttcaatttg   85920
gattctgtgc tattcatagc tcttccctaa gaccatttca ttattacctc ttatatttag   85980
ttgcaattta tcataatatg ttgttttgtc cctaaactta atctcctaat tttaagatcc   86040
tctctgattt ttgcatattg aaatttgcag aagtcacttt taagaagtct tttgaaagtc   86100
ttgcaatcct aaaataaatc aagcttgttt gttagaagtg tcatgagtct ccagtcttta   86160
ctattaaaaa gcagccctgc cttaacgcac attgttatgg gtgacaagtg acggacaaca   86220
agtgtagttt ctggatataa agagtgaagg actattgggt taaacatttt tagtggaata   86280
tacatagata tgtatattta gaaactttgg tgaagccagt atttgttttt aataaccttt   86340
```

-continued

| | |
|---|---|
| tcatttattt ccttctttga ttagcattgt cttctgtgtt aagaaatgtg gactcctgtg | 86400 |
| aggtgctgga ggtttgaatc atcttgaaaa cttttccagtc ttgtctagtt accactgcag | 86460 |
| agacactaag gaatttacca gaaaaagata tttgatacaa atgatttaag aaatctcaac | 86520 |
| atttcctgag gccatatcac tgggcaacca gtgatgaaaa ctatgaatga attgcacacc | 86580 |
| tggaagattt tttaagctaa cgacagtttc ttcaaagatg tcaattattt gccttggaaa | 86640 |
| ttttataaat tgcatttcta tgcacatctg cccctagtgc ttaccacttg gtttattatt | 86700 |
| cataatctgc aattcaataa aggctttgtg ctttcattta tcttcaaaac | 86750 |

<210> SEQ ID NO 4
<211> LENGTH: 49960
<212> TYPE: DNA
<213> ORGANISM: Macaca fascicularis

<400> SEQUENCE: 4

| | |
|---|---|
| aactacctgc tgtccggcag ccgcgcggct gctctcagcg gaggggggcgg ccccggggcc | 60 |
| caggcgccgc ggcccggcac cccgtggaag agccgcgcgt acagcccggg catccagggg | 120 |
| tgagtgcacg gggcggccgc gggggcgggg gcggggacca tggtcctggc cggcgcccgc | 180 |
| gttgcagaca ccggttacag gcgcccgggc ttcttttgga ggatgcatgt tgaaggccaa | 240 |
| ggcccgactc tgctctgaaa gttttttttg ttttttttt ttcttgctaa tatgaaactc | 300 |
| ctttataatg gagtgacttg cccagatcct gcaagtaaca atgcaagaaa ggggctgctg | 360 |
| aataggacct gtaggtattt gtctttttta ctcttgagac tggaaaggga aatcgactct | 420 |
| cccccctgcac cccgcctccg ggcaagtgag gaacccttg ttaaagtggg gcgtagataa | 480 |
| gtgtggagtt tcattaagtt aagttgcaga ataatttagc attaccagga actcagatca | 540 |
| cgtcgaaggt aaatattaac cgtttttatt tcatttaaaa caaaaattta actgtcaatt | 600 |
| tagaggtgat tcattggggg gggttgtgtg ctttaatttc gtgctgcagt taacataagc | 660 |
| atagtatata catattggct taattcaaag aaaaaaacag atatgtcata tatatctgtt | 720 |
| ctttggaaga tgccattatt atttttaaata cttccacatc cgcctggagg gaattagagg | 780 |
| ctctacttat atttagtgca cctacagacg gcaaggaatg aaagcaaagg tggtgtgtgt | 840 |
| ggggttggaa ttgccccagg tgaggctgtt caggtgtgat gctgttgacg cagctctttg | 900 |
| gccattttgg gcttttctga gcgtctggaa ataatttatg tgtgggttgt atgtcagtat | 960 |
| tttaagactt aaacgataaa ttttccttgc acgatttttt tccccccaat ttaaaaaga | 1020 |
| aggatttgcc ggggtatgag ggttgttaca tgcagtagag tcctacgaat aaccacaatt | 1080 |
| gctaggcgtt gggagttgtt acagtgcact ttttcttgta actctgtttc tcatgtgaag | 1140 |
| tatgttggga aacagagttg atacttcttt aaagcgtgtg atacactgta atagccgcat | 1200 |
| gttgtgtaac ttttttcacc tggcttgggc tacaagtgat gccttctaaa ttccctgaag | 1260 |
| gtgtaaacat gcattgcaga cactggcggg agggcagact cctctccctc cagttcttac | 1320 |
| ctgtagaact ttctgagagc aggtggttgg aagcggtttc ttcttgatgt atagtaatgt | 1380 |
| atacctcagg gctcgcttgg gaggaccttt aggtttccag cctgttatgg aactggcatg | 1440 |
| ggctctttct agtgtctctt agcactagaa aaaacagaca cgtcgtctct gcaagtcttg | 1500 |
| ggttgtacct ctgctcttag cggtagcgca tcaggcccca cgcatctcac ttggactccc | 1560 |
| caagctgttt cctcctggta actagtaagc ctcagtaggt cgtgttgctt ttgttagtga | 1620 |
| atgagcccac tagggtcagg tgctgtgttg ggatctgggg atctggtgca gagacgtat | 1680 |
| ggagacaatc tcatgatctt gacccaccct gaaacctgcc tacaagtgcc ccctgcctag | 1740 |

-continued

```
agcacaagag taccctgctc agttgtgcag gtccnctctc acgctcttcg tcacccacgc    1800
ccaatcaatc atcagatgct gttcgtttgg ccctttaat ctctccacac ctcatcctca     1860
ggcagtctct tgttacctct gtggagatcg ctcaagcagc cggaggtgcc ttcgatgcac    1920
tctcgtcctg cttgagtcct ttcccatcac tgctaatggg gtgatcttct ctgccggcag   1980
gtctggtcag gttcccctc acctctgat gtcacctcct ccatctccaa tccccacat      2040 taaagtctaa agcctaaaac tcagcaacac ctccagggtt ctgctactca gatgaccctg   2100
ggtcctggcc cctggcccca cgccccaccc cttgccaacc tgttagaacc cagctgtaag   2160
gcagtatggt gtagggcata agagagggct ctgaagcccg tcaggaggtc tggtttgatg   2220
ctacagtcat gctcttggaa ccttccttt cacctttgct ggagacctct ccttgcctgt    2280
ctccaggtgg cgtgtaccat gcctccagta tggccctggt gcatccactt cctgctgtct   2340
ctgcccaaag gggcccgtga ggactacctg ctatgagcct agaagggcac gttgacctct   2400
gcttgggctg ctactcaagc tgctctttca gaagtaaacc taagcggtgg tagagttggg   2460
cctatgacta gaggaggtaa ggtccccca gtgatcattt ccacatggcc cgttggtcct    2520
acatgaacta acctttttcgt gtcaagaaat agttccgtct agaactttct tctggccatc  2580
agcttaccca gagtgttgag aaaggccacc aaaaagtctt tcagttgtgc cttagagaag   2640
gaaataactg agttttaaag gcacacctga gctgaccaat agtaaaggat cttgttgctg   2700
ggaagctgct tggggttgtg atatagtccc aggacgtgca cttctgaaaa tgcagtgtgc   2760
gttcctcatg ggaggatgag cctgctgcgg agcactggct gaacccagtt gggtctttgc   2820
ctggtagccc atgtggcaac ccgcactatt tgtccttttc tggggaggag ttttctgtcc   2880
ttggacactt tgcctggtgg cttggccttg tgagactgcc agtctgcctt ctgctcaagt   2940
aggatgaaga aaaagcaggt gaaagaggac agggattggt gcaagaacct tcagaggaga   3000
ggaggtgaaa tgctccttt gactctggtt cttactccat tgtttgattg aaatcccaag    3060
cctttgtttt gggaatggtg tgcttagcgt gaactctgct gttgacctgg gcttctgacc   3120
ttgagatgtt gggcaggtgt gtggacaggc cctgggcccg ttgcatccca gcctctggct   3180
gctgttactt gcacgtgctc tcatgccctg acccagcagg gctttgagct gttgttactt   3240
tgccatggtc attctagcag cttttggaaac ctctccaggt taaaagtctt gcgtaagtga  3300
gagtgggagc atggccttca gatatttggc cacatccttc ctggtgtgtt acagagaccc   3360
aggaagagtg tagttgaacg aagacatgtg caggtgtccc gggccttgaa cagcttctat   3420
tcagagtttg gccttgcgaa ggctgtgcca tctcaggtgt gcctgcagtg tgcagcaggt   3480
gtttgcagct tcctctctgc aggttttcttg atatttaatt tcatcttta atatcttctg   3540 ttaactcaaa ggaaattctt agtttgacgt atgagagaga ctgaccactg tcagcatagg   3600
acatggtcag ccgtatctca caaggcccct ggtgagagtc gtttccaact tggtgcatgt   3660
ttttttcgat tctttcttgc aaaggagtca gagcttggag gcgcaaccag gatcccctcc   3720
tctccctcta gcctggcctc actgacataa agtagagcag gtgtgacctg tctggaacgt   3780
ccttgtgatg ctcagcaggg cctgctgcag agcacgggag gcatcactct aggggccttt   3840
ccctcccata ccttcctgtg agtgtccagg atacatagaa aggctgtcgt gagacctgcc   3900
gtaaaggatg gcggtggcac gtgtggacct tgctttctga gtttcactgt ctgagtccca   3960
gaggtataag cttgtggaga gaagtgtaca tgatcacact aagcagatac ttgctcctgc   4020
actgttggag gaggaggagg gattaatttc ataatttcat aaatcaactc ttccaacact   4080
```

```
cctcctgttt agtaatagca tcacttgttc ctgtcttttg ttccattgcc aagctcccca    4140
aggtgaaatt gaaatagag tgcaagacac aggctgtgtt ggagttgagg aaagttttgc    4200
tggagaactg cttgcaccac gtgtctggtc actgatagat gaggactggc caggtcagga    4260
cagctgacac tgggagaagg ggctgcccgg gggggcatga cagactctgg aaaaggaggg    4320
ttggagtatt aaactggctg ggaatgagag gcctctaatc ttttctccaa aagaaaaaa    4380 aaaaaaaaaa aaaaggctta atgctcatgc ggtggaagtc agagtgaagc aaagtgagtt    4440
ctgtctgtct tgctgctatg agcgtgtgat ggaacaacag tgtcatttgc tttttctcaa    4500
atatttaatg catgtttgtg acataatttt tttaagtaat ttcaaataaa tattttaaag    4560
taaaaagttc taagattttt gtgtctccag gtaaagtctc aaactgtctt tggtcactaa    4620
tatgagattt tgtcttcatt ttaaatggat tcatgtaagt gtcctgtggg agaagagtta    4680
atggttatcc ttggaaaata agaacttttt atgcctcagt taggtcatat ggtttaggat    4740
ctgattttgt agttgtggag taaaaaaggt tgtttaagaa aaaaaaaaca aaaaaccttg    4800
atattcaaat tcagaaactt gatttttgag gatgcaacca gaatttggac taacggtgga    4860
gagggctggc ggagtcagac cacccagact cgcagaagat tgaagaagct gcagtgctcc    4920
tgtggagagg ccctttctag gaggtgtggc tggcttgtca gtgctttctc ttctctgcag    4980
tgaattggat ggcaagcctc gccctctttg aaagctgcca ctctgagcct gccttgagag    5040
catctcaggg agggcagaga ggtggcctcg gtcagcgctg acaggtgccc aaattacctg    5100
acctgttgtg aacatgtgcc tgagtgaggt ggccaggatg cctttctcc caacactggg    5160 gatgtacact catgcaacat cctatttttg agatttctat gttgtggtag ttctctgttg    5220
ctgtgtagca aattagcgta aactcagagg catagaagaa cactcattta tggtcttgtg    5280
gattctgtgt gtcaaatcag ggatggctgg gctgggttct ctgctcaggc ttttgcaaag    5340
ctgaagggtg ttggccagct gtgttctcag ctggcactca gggtcctctt accagcgcat    5400
tcctgttatt gttagaattc agctccttgc aggatcgaag tccttgattg cttgctagct    5460
gccagcaggg gaattgggta gggctctctc agcttcttaa ggccacctgc attccatctg    5520
caaagcaagg tactttgaat ttctctgacg tttcccgcca gctgcttaga agcccatgga    5580 agcccctgc ttctatgggc ttgtgtgatt gagtcaggct cctgcgaata acctccctac    5640
ctgaaggtca tgtagtaata caacatgatc atggtgtgat aacctcatca gagccacagg    5700
ttccaaggag tagggtgtag gaccttgagg ggaggaggtt cttctgtggg tagacttccc    5760
ctggcgtgga atcggttgat gaggaggttg tggttcttct tgtccaacac ttttccctg    5820 actggactcc agcccatcgc aatgactctt gcagattgcc ggttctgtcc tctggcttgg    5880
tggttactgc tgaactcagg cagccaccat aaccaggaga acctttctgt gctgcagtca    5940
gatggacatt ctttaaaata tgtcgtttaa gaaaagtttg caggaaagcc gtgtgaatat    6000
atgaaactac ggtgattgaa aagtcctgtt tgtgaggtgt cctgcattgg ctggattagg    6060
aaaggggtca ttcctatgca ggtgggggtc gatgacttac ccaagagtca cctctggaac    6120
attctcgtat gttcatagca gtccatcttt gcagaaggtg tgggggacac ttgtcctgca    6180
agcccaggtt cgtaggaatg ttagcttccc cagaccttg gccgcagagc accgtgcctc    6240
ctttaggagg gacaagaaaa ctcccatatg gttcttccct ctgtcccttc ctgagcccct    6300
ctgagtgttt ggctcttgtg gagttactgc tgctataaca aagctgaccc gactgccctc    6360
ctgagtctcc tcagggaagg aggagctgta ttgtagcctg cattcttagt gccaagcaca    6420
cggtagccac taagtatgta tctcccaaga aagaagagca gaaagaggat ctgccagctc    6480
```

```
aggagggcag gtgggggatg gcaagtctgc ggagtgttca taaaccaaat gctaagggaa    6540
acttttgttg gttgtcttag aattttaaaa aataaagtct gttgcagttt atctgctttc    6600
cttcctggag agtggctaaa ctaatgttct cttttacaat atagaatgcg agagcagaaa    6660
acattcagga aaattctata ctgtatttga aaaacatcac catttagttt taactgctcg    6720
ctcttattat aaaaattaat acctaactat gaaaagttag aaagcctgga gaagtatgga    6780
gatgagttgt ccaccattgg gccacctaga gagtgcactg tgagcctgtc cctggtgtcc    6840
tgtactctgg tgatgtgcac tgcatttgct ggcagtgagc cagggagtgg accacatccg    6900
ggcctgggcc gggtggatct ctgcagaagt ttatctctcg gctgacaggg tgggctagat    6960
aggagcagct ctgagggtcc ctattggcag ggaatgtttt tgattatcaa tgacatgcct    7020
ttttgttgtg ggcttgtgat cttttctctt cctaaatcag ctgctgtgca taaccagtta    7080
ggctctcccg tggcttaaga ttggaattgg tttcccaatg ctaggatgtg ggtgttaggt    7140
ggtttctatc tttccgtttg aaagaggttt cagatcagtg taacatttct agaatcctgt    7200
tgatctgaag gaatggtaga atgtagtagt ttaagggaaa tgaaaagttg aattattttg    7260
atgtttctgc tttaaacctg ctgggtggag tccatttctg agcactggga gccacgtgct    7320
tggctcttga gagcctagct cgatcagccc atgtcacaca ctcacaggtc tggcttttgcc   7380 tggtttcgcc acggtttcta acttgagcct cagtttcccc aactgtgaag cggagcctgt    7440
ggcacccacc ttagagcaca tgaaagactt ggaagaggcc gggtagcctg taatcccagc    7500
actttggagg tcaggagatc gagaccatcc tggctaacac ggtgaaaccc catctctact    7560
aaaaaaatac aaaaattagc cgggcacggt ggcgggcgcc agtagtccca gctacacggg    7620
aggctgaggc aggagaatgg cttgaacccg ggaggcggag cttgcagtga gtggagatcg    7680
cgccactgca ctccagcctg ggtgacagag cgagactccc tctcaaaaaa aaaaaagact    7740
tggaagcact ctgtgagttg tcatgcaaga gattaaaaag gccaccactg ccctttttctc   7800 ctctctttaa ggaaattgaa accaaaaatt aagtccttct tcttgccagc tggacaggaa    7860 aagcctttt cttggttttt tgaaaataca gctttcactt tcagatcaaa gtgaaaactg     7920
ctaaagactg aatgttctga gttgtgggag tgggggggctg gaggggtgtt atgaattgaa   7980 agatacttt ctatttttaa aacatttaa caatgcctta ataatatctg ttctagtttt      8040
gtgttttttt tttttttttt tttaactgtt ctgaaggtac atcagcactg ttctacagct    8100
ttaaataaga atctcatctc cctagaggca agggtactct cgatgtattt ggtcaggggt    8160
gaatgtgctg ctctgtgtaa ctcgtttaaa gttggttaag gttttttta ttttgtgcac     8220 atagtagaag gagtgaatga agtgttttct gaactcttcc agcttttaac atagtattct    8280
gtgtatagcg aaagaaaaca aaattaaggg ccagggaaca ttaagaaggc aactagaaca    8340
gcactgtcca gtagagcttc ctgtggagat ggaataattc tagttttgca ctaatacagt    8400
agccactggc catatgtgac ttttgagcac ttgaaatgtg acaaatgcaa ctgaggagct    8460
gaattttaat tttattact tttaattaaa atttaaatgg ccatatattt agacagctct     8520
gaactgcagt aactttagac tctatttgaa acagcgtttg attcagtaac tgttgctgaa    8580
ataaattgaa actcatacaa cagtaaaaac tgtgttactc agcaagttac cactgtgaaa    8640
gctctagaaa ttgtttgaat ttccaatgca aatccttttc aaacagccgc tgttttaata    8700
gcacatgaag cataaaatag gtgcatagca gcgcaacaca gagcaacacg gagaaactat    8760
tgtgacctgg agtgtctcca gtccagcatg caggtgatag gtctctcagc gttttttgcac   8820
```

```
acaggttaat gatggtgcag acggtcactt ccttctctga acagccttcc tggtcaccag    8880
caccactgtg gctcatgtgt gtgaggctct tttggcttag ctctctacgt gagtttgctc    8940
cttgagttcc cagagctgac ccatgaaatg agtgatatta ctcctgtttt gtagatagaa    9000
aactgaagcc ttgacaggct gacatgacct ggcaaaaggt gctgcacttg gaaatgtcaa    9060
ttcacggctg acatctggac actttactcc taactgttca gtgaacaaga cgttgctaac    9120
atgcggggga tggaacctag caactcattc tacaagtatg gttcaaatat gttggtacag    9180
ggccttttgc tttgttttcc taaagagatt agattgagat gtggcggagt gctttgacag    9240
ccaccgcagg acaaagttga cagctctggg gttggggagt gttgaggatt tcggagggaa    9300
gccagtcctg ggcagtagtg cgctctgggt tcgtgctttc tcgaggtgtt ccagagctgg    9360
cctggaggga ggctgcggtg cggcagcggg atttctgtca cctggagtat tcttagaagt    9420
tgcattctat gaaaagtgga gcatctgatg agctgtttac tcgctgttgt atctgacggc    9480
agttgaaaga caaagcagga ctggcagcgc agccgcctca gtcagcactg ctgcgttggg    9540
ggcttgacct gcagtctcgc aatcctgggc aataactcat tttcaagaaa gaaaaattaa    9600
acattaagtg attgaagcgt cttgcccaag ccgctactag aaaataaagg tgctggtgct    9660
caggtgcagg tctgcatggt gtgcaaacct gggctccttc ccacacccc  tcagagaggg     9720 cactggtatg ttggagtgaa gagccacgca agacctctgt gaatgggcag agatgggccc    9780
gtggcgcaac acagtaaaat gtattttggt tatgggcatt gtctctaaac ttatgtaaaa    9840
cattataaaa aatggaagga caatgatgaa atgatggcca aaaacataga aaaggatacc    9900
ttgcatgtac tgtgaaatgc aaagaaattc taaagtgtca ttacgagtta cctcatggaa    9960
gaaagcaaaa ggtgaatcta tctagagttt gtggttctga ctcacaagag actgatgttc   10020
atgctgaagg acaagtgtga tgggtggaag gatagagcgc caagaccaca ctctaaagat   10080
gggaacctat gggaactgtc cagggagatg aaagcatgga atgaactgaa gcttgtggac   10140
ttgttgagta gaaagagcct tttaggattg gttttagaat aaaataataa ggcctgtggt   10200
tggggaagat gacttgctgt tcacagagcc tcccttaaca ggtggggacc tcagcttttc   10260
ctttgctgcc atcaagtgag tggtgtacag tcctagccac agtagtaatc tctactggcc   10320
tgactgagcc ctcacccttt atgcagtgtc tcctgccacc ctcctgggag aggctgttct   10380
cagcatagct ggcctggggt cacacagctg gtaggtgtaa agctggcgtc ggagtccagg   10440
tagtctcact ccatagcctg cctctttagc caccgcagat gtagagcaaa gcaagaattg   10500
tccaaagagg taagctaata aagaggaaaa caggctgggt gcagtggctc atgcctgtaa   10560
tcccagcact ttgggatgcc gagaggggtg gatcacgagt tcaggagatc gagaccattc   10620
tggccaattc tctgggcgtg atggcacgca cttgtagtcc cagttacttg ggaggctgag   10680
gcaggagaat cccttgaact caggaggcgg aggttgcagt gagccgggat cacgcaactg   10740
cactccagcc tgggtgacag agtgagactc catctcaaaa aaaaaaaaa  aaaaaaaagg   10800 aaaacaatta tgctgagttc cagtaatctc tgggtccaga gaagtgatat ctgacttctc   10860
aggagagatg ctgatgctgt ctgagggcct gcccagtctc cgaatgattc agacactcca   10920
gggatggaca gttagtgccc taattttccc aagaggattc tgagggtgac ttctctcaac   10980
ccaacaggag gacctggtgc tgtcatcacc agttggagag aggctgtttt gtgaggctgg   11040
ggaccacctg ctgtgtgtgc cgtcttacac tgccatttgc tgatcgcttt agagctagag   11100
gttgtttcta agagtacttc gtgctaacta aaaaatgacg acattgtttt tataaaactg   11160
attcatggtt tgttttttga agcagaaagc tctgaagtca ctcagtccca ccacccagaa   11220
```

```
ggacaattag gtgactgtca ctataggacc tctctaggct cgtgtagatg gacacatgga   11280
ttggtcagta gaaatactta cattaaaagt cttatcttta cataaatttg ccaaattatt   11340
aattttgctt gaaagggaaa gatgtctaac ttcagttgga aatactggtt tctgagagat   11400
agtgctgagg ctaagaacat aaaacatgaa aaccgtaagt ggctaagtgc agaaacatca   11460
gagtaaaatc tttgatgaag tcttggtttg cttgggctgt gtaggttgga ggctcagcct   11520
ttgtttctcc ctcctgtggt gcccagtggt ggtgtttctg tgtccatgaa ttttcagcat   11580
ctgtagtttg tagttatgac cactactgca cctagccctt actgagggcc agggcctgtg   11640
ctaagcactt cccagtgtgg attcattaag tcctcataac agcaccatgt gggggcagct   11700
gcgtccctat gtcgtacttg ggacgcgatc tgacccagt cacttcgggc tcctaaaggg    11760
tctgcagtct cgcctctgcc tgggaaacca cgatttgcag catattccac agacctcatg   11820
cttatcacca ggaggcttcc tgggactgct gtctgaggtt tctaagttcc taacgtggtt   11880
catgcttctg gtgagtttct ttgaggcgac atacccagca ttgcctctgg tcagctcagc   11940
cctgtggtcc cgcgtggcat cctgcagtgt cctctggctg tgactcgtgc cgcgccacct   12000
tgacctggca tccactgtcc tccactgcgt ttgcaggtgg gagccactgt tggtgccttt   12060
tgtcatgtgt gttgaatggt cagggtccca ataagagct gattggggtc attctccttg    12120
aatctgccat gtgcctggac cactctttgc ttcagaactc acacatgttg cctgtcctct   12180
ctggcttgga gggttgtgtg gaatcaaagg tgagacccag tccccaggga tgggcgtttg   12240
cctttgattg cccagctgtc ctgagcgccc tcgcttccgc gcccagctgc tgcctcggtt   12300
gcttgcttga ggatccggat gtagactgag gttggcctta atgtggcagg gggtttctct   12360
tgagccttgg atactttgct actggtccca tcttcctgtg agtgggagcg tcccgcctgg   12420
cccagcctcc cagcggtgac cttagctctc ttagtatatg ggctctgcct gccttggtcc   12480
ccagcttgcc accctagtgc agttgctgct tcgctcttgt tccgctcctt gtctctgtcc   12540
accctgtgct ttattgatgt gtccttactc ggtgttttct gtggagcagg gcatcctggg   12600
cttcctctct gatccctggc tcctgtgctc ttccctgctg ggctccctct tccttccgt    12660 tttctgctgt gttgccctca cacagctggc atgccacgga tgtcgctcac ccaagccctt   12720
cctagtgttg ctcaccaaac acctcccacc ttgcccccgg gaccttctcc ccttccaggc   12780
tgcaggcagg ctgagggcct ggcatctcag gagtgccgag gctcagcggg aggcagtggg   12840
gcctttgctg gcagctgggc tctgcatcct gactttctga gggcttagtc cttttggtcc   12900
atcttgaatc tcctccaggc ttttggactc tctgctctgt agctggccca tgggaacagg   12960
tacactcagg cctggtctta gactccacta cttgggctgt gccggtgccc ttggtgtcct   13020
cttagtccgt cccacctggg ggccccatcc tgctgtccct tgtgccagag tgctgtcctc   13080
ttgtctttcc acaactggct gctcattgcc tttcccatct cagactcagt tccagcccct   13140
tggtatcagg gaggctctcc ttgagcaccc aacctaaagt tcacagctgt ggttaccagt   13200
ttaaatttct gcctagcacc ttttggtttt attttggcta cttatctccc ccatcatgcc   13260
ccctgtccct cccatataaa ctcagtgagt agggaccgca tcatcatcct gcccacagct   13320
ctactgtctg tatcaaccgg gtgcgctacg cagaggctca tggtaaataa ctgcagacca   13380
cgaatcccat ctacttgctg tgctttaata ttggcttaca tctttggatc cagtgagttc   13440
ttttctctct ccctctctct cgctcagtca tacttacttt gtgtaattgg tgatttccag   13500
ccttttgtat agtcctttct tgaatagttg ttttctgtca tcttggcggg gcctcagggg   13560
```

```
gttgactgtg tggagggcag gggctgcaga gctgcagctg ctgcctgggc tctcatggcg    13620
cctgcgaagt ataggcaggt gctttgcctc tgagccatct gtagaatggg gtgacggtgg    13680
tttcatcaga ctcagtgaag cgtgtcatac agtgagcgcc tggtcacagc aggcagatga    13740
tgaatgtcag ctaatgagta ttcatcacca atgaatagta acaattttt ctactaaggc     13800 tatgtaatgt agcctcggaa tcccactcag cacagccccc tggcagcagt gcctttgaga    13860
gctggcatgg tcgagagacc ctggttggcc ttactagtgt ggttgggta cttgagagaa    13920 ctccttcctc acatagctct tccggtgttt agtctttgca tctggaggtt tttcgcgatt    13980
gtgggatagc tttttcaggg gccttgcctt tggcagggca gggacgtgta ctgctgcaat    14040
ctggggtatg ggataacttt ctaaaccaga cccagaactt gacggccgaa ggggcctctt    14100
agccatgcgg ggctaggagc tgacacaggg tcagcagcac gaggtcctgt ggtgctgggt    14160
ggcagagccc ggagggagcc cctgctggtg tgactttagt gtaaaggctg cgggatccca    14220
aattcttaca gaagacttaa gacgggcaca gtgatgtctg ctctttgacc tttgcagtat    14280
gaattagtaa aactgaaatg attacgcttc atttattagg attatgaaaa caataatgta    14340
cttattgaag aaaatgtgga aaatacagaa actacctata attttctat tgttaacatt     14400 tgagcatatt tcttgtcact tttaatgctg cttaaatat gtagcaaatg tatcattttg     14460 cattaaaaa aaatgctgct agcatttcct cctgtcttta aaagctctt ttaaacaact      14520 ttaaatatt gtatagatag atgtacacaa ttttctcaat aattggagtt atatttacat     14580
cttgtcactc tttaggaaag gactggccta cttctgtgtt gggttccttc ctgagtgtgc    14640
tttccagctc agtggctcgg acttcaagat ggagacttga gtcctggttc tgtatagtct    14700
tgggccagtt accatatgtc tgatgaatac ttagttttgt catctgtaaa atgaaaatag    14760
cagtacttgc ctcaaagact atttggagg atcagtgtg aatgttggta atgcggatat      14820
tgtgtagtgt cccagaatat taatgttttt agcctcttgg ctcttactct gtattgttgc    14880
cccaaaagat gatgttcgct tcttatttt catccagtgt aaggatatct ggaaagacaa     14940
agtatagctg ctttcatttc aaaagtgatc agctgcttga gctagcaagc aagctagctt    15000
ccaggcgcag ttatgcagtt tcacagcagg cgcggttccc tcggagcacc cagaggtgct    15060
ctgtggtcgt cagcagtgat gctgtggctg cactgccaga cggggtggca ggtggaccag    15120
agcagatgtg gctcaggaag tgccgtcttc ttcgcctctc cttaatctct ttcagagtct    15180
gtgggttctt gattgcgctg tgggttgctt cagactccag tattaggaga ttgaacccct    15240
tgggtttttg tgtgtgtgtg tgtgtgtgtg tgtgctgagc tgggttgagg acatgttaag    15300
caggtggggt gcctcccctg ggtttgctcc tggtggttcc tgtagtgtgg ggtggttctg    15360
agtagttctg gccccactgc tggggtatct gccgactcag tttgtgagat gtggagcttc    15420
atcctggtct ggtgcctcat tttcttcttt agcagtgggc ttagaaccaa tgcagattcc    15480
caagttaagt attttcctg tggcttaatt attacaagtt tctggtacct aagcccttc      15540 ttactttctg ttctgagggg aagaggagat tatggtgttt ctccccactc cgagtggccc    15600
caggaccttt gcatggcatt tgccgtgtgc ttgggtttgc tctactgggg tgaaagagta    15660
tcatgccccc cagcactcac aaaggcacct ctgctcaccc tccggtgagg ttctgactgg    15720
ccctgggaca tcacctgctc caggatcctc tgtggctcat cccaggagag atgtgggaga    15780
gggaagggga aaaaggctt acacttgtcg agtggaattc ctgtaggtct gagttccaca     15840
ttgattccta agctgcagaa cccttctgcc ctggctgttt tgtgaatggt agtcagtctt    15900
aaccttttta accaagttaa cattggctgt ctcaggaggc tcacagctcc tgctcctcct    15960
```

```
ccagggagt gcgccctcct cctctgtcgg tagctgtcag gcgccccttc ccccgcagc    16020 agattctcct gggtccttgc ctggccttct ccttacacgt gagcctgcag cttcattcac    16080
agccgctgtg tagaaagaca ggcacatcga taggtccctc cctgcccaga gtgggtggaa    16140
ctgaggcaga cactaaaagc agctgactgg cagccctaga aacacgaagg gtttcattta    16200
tagtttcagt ccttttcctt ctttcgagcc ttgatttaaa aaagaaagga aaaaaaaaa     16260 gccttgaaat cctgcttctg gattttctaa tttgtgcagg tattagttgc cttgtaatgt    16320
aattaaaaat aaataaaaat gatttataat tagctcatta actgtatcag taaatggatg    16380 cttttaaagag gatcattgat ccctcaaaac agaagcaatg cagtcgttcc ctcattatgc   16440
tgtacttgag atttgctcta gcaacccact cttcctaaag ttaaatatta atccagaccc    16500
tatcagtgca acgtagtagt gtctgaatca gttgtggttt tggtgtaata gcatcaaagc    16560
atgttataaa atctacaaaa ttgtagtggt taactccaaa tatttcactg agacattatt    16620
tttttgggca aaaatgcata gtgaacattg tggagctgag gtgaggaact tcgatttctg    16680
agaaaccacc cgttttaagg gttttgaagg aagagttgga ggagaagagg gagagaataa    16740
attaacagtg agtttccagt attttctgtc gcattttacg ttttagtgga aaaaactggg    16800
aactgaactc acatgcagtt tgtaaaatca ctttttccct agcattcagg attgatgaga    16860
tttaacgggg tgttaaaggt aaactgaggc acataattaa catggacaga actgtatacc    16920
tgagtgtcga gagctgtgag atttcagtga gttgggagac tggaagcgcc cattcttcag    16980
agtgcatctc ctcatgttca gtgggtttaa ggtgctgaag cctttttttt ttttttttt     17040 gaaatgggt cttgcactgg tgcccagact ggagtgcagt ggtgcaatca ccactcactg     17100
tagctttgaa tcctgggctc agcctatcct cccacatcag cctcctgact agctgggact    17160
gcagacctgg gccaacactc ctggcttgaa acaacttgta tccagattgg aggagggcgt    17220
gtttgttttt gtgaccttc ctttcccta aacattgaat aatatcagac ctttgaccat      17280
cactttgctt aaaagaagct actggattta aagtctagga gaacgtcctg gacaagcaaa    17340
cccatagtat gttcctgtat gttccccacc cagagacctg gattataaag tgtttggtgt    17400
gcttcttctg gccccactgt tctttctaaa gtgtttcatt ttacataggc tatcctggct    17460
tcagggttgt cacctctgcc tttgtgcccc ttagtacctt tgtcctttac ctactgcagt    17520
gcagctgcct gttcttcggt agactacaaa gaagtcactt ttgaacaact tagaaattgt    17580
gccttgtggg gaaggcaggg cagagccttg gggctgagat ggaggaggag ccagctctgc    17640 cctggaggg atacgaagct cgtgaggcag gggacgggtg gagttgcttc acctcttttgg    17700 ccccagcttc aaaaccagcc agtcctccct ggctttggct ttaattcaag tttggacaaa    17760
ctggaaaacc agttaatccc attagctcag cttctaaagc cgaaaatcat gcctgaaat     17820 gggtcatctg ttttcatcaa tagctttatt agctatggaa taatatagtt ttgttctcta    17880
actgtaggat cctcttttg ctcttaaaat agctcagtaa gttgggtctc ataaatacat     17940
gcagcaagca tataccagat aaatacgaaa acattgctga tcttgctttt tagtactaaa    18000
agcagaaaat cgggaattta ctaaatggag aagtcagtcg ttacctttg atgggtttgg     18060 actcttgcaa ggtagtgatt gtaaacaaga gtgatctttt gttgttttc aatgaacttt      18120 attctctaat ttttagtaaa gcacactagg aaataatgct tcagaattct gttttctagt    18180
agttccttga ttaaaatgaa aattcactaa aaaaaaaaac tctgctgtca ccgtttcctt    18240
ttttcttaag ataaccagga aatgaatcat tcagggtttg ctccatggtg atgggtcagg    18300
```

```
aagctgcccc tgctgtgtgt ggggcaggag gcttgctgat gtcccaggat ttcacttcgc   18360
ggagacaagc atcagaggct tgcttcattt atagatccta cttcttttct acaccacagc   18420
caactcaaaa tggtgacaaa atctaagacg aggctggaag tcaccgcaga gcagttggaa   18480
gctctgcccc cggttctggg ggcagtgttc ctggagttgt gtccttcggc cccacctcag   18540
tttgtccatt cagctcctcc actgagaatg agatttgtat cataaaggag tttcctgggc   18600
cactcgcagc ccccagctgg agagtgccag cctaatgtgt caggagtagg gggcgaggcc   18660
agagggctat gtgccagctc cttccctaag aagcctcctg ggaaagccct cccaggcact   18720
tcccaggtct cactggccgc ctgagggtgc tcaggccgcc tctccgctgg cactgcttcc   18780
cgacgtgccg ccagcctttc tcatggggac ggggatgatg gcatgcttgg ggggcagcag   18840
ggccttgggg ctgcctcggg ctgtcagtgt gtcctactgg ttctgagatg ccacctctgt   18900
gatccactgt agagagatat attctattat ggtcaatgca tagaaatttc ttcgatttag   18960
agactgaaca ctagtgagca gaactgaaat tgagctctta aaagattttg atgactggtc   19020
tgtggatagc agactttagt gtggttatta tgcggacatc ctgccagttg taaattccct   19080
ggaggtttgg tatgtgcgaa cataagacta aacttatttc tgttttgttg agaagaaatg   19140
attaaaactt ttcattgatg tacttctgta acagactttt ggagaattga agcagtgggt   19200
atattcagta tttgaagtca tagatgaata aaggaggtat gtcgtagttg gcactggtgg   19260
catggcctgt ggtcagcaag gcttttctgt gaaggtatgt gcacagcttt ctaaggcagt   19320
gaaaagtcct ggcaatgtta gtattgagat aatccaaaac acttagtgac tgtttacatt   19380
tttaaaggga tagttggcca tttaaatggt ttctgctaac agatcaaatt attcagtgca   19440
gaggtaaaat atttttcagaa tgttaatttt agatgtcatt ttatagagaa tgtatatgag   19500
caatgacaag gtcagcaaaa tatcttagca aaacttgatt gattcattcc atgcacaggc   19560
aagcactgtt ctgggcaccg gagatggagc agtgagccat tgcgtccatc cacagatggc   19620
ctccaggatc gtgcgggttg cagggaggcc gctgggtggg cacggctggg cagtgccctc   19680
atgtgggttt tgttgggctg ctcttactgc gcactgtttc tcagtttggt cggtgttcca   19740
cctcgctgcc tggcccccac ccctcgcctt ctgagggcct cacaaagagc caagcggaag   19800
gcaggctggg gactttgcag gtcagcccag aggcttcatg atgatggttg gtactgtccc   19860
gcggccacca tcagtctcac gctctgcctc gtgcgcagtc ctggcgtcgt gcggcacctc   19920
gctggtccct gctctcctgg aaggaagggc ccagtggggc gcttcgccag agccttcttg   19980
tctgactccc ttacccaaga ggcatggatg gcagggccgc cggctgtgtc ctttctgttc   20040
tgaaaaggca aaacaaaatt gttcttggct cttattatct aatatttgtt acaatagttg   20100
ctcactttta ggtccatttt attacagatt tcagacaggt gtggttatta gtgcccctca   20160
ttgtttggac acaatgccaa tgtcaggagg ccccgtgttc ccctgagccc cctttctgct   20220
aggagcacgg gcaggccacg cctcgccatt aatctctcct gttttagggg aggaatacca   20280
ggccaccccc tcttctctct gtgcaaggga acagacattt gacaaaaacg gatgccatgt   20340
taacgctaat tttgtttgtc tgaggcagat tgcagcaggt gttatctcca tactcttcct   20400
ttcctggagt gttgagcatg tcctgatagt aggggatgcc ccggagggtg gtgaatgtgg   20460
ctgcacaggg cctgaaagct atttgatgtt gctgttactt caggtagaac ttaaagttga   20520
cagtacattc tactctgcag gcagaaacct ggagtggcat tttgacaaat tggaatgccc   20580
tgtttatagt atgcttaat gagttaaatc tgggggatgt ggatagaatt ttagcatcct   20640
agccttggta ttcttccatg actttgggcc aattatttaa taattccaag cctgcatctt   20700
```

```
tgttagaatc tctctaagtt tctcctgttg ttatcctcag aacgggactg tgaggtacag    20760
gaggccacgt ggtgtagtgg tttaggtgga cagacttccc agtgctgttc tcatggagag    20820
cccaggcctg tgcctagctc tgcagtgaca gtgatagtga ctggtgaagg taaagggtc    20880 cacccagacg ctcttgctga tggagagagg ctggcctgtg gctcttccct ggggtggata    20940
ttaacctgct aacgtgccgt atctagtcct gcttacatta ctaagtggta ggaaatttta    21000
ggtaacatct cagactttaa agtggcctac tgagcgggta gaaaagatag ttaaatgcct    21060
agtatgtagt tggtgctcag taattgttga aaagatagaa gctttacttc aaagctcttg    21120
tagtttgttc agtttggaaa aaatatttta atgttgggat gtattaacag ctggactggt    21180
ggctgtctga attgggacca tggttagggt gacgtgtttt cttactttt tttttttttt    21240 tgggtgagac agtcttgctc tgttgcccag gctggagtgc agtggcagaa tctcggccca    21300
ctgcagcttc tgcctcccgg gttcaagtga ttctcctgcc tcagtctccc gggtagctgg    21360
gactacaagc tcgtgccacc atgcctagct aattttttt ctatttttac tagagatggg    21420
gtttcaccat tttagccagg atggtcttga tttcctgaac tcgtgatcca cccacctcag    21480
ccacccaaag tgctgggatt acaggcgtga gccaccgcat ccagacacat gttttttaa    21540 attaaatgtg atagataaaa ttaggctgca gggatggcct gatttgcagg tgcttcatga    21600
gcaagggtgc ccagcattta tttgctgcta ctggagtctc atgtgtgctt gcagcctagc    21660
cttaaaccct ctgtgggcgg tttggaatac ttcctccaaa tgactttttt ggcagggtgg    21720
gaagtggcga tacttcaggt gagagacagt tgaaattaac tttacacaag agccaaactg    21780
taggctgacg tggggccact cacctttgga ctcacccctg gcgggtcctg taagaggtgc    21840
tatatgcttc cactttgcca gctgttcgtt ggccctgttt tgtcttctgc tctttgcttg    21900
attagtgaaa cttagaatgg aaacaggcaa gtttgatttg ttataattcc taggagttct    21960
agcattaagg aagcagatga gtttgatttg ttataattcc ggggactgga taatttgctt    22020
tctcctctct ccatctttaa ttaatctctt aaaggaaagg aggacgacag cactttttcct   22080 gcagtcatcg gtgtaggctt cagccttaac tcatgacata ggctggtgcc actgaccaca    22140
gggctgacct cagctcttgg agcccatggg gtgacaggac atcagcacct ttgaggtggc    22200
ggcatgaggc gtcttccagg ccttgctcct agtgcttgaa acactgctt tagtttttg    22260 ttaagagaga cagaggccct acttactcct atcccacagg catctggctg ttgacctcct    22320
tgttggcctc ttaaggagag aatacttgag tattgaatta gatcaacttt tctgcctcca    22380
gggaccctgt ttctctctgc tgagactggc agatggaacc tggatttagt ggatggtcac    22440
caggtagctt gggcgacctg gccgctggg cccctgagga ctcacatatc ttttttcctg    22500
ttcatgtgtt ccttccccac accttggccc attctcagtc cctcccatcc tccttagctg    22560
aagcactcag ggaggtgctg atggggcctt gggacatgca ctggagctgg gtcccaccct    22620
cagacctgtg cccgactgtg ccacattcat tggaaagctg ctttcacact tcctggatgg    22680
aattctctca ttttttcag tgcagaatca ctgagatgat tttttttgga taaatcttta    22740
aaggccagtt gtaaatttat tgatacttgg aattgacaaa attcacttgt ttagtgttgc    22800
taagtcatac tgtgtaagtt tgttgaacac agagttttca ttttatactt tcagaggaga    22860
aatgaaactg aatttcatgg ccagaaatat gtttgagtgt catcctaatg taagaacaga    22920
acagaaagcg tggtgacgtt tcattgtaac tctagtatgt tttctctttt gtccattaga    22980
ctacatgagg aaataattga cttttataac ttcatgtccc cttgtcctga agaagcagct    23040
```

```
atgagaagag aggtggtgaa acggatcgaa actgttgtta aagacctttg gccgacggct   23100
gatgtgagta tgttctttgg ggttctgtgc cgcaagtcat gtgcgagtaa atttaaacgc   23160
cctgtggtga tgggtcggct ggatccacac agaccttttc ccatttgccc gagaaagcag   23220
ttctccaagt gtgctttgag agggccaggt cgcctgcaat gctaggaatg cacggccccc   23280
ggcccacctg cacctgatgc cttcgacacc tgcggtggcc acgggtctgt gtgacactgg   23340
cgcacactca agtgcgagga ccattggctg agggattttt ttttttttg gagcggggag    23400
aatgatgtga ttgtttctct taagttcacc ttaaatttag aaatttcacc ctgtcaccca   23460
cccctgcttc cccaccacca cacatggtag catataatgt gttcattttt gtaaaacttg   23520
gaagtgttcc ctcatcacac accactcttg cggtgaagga acaagtgttt ttgacatgtg   23580
gagaggggcc ttctggaatg cttggtgcag gcggtgtgaa gcctgcccct ggctggctct   23640
gctcagcagc cttccctgct gctggctggg ctcagggac cggcagggct ggccgtgctc     23700
tagctgtgag gggcatgtgt gctcttggtg ggcggtgggc aaggacgacc cagttttctg   23760
ctcctcttta aaatgatac atattttgg ctttaaactt cagagcccta ggacaaagcc      23820
ctgccccagt gccttagctg tgggtttaag aagaggttga agggttcaaa gctagctctg   23880
gaaagtcctc agctttgaag ggttgtaggg tgaagacaaa acttgtttca cttcttaact   23940
tagagttttt aaacattcct ttttgggca cgtctttaac ttataggaa ttttctggtt      24000
aattgttaca cagtcccctc catcagtttc caaggtagtt ttattttta cccaagggta     24060
tagtgagggc tttcttggag taagaagtaa tggtagtgtg gctgcttggt ctgtggtata   24120
cattttaaag caacctccct ttctttcagg tacagatatt tggcagcttt agtacaggtc   24180
tctatcttcc aactaggtga gtaccagact gcatggcatg ggctagtgtc tgtgcttatt   24240
tagaggctgg gatggtgtct gggcgatatt aagggctaca aatagattct ttgtaattga   24300
gtctaagggg aaaaaggcca gctgaaggaa aagactgtgg ttacagaagg aaattggcag   24360
aaagatttaa tttagtgtta tgaattcatt gctttgcatt ttgcctcaca cttaatttgt    24420
tgggtgcaa aaatgctggg tgctggaaac gtgaagaaga caggtgggag gactgtggga    24480
agtaaacgca atagaaaaca ttctgctgat actttagaac atgtgtttga aaaattgatc   24540
ttatgtttta atgaagattc aagcaaaatt ctcttttaaat agtattttct aagggttttt  24600
acctgataag aaaatgtcaa acaagtttgc attctaaaat gtaaactggt attttctcat   24660
taaggattct tgatatcaaa ataaatttca gtgcactatc tcattaaaag tttaccttct   24720
gttaacccac tgctagttag catttggagg ctgaagaggc tctaatctca ggatttgggg   24780
gttgatgtta gcagggccaa tgggtaattg aacaggttcg ggtatccagg aatccctgag   24840
tctgcaggag tgatccagtg taggtagtgc tggagtaggt gctgggagag cggggcctca   24900
gcctgctttg ggggcaggcg ttttcatctg aatcccctca catacctagt gctgttggga   24960
gaatcattta acctttgctt tccatcttat ggaagtcttc ccttcagttc agcgaggatt   25020
tgctgtagtt tatgaactgc atttcacttc cttaggggcc atagcctagt gggattgtgt   25080
cttggccttt gggggagacg caggcacatg tgcggtggtg cttatcctgc ccacacgagt   25140
gtgtaggctg tggtaagggg agcagtggct gacgtgcatt ttcttctgtc agcgacatag   25200
acctggtggt cttcgggaaa tgggagcgtc ctcctttaca gctgctggag caagccctgc   25260
ggaagcacaa tgtggctgag ccgtgttcca tcaaagtcct tgacaaggct acggtgagtg   25320
cctggctttg gccctctga ctgggcagga gcctcgtcac atcccaggtg gttacaggat    25380
acgcctgtgt cacgagctcg tggtatttta cacagttatt ggccacggtt tcgatgatta   25440
```

```
atctgcttct ggtatagaca agtgttttat gttttttgttt tatagtcatg atcaccaact  25500
gagaacgtgt ttagtgagtc tgaacttttg ggatttgtga gcccattaaa ctgttcttgg  25560
aatgaaaata tatgattgtg tctactcatg ttaggatgaa taggaaagga gagtcatatc  25620
tgaaagcgga cactgacgtt caggtgctgc ccattttgga gtgtttggct caatgattaa  25680
accatggttt ttatgattac catttgctac gttaaattca agaggaacaa cttagctgtt  25740
ccttcgttgt tccaaaatat atacatatat gaaaagcctc ttctctttgg gggaagtgtg  25800
gagatgagac tgtgtctggt gtgtacttgt taaagtttat gtcagttcaa gattctaagc  25860
ccccagtgac tgggaggtac ttgcctgtcg tatgacagtt cttagctcac ctgtgcgact  25920
ggctagcatt tcattttttaa atttgtctgt caacttatgt agtgtgtgat tcacatcctc  25980
ctagtgttta gcagagcgtc agttaaggcg ggagcttcct cctgcctgtg cggtggtagg  26040 ggaggggggca ttcacatgct tctcaggtga ttccttgtca ggtgcttttg attgggactg  26100
ggggcaaatt ttaaaacgtg atatatgcac tgaaaagtgc acatgtacca ggtgcacctc  26160
ttggtgaaag ttaacgaagt acatgtgctc acgtcattgt catgtggacc agagagagca  26220
ggcagcacca gaggcttcct ccaggcccag gttccaaaag gggctgttgg ctcttctcat  26280
gagcatgaga cgagccctgg ctggccactt tctcaaatgc ttatgggcct tattgcactt  26340
agctctccca gccactctca ccagcagaca ctgttgctct tctcattta caggtgagga  26400 aacaggtgca gagaggtgag gtagtaagcc caaggtgggt tggcggcagt gcgaggcagc  26460
acctgcgttt agcccaggcc gctgttgtct gctgctcctc tgtgtgtgcc aagggcagc   26520 ggggaggtgg atgggaatcc tgaccaggcg accaccttttg gagtagagaa ctaaggtgcg  26580
gttgtcctga ggacacacag taggttgagc agttgttgca gtaactgctt cgtcccagtg  26640
acctcattac tgtcgcatat tggctactaa gtacctcttc ctctgttgcc tgaaggccag  26700
tgtagactgc agggagatcc tggagcctgc cactgctcct ttccagggac cgtcctcacc  26760
atgcagccgg tctgtcatgg gcacaagagc cccggggcga gggccgagtt taaggtgaaa  26820
gcttgtctgt ttggaaggac aacccaaaac tgaatgttcc agtgttactc ctcacctcag  26880
gatttggggt tgctgcggtg agtgagtgtg tgcaagagta gggcaggaga gtgccaggag  26940
tgactgtggg gaggagtcca tgagatggaa aggaagctgc ttcctgaact ctgggtgtcg  27000
gggaaggcat agccatcgag tgttgacttc ttccaaagca gtttctgatg agttctttgg  27060
gaaagtgttt tgtttctctg ccttcttaga atgtgctggc ccccagagct taccgtgtct  27120
ggtggttgca gtggcgtcca ggtgactctg gccccactgg cctgtcctca cacgctgagt  27180
ccttggtggt ttgccctcaa gtgtagacat taaagcccag aataggtgtg tactgaatgc  27240
cccgtccctg tgttgccttt cactggtgtt taaacctttc atcagaccct gattgttttg  27300
gttaaaggaa ctccgttttt aatgcttcac ggctgaagga aaccaaacat tgccttttt   27360 cctggaagaa cacagtttca ctggtggggt gggcggtggg gcgtgagtgt ggcctggaca  27420
gttgctcagg caggttttga gtgccatttg gtgacagttc ttgttgggga gagtatttct  27480
aaaatagccc tttatttgct gaatctttta ggggaaaggt tttttttggta aaattatctt  27540 aaagagtgaa aacccaaagt agataaacaa taccagtatt gtttggagaa acagtatcag  27600
tataacgtac aatttaaaaa atggctttga agttacatta aattatttca aaaattcgac  27660
caaatagaag ttgggggcca ggcacctctc cccatcccag cacgtagggt gggcgtggca  27720
gagactaact catcatgttc cctgttagct ccctccccctc agtcctcttt gatgcttggt  27780
```

```
cacctccggt gctgatccag ggctgcaggg gcgggacaga acgtgggcct tgctgtgagg    27840
ggctggggcc tgggagttgt cctggattca gggactactg atgctgacaa tgttctctga    27900 cccccttca ttactaagaa aaacaccaa acctctgtac agctttggca gcattttgat     27960
gcctggctgt ggagagtcca gcatattaaa gcagttctta aaatgaaatc tttacaggta    28020
ccaataataa agctcacaga tcaggagact gaagtgaaag ttgacatcag ctttaacatg    28080
gagacgggtg tccgggcagc ggagttcatc aagaattaca tgaaggtact gtgcttggtg    28140
acctcgcgca gcgaaagtgc aggactggag tgcttatgct cggcggcatt tctcctacag    28200
atgtttacag ctgtcagctg cacacagggg tctttcgtaa tacagactac acttacatta    28260
tttctcctac aatactattt ctagagatac tttgaaatta catagctgtt tttaaaattt    28320
gcttttcttg agtaaccgtt ttatgaagtt gacaactatt ttagagggct tgttaaaat    28380 gttgtttcca gttattacaa agagactgct tctagctcag cgtgcctcat tggcaggttt    28440
tgcgcagggg tccagtggaa gttgataaat catgaggtgt cttagatata ctcactttgg    28500
gtggtctcag tgcctgagga tgggcagaga gatttggttg agctgatgta tttgggactc    28560
tgaccatgtt cacgaccccc gggtggtcgt gacttccttc ctgttactgt agagactgtg    28620
cagtccttag caggggcaaa tcctgttaca gtagaggcca ttgtagtcct tagcaggggc    28680
aaatccaccc ctgcaatctg gtccgtctt gttccatttt caagggcctt gcccttcagg    28740 ttccccttc cccttgtca tctggtctga aggagcacgt ctgcccccag cacaacgg       28800 acagcagcag ccaggctttc cctccctcct gtcatctcct gccgctctgc cttccttgcc    28860
accctcactc tgctctcctg ctccggaggc ccccactgtc ctcacggcct gcgtagcaag    28920
cacataaaca ctccagcgaa cgcactggtc tctccttgag ttcctttgtg cctgtggact    28980
cttcatggtg ggggtgcacc cctgctgagt cataaccgag ggagagctcc acagtctcga    29040
ttttcacaag cccctcagga aattaattct tagcgtctcc caaccagttt gagacttact    29100
gagagtcttc agatgggcaa gaggatggag gaaacgttcc tttctgtctt gtgtaatttg    29160
ctatgtgaaa tctctttgaa agtatggtaa ttactcaata aatcttttc ttttggaatt    29220 tacagaaata ttcattgctg ccttacttga ttttagtatt gaaacagttc cttctgcaga    29280
gggacctgaa tgaagttttt acaggtggaa ttagctcata cagcctaatt ttaatggcca    29340 ttagcttct acaggtacgt atgctttctt gcgaccgttt ctgttgagac atgtgtaaga    29400
gtagactttt ccaaccagtt gtcctgtagg ttccagcagc ctttgctctc cttttactat    29460
attgtttcaa tttgttagag gctgatttct gattcttata ttaaaaccct cttgatcaat    29520
gcacctttct ggaggctcct ttgtagctca ttttgtactg ggtgtaacgg ttagtgcggg    29580
gtgcccatct ggttctgtgg gtccagtgca catcagtgca agctcaagga gttctctata    29640
ttcagaaatg tccatttcat ggtaaacaat aaacatttgt tggtgcttgc ctgtgattta    29700
tattgaaaaa aaattgtctc agaataaagt ttggtaccac atatgagaaa aggatttaca    29760
agattgcttt ctcaattgat gaaacctcat tattttgtct gaaattatat gtggtcctta    29820
ttttgttgag taacatggaa aatctatcag tagaaacag atgtgtttta aaaatattg      29880 ttaaatgctg tgatgtattg ataaactgta cttacacttt ttaaacattt aaaatcatct    29940
ctaattgaaa cagtattgtg tttatatttt cttgagtgaa gaattctgtt ctttacagaa    30000
tctttcctgt ataatttagc tgcacaactg gatttgtcca tgtttaccat taatgttgta    30060
cttgtgattg tgctgagtga gccgtttctg ttcatgattt ggtaatgttc tcactgtcgt    30120
gaatgctatg atagtagaac cactgggtaa ccacctgtga tgatcgcagc ttccttggtc    30180
```

```
tgtctctgca gagatgcttt aagagtagtg aaaatggaat tccatgtctg ttttcttaca    30240
gttcaagtca cactgtcctg ttttcacttt cccctctgag atgtggccgt tagtgtatag    30300
cctttcttcc atagtttttg gacattattt tgaactaaac atgggcctat gttctttact    30360
aatatactcc tgacttgcac tattttcatg gccttgtagt aacaacagct acttaatact    30420
ttgatcatgc atgtgccatg tgtgcctggg cccagggcct cctgccaccc cctcaggggg    30480
tcctttcagt gatcctgtga ccccacagga ggccaccata gcatgagtcg gattcctggg    30540
ttcactgcca catccctgtg cctgtccagt gcccagagct tgtcctgcct cagcggtgtg    30600
actgtggcaa catttgagtt tcttgactga gtgaggggag gaggcccacc ctgccactgg    30660
ccaggctctt ggatatgtga ttttggctaa agacaagga ataaggaagg aataaaggt     30720 gaggccagaa ttggaatcct cctcttgtgt ggtggaaata cgcagagaac tccgggattc    30780
ttctgaacct taaaaacatt tgtatgcttt cgagctgcag ctcctcctgg cactctgtgt    30840
tataaatagt ttcaagcacc gtgcttctct gagggatttc tctcatgtgc ccttgtccat    30900 cccttttctag ttggcactgt ccgatagaat tctctgtgat ggtgacggcc acttctgcat   30960
ggtccggcaa ggggcttggt gccacatgtg gctactgagt attgcagtgt ggctggtgag    31020
agcaacaagc tggatttta attaatttgt tttagttcat ttaaatagac atgtgggcaa    31080
tgcaggtctg gacagctgag aattatgacc gtcaggaggt gtggtggaca gtggtttagt    31140
tcagaacaag cccaatgcct gcttttgaag acgatatggc actgaactga gagtggtgct    31200
catctgtgtg caagcaggat ggaagcttgc tatagatatt atgatgcaat actgatggcc    31260
tatactcagc tgaaatcagt catttcactt tctggtttta tgtgataccg ccatactgtt    31320
cagtctaaca ctgaccctg ttggttgtac ttcagcataa caaaattagg atggtgagaa     31380
tctgaaatta catctaccat ccacacaact aagttatgca gaatatagtc aacttatttg    31440
ccaatatttg gttaatcaag tatctgtgtt tgcaggaagt ttgctgtatg gattaacaat    31500
tccaaaaatt aaacgacaat aaaattgaga ttagtacatt gtattccttt tgaacactcc    31560
tcattgaaga ggctgctgtt caggcttcct cgtggtgctg gtgagtgagc gagtgcctct    31620
cactggtatt gccttgaaga ggctgctgga cggcagactt cgttgcatcc tatttctttt   31680
agaacatgcc ctgaatccat acaaattgtg gatgcattgc ttttacagtt gcatccaaga   31740
attgatgccc ggagagctga tgaaaaccttt ggaatgcttc ttgtagaatt ttttgaactc   31800
tatgggagaa attttaatta cttgaaaacc ggtattagaa tcaaagaagg aggtgcctat    31860
attgccaaag aggagatcat gaaagccatg accagcgggt acagaccgtc gatgctgtgc    31920
attgaggacc ccctgctgcc aggtaagggc tccccgacct ccactgctgg gagctaggcc    31980
agcttcgggg ggtggggggg aggtgtgggg gctatgttgg ggctctgaaa gcctcgggca    32040
attcatttgc tcttgatgca ggtttctctt ttttttttt ttttttgaga cagtctcgtt     32100
ctgtcgccca ggtggagtg cagtgacgtg atctcggctc actgcaagct ccgcctcccg      32160
ggttcacgcc attctcctgc ctcagcctcc tgagtagctg ggactacagg cacccaccac    32220
cactcccagc taattttttg tattttttagt agagatgggg tttcaccatg ttagccagga   32280
tggtctcgat ctcctgacct tgtgatctac ctgcctcggc cttccagagt gctgggatta    32340
caggcgtgag ccaccatgcc cagccacagg tttctcttat actaaccagt taataatgac    32400
actttgagaa atccttattt aatgcttcta attaacttt gtctttccaa ctgtttacat      32460
tctataataa agcagaatta aggaaaatct tttttttct gattatagaa gtattccgta     32520
```

```
ttcatcctaa atcatttgtt tcccagaagt atgtaatata gaaaaacagt agatgccata   32580
atcccttat ttggacatgt atttctccac ttttttcgta tatggatatt aatgtttatt   32640
attgttatct tgttgaacac atcccacaac gcaaacctgt tagtcacttg gcttttgact   32700
ttatttccta aagatcatct cagggaaaac acattggctg atgtgttttg tttttgcttg   32760
tagatggcgt gatttatgca ggctcttgag tggttttttt ggtagcacgg tgtggcagtg   32820
tatcatccat cttttgtct gttggatcag tcacattgga gacattgcca ttgtcttcaa    32880
gtgtctactg aaatgtactc aaaaaaacaa agacccacat aatcattgag atatataata   32940
taaacctaga aaagataaaa ttccggtact tagaatatat gtccttttaaa aaaaatctac   33000
acttaacctg attgtgaaga atgagttgta tgtagattaa aattcgaaac agtgcttttc   33060
tgatgaaaag taagctcctc ttgactgact tccttggtga cttctgtgac agatttcttt   33120
gatttgctgt cccagttttc cacacatgag aattcacatt ccattctaaa ggattcactt   33180
cctgcaggtt ccgttagtgt tgactgagtt ggggtgcact ttgggctagc tgcccttctg   33240
actgccttgt gaggcctcct gattgtcaga tcggctatca cactgggtcg gtgctccggt   33300
ctgcacaatg gtagcttttg gcttccttgt gtgtctgcca cctggagagc gggcttttg    33360
tgagctgttg ctccgtctgt gaatggcagc tgccttcatg aggtgggccg tgagcacgtg   33420
ggcaatgatg atgcagacca ggcccctcgg cactcacaga ccgtgccctg tgtatggtga   33480
ttgacagggc ctttgctagt gccaactgcc atgcgtgccc attgtgttcg cctgtctggg   33540
ctttgctggt gagggcctgc ttcagagtca cttgtatgac aagatctgaa atgtggacga   33600
tggtgtgcgt gtggggagag tctgacatag cctttttgct gcagggaatg atgttggccg   33660
gagctcctat ggcgccatgc aggtgaagca ggtcttcgac tacgcctaca tagtgctcag   33720
ccatgccgtg tcaccgctgg ccaggtccta tccaaacaga gacgccgaaa ggtaatgggt   33780
tgcgtgtctg tgtctgggct cagcatgcct gtgggatggt agttacccct ttcctgtgtc   33840
atttacctcc atgaaattta tgaagggatg ttctgtcgta tttcagtaga atttggatat   33900
gttggtgaag gaaggccttc taggaatgtg ggatggctgt atgggattca tccatggttg   33960
agagttgaaa atttctttct tggagatttg acatttctt cagggtcttt tgttttggag    34020
aggtgatttc tagctttcaa aactttggaa catgatgctt tttctccagc cttgaaagca   34080
taaacattca ctttctaagt gaatgtatct gatcacccaa tccctaccat cttctcttat   34140
gtacactcgt cccttgttct acatttgggg ccattttac agtcccaaaa tgtagtcaga    34200
tgtatttact tctgacccag atgatgctgt ggtggtggta gtggtgggat tggagggggt   34260
gggagatgag ataggaatgg gaaggaagag taacgtggtc gtcaagagtg gaatttgaaa   34320
cagtttgata aatctgttcc atggtggatg atgaataaaa cagatttcga ggcctggctc   34380
agcagctgct gcaggcgctg gtggtgctgg agctctgtgt gttcctgagc cgctgtctgc   34440
tcggtgtttt caggcggagc tctgggcccc gtgtagggca ctcatctcag taccatctcc   34500
attctcgcct gtgcagtggg aggtgaaatg tcagcactgt gtgaccatcg agggtgggaa   34560
ggccacgctc ccctacttgg agctgccttt cacagtggtc ttctgtaggt agatgtactg   34620
cgatccaggt tgtgctggag ctgaatcatt agaagtcata tatatttgta aatgtatttt   34680
agctcccttc ctactgtcct tcacctagtg agatgatctg ttaggggtat aaggtaactg   34740
ctcaagaggg gttctaactc cctgatacct gttgtactct gttgatctcc aacaatgtcc   34800
cttttgcagta ctttaggaag aatcatcaaa gtaactcagg aggtaattga ctaccggagg   34860
tggatcaaag agaagtgggg cagcaaagcc cacccgtcgc cggggatggg tgagagatta   34920
```

```
attcatttgt gttcatccta accactggct ggcgtgttca tgcagaagtg tctctattcc    34980
tttgtggtaa attggtcaaa ttaagaagat agctagtttt tctgatgagc attaattaaa    35040
aacacaataa gatctagagc agcactgtcc agtagaaaca atgccacaca tagaatttca    35100
aatgcatgcc acacatagaa tttcaaagtt tctagggccg tgtcaaatgt gaaaagaaac    35160
aggtgaaata attttggtag attttattca actgaagtca aaatgttaac atttcaacat    35220
gtaatcaaca taaaaatgat tgagatattt tatagccatt ttttgtacta agtctttgaa    35280
atccagtgtg tatttatttg tacttacagt acatccttat atgggtgcca aattttcata    35340
aaaaatactt gatctatatt tagattttag aaagttcaca tttgaagatg atttgcatac    35400
ccaagttgtt acaagcatgt ttaatgtttt ccataacta attgactata attttaaaa    35460 ttaagcaaaa cctaatgttg ggtttgtcag tcacattagc agcattcccg gctcagaga    35520 acccatgact gatgctgccg gggcggctcc acgccacagt tctcaggagt tattaaccaa    35580 gacttttcc ctccacagac aacaggatca agattaaaga gcgaatagcc acatgcaatg    35640
gggagcagac gcagaaccga gagcccgagt ctccctacgg ccagcgcttg actttgtcgc    35700
tgtccagccc ccagctcctg tcttcaggct cctcagcctc atctgtgtct tcactttctg    35760
ggagtgacgt tgtgagtgcc ctcccctcct ccgtgtgtct gttggacagt ttgtgtctct    35820
ggtaaatgtc catagctgtg agcttaaaat ctcccccctta ggtttgctca ggttttgttt    35880 cctttatgt gtgtggagtg ggtgggaggg tagccccgtg atgtcggcac caggcttcct    35940 ttccccact gtgaaccttc tgaacctgtc tggctcatgc ggctgtcgag ggcagtaatc    36000
ctcttcacag atttaaaaaa aaattaaatc caagtatctc ttctgtattt cctttaacat    36060
tctgtttcag ttttgatgaa attacttgaa ggaagcctgg gtagatttgg gctgcccgtt    36120
cagaagttag acttaattca ataaaccttt catagccagc ctggaggcag gagtttcttt    36180
tcatagcttg aaggaagtag tagtgcacct ttgtggtaca gctgtccttg ttgtttttgg    36240
taccgggttc aaggattcag acacaccgcc ctgcacaacg cctagtgttt accagttcag    36300
tctgcaagcg ccagctcctc tcatggccgg cttacccacc gccttgccaa tgccagtgg    36360 caaacctcag cccaccactt ccagaacact gatcatgaca accaacagcc aggtacgtgg    36420
ccctctggtg cccttcccgg tggtggcccc gggaagggca tctgagctgt gatatgcgct    36480
agagattcat ggtcctttga attcgaagag taacttttg agtctttggc cattgctgtc    36540
ttattctagg aaatcctgtc ttttttgtgg tgttgaggcc caccatgtag agtttcagca    36600
gtgaggagac tggttctcga gtgctgccgt ggcttttcac gggggccagg tcgactgcct    36660
tcctataagt ttcctcactg ccccagcatg agactgctgt cgaggatcat cttgagagag    36720
cgactcagtc gcgacccact tagccgggca ccaggcagcg ccagacactt gtccctactt    36780
cctctcagaa tctcagtgtt gagactttt taaaagtttt aatgtgaact tattggactt    36840
ttttcatgtt tcaaattagg catactttct aaggcttttt ctgttagaat gtactgtctg    36900
tttctaaaat ttagataaaa ttagaaatct aaaggagaat tttataaata ctaaattttg    36960
tatctacttc cgattataca tcactggaat atgtgtgggt ataaaaccca acatgttaat    37020
tgacttaaaa ccattttctg aaatgtgggg tgtaatttga gcataaaact atgtaggtat    37080
atgcaaaagt atcttgactc attacttgga gttttgcagt atgctctggg gaagacatgc    37140
tcacaggatc caccctgatt ctggcagagc ttctggaatg ctggctctgt aatgaccac     37200 agagttgatg agcagagcca tggcccagcc agacaccata acgtgtctaa ttactgcata    37260
```

```
aatgtaaaat tctgaggcaa ttatttacac tcttaaaatg aattatacca cagataaact   37320
tggttgcctt tttatggtca tcacactggc cctgacgtcc tgggccatgt gtcacaaagg   37380
tgtttgtttt aaccacccac aagccttggg gcccttgaga gcccagtgcg gctgctgagc   37440
tccagagcca cactctgcgg ctgcttgtgt ggttcgagcg tgaagtctag ggacgctgag   37500
ggtttctagg ttcttatcta agaagactct tgtccacagt cgatctccag aggtggttgg   37560
ggtaaatgca tgggatgcca agatgcaacg aggtcagtgt tgcaagtctg agaaaagggg   37620
ttcttgttag tgtgcttctg ctgctgacag taatgggtga tgctgacgta gaagcagccc   37680
gggacctgga cagcaggcaa ggatggatct gccggccgtc ccacggcccc ttgggccacc   37740
agtcaggcca gtctcggtct ctgaccccga gttcagtgtg tgagtcgtgg attcatcacg   37800
ggggtgacag ttgttattct gatgatgcta atgttttgag tcatttgatc ttcaatgagt   37860
tttaaacttt atgacttgga ttactgggca tactttatat tctaattgct gtttcagaat   37920
atgaggtatt tctaattcaa agcacaatat tgttaggtta tagtgaaaca aactgcttta   37980
tggagcccac atgcaactgt gccatttatg agctgccctg tggcggtgct gagctttaga   38040
agccggatgg ttttcctgtg attgatttgg tacccatggc cgtctctgtc gtttttcttcc   38100
```

tagaccaggt ttactatacc tccaccgacc ctaggggttg ctcctgttcc ttgcagacaa   38160
gctggtgtag aaggaactgc gtctttgaag gccgtccacc acatgtcttc cccggccatt   38220
ccctcagcgt cccccaaccc gctctcgagc cctcatctgt atcataaggt atagctcttt   38280
cctggtgcgt tcacctgttc aagctgccat gtgagaggtg gtgctgaatg ttttctcctc   38340
caaagagaat tccagagaga tcatttgaaa acggaatttg ctttcttgtc attcagcctc   38400
atgtttgctt gtctttccaa acaaaacttt aaaaagttaa actatttttaa gatgtaagat   38460
acagtttaat tggttgccac aaacatctct taattcctct gttgaactga ttagcataaa   38520
actaaaagtt gaaataaggc tcaaaatgaa gacttttctt ttcccattta tataattcat   38580
ttatatgcta aataccctcgg tttctaagaa gcaaatgata aaaccaagag cagatcttgc   38640
catgatgtcc catgtatgct gctgtcattc ccacgttgcc tgatccccac ctggggtagg   38700
agcaagcatc agggtgggca gagctgtgtg ctgggcctca gcaggatcct ggcatgcctg   38760
cccgtatggc tcctcacaag tgcagctgtg tgcacggaaa aaacaggtca cattaggttc   38820
ctatgttctt gaagtacctg aatgattggg agagccatga cgaggatctt ccaggtcagc   38880
ctctatcatg cgtgatgttc ccttgggctg tgcggatgct cggtactttc atcggtgtcc   38940
acacctctta ctctactcca ctcctccttt gcttgtctaa tcctactttg ccaggaagtt   39000
ttattcttga ggcttgcgtc tttggccctg tgttgtatga tggttgtttt taggagttaa   39060
gtcatagaac atttcctctt ggatttatgc atcccccata gacacattca gggtgaaaga   39120
acaacttcgc acagcagctc cttcgttgca ttttggcttt gctttcccag cctcctcctg   39180
ctgtttgtcc tgctctgaga cttccctaaa gccggcgtgt gtttcctctc agtctgcttg   39240
gccgggacct tgcagtgcgg agaatgtgct ttgggtgcag cccaagcaca ggctgctgca   39300
tgccgggatc gacaggctgc tgagggcgag agtaccaggc cctggcatgt gtgactcgct   39360
tgtttctaga aggtcacagt tgggggaaga acatgaccgg gaccttctta tttcttttttt   39420
tttgggacag aatctcactc catcccccag gctggagtgc agtggtgtga tctcagctca   39480
ctgcaacctc cgcctccggg ttcaagcaa ttcttgtgcc tcagcctctc gagtagctgg   39540
aattataggt gtgtgccgcc acacccagcc aattttgta ttttagtag agacggggtt   39600
tcaccatgtt ggtcaggctg gtctcgagct cctgacctca agtgagctgc ctgcttcagc   39660

```
ctcccaaagt gctggaatta caggcgcaag gcactggcac ctggccaggg accttcttat   39720
ttctatggat aagtagaaca agttagaagt gaggttctgc tgaatttgtg tggtttgatc   39780
ctggtatatg gttgttgcct tcagtcagtc acggaatggg aagaatactt ttctgtcaaa   39840
tggaagagtt ggaaagtccc agagggcagg tgtccatccc tcctccctac gtaacatcac   39900
gtcggcgctt agtgtggtca ctgccggagg acgtgggcat tgtgcctgtt gtctggctcc   39960
aacattgctg tctctctctt tctccagcag cacaacggca tgaaactgtc catgaagggc   40020
tctcatggcc acacccaagg cggcggctac agctctgtgg gtagcggagg tgtgcggccc   40080
cctgtgggca acaggggaca ccaccagtat aaccgcaccg gatggaggag gaaaaaacac   40140
acacacacgc gggacagtct gcccgtgagc ctcagcagat aatggctcct ggctgcgtcg   40200
gcctccccca cccctccgca gactgccccg cggcctcggc caccggcagg gaaccgaga   40260 ccagcacccc gcacgtcagc cgggctcacg gcacgcccgc cgctgatcac tctgcatgtt   40320
tctttgtgtg gtggtcgcgt ccatcttcaa gaacagctcg ttgtgctcat ctgtgaagcc   40380
ttattaaacg tggacgttgt tttctgcctt cccaggattc ttccttcagt gctgaggcag   40440
gtcaggctca ggaactgcag ggacgtgaac atgcgcttgc ggtttgcggt agccgtgtct   40500
gttccttcgc ggtttgctat tttcatttcc tgtttgtcaa agcagcagag gagatcaaac   40560
cccgttcgtg tgtctttcct ccatggatag gcttgggagg tcattgtttt actgccctca   40620
cattttgttt gaaatttcag aactgttttt ctatgtaaat attgaaaacc tatgatttgt   40680
gcaataactc agatattttt tatttaattt cctattttca cataagttat atttaaggga   40740
ggagggaatt ttttttaaac aagcttaggt cctttcccga gctgcatttt ctaagtttggg   40800 tcatcgtgtc ggctggttgt ctgacgagca tcgttacaaa caccatgatg aggggtttgg   40860
ggttttattt tgattctttt cttttggtcg gagtgagtga aggagtcagg tcgccctgac   40920
ggttttccag agggctcggc tccagagcca cctgacggac tgcccgtggc cctgctgtcg   40980
ggccccaggc cgttgtcttg ctctgaccac agagttttaa tgttttggtt ttcagttctt   41040
ttaaactgga caacaaatcc agcatttcaa gtgccagaag tataactttc taaggagaga   41100
agggttgtca cgttataaaa tctttaggaa aatgtgaact ggaaaatgtt tcagtcagtt   41160
ttagtgacat agcctgtgat gatgggtctg gtgactatta ttgcggaccg tggtacccag   41220
ttttaggaat gtggagaaag gaattctgtt gattccattg aggaatctgt agcgtatgca   41280
ttcgttctgt taagagcaaa tctaggagaa gtgcttcagc tgcccagtgc gccgtgggga   41340 gtgtttttaat ggatcatgtc gcaggagagc acagcccagc gttggggccg ggaccgctgg   41400
cgcccgacgt cggaagcata caggtatact atgcaagtgt attctgccac aacaaccact   41460
gtctttgtta ccttttttttg aacaagaata tatccatcct gcctaaccct gagttttttgg   41520 agcaccacag ttgtcctggg agttggttgc atcttgtagg ccatctgact tcctgttgtt   41580
aaaacagggg tctggtcttg ctaaacacta caggtaggtt ggtctttgaa gtccactagt   41640
ggagaatgtc gagacaagat acttattacc atgacatctg atggatgtgc agcagtgggg   41700
agttctagat tgatctctga atgtgatgga cgcccagcaa ggacaagctt taaaatgtct   41760
gcggtctgcc cttttgaagc aggactggct cactctgtca ttgggagctg tcggctgcga   41820
ctgcaggttc tctaggaggc attccagaat agagtagcac actgtgtctg cagttctcga   41880
tgaccgaaag ttatcaaaaa tatttaaaat atttaaattg tgaacctatt gataaagaat   41940
atttataaaa actgatctgt aggcctgtac taatctctac gcattagcaa tattgactgt   42000
```

```
aaacccacat taaggaaacc actacggggc cggcagtgag tgtcccgtgg ggtgtgcatt    42060
ttaaagctcg attcatagac acaggtacca tgttccattt ccgtcatggt gaagcagatg    42120
aattggcctg gctaccactg tggttgtgtg ctacaggttt gacaaaagat atcatgtttc    42180 gattttttg tgtgtggaca acaatatgga agctaaaatt gacatatttt tatgtaaagt     42240
ttttctattc tttgattttt aataaacttt ggaaaccagt tttgtgtttg tgttcaagtg    42300
tatgctttca agggtaagag cggcttccac attttcagtt ttgaatttct aaattagggc    42360
aatacgttaa ccagttattc taaataagat tcaaagaag gcagatgatc ccagtcctat      42420
aaagcaagtt gcggcaggga gattatgttg tcactggtcc attaaagtag gaggaggtga    42480
aaatacaaaa attagccggg catggtgact cactgagtag ctgtaatccc agctactcgg    42540
gagggtgagg catgagaaat gcttgaaccc gggaggcaga gattgcagtc aatcgagacc    42600
gtgctactgc actccagcct gggcgacaca gtgagaccct ttctccaaaa caaaaaacaa    42660
aaagtgggtg gaggttctag gctttgcaca aggcctatat aacagtaaca gaaacgtgct    42720
ctctgtcctc acattctgat gctaacaaat tcagtaaaac tgtttaaatg gttcttacat    42780
gcagtttctg gcaagctgct atgtgatatt gtgtacttag actgcccagg gcaacatttt    42840
tactttcttc atttcttta ggtcaacatt gcatcacttg caaacaagac attacaaacc      42900
aaacaatcat agtgtagctt aaaatgcaac ggacatttgg gatttatttg agaactgacg    42960
tttgggattt atttgagaca gagtctcgga gtctcgctct gttgcccagg ccggaataca    43020
gtggtgcaat ctcggctcac tgcaggctct gccttccagg ttcaaatgat gcttctgcct    43080
cagcctgccg agtagctggg attagaggca cccaccacca tgcctggctg atttttgtat    43140
ttttagtaga gatggggttt caccatgtcg gccaggctgg tcttgaactc ctgacctcag    43200
gtgatctgcc cacctcggcc tcccaaagtg ctgggattac aggtgtgagc caccatgcgc    43260
tgccgacatt tagaatttat aaggaaaggt ataagaattc ttctaggcca gtaagtgaca    43320
gaactgcatg tcccagcctg tgcagctgta gaactatcaa ctgagtgcat gttgtagaac    43380
tatcaactct agagttcttc cagttgtcaa ggtgggtgtt gtgggtaaaa cacgttcctt    43440
ccacccaaag aacagagtag ccctgtcctc ttggcacctg gttcctgagg gggtgcagaa    43500
gctgctcaca gcactgccta gtggtgctgt ggggaagatg gcaggcagct gggtgggact    43560
cgaaagcctc tccaggggggc cgagcccgtgt gcagggtctg catgagctgc catggtcagg   43620
gtggggctgg caggagctga gctgggcctc cgagggaact ggagggcttg tagccagggg    43680
catctggagg aggagcccac gacagtgctg aggtacaggg cactggagtg gggagatgtg    43740
gctgagttag cctctgttgg aggcgggact ggtgggtgtt gtgggggggc actctcggcc    43800
tgccccggat ttccccgtgg gtggtgatgc tgcctactga gccactggtg cctgtaggag    43860
agctgtcttt aggaggcttc caggagcagc cactggagca gccacgttac cagggagcct    43920
gaggccccac agaggcatct gaggtgtcag atttgggtcc cgctctcctc ggaagctgcg    43980
agtactggaa ggtaagggct ttctgggggc agagtgaacc tgtccaggcc actgcgtgaa    44040
catcagtaag cccaccacgt catctcggga ccccgtggac tggatttcat ggtaacaggt    44100 aacccctca tgaccggctt ttgtacatgc cttttgattt gtccggggtc tcgagtgcca     44160
cctctttacc ccgtgagata cccagagatc tctgtaaatg ctgtgcccag catgcctcgg    44220
cctgggcatg aaccgtacgc aggggaggtg gcgacatttg taatcgagat atggtttcgt    44280
tgtgactggg tcacctgtga tgccctaagc cttgagaact tgtcatgtgt gtgtcattat    44340
cctcttgctg tctaacttgt gagattcttg ccaagcctta ggtgactttg actacctttg    44400
```

```
gtccaaggta atcgcctaga atggacggtg gctcctgtta aacacacaca catcccagac    44460
accacgccgg gggctatgcc tgttgtttaa aatggcccc aaaatatgtt gcctgcactg     44520
tgtctccagg gcctgtgtgg gaggggtagc ttgggagggc cgggtcccgc tagccctggg    44580
ttgcaagggt aaaccgcctg tgtcattca tggtgagatt tacttacccc atgacttgat    44640
cctagagaag gccagctaag gacttcagag gtcttggagt gagttccagg caagggcaag   44700
aaaccaaggc ttttcatggg ttcttaggta aaggaagggg gtgtggacca gtcgcactgg   44760
gaggtcgagt cctgtctcct aggaagccac atggctgtgg ggtgagcttg cccagggttc    44820
cttcctgcca gtgtggatat ggcgtcctct gcccaggcct cttgagatgg aacgcttgga   44880
gctcagccaa tgctcaggtc gtcataggtg ctgtggggtc actcacactt ggttgagagg    44940
tatgtgactc gaggcagatt cctgtcattc ctgcttgtat ttcatcaagt cctgagcgag   45000
gtttgtggta atgagtgcag gtggctgtga ccgaatccag gtctcctcaa cagataggag    45060
acctccgcac atcctgccat gtcactgttg gaattttcaa gttgggagga atcttaagaa    45120
tcagctagag cagctcagcc ccaaaaatga gaaactgaag tcctgtgatg ggaagggctt   45180
ctaaaggtca cgtggcacat ccgccaggcc cccgagagcg tcctgggcct ggctcccacg    45240
ctgctgctct ttgcaaaggc ctgtggcccc tttttgttgt ctgacgacat gtagagaaat    45300
tgctgtgagt ttacgcagaa cactggtgct tacgctataa ttgagtctca ccaggttctg    45360
aagatgcgtc ttgtgcccat ggctcacatc tgtgggagcc tttcagggac agcggcatca    45420
ccagcctggc cctgtgtgtt gaaatggtta tggtggaact acgtgggctc atgaaacgtg    45480
ggaggcttcc agttggactt tttgtggcca atattgatag gatcctgcca gcggagagcc    45540
cgggcctagg gccaaacggc tggagttagg agctggggtg cgcagagccc tggaaggatt    45600
tggcagggca ggggagaagg gagtaacagc ctcactgtgc ttcaggcttt tccttgctgg    45660
ttcaagtgtc cgctgaaagc agctaacata atcagtacag cttctctgtt ttgggaaatc    45720
aaaccccaaa tctttaattt gatttaaaaa gctttccagg atcttgcctt tgcctccctt    45780
tccaatcttg ccgctcggca gttatttctg ctagaaaata ggtatttccc tctcagtgtc    45840
tccaaatgtg aaagaaaaat catcgtcatc aatagtcggg tataagagag gcagccttct    45900
ccggaagggg accagtgagc aggcagttca cagagcagaa gggagggtgg atctccaggg    45960
accgtcactg gcttcaagtc tcgcttctgt tgcttcctgg ctgtgtgtcc ctgggcatgt    46020
cactcaactc ctgtgctcca gtttcctcag cctcgcaatg ggccattgta cagactaaac    46080
gagtaaacgc acataaagca cctggagccg tgccaggccc gatgtgagca tttgggccgc    46140
atcgactcat gtgattagtc ctggtaggcc cggcgcaggg aaccaagcct gtcaatttaa    46200 agggagtgg caggaagaac tcattttttaa tgacaggcaa aaaggaaaaa tattgtaata    46260
catggcttcc tattttcctt ttccctttt cttgcctttg aatttataat gttgcttatt     46320
tggtatttaa gattcttgct ctggagcttc aaacattttg aaagaaaaag tagtgtcatt    46380
taataaatgc tgtcatttga cgctctggtt actattttag ggcagcatgg taggtagata    46440
ctgctagtta cttacccaat atccattttt ctttattact tgcaggattg ccaggtttag   46500
aaaatgaaaa cgcaaaactc caagttaaat ttgaatttaa gtagacaatg aatacttttt    46560
tggtggatgt tccaatattg catgggcaat ttaactaggt gtcctgtatt ttatctggct    46620
caactttgtt tagacagcag ggtgcacagc tgaaaagata acttgtataa catccttgca    46680
gctaggggtg gttgcaacag agtgctttcc tttggaatga aacttttctg ggataaagta   46740
```

```
ctttgcttcc ctccttggat tctggctgga attcaagtgc aatgcctggt gacacagcag    46800
ccatgttgta atcatgaagc ggctagctgt gtagtaaggc tgacagagca ggaagctgga    46860
aaggacccag agtcgtgagg ctttgggcct tctttatatg ttcatatata acatttgcat    46920
gaagaagaca cccgcatctg tttatgccac tgatattcag ggctctcagc tgaatacaat    46980
tttaactgat atatacagga aacgcacatt tcaaacaaaa tctcatgtga aactccatat    47040
gggtggttct ggttaaagca gtctggtagg gaggaaaaag gggacatcgc ttcattgctt    47100
gaatttcggc tccactccct ttcccttctc ccagattttg ggggatgccc tgtggaaccc    47160
ctcactttct atggaacaca tctttaagcc aggaaaccac ccattctttc ccgctcttat    47220
tctcattttt atttctcaa ctcttttggg caggggttga ggagggtgtc ctgtggtttg     47280
catagatgcc tgctggactg atcagagccc tggatcccat acctggagtc gggagcttcc    47340
cccagagccc tgcaactccc accctggttg ctgtgcacgg cggaaagggc ccgtcaggaa    47400
acaggaaggg agcctgctcc actcaggtca tttgtcctaa tccagctaag gcacaggctg    47460
gagatctcag gggagtccct tccctgtgcc cttaggaacg ctggcccac ctgggtgctg     47520 gtttcaccac tttgttacca aagtctttgt cacagacagg tatcgggtga gcttacagct    47580
cagcctgcag acatagcccc agggcagcat ggctggactg gttgtgcaca gatgcctgct    47640
gcgggctgtg gctccctgc gggtggaagt cttggcccct ggacctggta ttcgaggtct     47700
tctgagacat tctgccctcg gaatgcttgc ctcctattg atctgtcctg agtggcttgt     47760 tactatttt taatagtcat gtatcagtag ttatgtaaaa tgtggcaaaa atgaatgact     47820
gaagaaaaat gagatggaaa aagaaaaaat ctgaaaatat acaaaataaa gcccacact     47880 gttttgctat tggattcaaa gacctggaac tatccttgca ggagcccctc ggtgcccacc    47940
cgtaggccac actcaccaac tgcacccggg gctgtgcttc caggacccaa aagctccctc    48000
cttgagcggc acccaggcct gctcccacta acctcaccag ccgcacccgt ttctcccacg    48060
gcccgcccag gggaccattg atcctttagt cctcttcggc cagtgtaccc ccaatgcccc    48120
aggacagccc ctagtacaca atggctgttt cttgtggaca acgcgtggag gcacacatca    48180
gggccctgct tttaagaagg aagtgctgag acctgggtgc cacctcttcc aggagccatg    48240
gatgccgggg ctcacctcca gagactgaat taaacggtca ggagggagcc tgcacaccgg    48300
agagctctga gcaccgggcg agtctcccgt gtggccaggt tgggagccat cgctgttcac    48360
gtggccaggg ctgccttgcc agaggagctc atcttacttt gccactgtgt aactgttcat    48420
gtttatcaag tcatgacctc ccttgctaca gtcactcttg tctttcgtgt tctatttaat    48480
ttttttaaaa tgctggtggc ctcactcacg aaatttttt caccaccact catggacagg     48540
acctgtcacg tgagacatgc accaaagcac ggatagggat ggccacgatc ctgcctggaa    48600
cgggacttca gaactgggca gagcatggct ccttccggtg ggggcccag aactctttt      48660 caaaggcaat ggcaggacgg gatccacagt gcttgaccct ttgataagga gacatcctct    48720
ggccaaaggt gacaccacag ggataaggtc cacgtgctgc ttaacactgt tttgggtgca    48780
gaacaaaggg cagctgggac atttcttgtc tggtctcccc ctctacgtgt cctgaatttc    48840
tagcttgttc aaagtggtca aagacccaag gctggtctgg cacagaaggg gtcgtgccta    48900
catgtaggga ggcactgagg cttctgtctc ccgttgtatg tccccaggga caggacagcc    48960
ccctgcctgt tgttccgagt gtcctctgtg aatggggacc atctgtcctc cgggtaactc    49020
cctcctcctt cacctctgtc cacccgctct ggtagccacc ccttccacgt gcagtgcggc    49080
tctgcatccc ggagagcctc gaggactcct tttctcttct ctagtgttgg ctcccatatc    49140
```

```
tgtcagttaa ttacctattc attatatgaa catgtttctc ttgggtcatt atttaacttt    49200
tcaaatttat cttctttact caatatattg tgagcgtgga tgtctgttcc ttatgggatc    49260
accactgcca ggcatgtaga aattgcttga tgtagtttca ctggcttgtg gagaggcagt    49320
catgcttctc tgtgcttcta tgccaaagaa agtcagtagc aagcaaatag cagagcttta    49380
gtgaataaga acaatatttt accttgaaaa aggcagcagg aaggagagtt aagactcaag    49440
tttcctttat taaggaaaat tgaaatctag gtacctacag atgctctttg acttatggtt    49500
aggtcttagt aaacccattg taagtcaaaa atgcgtttaa tacacctaac ctaccgaatg    49560
tctatcttac atgtgcttag agcacttata ttagcataca gtcgggcaaa atcatctaac    49620
acaagccgat tctattaata ttaaaattga tgtaatatat gtacatattt tagtacatat    49680
gatagtttaa tatgttcata taatgtatac aggtcaaatc agagtaattg ggagatccat    49740
cgccttaaat atttctttat gctaaaaaca ttggaattat tctatctatt ttgaaatata    49800
caatagactg ttgtgaactt cagtgtccct actgatctag aactaccatg tgatccagaa    49860
atctcactgt tgggtatata tccaaaagga aaaattattg aagagatatc tgcactccat    49920
gtttattgca gcactattga caatagccaa gatgtggaat                          49960
```

<210> SEQ ID NO 5
<211> LENGTH: 60510
<212> TYPE: DNA
<213> ORGANISM: Mus musculus

<400> SEQUENCE: 5

```
actttccgcg gagtcggcag ccgcctcgtg tgcctcggcg gcgcttgagc ggcaacagag      60
tcctgcggcg gcgcgcgcgt ccgaggtgcc cggaggccca ggtacgtgcg accccagcta     120
agctagcgcg ggacggttga ccaggcggtt gcggccccgc tgcctgcagc ctgccgcggc     180
ctctgtgacg cgcggtgcgg cctcggggaa cccgcggacg gctggcagca gggacggggc     240
ggggcgagcg cggcggcggg gcaggcggag cggagcgagg ggcggagccg gcggaggccc     300
cgccccgggg ccgagcagca cggacgctac ggagcaggcg cgtcccgctg ccgccgccgc     360
tgccgccgcc gccgccgctg ctgctgccgc cgccgccacc accgccgccg ccgctcgccc     420
ttctcgggat ccgccgccgc catttgcacg ggaaccccgg tgacaggggc tcggcggagg     480
ggcggaggga gggggagggg cctgcgagcc ccgaggcgg gagcgacgcc gccggcgccg     540
gccaggctcc ctgcgctacc gcgccgcccg tgcggaaacc cgggtggcag cggcggcggc     600
ggccgagggc gggcgtgcgc ctgaggcagc ggcggcggcg gcggccctgc gggcggccgg     660
gaggggcggg ggcagcggcc gccgccgttt gatggatccg aggatcgcct ggttccagcc     720
agagcagctc ggaccgtcca atagtctgtg gatgcagatc tgggagacga cccagggget     780 gaggaacctc tacttcaacc accactgtca cagcagcggc gcgagcagcg cgagcggcgg     840
gagcggcagc ggccccggca gccccggcgg cacggccccg gccccggccg gcatgttccg     900
ctcgggggag cgcccactgg gcggcctcgc cgtgcccgcg gagcagcggg acttcctgcc     960
cctggagacg accaacaaca caacaatca ccaccagccg gcggcctggg cacggcgggc    1020
atcggcgggc cctcggcgt cgccggtccc atcggctccc tcgtccccgc gaccggcggc    1080
cgcactcccc gcctccgagt ctaccgaccc ggcctcgggc agcagcaaca agaggaaacg    1140
tgacaacaag gccagcacct acggactcaa ctacagcctg ctgcagccca gcggagggcg    1200
cgcggccgga ggcggacggg cggacggcgg cgggggcgtg tacagcggga ccccgtggaa    1260
```

-continued

```
gcgacggaac tacaaccagg gagtcgtggg gtgagtgctg gcgtcgtggc ctgcgtcttg    1320
gagggtcggc acacccgcac agcggggaac acgcccacag gcgggagggg gggatgatgg    1380 gtggggatg gggagcccca gtggggcctc cagagcatcg gtggccattc attccttcat     1440
agcttgacca gtctcggtgg acctttcttt ggaattcctt tggaaaaagt ggagctatcc    1500 tctcctttc gtagtcatct ctaccttcct cctctcctaa ctgtccacac cttcccgatg     1560
cattcttgct tgtccttctc ctggatcttt ctatgtctca gaattcagcc tgccctctga    1620 tcccttctg tcctccacac cttgctcccc accaccacac cccaagatga agcccttag      1680 catcgggcta gttaacttcc tgagaacgtt tctgccttag cgtctttaga tgttaggacc    1740
aggaggtgct cttcttgcca agaatagaaa catccagaat gctccttccc ctcccccagt    1800
ccacgacgaa aatctcctca gccctgaaag acactgcctg ctcttgatcc tttggcccat    1860
cttttatatt tacttaagga aaaaaaaaaa aaaagccagt gtttgccatg tctgtcgtga    1920
gcagaaagca ctgagtgaca gctagcttga agttgtcata gatggtgagc ttttctgagc    1980
cctgacagaa ctttgcagga gttcatggtc ggcagcttct cactgtgagg ttgtcactgt    2040
ggcagaggta gcagtggttt tcatttaggg gtgctggtgt tagtgtgtga atgttgcacc    2100
accggtgact ttgtgtttaa agttcagctc ttacaaaatg gaatcttacc tgagccctag    2160
tgaattatgt acataagctg ggaatgtttc cagcctgctt ttcctttggg aagagcccct    2220
gtgttggctg gattaggtta ctgagtcttt tcttctcgtt ctttttttt ccctttcat      2280 aaacttatgc ttttggattt tggtgtagtg tgtgtgtgag aagtgtagag tgtggtttgt    2340
gtagctccag tatggaaaac cagctctgaa ggttttgag ggcagtttct cgttttcagg     2400
tactgatctg tagttaggcc tcaggaaatc aatcagtaat cccgtgtgaa ctttcttaga    2460
ctcacccagt cagctctgcc ctggttttgg caaggagaga tagttgtgtg tacctttttg    2520
aaggtttggt aaaatgagtt ggtgggttcc atctgctgta gtgggctggt gtctgctcag    2580
tacactacta ttacaactcc caccttttat ggaaaaatgc agtcatgtgg ttcaggagtg    2640
atgctgggga atgcctcata gctgccctcg ttttccagag gagatccttc ctggctcagg    2700 cattttgcc agcttcaagg gcgctctcca tggtcatcac cttacattaa agatttgtgg     2760
ttccatcctg ttagccttcc catggcaaac ataaacctgt ggtttagtgg caacaactta    2820
atgctgaggg ttctggtggt cttgtcttcc tcgagtgagc tctgcttagg taatcactgt    2880
caaataatac ctggaaggtc cctagctgca tttcactgat gcctctggtc tgtttctaga    2940
aaagatatgc tataaatcca aagtgctggc tgccccttaa tcctgaaaaa gttcccacgc    3000
agaagcttcg gatactgcct tgccctcaga aggatcaggg aggaatgttc acttccctga    3060
gggattactg cttaaaaact gattgtaaac ttgctaagcg gcttatcact ccatcagact    3120
tgtattctta ccctgaagaa gacggcagca gttaggagtg gccctcctag tgtgagagat    3180
gcagtgaata gttcctaagg tttgttaaga gactctgggt tttcagtgat tccattcctt    3240
tccgatcttc gtggtccagt ttcttagctt ttaagggagt ttagttatta aattttcat    3300 ttacttattg tgtgtgtgtg tatatgcatg tgttcacatg catgtgtgca catatgtgcc    3360
aaagtaagcg agtggaagta acaggacagc atattgggag ttggcattct tcttcagggt    3420
cttgtagatt gaactcagtt caccagtgct tgatggcaaa cagcttttc tgatgagcca    3480 tcttgccagc ctagttttgc tttttttgt ttttgttttt gttttgttt tgttttgtt      3540 ttttaagaga cagggtttct ctgtgtagcc ctggctgtcc tggaactcac tgactggcct    3600
tgaactcaga aatctgcctg cctctgcctc cccaagagct gggattaaag gtgtgcgcca    3660
```

-continued

```
ccaccgcctg acagttttgc tattttagtt acaggtattt aaacagtagg acttctgagt    3720
gtacctcagt atggtgctat tcattatgtg acagaacttt ccctggggag acataacata    3780
catgtctact cactttagat agggaactca aaacagactt aagtgtgaat accataaaag    3840
ccaaaacttg gtgaaatctg acttttttggg gggttactta aaggaatatg ggtgaaaggt    3900
tacttaaagg agccagaaat gactcagaca tctgcatcac caaagcctat ccagctctca    3960
aagctaggga cctggagcac atggcacaga ccgcaggcag ctaaataggt agacagtgtc    4020
ctttctaggt gcctcagttt gtctaaaact cctccaggtt ttttctgctt ccaggtatcc    4080
agctggtccc tgagttgtca ttgcagctga gctctgctct tctgagtggg tctctcagct    4140
ttgtttgttt gtttgtttgt tgtttactt ttgcatggag tggcacagtg aatctggtta     4200
gtttcaggga tatccaagct gttttgagtt gtttacctcc ctgtttaagg agcttctttg    4260
tagaataaag atttcagtct cagaatacag cactgttcag aggtccagca ctgttcggac    4320
attaaatgta gtgtgactct tagcagtatc tcccacgtcc tgaggtttaa ctggtaccct    4380
gctggtagaa gaacaaattc tcgtgcctgc attcttgagt ggactctcca ggtagggact    4440
caggacatgg cagtagaact ctgtccttta tgccttgggg ctagtggctg acaaactcct    4500
gagttttcat taagagtttg aagccaactc ttaaaggtgt ccaggctctt gagtcttttg    4560
gtttccccta acatgcttca tgttcttgca agtgcaagat cctgtttaac cctctttatg    4620
tacgtatccc cttgtattca ctggatagac actctcagta gcccagtggg gcatcacttg    4680
tatggtacct taggtttcat ctctagtaat cccacaaaag gggaaaaagg tggaagagga    4740
ggaggaggag gaagatgaag aagaaaggaa ggaaggaaag aaacaaatat ttggatttca    4800
tcctaaagtc tctctctctc tctctctccc tctctctctc tttttttaaat gaaattactc    4860 tggatttagt tactgtctct caacctttgc ccctgaagc cgtaaaccca agtctagaga     4920
gggtatttgc attgtctgtt atttatttca gagattcaat ccaggggcctt gtgtatgtta   4980 taaaaggacc tctgaccaat gggctatttt ctcttgtgct ttttcctttt tttactgttt    5040
gagacagagt ctcagtaagt tacccaggct tgaacatact ctgtagccca ggtgggtttt    5100
gatactatga tcttcctgga tcagtctcct gaatggcagg aataacaccg gacccaccag    5160
gcccagcttg cttgcttgct tgcttccttc cttccttcct tcttccttc cttcctttat     5220 ttatttattt atacaactgt tttcatgtac cctttttgcta gggctggctg tgttgaagga   5280
tgctgtccgc cagcactttc ttgtccgtag aaatgagcca gatgcccttt tcttggaggt    5340
ttagcagtat ttgtggtaga gaaggaagga tacatagagc tacaagcatg ggaacttagt    5400
gaatcggagc cctcactcct gacctggttt tgagaaactt ctgtggaagg tgcctgatac    5460
tttccaacct cctgaggatg agacactgtg gctgccctga gaggtctctg tttgtcaagg    5520
ctaaatgact ttaacaatat agatatcaaa gagacttggg aaataacctc acttttggat    5580 atttggttg ctctaggaat tggacctggg ctcccacatt tgtgctagag agtgaagctg     5640
taccccagcc ccctgaaaac acaagtttaa gtaattggtt tttgagctaa ggaggtaaga    5700
atgagtggaa ggaagggcag gttaggaaag gatcctggct gagtggtggg cttagtgact    5760
acagctttga aggtcagggg ctaagaggct gtgctctcct gcagagggc cgcccattct     5820 ccattgtagt gctctccttt ggctgtcagt gctggtggct ttctttagtg ctgctgttgt    5880
gacatgtttc tttagcctaa ccacgcatgg gtttgctgac cctgctggat acctgctcag    5940
cccagcagat gagcacaggt tggtaggaaa gaagttagaa gactttactc tgcctttggt    6000
```

```
gctcacttta atttctgtgt gtttgaacat gcagcttact gtaattcttc agtgaaccga    6060
actcttccgg ctcttttgtt ttaccgattg ggatactgaa atgtattttc aagaagacat    6120
catattgtgg attctatgct acctgtaaat taatagttga gaattgctga attaattcca    6180
actgagattc gttccttctg agacctcatg tgagagttag tttgactggt gggtgagtgg    6240
tgtttctttt ggagtcattg gcacaggtag gcctttacaa ttcctgttat ggctctagct    6300
gttgagatgc aaagggaagc atcacccaga gcattttaga atctgccctg tgcttacacg    6360
ggagattagg acaccagaag gaagaaagga aggaaaagga agatgtgaga cgggtgagag    6420
agaggtcagg atcctggtgc actgggtggc cctcatctca gctgctttca ggaaatagct    6480
acctgcccta gtgttgggcc cagaaaggtt cttggtagga atgttatggg tttcttggtg    6540
cactggactg ggcagataga tggcagtctt ccttgatgag ttctttctca gacaatctga    6600
gaattgtaga aatgaggtag acatgagagc agtgaatagt aggcattctt gtttgttttt    6660
gttttttgttt tttttgaga cagggttttct ctgtatagcc ctggctgtcc tggaactcac    6720
tctgtagaca aggctggcct cgaactcaga atccacctg cctctgcctc ccgagtgctg    6780
ggattaaagg cgtgtgccac cacgcccggc atagtaggca ttcttatacc tgccgaagct    6840
gaggaaaatc atgggcacct tccctgtggg acacagagac gctgctcttg tctgacttca    6900
cacagctctc tctcctgctc tctgatgata gtgtttagtg gcggacacta gtccaggatc    6960
acacccacaa acactagact aaatcacata cacacgagt gccgtgttct caatgggtaa    7020
tgggccggga aagctgctgc ttttgaagac tctttgttgg tccactgatt agcatatatg    7080
catgtttctg cagagctgac tggacggctc ggagcctcct caggagctga gaggccagta    7140
gactgctctt tcagtttttg ctaaggactc agcacctgtg gaacatcaaa aaggcttcac    7200
atttgtcata ctgtatatat ttgttacaca taatgaactttt tttttaaatg attgtatatt    7260
gaatttgaag atggctttaa gctaggcttt ttattaattt acaatcacct ttaaattctg    7320
agaaatttct tgatgatata agtaagactc gaatactaag aactttggtc ctaaaaagtt    7380
gaatgtgggg ccgtttatga tgtctattgc ccagagatta cacattagta tttaatgaca    7440
aaacatagga attctcgctt aggcccttcc tgaaatagtg gtttgtaatt agtgcagaag    7500
tgcttgcttt cctatcagct tagtaagtag aagtgcgcat gaaaatagaa accgttatta    7560
ccacattcca aaaaaaaaaa aaaacctgtcg tacttgttac cataatcaac ctcttcatat    7620
gtagttatgt ttcttctttc ttttgagata atcgaaaggt tagtaggaca ttatagaaat    7680
tagtgattga tcattgtagt cttacttcac tgtcgtaaca tctcaatgac tagtttaatt    7740
cagaaccagg caactaatat tttcataatt tgtaacattt tgtattttgt caggtttaca    7800
agcaaatgtg tgttgagtac agctttatga catttgtaaa ttcatacaca ccaccacaat    7860
gaactttcag aactaggtta agttcatctt ggatactcat tatgtttccc tcatgggaa    7920
ccacaaaaaa aaaaaaaaga tacaactatt gtattaactt ggagatctct gatgcccgta    7980
gttagacaca tccttcttgg cactaaacct taacaagcac tagtctgtcc tcctctctgt    8040
agctttgccc ttttgagaat gtgatgtaaa tggaatcctg tcttctgtaa ctttggctgt    8100
tttcctgttg ctgaaatgtc tcggcgagtc attcagcttg tcttatgtgt cagtagttgt    8160
tctgttaccc agtagtgttc cattgtatgg aggcactagt tgaagaatat tccagaagag    8220
tgctttccag ttttttgactg ttacaaataa agctgctata acatttatg tacatatttt    8280
tatgtgaaca taaggcttca tttttggggga ataaatgccc aaaagcacca tatggtaagt    8340
acatgtttaa agaagtcgct aaccagtttt tatacttcct tcttttgtgt gtgtacatgt    8400
```

```
ggtataatca catgcatttg caggtcagag gttcacacca cgtcttcctt tttgctctct    8460
accttatttt tgaaacatga tttctctgaa cctggagtcc actgttttgg ttagactgat    8520
tggccatttg gccccagga tccacctgtc ttcgtcaatc tccggcatca cattgtgatt     8580
acagacaggc actgccacca tccaccttgt cttcaggagt catatctaaa ctcaggtctt    8640
catgcttgca tagcaatcac tgtactcact aggacatctt cctagactcc ttccactttc    8700
tacacttgat tttaggaggc tgagaatcaa aactaagcca ttttctacag tggctgcatc    8760
atgccaagtt cctgtatgaa ggggtccaga atctatctct ccagtacttg ccgtggccaa    8820
tgtactgtag tacagctctt ttcttctaat aggtgatacc aggcagctcc tgtgctgtgg    8880
tcataccaga ctgattggag taaccctgcc taataagtca tgcccttact ttccatctca    8940
atcatatctg ggattgcagc tcggtggtag aatcttttt ttaatcctat atgcacaaag      9000
tccctgtttt ctagccttgc attgaaaaaa aaatctgaat tcccaaggct tatgttttc      9060 tggggaaagg gagtgtgttc ttgaaatact cctctttctc ccctcagcgg tgtcttacta    9120
tatttgtcta ccggattggt cttgaactag ggctggtggt ctctgcacct cagattcctg    9180
actagctgga acttcagttg tatgccacaa tactacccct agtggttgtg gtgtcttgtc    9240
ttgtaataaa taaatgtaat agcaagagaa agaaaaataa attaagtaga tagagtctca    9300
ctatgtagct cactgtgtct tgaatactgg caatcctcct gcctcagcat gccgaatgtt    9360
ggaggacttg ccagtgatgg ctaccgtgcc tgcttgtagt tgttgagtgg aatgaaacat    9420
ccactgtttg tctcccagtt gtcctataat aacctcttaa aaacagcttg ttcaaagcat    9480
gatccaaata tggttctttc cctgctattt aaatcttttg atctataggt ttctctgcca    9540 tctgttccc tctctattaa atttgttgaa gaaattaggt tactttttc tttgttttag       9600 ttgagatttt tggatgtggt gtgtgtgtgt gtgtgtgtgt gtgtgtgtgt gtgtgtgtgt    9660
gtgtgtgtat gtgtttagac atgtgtgcct gtgtgtgcac atgcggcagc cagagaggac    9720
acgtgtggtg gtgccctgct cttttgcttt gcatttaatc cctttgagat gggcgctctc    9780
tctgtgtgtt tttggttagt ctggctggcg gacaaactct gggatctgtc tgtcttttcc    9840
cctgtcagca caggggttgc agacatgcat gtagggtcac atgtggcttt cacatgtgtg    9900 ctagggtct gagttcagat tctcatgctt aggcagtaac tgagccatct cctcagctct      9960
ctgtaaactt ccctgctctc tccttctcg aatcatggct ctattacgtc actttacttt     10020
gtctctttgg ttagatatta aattcataat tggaactaga gactgttctg atattttttt   10080
tcatgaatat tcttaccaat ggattataca tattttaaa aggaaaatag ccagagggat     10140
ggctcagtgg ttaagagcat tggttgctct tctagagacc taggtataat tcccagaacc   10200
cacatggttt ataattggtg gtaactccag tcctagtggg gatccaacac cagctgagtg   10260
tggtgttatg tgccttagat ccactgtgga tggaggcagg cagtggatct ctctgagttc   10320
aagaccagtc tggtttatac atgtcctgat ttcaggaaag ctagggctat gttgagagac   10380
cctgtctcaa taaactacaa caaccactta aaggtcaaat ctgaatagct tttgtgatgt   10440
aggtagccat taatgatgtt tgtctgatgg tattaatgca ctaggatttt aacctcatat   10500
ttggcttgga tccttcccct tgttagttgg tacttctaag agaaggtctc cttccttggc   10560
tccctctggt catgaggact cagttgtctc tctattggag tagagcttga gtgaggattg   10620
gggtgggaag acttacaggc acgagggaga agtaagggcc accgtgggaa ggggaaatgg   10680
gctttgggta gcttggggtg tgtacactcg tgtgcatgag tctgtgtgca tctatgtgtg   10740
```

```
tgtgtgtctt tctgtctgtc tgtgcgaaaa gagaaggaag ttctcacaat gaattgtact    10800
aggcctttgg tctctggtta gaaattgcat gagagcccct tgcccattgc caccctgtct    10860
tggcttttga tctgtggcag ccaagggaag ccatatgaga tctgtgacct gttagcctct    10920
gctcaggaga caaagttcac tcagccgtaa ttcagtattc aggaacagta ttttttggtt    10980
ttgttttgtt tttcctttca gattagcctt agattatttt tccttgtctg tttttttttt    11040
tttttttttt tttttttttt taaagattta tttatttatt atatgtaagt acactgtagc    11100
tgtcttcaga cactccagaa gagggagtca gatcttgtta cggatggttg ttagccacca    11160
tgtggttgct gggatttgaa ctctggacct tcggaagagc agtcgggtgc tctaacccac    11220
tgagccatct caccagccct ccttgtctgt ttttaatatt ggagccaatc attcttgttt    11280
tcaggctgat agagataagg ttgtaaggtg actccttccc cctcagacac tttaaaggga    11340
accacttata acagtagagc aagatcattg agggcatggt ggcctggaga gcaagactgt    11400
gaggactctg gaccctagcc ctaggtcagc tttagctttc tcaggagttc tttgtggagg    11460
cagcagtcag ttgtgggtaa gatggctgtc acaccctctt tttttggttt tctgagacag    11520
ggtttctctg tgtagccctg gctgtcctgg aactcactct gtaggccagg ctggccttga    11580
actctgcccg gtggctgtca cacacagtct aaataaagag ggtcttaaga tgggcagtgg    11640
tggtgcacgc ctttaatcct agcacttggg gagcagaggc aggcagatta ctaagttcga    11700
ggcctgcctg gtctacagag tgagttccag aacagccagg gctacacaga gaaaccctgt    11760
ctggaaaaaa agaaaaaaag aaaaaaagaa aaaaagttc tcttcctttt tgtgtcctcc    11820
tcaaagtata tgaacttggt tgagttttga caagcagttt aggtttatgg aaaagtgagt    11880
gggcagttag tccagtttcc atgtgtcctc tgcgcccagt ttcccatact aagatcttgg    11940
tgtacggtga tgaacttgat gggcctgatg ccgttaagtt cctggagctc aggaaacatg    12000
tgacaagatg gttctgttga ccacccaatt ctctttatc cacctagtca cccccccccc    12060 cccttttct tcctgttcct gaacacctgg caaacacctg tcctttctt gtctcttccg    12120 tttgccatac cctgggctgt attctaagtc gccatcacta agtcttttcc tgttacctt    12180 cgctcggcag cctgcttttg agatccttta tgtattttcc tggcttggtt tagctgattt    12240
atgtagtgct aagtaatact gcatggtata gatatgttgg tctgtttatc cactcaccta    12300
ctggagaata gagtgttgct tccaagtttg gcattggtgc acaaagctgc tgtaaatatc    12360
cacgtgtgag ttcttgtgtg gccatacttc tagcactttg aataaacacc agggaacaca    12420
actgctgcat tatatggtaa gaatactgcc aagagggtct tccaaagtgg ctgtgtcatt    12480
ttttgcattc ataaaacaga aaatagggtt tcttgttatt tcacttcttc ccctgggtta    12540
ttgttttggc tttttgccat tctagtatat gaatagtgat agcaatttaa tttgtggttc    12600
tgatttcctt catgtgctgg aagtatctga atgcatcaat gttgagtgtt ggggcggctg    12660
agacaggaag gtggtgcatt caaagccagt ctgggcttca tggcaagaca ctgcctttta    12720
gggcttttag tggccaaacc taggatctca tacatgttag gggtgcacac ttgtcactga    12780
gatacatcca agcccaaggc cctgcctcaa gatgaagtaa attagtaata aatgttaggt    12840
tatgagagct ctgccctcat gactagattg atattattct tgttctttt ctcccttct     12900 ccatttcat atgtattgta tgcatgcata tgtatgtgtg cctatgatgt gtgtgtgtgc    12960
atgcacatgt atacacatgt atatggaggc ctgaggctga tgtggagact caccctcagt    13020
tgctcttcca ttactggtgc aggatctctc aagcccctag cttgctgatg tgcctatagt    13080
atcactagcc agcttgcttg gggggatccc ttgcctctgg cgtctctgta attataggca    13140
```

```
ggccactatg ccttttctt ttttttttta agttttgttt attattatac ataagtacac   13200
agtagctgtc ttcagacact ccagaagagg gtctcagatc tcattacata tggttgtgag   13260
ccaccatgtg gttgctggga tttgaactca ggaccttcgg aaggtgcttt taaccgctga   13320
gccatctctc cagccccact tccttccttt taaagaatt atttatatat tatgtgagta   13380
tactgttgct gtcttcagac acacaggaag agggcatcag atcctattac aggtagttgt   13440
gagccatcat gtcgttgctg cgagttgaac tcaggatctc tggaagagca gtcagtgctg   13500
ttaaaccacc aaggcatttt ccagcccttc tcttactttc ttacattgct gccttgtgtg   13560
tcggtgttga catttctctt tcatatgctt cccaccatgt cgtgcctgtc atgagggagc   13620
agaaaggctc acaagtgagg gatagttatt ttcttccttg tttttccctt tggtgaatta   13680
agatctgttt ttgctgtgta gcccaggctg gccttgaact tgagttctgc ttcagcttgt   13740
ctagcactgg ggttacagac atggctaaat catctttatc cttccagctg ctagaactat   13800
gggccaaata aagttttgtc cattgtaagc tacctggtct gataaagtct attgtagttg   13860
tataaacaca gacaaagagc accagtgtag caaaaagcta cacctccacc cccatacaat   13920
tactaaagta tctgttctga tagtttgcgt attatttatt tgggatattt ttcttgttga   13980
aatttaagac ttcttggtat gttttatttg agatatttt cttgttgaat tttaagactt   14040
cttagtatgt tttagaatca gcctatcaga taaggacttg cagatacttt cttgcagtct   14100
gtggcttaca ttatcccatc tccccacccc cgaaaagttt aatttcagag tagtcaaata   14160
attataatct ttcagagttt gtgcttttgg taatatgtct accaaaacca agaacactta   14220 cccttttct taatatttag aagttgctcc atttattgat tgtttagaga caagtcttgc   14280
tatttagctc aggatagtcc aggttagcct tgaagccaca gtcttatctc aaggttgtag   14340
gtatgagaca ttgattgttt ttcttccctt tccttcctt tccttcctt tcctttcctt   14400 tcctttcctt tcctttcctt ttctttatt attttttgg tttttcgaga cagggtttct   14460
ctgtgtagcc ctggctatcc tggaactcat tttgtagacc aggttggcct tgaactcaga   14520
aatccgcctg cctctgcctc ccaagtgctg ggattaaagg tgtgcgccac cattgcctgg   14580
ccaattgttt gctaagctgg agtcttactg cattgtccag gttgctctct atatcctcaa   14640
gtgacccgtt cccttctctt cctgagcccc cggcaatact gcccacttca ctgtctccac   14700
aattttgttt ttcagaaaag tcacatatga tgatgtagtg tcttggtttg gcctcactta   14760
gcaggagctt tttaagattc taccatgtct tttttgtttt ttgttttt ccttctattc   14820 ttttttttt ttttcttcct ttccctgcct ctgcctccta agtgctggga ttaaaggcat   14880
gccccaccac ggactggtac ttccatgact tgatagtctt ccttccattt agaatgactg   14940
gcatgtgcca ccagacccat atttttttgg agttttataa ttttgtgttt tacatttag   15000 tttgtggccc atttaagtg tgtgtgtgtg tgtgtgtgtg tgtgtggtat agtatctgtg   15060
tctagaattg tttcatttgt ttaggtttat ttatttaatt tatatgtgtg agtgtttagt   15120
ctaaatgtct gtatgccaac catgtgtgtg agaagtcaag agagggtgca gattccctgg   15180
tactggagtc atggatactt gtgagttcc gtgtggctgc tgtgaatcaa acctagggcc   15240
taaggttaat aagggctcta aattgccgag ctatctcttc agcctctaga atctgtgccc   15300 cgcccccac ctttgtatag ctctgattgt ttgggaattc tgtctgtaga ccaggctggc   15360
cttgaactca cagatatctc tacctgcttc tgcctctcaa ataatgggat taaaagcgtg   15420
caccactgtt gtgggaaata tttaagaagt taacccacca tctctctgct ccactggtcc   15480
```

```
gtgctcctgc tccagtaccg gtactggcct gccacaacac tatgtcctgg cgcgtcccac   15540
tttggcctgt tctcaccgct gagctactct ctcccagcta gcgggttgat cccgctttca   15600
tgcaacaccc tacacacccc atgatcagcc atctcaacac ctagttaccc agtagaaaac   15660
tgacacttaa agcttaataa tccaatcaga tgtatataac aataagatca caagttacaa   15720
gatgccaata caataatttc agagccaact gataaggata aagctttacc ccaattattc   15780
taatctttgt gacaatctta gctacttgtg gctgttcaaa accatgtggg atcaggatca   15840
tcttcctgtt tgtctgcctc catgttggct ctcccctcc tcctacctct ctctccctgt    15900
cccccaaact cttagctcca actccccttt cctgaagtag caatgaaata atgttatggc   15960
tcggggtcac tccagcacga ggaactgtac taaaggtcac accgcattag gagggctggg   16020
aaccactggg atccttgttt ctttcattaa agtttcagag tctccttcat atagggcctt   16080
tgcatatttt gttagagttc agagttagat tgtttgtttg tacgtgtgct agtataaatg   16140
atattatgct tcaagtttca aattctagac ttatttaata ccttgtatct ttaatcccaa   16200
gtgctgggct taaagcatgt gccaccactg ccctgctctg gccttgttct taatcggagt   16260
gggtgggaaa acatctccct tctcgctgtt ggcttttga agattgtttt gaaaatcagg     16320 ttgaacttc cttttctaat tgctgaggtt ttttgtgaaa gtagttaaaa gtttaaccct    16380
tttttgccta ttaatatgat tatagaattt ttcttctctg gttgcagtaa tggatattat   16440
ttttgaactt tgaactaatc ttgcatatct ggagcaagtt cattcggtta tgtttattta   16500
ttaatcatcc tgcttcagcc tctttaagtg ctgatatacc agctgtgcac caccaagccc   16560
agcgtcttat ttaagtcttg gtagttatat cttcatgcat tggtatgtct catttaggtt   16620
aacagatctg agggatattg ttcttcatga cacttattaa tggctgtaag atcagtagtg   16680
attatttgcc tttcattttt tgtttgttta tttatttatt tttgattttt cgagacaggg    16740
tttctctgta tatccctggc tgttctggaa ctcactttgt agaccaggct ggcctcgaac    16800
tcagaaatct gcctgcctct gcctcccaag tgctgggatt aaaggcttgc gccaccaccg   16860
cccagtttgc ttacttattt ataagttgta tgtttttagc caggtggtga cccatgcctt   16920
taataatccc agcttttggg aggcagaggc aggcagatcc ctaaaattcg aggccagatt   16980
ggtccaagga atggcttcca gggcagccaa agctacatag gaaaatcctg tctcaaaatc   17040
caaacaaata aacaaaaaaa ttgtatgtat gagtgtgtac ttctatattg gctttgtgaa   17100
tatgggtgta gtgtctgcag aagccagaag agagcattct gttcccagga gctgcgggta    17160
ctggggactg aatgctcaga atcgctgagc tgtctctcca gcctcctttc actgctagta   17220
ctagtaactt aatatttgta tgtgtatttg cctgggagta tgtttgtgca ctagataggt   17280
gcttggccag aaggcatcag gtctcctgga actggagtca caggtggttg tgagccacca   17340
tgtaggtact gggagcagaa ccgggttcct ctgcaaaagc aactggtgtg cccttaacca   17400
cttataattc tccagccctg atattggcag ttttttatatg ttcttcacta atctggctac   17460
aagttgacca gttttggtt ttttttgttg ttttttttaag aatttattta tttatttttat   17520 atatatgatg agtatgctgt agctgtcttc agacacacca gaagagggca tcagatccca   17580
ttacacatgg ctgtgagaca ccatgaggtt gctggaaaac agtcagtgct cttaactgct   17640
gagccatctc ttcaacaccc tgttagtttt tttgtttttt tgtttttta ataaaagtat    17700 acatatacat tttaaatttt atatttattt tatgttttca tttttctgc ctgtaattct    17760 gtgccccatt cccattcagt gtttgcaggt gccaaaggaa ggtgtcagat cttttggaac   17820
tggagttaag ggtggtggtg agctaccaca taggtgcagg gaaatgaacc cttggtcctt   17880
```

```
tgcaagaaca gccagtacat gtaacctgtg aaccatctct ctagcctatt aaggttttat   17940
agctgaaaat atgcccttct ccctttaaaa aaaaaaagt gctggatata tcagtttctc    18000 ttttttgtc tgtgtgactt caaagtgcca aatatgtaaa acaaccagag gccagctatg    18060
gtggcacagg cctttaatcc cagcacttgg gaggcagagg caggtaaatc tcttgagttc   18120
gaggacagcc tggtctacag agtgagttcc aggacagtta gggctctgtt acccagagaa   18180
cccggtcttg aaaaagcaaa gcaaagcaaa ccaaaaaaaa aaaaaaaaaa aaaaaaaaa    18240 tccctaaacc aacaaaccaa agaacaacaa caggaaagaa ctaatgagaa tgctatatcc   18300
atggtccatt gatggtgaag tgataaacaa catggtgtag ctctacacag taggctgctg   18360
tttactgtta agaggagaaa ttctgctgtg tgaaaagcag gcacagagga caagtattat   18420
acagtgttgc atattatagg aaccacctag gcagtggaac atacagaggc agaaatcatg   18480
atggttattg ccaaaggctg ggggaaagag gaaatcgggt accatgaacc ctaacagttt   18540
caactgagaa tgttaaaaac ttgaggagag ccggggagtg gtggcgcatg cctttaatcc   18600
cagcacttgg gagacagagg caggcagatt tctgagtttg aggacagcct ggtctaaaaa   18660
atgagttcca ggacagccag ggctatacag agaaacgctg tctcaaaaaa caaacaaaca   18720
aacaaaaaaa ccaaaacaaa acaaaaaaaa aaacttcagg agaacaggta gtggcaatag   18780
ttaaacacta aggtgagtga atgtactaat gacatagatt gtgtaattaa agtggctga    18840 aagcacacta ctacttggtg agcataccta gggtcctggg tttgagccct atattgggag   18900
gaaaacaata gttgtaatgt taaattatgt attatatata ttttaccata atttgtgaaa   18960
atgagaaaaa aatttaaaat tattttattg tgtcttatgt gtgtcttatt tgtgttggca   19020
cccatcatgt tacagaaagg tgcgagccag ctggtgtgag ttttgggaac agaccttggg   19080
ttctctgtcc tgggtgctta taactgcaga gccacttctc cagcctggat gatttattta   19140
ttttttaaaa aatctgtgtg gtattgataa tggaaagggt ttaaaggaag ctatttgaaa   19200
tgtttaattt tcatggtggg aagtgactgg ggatattttg agcctctgct actgagctac   19260
atttccagct ttcaaaattt taacttaatg ctagtattag cattatttaa ttttcatttg   19320
ttactgtttt gatagaattg ttatatatag ttaggatgtt ttatgatgag taaatcagca   19380
caaaatcgtt tatttgtgtt gagtcttgta agggtctaag aatcgctgaa agaagacccc   19440
agactcaata gtattcaaag acaaagagtg ttctgtagaa acagccagca tgagtgggtg   19500
gaggatgggt gggggactga aggggtggt caaccatcca agcaaaatgg caaccatggg    19560 ggagggtct cacagaccca tttttaaagcc agttacggag ttttccagttg tggttgggtc   19620 atcttcaatc aggattggtt gagcttatgg tatgggatat ttgtacactt ctgattggtt   19680
cctacctgga gggagagagg gttaccttat agggactatt tctgtatctg ttataagccc   19740
ctggccagat gtcagagcag ttgctgattg gttgctcttt tcttcgtttt tttccaagaa   19800
gcctgggatg tcctgggaaa ttgaggctta aggcctaaca tggctgccta ttattctaaa   19860
atggagtgag ttaggtcctt tcagtttgat actgtagaac atatggatgc cttcactgct   19920
ctgcttattt gtagccagat tctgagattt gggttttgag attgaaggat cttcaggggt   19980
cagtggagca tagctgtgtt tagagtgttt gctcaccatt caaaggtccc tatgtttgat   20040
ccaacaactc ttcaaatcaa cagaacacca aaataaatta cttaagcctc agagattcta   20100
cctggttttt ccttactaag tgcagaagct gatactgccc ttccctggag ctgagcccgt   20160
ttgcccagca tgctgggtcc ctgtgaacac ctgaatctgg tcctgtcaac ccaggcccgt   20220
```

```
gataacataa aacctggggc ctctgtccat gcctgctgcc tcttttcaca gctttgcagg    20280
taacagagca tgcgtggtgg gcttgacact tctttattta ttttatgtat atgagtacac    20340
tgtagctgtg tagatggttg tgagccttca tgtggttgtt gggaattgaa tttaggacct    20400
ctgcttgttc tggccaaccc tgctcgcatc agaagagggc gtccgatttc attatgggtg    20460
gttgtgagcc accatgtagt tgctggaatt tgaactcagg accttcagaa gagcagtcag    20520
tgttgagcca tctcgacagc tcttcttcat gccttttaag tcctgattgg taactgggat    20580
tgaggactgg aaccttctcc tgggggactg acctaacagg tggtgtagtg tgtggtggtt    20640
ttgacaccat atttataaat gatcatgcgg cacaaattca gaactaccat tcaaggatct    20700
attgacggga tcccagagct ggccggttgt cagaacacat ggaccattag atgcctcaga    20760
ctcattgctg tgaccagagc tagtgtggaa gtgggggggct gagaattcca ctcaggatgc    20820
agtatctctt cctcactact cactcttctg aattaaggcc aggccaagtg aggtcaacct    20880
taaaacttaa catgggccgg gtgtggtggc acattccttt aatcccagca ctcgggaggc    20940
agaggcaggt ggatttctga gttcgaggcc agtctggtct acaaagtaag ttccaggaca    21000
gccagggaaa cagagaaacc ctgtcttgaa aaaccaaaaa aaaaaaaaaa aaaaaacctt    21060
aacatgagca agtggattgg tttaggcctt aacaccatgc tttttaaagt taaaagtgaa    21120
aatgcttatt aaggaatctg aggttatatt gcaaggtttc tcttattaaa cttttttggtc    21180 tttaggcagg ccagcttgtg acaggcagag gtaggcagag ttttgaggcc agactggtct    21240
acaaagcacg tcctaagcca gccagaacta tatagtaaga ctttgccttt gaaaaaacag    21300
aaaagacgag aaattggtct tgcagtgaaa gtgttgggtc ttttttgtttc cttttggctg    21360 ggtttacttt taagtgagac agtgagttag aggaagaggg tgtacctgtt tacatgtgaa    21420
cattgtgtgc cgggagctcc ttactaagtt ttgaatttttc cttaatggaa tcttagataa    21480
attacctata cttttttgatc tggaattttt tcttaaagt ttatctttgt aacaacttaa    21540
aacaggaaaa agaggggtta gagtcgtaca taactaccat tctgagttct gaccttgtct    21600
tgggaggtgt aattgtttct agtgttctga ggagtcttgc aaacctgcca ggtaaactgg    21660
acaggaacca aagaagtcat tatttagtaa tttatgtgt gtatttttaa acttattcac    21720
atgtaacctc tcttagtctc ccctcgccc tctttgtgga agtcatgtga atgttctgta    21780
gacttcagtt gtagggctgt gcagttgttc ctgctatgga gattgaacac ttgctgctct    21840 ctctttttttt ttttttttga cagggtttt ctctgtgtag tcctggctgt cctggaactc    21900
actctgtaga ccagactagc ctcaaactca gaaatccgcc tgtttctgcc tcccaagtgc    21960
tgagattaaa ggcctgcgcc accacgcccg gcacacttgc tgctcttgta gaagacctga    22020
gtcctgagtt tggttcccag tacctatgta gggtgactca caaccacatg taactctagc    22080 tccagggga tccaatatct ctggcctcat caggcacctg catatataac ccctatgcat    22140
taatgttgtt ttgttttgtt ttgttttgag atagcacatc tgcttgtctc ttagttcact    22200
atagagaatg acactggcta cgtaggatgc caagtaattt aaaagttatg agctgtgtat    22260
tcctggaatt tcctgtgtag ttttgaaact gtagttgagc atggataact gaaaccacta    22320
aaaggaaaac ggaggtaagg ggtaggagtg gcgggggcct gctttacagt gctctgctga    22380
gccactggcc cagggatgag tgctgaagtg ctttctgtgt ttcctaacct gctgctgctg    22440
cgagcattct ctgtgcctgc tggagtctct ctgcttgtag aacagagctg agcagttcac    22500
tgtccaacag gatctgccta aggatctgga gctggccctg ttgctgagat gataagaggt    22560
aaagcgacac tcaggagatt gctggaaccg ggcagcggtg gcgcacacct ttactcctag    22620
```

```
cacttgggag gcggatttct gagtttgagt ccagcctggt ctacagagtg agttccagga   22680
cagccaggcc agggctacac aaagaaaccc tgtctagaaa aaaaaaaaag gagattgctg   22740
gatctcactg acactgctcc acaactcctg ggaaggtgga cagggcaggg ccggtctgct   22800
gggcgccact atagaaatat ttgttaaaat gctaggatgg tgatatgaag gtggttggca   22860
gatgttggtg gttggactga ttgtgtcaaa acatcaagca tcaagagaag gcttaaaaaa   22920
tctaatatct aaagtctttg tcttctacta cttgaataca gcatgcttca agcatccctt   22980
acagttggac atctaaattg tttccttttt gtctgttgga aatgaagctc tagaaacatg   23040
cccagcattg gctttgcagc tattgtcttc gtctgcgttg cttagaatac gcttcttaaa   23100
tgttgccagg gatcttgtga ggcccagcag tgagggaggg agcctggcac tcagcttgga   23160
gcctcttctc cacccatgaa gagtagagat ccactctttt gtttgttggg atggtgcttg   23220 tcaaatttt gcctttcaga ctcttggggt gtgtgtttca caatggaaat gagttacttg   23280
ctgttgacta tggagtttga ctagtgtgtt aggttttag ggaagaact gggggtactt    23340 cgcatcacca aagtggaaag gtgtttgtcc ttggctataa gatcctgcac gtaggactta   23400
ggtagggtgg atacaggtcg gtgctagagt gcttgcttat tactgtatcc caggaacttg   23460
ggcttggtcc tcagtgatgt tgagcgaaca agcagattaa tgggaacttg ttagttcagc   23520
agcagctctg tctgccagtg agtgatctgt cataaaatga agcggggctc ctcggtcagg   23580
gtcagtgtaa gtgcgtgccg taggtgcttt ttggtgaaga agttaaggta ggaagggct    23640 ttgagtttgt gaggattatt gaatattatc ctgtgaaaac agcagaccag gagagagaga   23700
gagcttagct gggtacacgc cacaggttga aaactgctga tgtagaatga ctcaggagag   23760
ttttattttt acatttcatt gatttgtctt tcctgttttc cttccatttt tgtttattgt   23820
gttctacatt ttttctaag gacagttta attccttttg tgggcttgat agctagtcat     23880 attttaaga tttgttttac tttatgtata tggatgcttt gcctgaatgt atataaatgt     23940
actatgtctg tgcctgatgt ttttagagac cagagacatc tttaactgga tttacaagtg   24000
tgggccatca tttgggtgct gggacaggat ctcagtctat acagtgacag ccagtgctct   24060
taaccagtga gacatctcat caatcatttt taaattattc ttcttttaac tgtgtgtgtt   24120
ttagtgtctt tgtttatctg atgaatgtat ggagatgaga aaacaggttc tgaactcagt   24180 tcttttact ttttttttt tttttgaga caagtgtctc acaatgtagc tctggctacc     24240
ctggaatttg ctatgtagac caggccttga ttcacaggca tccttctgcc tctgctgccc   24300
acgtgctggg attacaggtg taaaccacac atcagacctc atttacaatt ttacttgtgt   24360
tatttcaagt atgtggtaag gaatacagag taacatcgaa tctttgagca tctacccctg   24420
aatttaagaa actctaattc tatttttaaac ttattttctc cttcccttcc ctccttaagg   24480
acaacagctt tcagatgta ttacacacta cgtggtgccc ctcctgcttt ccaggtgatt    24540
gttgccacag gcaggacagg accttccctg ttcttcccaa gtaatgcgcc atagtctgta   24600
cttacatcca tgagcaatgt gcactgtatt ctgtacttac aaacattgta ttagtgggtt   24660
atctttctta ctttagaaaa ctatacgtgt gagcattcat atatacatat ggcacagctc   24720
tgtagttcag aagataactt ggaatttgtt tatgtgcacc aacacttcag tgtctttgtg   24780
ttttaggaga gcttaatttg agaaacatgg ctgcagaata gaaatttaaa acccatgtat   24840
tgccaggcct ggtggaatgt gcatggagct cgaggtgctt acaagaccat ttgcaggttg   24900
tgtcaggatg ctaacatttg ccacctgttt tcaagccatg taacctcttt ctagtggaca   24960
```

```
ggtgtcatta tgtccacttg atagatgaag aaaatgaggc tgaaggaagt atagggaccg  25020
gtatataaat gtgtgtcaga agcaggtata gaatctataa ggcaaggctc cttttgcagt  25080
gatcaaggga ctatagtcag tgatcttggt gcttccagga agcctgtggt agagtaggac  25140
caccgaagtc tcagcgagca cttacgtggg tgctggggag tctgaactgg ttctcatgct  25200
tgcatggata gcatgggctt tacctactga gctttagctt gttaaatatg tcatccagtg  25260
gcattcagca cgtttacatc attatgcaag cctttgtttt tgtttttaa cttttttatt  25320 tattttatgt gtgtgagtgt tctgcctgtg cgccatgtgt ttgcattgcc tgcagaggga  25380
ctggagttac agatggttat gagggaattg aacctgggtt ctctgggaaa gcagtcaagg  25440
gctgttaggc tgtttagtgc tatagattga acccttgaat gcaaatatcc taccaaagcc  25500
ctgctattat ccattccttt ttaagcagtt aaatatttgg gttgtttgct tattttgtct  25560
tttgtggccc tggttgttct ggaactcact ttgaccaggc tggcctcaaa ttcacagaca  25620
tccacctgcc tctgtccccc aagtgctggg atttacgaat ctctgctttc agctccttta  25680
tatttatatc tgggagggaa attgttaggc cagatggcaa ctctgtgttt aagtttgaaa  25740
tgacatttta tatttttat tatttttagg tagggccttt gttgcctagg accttgagtt  25800
cccaagccta ctggatggat tgctagaaga gacttaaaga cttaaagatt tgtgttagac  25860
ttcagaagcc agagccaggg ctagtcgtgt aagcctgtga atttgatccc tggggcctgt  25920
gtgaggttgg aaggaggaca accatagagt tgtcctctca cctccactta ggtgatgtgg  25980
cacaggttgg acatgggatt gcataagtgt gtgcatgtac acatgtgcat tcatgcacac  26040
atacactcac acacacagaa taaaaaattg tttttaaaga taagcatcta gaaacatgac  26100
taagccacag gttggtggtt cgccatatgc tttccactga actgggagtg ttagcagctt  26160
ggttggtcag cattgtgaac ggcagcaggc agcagcagca ggagcttctt acaggtctta  26220
gacagcctca gctcctggga cccctgccct gaagcggcag cccttgagag tgacacatgt  26280
cacagtcctc tgacctaggt gccaggatct ccatcctttg agagaagcta gtgttgcgtg  26340
tcttaggcct gtaggagcgc tccctggaga gagaagcttc tgctgcgtct agagcccagg  26400
cctacattgt cttcagctcc tcacagccct cattgtttct gctgcctctt tgtttctgc  26460 cctgacaccc tagctgccct tgtgtattta ttgtcactgt ctctacaatg gctgcttcca  26520
ccctctcttt tttatggcag cagcctagcc agctctgcta attatatagt tagaagcaaa  26580
gaaaaaggca caagaatcct tttattggtc ccagtgttgc agtaccagcc caggagcccc  26640
tctccagcgt ggttaacaga gagctgagca gccttcagtg tgaccagaaa tggaccagaa  26700
atggacatct ctatctcaga atttcatgaa aaagaacaac tgtctgaacc aaaaaaatgg  26760
cacagtccct tatgcaaatg aagaactctc cttacactaa ttgtaggctt tctgtttccc  26820
cttgtttggg tgaaaatgcc tgcaaggtaa actgtcatct ggacctcact gagtctttca  26880
tggtaaaatg tctagggcaa tgcgtttcac acaggccagc cccctgcttt ctggagctgc  26940
agttactact ctcgggtagc aagcagcagt ggcagctgag gaacttcatc tgatacctca  27000
gtgcagtatt cacagccaga cctatgtgag gatagtcctg cagctgatgg atggcagcct  27060
gggtgccagg gagagctctg atagctgtca gttaggcagg tggcccttag aaggatgctt  27120
atagaaaaga caagccttcc tgctgcagcc ttcatatcat agtgggtttg ttttctgttt  27180
tgtttgtttt gttttaatgt ttttaaaat ggggaatgtg ggaggggat gtatgctgca  27240 tgtatggagg gaggtcagag gacaacttgt ggaagttact tctctatttt cactatgtgg  27300
atcttaggga ttggacacag gcagcaagta ccttttaccct ctgagccacc caatagcaac  27360
```

```
tctgtttgtt ttaatgtagt tatcctctta gatgtaaatt gatgtctgat tgtggttttc    27420
attagttaaa ctgtggtggt ttgaataggt atgtctccca tagacttctg tgtttgaatg    27480
cttggcacta ttgagagatg tggccttact ggagtaggtg tgggcttatg ggagggagtt    27540
tgtcactgtg ggggcaggct ttgagatctc ctatgctcaa tctctagccg gtatggaatt    27600
cagtctcctt gctagctaag gatttagatg tagaactctc agttatctca tctctgtgct    27660
gccatggact gaacctctga acatgtaagc cagcctcaga taaatgctgt cttttataag    27720
agttgccttg gtcatggtgt ctctgcacag aaataaagcc ctatctaata taatggctaa    27780
cagtgcattt ttatgtgtct attgcaatct gtctttcttc tttggagaaa tgtctgttta    27840
gacctttctt ttttcccttt tgcattgttg aatcatgctt cttacataat ctgtcaggat    27900
agtatttctt tatcaaatat ataacttgca aatatactct cccattctgg ggattttctt    27960
tttactttca gtttttaaa aattggcttt aaaaatttt atgtgtatga gtgttttcct    28020
gcatgcatgt ctgtgcacca tgcctggtgc ccttggtggt cagacgagag cattcggtat    28080
cctgaaactg gagttacaga tgttgtgagc cagcatgtgg gtgctaggaa ttgaaccctg    28140
agtactctgg aagaccagca ggctctccta aacatgagcc atctctccag cccagtcctt    28200
tactctctta atactttact cttttgcaca aaggtttaca attttttgatt aaattcaatt    28260 ggttcttcct tttatatgtg tgtttagtgt catgtcttaa gaagtcagtg ccaaatgtag    28320
tgtttcctac agtgtgcttt ccagagtttg aggttttaag tgtggctttt tggcactctg    28380
agtgaattat tgaatattgt tgaaggtaag tgtctggcct tattcttttg tatgcggata    28440
tccagttccc tcagcaccat tgttgcatg atctattgaa cagtctttgc tcactagttt    28500
gagttatttt tattatgtta actaagagtg cacagaaata gaaacttctt gtgttcaagg    28560
atgatttaaa aggaaacaaa tttacgagtt agagatgcta ttgaaatcgt ataagatgtt    28620
aattttcatg gcatctcatg ataccactcg aagtgaacat tggtggtgtt gtgtgatgtg    28680
gaagtgtatt taggtcctgg ccagagtgac acccttcggt tatgaaaatt tggcccttgc    28740
agcagtgtca cctgctctta cttggcatgc atgcatgcat gggtcaccaa gttgtgcttt    28800
gctcttggct gttaatacag accaggtaaa tctcttgcgt ggcctgagcc ggacaagcag    28860
gtgcagcagt atgtatgtgc tgggacacag ggcagccctg tgctcccaag gaaggctagc    28920
ccttagccca aacagaaacc atgtgagact tcctgtggca ccgtccactt tctcttgtgc    28980
tcctgaaggg ttaattcccc ccaccctga gagttagccg ggaagaggga attatttaca    29040
cctcgtctga caaagggagc ttgttttgct tttcccagag gaattattta caggatcctt    29100
gcttctgtgc tccttctgtg gttggttagg gtgcttcctc atggctagtg accccacctt    29160
tgcctcagtt ccactgtaac cacagctttt cattgactgc aactagattc aaagcttgtg    29220
ctcccagtct tagatgggat taggatgttt gctcttaaca ctgattttac tgccaagatt    29280
ctgtcaagtt gaagattcac tacatcagtt ttgtttgcat gaccatagag ttcttcacag    29340
ctaaattctt aactgggttg tccctccctg tttaaagtgc tagactaccc atttgatttt    29400
taactattga aaatgagtga tgctgagata agcttccggg tgaggacctc atgccctgg    29460 ggcagagagg ttctttagct gttttctgct tggatacagt ttggtttaga tattcagttt    29520
ggttttggtt gtttggttgt ttgttttgag acagggtttc tctgtgtcat cctggctgtc    29580
ctggaactca ctctgtagac caggctggcc tcaaactcag agagatctcc tgcctgtgcc    29640
tcctgagtgc tgacattaaa ggtgtgtgcc accaccacct ggctagaaga tggagtcttt    29700
```

```
ttatgctgtt ctgagcaaag agtctccact ttgtaggctg tgaaggcaag tggctgaaac    29760
tggaagtgaa gctctgccta gctgctggaa ggagtggctc tccccccccc cccccccagg    29820
cggaagtgtt ccttgtcttg tatgcatgtc aggaagtgta gtaatcttgt atgacttcag    29880
gatgggattc atttagtatg atagtataca acatttttct aagtttgtat caagtcatag    29940
ctaagcagat tatatatata tatgtgtgtg tgtgtgtgtg tgtgtgtgtg tgtgtgtgta    30000
tatttttttt tttaaataac caaaacaaga gtgttatgtg aattaacaca ttatgggcta    30060
ggtatggtgc cacacccacc agtgagagtt tgaccatgct ctagtgaata tatagacaat    30120
acaaactggg cttttccct ttgatttta cttattattt taatctatct atccatctgt    30180
ctatctgttt attttgatgg gggggaataa caagggcaag gtggtcatgg aaagactggg    30240
aagtgagtgt gatgggttgc ataatgtgag tcccagagga tcactgaaaa tactacatgg    30300
aaaaaaaaag agaatttcaa catatgaacc agggaaatgg cctaggatgg agagagctga    30360
gtggcagagc acttgtctgt gtgcaaggct tcgggtgtga ccccagcact gcaaataaat    30420
aataacaaaa gggaaagggt tcactgatcc agcaatgtag gtagatatca aaatattgac    30480
actgaaagac taaatgagta accctacaag tattttctgc ataatttgct ttatatgctt    30540
tttataaaat tatatataac tatacagagt gcaaaactaa agtagtaaaa aggacatatt    30600
aattgttgct gacgatgggt aaaaataaaa gcaggctgaa ttatagagac ccaagaaagc    30660
ttgggaaggt gtcagtgtgt tcactattac gattataaag atagtctgac atccactggc    30720
caaaatcaag ttttaatgtg tagcttatta ttatacttaa gtgttatgga gctaaaataa    30780
taccggtaaa aacctcagct tcactgggtg gtggtacaca cctttaatcc caacactcaa    30840
gaggcagagg cagggaggca gagaggcaga ggcagaatct gtgagttcaa ggccagcctg    30900
atctgcacag agaattctag tacagccagg gccaaataat acagaataag acaagtcctt    30960
attctcatcg atgtgtatcc tcattagctg ggtaatagca cacgagctga tagttctggg    31020
gacttgggcc caggcctcac atgctaagaa agagcactat cactaagcta catgtctatt    31080
cagtgttttg agatagggtc ttgctgcata gtttagacag gcctagaact catgatcttt    31140
ctgtctcagc ttcctgagtg ctagaattac aaacatgcac accactttgg ctgatagagt    31200
agtttattct aaaatgcttt taaaattgga accatgtaaa acaatcaatt ttagtaatat    31260
aatctcttgt tcatttttaa agttttaatt atgagggatt tattttcttt ttaagattga    31320
ttttatttta cgtgtgtgtt ttgcctgtgt cctgtggagc tcagtagtgg ttgactactg    31380
gagctggagt taaggatggg tgtgaagtac atgtgggtcc tgggaacaca acctgggtcc    31440
tctgcaagag cagcaagtgc tcttaactgc tggatcactt ttattagttt aaaaaaaatg    31500
tgtatattat ttttctgcat acatatctgt gcacctcttg catgtctggt gcttgcagaa    31560
accagaatag agcatctaat ctcctggagt gaactacagt tggaagccaa tatgttggtt    31620
cggagacttg aactgggccc cctggaagag cagcaagttt tttcttaacc agtgagtgag    31680
ccatttctcc aaccctaatg tgattctctt cattagttta tctatttact tatttgagga    31740
aaagcctcac tatgtagctc tagctggcct ggagctggcc ttgaactcac aaagatctgc    31800
ttcctgaacg ttgggattaa agttatgctc cagcatacct tgactctcaa gtacaccata    31860
gtttatggca ttaagtatag tcacaatgta ttgtggcaat tgtcactatt aagttccaga    31920
acattcatca ccaaatagga attctgtttc tttccagccc ctggcaacca agaggctctg    31980
gattttctta ttcttcatgt gtcatgtaat agactcatac tgtatggggc tggttttata    32040
gcttcagggg tttagtgcat ggttctcatg ctgggacaca tggtgggatg taggcagaca    32100
```

```
gggtgctgaa ggtaagttta gaattctaca tctagattag taagctgtag gaagacatgc    32160
acgcacacat gcatgcacac tgagcctgat ttgagcattt gaaacccoaa agcccatctc    32220 caagtgacat acttcctcca acaaagccac acctcctaat tcctgtcaag tagtgccact    32280
ccctaaagac caagcatcca cataaacgaa cctgtagtgg ccactcctct tcaaaccacc    32340
gtgtgtgtgt gcgtgcgtgc gtgcgtgcgt gcgtgcgtgc gtgcgtgcgt gcgtgcgtgc    32400
gtgtgtgtgt gtgtgtgtgt gtaacttaat atcaaccatt tgaaagcata caatttatgt    32460
tgttgtcatt gcccgtctcc agaaattttt atcctcccca actgaagctg aaaatactgc    32520
tatattttct cttccatcct tgcccctata gccatgattg tctattatgt caggattatt    32580
cctgggattt gacttctcta gagacctcat aaaaatggga tcaaacagta tccttttgag    32640
tccagctgat ttcactctgc gtaacagtat tctcaaggtc cactcacttt ttatccacca    32700
ttcctcgccc atagactcct tcacttggct ctgcctcagg ctagcatgaa taacactgca    32760
gtgaacaggt ctcttctgga gacctgctct cagttctttg ggggatgcac ccatgtgata    32820
attctgtgtg tgtttgttag ttttttcttta acaaattgcc atgattctct ccccatgctg    32880
tccattttat attcccggaa gcagagacaa gggtcctcca gctgtgtcac gtgcttgtct    32940
gcacacgaca acgtgtttcc ttttgtttgt tttatagaaa tcaccctaat agctactata    33000
aaattttcat acactttaca ttttaatgta taaccaagtc ttaatgtact gctgacagc     33060 agttacccct aaaccttgt ggaagtgtgg aggactctga caactgtcag tctcctcctc    33120
agccttactt actcccaaat atcaaggcgg cccaggaag tacacagtgt accttggtct    33180
ggcatgtaac ttttgaagac tttatggaac ctacagatgg cagaggtcag caggtgttcc    33240
ctgtagagac aatacgtact ccttattggg tctgtggtct ctgtctcagc cgctgcactc    33300
tggtgtgctg gtgacaagca gctggagtca acgtggaaag gagtgagggg tgttgattgt    33360
attctagaat agttattcat atgtgcttga atttgaatta tatatacttt ttaaaaattt    33420
attttgctat tttatgtgta tgagtgtttt gcctccatgt atgtgcgtgt gccacactca    33480
tgcttggtgc cggaggaggt ggtgagcctc tatgtgggtg ctgggaaccg agccctcctt    33540
tgcaacaaca gtactcttaa gcactgagcc aactctctag cccattatat atgcttatcg    33600
tgtgtcgcag tataattctg acttcttttc aaccatttaa aaatgaaact ataaaagcac    33660
ttttaacttg tggagtgtat acaaatggcc tttgttttgc tctttgggca tgaactctgt    33720
taagagagag ctgagtagat gtcgggggag ggggacgaa tgtggtttgt tagaacttt     33780 ggaaattcca ttttctggtt aaggcaaagg gtacagtact tagctgatgg caagaagtgc    33840
tatgctcaga gtagaagacc ctagaattac agatggggta ggtgtgtcta taacaactta    33900
catgaagaga ccaggacctg gcacagtgct cagcatgttg tctactgtta agtgttttat    33960
gggacatagg tgggaggagt gtctataaga acaagaagga tggttagtgg ctaccattgc    34020
taaatgatta ttttattggt ggacctgtct cagagacaca tggtcattgc tctgtgcctg    34080
agagagtcca tgaagagctg agagagctga ggtctgggag tcatatcagg acttggacgc    34140
atatggaggg acaggcagta ggtgaagcct cctagcttgt tacacacaca catgggactga    34200 aaatgaagga aggtgccatc ttcctgtttc tgctgtaatg aaacaccaga gacagttttt    34260 ttttttttttt tgaacagagg ttgcttttat ttagctgaag ctgagaagcc caaagtcaaa    34320
gggcccatgc cagattcaga gctgcttgct gcacatgtct tcctagcccc tcactagaat    34380
tgttcttacc ccatgcctcc aaactctgcc agcccctgcc caatacctgc ctccagatgt    34440
```

```
ttcagcacct cggatagtta tagcagcaac cccactctga gtgccaaatc ggtagtagaa    34500
ttttgacaga agcagaaaca atagggatgt agacagacag accagtgatt tattaggaaa    34560
atcagcttgt gtggttatgg agggacagaa atccctaagc aggctgtcta gaagtggaag    34620
gtgctgggac gccagtactc tgtaactctt gtttctgtcc agaggtctca gagttaggga    34680
gccagcaggt ggtgtttctg tcagtttgag accaaaggcc ttacagattc agggatgggc    34740
tgctataaat tctggagttc aaaggccaga gaacctaggc ttctgatggc cagagaggcc    34800
tcatagttgt gtcgctatga ggaaatctct agatgtattt ctctttgatt ctctctgtta    34860
atgaaatgga ctggtttcca taaaagttct taaaattaga aattaacttt tttagaatct    34920
atctgatgtt aatagcatta tggatacttg gaccagagat taagtaagag cctatggaca    34980
caataaaagt ccctcttcaa agctagaggc acggctttgc acagcacagg aaggaatatg    35040
gaagatggcc attctccatg tgactctcca agccagcacc agaattacag gttttattct    35100
tatgtgagaa cttcagatgc tctgtgagtt tgttgtctct agtgactgta ttaagcagaa    35160
cagaagctaa agatggatgg agagaagtca gaatgatatc atcaaaaggg accaattgca    35220
gagcccaaat atagacccct aagctgctct gaatgaatga tgggtgttgg ctttaagtta    35280
ggtcaaccct agtcacaggc tttttttttt ttttatgata gggtttcatg tcattcaggc    35340
tggctttgaa ctcactgttg ttgctgaagg tgaccttaaa ctcctggtaa ccccacctgc    35400
aattcttgaa ttgtaggcat gcgttgcagg aaatattaaa aaaggaacag gcacattcct    35460
gtgcttgtgt cggcaactct ctgccctggt ggcatggctg ccatgcact ggtgacctgt     35520 ttttatcaag tggaggctct aactcacaac tccaagatct ctccacccaa cttgctaggt    35580
tccctctggc aggtcgctac cacgccaatc ccatgattca aatcccccac accgctgtgg    35640
tgcacctcag gcagacccac actttgctgc catacctttc tctcttgaac ctggaggaga    35700
cgggagggaa agcatcacat aaacttagtt cacgatagtc gcaagtaagt gttagttttt    35760
aaaaaaaaca gggctggaga gatgatggct cagaggttaa gagcactgac tgctcttcca    35820
gaggtcctga gttcaaatcc cagcaaccac atggtagctc acaaccatcc gtaacgagat    35880
ctgactccct catctggagt ctctgaagac agcaacagtg tacttacata taataaataa    35940
ataaatcttt taaaaaaaaa gttgaagccg ggcgtggtgg tgcacgcctt taatcccagc    36000
actccggagg cagaggcagg tggatttctg agtttgaggc cagcctggtc tacagagtga    36060
gttccaggac agccagggct aaacagagaa accctgtctc gaaaaaaaaa aaaagttgaa    36120
aaaatatagc ttaatgtttt ttgttttttgt ttttgttttt ttcgagacag ggtttctctg    36180
tgtagctctg tagatcaggc tggccatgaa ctcagaaatc cggctgcctc tgcctcccaa    36240
gtgctgggat taataaaggc atgagccacc actgcccggc aaattttttt ctgtagaact    36300
tatatttagc tttacaaagt ttatagcaga attgagtgga aggtacaggg attccctgta    36360
tagccccggc actcccttga gtcccttat atgacgttct gcccagagca gtatagttgt     36420
tcagttagtt aatcttcatt ggcttgttgt tagcgagtgg tccctgatgt gtattggtgt    36480
tgtagtaaat agttaatctc agttgatcat tcagttgatc attcaacttg atcattcagt    36540
tcccagagaa aagacacaca acctttttat ttatttattt atttatttat ttatttattt    36600 attttttaaag atttatttat tatgtgtaag tacactgtag ctgtcttgag acactccaga    36660
agagggagtc agatctcgtt acggatggtt gtgagccacc atggttgctg ggatttgaac    36720
tcgggacctt tggaagagca gtcgggtgct cttacccact gagccatctc actagccccc    36780 aaccttata tttataataa gccttaatca gctctagagc tgggcagtta tctaccctct    36840
```

```
atggctatta tgtctactac tctatcaata actacgagtt ataacttgcc atgttgcctc    36900
tggacagctt ttaactccag ttggccagcc ctcatggcca tgttttatt tctcacccat     36960 cgagtcttct ctccaccttc tccctctcct agaagtcctt gcctccagcc ccagcccaaa    37020
tcaaactccc acttctctgt cttctgtcca gctataggct gtaggcatct ttattcacct    37080
atggggataa cttggggtc aaggttacat agcattactt gggtcaaccc aagaatctgc     37140
tccctgggac aactagggct gtatttagca ttacaacaca tagaacagac taaacatcaa    37200
catatcagta ttgctggaac ttcttactta gtggaatgat ggatccaaga tgcatcacat    37260
agaattggtt ttattgcccc aaaattcttt gctctgtctc ccaactcttg caaccactg     37320 agccttcttc ccccatcttc agtttgactt tccccaagat gtcttacagt tggaatcaca    37380
cagtttacag cctttgaatt tggcttcttt cactcagcag ccagcattta aggccctta    37440 aatttgtcct ggcttggtag ctctcctcgt tctcatgctg tgtgatcttc ctttgtacag    37500
atgcactaga ccacatttcc tctgctgaag gccatgttgg gtgcttccat ctgggcagcc    37560
atgaaaggcc tgttctatat gtcctggtgt aagcttttga gagcatgttt ttagcttcct    37620
ggattgctgg attataaact ttgagaatgt ttgtttgtct attgattgat tggcagacag    37680
gttctcactg tgtagtccta gcacggaact caaagagatg tgctggcctc tgttgggatt    37740
agaggcatac accaccactt ctggcctcta gctatgttt tcattctcac ttaaattttt      37800
tttcttcccc aaaaccttta aaacacacaa acaaacaaaa agatagaaag tatgtggaag    37860
ctggggccat ggcttagtgg ttaagagcac tcgcagtttt atttccagca cccacgtgtt    37920
ggctcctaac tgtcttatgc cctctctggc ctctgagtac acagacatgc aggcaaaata    37980
ccgtacacat aaaatgtaat aattaataat gacaagaaca acacagattg tgagtggtga    38040
ccccgtgact gggatcagac ctgcacacac attaaattat gcctgtattg aattgtcttg    38100
taaaattaat tatctgataa tggtgcttat ttcccgaggg tttgctttgt gcttggtaaa    38160 cagtaaaacct tgtagagata cagatagaag ctgcctgtat ctgcactcct gctctcccca   38220
ctcagcaagt gggaaggagg ctgtctgtgt aaaatgcttc ccccagcaca ggctggctgt    38280
gtaaagctca ggttttgttt ttgttttgt tttgtttttg cttgtttgtt tgtttattgc     38340
tactttaagg aagaaaggga acctgggaca tgtggcccag ggtgcttgga ccggagtgcc    38400
tctgcgtgtg tgcctttggt tggttttgag cagaaagaat ttggtaagct atcagatcag    38460
catgagaaga aaggtggacc tgggaagcag agagcagagg aggaagtcct ggtgaccgtt    38520
gggactggga gtaagatgat ctttggttct ggtcttgtgg catttgaggt gacagcctgg    38580
caagaggtct ctggcattga gctggaatgc tgaactggct aactatgttt ctgtttctac    38640
catgaattct ggaaccttct ggagccactt acattgcttt gtggttttgt agggcttgat    38700
tgctcacttc ccttagtgtc ttggtatagt tgagaaaaat taagtggtat agaaagttgt    38760
aagtgcctgg cctccctgg aggaaaatac caccagctgt tatagctact ttggaagttt     38820
gtctcaaatt tgaatacgta attctgacac cagcagacac tccttgaatg tgtatgaaac    38880
cgaccatgac ttgttagtgc tctgtaccaa agtgctgaca ctgagtcctg ggcttggggt    38940
cctccttgct ccctggtggc cgtgctgccc cacatttgac cacagaatcc cttctacagt    39000
tgctcaggct ccctagttac gcaggtagaa cctttgctct acagggtaag attattaaaa    39060
taattttctc tagttgatat atttccttgt tacaaagatt tagttttaa aaaaatacat     39120 gccattaaca tacattttat aaaatgggtc agtaaaagta tacatttcaa aacagtaaat    39180
```

```
ccctctcttt catgtcactg cttaaactta atcactgctg atagtaagtt ccagatcttg   39240
ctttgtggga acagggaaat gtacagctat ccaagccaag cgcattcatg tgtacatagc   39300
atgtatcacg tgggacacca actgtggaga agacgactct taggaccggt atgtcactaa   39360
gcagactgta atcctcactg gaagggtaga caacagattc ttgccggtga tggaaatcct   39420
tctgggttct gttgttgact gtaagttttt agcatttcct gatcatgagt tctgtgctgt   39480
gcatccttgt acccatgcct ttatattaat ccttatggaa tatttctgaa ggatagggtt   39540
agggagtttg gaaattacat gaacctcttg agatatttgg taacttatac ttccacctgt   39600
agcatctatg cttttttcat catccttttc aaaaagtgtc cgctcttagc tacactaaga   39660
cttaactaag actagttact aatagttctt gggtgaatat agtcagtgct tttgtgtagc   39720
attagatcct tgtgttaaaa agcctggatg gtggttgtaa cagaccttgt tttacctttg   39780
tgtttgtgtt tgcatattcc atgcccttat aagagaattg tgattctttg cctactttaa   39840
cttttagaag gaaagtacta ttatccaaat ggaggacact tgggtacaac aatcaaatcc   39900
agcttctctt gttctctcaa aacacagacc actgttgtgt ccaagtgtgt aggggtttcc   39960
agtctgtacc tgggaagcta ccaattctgt agcagacgcc agctgggtgt ctatcgttct   40020
agttctgtag tccctggtc tagttcatgc taaccttact tacccaggga tagcaacaga   40080
gcttttatca ctggtgtccc cagcccaatt gcaagcccca ggttgttggg gtagtatgca   40140
acacttttac tagattatct tagaaaagct gccttcgagg aataaatggc agagatgcag   40200
aaacacagga tggtctggag gctccccagc ttctgtgcca gtggagttga gatgtgcccc   40260
cgcctggctc ttgctccccc gcagggaagc gccagcatgt tctgtcagta agtaagctct   40320
gctagaccag gccttttggg caggtgtggg aagcttttc ctgtaaacat gatcaactcg   40380
gatcttctcc ctgatgtcaa ggtggcaggg aagaacagga agcccagagc ttcttctctt   40440
accctggtct tcacagcatc atcccgatgc agtccaccat cagccagtta tcagtggaca   40500
gaaaagcatg gagtgcctaa atggttccaa agattacaag gctgtatttc aggaatcaga   40560
agtctcacaa tcagggcagt gttgcatagt gtagtcacag agctcagttc tcaagatctg   40620
caatttataa tttcatctga gcttcacggg ggtgggggat gggggtgggt gggggtgat   40680 gtttcacaga acttcctggt gttactatga tccagaccct ggagaaactg ttttctgtgc   40740
atagttagat ggttctagag gcatacagct gcattggtgt gtgaaagaca gcctacagaa   40800
cttgtctctg tcctaattta ttctatcatg atatcaagct tatactcagc caagagtggg   40860
cacttcagac acagacttta gtctgtgcag tacttagtca ataagcactt agattcactg   40920
tgattctatg ttagcaaagt catgtaggcc aggctggaga gatggtttac tggttaagag   40980
cgttggctgc tcttccagag gtcctgagtt caattcccag caaccacatg gtggctcaca   41040
accatctgta atgggatctg atgctctctt ctgatgtgtc taagtgtact catatacata   41100
aaataaataa gtaaagtcta aaaaaaaagt tttaagaaaa agaaaaaagt ctaacaagcc   41160
aaagagactc aaaagtactg aagtctgctt tgaatgttta tgaagaatgt accaagattt   41220
attactgctt gcattgtgca tgccactagt tgcatagaga aagaaagggt gtgtttggca   41280
tgactaagag gaccctaccc ggcctgacat gggtctcctt ttcttactga tgaaaggcat   41340
tttgctttat tagcttggcc ttctaccttc ttcacacaga tggttgtgtt ggcatatgat   41400
catctaaaac cctagcaccg gggacaggaa gacagcaggc ctgcctgagc tgcataacaa   41460 gacccctggtt taaaaaaata aaataaaata aaataaaatt gtgggggctg gagagatggc   41520
tcagtggcta agagcactgt ctgctctttg aaaggtcctg agttcaattc tcagcaacca   41580
```

-continued

```
catggtggct cacaaccatt tataaaggga tctgatgccc tcttctggtg tgtctggaaa    41640
cagctacagt gtattcataa ataaaacaaa tctttaggaa aaaaaaatag agaatccttt    41700
aaaaaataat aaataaataa aactgtggcg gggattctct tgacaagcac tcacacggcc    41760
ccaggttctt ctagcaactt aaggagctaa agaaatacag taacttctgg gagcagaagg    41820
gagatgatag ttcatagact attaagtact tgcatagtcc tttctttat agtgctgggt    41880 atccaatccc gggctccaca tcacatgcta ggcaaatact tttacggcta aactgcaacc    41940
tagcccttag gggaatcctg tcttaaaact tgtagaaccc tgaataactt gctgtcaaat    42000
taatgtgctg acagaaagcc caggatcaca gcactgaaag cagattttag aatcttccct    42060
accttaccat tgtgttcaga aaatcccttc tgtagggtct ttgctttatg atagtctagt    42120
ttgttttcat gtatagtaac aagaacctgt ggtcccttc tgaagcctgt ctgtggtgaa    42180
gcagtgcaga acagaccact agcacccttt acaaaccctg ctttgatgaa ttttttctc    42240 tgttcttgga tagagatggc tcagtttgac aagttctgtt catactatac acattcccag    42300
cgtgcacatt cagagaacag actctcttga ctggtgtctt ctgacataaa ctttaactgg    42360
caggtggact ctatacttct gtctgcattg aatcagaaac catgtaagga aaccttcata    42420
tggtagaggt agtcaagttt tcagttcttc cctcgctagg atgctttatc tggaagctac    42480
agataaactc tcaaaatgca cccctgacct cttcacctgc ccagtcccag aagtgcctta    42540
cctcaggcag ggcctcagct agaactcaga gggttttta ggcagcagaa gaggcaagaa    42600
caaaaggttg cttgctccca ctggttccat tttttaagac atcagtgcct catgaggtag    42660
aagttgcagc cagtgaaagt gaaaagaaa ggattttcc cttcttcaaa actagttttg    42720
gtctacttga gtttctgtct tcccactcca tggccagtgg atttctaat tgcagacact    42780 ccctctaggg taccctgac ttcttcacct tccaatccta gggagagttt aatgcgtgct    42840
tctcttcagt ctcttttcac ttcctctttc cacggtaact ccccagggtc tcagggactt    42900
ggaagcaagg agtgtctttg gttctgccca aggcccagtt gtcttgttcc cagccagctg    42960
tctgtgtgta cagtgtttcc gagcttctgt cctaggtctt ctgtgatgat gtgttctagg    43020
ccttgctgct ctgtccatct gatacgatct tcttaaatgc tcacattgta gtctctccaa    43080
ccctcccttt taatttcccc tttttctttc tttcccttcc ttctctcttt tgctttttt    43140 tcaagacagg gtttctctgt atagccctgg ctgtcctgga actcactctg tagaccaggc    43200
tggcctcgaa ctcagaaatc cacttgcctc tgcctcccga gtgctgggaa taaaggtgtg    43260
tgccaccaag cccggctccc tctctttctc tccccttctc ttttcattga acataccagg    43320
gcgcatgctc taccaccaag ccacaccttc agcctagcct gaccttctta gctttgtcgt    43380
tatcctgagc ctgtattccc ttcctgacgg gcctgtctac atgagatgct ttggtttcat    43440
gccttgccca ctgtagtctc tggaagcctg cagctttctc agagcccttc tctgcctgac    43500
attcttctca gggcactgct gggtcactga ctagcttgtt catttgacag ttaattcatt    43560
aagcaagtgc catactgttt tgctccttgt ggcgaggtgg atagtcagg aagctctgct    43620 gcctgggctc agggcctgcc ttcctggtct atgcctgcag agtatgagac ctggcctgta    43680
tgactttaaa aagaaaaagg aaggcaaaaa ctcacctaca gcttagtaga ggaacacaca    43740
agggatttct tactttcttt taattaaatt ctgtatatta cctctttaac ttgtatgatt    43800
ataatattaa aatgaaggca aaaattgcaa gtataaattc atcagctgaa ttataagact    43860 ttttttact attttttat tacgtatttt cctcaattac attttcaatg cgatcccaaa    43920
```

```
agtccctcat accctccccc cgaattataa gacttttaag attattcatg aaactgactt   43980
catattggat cggcccgcct cacatttgct ttctgctttt ttcttcagtc tgcatgaaga   44040
aatcagtgat ttttatgagt acatgtctcc cagacccgag gaagagaaga tgcggatgga   44100
ggtagtgagc aggatcgaga gtgtgattaa agagctctgg cccagtgctg atgtgagtac   44160
ttgtcctgga cctgggcttg aggcagagcc tgccccagac tgtctctcat agagactcac   44220
tcacactgta agtgctttgg tagaggtagt ctactttatt ttgcagcagg gtcttacgat   44280
gtcataccca tggctagccc tgaactcaag cctccttaag cttcccagac atgtgccaca   44340
cccagctttg gtcaaatcac atcttaaagg caaacaggga cctgcagcct gtagactttg   44400
gggtttgttg atgactttct tccactcaga tgctttactc taaacctctt cctctcagtt   44460
ctgagtagca cccaataaag tggacagaac ttaggcttat taatgcaagg aaaagagagg   44520
tccagcctca gtacagtagt tagttgctgg aagggattta tcaaggcttc atctttgttt   44580
ttactctagc ccgtcagtgt aaacattgca gttggcttgt agctgacggc atttcttttg   44640
ctacttgaag ttgactgtct tgggcaaatg caggcgagtg tatgcctctc attgcaaacc   44700
actctttgtt ccccgggcca acttcttttg attactcagt cagtgagcag atttgttgcc   44760
ttagtctcca ctttgtgtgt atctcttttt tttttttttt tttttttttaa gattatttat   44820 ttatttattt tatgtatgtg agtacacagt agccgtcttc agatacacca gaagagggca   44880
tcagatctca ttacagatgg ttgtgagcca ccatgtggtt gctgggaatt gaactcagca   44940
cctctggaag agcagtcagt gctcttaacc gctgagccat ccctccagcc ccgtgtgtat   45000
ctcttattat tggcattaat acttaatttt ttagggattc tttcaggtct gctgtagaat   45060
cctccctgag caaagagtaa ctgactttgt tgcatagatt ccttagacct tcctgaagtg   45120
atgtaaggga agccagggcc aggtttgtcc atttggcaaa agaaagaagt tcaaatatag   45180
gtaaagaata gaagggaagg cacaggtgcc cttcactgca ctggggcaca gcagagatgg   45240
ctccgcctgg catgcctctg taagcactgc tgacatctag tggctagaaa gggaagctgc   45300
tggcagtgcc atgacctgca cagaccctat agcaagggag aacctgcccc aggttaagat   45360
gcctccatct ttccgaaacc tttctgaggt aggcaattgt attcatacaa atagaagtgc   45420
agagatacgg ctaggttccc ggaactttt ttttttttt ttttttttt ttaccagaat     45480 ggtttagcat tttcctgact tggcttacag acacatgtat aattgcctgg gtgcctctgt   45540
cctcagtgga ccaagattct cagttgatag cacatcagga tcttgtatag actgctcctg   45600
gtactctctc gcactgacct acacatcagc acatggtcag cagctaaata ttctgaattc   45660
atgagagaac tcctgcagag aggacagaat taaggatttg tgacattcct tatcttgtaa   45720
aagaatacta actagccttt gaaacataac ttgtgaaact tctgtataat gtgtacacat   45780
gtatattatt atatgtatat gtaggcatgt gtgtagaagt cagaggacag ttttttttc    45840 ccattttta ttaggtattt agctcattta catttccaat gctataccaa aagtccccca    45900
tagccaccca cccccactcc cctacccacc cactcccctt ttttggccc tggcgttccc    45960 ctgtactggg gcatataaag tttgcgtgtc taatgggcct ctctttccag tgatggccgc   46020
ctaggccatc ttttgataca tatgcagcta gagtcaagag ctccgggta ctggttagtt    46080 cataatgttg ttccacctat agggtgagga cagttttat agtcaggttt tgtctacctc    46140
tatatgtggt ctgggcatca ggcttgcata gcgagcatct tcaactgctg agccatctca   46200
atggcctcaa cgtctctgat ttagattata agccatgctc tgagtgaatg cccgtgaggc   46260
atggtgtccc tactttagga aagccttgta tttggacctg tccattctaa aacaccagta   46320
```

```
gaggacaaaa gggacgtgca tttctctgta ggcaccttaa tgtgattttt cttcccttgt   46380
tctaggtcca gatatttgga agttttaaaa ctggcctgta tttacctacc aggttagtat   46440
gttgatgaag ttttgaagga ttattatttt gaagggatta ttgtccactg gggctattga   46500
atatgtctga gtagaaatgg ggcttgtttg tttattgttt ttgagatagg gtctctgtgt   46560
agtctgggct gtcctaaagc ttggtgagaa cagttgtcat aggtgagata tggaaaaggc   46620
acataaataa tgagattgga agtaaatgcg tgtatttaca cactgagagc cagcatgatg   46680
ctctggcttt atgcagctta atagtcaggt cacatctcat tgaggcagca cacgtgaagt   46740
ttaataccag aaggctctag gaaaaaccaa acaaaccaaa aaaccattca ctaatagaat   46800
ttaatatgtt tgaggttttg tttctgtcag cattatctca tgtcctgggg cctgagatct   46860
gtgaaatacc tgagggtatg aggttgctaa aattgacact ccctgcttct cctctcctct   46920
cctctcctct cccctcctct cccctcccct cccctccccct cccctcacct cccctcccct   46980
cccctcccct ctcctctgct tcccttccaa aacttaccat cagcacactg atgctctgaa   47040
gcagagaggg aaagggattc ttgttaccct aacttaaagt tggtaagcat aattgtcagc   47100
tacaatagag acctgattga tgcttcttga aacctcacac gtgtccctac agtgacatcg   47160
atcttgtggt gtttgggaag tgggagaacc tgcctctctg gaccctggaa gaagcccttc   47220
ggaaacacaa agtcgctgac gaggattccg tgaaagttct agacaaagca acggtaagtt   47280
cttagcattg tgtctttgtg agccttatta cctgcaggag aaacttggac tctaatctcg   47340
aatagcacag ttggaatgtg actcagtgaa tcattttttg aatgtcacag tgactatgca   47400
taaagactgt cattggagaa tcaaagtaac ttgtccaggc tatacatttc tttaagaata   47460
atacccaatt tttcatgcgt aatgaaatat aaaaatagat tactagctgg gcattggtgg   47520
cgcaggcctg taatcccagc acttgggagg cagaggcagg tgatcttagt ttgaggccag   47580
cctggtctac agtgtgagtt tgtttctgtt aaatagcccc tagttataac aaaagatatt   47640
gttctcttat tttgcacttg agatcttgtc aaggccttt ttttttttt aattaaaaag   47700 gatatgtttt tattttgtgt gtgtgttttg gggctacagc agagggcttt ggatcctcta   47760
gagctgagct gcaagcagat tgagccacaa tgtgggtgct aggaattgaa cttaaactca   47820
ctaagtgatg actcttagcc attgagccat ctctatagcc tctgaagtca tgctttctat   47880
agagaagtcc tgtcgcaaac aatgttttaa atagaatata ttgtatttt atgaatttat   47940 tgcttttag aatttttaga atttattgcc ttctatgaac ttttcatttt tacttatgtg   48000
cgtgcacaca cacccccac gctccccctc cccccatgcc ctgtgtaggt ctgtgcgtga   48060
gaggacagta tggtgcagtt tctccactct gagctggagg tccagctcag gttatcaagc   48120
ttggcagcag acgcctttgc ccgctgtgtt ggctggtgcc tggtcctcag agcacttcat   48180
ggttttgtgg tctcgtgaga agtgtagagg tcacaggtct agctagtaac cttgtgtcct   48240
gattctgcca cttactttgg gagactattt taaactttta tgtcttcttt ttctaggttc   48300
ctattattaa attaacagat tcttttactg aagtgaaagt tgatatcagc tttaatgtcc   48360
agaatggcgt gagagcagca gacctcatta aagattttac taaggtcaga tacagtctat   48420
attgtgaagc tattaagttt gtctcgagcg actgctgtgc tgtgctgtct tctgcccagc   48480
ttatgtatgc gtgcggctga cacatgactg catttcgtgt gcttcctgtg gacgggtttc   48540
tgaaaggttg tggacacttg tgaagaccac tctgttcctt aggctgagtg gcatgggagc   48600
tgagattgta caacaagctg actctggcca gttttttaatc tccaagttta gattagaatc   48660
```

| | | | | | |
|---|---|---|---|---|---|
| tttcccaggg | agccttttt | tttaatccca | aattctctgt | caggagatac | ttgctacttt | 48720 |
| atcttgaggt | aatgttagtt | tatttcaatt | ggtttcaaaa | taaagaagtt | gccagcatta | 48780 |
| tatatactca | gaacatttta | cagccccaga | cctgaaagca | ttctgtccaa | tgcagtcacc | 48840 |
| tttcttaagc | agttctccag | tttctagaca | tttcagtttt | tgtattttgg | tgtttttagt | 48900 |
| ttttcaaaca | ggatttctta | tgtagccctg | gctgtcctgg | aactaactct | gtagaccagg | 48960 |
| atggccttga | actcacagag | atcctcctgc | ctctgcctcc | cacatgctgg | gattaaaggc | 49020 |
| atgctccacc | actgccctgc | ttttttgcttg | ttattttgag | gcagagtctc | actatgtggt | 49080 |
| tggcctcaag | cttttaatct | ttctagcaca | gtatctggga | ttgctgggat | catagttgtg | 49140 |
| tcctactgcg | gcttctgcct | gctgtacctt | gcttccttt | tcctatcagg | catgaaagaa | 49200 |
| tatagaagat | agaaagaaaa | agaaaaatat | ctcttttgca | ggggctatgt | atatgtgtat | 49260 |
| agcttttcat | aaaagaaac | taaacgttcc | aaattgtttg | cttactaaca | aacaatagaa | 49320 |
| gatgacatga | aaagccatgg | ccatcctctg | tagcggacct | tgtgttctgt | gcctggagcg | 49380 |
| ttaacagttc | tggagggtta | tatctgtcag | ctctaagagc | cctgctcatc | ttctgtaaag | 49440 |
| caggaagtga | tctgggtggt | gacctgtcca | ctgggtgaca | gcgggcaaga | ctgtgtgtgc | 49500 |
| tcgggcagct | gcagaatgga | ataggggacc | ttgctgtaca | gcagaaggcc | acacacaaat | 49560 |
| gatttcttga | cttttcttact | ggattagtgc | cttaaatgtt | gaggtgcttt | ggcctttgtg | 49620 |
| ctatttctgt | tgtctgtttt | aagagacctt | tctgtgatca | taataatatg | gttagatagt | 49680 |
| tagtatgtct | gttcagacag | catgtggccg | ccattattta | cgtcaccatg | aggagaaagc | 49740 |
| cttttattac | ttagaagggt | gactttgaaa | ttgaatatat | tacatatatc | taccaaattt | 49800 |
| tgtattataa | ggaccaattt | atgcccctgg | tgatgctttg | ggctattaaa | atataggaat | 49860 |
| tcattgaaaa | tgtaatttca | tttctctttc | agaaatatcc | tgtattgcca | tacttggttt | 49920 |
| tagtattgaa | acagttctta | ttacagaggg | accttaatga | agtatttaca | ggtggaattg | 49980 |
| gttcttatag | tctctttta | atggcagtca | gtttccttca | ggtaagttgt | gtgggtgtgc | 50040 |
| tatatcagtg | tgcactggaa | aaaagataaa | ctacttgcag | agacatttgg | ggagaaaatt | 50100 |
| taaatcagga | attttacag | tacttctcct | ttaaactggg | taccttttat | atagtttagc | 50160 |
| aaattagtat | ttaaacattc | ctaggagaga | gattgagact | ttactaggta | tgttaacatg | 50220 |
| taatgtttgg | cctggtttct | gtaaatgtga | atgcaataac | agccaaaaca | cagggctgtc | 50280 |
| tggagctcac | tggtcagtca | tcaagctctg | ggttcagtaa | aagaccttat | ttcagatgga | 50340 |
| aagtgattat | ggaagacagc | tgatgtcagc | agcagacctt | tggctcctgc | atgcctctct | 50400 |
| acttacactt | agacattcat | ttgtacatac | aagtacacat | accacttgaa | catacacaca | 50460 |
| cacacagcag | cagtgcgcgc | gcacacacac | acacacacac | acacagcagc | agcatttgta | 50520 |
| catacaagta | cacataccac | ttgaacatac | acacacacac | acacagcagc | agcagcagca | 50580 |
| gcacacagag | ggactgggaa | atggctcagt | cagtaaagta | cttgccattg | caagcatgag | 50640 |
| aatctgagtg | tagatcgcta | aagcccacta | acaagctgga | cacagcagca | ggtgcttata | 50700 |
| gtcccagcac | tggagaggga | gagacaagag | gatccctggg | gctagctggc | ccaccagtct | 50760 |
| agcccactgg | gttcagtact | tcagtgacag | acactctttc | acttgcctat | catgcataaa | 50820 |
| gtctaggttc | cattccttag | caccgttatc | tgaaaaacaa | caagtatggt | ggccagatgt | 50880 |
| ggcaggtaga | tctccatgag | ttcaaggcca | gcctggtcta | cacagtgaat | gccaggacag | 50940 |
| ccagaactac | atagtgagac | cctgtgttga | taaacctaaa | tatatatatt | ataatatatt | 51000 |
| gtgggcagtg | acttaggaag | acacctctca | tcaactgctg | tctttgatat | acatgtacac | 51060 |

```
acacacacac cagaaataag agtacattta aagcagttac ccatggaagc tcagctataa    51120
ctgacacatg ttctttggat aagagcttta gttttgcctg tttggcagtg gttgccagta    51180
accagactgc taagtgagat gaattccctg atgtggctca cactcagcct tacctacctg    51240
gtctataccc atggtgcatt gcatgagctt tgtagcatag ctgtcaactg gtccaagatg    51300
atgatgatga tgatgatgat gatgatagcg agtgctcgta gaagttggga tctcacttat    51360
accccctcct tcataacaga gaaaatccaa ataatttct tccttttttt ttttttttct     51420
gttttagtta catcccaggg aagatgcttg catccccaat acaaactatg gtgttctctt    51480
aatagagttt tttgaattat atggacggca cttcaattac ttaaagactg gcatccggat    51540
aaaggatggt ggttcctatg tggccaaaga tgaagtacag aaaaatatgc ttgatggcta    51600
ccggccgtca atgctttata tcgaagatcc tttacaacca ggtactgcga ttcggtgtct    51660
gtaggcttca gagggcgtc acagtccacc catgctttac tctgttcaga tgaaaatgct     51720
tatttctaag tagcacttgt tcagaatatt cttatcatac taaagagac acatactcca     51780 gaaaaccac ctgctagact tgcacataag ttgaggtagt gtccatttga cttcaaagc      51840 caagcagaga ggaattcact gtggggtggg tttgcagcca tctctcctcc tgtgggctgc    51900
catttccagc tagttgtcag cagggcttta gtgaggtaag atgggggctg gagagatggc    51960
tcagccgtta agagcactga atgctcttcc aggggtcctg agttcaatac ccagcaacca    52020
cgtggtggct cacaaccatc tgtaatggga tctgatgccc tcttctggtg tgtctgaaga    52080
cagtggcagt gggcagtgta ctcacataca taaaataagt aaatctttaa aaaaaaagaa    52140
agaaagaaag aaagaaagaa agaaagaaag aaagaaagaa agaaagaaag aaagaaaaga    52200
aaagaaaaga aaagaaagaa aggaggaaag gtggaagtcc tcagacagca gggagcatgg    52260
gcagaaaagc tccaggagac cgctcttact catgttctga ctgctgcttt cttttgtgt     52320 gccctctctg tatggctcta gctttgggag tggcttgaga gtgaacgag tgcaagtttc      52380 tgcctcactt tcacaacgtt aaatgtattt gcttatgatg tgcagatgta tgttcatagc    52440
taattcagac aaagaccagg cagcacccct ccttccttac tgttttcaat gtagcttggc    52500
tttattccga ggagaaaata gccagctgtt tgtttgtatg tgataggaga atccttgctg    52560
ggctaaagtt gtatgcaggc agtgggtggg tgtaccatag caaagcactg tgcaggtctt    52620
ccaaggctga cagcccactc atgagcagct gtcacccttg ttcctgggca agggctcatc    52680
agcctttatt cataataacc agcagccagg tttacttgtc ttcgtatcca tttctttaa     52740 aggtaatgat gttggaagga gttcctatgg ggccatgcag gtgaaacagg cctttgatta    52800
tgcctatgtg gtattgagtc atgcagtgtc accgattgca agtactatc ccaacaatga      52860 aacagagagg taaagtcta gcccaggcca gcctgtgtgt tgagagtggt tggtacttct      52920
tatcttcaac ttaatgtaca cctctttgt ttttttttaa cctgtgcagc atattaggta      52980
gaataattag agtgacggat gaagttgcca cgtatagaga ttggatatca aaacagtggg    53040
gcttgcagaa taggcccgag ccatcatgca acggtaagac ctccttgatg gtggactggg    53100
tcttagaggc ttttttctatg ttttgtgtat ttaatgggaa gaaacgtttt ccaatctttt   53160 gccactttt caggaaatgg tgttaccttg atagtagata ctcagcagtt agataagtgt     53220
aataataatc tgtctgaaga aaaggaagcc cttggaaaat gtagaagtaa cgcctcggaa    53280
cctcttagta aacactcttc aaactcttca tcaggtccag tgtcctcctc ctctgccacg    53340
cagtccagct ctagtgacgt cgtaagtatg acacatgctg ccccagcctg ctctttggag    53400
```

```
ggccctcaca ggcaccaggg atatttccaa tacctttcat tcttgtactt tttccctaac    53460 atttttttt  aaagaaattt gaaaatctag tgaaggtaga acccgtcagt ggctgtagca    53520
ttccatactc cattagcatt gacctgctta ttatattcct gacactctgt cccgtaggca    53580
gctcctcttc ctctttgatc tgcttcaaag atggcagatg tcacacttca ccccagcctc    53640
catagcatgc atcctggatt tagatggctt gcttattctt tattcctcac taagttttat    53700
gaccatgctc aggtcactca gagctctagt aagagaatgt cctctcacta acccacagtc    53760
cccagtctcg cctccagagg gcatccttgt ccttgtaaag gattttctac atcacatatt    53820
ggttttccat gtcggggttc ctagagcttt gatctcatgc tatagaatat tatttgtaaa    53880
gcagctttca cttctttttt tttttttctt ttttttcttt ttgtttgttt gtttttttgt    53940
tgttgttatt gttgttgttt tcgagacagg gtttctcttt ataaccctgg ctgtcctgga    54000
actcactttg tagaccaggc tggcctcgaa ctcagaaatc cgcctgcccc tgcctcccaa    54060
gtgctgggat taaaggcgtg caccaccacc gcctggctgc ttttactttc ttaagctttt    54120 tttttcttt  acttgttttt gagatcccta attgaaattg ttaattgata aaacttgcat    54180
ttaataaaag tataattcag ggttcccagc aatgatatca ggcagctctc aactgcctgt    54240
atgtaactct aggagtgtgt gtgtgtgtgt gtgtgtgtgt gtgtgtgtgt gtgtgtttgt    54300
gtttgtgttt tctggaactc actatgtaga ctaagctggc ctcaaactca gattcaactg    54360
cttctgtctc ccaagttcta ggattaaagg ctcagttttg agtttctaat gtattcagta    54420
ttacacagct actttcactc ttaatttaag gatgtttcca gctaggcatg gtggcacatg    54480
ccttcagtcc tggcactcgg gaggcagagg gagacagtcc tccaccaggg ccatatagag    54540
agatggtgtc tcaatccccc tgccttcccc ccaatatcca tgttatttag taacctctcc    54600
cagctcccct ttcccataac ctttggtcta cttcctgtct ctatcatgat gaataacatc    54660
tcacattaaa ttttcgttgt aaaaaatttg agtctactta attaaagttt aaggtagatt    54720 tgtcttttcct ttgaatttg actttaatat gtgattgcaa aatgtcctat tagggtcatg    54780
gaggtactag catgtgccct gggtttagtc ctctgcactg cataaatcag gcttggtagt    54840
acatatctat aatcccaata atagggaggg tggaagcagg agactcagga gcaggagtta    54900
aagacatgct ctgttgcaga gtgagttgga gcccagcctg cattaaatga gactgtgtct    54960
caaagaaaaa ggaagaaaga aagaaccaat tttccacata gcaatatgat ggcatattgt    55020
tatggagtca taaatactga tatactggat ccttgtgtct gggttctgga gtggtgcttt    55080
ggaaggtgga atgaatgcta agctagatgt ccctgtagag actgccttga aaagaagaat    55140
ttagctatgc cgctgacgtg tcaggcagtg taccaacata aagcagccaa gagagcagat    55200
ggagcttaga acaagcatcc ctgtcctaga cactcagttg tgccacttga acctgccatc    55260
ttgcaataag gtccctccct ctttatggtg atcttccatt gtttatatga cttgctattt    55320 taaaagttc  acatcaactg gaactcacaa tgattgacat tcacaactga tttaaaaatc    55380
agctagatgt ggtcagtgac ttggcaataa ctagaagcat acagtagaat agatcacctc    55440
acatgtctgc agaaggggct gggaaatgac tcaatggggt agaggtgcaa gctgtgcaag    55500
caaaaggacc tgagtgtgaa caccccatgt cctctgactt gagtgtgaat accctgtgtc    55560
ccctgacctg agtgtgaccc gaatcccttt gaaacagtca tgactgtgtt tgcctgcagc    55620
tgtactgttg ggagcagaag ctctcattca gtgagggacc ctgtctcaga aaataaagtg    55680 gagggggtaga ggaagacaga agctgttgtc tggtctctga ctgcatgctt tggatgcgca    55740
cacacacctt ccttcacaca gcatttgaag taaagcctcc tcaggtccca gatgtgtctg    55800
```

```
tttagactag aaagtactta gccgaaattg ttgcccctct gagttctgaa tatgaaaatt  55860
actaatatat tgctttaccc atgtgacttg tgttaggatt ctgatgcaac gccatgcaaa  55920 accccaaac agctgctctg ccgtccaccc actgtcaccc gggtaggctc acaggatgtc  55980
tccttggagg tctctcaggc agttgggaaa atgcagagca ctcaaaccac taacacaccc  56040
aacaacgcca acaaatcaca ggtgggtaga atctgtgctt gttactctta gcgttcagtt  56100
ttagatagtt agaagttctt ttttcgcttc taattttaaa atgtgtattt attaaagcat  56160
ttataacaag tatgaatagc ctatccttat ttactagagt tgataaaaat gtccacggca  56220
tttgttgctt ctttccatgt ttataagctc catcaaaccc acacattctc acgcctctac  56280
taaacactaa tatttcacag gggtaaattt tttcagtact ttctaaagta ttgagaaaat  56340
acattatttt gttgtactta ctgttgttgg acagatcaga taacagttgt gtttttatag  56400
attgaaaatc acataaaatt atccaattag aattaaattt caattcttgt ctcatactat  56460
tattggaaga ataaataatg aaacacagcc tgagaaagca gaagtcataa agtggcagca  56520
tggatagtgt cccgttgact agcacgggct caggtgtgtt ccttcctgtt ctcagcagtg  56580
ggaagtgtgg ccttgaaaag cccatctggc ccctctgttt ttctcatctg ctagacagac  56640
ttaattatgt acctcccttt tctataaaat gatgacaaga atagtctacc ttcaaattta  56700
tagtgaatac tatgttaata attatagaaa tgcttagaac aattgagaaa tgttgagcat  56760
atattaagca tcatatagtt agaatttctt acatgtgcac agttgctaca cataaagaac  56820
tctcttagtt aaagaatgaa ctgttttgtc aaaccagatg tcctgaagct ccttttaaga  56880
tagggttgta acatagtaac atagatctta gtgctagcca agcccattga gcattgggc  56940 tgaggatgta gctgagtgta gagcaggctg atgagtggtc tccgtggctg tgcttgaggt  57000
gcactggcat ggaatgtctg cagcatccct agaaacagct agttctttgt tcttatttga  57060
tacttgttgc tgaggacaat taccaggtac ctgggagaca ggttcagttg attaacatca  57120
gctttgactt acttaagtat ttttagttgc caaatagtat tactaatttg ccatgaataa  57180
ctaatcaggc aagagaagaa gcttttgata ctgatctgtg gtaaaaattt tctttcccat  57240
cctcagatgt agcaggttcc ataggaaaag gtctgtcttc ttggaagttg tgatttgatt  57300
ctcccggttc actgtacctc cacagtctta gcatgggcac caaatgcagg tgcagggagg  57360
ggcaggacta accagagact ggtgccagta ggcaccacaa gagctgtcac tgggaacagg  57420
aaagaaacac ctaaactgtt taggtctctt gacctcctcc ggtagtgcac acaacatgat  57480
aaggaggagg taaggtagac ctcctcctta tcatgttgtg tgagcagtag gatccttgag  57540
gaagctttca tgttgtacac atgctgtcag aagggagc tatagagttc accctgtta  57600 gtcctcgttt tctagcctct agaacagtgt gtgatagctg ggtgtgatgg cacacccctt  57660
taatcccagc acttgggagg ggaggtaggc ggatctctga gtgtttgagg ccagcttgaa  57720
ctgcatagga aggaagggcc agactggcca gagtgacagt gtgggagttg tcagtggggg  57780
accatgttaa gtgcgcgcct gcccctttct agtctgggag cggccctgca tgcggtttgc  57840 caggggggcag ctctgctccg attctcactg cttttcttctt ctgcagcatg gatcagcaag  57900
gctcttccgt tcttccagca aaggcttcca aggtacagct caaaccagcc atggggcctt  57960
gatgacaagc aaacagcatc aaggcaaatc caatactcag tattaccatg gcaaaaagag  58020
gagacacaag agggacgcgc ccctctcaga gctttgtaga tagtcggcgc tctgcgacag  58080
actgtcttct gtgtgcaatg atctcgtgct caggacagtt gcacagggac tcctgggacg  58140
```

```
gcaggagcct cacactgttc agacgttgat ttagcaactg cgttttttcc cagctcgcca   58200
cggaatggat catgaagact gacaactgca aaaacaaaaa gcaagcaaaa aaaaggggga   58260
aaggctgctt atgtgataag tcatgtgcta caacagggtc attttaagat ttaaagcttg   58320
aatgtaaaat aaatatattt ctcattggct ttatgcagag ttatagggc tagtgctcag    58380 tgtgggtagc tgacaggaag agagcagtgt caaggagatg ggtgggcagg tcagcaggag   58440
catctcatgg gaagtcagac tccgagggaa aggagtttgt gcatggtttt ttttaaaaaa   58500
taattttgca tatatttgcc attttattgt gtgtatatat agaagaccat ataggaaatt   58560
gatatttgta atagtggatt tgttaatact ttttacataa cattactatt tgaattgtaa   58620
acagattttt ttctcaggat tagtttgaag aataattgag ttgtcactct taacacatgc   58680
agggaagtga ttagctctgg tcctgtctgt tttcttcagc attgaaatga cttcatagaa   58740
cccttgtgac ctgcttcaaa attctttcct ctctaagcaa aaggtttatg gtggcaaatg   58800
atgtttattt tattttgtaa aaagagaaa aatgtactgt gtacttgtgt atacactgaa    58860
caacctctag ctgtctctcc gaatgaacac acctgctctg gatccagtgc tgttgtcttc   58920
ctgggcactg ggccgtagca ggccttgtgt gtgtttccta gcagtctttt cttcccctcc   58980
ctcctcttct tcctcaaagg aaacgaaagg cctccctggg cctgggctgt tcctgtcaca   59040
gtgtggctga cctctagctc cacagccctt gttagctcgc atgctggttc ctctgaccct   59100
gcgttccatg tgcttgtggc gtcctctcat tctttctagg ttcctgctta ctgctgtggg   59160
agagagtaac tgtaaacagc tttaatgaaa tcatacttat aaaaactatt ttcttatact   59220
ccactttatg cttttggtat tgtcgatctt taaaaattaa atggtctttg ataatggatc   59280 gattttgta ttgccttatt aagaccaaat acttcttgtc atcccattct ttatcctctc    59340
ctttaatgga attgctgtct ttaattaaaa ctttgtaaac actggcttgt tttaatcatc   59400
ctgtaactta ggctgtggtc agctacaagc gcagatgtgt aatcctgtta ctcattgcca   59460
gctgagtctt gagactcggg tggggtactt aacacaatgc atcgtacacg ctctgctcgc   59520
tcgctcgtca gcagagtggt cttggaggtg aaagccctcg tgtctagcat cagtgtgtgt   59580
gtgtgactct gttcagtacg gccgtttccg agatgggatt ctttatatg tgtatgtgtg   59640 aagtactgtt ggcatttagg catttctttt ctatacactt aggaaatact gaagaccaat   59700
cagaccatta atggacactt agtgcaactt tttataatga gaataatgct ataaagtaag   59760
accaaaaccg gtgtcatcac tgaaattaac aatttcaat atgttcatat tttaatttac    59820
aatgggaaaa aatgtgttcc acaactggaa actcacagta ctgtgtaaac tgtgtaagat   59880
tttaaatgtg atgttatttt gactgttctc aattttagag tcacatttta ttctgatcag   59940
aatttttatc aagatgttga agtttgtttg tttttgaaact agtttgtcat aacatattgt   60000
gcataatcac agtatttatt ttgtagggct tgtggatgtg tagacttatg tttactgcta   60060
agggaacaat tatttataaa aaaaatatta aatccagtat tagctgccta tttcagacac   60120
ttaacacctg cagagatctg tgttacattt accacactga agttttttta aagaatcacc   60180
ctcattgttg aaagtaaatg tactcttagg tgggttatta gtgtccaata agcatgtgat   60240
tatattaagg tggtggtagc gggaagataa tcttgattcc attgggaatc ttaggttttc   60300
gtaaatttat tgggaaaata gttttttcctg tactgctgat gtttcttttt ggtaaacagt   60360
atctttctaa aagaaaaagc atgaaggaga attgaggtgt gtatacattt ccccagatga   60420
ccagcattgt attcgtgaat actgtgtatc tggaatgagc agtgtgcaag ctgttcattt   60480
ttcaatctga agtaaaatac tttcaagaac                                    60510
```

<210> SEQ ID NO 6
<211> LENGTH: 36659
<212> TYPE: DNA
<213> ORGANISM: mus musculus

<400> SEQUENCE: 6

| | | | | | |
|---|---|---|---|---|---|
| ccgccgcccc | cgcgccgcct | ccccgccccct | cattggagct | gaggcggcgg | cccccatccc | 60 |
| tctccgttcc | cggccgccgc | cgagggcgtc | tttccgccgc | cgcgccgcag | gagcgccgtg | 120 |
| actgactgac | ggcccgacgc | tctgggcccg | ccccctcggc | cggtcaccgc | cccttcgatg | 180 |
| gcctctccct | gccgccgca | cgctacgccg | ccgccgccgc | ggcccctcg | ccctccccgc | 240 |
| gccgcctgag | ccaccgggac | cgcagctgcg | ccgcgcgccc | caccgagcgc | cgcccgcgcc | 300 |
| catccgcgcg | caccggagcg | cggcccaggc | ccgtccgtcc | gtccgtccgc | gcggccggcc | 360 |
| cggggcgcgg | cggggcgggg | cgcggcgggg | cggggcgcg | gcgggcgacg | cgggccccgc | 420 |
| gggggcggcc | cgtggatgga | tccgcgcgtg | gcctggatcc | agccggagca | gaaggggccg | 480 |
| gccaatgccc | tgtggatgca | gatctgggag | acctcgcagg | gcgtgggccg | tggcggctcc | 540 |
| ggcttcgcgt | cctacttctg | cctcaactcg | ccggcgctgg | acacggcggc | cgcgcccggg | 600 |
| gcggcggggc | gcgcagcacc | agcagcagga | ggcccggggc | cggcgcccgc | cgcctcgtcc | 660 |
| ccgccgccgg | cgcccggccc | cgccgcgctg | ccccccgcgc | tgcttaccgc | gctagggccc | 720 |
| gcggcggaca | gcgcaagacg | cttgcacaag | tccccgtcgc | tgtcgtcgtc | gtcgtcctcg | 780 |
| tcgtcgtcca | acgccgagtc | gggcaccgag | agtcccggct | gctcgtcgtc | gtcctccagc | 840 |
| agcacctcgc | tcggccgcgc | cggcagcggc | cgcaccttct | tcagcttcgc | cgacggtgct | 900 |
| gcccacgcac | acccgggccc | acgcggctcc | acgcccgccg | gctcgccgcc | gcagcaccag | 960 |
| ttccacccgg | gtcggcggaa | acgcgagaac | aaggccagca | cgtatggcct | caactacctg | 1020 |
| ctgtcgggca | gccgcgcggc | cacgctgagc | ggaggggggcg | gccccggggc | ccaggcggcg | 1080 |
| cggcccggca | cgccgtggaa | gagccgcgcg | tacagcccgg | gcatccaggg | gtgagtgcgc | 1140 |
| ccgagccgcg | gggctgccag | cggcgcgggc | actttaaaaa | ctccgttgga | tcgagatcca | 1200 |
| ccaggcaggg | gggattgaca | gttcgggatg | gaggcctagg | gctagactag | aaagtggttc | 1260 |
| ctttctttcc | tctgctccag | ggcagggaag | caagggctgg | ctgtcagagt | gggaagcgtt | 1320 |
| tacgcgtgtt | ctttcctgta | ggctaaatcc | tgtatcttag | tgtagtgagg | ttgaatgtaa | 1380 |
| aaaattttg | ttccctttt | ttgagacagt | aggttttgg | tattggtgca | gtttagccat | 1440 |
| caagtgaggt | ttagaagtgg | agtcttgtgt | gtgttgaggt | tacctcgtac | gttttaattt | 1500 |
| tgggcagacg | ttcacagaaa | gaccgtcacc | tggggtttct | gaaaaccacc | taatagtact | 1560 |
| caggtttttt | tcctgtgaac | tcacaggaag | gtgttttcat | ttaaaaattt | ttccataagg | 1620 |
| ctcagaggac | cttagcggtt | taatgtcccc | aatgacagca | aggtgggggt | gttggtctgg | 1680 |
| aattgcccca | ggtgagactt | ttctagtatg | aagctcttca | ttcaacctat | tggttgaatt | 1740 |
| tctgaacatc | tagaaacaaa | atagtggttg | tgtagtctca | agactggtga | gcttgatttg | 1800 |
| cctcagttcc | tgccgctctt | aaagggcgtc | taacctcccc | ccctcccct | cactccaggg | 1860 |
| agcgacatcc | ccagttcaag | tccacccggg | tggttgctag | gccctgggac | tccttttgagg | 1920 |
| taacttctta | gggggctgtt | tgcggtttga | ggtctgtggg | gaacacggat | actctttaag | 1980 |
| gggttgggggg | tgttacatag | aaacagttgt | ccctctgca | acttgtttca | cctgccttgg | 2040 |
| atctttgggt | cgggattctc | cagcatgcac | tacaaatcca | ggaggagcct | ggtttcttct | 2100 |

```
gccagttccc ccgcagtgct tgcttgtaga actttgtgag acaggtgtgg ccgtggacct    2160
acgggaggtt tctggattgt tacataactg taatggacat ggtgtctgcc gggagacgga    2220
tcctagcctc tgacagagtt ccacttgggt acttaggcat cagcagcatg atctgcccct    2280
cggtgagagt tgtgtccctt gatgtggtct ctctggtggt ctgtaaagct ggtcagcctc    2340
tgtgtgttct tctgtggcgt tttgttagta tgtgtgcctc tgtgggctag gtgtgctttt    2400
agagtctagc atgggtgcag ttggcatggg tggcatgtat ttctattgat cccacaagca    2460
tggtcccttc tttaaatacc ctcccttcct ggtacagatg aacattgcca cctgggtatt    2520
catacttggc tcctgtcacc ctactcccaa gtctgtagtt cttgattagc cgctgtcccc    2580
caagtctggg tctctcttcc tatgtcaagc acattgtaac cactctctgg aggaggatgc    2640
tcaggcagtc caagactggg gtcttctgtg cactgtggcc tagcctgtgt ccttggtcag    2700
cagggtcagt gggatgaggt tctaccagcc cccaactttc acgagagcct ccattacttc    2760
ccccacccac ccaagagaga tgaaggcctg actcggtggt gcttgggctc tgccactctt    2820
cttgcctgag ccctgcctca gagccccact tgctcacttt agggttcaaa cccagctag    2880
agtttagcgt tggatgctgc ctggtgactc ttccttttct gtctaggtgg catgtgttga    2940
atggtgactc ctggaggagg agcttgctaa ctggcttggc atgtgtgcgt gagagagtgc    3000
ctcctgagag ggtaccttgt ctgtttccta ctgtgactga cctctcgagg gggtgggaag    3060
gaattagtga acgggcacca gtagagctga gccctatatg ttaacagtaa aggtggctcc    3120
aactattgct ggttgctctc acgtgagctg atcttggatg gcaaaaaag gacctgtctg    3180
aagctagtct tgtgctgtgt ggggccagca ccaagcctgg cttagcaaga gacacaagta    3240
aggttaagtg ttggcttgag cgtggcccag ttaacagtga gggggcctgt tatgttagtg    3300
agaggctgct gagcttgctt tctgctgctg gggacgtgcc tttgggggac tccgcagacc    3360
tccagaaagg gtgagtggtt ttctggtggg gtgagagtct gggtctctgc ccaggtggac    3420
acggggcact tgcaccttc agctctctgg gtggagtttg cccttggaaa ctgctagact    3480
gctttcgatc ccgggtagga tgaagaaagc ggacagggct tagtgtaatg agcttgggga    3540
ggagagaagg tgagccctgc tatgggagct cccctgagcc cagctctgaa accttccttg    3600
ggacatggca ggcataatgt cagatgtgcc tctgcatgag tttcttgctt aggatggagg    3660
caggcatggg caggctctct gggtcctccc tcccccctt aactaactca ctgtgccttc    3720
tgagtcctta actctgaccc acagtgtgat tccttagtcc tgggcagtct cagtggcttt    3780
agaagctgct ttgggttaaa agtaaagagc attccctgg aagtgaggat tggagtgtgg    3840
tcctgacctc cctggtgtct tgcaggagtg cagatggaca ggggaggccc cagcccttgc    3900
atacacctgc agccccatga cttgagttga ctctgaaggt tgtgtcctcc caggtgtgcc    3960
tacagtgggc agcttctctg caactctctt caccatagtt agtctttgaa tgtgtcctgt    4020
gcccttggcg acaggagtcc cgttgtccgt ctgaagccgg agaagcctcc agtgtcagca    4080
gttacagctt ggctgtgact gatggtgctc tcagggctgt ggggtgattc cctcccagct    4140
ccatgactgc tcttttgct gttctcctgt gagggagtca gagctcggtg gagcagccag    4200
gttccctctc ctgcagcaca gctcctggct gttctgacag aagcagatgg cctttcctca    4260
gaaggctcca ttgggaaggc acaggtgagg gcccagtggg ttgtgctgtg aacacaagt    4320
gtagtcactg ctatctccct ccctgtcttc cagtgagcat caggggatgc acgggaggga    4380
agagggaatc agggaagctg taaacccgc ctgtgcaggt gacagtggca taagaggttt    4440
cttttcacaga gatgctcaag gttgaagagg gagatgagaa cagtatacta cacagagctt    4500
```

-continued

```
gttgtcatat ggacagtgtt acctcctgtg caaccttctc caactaaaca gcaccactct   4560
cttgtcatgg ccagtctcca tacagaactg gaaaggctag tgagatgctg tcccgggcag   4620
ctgaggggag tcccggagaa ctgctgcacc acggcttgct caggatggag agctgatgct   4680
ggggaaggct gcccaggagg acaaggccag tcttctctta gactagaata ttaagcaggc   4740
tggcgcagtc ctttggaaaa gaggccctag ggttggggag gccttgggtt tggttcctaa   4800
caccaaggag aaaagcaata gaaacaaaga aacaaacaac cataaaaata aaaatggagt   4860
ccctgagtaa ttttgaagaa aaaccatcta atgctcatgc tgtgtaagtt aaggagggcg   4920
ggcatccggg tgtcctggcg tctgggtgtc ctggcgtcct gtggctggga tatttggatg   4980
aagaagcagg gctgcttccc ccttagaagc aacacacctg tggcttaaaa gtaattttta   5040
agtaaaaaaa ttttttttaga ttttttttca tactgttatt tacatatttg attcttgtgt   5100
atgtgcttat gtgagtttat gtgcatcaca tttacaaatg tctgcggtcg ccagaagagg   5160
gcattggatt cctctggacg tgtaatgaca ggcagctgtg ggcagccaga tgtgggtgct   5220
gggaacaatc tggattctct gcacgtgctc ccaactgctg gacagcccat ctagctcttt   5280
aagtagacat ttaaaggaa aaaagaaaa tatgacttta agacttgtgc ttcaaagtct    5340
tggttatttt tgatgacaga tgtgagcttt tgggcatcac cttgaaagat ttcataccaa   5400
gtatcctttg ggagcaggga taccagtcag tgcaccatgg acagaaagga tgctgtgcct   5460
tggtaaggtg gtatacctaa gaaagtaaac ccggatgctc acattcagag acatggtttt   5520
gatgatgcag acagaactca agctgcaggg gtgcccgccc tttccaggaa ccatctctag   5580
tgcttgctat ggctggtatt gctgtgatga ggctaggcca gaggctctgc ccagcctgtc   5640
agggttgctt taaccttaaa taaagttgga tggtatgcta accccataag gctgcccagg   5700
agagtgtggc ttacagcaaa gtgaagttgg tgatgccctc tgcatgcctc tgagtggggc   5760
agccatgtcg tcttcccatt tggcatgtgc acggactcag acagcattga actcttgata   5820
cgtctccatt gttcactgtt tctgtggtca ggtagcaaag tccagtgcac taggcttgga   5880
ccggttatct catcagtcac atccttccgg tcacttgagg atggcttggg tgagttctct   5940
attcagcagg gcagagggct gagtgtcagc tgcttgttgt cacatctgtc tccagagccg   6000
gctcataagc acattcctgt agtttcagca cttggggaga ctcctcagag ggctcacatg   6060
attgcatagg ccaattcgga tggtctgtct tcaggccatg caatgcagtg tggtctatag   6120
actattccat cagaaccaca agtttgggca tgggttgctg tctgccacac actggcattg   6180
tttagtagga agacagcatt gatgtgggaa gaggaggcca tggttgtctt gtccaacact   6240
cttgtcctct gcttggacat cagcttatca caagtgactc tttttatattg ccagtcccgt   6300 cttctggctt gattgtcacc cctgaagctg ggctaattga tgacaagaac agtgtgcact   6360
tttctctgcc tctcacagat gaaccattct ttagtgtgcc atttaacaaa gtctatacaa   6420
gagccacgtg attgcacaaa aactgtttca gccatgaggg cacctgcatt catcagattg   6480
tcaccgtggc ccatttaagt tgccacttga taatgacaaa acagcccatg gttgctctgt   6540
gtaagatgtg gcccacaccg gatctgcatg ctccgttgat ggggatggtg gtttgcccat   6600
ggcctcagct gcagaacatg tgcctctccc tggaggagca aaaagacccc ccacaattct   6660
tgccttgtct cttcctgagc tcccatctga atctttagtt tctacggagt tagcttttac   6720
tgtcccctgc ctacctacac tcccagaacc aagacgtgc atactaagaa agatgcaaaa    6780
gacaaatagg ttttgtatgc aaagtaaac tttagttttt tgtcttaggc attttaacat   6840
```

```
agattgtgag ctttgcagtg attttttgtt gttgttgttg ttgttgtttt gtacatgcaa    6900
aacagtatgt tagtttctct ctgagtgtag ctaagacccc tagtgcagga tgaaaacatt    6960
aacatacaca caggatgaaa acatgtaga gaagtctcat gccacatctg aaaggtattc    7020
ctatttgctg gcatccttt cttttttaaat actggataac aaccaaaaag tcagagaacc    7080
tctgattgga ccacctgccg agagtctctg tcatctgtgt tgcctgttgg cctcccgcat    7140
gagctggctg ggctgtggca agacttctgc acaggcttat cttttcccag atgacaggcc    7200
caactagatg ggatgtcccg gacatccttg agtcagtggc ttgtgacact catttgcctt    7260
ttagaaaatt ttttatttta tttatttaca ttccaaatgt tatcccctc ctgttagctc    7320 cagatttctt tgccccatcc cctcttccct ttgcctctga gcaggtgctc tcccccaaac    7380
ctcacctctt accccccccc cccagcatcc cccttccctg aggcatcaag tctttacaga    7440
atttaggcac atcctctccc actgaggcca gacagggcag tcctctgcta catatgtgct    7500
gggggccaca gagaagccca tgtttgctct ttggttggta gcttagtctc tgggagctat    7560
gtggagtctg ggttagttga tactgttggt cttcctatgg ggttgctgct ttgcacaact    7620
ctagcttttc ctggtgtttg ttttctgaga tacagcagtg ggcatgattg ggacacagag    7680
tcaaattagt cccttttttt ctttttttt aaacctcatt tttttttctca tattgggaag    7740 catgcacttg gtttggagtt gactttgtgc aactttatgt tttacttgaa atagtttaac    7800
ttggtaagtt actgaaataa attgaaactc aacttcatta gcccagccac atacttgggg    7860
gtctggttct ggctggtttt acctgtgctc taactcccac acctcagttt ccccacctga    7920
gaagtagggc ctgtgacata actcagtcag tttctgagct ggtcagcatg tgtgagaaag    7980
gctactcctt ctcccttcc tcctctcagg aaatggaaac caaaaatgag cttcttgttg    8040
ccaacaggaa agccttcctc ttcttccttt tcttaaatga cgaagctaca gactcaaagc    8100
tccacatctt agagagggga gagggactca gactcagctg ggagttctgg aatcccctg    8160 cccctagtc cttgtatttt aaatgcagac gacactttag cccattgtca cagcgtgtgt    8220
gtgtgtgtgt gtgtgtgtgt gtgtgtgtgt gtgtgtgtac accgtgtgcc tgctgtgctg    8280
cagctggagt taggttgggt tcagttctta gcctctgctc cgaggggagg tttgagtggc    8340
cgtggatgac gatgacccctt actctgagtt ctttgccact tcctacacag agttagtggg    8400
tttagaggga agagagcagt gtgctgggga gccacgacag tgcagggtgg cacagtcctg    8460
tgcagaggag gagatgcagt gtctgtcctg agtagtggcc acacttcatg tgtcctagct    8520
agcacttgga gggtggccag tgcaggtgaa aagctaagtt gaactttaat gtgttgactt    8580
gttttgtggc attgggaatc aagctgagct ctttgagcat gccaggcgga ccgtctacca    8640
gtgaggaccc tcccgagctc ttacttaatt ttagttaaaa tttaaatggc cctgtgtttg    8700
aacagtgctg actttgtgca actttatgtt ttacttgaaa tagtttaact tggtaagtta    8760
ctgaaataaa ttgaaactca actgcagtaa aaagagtgtt gcttagtaag ttgctatgga    8820
gaaagctcta gagttcatgt ttctgagttt ccaatgcaag tcctttatga aaggctgata    8880
tctttgtgcc ggaggcagca gggaacgggg cagtgcagcc cagagcattc tgaggagggg    8940
agcatttctg gtcagcatgc aggagcgagc gagtaggcag gcaggctgct ggtggtgtgg    9000
cgaatgggtt gccttcaggt ctctgcaggt gtcacagctt cccgccacat ctcctagcag    9060
ctctgtgctc aggattcctg gaggctagtg agccctgctc cactgtactc tttgacgtcc    9120
tggttcaaag ccacacagag gcaatatttc ttgtgtttta caggcacaaa cccagtctag    9180
attagctaaa atagtctgac caagaggtct gcacttgtgc atattgctgt tgctgaggga    9240
```

```
aatagctacc acagactgag gatttagcac agcactaggc agagccaaag gtaagttcat   9300
gcggagcctt tcctaatgag aacaggcaaa tacagagcct gcctgtgctg tgcttcctct   9360
gtgcagccgc gtcctgcaga ggggcgcagg gagccctttg gggtggatct ggcttcctgg   9420
gctgtttaga ggttgaattt tgggagaggt gaagaagctg tgagttctga catgtcctgg   9480
aagggccagg cttccctgca gtcccaaaac agctcgtttg aacgagatga gagcaatttt   9540
caggagatgt tctgattttg tccaagagtc acctaggaag tgatagaact aggctcagat   9600
gcaggcttct tgcctggcaa gtccatgcac ttgaccagtg ctttccagag agtgagaggg   9660
aacacgagtt gagagtcaga agcatgactt ggtgaaatgg cagagacaag ttgaagcata   9720
agaaagagta ctttggtcac aggcatcttc tctcaattga agtaacattt tagaaagtga   9780
agagcagcta tgatatggta tccaaaagta aagagagcac ttggcatgat aaagaaacaa   9840
aggaattcgg aatataacta ctagttatct tgtgaatgag tcatgagaca ctagtgtggg   9900
catgaaggaa aggtcactgt gttggcatga cactctgaac tacagggtgg gctactgaac   9960
agtttgaagc ttgtgggggg ctgcttgggg ctggaagaaa gctcactgtg catgagactt  10020
tccttagcag tgagctctgc ctctttcccc ttttccccac ctggctgtag ccggctgtac  10080
tagctagcta gagccttact ggctccactg acccacacct gggccaggcc tctcttttt   10140 atccctttat acagtgtttc cggctgccct ccaggatgct ccaggaggta tggcactgag  10200
agaaacagtc cacccacaca ccacaacaca gcacagggct gtcagtggag ctcaggcctc  10260
gtgattccct agctcactca ttacctagga actaggtaga gggacttgcc aaagaggtga  10320
ggttggtagg agcaatgctt gtgaattcca ggctctgact cctctggaga gaggccagat  10380
gctgccagaa ttctttgctt ctgaggacag gtctttgaac atcccagagg aatgtgagtg  10440
acacttctca ctaatctagc agcagcagga cagggagctc tgtcctactt gagagggct   10500 cttctccttt ctgtaagaca gtttataggt gactcttcag agcattgatg cctatcgttt  10560
attcactgtt tcttacataa gggtaccccc tgctgatgta aacttaaggc tgttctgtct  10620
cagcctccca gcttccaaga ttacaaacgt gagccatcat ttctggcacc aattctaaaa  10680
tactgatgaa tcggtaaaac tggctcatat ttttaaaagt ggaagcttta aagtatctca  10740
gtcctatcac ccagaaatcg ccaggataat tagatgacca cagctgcaga tggtattctc  10800
caagatcctg gagatagtac ttggagccac caacagaaaa actcactaga atcatcttca  10860
tgaaaactct agtaaattat ttattttgct tcagtaagaa acgtgcagtt tcaaatagaa  10920
acccgggctc ctgagagcga gtgctgtggc tgagaatgta aactgacaaa gcccgagtgc  10980
agaaggtcgt gctaacaagg caccaaccgg tttgctctca gtttatgggc tgagaagtcc  11040
gcccttctgc atcttccctc ctgactgaac atgaggcgtt gctgtgagtt tgctattttg  11100
ttgtgtggtt tcattcacta gtatttgttg attgagccct tactgagcca gtgtcgcagg  11160
cggtgttttc aggaggttca ttgctggccg tgctgctcct ctgtgctgtc ctgtgctctc  11220
agtagctctg cagggccagc cctgcatccc tgggctctgg gttgctctgc tctgaccctg  11280
tgtgtgtagt ttttgcctga gatgtggttt ggttcttcat actgcatagt ggctgctgcc  11340
agtgtctttt tatgaaggga ctggatagat gcattttttg tagagtggat aagggctcta  11400
ctccctgaag cctgttgtgg ccctgtaggg ttgcttggct ttcttctccc atggcagaac  11460
agtgccacca ccacctgtcc tccgagacag gaccttgtct cctctggtct gaagattgat  11520
actaattgct gacctgtcta gacatctctg tctaagctgg cctctttgtg aggcagactt  11580
```

```
ttctggacct cagatgcttg tgcactgcag gctgaagttg gcctgcagtc tagggggagg    11640
ctctgtcagg tccttgctcc tgtgttgctg gctttgcctt cctggggtga caagtgtctg    11700
aatgtctgtc catctttgga tgctgcttgc cttggctctg tcactgacac ccagcagctt    11760
cttcctgact cctgactttt ctcaacatta gggacacgct ctgattttt ttctgtggaa     11820 ctggcagtga ggtagctttc tcttctgggt tcactgtttt tgtgatacac tgtgtccctt    11880
atgccatccc tcttactcta cctgtgcaca gcatatttcc cccctgctca ttttaatact    11940
caataagtct taatactgac ttgctgtgga tattttccta tggaagcagc cgccacccc     12000 aatccatctg cagatctgaa agtctgcctg ttccatggga tgactattct ctggccttct    12060
ggtaccagat tgtgggcagc agagattcag gctgagctag ggcattacct tgttgggacc    12120
tggactctgc tttgagttgt ttcagctttc cagggtcagt gctcttggct tacccctggg    12180
cttcctagaa ggccttctgg cctcttgttt acagtcagcc cctggggaca ggagtggccc    12240
tgggctccag tgctcagtgc tgctgtgtag ggatgctgcc ttctctccag ggtttccttg    12300
cctgggggcc tgctgtttca atccagctgc tgctgctgct tccttctca gccttagcac     12360 cagctccttg gaaggcagtc cctgacaact gtcctgtgcc acatgaaacc agtttggatt    12420
tcttcactgt ttattcattt cccctagccc cagggaggac ccttctagtg tgagcaaggg    12480
cctcagtttc tcctgtctgg ctcactggtc tgcagaacga gccacacagg agtaaactac    12540
tggagtatgc aggtcacttc tgctttctct actggtgtac tgagagaaac ctttgcacct    12600
gttgggttat tttctctccc tctgtcttaa ttcctgcctt ttctttctat atttttggta    12660
aatttccact gttagggtct ccttttctc ataaggtcct ttttgtcatc ttgagtgagg     12720
gcagaaacta ctgccctggt cccagttttcc gtatgtgggg ctgtgtgcag agtggttgac   12780
agtggtacca ggactctact cagtggccag tgtcacacag gagaggccca agcacctgtc    12840
acatgcaggt gcagccgtga tgcttccttc cagtctgaat gcagcagcag agctctctgc    12900
atagtgcctg ggcttgtgtc tctaaggagg ctgagtggct ggtctgctga gaggaggga     12960 gtggctgttc agggactaag tcattgagaa tcacacaccc tccatgtgga agggtttcct    13020
aagcaaggag gtatttctga gcaagatggg tgtctgtgtc tgagtttgtt gctcatggca    13080
tgaaggggat ctgggatgtg tcccttatat ccagtgcaaa gtggctcagt cctgctctct    13140
gctgcatttc agtatgctca gtgcctaagt actggcactg cttcatctgg tccagcgctt    13200
accagacttc cctctataga gaccaagggg ctgtagtagg tagccatgtc agaggcattg    13260
ctagcactgc ggcaggaagt gcgtactcta gttaacgctt tgttcatggc ctacctgctg    13320
ttgagaagtg atgctcttgc tttgcctgaa agtggcttct cggtgccctt ggggcttgct    13380
ctgcctgggg catagtcttg agtcttggag catgcacata gagcctctta gaaccccctcc   13440 ctcgttaggc tctggaaggc tcttagacat ctatctgttc agagtccaga ttggtaatgt    13500
tgatcagaaa gttgaggagc cctcccttt tttttttttt ttttggtttt ttcgagacag     13560
ggtttctctg tatggccctg gctgtcctgg aactcactct gtagaccagg ctggcctcga    13620
attcagaaat cgcctgcctc tgcctcccaa gtgctgggat taaaggcatg cgccaccacg    13680
ctcggctcga gccctccctc tcttatcttg tgtattaacc tgttgtaatt agcttttact    13740
gtaaacttga ccagactggt cagtgggctt gtctgtggag acttggcttc ttgttaatta    13800
tgtgagaggg accccactct gtacaagaca aacactgtta tctgggcagg tggtcctggg    13860
ctatatgaga agtctaccta agcgtgagcc tcagtgaacc agcaagcacc attccctgc     13920 ttcaggtctg ctgagttctt gctgttggat gtccttcaat gatagactgc aacctggaga    13980
```

```
ggtgcaggcc acatagtgat gggctgcgac ctagaagtat agccacataa acccctttct   14040 cccccaggctg cttttgatga gggttttatc acagcaacac cattttaacc ctagcctctc   14100
ctgactgccc agggagtagc tgctgcacag agatcttcct tctctcttca gctttctcag   14160
gccaagcttg tcctatgcgg tagagcagtc atgtgcaccc cactccacct tccttcagag   14220
ccgtgctctc tataccattt agagccctgt gtagaagata ggtaccagaa agattcttgt   14280
agctattcag aacatctagt gggagtcccc taaacaccca taggctccgt tccagcctac   14340
agccttccac ttattttgag actgcagggt tttcttgttt tttgtgtttt ttttgttttt   14400
tgtttttttt taaaaagcac gtttgatagt ctgaggcaag gttttctaat ttgttcagat   14460
actagttacc ttgtgacata attaaataaa agtgatttat aattagttca ttaaccatgc   14520
catttaatga tgctttaaag aagattaccc gccctcagag ttgtggaagc agctcactta   14580
ttcttctata ggtacttgtg cttgccttgc tcagcagctc attccttctg atgaataaag   14640
aggcccctac agctcagcac agtgggtcag ttgtacttgt gtcaaagaaa gctgcaagac   14700
cctcctgtcc tggctgctct gtgtatgcta cttggtccta ctaacctgct gctgttagct   14760
ttaactgtta gcttggcatg tgtgtgtgtg tggggggggg ggagaattgt tttatttttct   14820 ggcaaaaatg gttcctgaag tgaagggttt tggtctcaga aacttactga ttttaaagtt   14880
ttttgagact gggtgtagtg ggccacacct ttaacgctag cactagggag gcaaaggcag   14940
gtgcatctat gtgagttcaa gtccagcctg gccagcatag caagtttcag gtcagcacag   15000
ctatggagta agatcatgtc tgaaagcagc aacagtaacc actgaagaag ttggtagagg   15060
ggaaagaata acttaacagc tgaggaactg aggaggtttc agagttttga tcaacagtct   15120
ggaaagggaa atcagtgcct gaagtcaatg caggtcctag catcactttc cagtagaagt   15180
gggaactgat gggatgaatg ggcagctctg cgggtaaagg gggtgagggt aacagttaca   15240
gagccctagg tctgtgggca gcagagaagc cacgtgctag cagctcacag ttggtgaatt   15300
acatgctgtg gcaacaccca gggagggcca ctggttcttc ctgtgcgtgc gttctcactt   15360
gtgcgcgtcc tccctctccc cctctccccc cttttttagtt tatgtatatg agtgttttgc   15420
ctgcttgtgt ctgtgcacca gctgagatcc tggtgctctg gggaggttgg aaaaatatgt   15480
tgggtctcct ggaattggag tacaaatggt taggagcctc catgtgggtg ctaggagcag   15540
aacctgggtc ctctgaactc ctgaaccatg tctctagcac cagacctctt tttctttgga   15600
taaaggtgcg tcatgaagcc taatgtcaca tttgggtgtt tctctgcctg ttgttgtgtg   15660
gttcttgtgc ctccgtcatg cttgctgcag gccaaggctc tgtttctgct ctgtttctgc   15720
tctgtttcct tgtgctgatg cagtgcagtt gctggctgag gttgaaaaca gcaccttcca   15780
acagtttaca gcttgtgctt gtttcgagtg gggatcccaa gcctgaaggt ctgcgatctt   15840
gggagtagag aaggagccag ctttgcccag gtaggaactg gaaggaatag gaaccaggaa   15900
cctaaggtcg gggctgcact agccagcttg gatttgcttg gattacctgg gacagcactt   15960
cggaagtgaa aaccattctc gcaggatgac catctctttc cttggtagct agatttggta   16020
tggagagagt tggtttggct taatagctgg gatccttat tcttaagact agcccagaga   16080
tccaagctcc atgtccctga cttgggcatt aaagacagaa actgatgaa tatacaaaaa   16140 ataggagaaa atctgtcgta ttttcctctg gtgttctgag atggtctctt gtggtccagg   16200
ctggcaccaa ctccccattc tcatgcctcc acctccaag tgctgggtta tagacatgga   16260
ctgccacact cctcctgcag ttggagactt ataggcccca gggtatgaaa gagtagctct   16320
```

```
gacacagtga gcatgcaggc ctctagcacc ctctttgcct gcttccttca tctgccccta   16380
ttggaggctc caggatctag gaaagtatag gagtagggct ccctccaggc ttccaggcca   16440
cctgaagcaa gaggtttctc agcattgtcc cttacctggc aggtacctta cctgcacagg   16500
tgtggctttt agtgctaaca gcaggcctag tggacagcag cagagtaatt tttgactccc   16560
acaggctttt gcgtgtgccc agacaggagg tggtgctctg ctacctcttc ccatggctgc   16620
taacagctat tgtcaatcat caagctgcct gtctttgctg actacagttt ggtggtgacc   16680 ctgcttttg gggagggcca ataggaggct tggcttttt tctaaccccc tcatctcaaa     16740
ggcttaaagg caattcctgt gcagtgtcct gttctgagaa cacaaagcac attctttcct   16800
gatttttccc cccagatcag tttgtaatat ttatatcccg tttgtaatga cttcagaacg   16860
atgcgtgcct tgctgatagg accacagcac agcactggat ttaggacacc tgtgtttgac   16920
tgcgcaccac ttcttactct gggcacttac aggccatggc cttactcctg gaggaatgcc   16980
agccacttcc ttcttggccc caagtgagtg atcagtatga ttgcacactg tgctttactg   17040
atggcagggg ttttgctgtg gatcagagga ccctttccag ctttcttctc tggagtatca   17100
gggaaggccc taagggtaaa gtgcacctga gtgaggaagc ccagcatgag acccgaggag   17160
cgggtgtgtg tgtgtgtgtg tgtgtgtgtg tgtgtgtgtg tgtgtgtgtg tgtgtgtgtg   17220
agactgtctc atgctgttgg tatttcagat agagcttgaa agcttggcca tatgtactgc   17280
tttgcaagtg aagaccttga gtcatgtttt ggctattgga cctctctgtc tacaggatgt   17340
ttgagtgtgg ctagtttgag ctatgcatga gattttgta agctagcctc agtgttctgt    17400
tgtgaccggg ccagttattt aattttctt tttgtctttg aaacctgctg ctctgaggct    17460
ttaaactctg ctgttctcat cttgagctcc tccctctgg acctagtgga cagccagcag    17520
gacctcctgt ggatttgtat gtcttttcctg tctcaggctg tgtgttacct atcatgaggt   17580
atgcagtgag ctgcctgtgt gactcaggat gtcttggcta gggcttgaac cttggctgg    17640 gtactgtgct gcactgcagt tcattgaaaa atgtctgtcg tgagtgtagc tttccgactg   17700
gcattgtttt gaatgcatct ttaaaggtta gttataaata cattaatgct tgggactgac   17760
aagaattcat ctgtggaact ataccatcct gtgagatttt atttcattat atatgttcac   17820
agaaaagaaa cagggagggt agggtgggct ggaaagaccc tcagcaatta agagcactgc   17880
gtgtgctttc agaggacttg gggttggttc ccagtactca cgtgggaggg acctctctac   17940
tgtgcataac tggttccaag ggatctgata ccctcttatg gcctctgagg gcactctgtg   18000
tgcaaatggt atgcagacat acgtgcaggc aaaactccca tacacttaca gtagatacta   18060
ataaataagc tggacttaaa ttttcatttt atgtgtatga atatttggta tatatcagtg   18120
taatgtgtgt gctatgcctt cagaatccag aagagggcat tagatccttt agaactagtc   18180
ttacaaaggc ttttgagcca cattatggct gctgggaatt gaacctgggt cctctggaag   18240
accccagagg agcaagtact tctaataaca gagacatcac tccagtccca gaagctgggt   18300
tctgagtggc tccaatataa tttgaactat agcaaaaggt agaattctgt ttaattgtaa   18360
ctctccttct tcttcttctt cttcttcttc ttcttcttct tcttcttctt cttcttcttc   18420
ttcttcttct tctcctcctc ctcctcctcc tcctcctcct cctcctcctc ctcctcctcc   18480
tcctcctcct cttcttcctt cttcttcttc tttcttcttc tttcttcttc ttcttctttt   18540 cttttttttgg tttttttgaga cagggtttct ctgtatagcc ctggctgtcc tggaactcac   18600
tttgtagacc aggcaggcct caaactcaga aatccgcctg cctctgcctt ccaagtgctg   18660
ggattaaagg catgcgccac cacgcccagc ttcctttttc tcttttttcc acagacttca   18720
```

```
tgaggagata atcgactttt ataacttcat gtccccttgt cctgaagaag cagccatgag    18780
aagggaggtg gtgaaacgga tcgaaactgt ggtgaaagac ctctggccca cagctgatgt    18840
gagtatcttg ttcacgtacc agtccatgag gttgtgtcag ctttatccac atgtgcccac    18900
gcttcctatt cccacagtag agcagctccc caggcctagt cccgggagca tcgcctggga    18960
gggaacggct tagacgagca ctctcccctc tactgcgtct agccctggtg tagtccagcc    19020
tctggttagc ctgtgaaacc cataaatagg aatatttata ttcttatggt ccttcattcc    19080
cctcctcttt cattcttgtt taaaaattgc gttaaggtta gaaatctccc tcctgctcca    19140
cccacacttg cagtcactgc agttcacagc atggaacatg tttgcgtcat tagaaattgc    19200
aagtggcagc agagcatggt ggcacatgcc tttcatccca gccctcaggc agcaaaggct    19260
ggaagtttga ggctcaagtg ggctacgtag ggaaactctg tcttaaaaca taacagaata    19320
caagtgttcc tggtgtagca ctcacatgaa tgagtgtgtg tctgtggaaa tgaggtactt    19380
gcctatttgt agtccttggt gcaggcagcc tgtggtatgt cagctgacca gggagctaac    19440
cgcctggcct ggattttgat gtaaataaat gtacaaagag ttttctagtt tgttgcacca    19500
tttcatctgc ttcttcccct aatgtccaag ctggttttgt ttgtcctcgt gtttttcaag    19560
gcatggtggg ggtctgctgg cttgaactct gggacttctc tttcaggtgc agatatttgg    19620
cagctttagt acaggcctct atcttccaac aaggtgagtg tcaaggctga cggcacactt    19680
gggtgttggc ttatggagtg gcagtgtctt tgcttctaag gcttgaatag ccagctaagg    19740
ggaaggattg tggaacacag gggaaatagg cagaaagttg catttattag tttagtatta    19800
aggcaggaga ttgcttgctt ggcattttc ttcttgcatt taatttcttt cttttttttt    19860
gggggggggt atatttggat aatagtttat tggttaaaag aatatatttc cacaaagatt    19920
tttttgattt gtttacagag ctacccatat tttatagaat acctgaagaa gctggaaagc    19980
tgttcagatt tcatgtgcta aaaaagaat attcttaatt aaattgtaag aaaaacacta    20040
aaatacacag gacaaataag cctcaagaga aaatatggct gaacaaaaat aatcagcaac    20100
tacatcactt tataacacag gaattataat gaaatgaagt tctctctgga cgactccagc    20160
tatacatgaa atgaaaagta ttttcaacat acatccaatt tccaaagtac aacataatga    20220
aacatttaaa acttcagtgt attttgatta gttcttaaag ccccttcccc caaacatttt    20280
ggcaccaaac aaacttttgc tacaaatggg gattttttc ctttgagatt tcctgcatga    20340
ccagtgttga taaataagg aaaggggaaa ggctgattga caagaacagc tacataaact    20400
attagaagac cattcctaat cgagaaatga attggtacta accactgtgt gcatacactt    20460
agatcaatgc ctgtcagagc cttacaacaa cgaatggcag tcttaatcaa cacagaggga    20520 tcttttctg ggtttggtcc atccagcgaa ggagaccagt ggcctccaat ggccatggct    20580
tcatccttgc ctttcattcc cactagaaac taattcaaac caaagaatca tttatatata    20640
tataacacag cccatcaaat tataatagat acttagaaaa ttaggaaggt acaaaccttc    20700
ccaatactac ttttactacc tctgatatct gtcagtcaag gacgagttca gttcagcatt    20760
taatttctta agcacagaaa tgttgggtgt cagacagaaa atggatggga actgccttgg    20820
tctcctgctg ccatagaaca ggaccccggg ttggctgaac tgtaaactgt agaagcttcg    20880
ttagctctca gttctgggga ccgagaagtc ttaagattca gaggcttatc tgggtctaac    20940
tcaccccgta gcagaggtct tgatccattt agaaaacatt gccccagagc ctactcacct    21000
caggaaggag aaaggcctga cctgttggtt ggggggggcca catttcagtg ggagtctttg    21060
```

```
gggttttgat agtgaataga aaatgttagc gaaccttcaa gcacacttct gttagaacag    21120
tattttatga agctctttat gtagaagtgt cagatttaca tcctaaaatt gtcttctggg    21180
ttcatattgt catatatata atgtataggt ggttttgtt gtacatgctg gttagcattt    21240
ggaactagcc tgctagtata gcatttggct gtgatgtcag gacttaggaa ctgacatggg    21300
caaaggctct ggaagccaag tagattaaaa gtcttcaggg atctccagac cttgaagcaa    21360
gagccagtga cgatagaata gactgctgaa aacagtttat cctgtcacct gttggttcct    21420
gggactctga ggcccttttc actctggctt tatatactta gatgactcaa gagctgcatt    21480
cagggctcat ggcttaggta cttagggggac cttgttgata agaggcaaca tgctgtggtg    21540
ctggccttcc catgggaggc cacctggtga ggtttgttgt gactgacaca gtttctcttc    21600
tgtccagtga catagacctg gttgtctttg gaaagtggga acgccctcca ttacagttgt    21660
tggaacaagc cctccggaag cacaacgtgg ctgagccgtg ctccatcaaa gttcttgaca    21720
aagctacagt gagtattggg ggacagatac cttcacctga agtccccaca tggggtcagt    21780
gtcctctggt tttcttacag tggttactgg ttatattttg attgtcctct tgtggtataa    21840
ccataccagt gaccatcttc atgatttacc agctgagaac ctgtttggtg ataagtggat    21900
ttgttctcat tgtgagatct tagattttca ctcttggcct taaaagactt gtgtctgtct    21960
gtgtctgtag agtaaagcaa ggcagaggat cactacggag gaactagcac tccacctgct    22020
gttgtcctgg tttgcagctt agagatctgt gtggcagtgg tgtgtgtgtg tgtgtgtgtg    22080
tgtgtgtgtg tgtgtgtgtg tgtgtgtaag accgcacact aacttacgct gaaggaggaa    22140
aacctggagt tccctttgtt gctcagccct gtgtcttctt aggaaaggca ctgtctcagg    22200
ggaaactgaa agataagatt gcttctaaga agttcctggg acgattcatt gaaatggttt    22260
atgttagaca gcttatgatc tcagtctgtg gccctggtat gcaccagaca ccagctctgc    22320
tgccatggac tggtgtttca gttttgagtt ggtgtgttac ctcgtctgta gggttttggg    22380
ggaaagtgtg agtttcaatc cagtggctgc aagctttgtt ggtacttttg cctggggtgg    22440
gtgagtgttt agatggaagc atgcccactg tggattggat cttcacaaag tgtctagact    22500
gtcccttccc agtggttgtc cctccaggcc tggctaccat actgccttt attttattca    22560
ccggaactct gcttagtcat gaaccttggg taagatgcag aaggccatgt tgtactcagt    22620
cagtcctcca actcaccggc aggcacatga ggaaacaccc acaatgaata gcaagggaaa    22680
ggctttgagc tcctttaaac acagtgggca gaggtgacac cttgctatga ccagggtcct    22740
gctgtggtcc agggtcctgt tgtgatccag ggaaggtcct gctgtgatcc agggaaggtc    22800
ctgctgtggt ctggggtcct gctgtggccc catctgtgcc atggttgttc ttttgtctt    22860
taattcttca tccagggaga aatccagctg tcttaggcac tctgaccact cagtcttgca    22920
cagttagtga agtgaggccc tttgacaatg tggaggcaat ggggacttgc tgttggtggt    22980
ggtattcaga tgtaggagag cttatgggtg gcctgaggtt cctgagttgt tgaactttc    23040
aagatccaga cagagcattt gaggattgtt gggtataact gcttagtcct cccagactcc    23100
ctgctccagc atgttgaaaa atatatacct caattacttg aaggcatccc atcctggctg    23160
gtgtgtgtgt gtgtgtgtgt gtgtgtgtgt gtgtgtgtgt gtgtgtgtgt gtgtgtgtgt    23220
gtgtgtgtgc gctcttctct tctcttctct tctcttctct tctcttctct tctcttctct    23280
tctcttctct tctcttctct tctcttctct tctcttctct tctcttctct tctcttctct    23340
tctcttctct tctcttctct tctcttctct tctcttctct tctcttctct tctcttctct    23400
tctcttctct tctcttctct tctcttctct tctcttctct tcttctcttc ctctccctcc    23460
```

```
tgctcgtcct gtgatgataa ccatggatct ggatcttgaa gtgcaagggc tttgtgctgc   23520
tgtgtatttc tcagtgtctg gtctaacaga gcagctgtgg tgctctcacc cttgggtgtg   23580
tagtgtgact ttgtagggtg catgtgcagg tcaggcctct cacctgagtc ctctctcagg   23640
ctcccattcc cctcttgctg tcccacttca gagttggcct gtaggagatg gtagagtggg   23700
agtcctgcta ggagaagaca ggtcatggac gttgtgtgga gcttcatgac cactgatttt   23760
aactcctgac agagcccttc tctttaaaac tgacatcctt gaccaccaat tcccttttgt   23820
gaagagagaa cggtgagtga ctgtctggag atgtagatgt cacagcagtt tgtcaactac   23880
atcctcatag gtgcccatca taaagctcac agatcaggag actgaagtta aagtcgacat   23940
cagctttaac atggagactg gcgtgcgggc ggcagagttc atcaagaatt acatgaaggt   24000
actgttgtct caggtgccca gtaggacaga ggtgtgagac cttgttactc attttctca   24060 tgaatgttaa aaaccttagg atgggtcatg ggtagcaata cagacagtgc aatttccagg   24120
ttctgtcatg gggtctgtgg gggcactcag gaagtgtgta gttgctttct gattggcttt   24180
gagtgactgc ttcttttaga gcactctggg gaaatgttct gtgttagtgc acagcctcgc   24240
tcctgctccc ggctttgtgc tactctccca acctactttc tcacttgcca gactccgtct   24300
aggttggctt agtttagagg cctcagtgct tgtgaatgtg agagtggctg gtgcctgagc   24360
tgctgctttc tggagctttg agtgttggca ctcaggccac acagccaagc ctgtggtctc   24420
tttcctctgt cagttcccct tgtctgtcat tgatctgcag gagcatttgc ccacttccct   24480
cgctctctgt ccctgctttc cctagttctg ttcagggctg agccacctgc ttactgagtg   24540
ctgggattct tgtgtcccac tgatggggtc atggcttggg cctggggtg tggggcagt   24600 accctcagct agtgtgaatc cttaagccta aaattggagt caagagtttt tggggggagg   24660
gagcaggaga atgggtgagg agttcttttt ctcccaggaa gcttgtctag agtcccttca   24720
aaagtacatc agctacgggg ctggagagag agctcagagg ttttaagagt tttttcaatt   24780
caattcccag caaccgccca gtagcttata gctatctata atgagatcta gtgccctctt   24840
ctggcctgca ggtgtacatg caggcataat taaaacaata acaaaaaaaa tatcagctga   24900
cctgtatgcc tcttcttggg tttcagaagt actcgctact gccatacttg attttagtgc   24960
tgaaacagtt cctgctgcag agggacctga atgaggtctt cacaggcggg atcagctcct   25020
acagcctcat cctaatggcc atcagctttc tgcaggtgag cggcctccgc actgtgctct   25080
cctcaccctc actgggctga ggaggcgccc ttttctgctt ctcctcacaa tgctttcttg   25140
gtcagccccc gtcctgtagg ttgattctgt gggtgtaggt ttcagaccct gggtgatgcc   25200
tgcctgtgct tcaggaagct ccaactttta ctatactgag aactgtggat tgtcagtttg   25260
gagcaggaga gcaagaattg gtttattcct atataaatca taaaaagcct tttccactgg   25320
cgcttatctg taaattactc ccaaataccc tgagagtaaa gggtagttac caacatgggg   25380
atgagatgga gacatttcct tttgtgtttt tgagataaag tcactctagt cctgatgac   25440 ctagaactca tgtgcagccc agcctggctt tggacccatg gcagtcctct tgactcagtt   25500
tccctggcac tgagactgca catgtgagcc actctgcctg gcaagccctc tgtgattatt   25560
ggtcttaaat tcggtgtcat ctctgctttg cgagtagagc actaggagct gccctgtcag   25620
cagctggcct cccaagcaag gcgctcctct ccttgctggt tggttggttg gtgatgttga   25680
gccagaacct cttacatact gacctggaat tcactttgta gcccaggctg gccttgaact   25740
agtagcaagt cttctgtctt aggctcctga gcactgagat tatagatgtg agctcttaca   25800
```

```
cctgctaact catatacaaa atagcacctg tgttaaagtt ttattgcatt tctattggct    25860
tgagaaaaca tttgcctgtg tgtgttagtc acctgagtgt atgtccccat gtatatcact    25920
gagagtgtat gtatgtcccc atgtatatca ctgagagtgt atgtatgtcc ccatgtatat    25980
cactgagagt gtatgtatgt ccccatgtat atcactgaga gtgtatgtat gtccccatgt    26040
atatcactga gagtgtatgt ccccatgtat atcactgaga gtgtatgtat gtccccatgt    26100
atatcactga gagtgtatac atgtccccac gtatatcact gagagtgtac gtatgtcccc    26160
atggctgccc aagtctcttt ccccacgtat atcactggtt ctcctttgtg agtgcttgct    26220
gagggtttgt tattcccaat gacactgcta gcctgcaagt cagactgtag ctcggactgt    26280
ggtgagcttt gatgcagacg tgttgccct gaagcattag tccccaggtg tgacagcgga    26340
gaggcttaca gtgctgagcc atcacagtgg gtgacattac tgttagcgac atggcctctg    26400
tttatatctt gagtacccct gatttgaggt aatgtgtttg gatatcttgt caggacaggt    26460
gacgttacct tgagtggggt ttcccaaggc ttcctggtgt gctgttacta ggatccttct    26520
ggctgtcaga cctcacagag ctatatagat gggatagccc tccttctgtg cctgtgttgg    26580
agaccaccca cctgaggctg gacctggtgt agcattctgc ttatctcact gctgctgcct    26640
gagggaagaa ggccaggccc tgtactgggc tgccttgagt atttgatttg gctcaaaagc    26700
aaggacataa aggcttggca agaggactgc cctgttatgt agaggaggga agaactctga    26760
cattatgagg gattattcct ggaaggccac attcatgctt cagccctgtg ctaccaggac    26820
ttggacacta gggaggcttg accgtcacca tctagaattg tgcaaaggac aagttctctg    26880
tgtgaccatg gaagcgatga gccacacgct actcttggat gctgagagta actggcatgc    26940
ccacactcat tctgtagtgg gcagctcagg tctataaagt tgctggcacc tgggagttag    27000
ttatcaggga ccgtgggcaa gcgtcacaga gaggctgtgg cttgctagaa caaagtgtgc    27060
aggtgaaata gcctgacagt gatgtgtgaa agctggaagt gagttcccag gcagagttag    27120
ctctgtccac tcacatcctg gtccaatgat tgtgatactg ttcagtctca tcctgctccc    27180
tcctggtagc atgtcaggat gatgacattg atgtgaacca tgcagccacc atccagatga    27240
caatgtggaa aacttaccat tgcagcatga gggtaactag atgtgtgtgc ttggatgtcg    27300
tggtctgaat ggatgttgag atgtgttctt tctttcaagc ctcccaccaa cagaggctgt    27360
ccattgtctt gtgttttctc aggtgctatc gagtggggac ccctcagtgg gttcctggag    27420
agctgctagg tgagtgttgt tggagtgtag cttgaattca tatgctggtg gctctcttgc    27480
ttttacagtt acatccaaga atcgatgccc ggagagctga tgaaaacctg ggaatgcttc    27540
ttgtagaatt ttttgaactt tatggaagaa attttaatta cttaaaaact ggtattagaa    27600
taaaagaagg aggtgcctat atcgccaaag aagagatcat gaaagccatg accagtgggt    27660
accgaccatc gatgctgtgc attgaggacc ccttactgcc tggtgagctt gcccctctgg    27720
ctggaagcac agtgctggct tatctctacc agcagaactc agtgggaaca ctttcaggtt    27780
tctaacgagt ttactgcact ttaaaatgtt tacattctgg aaatatcata actaggaaag    27840
gctaatcagg gaatcctcac aggaaacatt cacttcagga aggaagcatg ggccaggaag    27900
tgaagaatgg ggactcctgc aggtgattct cctggctttc ctatgtcact gcaaatgttg    27960
ctcttgcagt atgtggtggc tgagctagga ctccaagccc cactccattg gcacgtgtaa    28020
gggtgcttat ctcacccacc gtggtaacac ttggtcttta agtccttgcc aatctgataa    28080
ctgctgcaca ttcttatttta gttatagtcc ttcctggtgc ttgctcttca actctgcata    28140
tgcctgttga gcctgtcttg ggtgataggc taagtgcatg atgggatcag gcaggctgt     28200
```

```
gacaacagga cgacgggagg ctgcaaacgc cttggctttg ttcttctttc gtggaactgt   28260
gcgctgcgct gcagccatgg tctcctgagc tggccacgtt ggtgttctgt gctaggggag   28320
ccttgtccac atgactctca gatcccagct tgtgctttca tttgtattca gtcgcttatt   28380
attctgctcc tattccttat ttatttacta tcctcatttt tttaaataat gtttttatta   28440
aatattttct ttatttacat ttcaaatgtt atcccctttc ctggtttccc ctccgaaaac   28500
cccctatcct catccccact tcccctgct caccaaccca cccactccca cttccctgtc   28560
ctgttattcc cctatactgg gccttcgagc cttcacaaga ccagagggcc tctcctctca   28620
ttgatgtcct acaaggccat cctctgctac atatgtggct ggagccatgg gtccctccat   28680
gtgtactagc tggttggtgg tttagtccct gggagctctg gggggttctg gttggttgat   28740
attattattc cttctatggg gctgcaaacc tcttcagctc cttcagtcca ttctctagct   28800
tctccattgg ggactctgtg cagtggttgg ctgtgagcat tcacttctgt atttgtcagg   28860
ttctggcaga gcctctcagg agacagctat atcaggctcc agtcagcaaa cacttgttgg   28920
catccacaat agtgtctggg tttgttgtct gtatttggga tagatcccca ggtgggacag   28980
tctctggatg gcctttcttt cagtttctgc tctatacttt gtctccgtat ctcctcccat   29040
ggatattttc ttcccctac tgtcctcaaa tttaatgatt attttaaac tgttcgttct   29100 agggtgagac taatttcttt aaaaatcttt tgaaaggaaa atagacaatt ctagtgagct   29160
gtcttcaagt ggctaacgga tcccataaat ggggaggtgg ggttttcgtg gaaacgtcct   29220
gacagtgtgt catctacttg agtgtcccat gtcttcaggt tctatttcag tgtgcctgca   29280
ttactcctgg actgtagctg tgtctaggaa gatgaaattc ccatatcctc cctaaaatcc   29340
catacttgag atgactgagc agtgaatcta tgtaggagtt acagttcctc ttgatgctag   29400
tggtagcttc atttgctttg ctctgtgagt ttgtaataca gcattcttcc cttaaagggc   29460
ttccttccag ttctgatact ctgttcagtg tgagcgaccc cgttacactg tgtgccactc   29520
agggcttatc atgacattga tcatgccaag tccacactgc tggttggtgt gttggatatt   29580
ctggatttcc ttgtggtgtg ggcttcccct ttttttttctt tttcccttttt ctgctacctg   29640 gggtcttagc agactctgtg aactgtcaga cacttgtggc tgccccctttt ccattgttag   29700 gaatagactg gtcacagagt ctgaagcact gaacctgtgt gcaattatat accatgcact   29760
tgcagcagct cgctcgggtc tgtgtttaca tgcctgttgc ttgagctgct gtagttggga   29820
ggcatttggt ggtgagcccc tattcacagt accttgtatg agagacaggt gcctttgtgt   29880
tgcaggaaat gatgttggac ggagttccta tggggccatg caggtgaagc aggtgtttga   29940
ctacgcttac attgtgctca gccacgctgt gtcaccgctc gccaggtctt accccaacag   30000
ggattctgaa aggtaatggg tcttgtgcct gggttctagg ctcctctttc ctgtagagta   30060
gcaggtgtac tttttcatgt gcttctgtgg catggatgga tacactgtca tacttgagtg   30120
gaccttgagg aaagcttttt tgggggcaac aagatggctt ttgggtagcc cgtggcctag   30180
gacagcattt cttagtgggg tggtattgta cttgggacat tctgtattag agcagattcc   30240
tgactttgaa aacctcggtt ggtgcctgtc cagcagctgt caggtgtgct tgcttaggtt   30300
gtgagtgggt tcagatctga acacactgct ctgcctctac agctgtttag ccgtccttca   30360
ctttacagtt gaggatagtc tacagtgtct cctttagtgg ttgtcaggca tatttatttc   30420
cagttcagct tagctgctat agtatgtgca catgggagc aggaggagac aagagtggaa   30480
ggggagaaat gggctgaaca gactgctgtc agcagtgtgt gaatgtctgt tccagagctg   30540
```

```
gctgcctcag gaaactgtta ggaatgggcc tggctttcca tgattgtcca cacacagtgt    30600
tgcaggccag cccctagcct gtaatgggcg cctgggtatc tctccacacc tgtgcagtgg    30660
aaacaaagtg tcaggacttc atggctaccg cttaaactgg attgaagcca tcatttgtag    30720
acagatcttg gttaaggact tctacatagt gaacctacct ttatctgtac cgtgatctca    30780
tggtactatg aatgtaaaca tgtcagacct catgctctct cctgtcttta atgagcctca    30840
catctgacac ctagtgctta tgtccaaccc tgttctctgc agtactttag gaagaatcat    30900
caaagtcacc caggaagtga tcgactaccg gaggtggatc aaagaaaagt ggggtagcag    30960
aatcctcccg tctccagacc ttggtgagag actgacagtg tgaggcgtgg cctctcacca    31020
tagcacagaa gcatctctgc cctcttgtag ggttggccaa gctgtgaaag tagttccttt    31080
tctacttttt ctgataggct atccgttctg taagctctgg accctataga aatacagtcg    31140
tagctgcagt aaacgaaggg aaggagcaga tggaagtggt tgctaatgtt gcatttgatt    31200
aaacgaaggt atactccaac acagtggcaa gaaatcactg agatgcagat aggttttgtt    31260
ccaaatctta gaaatccagt atgtatttgt ttcagaattc tacattctac attgacattg    31320
gacatatttg ttttatgttt atagtttatg acagctacag gttaagactt acacagcact    31380
ggacaaatta tagtgttttc tggtgactag tttgattcac atttaaaatt agattaactc    31440
agatacaagg tttggtttgt taacattcag agttcagcag ccttgtgctt cgagcacatt    31500
gtactaatca ctaacctgga ctttgctttc ctgccccaga caacaggatt aagataaagg    31560
agagaattac cacgtgcaat ggggagcaga tgcagagccg ggagcccagc tccccttaca    31620
cccagcgcct gactctgtcc ctgtccagtc cccagctgct gtcttcaggc tcttctgctt    31680
cttctgtgtc ctcactttct ggaagtgaca ttgtgagtgg gcttttgctc ttgactcgtc    31740
cttctcatgg ggtgggggtgg ccactgtcct tgttatctgt agcagggagt tcaagaccta    31800
ttcctcctcc atctcagtcc cttgctgggg tgtgaggatg tgtgtgtgtg tgagagatgt    31860
atgtgtgtgt gtgagatgta tttgtgtgga tatctatgga gtatatgtga ggtacgtgtg    31920
ggtgggaggt tggggtgtgt gtgtgtggtg tcgtgtctgt cttttgttggg tgttctttga    31980 cataggcttt aagaacccct ggctgtgttg ctccgatgac ccatcaatag cactcagcca    32040
aactttggac tttgagtggt tttttttgag aaatggttta gagatttacc ggttaggtcc    32100
atgtgcctca tctgcatttt ctgcagccta gtctttctcg tgctgcagtg actgaggaag    32160
gataggtttg ctgtaatggc cttttcctagc ttcctcctta aaggcgcctg gctcacactt    32220
cagctgcgct gtgcttatga ctctccttgt ctctgtgctg cgctctagga ctccgacaca    32280
ccgccctgca ccacacccag tgtttatcag ttcagcctgc aagcacccac taccctgatg    32340
gccagcctgc ccacagcctt gccaatgccc agcagcaaac cccagcctgc tgcttccaga    32400
acgttgatca tgacaacaaa caaccaggta caggcttcct ccccggggac ggcatccggg    32460
ccaagcagga ccctagatca gcgttcttgt ggacgactgg gtctagtgct gtctcccggc    32520
agtcatcgtg ctttggtggc tgcagttgtt actcagcctg ttgtgtaacg cagtctctga    32580
cctggagtct gatgttgttc tggagcactg gatgcctctg acaggtgctc tctcagtgcc    32640
gctttgcatg cagtagtgtc cagggcacgc actgctggct gcgtagacac ttgctctctc    32700
tctccagaaa ctcagtgtca gcatgggctt agactctctg ttagtcagtc agtactcggg    32760
acttctcttt ttaaatttta tataaagtga atcaaaagaa aagtatagaa attcagtatt    32820
gtgttgggtt tgtacaaact cagtgcatta ttaactggga aggagaagca gcatttgacg    32880
tgggagttga gtgggaaaca gaacagaagc atgtagatgg ctttcctgga gtcctttggc    32940
```

```
cctgctgaga tccattccca cacagctgct ttgaagctga gctctacgaa agcatgtgac    33000
tctgatgttg gtgagcgttg gacacccttc ccccagtgta gcccagacta cagacctcaa    33060
cgagtgcacg cgaggaactt tccaaggcag ttgttgaagc tattaaattc taccccactt    33120
caacttgact gtcagcttcc ggaaaggaca ctgcccaccc ttccactctg gaggcctctt    33180
tgtcactcgc caggacagtg tcttggagag cccgatgcag gccagcttc  agtttcctgc    33240 cggaggtgtt ttggacctgt ggtgtctaag aaagtatagg tgtggatccc agttggttgt    33300
cacagttgta tgattatcct gtgtgagtgt gagtcaggct gagcttgaaa ccaaagtttg    33360
ctgtaatggc ctggagcaga gtgctggcat ccgattctcc accatgtgct ttctacagag    33420
gtagccaggc tgctgcctct cccagcagct gctatccccc tatggagctc tgctgtcaaa    33480
ggttagctcc tactgtagca agtctctctg caagtgctgg gtaaagcagc gatacctgca    33540
gtgtcaggct gagagtggca cttaccagct ttcttttgct ttgggtggga cagataatgc    33600
ggtggccaga aagagccgcc ctctttgact cttcttgtgt tcctctgttc ctctggggtc    33660
tgagggttgt tcactttggg gctcattcta gggactaaag tgacagttgc tgttttggtg    33720
gctctaattg ttttgaattt ggtttgatct ttggagaatg ttagatttta tgacctagtg    33780
actgttataa cttggtattg taattgctat ttgagaagat gagatgattg taattccaag    33840
gccacagtgt ccttaggtca aacagaagc  tgtgctccgt gggcatgtgt gtgagtggat    33900
tcgcacagcc agccccacac tgctttcact tggtgtgaag tttcacttgt gggaagctca    33960
tgtttctctt ttccttctag accagggtta ctatccctcc accaaccctc ggagtcgccc    34020
ctgttccttg cagacaggct ggtgtcgacg gaaccacatc tttgaaggct gttcacagtg    34080
taacttcccc agccattccc tcggcatccc ccaacccact gtctagtcct catctgtatc    34140
acaaggtaag tgtcgtctgc tgctgggcta ctttactgca gccgcttgct cactcggggc    34200
cctgcacccc ttggaactga attccccctgc atgctctctg gttggtggtt cagtctctgt    34260
gagcccccat gggcccgggt tgttgactc  tgaccctgca gggaccttct cacacccatg    34320
aagaggcaga gcagattaaa agcctgtagg ctctgagtgg agccatagtc tgttcagagg    34380
gaagggttcc ctcagcttac tgcacgccgc agcagggatt atgtggctat gggttcctgt    34440
tgtacattgt gtcttttcac ctcatggtct gtgtgctgca ctccagccct gctttctctc    34500
tctccagcag cacaatggca tgaaactgtc catgaaaggc tcccacaacc acactcaggg    34560
tggcggctac agctctgtgg gcagtggagc tgtgaggcct cctgtaggca accgaggaca    34620
tcatcagtac aaccgcaccg gctggaggag aaaaaagcac gcacacacaa gggacagcct    34680
gcccgtgagt ctcagcagat aatggtcctg actgactgcc caaaggcctc gctcgggcac    34740
cacaggggag ccgagaccag catccagcac ctccaccgct gtctgccaag cgcagcccag    34800
cactggtcac tctgcatgtt tgtgtggtgg ccgcatccat cttacagaac agctccttgt    34860
gctcatctgt gaagccttac tacatgtgga tgtgcgtctg cctgcctaga agtcttcatc    34920
tgtgcccagc agggcggcct aggagtgtca gggactggat gtgcggctgt gcagccgggt    34980
cagctaggtg gccatttggg gttctcatcg tgtctgtcac aggcagagac gccaagccct    35040
gctccgtgtc ttctgacgga gtgggcaggc tgctgtttta ctgccctcat gtcttgtttg    35100
aaaatttggg actgttttc  tatgtaaata ttgaaaactt atgatttgtg caataactca    35160
gatatttttt atttaatttc atattttcac ataagttata tttaagggag gagggaattt    35220
tttttaaaac acgcttaaat cctttcccaa tttgcatttt ctaagttggg ttcctcgtgt    35280
```

```
tggctggtta tctgatagca tcctgacatg aacaccgtga ggagggaggg gcctgtgggc   35340
tttgttttta tgtcttttct tttggtcaga tgcagtgaag gagccaagtc aacttgatag   35400
ttctgtgagg ccagtgtgta cctggcagcc tggctgtcgg ccttgggcct ttgtcctctc   35460
tgaccacgag ttctgacatt ttggtttggg ttttttaaaaa ctagacacca aatccagcat   35520
ttaaagtgcc agaagtaaga acctctaaga ggagaagagg ttgtcacgtc gtataaatcg   35580
taaagaatcg tgactctggg cgtgcttcgg tcattaagtg acgtggtcta gagtcacggg   35640
cctggtgagt atcgttacag acaatggcac ccagatttag gaatgtggag aaagggattt   35700
tgttgattcc attgaggaat ctgcataggt atgcactcgt tctgttaaga gcaaatatct   35760
gaaaaggacc tccgttgtcc aggcacatgg gggtatttta atgtatcaca ggagagcaca   35820
gccccagtgt gggcccagga gcggctggtg cctggcgtca gaagcataca ggtatactat   35880
gcaagtgtat tctgccacaa ccactgtctt tgttactttt tttgaacaag aatccatcca   35940
ttgcctgacc ctgattctca agcaccacgg ttgtcctgga gtgcttgcag ttgtaggccc   36000
tctgacttct gcttctaaaa cggggggtctg gacctgctgc acaccacagg caggttgctt   36060
cttgtccacc agtacagagt gtcaagccga gtgctgtgcc acctgattga catgcagcag   36120
tggaaattct gaatggatgt ctgagtgaca ttggacacct cgccaaggac aagctctgtg   36180
tgtctgggtc tgcctcctgc tgccgtggtg aggctgttga ctctgggagg cattccagag   36240
cagaggagca catgggtctg cagctcatga ggattggagt catccagaat atttaaaatt   36300
atttaaattg tgaagcctgt tgctaaagaa tatttatgaa cactggtcca tagcctgtac   36360
taatttacac attagcaata ttgactgtat ctgcattaag gagccaccgt ggggccgttc   36420
gagtgacccg cagatgtgcg ttttaaagtt ctgtcatcca caggcacagg tatgtgtccg   36480
tctccgtcat ggtgaaccag atgaattggc ctggcgacca ctgtggccat atgctacagt   36540
ttacaaaatg ataccatgtt taaattttct gtgcggacaa caatgtggac actaaaatta   36600
acatattttt atgtaaagtt tttctattct ttgatcttta ataaacttta gatgctaga    36659
```

<210> SEQ ID NO 7
<211> LENGTH: 16
<212> TYPE: DNA
<213> ORGANISM: Artificial sequence
<220> FEATURE:
<223> OTHER INFORMATION: oligonucleotide motif

<400> SEQUENCE: 7
agatctgcat ccacag                                                  16

<210> SEQ ID NO 8
<211> LENGTH: 17
<212> TYPE: DNA
<213> ORGANISM: Artificial sequence
<220> FEATURE:
<223> OTHER INFORMATION: oligonucleotide motif

<400> SEQUENCE: 8
cagatctgca tccacag                                                 17

<210> SEQ ID NO 9
<211> LENGTH: 18
<212> TYPE: DNA
<213> ORGANISM: Artificial sequence
<220> FEATURE:
<223> OTHER INFORMATION: oligonucleotide motif

<400> SEQUENCE: 9
ccagatctgc atccacag                                              18

<210> SEQ ID NO 10
<211> LENGTH: 17
<212> TYPE: DNA
<213> ORGANISM: Artificial sequence
<220> FEATURE:
<223> OTHER INFORMATION: oligonucleotide motif

<400> SEQUENCE: 10
ccagatctgc atccaca                                               17

<210> SEQ ID NO 11
<211> LENGTH: 17
<212> TYPE: DNA
<213> ORGANISM: Artificial sequence
<220> FEATURE:
<223> OTHER INFORMATION: oligonucleotide motif

<400> SEQUENCE: 11
cccagatctg catccac                                               17

<210> SEQ ID NO 12
<211> LENGTH: 16
<212> TYPE: DNA
<213> ORGANISM: Artificial sequence
<220> FEATURE:
<223> OTHER INFORMATION: oligonucleotide motif

<400> SEQUENCE: 12
cccagatctg catcca                                                16

<210> SEQ ID NO 13
<211> LENGTH: 17
<212> TYPE: DNA
<213> ORGANISM: Artificial sequence
<220> FEATURE:
<223> OTHER INFORMATION: oligonucleotide motif

<400> SEQUENCE: 13
tcccagatct gcatcca                                               17

<210> SEQ ID NO 14
<211> LENGTH: 17
<212> TYPE: DNA
<213> ORGANISM: Artificial sequence
<220> FEATURE:
<223> OTHER INFORMATION: oligonucleotide motif

<400> SEQUENCE: 14
gtctcccaga tctgcat                                               17

<210> SEQ ID NO 15
<211> LENGTH: 16
<212> TYPE: DNA
<213> ORGANISM: Artificial sequence
<220> FEATURE:
<223> OTHER INFORMATION: oligonucleotide motif

<400> SEQUENCE: 15
tctcccagat ctgcat                                                16

<210> SEQ ID NO 16
<211> LENGTH: 16
<212> TYPE: DNA

```
<213> ORGANISM: Artificial sequence
<220> FEATURE:
<223> OTHER INFORMATION: oligonucleotide motif

<400> SEQUENCE: 16
gtctcccaga tctgca                                                      16

<210> SEQ ID NO 17
<211> LENGTH: 17
<212> TYPE: DNA
<213> ORGANISM: Artificial sequence
<220> FEATURE:
<223> OTHER INFORMATION: oligonucleotide motif

<400> SEQUENCE: 17
tcaactttca cttcagt                                                     17

<210> SEQ ID NO 18
<211> LENGTH: 16
<212> TYPE: DNA
<213> ORGANISM: Artificial sequence
<220> FEATURE:
<223> OTHER INFORMATION: oligonucleotide motif

<400> SEQUENCE: 18
tcaactttca cttcag                                                      16

<210> SEQ ID NO 19
<211> LENGTH: 16
<212> TYPE: DNA
<213> ORGANISM: Artificial sequence
<220> FEATURE:
<223> OTHER INFORMATION: oligonucleotide motif

<400> SEQUENCE: 19
tgtttcaata ctaaaa                                                      16

<210> SEQ ID NO 20
<211> LENGTH: 18
<212> TYPE: DNA
<213> ORGANISM: Artificial sequence
<220> FEATURE:
<223> OTHER INFORMATION: oligonucleotide motif

<400> SEQUENCE: 20
catcaacttt cacttcag                                                    18

<210> SEQ ID NO 21
<211> LENGTH: 19
<212> TYPE: DNA
<213> ORGANISM: Artificial sequence
<220> FEATURE:
<223> OTHER INFORMATION: oligonucleotide motif

<400> SEQUENCE: 21
catcaacttt cacttcagt                                                   19

<210> SEQ ID NO 22
<211> LENGTH: 20
<212> TYPE: DNA
<213> ORGANISM: artificial
<220> FEATURE:
<223> OTHER INFORMATION: Oligonucleotide motif

<400> SEQUENCE: 22
caacataagt ctacacatcc                                                  20
```

```
<210> SEQ ID NO 23
<211> LENGTH: 19
<212> TYPE: DNA
<213> ORGANISM: artificial
<220> FEATURE:
<223> OTHER INFORMATION: Oligonucleotide motif

<400> SEQUENCE: 23
cagttttacc gattcatca                                                 19

<210> SEQ ID NO 24
<211> LENGTH: 19
<212> TYPE: DNA
<213> ORGANISM: artificial
<220> FEATURE:
<223> OTHER INFORMATION: Primer

<400> SEQUENCE: 24
ctgtgccttg ggtggcttt                                                 19

<210> SEQ ID NO 25
<211> LENGTH: 24
<212> TYPE: DNA
<213> ORGANISM: artificial
<220> FEATURE:
<223> OTHER INFORMATION: Primer

<400> SEQUENCE: 25
aaggaaagaa gtcagaaggc aaaa                                           24

<210> SEQ ID NO 26
<211> LENGTH: 34
<212> TYPE: DNA
<213> ORGANISM: artificial
<220> FEATURE:
<223> OTHER INFORMATION: Prope
<220> FEATURE:
<221> NAME/KEY: ZEN
<222> LOCATION: (9)..(10)
<223> OTHER INFORMATION: internal quencher

<400> SEQUENCE: 26
agctccaaat tctttataag ggtcgatgtc catg                                34

<210> SEQ ID NO 27
<211> LENGTH: 16
<212> TYPE: DNA
<213> ORGANISM: artificial
<220> FEATURE:
<223> OTHER INFORMATION: oligonucleotide motif

<400> SEQUENCE: 27
agcgaagtgc acacgg                                                    16

<210> SEQ ID NO 28
<211> LENGTH: 13
<212> TYPE: DNA
<213> ORGANISM: artificial
<220> FEATURE:
<223> OTHER INFORMATION: oligonucleotide motif

<400> SEQUENCE: 28
gcgtaaagag agg                                                       13
```

```
<210> SEQ ID NO 29
<211> LENGTH: 18
<212> TYPE: DNA
<213> ORGANISM: artificial
<220> FEATURE:
<223> OTHER INFORMATION: oligonucleotide motif

<400> SEQUENCE: 29
caagcgaagt gcacacgg                                                 18

<210> SEQ ID NO 30
<211> LENGTH: 15
<212> TYPE: DNA
<213> ORGANISM: artificial
<220> FEATURE:
<223> OTHER INFORMATION: oligonucleotide motif

<400> SEQUENCE: 30
cagcgtaaag agagg                                                    15

<210> SEQ ID NO 31
<211> LENGTH: 18
<212> TYPE: DNA
<213> ORGANISM: artificial
<220> FEATURE:
<223> OTHER INFORMATION: oligonucleotide motif

<400> SEQUENCE: 31
caaaggttgt tgtactct                                                 18

<210> SEQ ID NO 32
<211> LENGTH: 17
<212> TYPE: DNA
<213> ORGANISM: artificial
<220> FEATURE:
<223> OTHER INFORMATION: oligonucleotide motif

<400> SEQUENCE: 32
cagttttatg ctaatca                                                  17

<210> SEQ ID NO 33
<211> LENGTH: 17
<212> TYPE: DNA
<213> ORGANISM: artificial
<220> FEATURE:
<223> OTHER INFORMATION: oligonucleotide motif

<400> SEQUENCE: 33
gtattcttat tcttgct                                                  17

<210> SEQ ID NO 34
<211> LENGTH: 19
<212> TYPE: DNA
<213> ORGANISM: artificial
<220> FEATURE:
<223> OTHER INFORMATION: oligonucleotide motif

<400> SEQUENCE: 34
cattgctttt ataatccta                                                19

<210> SEQ ID NO 35
<211> LENGTH: 19
<212> TYPE: DNA
<213> ORGANISM: Homo sapiens
```

```
<400> SEQUENCE: 35
ggtcctggcc ggcgcccgc                                                    19
```